US007576117B1

(12) United States Patent
Shiota et al.

(10) Patent No.: US 7,576,117 B1
(45) Date of Patent: Aug. 18, 2009

(54) CYCLIC AMINE CCR3 ANTAGONIST

(75) Inventors: Tatsuki Shiota, Tokyo (JP); Masaki Sudoh, Aichi (JP); Tomonori Yokoyama, Tokyo (JP); Yumiko Muroga, Tokyo (JP); Takashi Kamimura, Tokyo (JP); Akinobu Nakanishi, Tokyo (JP)

(73) Assignee: Teijin Limited, Osaka (JP)

( * ) Notice: Subject to any disclaimer, the term of this patent is extended or adjusted under 35 U.S.C. 154(b) by 275 days.

(21) Appl. No.: 10/031,698

(22) PCT Filed: Aug. 4, 2000

(86) PCT No.: PCT/JP00/05260

§ 371 (c)(1),
(2), (4) Date: Jan. 23, 2002

(87) PCT Pub. No.: WO01/10439

PCT Pub. Date: Feb. 15, 2001

(30) Foreign Application Priority Data

Aug. 4, 1999 (JP) ................................ 11/220864

(51) Int. Cl.
*A61K 31/40* (2006.01)
*A61K 31/38* (2006.01)

(52) U.S. Cl. ........................ 514/408; 514/422; 514/447

(58) Field of Classification Search ................. 514/408, 514/422, 447
See application file for complete search history.

(56) References Cited

U.S. PATENT DOCUMENTS

| | | | | |
|---|---|---|---|---|
| 4,443,461 A | | 4/1984 | Ward | |
| 6,166,015 A | * | 12/2000 | Rogers et al. | 514/243 |
| 6,362,177 B1 | | 3/2002 | Shiota et al. | |
| 6,410,566 B1 | | 6/2002 | Shiota et al. | |
| 6,451,842 B1 | * | 9/2002 | Shiota et al. | 514/422 |

FOREIGN PATENT DOCUMENTS

| | | | |
|---|---|---|---|
| CN | 1279668 | A | 1/2001 |
| EP | 217286 | A1 | 4/1987 |
| EP | 903349 | | 3/1999 |
| EP | 1 201 239 | A1 | 5/2002 |
| GB | 2106108 | A | 4/1983 |
| WO | WO 97/24325 | | 7/1997 |
| WO | WO 97/40051 | A1 | 10/1997 |
| WO | WO 97/44329 | | 11/1997 |
| WO | WO 98/02151 | | 1/1998 |
| WO | WO 98/04554 | | 2/1998 |
| WO | WO 98/06703 | | 2/1998 |
| WO | WO 98/25604 | | 6/1998 |
| WO | WO 98/25605 | | 6/1998 |
| WO | WO 98/25617 | | 6/1998 |
| WO | WO 98/27815 | | 7/1998 |
| WO | WO 98/30218 | | 7/1998 |
| WO | WO 98/31364 | | 7/1998 |
| WO | WO 98/38167 | | 9/1998 |
| WO | WO 98/50534 | A1 | 11/1998 |
| WO | WO 99/01127 | | 1/1999 |
| WO | 99/25686 | A1 | 5/1999 |
| WO | WO 99/25686 | A1 | 5/1999 |
| WO | WO 00/9377 | | 2/2000 |
| WO | WO 00/31032 | A1 | 6/2000 |
| WO | WO 00/31033 | | 6/2000 |
| WO | WO 00/35449 | | 6/2000 |
| WO | WO 00/35451 | | 6/2000 |
| WO | WO 00/69815 | A | 11/2000 |

OTHER PUBLICATIONS

Frade et al. "The amino-terminal Domain of the CCR2 chemokine receptor acts as coreceptor for HIV-1 infection," J. Chinical Investigation, 1997, vol. 100, No. 3, pp. 497-502.*

Khalid et al, "N, N'-disubstituted L-isoglutamines as novel cancer chemotherapeutic agents", Drugs Exp. Clin. Res. (1987), vol. 13, Suppl. 1, p. 57-60.

International Search Report.

N. Zimmerman, et al. "Polymorphisms in the human CC chemokine receptor-3 gene" *Biochimica et Biophysica Acta. Gene Structure and Expression*, Elsevier Amsterdam, NL, vol. 1442, No. 2-3, Nov. 8, 1998, pp. 170-176, XP004275252

H. Choe, et al. "The Beta-Chemokine Receptors CCR3 and CCR5 Facilitate Infection by Primary HIV-1 Isolates" *Cell, Cell Press*, Cambridge MA, US, vol. 85, No. 7, Jun. 28, 1996, pp. 1135-1148.

Chen, et al. "CCR3 and CCR5 are co-receptors for HIV-infection of microglia" *Nature, Macmillan Journals Ltd*., London, GB, vol. 385, No. 6617, Feb. 13, 1997, pp. 645-649, XP002107165.

Krishna Vaddi, "Chemokine Facts Book, Acad. Press," 1997 San Diego, CA, pp. 1-2, 10-37, 86-130, 135-137, 142-143, 158-164.

Franklin H. Epstein, M.D, Luster, D. Andrew, "Chemokines—Chemotactic Cytokines that Mediate Inflammation", The New England Journal of Medicine (Feb. 12, 1998), vol. 338 pp. 436-445.

Marco Baggiolini "Chemokines and leukocyte traffic" Nature vol. 392 pp. 565-568 Apr. 9, 1998.

(Continued)

*Primary Examiner*—Shengjun Wang
(74) *Attorney, Agent, or Firm*—Sughrue Mion, PLLC

(57) ABSTRACT

A medicine containing, as an active ingredient, a cyclic amine derivative represented by the following formula (I), (I)

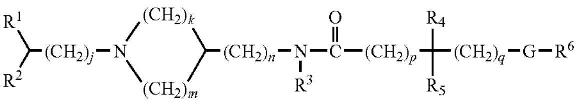

a pharmaceutically acceptable acid addition salt thereof or a pharmaceutically acceptable $C_1$ to $C_6$ alkyl addition salt thereof. The medicine has an action for treating or preventing diseases in which CCR3 participates, such as asthma and allergic rhinitis.

2 Claims, No Drawings

OTHER PUBLICATIONS

Joseph Hesselgesser "Identification and Characterization of Small Molecule Functional Antagonists of the CCR1 Chemokine Receptor" The Journal of Biological Chemistry vol. 273, No. 25, Jun. 19, 1998 pp. 15687-15692.

European Communication Nov. 29 , 2002.

Bright, Colin, et al. Identification of a Non- Peptidic Rantes Antagonist, vol. 1, No. 1, Bioorganic & Medicinal Chemistry Letters, 1998 pp. 771-774.

Ward, G. Stephen, et al., "Chemokines: understanding their role in T-lymphocyte biology", Biochem. J. (1998) 333, pp. 457-470.

European Communication Sep. 17, 2003.

Rapport, Carol A., et al., "Molecular Cloning and Functional Characterization of a Novel Human CC Chemokine Receptor (CCR5) for Rantes, MIP-1β, and MIP-1α," The Journal of Biological Chemistry, The American Society for Biochemistry and Molecular Biology, Inc., 1996, pp. 17161-17166, vol. 271, No. 29, Issue of Jul. $19^{th}$, USA.

Murai, Masako, et al., "Active participation of $CCR5^+CD8^+$ T lymphocytes in the pathogenesis of liver injury in graft-versus-host disease," The Journal of Clinical Investigations, Jul. 1999, pp. 49-57, vol. 104, No. 1.

Balashov, Konstantin E., "$CCR5^+$ and $CXCR3^+$ T cells are Increased in multiple sclerosis and their ligands MIP-1α and IP-10 are expressed in demyelinating brain lesions," Proc. Natl. Acad. Sci., Jun. 1999, pp. 6873-6878, vol. 90, USA.

Bradley, Linda, et al., The Journal of Immunology, vol. 162(5), pp. 2511-2520, Mar. 4, 1999.

Zimmerman, N. et al., "Polymorphisms in the human CC chermokine receptor-3 gene", Biochimica et Biophysica Acta, 1998, pp. 170-176, vol. 1442, Elsevier Science B.V.

* cited by examiner

CYCLIC AMINE CCR3 ANTAGONIST

This application is a 371 of PCT/JP00/05260, filed Aug. 4, 2000, which claims the priority of Japan application Ser. No. 11/220,864, filed Aug. 4, 1999.

TECHNICAL FIELD

The present invention relates to a CCR3 antagonist which can be expected to have effects as a remedies and/or a prophylactics against diseases, for whose progress and maintenance the increase and tissue infiltration of eosinophils, basophils, activated T-cells and the like play main rolls, for example, allergic diseases such as asthma, allergic rhinitis, atopic dermatitis, urticaria, contact dermatitis and allergic conjunctivitis, inflammatory bowel diseases such as ulcerative colitis and Crohn disease, eosinophilia, eosinophilic gastroenteritis, eosinophilic enteropathy, eosinophilic fasciitis, eosinophilic granuloma, eosinophilic pustular folliculitis, eosinophilic pneumonia, eosinophilic leukemia and the like, or AIDS (acquired immunodeficiency syndrome) caused by the infection of HIV (human immunodeficiency virus).

BACKGROUND ART

In recent years, a concept that the essential pathosis of allergic diseases such as asthma is chronic inflammation has been established, and the accumulation of eosinophils at an inflammatory region is especially thought to be one of the principal characteristics of the diseases (refer to, for example, Busse, W. W. J. Allergy Clin. Immunol., 1998, 102, S17-S22; Takao Fujisawa, Gendai Iryo, 1999, 31, 1297, and so on). For example, when an antibody against intercellular adhesion molecule-1 (ICAM-1) was administered into a simian asthmatic model, the accumulation of eosinophils was inhibited, and the manifestation of a late asthmatic response was controlled. Thereby, the importance of the eosinophils in allergic diseases was strongly suggested (Wegner, C. D. et al., Science, 1990, 247, 456).

Eotaxin was identified as a specific chemotactic factor causing the accumulation/chemotaxis of eosinophil (refer to, for example, Jose, P. J., et. al., J. Exp. Med., 1994, 179, 881; Garcia-Zepda, E. A. et al., Nature Med., 1996, 2, 449; Ponath, P. D. et al., J. Clin. Invest., 1996, 97, 604; Kitaura, M. et al., J. Biol. Chem., 1996, 271, 7725, and so on). Further, it was elucidated that eotaxin bound to a CCR3 receptor expressed on eosinophil to display the action, and it is also known that chemotactic factors such as RANTES (abbreviation of regulated upon activation normal T-cell expressed and secreted), MCP-2 (abbreviation of monocyte chemoattractant protein-2), MCP-3 (abbreviation of monocyte chemoattractant protein-3), and MCP-4 (abbreviation of monocyte chemoattractant protein-4) can exhibit the same actions as that of the eotaxin through CCR3, although the action potencies of the chemotactic factors are weaker than that of the eotaxin (refer to, for example, Kitaura, M. et al., J. Biol. Chem., 1996, 271, 7725; Daugherty, B. L. et al., J. Exp. Med., 1996, 183, 2349; Panath, P. D. et al., J. Exp. Med., 1996, 183, 2437; Hiath, H. et at., J. Clin. Invest., 1997, 99, 178; Patel, V. P. et al., J. Exp. Med., 1997, 185, 1163; Forssmann, U. et al., J. Exp. Med. 185, 2171, 1997, and so on).

Not only an action for causing chemotaxis but also actions related to the activation of eosinophils, such as the enhancement in the expression of adhesion molecule receptor (CD11b) (refer to, for example, Tenscher, K. et al., Blood, 1996, 88, 3195, and so on), the stimulation in the production of active oxygen (refer to, for example, Elsner, J. et al., Eur. J. Immunol., 1996, 26, 1919, and so on), the stimulation in the release of EDN (abbreviation of eosinophil-derived neurotoxin) [refer to El-Shazly, et al., Int. Arch. Allergy Immunol., 1998, 117 (suppl. 1), 55], have been reported as the actions of the eotaxin on the eosinophils. It has also been reported that eotaxin has an action for stimulating the release of eosinophils and their precursor cells from bone marrow into blood (refer to, for example, Palframan, R. T. et al., Blood, 1998, 91, 2240, and so on).

Many reports show that eotaxin and CCR3 play important roles on allergic diseases such as asthma. For example, the inhibition of eosinophil infiltration with an anti-eotaxin antibody in a mouse asthma model (refer to Gonzalo, J.-A. et al., J. Clin. Invest., 1996, 98, 2332), the inhibition of eosinophil infiltration with an anti-eotaxin antiserum in a mouse dermal allergy model (refer to Teixeira, M. M. et al., J. Clin. Invest., 1997, 100, 1657), the inhibition in the formation of pulmonary granuloma with an anti-eotaxin antibody in a mouse model (refer to Ruth., J. H. et al., J. Immunol., 1998, 161, 4276), the inhibition of eosinophil infiltration in an asthma model and an interstitial keratitis model using eotaxin gene-deficient mice, respectively, (refer to Rothenberg, M. E. et al., J. Exp. Med., 1997, 185, 785), the increase in the expression of eotaxin and CCR3 in the bronchus of an asthmatic patient at a genetic level and a protein level in comparison with a healthy subject (refer to Ying, S. et al., Eur. J. Immunol., 1997, 27, 3507), and the increase in the expression of eotaxin in the nasal subepithelium tissue of a chronic sinusitis patient (refer to Am. J. Respir. Cell Mol. Biol., 1997, 17, 683), have been reported.

Additionally, since it has been reported that eotaxin is expressed in large amounts in the inflammatory regions of Crohn disease and ulcerative colitis which is an inflammatory large bowel disease (refer to Garcia-Zepda E. A. et al., Nature Med., 1996, 2, 449), it can be understood that the eotaxin also plays important roles on the diseases.

From these data, it is strongly suggested that the eotaxin accumulates and activates the eosinophils in the lesion regions through CCR3 and thereby deeply participates in the initiation progression and maintenance of diseases in which the deep participation of the eosinophils in the progresses of the lesions can be supposed, for example, allergic diseases such as asthma, allergic rhinitis, atopic dermatitis, urticaria, contact dermatitis, and allergic conjunctivitis, inflammatory bowel diseases such as ulcerative colitis and Crohn disease, eosinophilia, eosinophilic gastroenteritis, eosinophilic enteropathy, eosinophilic fasciitis, eosinophilic granuloma, eosinophilic pustular folliculitis, eosinophilic pneumonia and eosinophilic leukemia.

Further, since they have been reported that CCR3 receptors reveal not only on eosinophils but also on basophils and Th2 lymphocytes and that the increase in the intracellular calcium ion concentrations of the cells and the chemotaxis of the cells are caused by the eotaxin, the eotaxin and the CCR3 are supposed to have relations with the initiation progression and maintenance of the diseases in which the cells participate, such as allergic diseases, also by the accumulation and activation of the cells (refer to, for example, Sallusto, F. et al., Science, 1997, 277, 2005; Gerber, B. O. et al., Current Biol., 1997, 7, 836; Sallusto, F. et at., J. Exp. Med., 1998, 187, 875; Uguccioni, M. et al., J. Clin. Invest., 1997, 100, 1137; Yamada, H. et al., Biochem Biophys. Res. Commun., 1997, 231, 365; and so on).

Thereby, a compound for inhibiting the binding of eotaxin to the CCR3, namely, a CCR3 antagonist, is supposed to be useful as a medicine for treating and/or preventing diseases such as allergic diseases and inflammatory intestinal diseases by inhibiting the action of a CCR3 ligand represented by the eotaxin on a target cell, but a medicine having such the action is now not known.

In addition, since it has been reported that HIV-1 (human immunodeficiency virus-1) utilizes CCR3 on the infection of a host cell, a CCR3 antagonist is supposed to be useful for a medicine for treating or preventing AIDS (acquired immunodeficiency syndrome) caused by the infection of the HIV (refer to, for example, Choe, H. et at., Cell, 1996, 85, 1135; Doranz, B. J. et al., Cell, 1996, 85, 1149).

Recently, it has been reported that xanthene-9-carboxamide derivatives (refer to WO 9804554), piperazine or piperidine derivatives (refer to EP 903349; WO 0029377; WO 0031033; WO 0035449; WO 0035451; WO 0035452; WO 0035453; WO 0035454; WO 0035876; WO 0035877), pyrrolidine derivatives (refer to WO 0031032), phenylalanine derivatives (refer to WO 9955324; WO 9955330; WO 0004003; WO 0027800; WO 0027835; WO 0027843), and other low molecular compounds (refer to WO 9802151) have antagonistic activities to CCR3 receptors. However, these compounds are different from the compounds used in the present invention. And, the compounds used in the present invention are the same as the compounds mentioned in WO 9925686, but it is not known that these compounds have antagonistic activities to CCR3 receptors.

DISCLOSURE OF THE INVENTION

Thereby, the object of the present invention is to provide low molecular compounds, which have activities to inhibit that the ligand of CCR3, such as eotaxin, binds to the CCR3 on a target cell.

Another object of the present invention is to provide a method for treating and/or preventing, with a CCR3 antagonist, such a disease that the binding of the ligand of CCR3, such eotaxin, to the CCR3 on a target cell is an etiology.

The inventors of the present invention have zealously made studies, and have consequently discovered that a cyclic amine derivative having an arylalkyl group, a pharmaceutically acceptable $C_1$ to $C_6$ alkyl addition salt thereof, or a pharmaceutically acceptable acid addition salt thereof has an activity to inhibit the binding of the ligand of CCR3, such as the eotaxin, to a target cell, and further have found that the compounds can be used as medicines for treating or preventing diseases in which the participation of CCR3 is supposed. The studies have further been continued to accomplish the present invention.

Namely, in accordance with the present invention, there is provided a medicine, which contains, as an active ingredient, a compound represented by the following formula (I), a pharmaceutically acceptable acid addition salt thereof or a pharmaceutically acceptable $C_1$ to $C_6$ alkyl addition salt thereof, and which has a $CCR^3$ antagonistic action, (I)

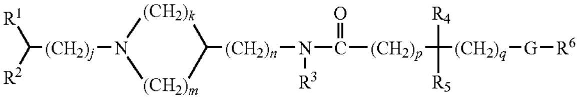

[wherein, $R^1$ represents a phenyl group, a $C_3$ to $C_8$ cycloalkyl group, or an aromatic heterocyclic group having one to three atoms of oxygen, sulfur and/or nitrogen as heteroatoms, provided that the phenyl group or the aromatic heterocyclic group in the above-mentioned $R^1$ may be condensed with a benzene ring, or an aromatic heterocyclic group having one to three atoms of oxygen, sulfur and/or nitrogen as heteroatoms to form a condensed ring, further provided that the phenyl group, the $C_3$ to $C_8$ cycloalkyl group, the aromatic heterocyclic group or the condensed ring may be substituted by the arbitrary number of halogen atoms, hydroxy groups, cyano groups, nitro groups, carboxyl groups, carbamoyl groups, $C_1$ to $C_6$ alkyl groups, $C_3$ to $C_8$ cycloalkyl groups, $C_2$ to $C_6$ alkenyl groups, $C_1$ to $C_6$ alkoxy groups, $C_1$ to $C_6$ alkylthio groups, $C_3$ to $C_5$ alkylene groups, $C_2$ to $C_4$ alkylenoxy groups, $C_1$ to $C_3$ alkylenedioxy groups, phenyl groups, phenoxy groups, phenylthio groups, benzyl groups, benzyloxy groups, benzoylamino groups, $C_2$ to $C_7$ alkanoyl groups, $C_2$ to $C_7$ alkoxycarbonyl groups, $C_2$ to $C_7$ alkanoyloxy groups, $C_2$ to $C_7$ alkanoylamino groups, $C_2$ to $C_7$ N-alkylcarbamoyl groups, $C_4$ to $C_9$ N-cycloalkylcarbamoyl groups, $C_1$ to $C_6$ alkylsulfonyl groups, $C_3$ to $C_8$ (alkoxycarbonyl)methyl groups, N-phenylcarbamoyl groups, piperidinocarbonyl groups, morpholinocarbonyl groups, 1-pyrrolidinylcarbonyl groups, divalent groups represented by the formula: —NH(C═O)O—, divalent groups represented by the formula: —NH(C═S)O—, amino groups, mono($C_1$ to $C_6$ alkyl)amino groups or di($C_1$ to $C_6$ alkyl)amino groups, and further provided that the substituents of the phenyl group, the $C_3$ to $C_8$ cycloalkyl group, the aromatic heterocyclic group or the condensed ring may further be substituted by the arbitrary number of halogen atoms, hydroxy groups, amino groups, trifluoromethyl groups, $C_1$ to $C_6$ alkyl groups or $C_1$ to $C_6$ alkoxy groups.

$R^2$ represents a hydrogen atom, a $C_1$ to $C_6$ alkyl group, a $C_2$ to $C_7$ alkoxycarbonyl group, a hydroxy group or a phenyl group, provided that the $C_1$ to $C_6$ alkyl group or the phenyl group in $R^2$ may be substituted by the arbitrary number of halogen atoms, hydroxy groups, $C_1$ to $C_6$ alkyl groups or $C_1$ to $C_6$ alkoxy groups, and provided that when j is 0, $R^2$ is not a hydroxy group.

j represents an integer of 0 to 2.

k represents an integer of 0 to 2.

m represents an integer of 2 to 4.

n represents 0 or 1.

$R^3$ represents a hydrogen atom or a $C_1$ to $C_6$ alkyl group which may be substituted (by one or two phenyl groups which may be substituted by the same or different arbitrary numbers of halogen atoms, hydroxy groups, $C_1$ to $C_6$ alkyl groups or $C_1$ to $C_6$ alkoxy groups, respectively).

$R^4$ and $R^5$, same or differently, represent a hydrogen atom, a hydroxy group, a phenyl group or a $C_1$ to $C_6$ alkyl group, respectively, and the $C_1$ to $C_6$ alkyl group in $R^4$ and $R^5$ may be substituted by the arbitrary number of halogen atoms, hydroxy groups, cyano groups, nitro groups, carboxyl groups, carbamoyl groups, mercapto groups, guanidino groups, $C_3$ to $C_8$ cycloalkyl groups, $C_1$ to $C_6$ alkoxy groups, $C_1$ to $C_6$ alkylthio groups, phenyl groups (which may be substituted by the arbitrary number of halogen atoms, hydroxy groups, $C_1$ to $C_6$ alkyl groups, $C_1$ to $C_6$ alkoxy groups or benzyloxy groups), phenoxy groups, benzyloxy groups, benzyloxycarbonyl groups, $C_2$ to $C_7$ alkanoyl groups, $C_2$ to $C_7$ alkoxycarbonyl groups, $C_2$ to $C_7$ alkanoyloxy groups, $C_2$ to $C_7$ alkanoylamino groups, $C_2$ to $C_7$ N-alkylcarbamoyl groups, $C_1$ to $C_6$ alkylsulfonyl groups, amino groups, mono ($C_1$ to $C_6$ alkyl)amino groups, di($C_1$ to $C_6$ alkyl)amino groups or aromatic heterocyclic groups (having one to three atoms of oxygen, sulfur and/or nitrogen as heteroatoms) or condensed rings formed by the condensation of the aromatic heterocyclic group with a benzene ring, or $R^4$ and $R^5$ may together form a three to six-membered cyclic hydrocarbon.

p represents 0 or 1.

q represents 0 or 1.

G represents a group represented by —CO—, —$SO_2$—, —CO—O—, —$NR^7$—CO—, —CO—$NR^7$—, —NH—CO —NH—, —NH—CS—NH—, —$NR^7$—$SO_2$—, —$SO_2$—$NR^7$—, —NH—CO—O—, or —O—CO—NH—, provided that $R^7$ is a hydrogen atom or a $C_1$ to $C_6$ alkyl group, or $R^7$ may form a $C_2$ to $C_5$ alkylene group together with $R^5$.

$R^6$ represents a phenyl group, a $C_3$ to $C_8$ cycloalkyl group, a $C_3$ to $C_6$ cycloalkenyl group, a benzyl group or an aromatic heterocyclic group having one to three atoms of oxygen, sulfur and/or nitrogen as heteroatoms, provided that the phenyl group, the benzyl group or the aromatic heterocyclic group in the above-mentioned $R^6$ may be condensed, to make a condensed ring, with a benzene ring or an aromatic heterocyclic group having one or three atoms of oxygen, sulfur and/or nitrogen as heteroatoms, further provided that the phenyl group, the $C_3$ to $C_8$ cycloalkyl group, the $C_3$ to $C_6$ cycloalkenyl group, the benzyl group, the aromatic heterocyclic group or the condensed ring in the above-mentioned $R^6$ may be substituted by the arbitrary number of halogen atoms, hydroxy groups, mercapto groups, cyano groups, nitro groups, thiocyanato groups, carboxyl groups, carbamoyl groups, trifluoromethyl groups, $C_1$ to $C_6$ alkyl groups, $C_3$ to $C_8$ cycloalkyl groups, $C_2$ to $C_6$ alkenyl groups, $C_1$ to $C_6$ alkoxy groups, $C_3$ to $C_8$ cycloalkyloxy groups, $C_1$ to $C_6$ alkylthio groups, $C_1$ to $C_3$ alkylenedioxy groups, phenyl groups, phenoxy groups, phenylamino groups, benzyl groups, benzoyl groups, phenylsulfinyl groups, phenylsulfonyl groups, 3-phenylureido groups, $C_2$ to $C_7$ alkanoyl groups, $C_2$ to $C_7$ alkoxycarbonyl groups, $C_2$ to $C_7$ alkanoyloxy groups, $C_2$ to $C_7$ alkanoylamino group, $C_2$ to $C_7$ N-alkylcarbamoyl groups, $C_1$ to $C_6$ alkylsulfonyl groups, phenylcarbamoyl groups, N,N-di($C_1$ to $C_6$ alkyl)sulfamoyl groups, amino groups, mono($C_1$ to $C_6$ alkyl)amino groups, di($C_1$ to $C_6$ alkyl)amino groups, benzylamino groups, $C_2$ to $C_7$ (alkoxycarbonyl)amino groups, $C_1$ to $C_6$ (alkylsulfonyl)amino groups or bis($C_1$ to $C_6$ alkylsulfonyl)amino groups, and further provided that the substituents of the phenyl group, the $C_3$ to $C_8$ cycloalkyl group, the $C_3$ to $C_8$ cycloalkenyl group, the benzyl group, the aromatic heterocyclic group, or the condensed ring may further be substituted by the arbitrary number of halogen atoms, cyano groups, hydroxy groups, amino groups, trifluoromethyl groups, $C_1$ to $C_6$ alkyl groups, $C_1$ to $C_6$ alkoxy groups, $C_1$ to $C_6$ alkylthio groups, mono($C_1$ to $C_6$ alkyl)amino groups, or di($C_1$ to $C_6$ alkyl)amino groups.].

In accordance with the present invention, there is also provided a medicine which contains, as an active ingredient, the compound represented by the above-mentioned formula (I), the pharmaceutically acceptable acid addition salt thereof, or the pharmaceutically acceptable $C_1$ to $C_6$ alkyl addition salt thereof, and which is used for treating or preventing a disease concerned with CCR3.

The compound represented by the above-mentioned formula (I) has an activity for inhibiting that the ligand of $CCR^3$ receptor, such as eotaxin, binds to a target cell, and an activity for inhibiting the physiological actions of the ligand of CCR3, such as the eotaxin, on the target cell. Namely, the compound represented by the above-mentioned formula (I) is a CCR3 antagonist.

BEST MODE FOR CARRYING OUT THE INVENTION

In the above-mentioned formula (I), $R^1$ represents a phenyl group, a $C_3$ to $C_8$ cycloalkyl group, or an aromatic heterocyclic group having one to three atoms of oxygen, sulfur and/or nitrogen as heteroatoms, provided that the phenyl group or the aromatic heterocyclic group in the above-mentioned $R^1$ may be condensed with a benzene ring, or an aromatic heterocyclic group having one to three atoms of oxygen, sulfur and/or nitrogen as heteroatoms to form a condensed ring, further provided that the phenyl group, the $C_3$ to $C_8$ cycloalkyl group, the aromatic heterocyclic group or the condensed ring may be substituted by the arbitrary number of halogen atoms, hydroxy groups, cyano groups, nitro groups, carboxyl groups, carbamoyl groups, $C_1$ to $C_6$ alkyl groups, $C_3$ to $C_8$ cycloalkyl groups, $C_2$ to $C_6$ alkenyl groups, $C_1$ to $C_6$ alkoxy groups, $C_1$ to $C_6$ alkylthio groups, $C_3$ to $C_5$ alkylene groups, $C_2$ to $C_4$ alkylenoxy groups, $C_1$ to $C_3$ alkylenedioxy groups, phenyl groups, phenoxy groups, phenylthio groups, benzyl groups, benzyloxy groups, benzoylamino groups, $C_2$ to $C_7$ alkanoyl groups, $C_2$ to $C_7$ alkoxycarbonyl groups, $C_2$ to $C_7$ alkanoyloxy groups, $C_2$ to $C_7$ alkanoylamino groups, $C_2$ to $C_7$ N-alkylcarbamoyl groups, $C_4$ to $C_9$ N-cycloalkylcarbamoyl groups, $C_1$ to $C_6$ alkylsulfonyl groups, $C_3$ to $C_8$ (alkoxycarbonyl)methyl groups, N-phenylcarbamoyl groups, piperidinocarbonyl groups, morpholinocarbonyl groups, 1-pyrrolidinylcarbonyl groups, divalent groups represented by the formula: —NH(C═O)O—, divalent groups represented by the formula: —NH(C═S)O—, amino groups, mono($C_1$ to $C_6$ alkyl)amino groups or di($C_1$ to $C_6$ alkyl)amino groups.

"The $C_3$ to $C_8$ cycloalkyl group" in $R^1$ means a cyclic alkyl group such as a cyclopropyl group, a cyclobutyl group, a cyclopentyl group, a cyclohexyl group, a cycloheptyl group or a cyclooctyl group, and includes a cyclopropyl group, a cyclopentyl group, a cyclohexyl group and the like as preferable concrete examples.

"The aromatic heterocyclic group having one to three atoms of oxygen, sulfur and/or nitrogen as heteroatoms" in $R^1$ means an aromatic heterocyclic group such as a thienyl group, a furyl group, a pyrrolyl group, an imidazolyl group, a pyrazolyl group, an oxazolyl group, an isoxazolyl group, a thiazolyl group, an isothiazolyl group, a pyridyl group, a pyrimidinyl group, a triazinyl group, a triazolyl group, an oxadiazolyl (furazanyl) group or a thiadiazolyl group, and includes a thienyl group, a furyl group, a pyrrolyl, an isoxazolyl group, a pyridyl group and the like as preferable concrete examples.

"The condensed ring" in $R^1$ means a bicyclic aromatic heterocyclic group which is formed by condensing the above-mentioned benzene ring or aromatic heterocyclic group with a benzene ring or an aromatic heterocyclic group having one to three atoms of oxygen, sulfur and/or nitrogen as heteroatoms at an arbitrary possible position, and includes a naphthyl group, an indolyl group, a benzofuranyl group, a benzothienyl group, a quinolyl group, a benzimidazolyl group, a benzoxazolyl group, a benzotriazolyl group, a benzoxadiazolyl (benzofurazanyl) group, a benzothiadiazolyl group and the like as preferable concrete examples.

A phenyl group, a thienyl group, a pyrazolyl group, an isoxazolyl group, a benzofuranyl group or an indolyl group is especially preferable as $R^1$.

"The halogen atom" as the substituent on the phenyl group, the $C_3$ to $C_8$ cycloalkyl group, the aromatic heterocyclic group or the condensed ring, in $R^1$, means a fluorine atom, a chlorine atom, a bromine atom, an iodine atom or the like.

"The $C_1$ to $C_6$ alkyl group" as the substituent of $R^1$ means a $C_1$ to $C_6$ straight-chain or branched alkyl group such as a methyl group, an ethyl group, a n-propyl group, a n-butyl group, a n-pentyl group, a n-hexyl group, a n-heptyl group, a n-octyl group, an isopropyl group, an isobutyl group, a sec-butyl group, a tert-butyl group, an isopentyl group, a neopentyl group, a tert-pentyl group, an isohexyl group, a 2-methylpentyl group or a 1-ethylbutyl group, and includes a methyl group, an ethyl group, a propyl group, an isopropyl group and the like as preferable concrete examples.

"The $C_3$ to $C_8$ cycloalkyl group" as the substituent of $R^1$ is the same as the definition of "the $C_3$ to $C_8$ cycloalkyl group" in the above-mentioned $R^1$, and includes the same groups as preferable concrete examples.

"The $C_2$ to $C_6$ alkenyl group" as the substituent of $R^1$ means a $C_2$ to $C_6$ straight-chain or branched alkenyl group such as a vinyl group, an allyl group, a 1-propenyl group, a 2-butenyl group, a 3-butenyl group, a 2-methyl-1-propenyl group, a 4-pentenyl group, a 5-hexenyl group or a 4-methyl-3-pentenyl group, and includes a vinyl group, a 2-methyl-1-propenyl group and the like as preferable concrete examples.

"The $C_1$ to $C_6$ alkoxy group" as the substituent of $R^1$ means a group comprising the above-mentioned $C_1$ to $C_6$ alkyl group and an oxy group, and includes a methoxy group, an ethoxy group and the like as preferable concrete examples.

"The $C_1$ to $C_6$ alkylthio group" as the substituent of $R^1$ means a group comprising the above-mentioned $C_1$ to $C_6$ alkyl group and a thio group, and includes a methylthio group, an ethylthio group and the like as preferable concrete examples.

"The $C_3$ to $C_5$ alkylene group" as the substituent of $R^1$ means a $C_3$ to $C_5$ divalent alkylene group such as a trimethylene group, a tetramethylene group, a pentamethylene group or a 1-methyltrimethylene group, and includes a trimethylene group, a tetramethylene group and the like as preferable concrete examples.

"The $C_2$ to $C_4$ alkylenoxy group" as the substituent of $R^1$ means a group comprising a $C_2$ to $C_4$ divalent alkylene group and an oxy group, such as an ethylenoxy group ($—CH_2CH_2O—$), a trimethylenoxy group ($—CH_2CH_2CH_2O—$), a tetramethylenoxy group ($—CH_2CH_2CH_2CH_2O—$) or a 1,1-dimethylethylenoxy group [$—CH_2C(CH_3)_2O—$], and includes an ethylenoxy group, a trimethylenoxy group and the like as preferable concrete examples.

"The $C_1$ to $C_3$ alkylenedioxy group" as the substituent of $R^1$ means a group comprising a $C_1$ to $C_3$ divalent alkylene group and two oxy groups, such as a methylenedioxy group ($—OCH_2O—$), an ethylenedioxy group ($—OCH_2CH_2O—$), a trimethylenedioxy group ($—OCH_2CH_2CH_2O—$), a propylenedioxy group [$—OCH_2CH(CH_3)O—$], and includes a methylenedioxy group, an ethylenedioxy group and the like as preferable concrete examples.

"The $C_2$ to $C_7$ alkanoyl group" as the substituent of $R^1$ means a $C_2$ to $C_7$ straight-chain or branched alkanoyl group such as an acetyl group, a propanoyl group, a butanoyl group, a pentanoyl group, a hexanoyl group, a heptanoyl group, an isobutyryl group, a 3-methylbutanoyl group, a 2-methylbutanoyl group, a pivaloyl group, a 4-methylpentanoyl group, a 3,3-dimethylbutanoyl group or a 5-methylhexanoyl group, and includes an acetyl group and the like as preferable concrete examples.

"The $C_2$ to $C_7$ alkoxycarbonyl group" as the substituent of $R^1$ means a group comprising a $C_1$ to $C_6$ alkoxy group and a carbonyl group, and includes a methoxycarbonyl group, an ethoxycarbonyl group and the like as preferable concrete examples.

"The $C_2$ to $C_7$ alkanoyloxy group" as the substituent of $R^1$ means a group comprising a $C_2$ to $C_7$ alkanoyl group and an oxy group, and includes an acetyloxy group and the like as preferable concrete examples.

"The $C_2$ to $C_7$ alkanoylamino group" as the substituent of $R^1$ means a group comprising a $C_2$ to $C_7$ alkanoyl group and an amino group, and includes an acetylamino group and the like as preferable concrete examples.

"The $C_2$ to $C_7$ alkylcarbamoyl group" as the substituent of $R^1$ means a group comprising a $C_1$ to $C_6$ alkyl group and a carbamoyl group, and includes a N-methylcarbamoyl group, a N-ethylcarbamoyl group and the like as preferable concrete examples.

"The $C_4$ to $C_9$ N-cycloalkylcarbamoyl group" as the substituent of $R^1$ means a group comprising a $C_3$ to $C_8$ cycloalkyl group and a carbamoyl group, and includes a N-cyclopentylcarbamoyl group, a N-cyclohexylcarbamoyl group and the like as preferable concrete examples.

"The $C_1$ to $C_6$ alkylsulfonyl group" as the substituent of $R^1$ means a group comprising a $C_1$ to $C_6$ alkyl group and a sulfonyl group, and includes a methylsulfonyl group and the like as preferable concrete examples.

"The $C_3$ to $C_8$ (alkoxycarbonyl)methyl group" as the substituent of $R^1$ means a group comprising a $C_2$ to $C_7$ alkoxycarbonyl group and a methyl group, and includes a methoxycarbonylmethyl group, an ethoxycarbonylmethyl group and the like as preferable concrete examples.

"The mono($C_1$ to $C_6$ alkyl)amino group" as the substituent of $R^1$ means an amino group substituted by the $C_1$ to $C_6$ alkyl group, and includes a methylamino group, an ethylamino group and the like as preferable concrete examples.

"The di($C_1$ to $C_6$ alkyl)amino group" as the substituent of $R^1$ means an amino group substituted by the same or different two $C_1$ to $C_6$ alkyl groups, and includes a dimethylamino group, a diethylamino group, N-ethyl-N-methylamino group and the like as preferable concrete examples.

Among the above-mentioned groups, the substituents of the phenyl group, the $C_3$ to $C_8$ cycloalkyl group, the aromatic heterocyclic group or the condensed ring in $R^1$ include halogen atoms, hydroxy groups, $C_1$ to $C_6$ alkyl groups, $C_2$ to $C_6$ alkenyl groups, $C_1$ to $C_6$ alkoxy groups, $C_1$ to $C_6$ alkylthio groups, $C_3$ to $C_5$ alkylene groups, $C_2$ to $C_4$ alkylenoxy groups, methylenedioxy groups, phenyl groups, N-phenylcarbamoyl groups, amino groups and di($C_1$ to $C_6$ alkyl)amino groups as especially preferable concrete examples. The substituents especially preferably include halogen atoms, hydroxy groups, $C_1$ to $C_6$ alkyl groups, $C_1$ to $C_6$ alkoxy groups, $C_1$ to $C_6$ alkylthio groups, methylenedioxy groups and N-phenylcarbamoyl groups.

Further, the substituents of the phenyl group, the $C_3$ to $C_8$ cycloalkyl group, the aromatic heterocyclic group or the condensed ring in $R^1$ may be substituted by the arbitrary number of halogen atoms, hydroxy groups, amino groups, trifluoromethyl groups, $C_1$ to $C_6$ alkyl groups or $C_1$ to $C_6$ alkoxy groups. The halogen atoms, the $C_1$ to $C_6$ alkyl groups and the $C_1$ to $C_6$ alkoxy groups are the same as defined as the substituents of the phenyl group, the $C_3$ to $C_8$ cycloalkyl group, the aromatic heterocyclic group or the condensed ring in $R^1$, and include the same groups as preferable concrete examples.

In the formula (I), $R^2$ represents a hydrogen atom, a $C_1$ to $C_6$ alkyl group, a $C_2$ to $C_7$ alkoxycarbonyl group, a hydroxy group or a phenyl group, and the $C_1$ to $C_6$ alkyl group or the phenyl group in $R^2$ may be substituted by the arbitrary number of halogen atoms, hydroxy groups, $C_1$ to $C_6$ alkyl groups or $C_1$ to $C_6$ alkoxy groups, provided that $R^2$ is not the hydroxy group, when j is 0.

The $C_1$ to $C_6$ alkyl group and the $C_2$ to $C_7$ alkoxycarbonyl group in $R^2$ are the same as defined as the substituents of the phenyl group, the $C_3$ to $C_8$ cycloalkyl group, the aromatic heterocyclic group or the condensed ring in $R^1$, and include the same groups as preferable concrete examples.

The halogen atoms, $C_1$ to $C_6$ alkyl groups and $C_1$ to $C_6$ alkoxy groups as the substituents of the $C_1$ to $C_6$ alkyl group or the phenyl group in $R^2$ are the same as defined as the substituents of the phenyl group, the $C_3$ to $C_8$ cycloalkyl group, the aromatic heterocyclic group or the condensed ring in $R^1$, and includes the same examples, respectively, as preferable concrete examples.

Among groups, a case that $R^2$ represents a hydrogen atom is most preferable.

In the formula (I), j represents an integer of 0 to 2. A case that j is 0 is most preferable.

In the formula (I), k represents an integer of 0 to 2, and m represents an integer of 2 to 4. Among them, the 2-substituted pyrrolidine compound in a case that k and m are 0 and 3, respectively, the 3-substituted pyrrolidine compound in a case that k and m are 1 and 2, respectively, the 3-substituted piperidine compound in a case that k and m are 1 and 3, respectively, 4-substituted piperidine compound in a case that k and m are 2 and 2, respectively, and the 3-substituted hexahydroazepine in a case that k and m are 1 and 4, respectively, are preferable. Especially preferably, the 3-substituted pyrrolidine compound in the case that k and m are 1 and 2, respectively, and the 4-substituted piperidine compound in the case that k and m are 2 and 2, respectively, are included.

In the formula (I), n represents 0 or 1.

Especially, the 3-amidopyrrolidine compound in a case that k, m and n are 1, 2 and 0, respectively, and the 4-(amidomethyl)piperidine in a case that k, m and n are 2, 2 and 1, respectively, are preferable.

In the formula (I), $R^3$ represents a hydrogen atom or a $C_1$ to $C_6$ alkyl group which may be substituted (by one or two phenyl groups which may be substituted by the arbitrary number of the same or different halogen atoms, hydroxy groups, $C_1$ to $C_6$ alkyl groups or $C_1$ to $C_6$ alkoxy groups).

The $C_1$ to $C_6$ alkyl group in $R^3$ is the same as defined as the substituent of the phenyl group, the $C_3$ to $C_8$ cycloalkyl group, the aromatic heterocyclic group, or the condensed ring in the above-mentioned $R^1$, and includes methyl group, ethyl group and propyl group as preferable concrete examples.

The halogen atoms, the $C_1$ to $C_6$ alkyl groups and the $C_1$ to $C_6$ alkoxy groups as the substituents of the phenyl group as the substituent of the $C_1$ to $C_6$ alkyl group in $R^3$ are the same as defined as the substituents of the phenyl group, the $C_3$ to $C_8$ cycloalkyl group, the aromatic heterocyclic group or the condensed ring in the above-mentioned $R^1$, and includes the same examples as preferable concrete examples.

Among them, the case in which $R^3$ is a hydrogen atom or a non-substituted $C_1$ to $C_6$ alkyl groups, is the most favorable.

In the formula (I), $R^4$ and $R^5$, same or differently, represent a hydrogen atom, a hydroxy group, a phenyl group or a $C_1$ to $C_6$ alkyl group, respectively, and the $C_1$ to $C_6$ alkyl group in $R^4$ and $R^5$ may be substituted by the arbitrary number of halogen atoms, hydroxy groups, cyano groups, nitro groups, carboxyl groups, carbamoyl groups, mercapto groups, guanidino groups, $C_3$ to $C_8$ cycloalkyl groups, $C_1$ to $C_6$ alkoxy groups, $C_1$ to $C_6$ alkylthio groups, phenyl groups (which may be substituted by the arbitrary number of halogen atoms, hydroxy groups, $C_1$ to $C_6$ alkyl groups, $C_1$ to $C_6$ alkoxy groups or benzyloxy groups), phenoxy groups, benzyloxy groups, benzyloxycarbonyl groups, $C_2$ to $C_7$ alkanoyl groups, $C_2$ to $C_7$ alkoxycarbonyl groups, $C_2$ to $C_7$ alkanoyloxy groups, $C_2$ to $C_7$ alkanoylamino groups, $C_2$ to $C_7$ N-alkylcarbamoyl groups, $C_1$ to $C_6$ alkylsulfonyl groups, amino groups, mono ($C_1$ to $C_6$ alkyl)amino group, di($C_1$ to $C_6$ alkyl)amino group, or aromatic heterocyclic groups (having one to three atoms of oxygen, sulfur and/or nitrogen as heteroatoms) or condensed rings formed by condensing the aromatic heterocyclic groups with a benzene ring, or $R^4$ and $R^5$ may be bound to each other to form a three to six-membered cyclic hydrocarbon.

The $C_1$ to $C_6$ alkyl group in $R^4$ and $R^5$ is the same as defined as the substituents of the phenyl group, the $C_3$ to $C_8$ cycloalkyl group, the aromatic heterocyclic group or the condensed ring in the above-mentioned $R^1$, and includes the same examples as preferable concrete examples.

The halogen atom, $C_1$ to $C_6$ alkoxy group, $C_1$ to $C_6$ alkylthio group, $C_2$ to $C_7$ alkanoyl group, $C_2$ to $C_7$ alkanoyl group, $C_2$ to $C_7$ alkoxycarbonyl group, $C_2$ to $C_7$ alkanoyloxy group, $C_2$ to $C_7$ alkanoylamino group, $C_2$ to $C_7$ N-alkylcarbamoyl group, $C_1$ to $C_6$ alkylsulfonyl group, mono($C_1$ to $C_6$ alkyl) amino group and di($C_1$ to $C_6$ alkyl)amino group as the substituents of the $C_1$ to $C_6$ alkyl group in $R^4$ and $R^5$, are the same as defined as the substituents of the phenyl group, the $C_3$ to $C_8$ cycloalkyl group, the aromatic heterocyclic group or the condensed ring in the above-mentioned $R^1$, and includes the same examples, respectively, as preferable concrete examples.

The $C_3$ to $C_8$ cycloalkyl group, and the aromatic heterocyclic group having one to three atoms of oxygen, sulfur and/or nitrogen heteroatoms as the substituents of the $C_1$ to $C_6$ alkyl group in $R^4$ and $R^5$ are the same as defined in the above-mentioned $R^1$, and includes the same examples, respectively, as preferable concrete examples.

The halogen atom, the $C_1$ to $C_6$ alkyl group and the $C_1$ to $C_6$ alkoxy group as the substituents of the phenyl group as the substituent of the $C_1$ to $C_6$ alkyl group in $R^4$ and $R^5$, are the same as defined as the substituents of the phenyl group, the $C_3$ to $C_8$ cycloalkyl group, the aromatic heterocyclic group or the condensed ring in the above-mentioned $R^1$, and includes the same examples, respectively, as preferable concrete examples.

The preferable concrete examples of "the three to six-membered cyclic hydrocarbon" comprising $R^4$, $R^5$ and the adjacent carbon atom includes cyclopropane, cyclobutane, cyclopentane and cyclohexane. Among the groups, the hydrogen atom and the $C_1$ to $C_6$ alkyl group are the especially preferable examples of $R^4$ and $R^5$.

In the above-mentioned formula (I), p represents 0 or 1, and q represents 0 or 1. A case that both p and q are 0 is especially preferable.

In the above-mentioned formula (I), G represents a group represented by —CO—, —$SO_2$—, —CO—O—, —$NR^7$—CO—, —CO—$NR^7$—, —NH—CO—NH—, —NH—CS—NH—, —$NR^7$—$SO_2$—, —$SO_2$—$NR^7$—, —NH—CO—O— or —O—CO—NH—. $R^7$ represents a hydrogen atom or a $C_1$ to $C_6$ alkyl group, or $R^7$ may form a C2 to C5 alkylene group together with $R^5$.

The —CO—, —$SO_2$— and —CS— means a carbonyl group, a sulfonyl group and a thiocarbonyl group, respectively. The especially preferable example of G includes a group represented by —$NR^7$—CO— and a group represented by —NH—CO—NH—.

The $C_1$ to $C_6$ alkyl group in $R^7$ is the same as defined as the substituents of the phenyl group, the $C_3$ to $C_8$ cycloalkyl group, the aromatic heterocyclic group or the condensed ring in the above-mentioned $R^1$, and includes the same examples as preferable concrete examples.

"The $C_2$ to $C_5$ alkylene group" comprising $R^5$ and $R^7$ means a $C_2$ to $C_5$ straight-chain or branched alkylene group such as a methylene group, an ethylene group, a propylene group, a trimethylene group, a tetramethylene group, a 1-methyltrimethylene group or a pentamethylene group, and includes an ethylene group, a trimethylene group and a tetramethylene group as the preferable concrete examples. Among the groups, $R^7$ includes the hydrogen atom as an especially preferable example.

In the above-mentioned formula (I), $R^6$ represents a phenyl group, a $C_3$ to $C_8$ cycloalkyl group, a $C_3$ to $C_6$ cycloalkenyl group, a benzyl group or an aromatic heterocyclic group having one to three atoms of oxygen, sulfur and/or nitrogen as heteroatoms, and the phenyl group, the benzyl group or the aromatic heterocyclic group in $R^6$ may be condensed, to make s condensed ring, with a benzene ring or an aromatic heterocyclic group having one to three atoms of oxygen sulfur, and/or nitrogen as heteroatoms. Further, the phenyl group, the $C_3$ to $C_8$ cycloalkyl group, the $C_3$ to $C_6$ cycloalkenyl group, the benzyl group, the aromatic heterocyclic group or the condensed ring in $R^6$ may be substituted by the arbitrary number of halogen atoms, hydroxy groups, mercapto groups, cyano groups, nitro groups, thiocyanato groups, carboxyl groups, carbamoyl groups, trifluoromethyl groups, $C_1$ to $C_6$ alkyl groups, $C_3$ to $C_8$ cycloalkyl groups, $C_2$ to $C_6$ alkenyl groups, $C_1$ to $C_6$ alkoxy groups, $C_3$ to $C_8$ cycloalkylthio groups, $C_1$ to $C_6$ alkyloxy groups, $C_1$ to $C_3$ alkylenedioxy groups, phenyl groups, phenoxy groups, phenylamino groups, benzyl groups, benzoyl groups, phenylsulfinyl groups, phenylsulfonyl groups, 3-phenylureido groups, $C_2$ to $C_7$ alkanoyl groups, $C_2$ to $C_7$ alkoxycarbonyl groups, $C_2$ to $C_7$ alkanoyloxy groups, $C_2$ to $C_7$ alkanoylamino groups, $C_2$ to $C_7$ N-alkylcarbamoyl groups, $C_1$ to $C_6$ alkylsulfonyl groups, phenylcarbamoyl groups, N,N-di($C_1$ to $C_6$ alkyl)sulfamoyl groups, amino groups, mono($C_1$ to $C_6$ alkyl)amino groups, di($C_1$ to $C_6$ alkyl)amino groups, benzyl amino groups, $C_2$ to $C_7$ (alkoxycarbonyl)amino groups, $C_1$ to $C_6$ (alkylsulfonyl) amino groups or bis($C_1$ to $C_6$ alkylsulfonyl)amino groups.

The $C_3$ to $C_8$ cycloalkyl group, the aromatic heterocyclic group having one to three atoms of oxygen, sulfur and/or nitrogen, and the condensed ring are the same as defined as the above-mentioned $R^1$, and includes the same examples, respectively, as preferable concrete examples.

"The $C_3$ to $C_8$ cycloalkenyl group" in $R^6$ means a cyclic alkenyl group such as a cyclobutenyl group, a cyclopentenyl group, a cyclohexenyl group, a cycloheptenyl group and a cyclooctenyl group, and includes a 1-cyclopentenyl group and a 1-cyclohexenyl group as preferable concrete examples. Among the groups, $R^6$ include a phenyl group, a furyl group, a thienyl group, an indolyl group and a benzofurazanyl group as especially preferable examples.

The halogen atom, the $C_1$ to $C_6$ alkyl group, the $C_2$ to $C_6$ alkenyl group, the $C_1$ to $C_6$ alkoxy group, the $C_1$ to $C_6$ alkylthio group, the $C_1$ to $C_3$ alkylenedioxy group, the $C_2$ to $C_7$ alkanoyl group, the $C_2$ to $C_7$ alkoxycarbonyl group, the $C_2$ to $C_7$ alkanoyloxy group, $C_2$ to $C_7$ alkanoylamino group, the $C_2$ to $C_7$ N-alkylcarbamoyl group, the $C_1$ to $C_6$ alkylsulfonyl group, the mono($C_1$ to $C_6$ alkyl)amino group and the di($C_1$ to $C_6$ alkyl)amino group as the substituents of the phenyl group, the $C_3$ to $C_8$ cycloalkyl group, the aromatic heterocyclic group or the condensed ring in $R^6$ are the same as defined as the substituents of the phenyl group, the $C_3$ to $C_8$ cycloalkyl group, the $C_3$ to $C_8$ cycloalkenyl group, the benzyl group, the aromatic heterocyclic group or the condensed ring in the above-mentioned $R^1$, and includes the same examples as preferable concrete examples.

The $C_3$ to $C_8$ cycloalkyl group as the substituent of $R^6$ is the same as defined as the $C_3$ to $C_8$ cycloalkyl group in the above-mentioned $R^1$, and cludes the same examples as preferable concrete examples.

"The $C_3$ to $C_8$ cycloalkyloxy group" as the substituent of $R^6$ means a group comprising the above-mentioned $C_3$ to $C_8$ cycloalkyl group and an oxy group, and includes a cyclopropyloxy group, a cyclopentyloxy group, a cyclohexyloxy group and the like as preferable concrete examples.

"The N,N-di($C_1$ to $C_6$ alkyl)sulfamoyl group" as the substituent of $R^6$ means a sulfamoyl group substituted by two same or different above-mentioned $C_1$ to $C_6$ alkyl groups, and includes N,N-dimethylsulfamoyl group, N,N-diethylsulfamoyl group, N-ethyl-N-methylsulfamoyl group and the like as preferable concrete examples.

"The $C_2$ to $C_7$ (alkoxycarbonyl)amino group" as the substituent of $R^6$ means a group comprising the above-mentioned $C_2$ to $C_7$ alkoxycarbonyl group and an amino group, and includes a methoxycarbonylamino group, an ethoxycarbonylamino group and the like as preferable concrete examples.

"The $C_1$ to $C_6$ (alkylsulfonyl)amino group" as the substituent of $R^6$ means a group comprising the above-mentioned $C_1$ to $C_6$ alkylsulfonyl group, an amino group and the like, and includes a (methylsulfonyl)amino group as a preferable concrete example.

"The bis($C_1$ to $C_6$ alkylsulfonyl)amino group" as the substituent of $R^6$ means an amino group substituted by two same or different $C_1$ to $C_6$ alkylsulfonyl groups, and includes a bis(methylsulfonyl)amino group and the like as a preferable concrete example.

Especially, the substituents of the phenyl group, the $C_3$ to $C_8$ cycloalkyl group, the $C_3$ to $C_8$ cycloalkenyl group, the benzyl group, the aromatic heterocyclic group or the condensed ring in $R^6$ include a halogen atom, a mercapto group, a nitro group, a trifluoromethyl group, a $C_1$ to $C_6$ alkyl group, a $C_1$ to $C_6$ alkoxy group, a phenyl group, a benzyloxy group, a phenylsulfinyl group, a $C_2$ to $C_7$ alkanoyl group, a $C_2$ to $C_7$ alkanoylamino group, an amino group and the like as preferable examples. The halogen atom, the nitro group, the trifluoromethyl group, the $C_1$ to $C_6$ alkyl group, the $C_1$ to $C_6$ alkoxy group, the phenylsulfinyl group and the amino group are included as especially preferable examples.

Additionally, the substituents of the phenyl group, the $C_3$ to $C_8$ cycloalkyl group, the $C_3$ to $C_8$ cycloalkenyl group, the benzyl group, the aromatic heterocyclic group or the condensed ring in $R^6$ may further be substituted by the arbitrary number of halogen atoms, cyano groups, hydroxy groups, amino groups, trifluoromethyl groups, $C_1$ to $C_6$ alkyl groups, $C_1$ to $C_6$ alkoxy groups, $C_1$ to $C_6$ alkylthio groups, mono($C_1$ to $C_6$ alkyl)amino groups or di($C_1$ to $C_6$ alkyl)amino groups.

The halogen atom, the $C_1$ to $C_6$ alkyl group, the $C_1$ to $C_6$ alkoxy group, the $C_1$ to $C_6$ alkylthio group, the mono($C_1$ to $C_6$ alkyl)amino group and the di($C_1$ to $C_6$ alkyl)amino group as the substituents of the phenyl group, the $C_3$ to $C_8$ cycloalkyl group, the $C_3$ to $C_8$ cycloalkenyl group, the benzyl group, the aromatic heterocyclic group or the condensed ring in $R^6$ are the same as defined as the substituents of the phenyl group, the $C_3$ to $C_8$ cycloalkyl group, the aromatic heterocyclic group or the condensed ring in the above-mentioned $R^1$, and includes the same examples as preferable concrete examples.

By making a therapeutically effective amount of the compound represented by the above-mentioned formula (I), the pharmaceutically acceptable acid addition salt thereof or the pharmaceutically acceptable $C_1$ to $C_6$ alkyl addition salt thereof into a pharmaceutical composition together with a pharmaceutically acceptable carrier and/or a pharmaceutically acceptable diluent, the medicine for inhibiting that the ligand of CCR3, such as eotaxin, binds to the CCR3 on a target cell, the medicine for inhibiting the physiological actions of the ligand of the CCR3, such as the eotaxin, on the target cell, and further the medicine for treating or preventing diseases in which the CCR3 is supposed to participate, as the medicine of the present invention, can be prepared. Namely, the cyclic amine derivative represented by the general formula (I), the pharmaceutically acceptable acid addition thereof, or the pharmaceutically acceptable $C_1$ to $C_6$ alkyl addition salt thereof can be administered orally or parenterally such as intravenously, subcutaneously, intramuscularly, percutaneously or intrarectally.

The dosage form of the oral administration includes tablets, pills, granules, powders, liquids, suspensions and capsules.

The tablets can be prepared using a vehicle such as lactose, starch or crystalline cellulose, a binder such as carboxymethylcellulose, methylcellulose or polyvinylpyrrolidone, a disintegrator such as sodium alginate, sodium bicarbonate or sodium lauryl sulfate, and so on, by a conventional method.

The pills, the powders or the granules can also be prepared using the above-mentioned vehicle and so on by a conventional method. The liquids or the suspensions are prepared using a glycerol ester such as tricaprylin or triacetin, an alcohol such as ethanol and so on by a conventional method. The capsules are prepared by filling capsules made from gelatin or the like with the granules, the powder, the liquids or the like.

The dosage form for subcutaneous, intramuscular or intravenous administration includes injections in the forms of aqueous or non-aqueous solutions. The aqueous solutions include, for example, isotonic sodium chloride solution or the like. The non-aqueous solutions include, for example, propylene glycol, poly(ethylene glycol), olive oil, ethyl oleate or the like. The solutions, if necessary, further contain a antiseptic, a stabilizer and so on. The injections are sterilized by suitably carrying out the filtration with a bacterial filter and the treatment by the addition of a disinfectant.

The dosage form for the percutaneous administration includes an ointment and a cream. The ointment is prepared using a fatty oil or a fat such as castor oil or olive oil, petrolatum or the like by a conventional method, and the cream is prepared using a fatty oil or an emulsifier such as di(ethylene glycol) or a sorbitan monofatty acid ester by a conventional method.

Ordinary suppositories such as gelatin soft capsules are used for intrarectal administration.

The dose of the cyclic amine derivative of the present invention, the pharmaceutically acceptable acid addition salt thereof or the pharmaceutically acceptable $C_1$ to $C_6$ alkyl addition salt thereof depends on the kind of a disease, an administration route, the age and sex of the patient and the severity of a disease, but is usually 1 to 500 mg/day/adult.

The suitable concrete examples of the cyclic amine derivative of the above-mentioned formula (I) includes compounds containing substituents, respectively, shown in the following Tables 1.1 to 1.221.

In the Tables 1.1 to 1.221, "chirality" means "an absolute configuration", namely the absolute configuration of an asymmetric carbon on the ring of the cyclic amine. "R" means that an asymmetric carbon on the ring of the cyclic amine has the absolute configuration of R, and "S" means that the asymmetric carbon has the absolute configuration of S. "-" means that the compound is a racemate or does not have an asymmetric carbon on the cyclic amine.

TABLE 1.1

| Compd. No. | 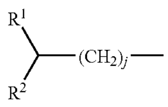 | k | m | n | chirality | $R^3$ | 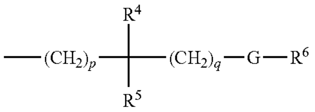 |
|---|---|---|---|---|---|---|---|
| 1 | 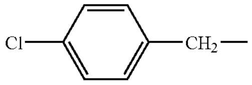 | 1 | 2 | 0 | — | H | 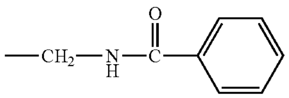 |
| 2 | 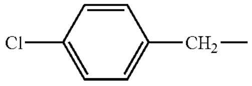 | 1 | 2 | 0 | — | H | 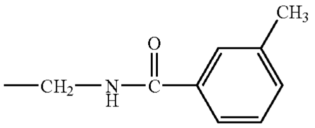 |
| 3 | 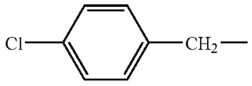 | 1 | 2 | 0 | — | H | 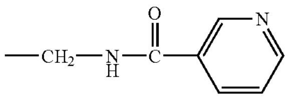 |
| 4 | 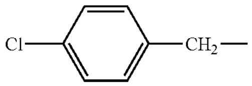 | 1 | 2 | 0 | — | H | 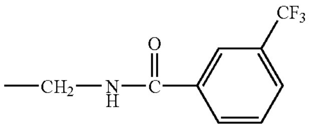 |
| 5 | 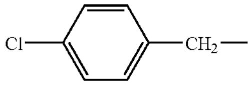 | 1 | 2 | 0 | S | H | 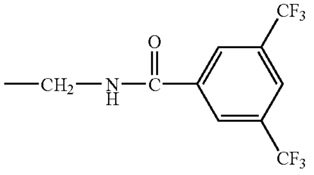 |

TABLE 1.1-continued
| Compd. No. | 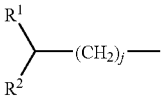 | k | m | n | chirality | $R^3$ | 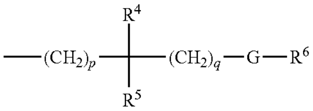 |
|---|---|---|---|---|---|---|---|
| 6 | 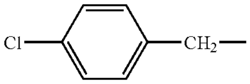 | 1 | 2 | 0 | S | H | 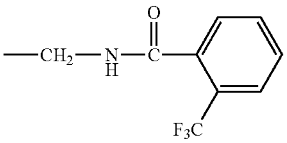 |
| 7 | 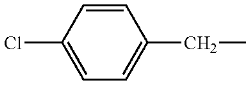 | 1 | 2 | 0 | S | H | 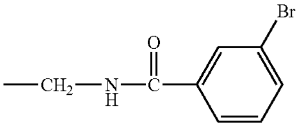 |
| 8 | 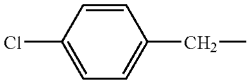 | 1 | 2 | 0 | S | H | 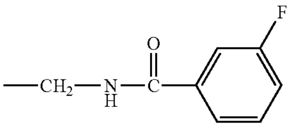 |
| 9 | 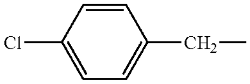 | 1 | 2 | 0 | S | H | 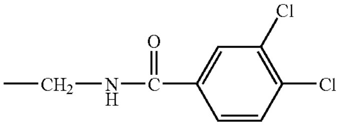 |
| 10 | 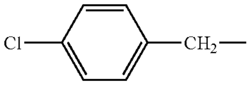 | 1 | 2 | 0 | S | H | 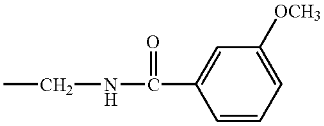 |
| 11 | 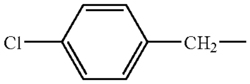 | 1 | 2 | 0 | S | H | 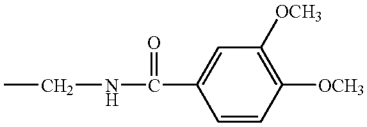 |
TABLE 1.2
| Compd. No. | 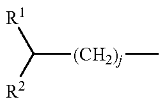 | k | m | n | chirality | $R^3$ | 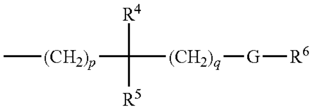 |
|---|---|---|---|---|---|---|---|
| 12 | 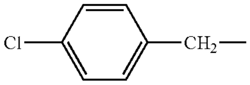 | 1 | 2 | 0 | S | H | 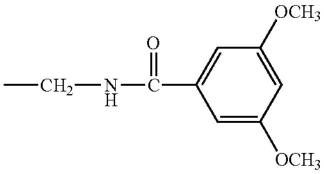 |
| 13 | 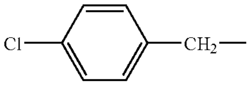 | 1 | 2 | 0 | S | H | 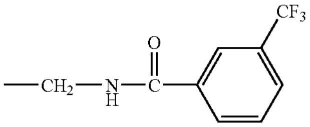 |

TABLE 1.2-continued
| Compd. No. | 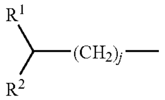 | k | m | n | chirality | $R^3$ | 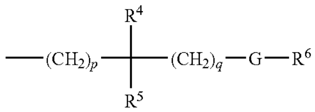 |
|---|---|---|---|---|---|---|---|
| 14 | 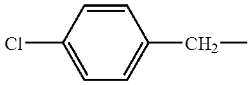 | 1 | 2 | 0 | S | H | 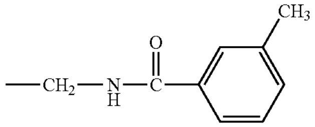 |
| 15 | 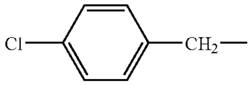 | 1 | 2 | 0 | S | H | 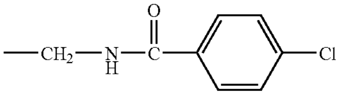 |
| 16 | 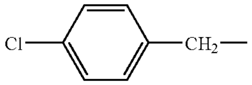 | 1 | 2 | 0 | S | H | 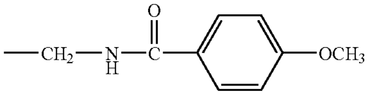 |
| 17 | 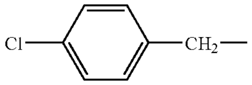 | 1 | 2 | 0 | S | H | 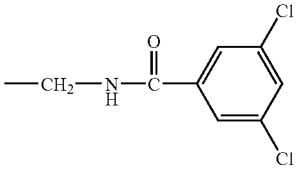 |
| 18 | 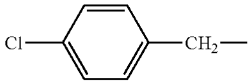 | 1 | 2 | 0 | S | H | 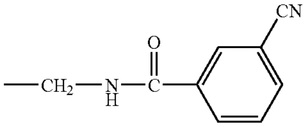 |
| 19 | 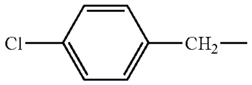 | 1 | 2 | 0 | S | H | 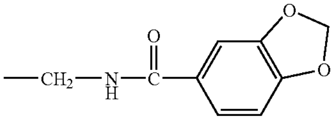 |
| 20 | 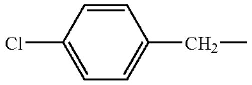 | 1 | 2 | 0 | S | H | 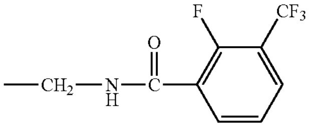 |
| 21 | 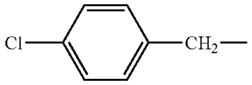 | 1 | 2 | 0 | S | H | 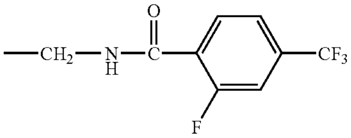 |
| 22 | 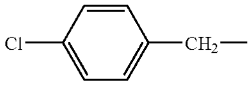 | 1 | 2 | 0 | S | H | 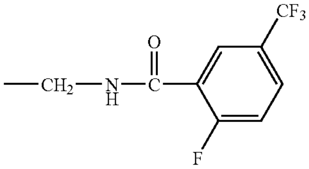 |

TABLE 1.3
| Compd. No. | 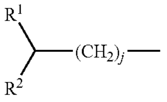 | k | m | n | chirality | $R^3$ | 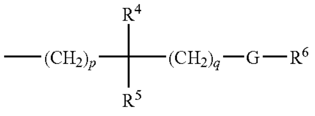 |
|---|---|---|---|---|---|---|---|
| 23 | 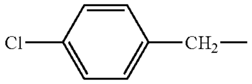 | 1 | 2 | 0 | S | H | 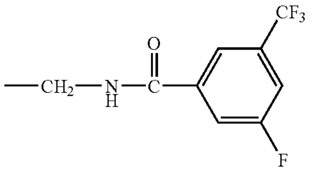 |
| 24 | 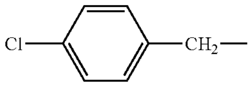 | 1 | 2 | 0 | S | H | 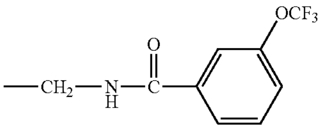 |
| 25 | 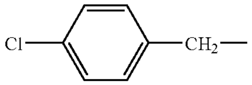 | 1 | 2 | 0 | S | H | 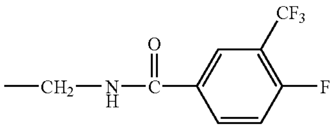 |
| 26 | 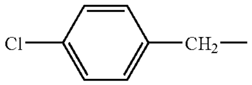 | 1 | 2 | 0 | S | H | 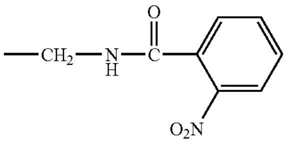 |
| 27 | 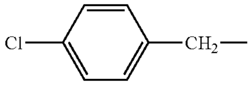 | 1 | 2 | 0 | S | H | 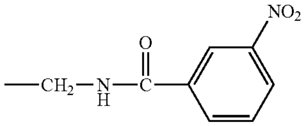 |
| 28 | 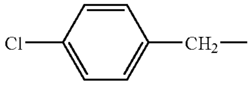 | 1 | 2 | 0 | S | H | 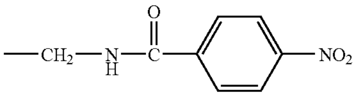 |
| 29 | 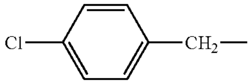 | 1 | 2 | 0 | R | H | 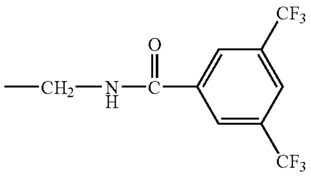 |
| 30 | 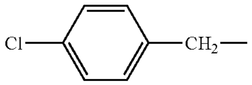 | 1 | 2 | 0 | R | H | 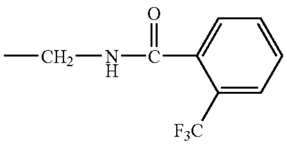 |
| 31 | 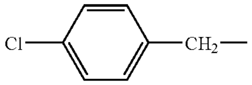 | 1 | 2 | 0 | R | H | 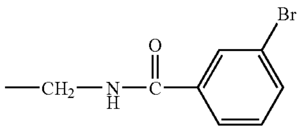 |

TABLE 1.3-continued
| Compd. No. | 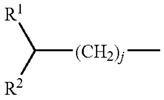 | k | m | n | chirality | $R^3$ | 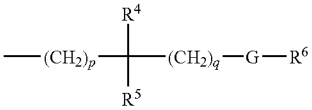 |
|---|---|---|---|---|---|---|---|
| 32 | 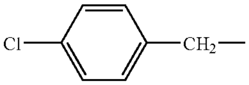 | 1 | 2 | 0 | R | H | 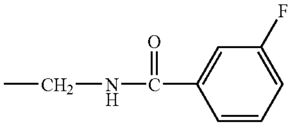 |
| 33 | 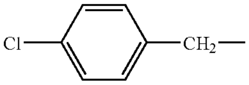 | 1 | 2 | 0 | R | H | 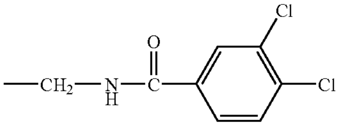 |
TABLE 1.4
| Compd. No. | 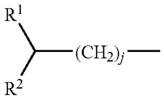 | k | m | n | chirality | $R^3$ | 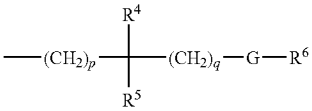 |
|---|---|---|---|---|---|---|---|
| 34 | 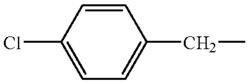 | 1 | 2 | 0 | R | H | 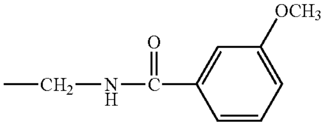 |
| 35 | 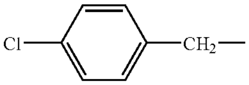 | 1 | 2 | 0 | R | H | 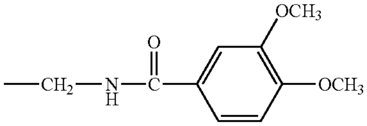 |
| 36 | 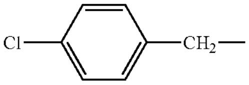 | 1 | 2 | 0 | R | H | 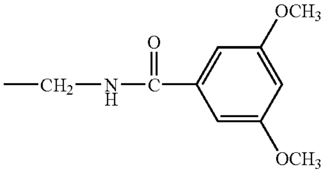 |
| 37 | 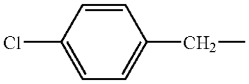 | 1 | 2 | 0 | R | H | 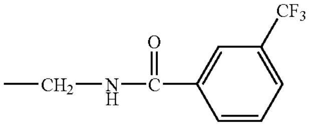 |
| 38 | 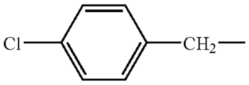 | 1 | 2 | 0 | R | H | 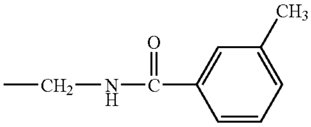 |
| 39 | 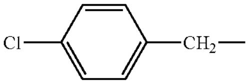 | 1 | 2 | 0 | R | H | 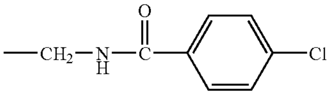 |
| 40 | 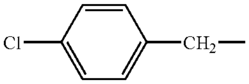 | 1 | 2 | 0 | R | H | 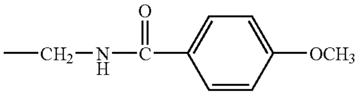 |

TABLE 1.4-continued
| Compd. No. | 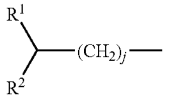 | k | m | n | chirality | $R^3$ | 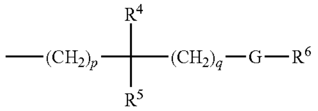 |
|---|---|---|---|---|---|---|---|
| 41 | 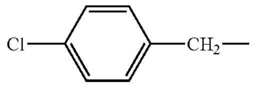 | 1 | 2 | 0 | R | H | 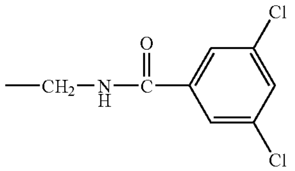 |
| 42 | 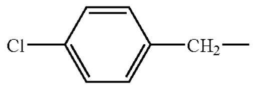 | 1 | 2 | 0 | R | H | 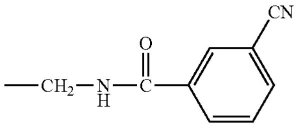 |
| 43 | 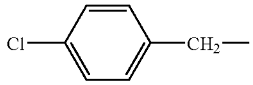 | 1 | 2 | 0 | R | H | 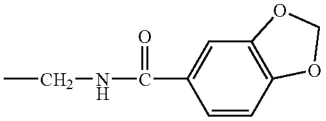 |
| 44 | 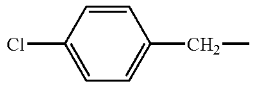 | 1 | 2 | 0 | R | H | 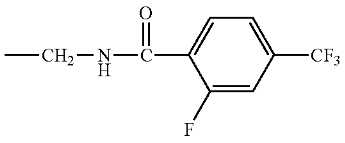 |
TABLE 1.5
| Compd. No. | 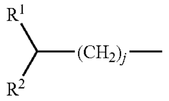 | k | m | n | chirality | $R^3$ | 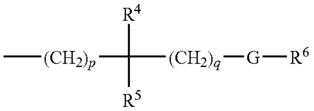 |
|---|---|---|---|---|---|---|---|
| 45 | 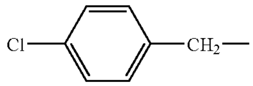 | 1 | 2 | 0 | R | H | 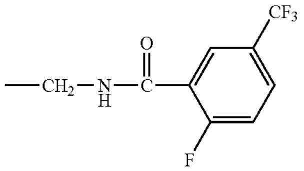 |
| 46 | 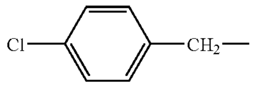 | 1 | 2 | 0 | R | H | 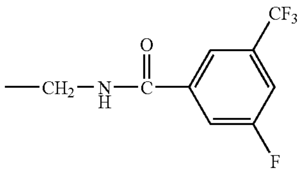 |
| 47 | 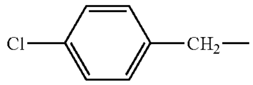 | 1 | 2 | 0 | R | H | 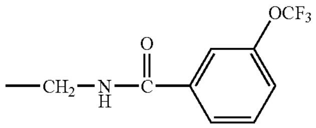 |
| 48 | 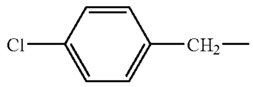 | 1 | 2 | 0 | R | H | 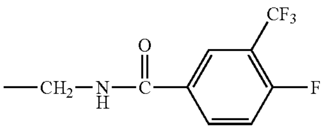 |

TABLE 1.5-continued
| Compd. No. | 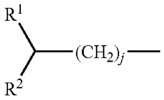 | k | m | n | chirality | $R^3$ | 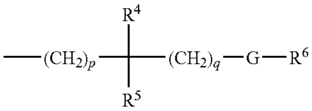 |
|---|---|---|---|---|---|---|---|
| 49 | 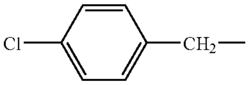 | 1 | 2 | 0 | R | H | 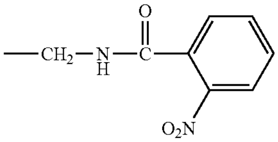 |
| 50 | 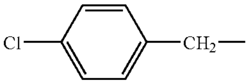 | 1 | 2 | 0 | R | H | 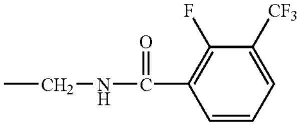 |
| 51 | 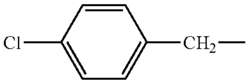 | 1 | 2 | 0 | R | H | 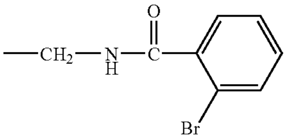 |
| 52 | 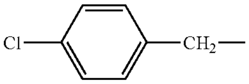 | 1 | 2 | 0 | R | H | 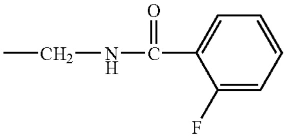 |
| 53 | 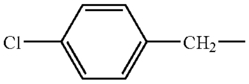 | 1 | 2 | 0 | R | H | 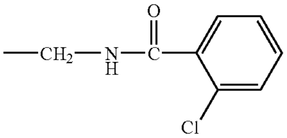 |
| 54 | 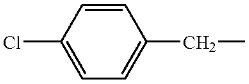 | 1 | 2 | 0 | R | H | 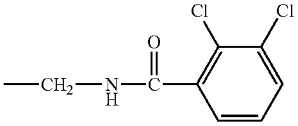 |
| 55 | 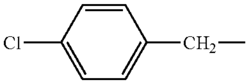 | 1 | 2 | 0 | R | H | 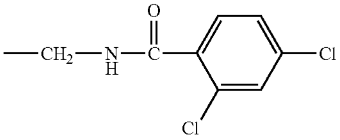 |
TABLE 1.6
| Compd. No. | 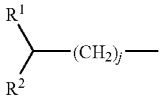 | k | m | n | chirality | $R^3$ | 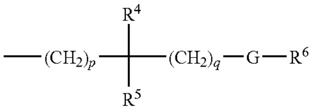 |
|---|---|---|---|---|---|---|---|
| 56 | 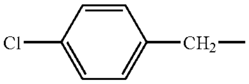 | 1 | 2 | 0 | R | H | 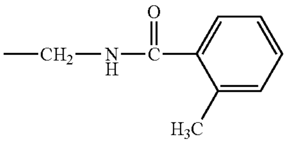 |

TABLE 1.6-continued
| Compd. No. | 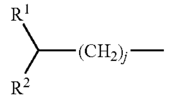 | k | m | n | chirality | $R^3$ | 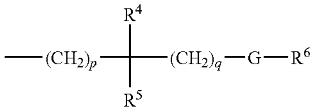 |
|---|---|---|---|---|---|---|---|
| 57 | 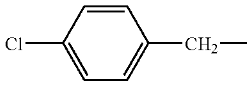 | 1 | 2 | 0 | R | H | 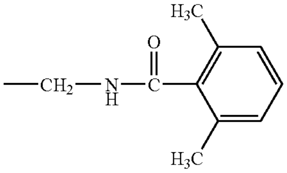 |
| 58 | 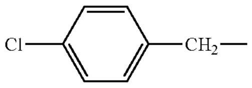 | 1 | 2 | 0 | R | H | 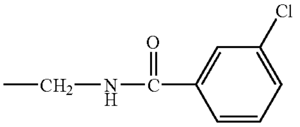 |
| 59 | 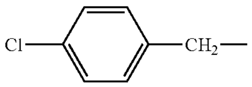 | 1 | 2 | 0 | R | H | 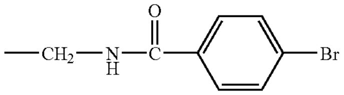 |
| 60 | 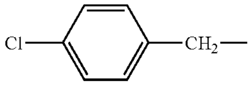 | 1 | 2 | 0 | R | H | 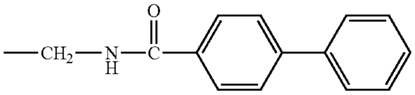 |
| 61 | 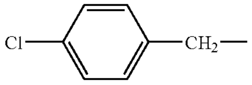 | 1 | 2 | 0 | R | H | 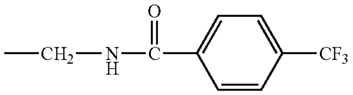 |
| 62 | 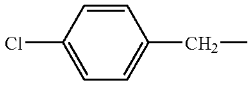 | 1 | 2 | 0 | R | H | 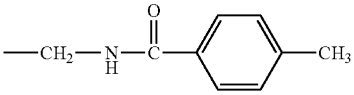 |
| 63 | 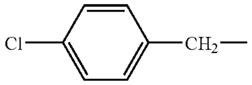 | 1 | 2 | 0 | R | H | 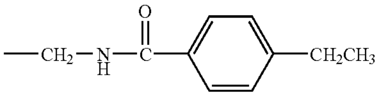 |
| 64 | 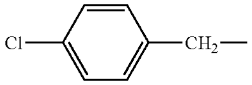 | 1 | 2 | 0 | R | H | 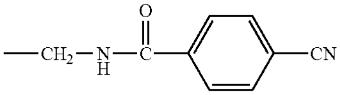 |
| 65 | 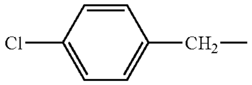 | 1 | 2 | 0 | R | H | 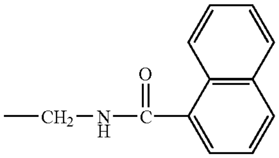 |
| 66 | 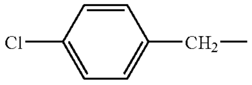 | 1 | 2 | 0 | R | H | 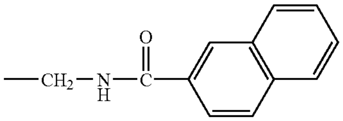 |

TABLE 1.7
| Compd. No. | 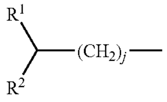 | k | m | n | chirality | R³ | 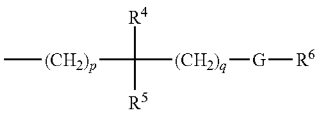 |
|---|---|---|---|---|---|---|---|
| 67 | 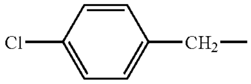 | 1 | 2 | 0 | R | H | 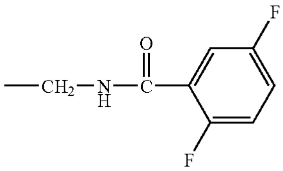 |
| 68 | 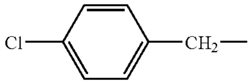 | 1 | 2 | 0 | R | H | 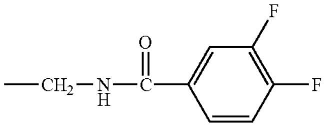 |
| 69 | 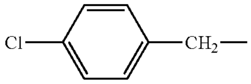 | 1 | 2 | 0 | R | H | 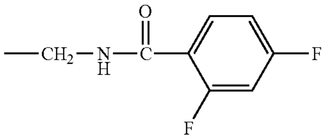 |
| 70 | 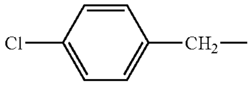 | 1 | 2 | 0 | R | H | 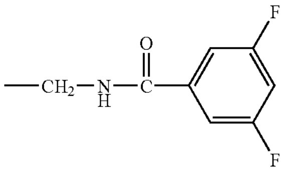 |
| 71 | 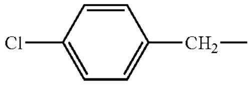 | 1 | 2 | 0 | R | H | 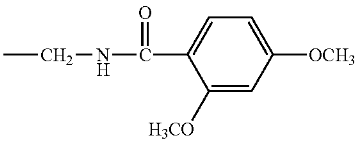 |
| 72 | 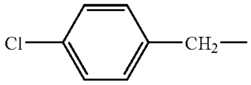 | 1 | 2 | 0 | R | H | 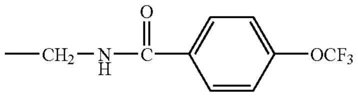 |
| 73 | 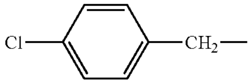 | 1 | 2 | 0 | R | H | 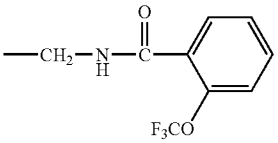 |
| 74 | 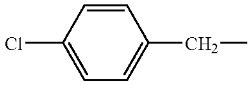 | 1 | 2 | 0 | R | H | 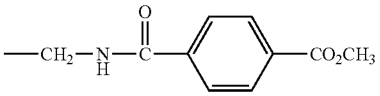 |
| 75 | 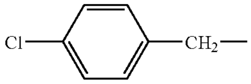 | 1 | 2 | 0 | R | H | 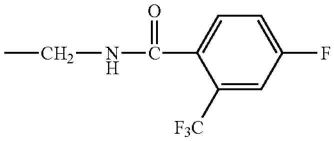 |

TABLE 1.7-continued
| Compd. No. | 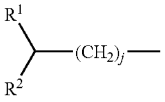 | k | m | n | chirality | $R^3$ | 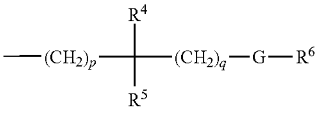 |
|---|---|---|---|---|---|---|---|
| 76 | 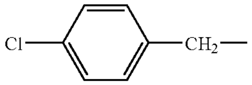 | 1 | 2 | 0 | R | H | 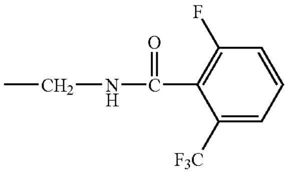 |
| 77 | 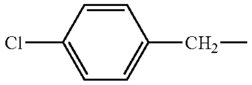 | 1 | 2 | 0 | R | H | 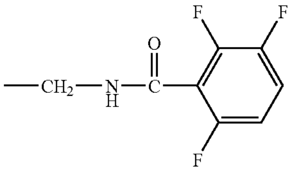 |
TABLE 1.8
| Compd. No. | 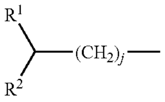 | k | m | n | chirality | $R^3$ | 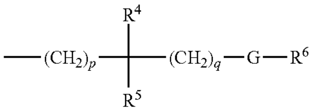 |
|---|---|---|---|---|---|---|---|
| 78 | 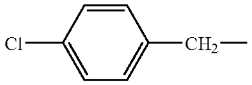 | 1 | 2 | 0 | R | H | 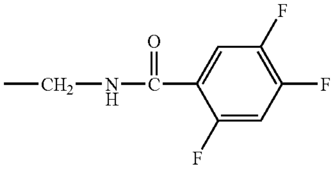 |
| 79 | 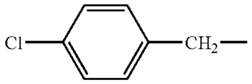 | 1 | 2 | 0 | R | H | 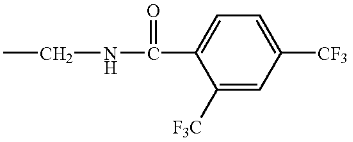 |
| 80 | 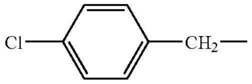 | 1 | 2 | 0 | R | H | 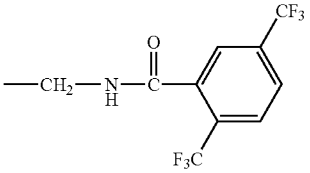 |
| 81 | 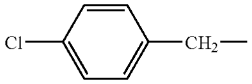 | 1 | 2 | 0 | R | H | 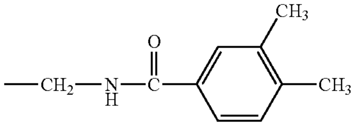 |
| 82 | 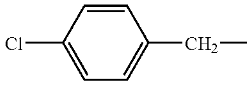 | 1 | 2 | 0 | — | $—CH_3$ | 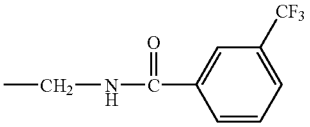 |

TABLE 1.8-continued
| Compd. No. | 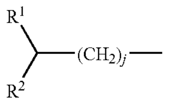 | k | m | n | chirality | $R^3$ | 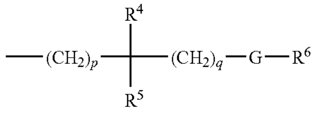 |
|---|---|---|---|---|---|---|---|
| 83 | 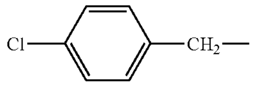 | 1 | 2 | 0 | R | H | 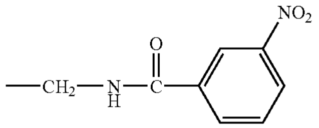 |
| 84 | 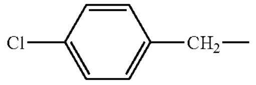 | 1 | 2 | 0 | R | H | 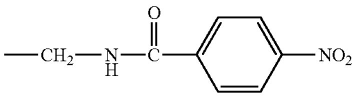 |
| 85 | 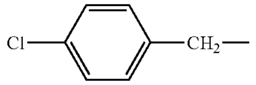 | 1 | 2 | 0 | — | H | 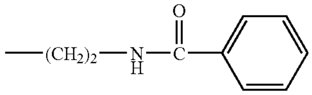 |
| 86 | 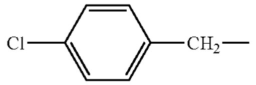 | 1 | 2 | 0 | — | H | 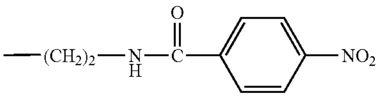 |
| 87 | 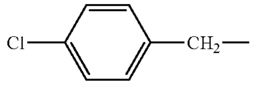 | 1 | 2 | 0 | S | H | 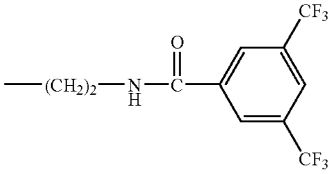 |
| 88 | 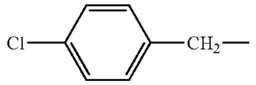 | 1 | 2 | 0 | S | H | 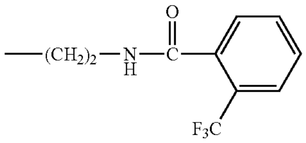 |
TABLE 1.9
| Compd. No. | 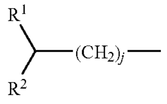 | k | m | n | chirality | $R^3$ | 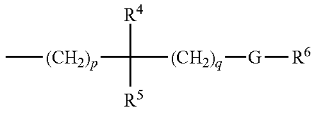 |
|---|---|---|---|---|---|---|---|
| 89 | 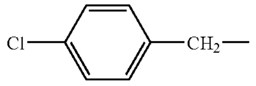 | 1 | 2 | 0 | S | H | 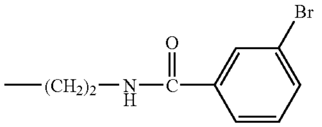 |
| 90 | 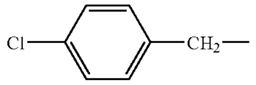 | 1 | 2 | 0 | S | H | 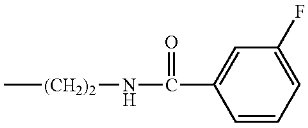 |
| 91 | 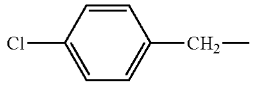 | 1 | 2 | 0 | S | H | 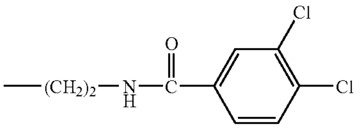 |

TABLE 1.9-continued
| Compd. No. | 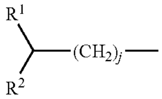 | k | m | n | chirality | $R^3$ | 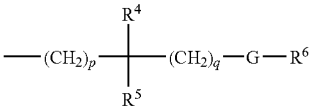 |
|---|---|---|---|---|---|---|---|
| 92 | 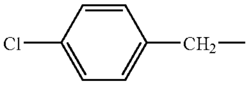 | 1 | 2 | 0 | S | H | 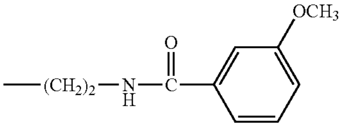 |
| 93 | 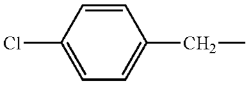 | 1 | 2 | 0 | S | H | 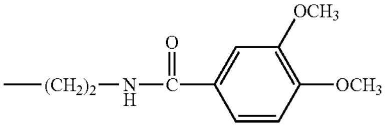 |
| 94 | 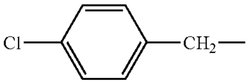 | 1 | 2 | 0 | S | H | 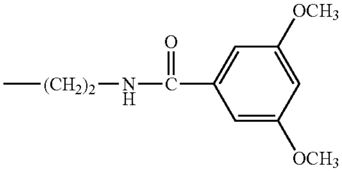 |
| 95 | 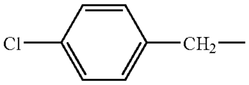 | 1 | 2 | 0 | S | H | 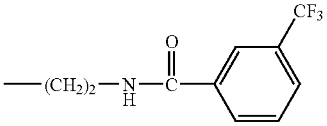 |
| 96 | 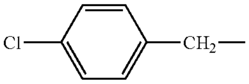 | 1 | 2 | 0 | S | H | 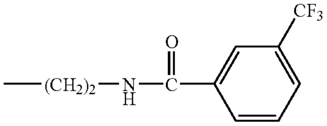 |
| 97 | 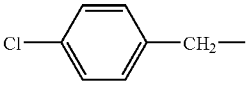 | 1 | 2 | 0 | S | H | 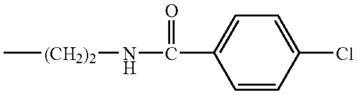 |
| 98 | 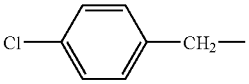 | 1 | 2 | 0 | S | H | 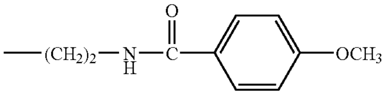 |
| 99 | 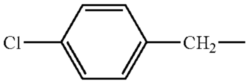 | 1 | 2 | 0 | S | H | 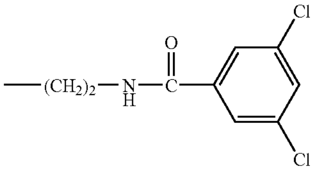 |

TABLE 1.10
| Compd. No. | 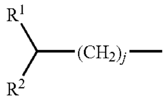 | k | m | n | chirality | $R^3$ | 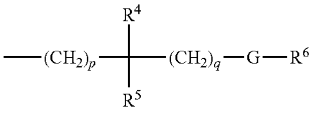 |
|---|---|---|---|---|---|---|---|
| 100 | 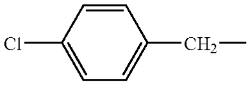 | 1 | 2 | 0 | S | H | 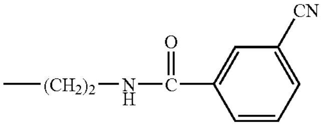 |
| 101 | 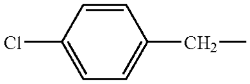 | 1 | 2 | 0 | S | H | 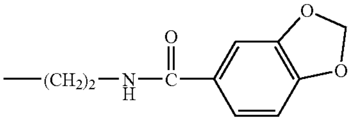 |
| 102 | 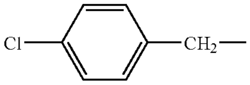 | 1 | 2 | 0 | S | H | 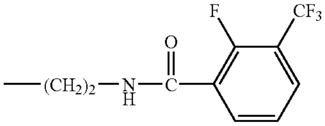 |
| 103 | 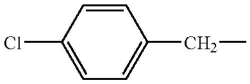 | 1 | 2 | 0 | S | H | 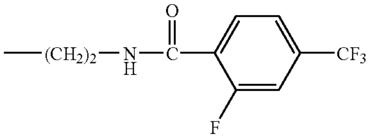 |
| 104 | 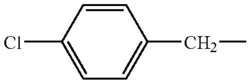 | 1 | 2 | 0 | S | H | 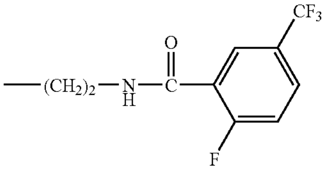 |
| 105 | 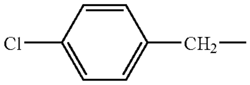 | 1 | 2 | 0 | S | H | 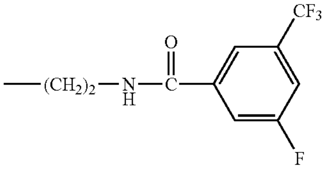 |
| 106 | 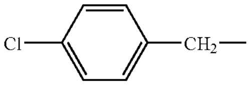 | 1 | 2 | 0 | S | H | 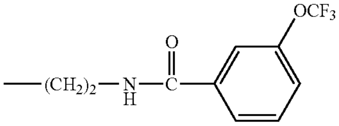 |
| 107 | 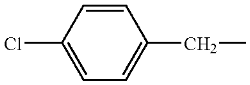 | 1 | 2 | 0 | S | H | 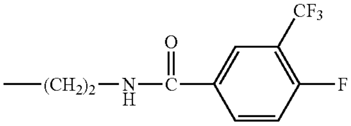 |
| 108 | 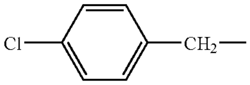 | 1 | 2 | 0 | S | H | 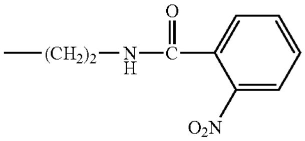 |

TABLE 1.10-continued
| Compd. No. | 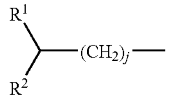 | k | m | n | chirality | R3 | 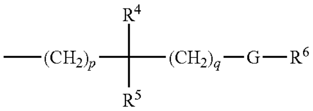 |
|---|---|---|---|---|---|---|---|
| 109 | 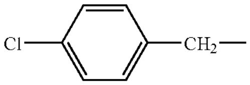 | 1 | 2 | 0 | S | H | 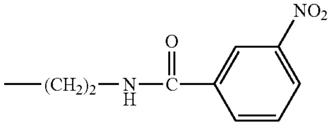 |
| 110 | 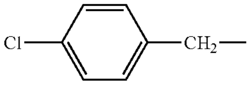 | 1 | 2 | 0 | S | H | 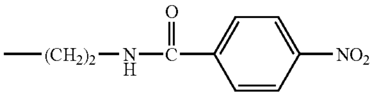 |
TABLE 1.11
| Compd. No. | 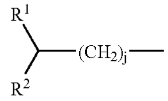 | k | m | n | chirality | R3 | 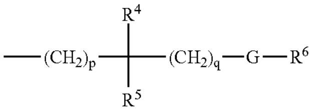 |
|---|---|---|---|---|---|---|---|
| 111 | 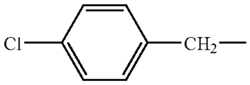 | 1 | 2 | 0 | R | H | 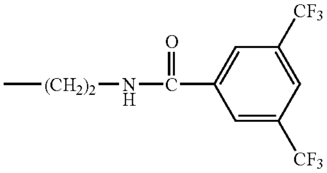 |
| 112 | 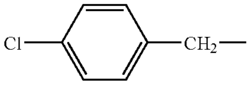 | 1 | 2 | 0 | R | H | 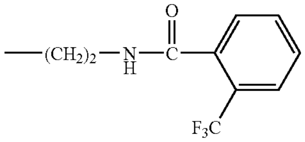 |
| 113 | 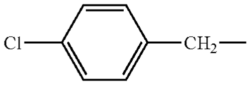 | 1 | 2 | 0 | R | H | 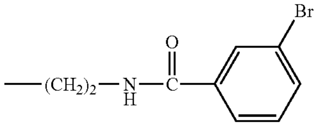 |
| 114 | 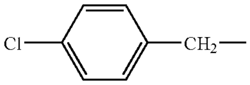 | 1 | 2 | 0 | R | H | 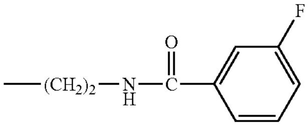 |
| 115 | 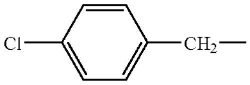 | 1 | 2 | 0 | R | H | 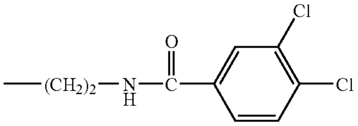 |
| 116 | 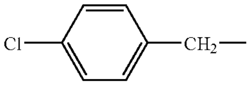 | 1 | 2 | 0 | R | H | 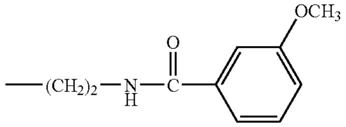 |

TABLE 1.11-continued
| Compd. No. | 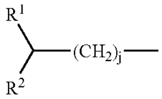 | k | m | n | chirality | $R^3$ | 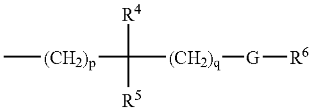 |
|---|---|---|---|---|---|---|---|
| 117 | 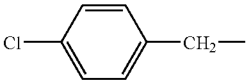 | 1 | 2 | 0 | R | H | 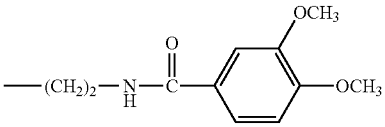 |
| 118 | 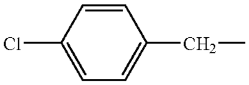 | 1 | 2 | 0 | R | H | 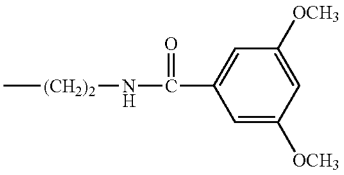 |
| 119 | 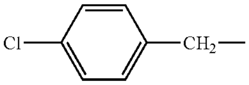 | 1 | 2 | 0 | R | H | 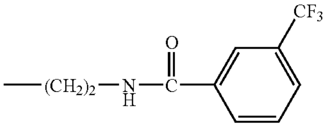 |
| 120 | 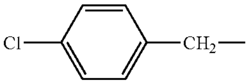 | 1 | 2 | 0 | R | H | 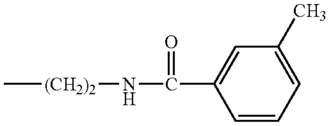 |
| 121 | 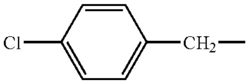 | 1 | 2 | 0 | R | H | 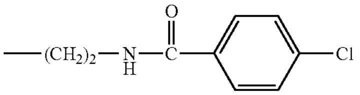 |
TABLE 1.12
| Compd. No. | 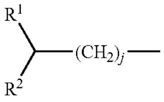 | k | m | n | chirality | $R^3$ | 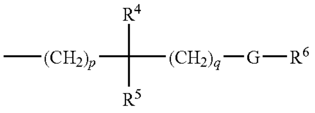 |
|---|---|---|---|---|---|---|---|
| 122 | 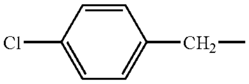 | 1 | 2 | 0 | R | H | 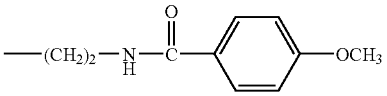 |
| 123 | 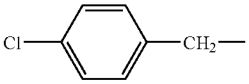 | 1 | 2 | 0 | R | H | 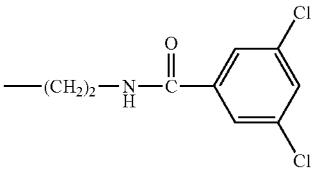 |
| 124 | 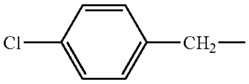 | 1 | 2 | 0 | R | H | 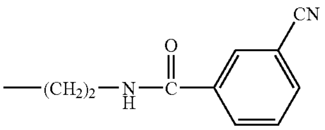 |

TABLE 1.12-continued
| Compd. No. | 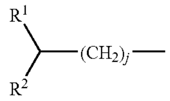 | k | m | n | chirality | $R^3$ | 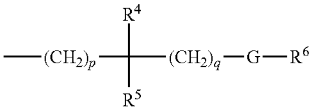 |
|---|---|---|---|---|---|---|---|
| 125 | 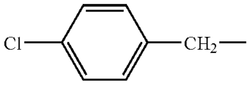 | 1 | 2 | 0 | R | H | 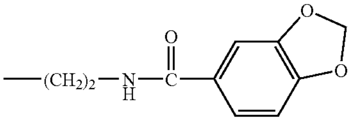 |
| 126 | 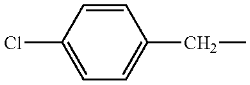 | 1 | 2 | 0 | R | H | 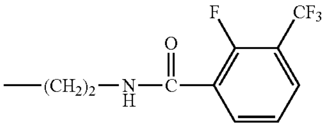 |
| 127 | 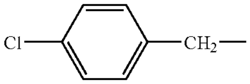 | 1 | 2 | 0 | R | H | 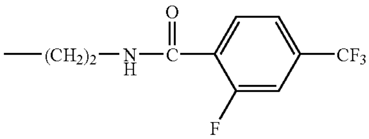 |
| 128 | 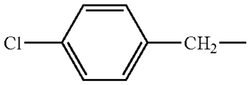 | 1 | 2 | 0 | R | H | 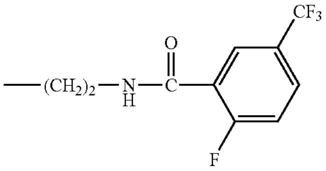 |
| 129 | 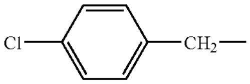 | 1 | 2 | 0 | R | H | 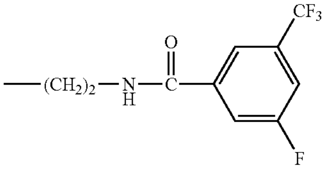 |
| 130 | 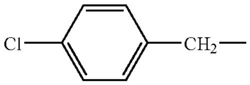 | 1 | 2 | 0 | R | H | 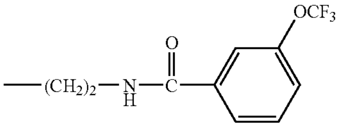 |
| 131 | 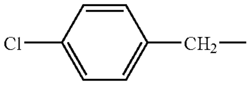 | 1 | 2 | 0 | R | H | 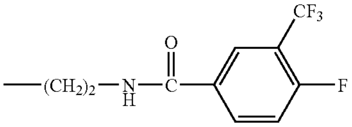 |
| 132 | 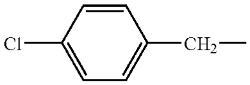 | 1 | 2 | 0 | R | H | 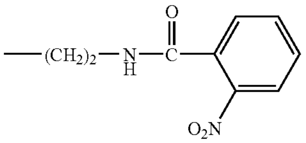 |

TABLE 1.13
| Compd. No. | 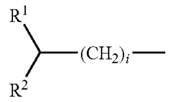 | k | m | n | chirality | $R^3$ | 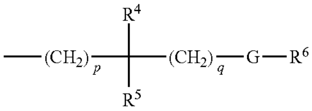 |
|---|---|---|---|---|---|---|---|
| 133 | 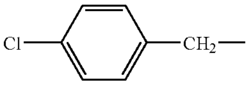 | 1 | 2 | 0 | R | H | 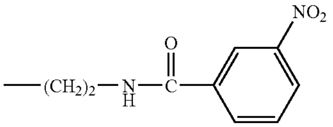 |
| 134 | 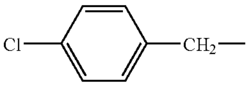 | 1 | 2 | 0 | R | H | 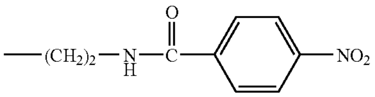 |
| 135 | 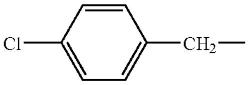 | 1 | 2 | 0 | R | H | 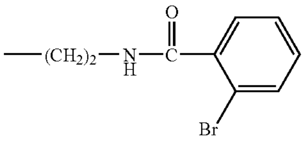 |
| 136 | 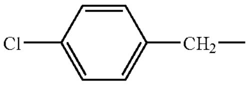 | 1 | 2 | 0 | R | H | 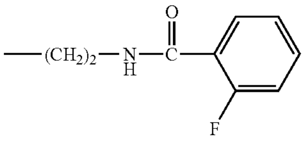 |
| 137 | 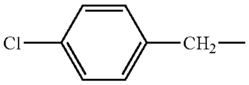 | 1 | 2 | 0 | R | H | 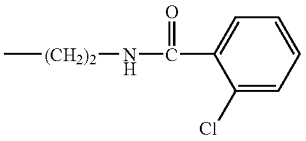 |
| 138 | 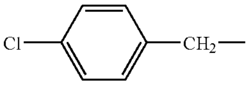 | 1 | 2 | 0 | R | H | 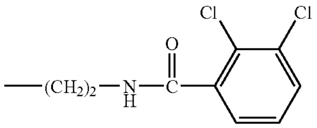 |
| 139 | 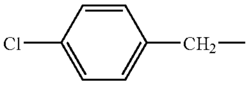 | 1 | 2 | 0 | R | H | 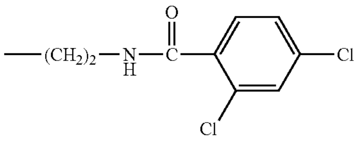 |
| 140 | 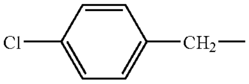 | 1 | 2 | 0 | R | H | 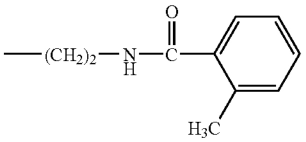 |
| 141 | 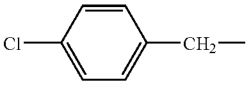 | 1 | 2 | 0 | R | H | 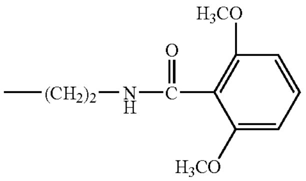 |
| 142 | 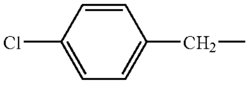 | 1 | 2 | 0 | R | H | 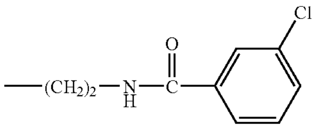 |

TABLE 1.13-continued
| Compd. No. | 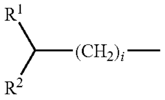 | k | m | n | chirality | $R^3$ | 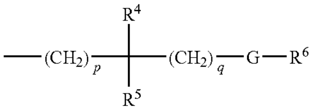 |
|---|---|---|---|---|---|---|---|
| 143 | 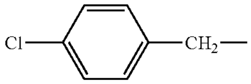 | 1 | 2 | 0 | R | H | 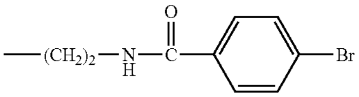 |
TABLE 1.14
| Compd. No. | 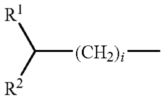 | k | m | n | chirality | $R^3$ | 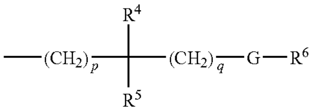 |
|---|---|---|---|---|---|---|---|
| 144 | 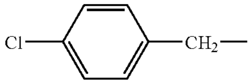 | 1 | 2 | 0 | R | H | 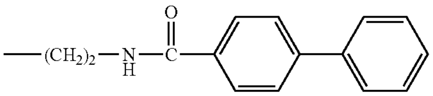 |
| 145 | 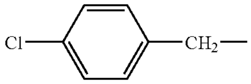 | 1 | 2 | 0 | R | H | 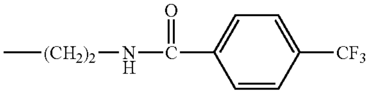 |
| 146 | 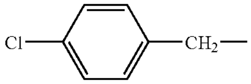 | 1 | 2 | 0 | R | H | 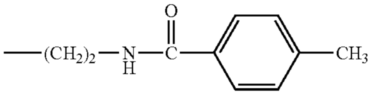 |
| 147 | 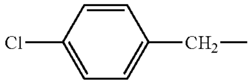 | 1 | 2 | 0 | R | H | 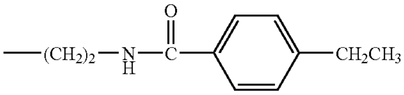 |
| 148 | 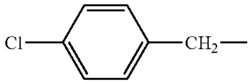 | 1 | 2 | 0 | R | H | 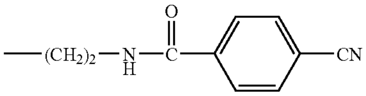 |
| 149 | 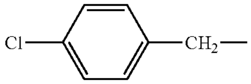 | 1 | 2 | 0 | R | H | 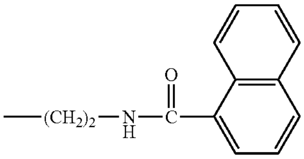 |
| 150 | 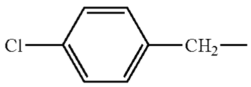 | 1 | 2 | 0 | R | H | 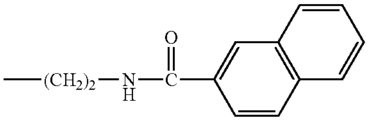 |
| 151 | 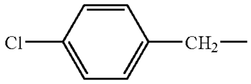 | 1 | 2 | 0 | R | H | 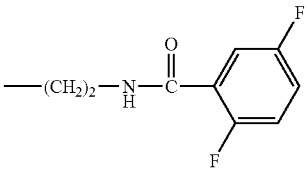 |

TABLE 1.14-continued
| Compd. No. | 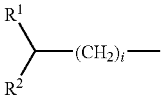 | k | m | n | chirality | $R^3$ | 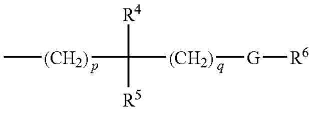 |
|---|---|---|---|---|---|---|---|
| 152 | 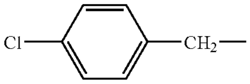 | 1 | 2 | 0 | R | H | 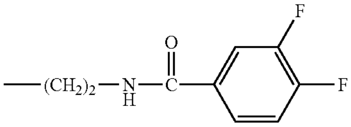 |
| 153 | 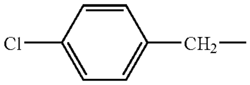 | 1 | 2 | 0 | R | H | 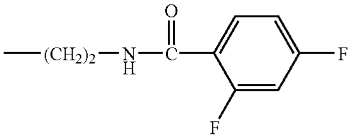 |
| 154 | 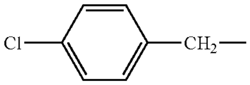 | 1 | 2 | 0 | R | H | 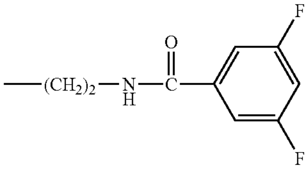 |
TABLE 1.15
| Compd. No. | 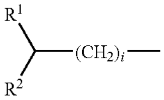 | k | m | n | chirality | $R^3$ | 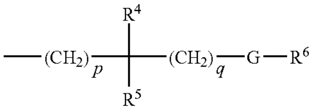 |
|---|---|---|---|---|---|---|---|
| 155 | 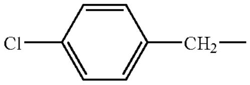 | 1 | 2 | 0 | R | H | 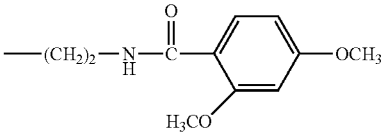 |
| 156 | 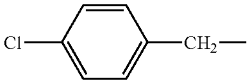 | 1 | 2 | 0 | R | H | 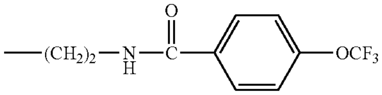 |
| 157 | 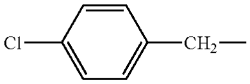 | 1 | 2 | 0 | R | H | 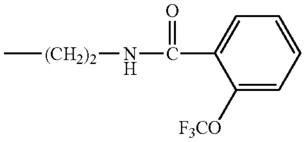 |
| 158 | 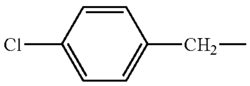 | 1 | 2 | 0 | R | H | 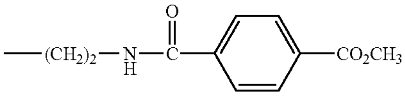 |
| 159 | 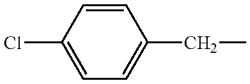 | 1 | 2 | 0 | R | H | 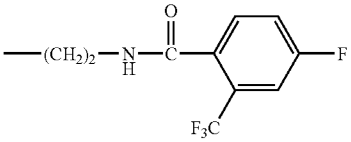 |

TABLE 1.15-continued
| Compd. No. | 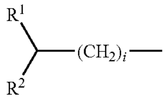 | k | m | n | chirality | $R^3$ | 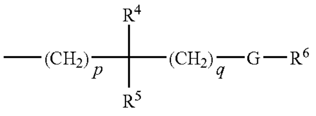 |
|---|---|---|---|---|---|---|---|
| 160 | 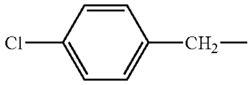 | 1 | 2 | 0 | R | H | 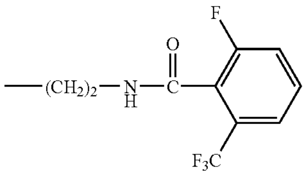 |
| 161 | 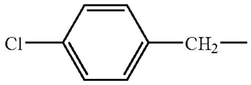 | 1 | 2 | 0 | R | H | 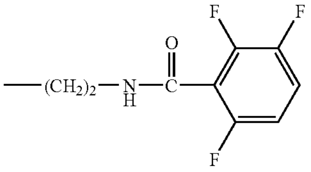 |
| 162 | 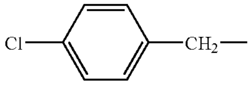 | 1 | 2 | 0 | R | H | 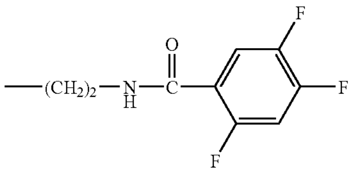 |
| 163 | 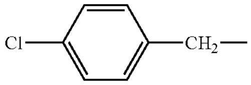 | 1 | 2 | 0 | R | H | 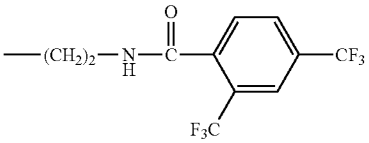 |
| 164 | 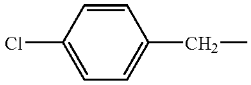 | 1 | 2 | 0 | R | H | 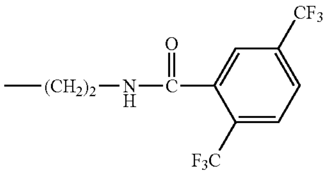 |
| 165 | 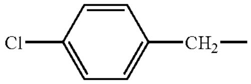 | 1 | 2 | 0 | R | H | 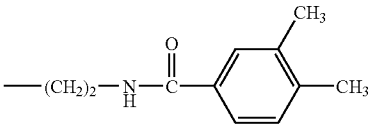 |
TABLE 1.16
| Compd. No. | 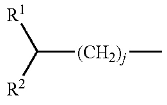 | k | m | n | chirality | $R^3$ | 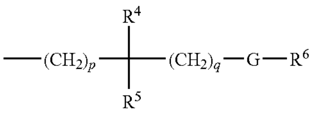 |
|---|---|---|---|---|---|---|---|
| 166 | 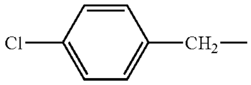 | 1 | 2 | 0 | R | H | 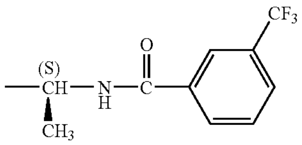 |

TABLE 1.16-continued
| Compd. No. | 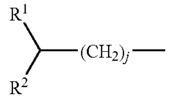 | k | m | n | chirality | $R^3$ | 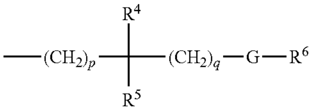 |
|---|---|---|---|---|---|---|---|
| 167 | 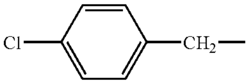 | 1 | 2 | 0 | R | H | 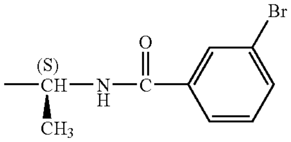 |
| 168 | 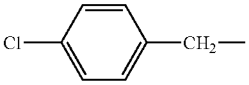 | 1 | 2 | 0 | R | H | 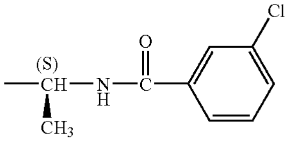 |
| 169 | 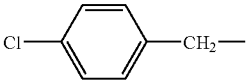 | 1 | 2 | 0 | R | H | 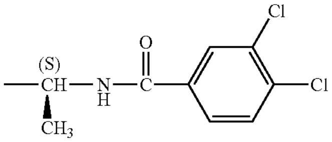 |
| 170 | 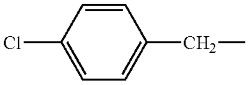 | 1 | 2 | 0 | R | H | 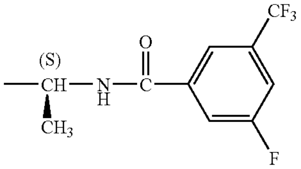 |
| 171 | 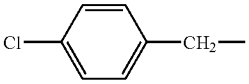 | 1 | 2 | 0 | R | H | 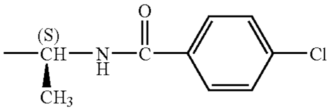 |
| 172 | 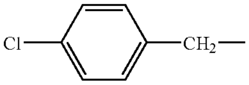 | 1 | 2 | 0 | R | H | 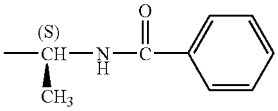 |
| 173 | 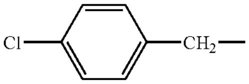 | 1 | 2 | 0 | R | H | 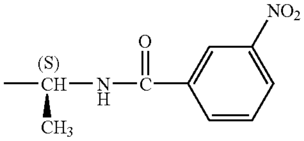 |
| 174 | 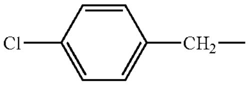 | 1 | 2 | 0 | R | H | 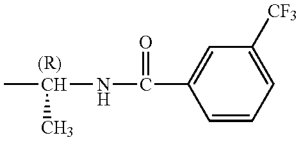 |
| 175 | 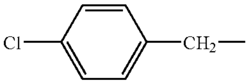 | 1 | 2 | 0 | R | H | 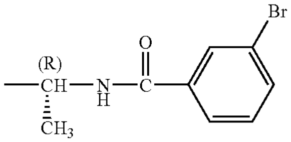 |

TABLE 1.16-continued
| Compd. No. | 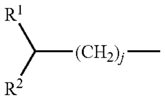 | k | m | n | chirality | $R^3$ | 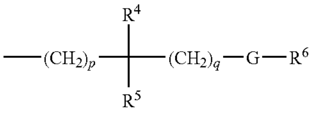 |
|---|---|---|---|---|---|---|---|
| 176 | 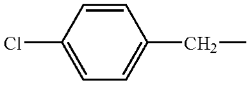 | 1 | 2 | 0 | R | H | 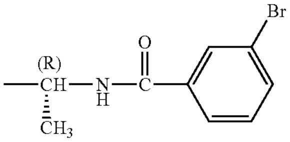 |
TABLE 1.17
| Compd. No. | 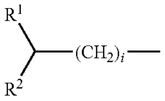 | k | m | n | chirality | $R^3$ | 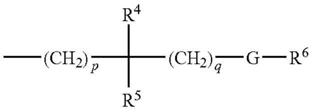 |
|---|---|---|---|---|---|---|---|
| 177 | 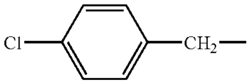 | 1 | 2 | 0 | R | H | 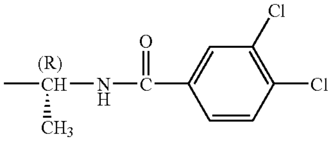 |
| 178 | 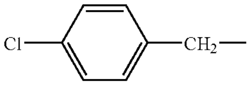 | 1 | 2 | 0 | R | H | 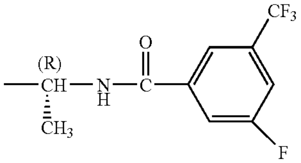 |
| 179 | 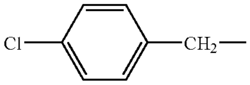 | 1 | 2 | 0 | R | H | 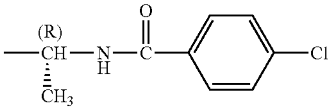 |
| 180 | 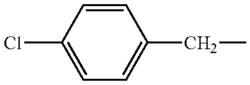 | 1 | 2 | 0 | R | H | 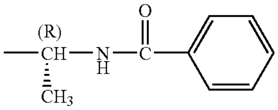 |
| 181 | 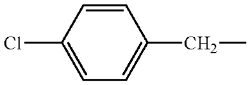 | 1 | 2 | 0 | R | H | 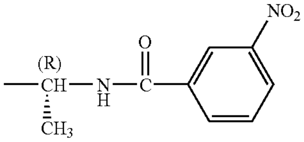 |
| 182 | 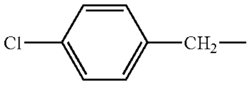 | 1 | 2 | 0 | R | H | 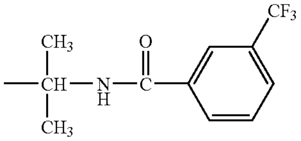 |
| 183 | 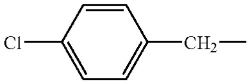 | 1 | 2 | 0 | R | H | 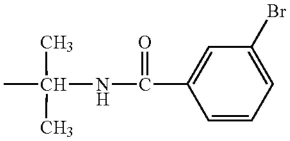 |

TABLE 1.17-continued
| Compd. No. | 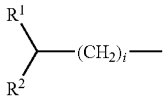 | k | m | n | chirality | $R^3$ | 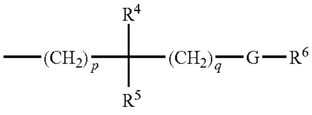 |
|---|---|---|---|---|---|---|---|
| 184 | 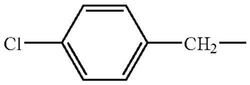 | 1 | 2 | 0 | R | H | 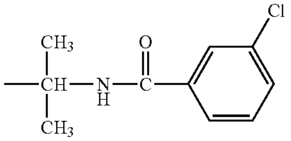 |
| 185 | 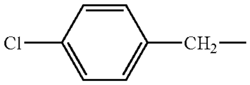 | 1 | 2 | 0 | R | H | 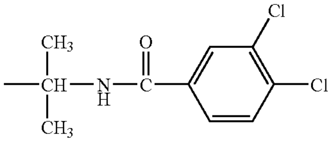 |
| 186 | 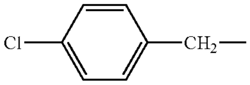 | 1 | 2 | 0 | R | H | 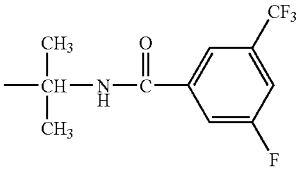 |
| 187 | 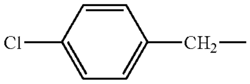 | 1 | 2 | 0 | R | H | 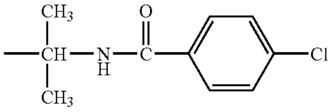 |
TABLE 1.18
| Compd. No. | 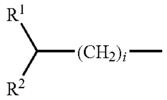 | k | m | n | chirality | $R^3$ | 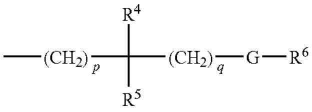 |
|---|---|---|---|---|---|---|---|
| 188 | 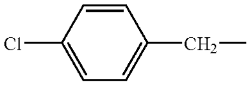 | 1 | 2 | 0 | R | H | 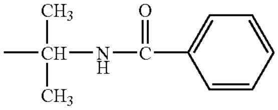 |
| 189 | 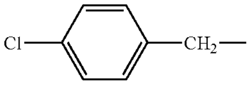 | 1 | 2 | 0 | R | H | 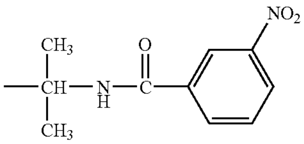 |
| 190 | 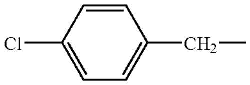 | 1 | 2 | 0 | R | H | 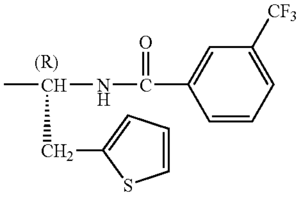 |

TABLE 1.18-continued
| Compd. No. | 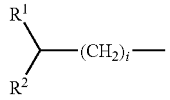 | k | m | n | chirality | $R^3$ | 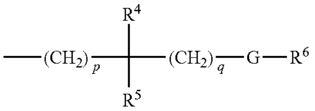 |
|---|---|---|---|---|---|---|---|
| 191 | 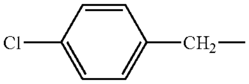 | 1 | 2 | 0 | R | H | 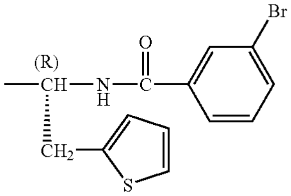 |
| 192 | 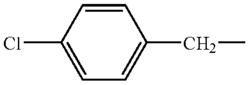 | 1 | 2 | 0 | R | H | 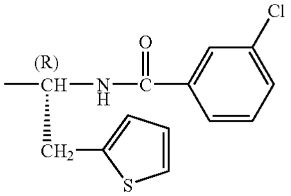 |
| 193 | 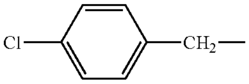 | 1 | 2 | 0 | R | H | 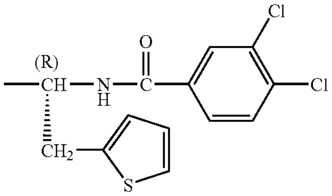 |
| 194 | 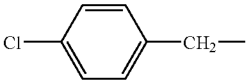 | 1 | 2 | 0 | R | H | 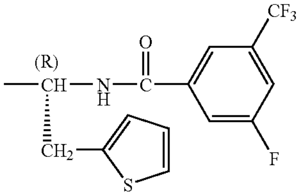 |
| 195 | 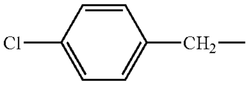 | 1 | 2 | 0 | R | H | 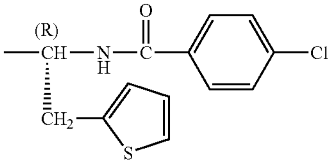 |
| 196 | 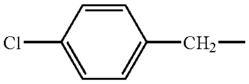 | 1 | 2 | 0 | R | H | 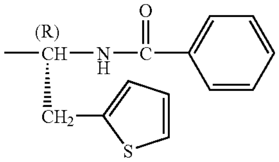 |
| 197 | 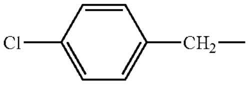 | 1 | 2 | 0 | R | H | 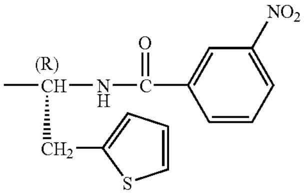 |

TABLE 1.18-continued
| Compd. No. | 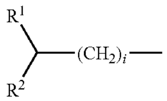 | k | m | n | chirality | $R^3$ | 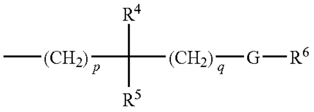 |
|---|---|---|---|---|---|---|---|
| 198 | 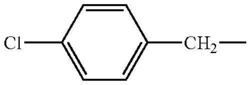 | 1 | 2 | 0 | R | H | 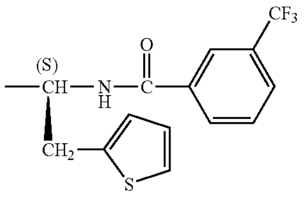 |
TABLE 1.19
| Compd. No. | 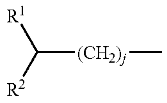 | k | m | n | chirality | $R^3$ | 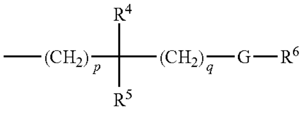 |
|---|---|---|---|---|---|---|---|
| 199 | 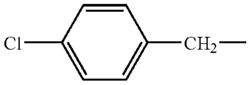 | 1 | 2 | 0 | R | H | 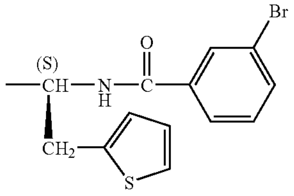 |
| 200 | 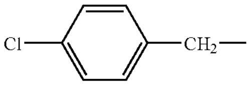 | 1 | 2 | 0 | R | H | 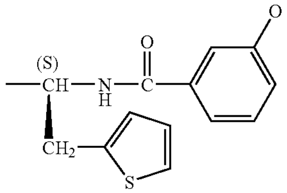 |
| 201 | 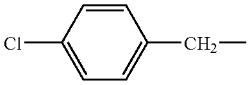 | 1 | 2 | 0 | R | H | 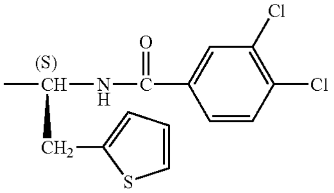 |
| 202 | 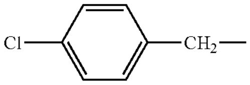 | 1 | 2 | 0 | R | H | 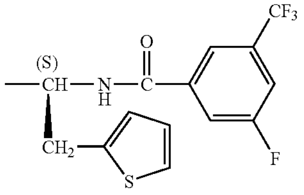 |
| 203 | 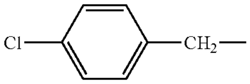 | 1 | 2 | 0 | R | H | 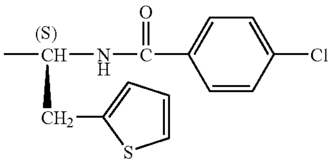 |

TABLE 1.19-continued
| Compd. No. | 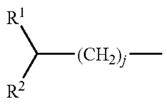 | k | m | n | chirality | $R^3$ | 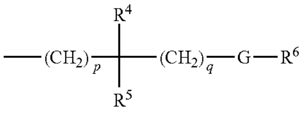 |
|---|---|---|---|---|---|---|---|
| 204 | 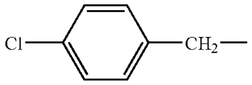 | 1 | 2 | 0 | R | H | 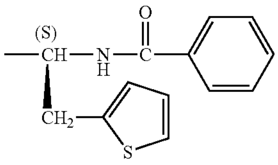 |
| 205 | 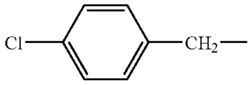 | 1 | 2 | 0 | R | H | 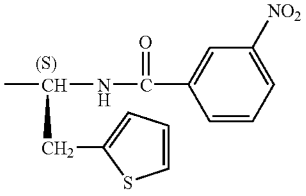 |
| 206 | 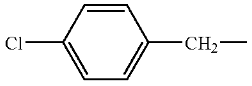 | 1 | 2 | 0 | R | H | 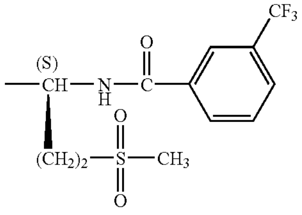 |
| 207 | 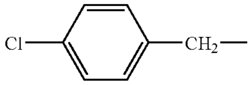 | 1 | 2 | 0 | R | H | 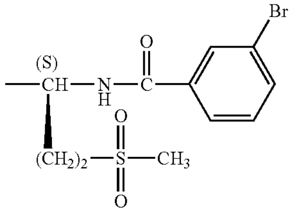 |
| 208 | 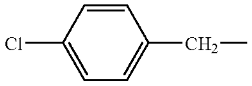 | 1 | 2 | 0 | R | H | 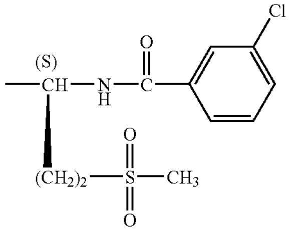 |
| 209 | 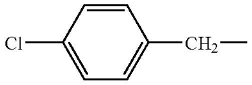 | 1 | 2 | 0 | R | H | 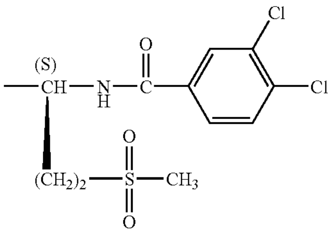 |

TABLE 1.20
| Compd. No. | 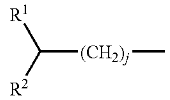 | k | m | n | chirality | $R^3$ | 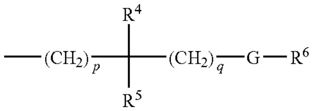 |
|---|---|---|---|---|---|---|---|
| 210 | 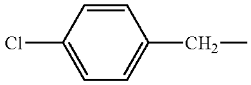 | 1 | 2 | 0 | R | H | 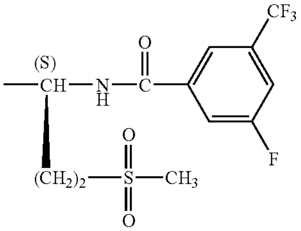 |
| 211 | 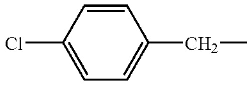 | 1 | 2 | 0 | R | H | 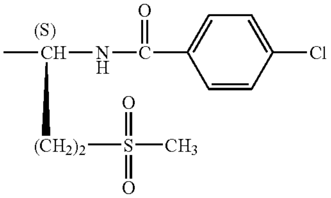 |
| 212 | 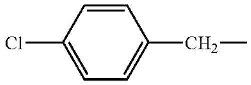 | 1 | 2 | 0 | R | H | 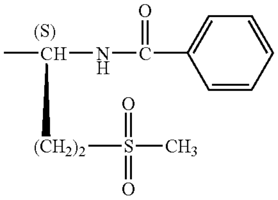 |
| 213 | 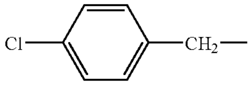 | 1 | 2 | 0 | R | H | 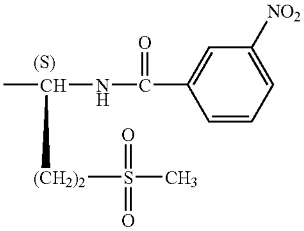 |
| 214 | 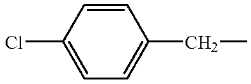 | 1 | 2 | 0 | - | H | 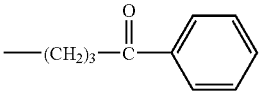 |
| 215 | 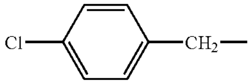 | 1 | 2 | 0 | - | H | 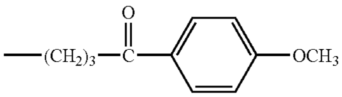 |
| 216 | 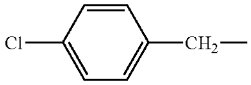 | 1 | 2 | 0 | - | H | 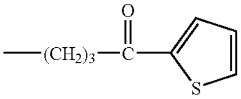 |
| 217 | 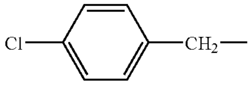 | 1 | 2 | 0 | - | H | 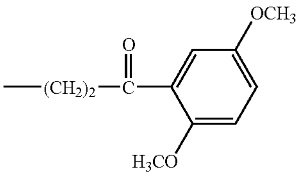 |

TABLE 1.20-continued
| Compd. No. | 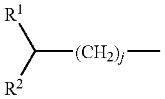 | k | m | n | chirality | $R^3$ | 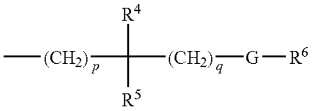 |
|---|---|---|---|---|---|---|---|
| 218 | 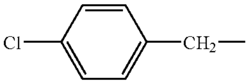 | 1 | 2 | 0 | - | H | 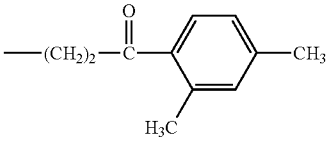 |
| 219 | 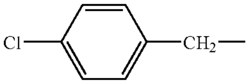 | 1 | 2 | 0 | - | H | 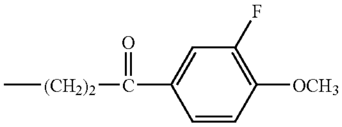 |
| 220 | 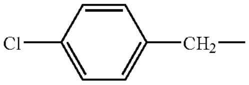 | 1 | 2 | 0 | - | H | 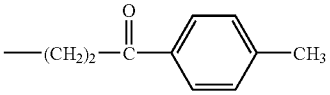 |
TABLE 1.21
| Compd. No. | 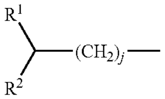 | k | m | n | chirality | $R^3$ | 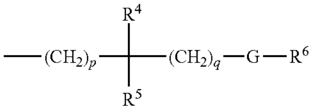 |
|---|---|---|---|---|---|---|---|
| 221 | 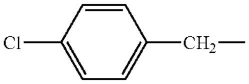 | 1 | 2 | 0 | - | H | 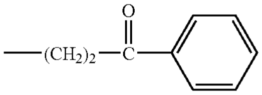 |
| 222 | 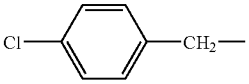 | 1 | 2 | 0 | - | H | 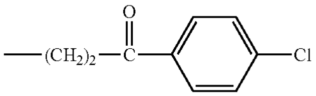 |
| 223 | 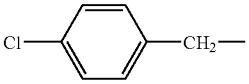 | 1 | 2 | 0 | - | H | 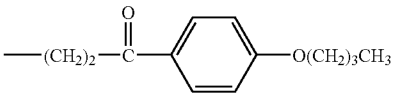 |
| 224 | 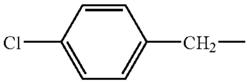 | 1 | 2 | 0 | - | H | 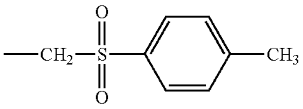 |
| 225 | 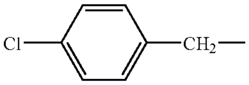 | 1 | 2 | 0 | - | H | 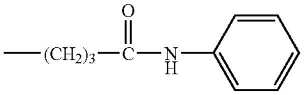 |
| 226 | 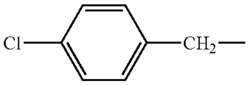 | 1 | 2 | 0 | - | H | 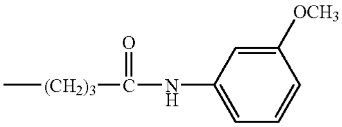 |
| 227 | 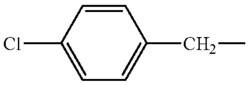 | 1 | 2 | 0 | - | H | 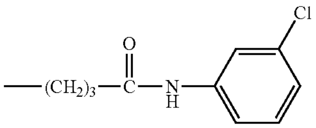 |

TABLE 1.21-continued
| Compd. No. | 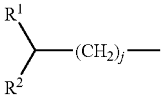 | k | m | n | chirality | $R^3$ | 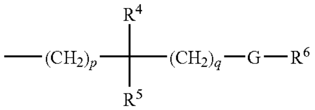 |
|---|---|---|---|---|---|---|---|
| 228 | 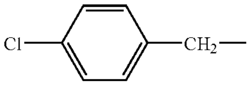 | 1 | 2 | 0 | - | H | 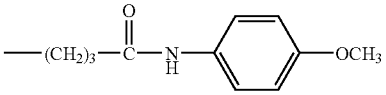 |
| 229 | 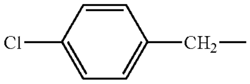 | 1 | 2 | 0 | - | H | 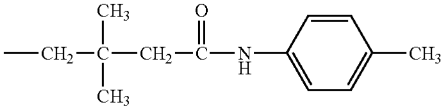 |
| 230 | 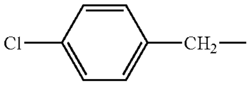 | 1 | 2 | 0 | - | H | 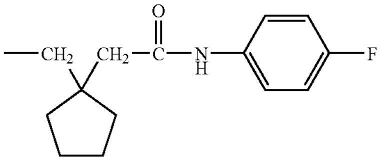 |
| 231 | 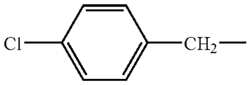 | 1 | 2 | 0 | - | H | 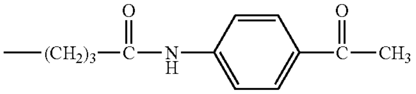 |
TABLE 1.22
| Compd. No. | 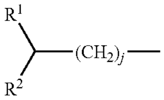 | k | m | n | chirality | $R^3$ | 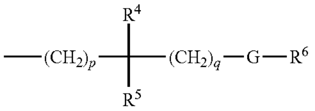 |
|---|---|---|---|---|---|---|---|
| 232 | 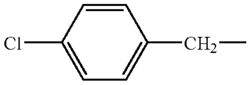 | 1 | 2 | 0 | - | H | 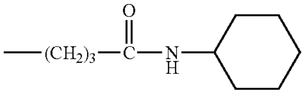 |
| 233 | 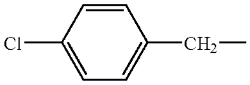 | 1 | 2 | 0 | - | H | 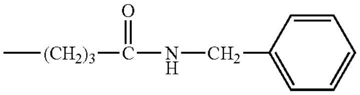 |
| 234 | 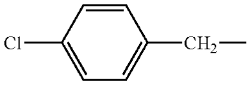 | 1 | 2 | 0 | - | H | 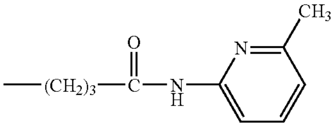 |
| 235 | 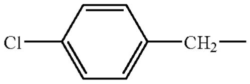 | 1 | 2 | 0 | - | H | 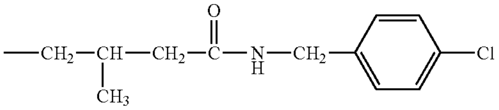 |
| 236 | 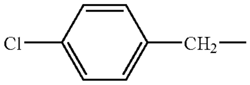 | 1 | 2 | 0 | - | H | 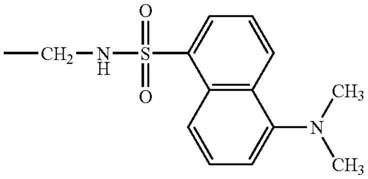 |

TABLE 1.22-continued
| Compd. No. | 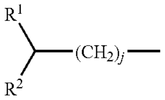 | k | m | n | chirality | $R^3$ | 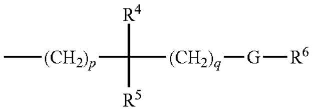 |
|---|---|---|---|---|---|---|---|
| 237 | 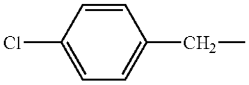 | 1 | 2 | 0 | - | H | 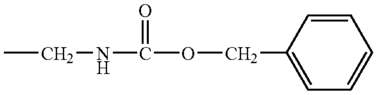 |
| 238 | 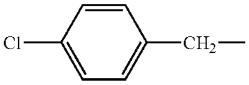 | 1 | 2 | 0 | - | H | 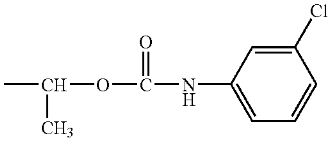 |
| 239 | 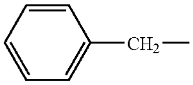 | 1 | 2 | 0 | S | H | 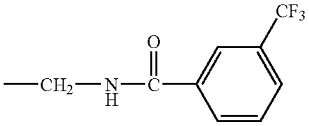 |
| 240 | 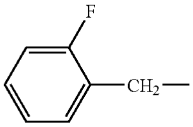 | 1 | 2 | 0 | S | H | 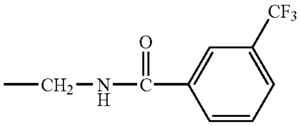 |
| 241 | 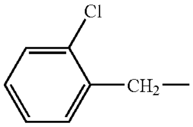 | 1 | 2 | 0 | S | H | 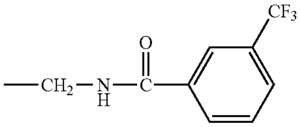 |
| 242 | 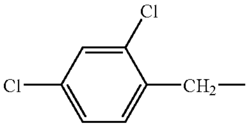 | 1 | 2 | 0 | S | H | 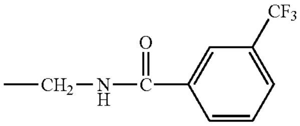 |
TABLE 1.23
| Compd. No. | 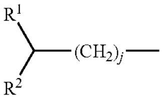 | k | m | n | chirality | $R^3$ | 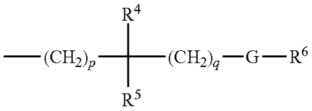 |
|---|---|---|---|---|---|---|---|
| 243 | 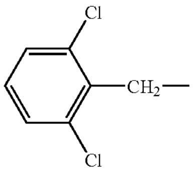 | 1 | 2 | 0 | S | H | 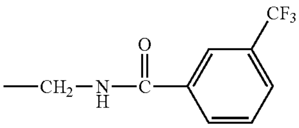 |
| 244 | 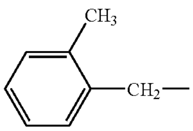 | 1 | 2 | 0 | S | H | 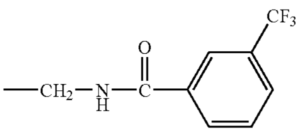 |

TABLE 1.23-continued
| Compd. No. | 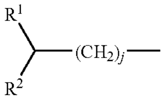 | k | m | n | chirality | $R^3$ | 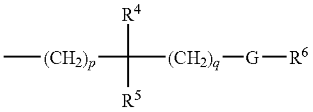 |
|---|---|---|---|---|---|---|---|
| 245 | 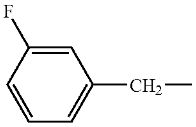 | 1 | 2 | 0 | S | H | 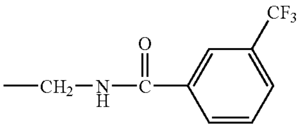 |
| 246 | 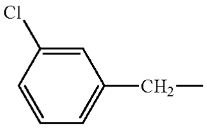 | 1 | 2 | 0 | S | H | 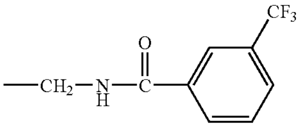 |
| 247 | 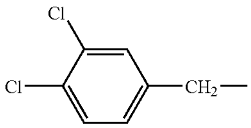 | 1 | 2 | 0 | S | H | 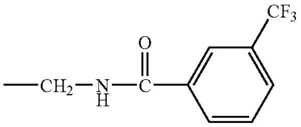 |
| 248 | 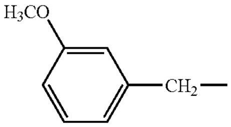 | 1 | 2 | 0 | S | H | 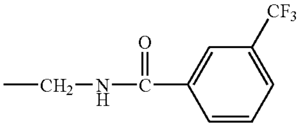 |
| 249 | 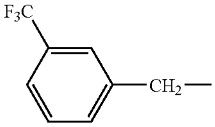 | 1 | 2 | 0 | S | H | 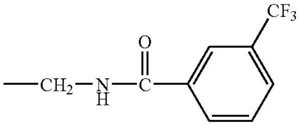 |
| 250 | 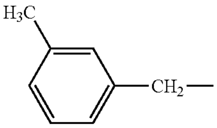 | 1 | 2 | 0 | S | H | 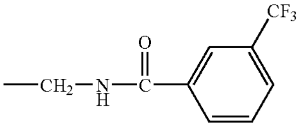 |
| 251 | 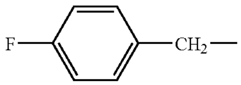 | 1 | 2 | 0 | S | H | 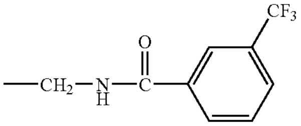 |
| 252 | 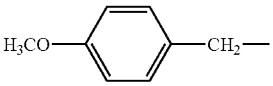 | 1 | 2 | 0 | S | H | 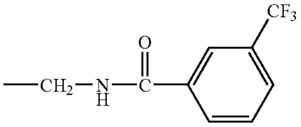 |
| 253 | 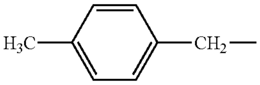 | 1 | 2 | 0 | S | H | 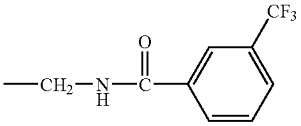 |

TABLE 1.24
| Compd. No. | 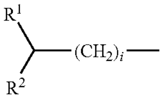 | k | m | n | chirality | $R^3$ | 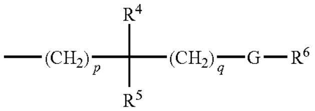 |
|---|---|---|---|---|---|---|---|
| 254 | 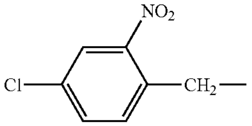 | 1 | 2 | 0 | S | H | 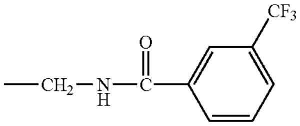 |
| 255 | 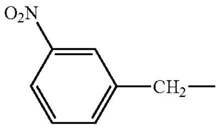 | 1 | 2 | 0 | S | H | 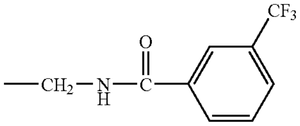 |
| 256 | 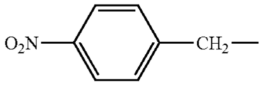 | 1 | 2 | 0 | S | H | 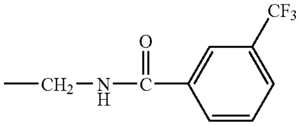 |
| 257 | 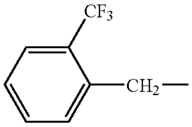 | 1 | 2 | 0 | S | H | 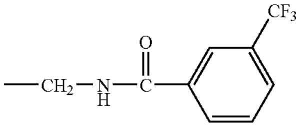 |
| 258 | 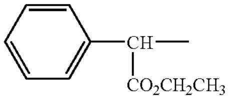 | 1 | 2 | 0 | S | H | 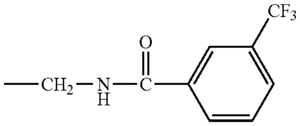 |
| 259 | 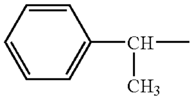 | 1 | 2 | 0 | S | H | 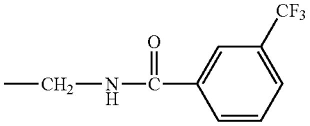 |
| 260 | 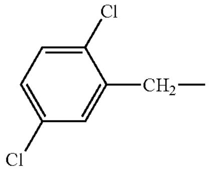 | 1 | 2 | 0 | S | H | 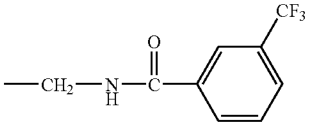 |
| 261 | 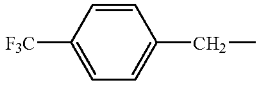 | 1 | 2 | 0 | S | H | 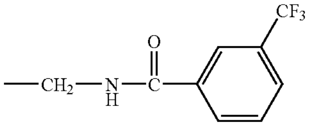 |
| 262 | 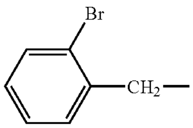 | 1 | 2 | 0 | S | H | 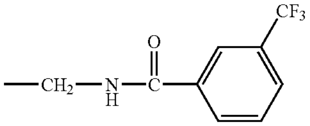 |
| 263 | 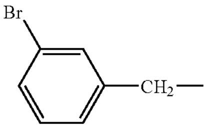 | 1 | 2 | 0 | S | H | 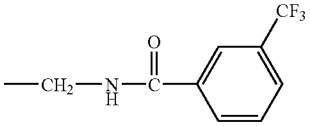 |

TABLE 1.24-continued
| Compd. No. | 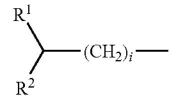 | k | m | n | chirality | $R^3$ | 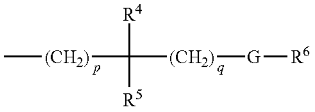 |
|---|---|---|---|---|---|---|---|
| 264 | 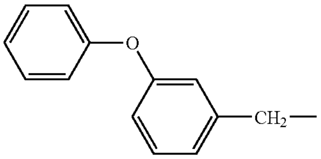 | 1 | 2 | 0 | S | H | 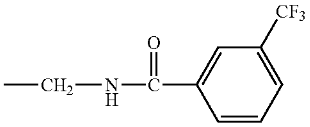 |
TABLE 1.25
| Compd. No. | 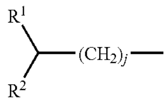 | k | m | n | chirality | $R^3$ | 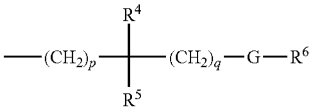 |
|---|---|---|---|---|---|---|---|
| 265 | 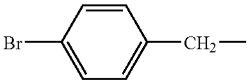 | 1 | 2 | 0 | S | H | 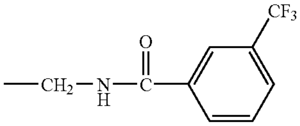 |
| 266 | 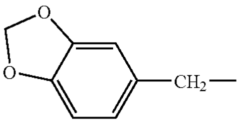 | 1 | 2 | 0 | S | H | 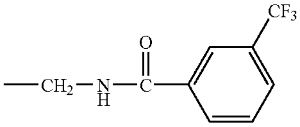 |
| 267 | 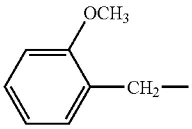 | 1 | 2 | 0 | S | H | 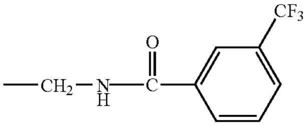 |
| 268 | 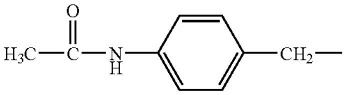 | 1 | 2 | 0 | S | H | 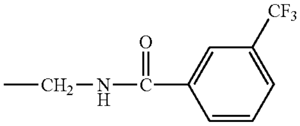 |
| 269 | 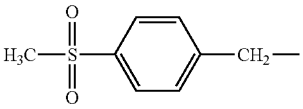 | 1 | 2 | 0 | S | H | 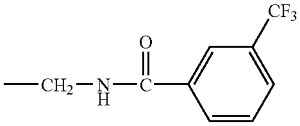 |
| 270 | 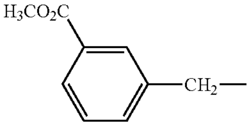 | 1 | 2 | 0 | S | H | 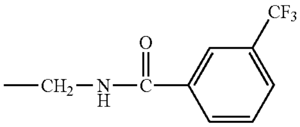 |
| 271 | 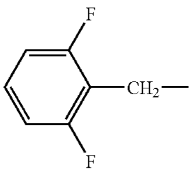 | 1 | 2 | 0 | S | H | 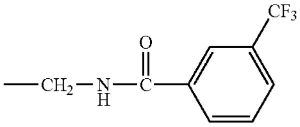 |

TABLE 1.25-continued
| Compd. No. | 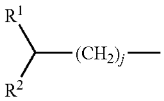 | k | m | n | chirality | $R^3$ | 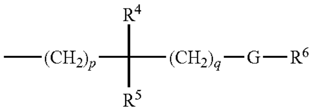 |
|---|---|---|---|---|---|---|---|
| 272 | 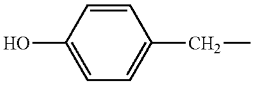 | 1 | 2 | 0 | S | H | 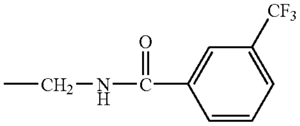 |
| 273 | 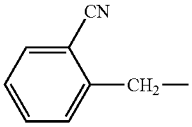 | 1 | 2 | 0 | S | H | 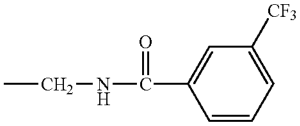 |
| 274 | 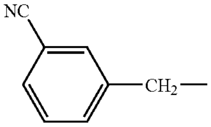 | 1 | 2 | 0 | S | H | 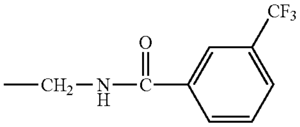 |
| 275 | 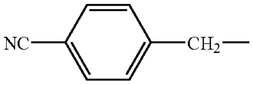 | 1 | 2 | 0 | S | H | 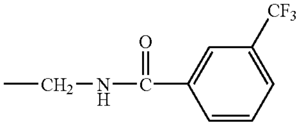 |
TABLE 1.26
| Compd. No. | 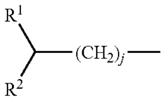 | k | m | n | chirality | $R^3$ | 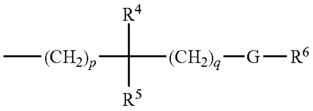 |
|---|---|---|---|---|---|---|---|
| 276 | 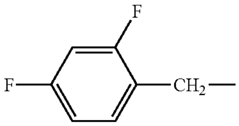 | 1 | 2 | 0 | S | H | 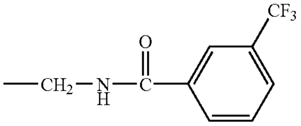 |
| 277 | 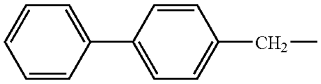 | 1 | 2 | 0 | S | H | 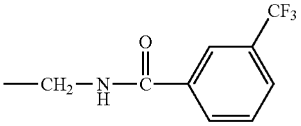 |
| 278 | 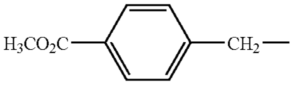 | 1 | 2 | 0 | S | H | 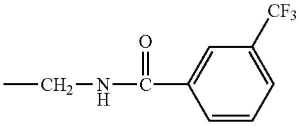 |
| 279 | 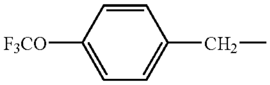 | 1 | 2 | 0 | S | H | 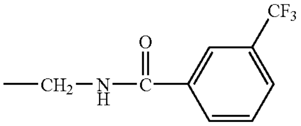 |
| 280 | 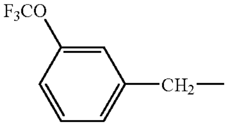 | 1 | 2 | 0 | S | H | 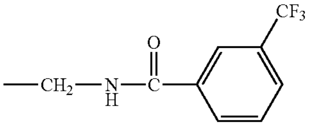 |

TABLE 1.26-continued
| Compd. No. | 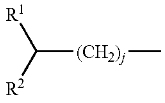 | k | m | n | chirality | $R^3$ | 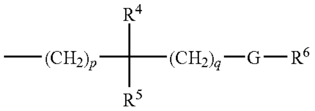 |
|---|---|---|---|---|---|---|---|
| 281 | 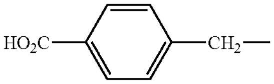 | 1 | 2 | 0 | S | H | 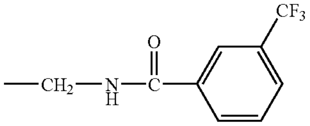 |
| 282 | 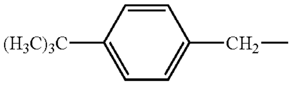 | 1 | 2 | 0 | S | H | 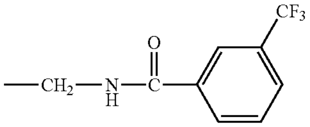 |
| 283 | 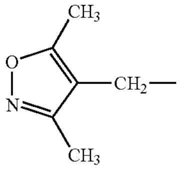 | 1 | 2 | 0 | S | H | 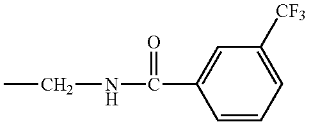 |
| 284 | 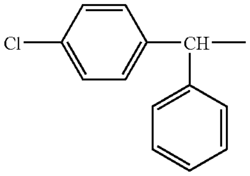 | 1 | 2 | 0 | S | H | 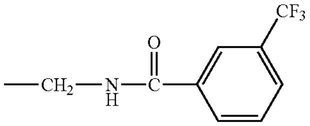 |
| 285 | 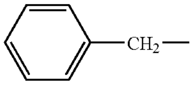 | 1 | 2 | 0 | R | H | 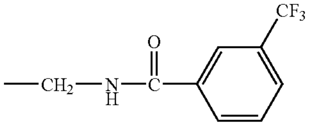 |
| 286 | 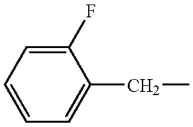 | 1 | 2 | 0 | R | H | 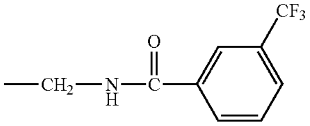 |
TABLE 1.27
| Compd. No. | 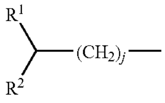 | k | m | n | chirality | $R^3$ | 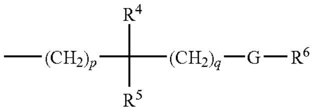 |
|---|---|---|---|---|---|---|---|
| 287 | 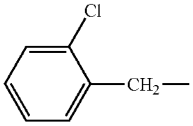 | 1 | 2 | 0 | R | H | 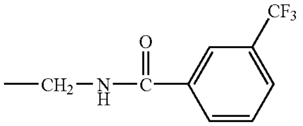 |
| 288 | 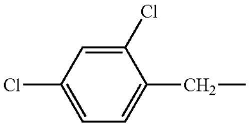 | 1 | 2 | 0 | R | H | 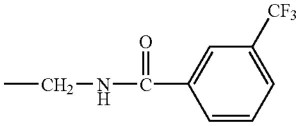 |

TABLE 1.27-continued
| Compd. No. | 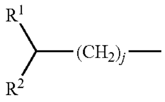 | k | m | n | chirality | $R^3$ | 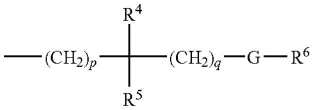 |
|---|---|---|---|---|---|---|---|
| 289 | 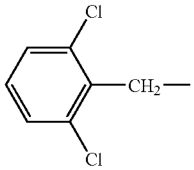 | 1 | 2 | 0 | R | H | 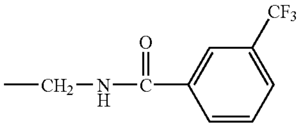 |
| 290 | 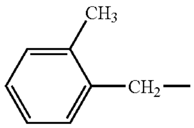 | 1 | 2 | 0 | R | H | 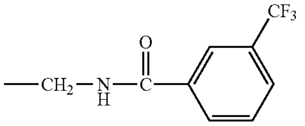 |
| 291 | 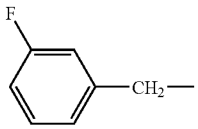 | 1 | 2 | 0 | R | H | 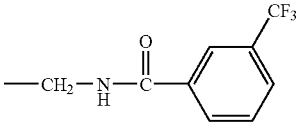 |
| 292 | 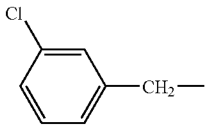 | 1 | 2 | 0 | R | H | 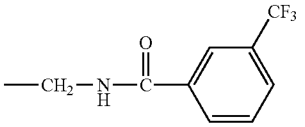 |
| 293 | 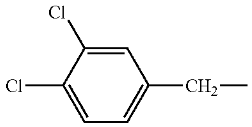 | 1 | 2 | 0 | R | H | 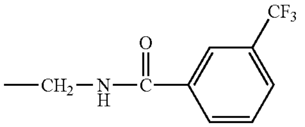 |
| 294 | 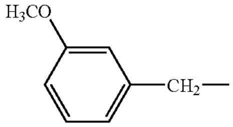 | 1 | 2 | 0 | R | H | 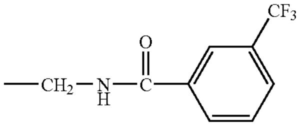 |
| 295 | 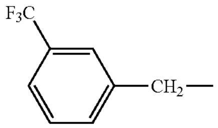 | 1 | 2 | 0 | R | H | 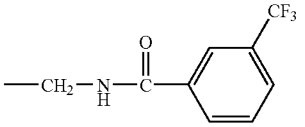 |
| 296 | 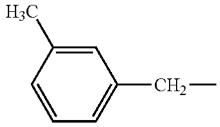 | 1 | 2 | 0 | R | H | 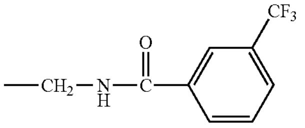 |
| 297 | 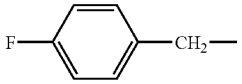 | 1 | 2 | 0 | R | H | 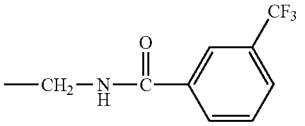 |

TABLE 1.28
| Compd. No. | 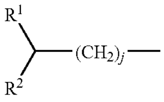 | k | m | n | chirality | $R^3$ | 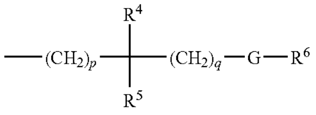 |
|---|---|---|---|---|---|---|---|
| 298 | 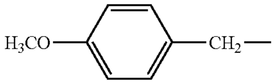 | 1 | 2 | 0 | R | H | 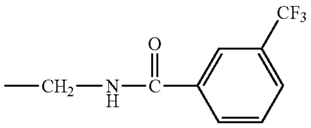 |
| 299 | 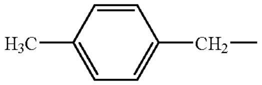 | 1 | 2 | 0 | R | H | 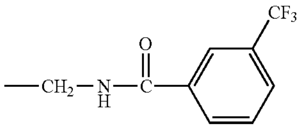 |
| 300 | 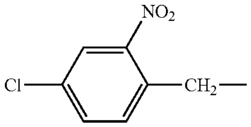 | 1 | 2 | 0 | R | H | 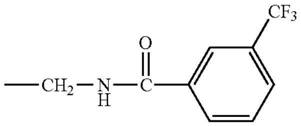 |
| 301 | 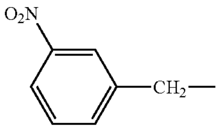 | 1 | 2 | 0 | R | H | 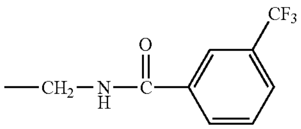 |
| 302 | 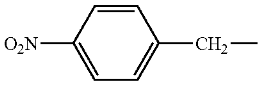 | 1 | 2 | 0 | R | H | 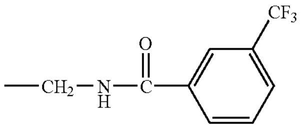 |
| 303 | 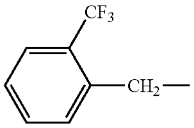 | 1 | 2 | 0 | R | H | 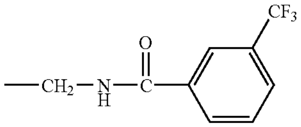 |
| 304 | 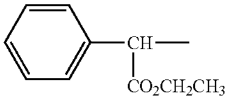 | 1 | 2 | 0 | R | H | 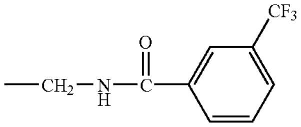 |
| 305 | 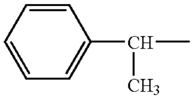 | 1 | 2 | 0 | R | H | 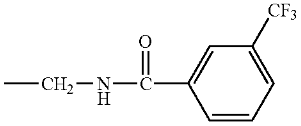 |
| 306 | 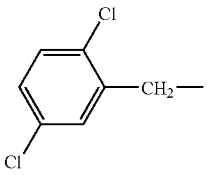 | 1 | 2 | 0 | R | H | 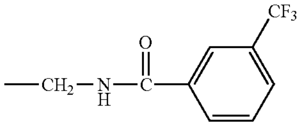 |
| 307 | 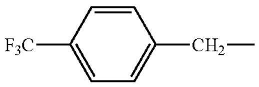 | 1 | 2 | 0 | R | H | 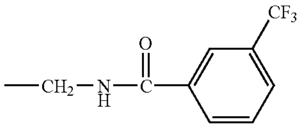 |

TABLE 1.28-continued
| Compd. No. | 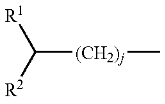 | k | m | n | chirality | $R^3$ | 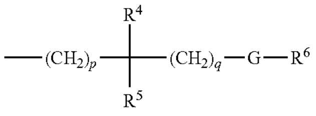 |
|---|---|---|---|---|---|---|---|
| 308 | 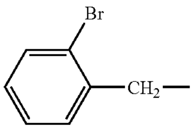 | 1 | 2 | 0 | R | H | 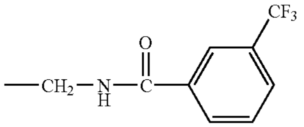 |
TABLE 1.29
| Compd. No. | 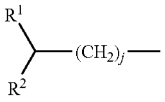 | k | m | n | chirality | $R^3$ | 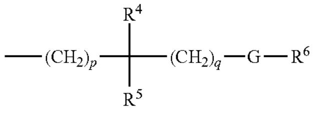 |
|---|---|---|---|---|---|---|---|
| 309 | 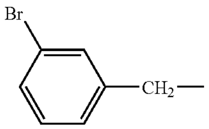 | 1 | 2 | 0 | R | H | 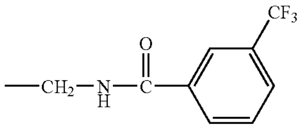 |
| 310 | 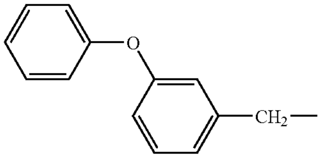 | 1 | 2 | 0 | R | H | 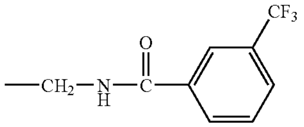 |
| 311 | 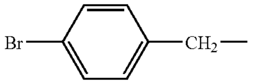 | 1 | 2 | 0 | R | H | 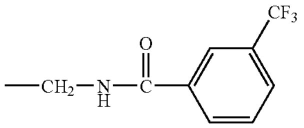 |
| 312 | 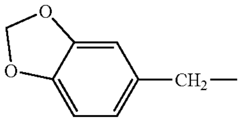 | 1 | 2 | 0 | R | H | 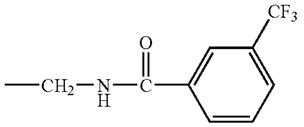 |
| 313 | 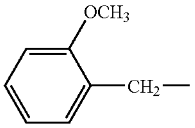 | 1 | 2 | 0 | R | H | 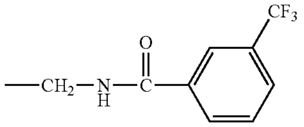 |
| 314 | 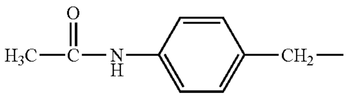 | 1 | 2 | 0 | R | H | 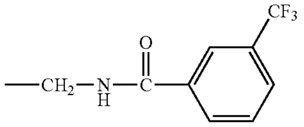 |
| 315 | 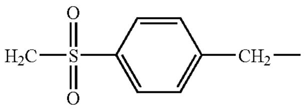 | 1 | 2 | 0 | R | H | 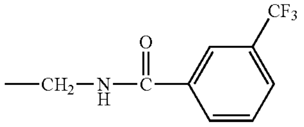 |

TABLE 1.29-continued
| Compd. No. | 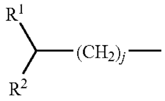 | k | m | n | chirality | $R^3$ | 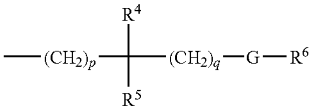 |
|---|---|---|---|---|---|---|---|
| 316 | 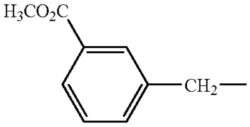 | 1 | 2 | 0 | R | H | 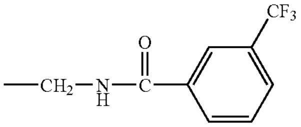 |
| 317 | 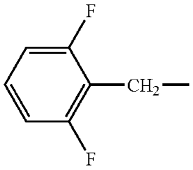 | 1 | 2 | 0 | R | H | 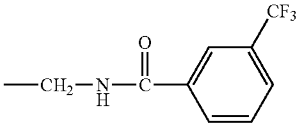 |
| 318 | 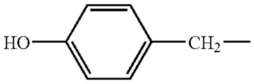 | 1 | 2 | 0 | R | H | 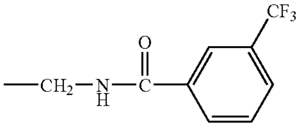 |
| 319 | 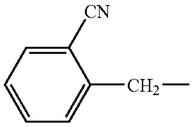 | 1 | 2 | 0 | R | H | 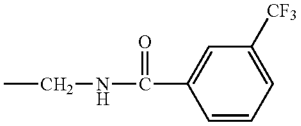 |
TABLE 1.30
| Compd. No. | 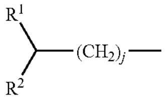 | k | m | n | chirality | $R^3$ | 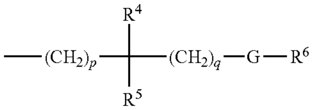 |
|---|---|---|---|---|---|---|---|
| 320 | 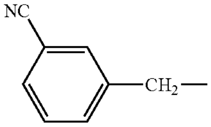 | 1 | 2 | 0 | R | H | 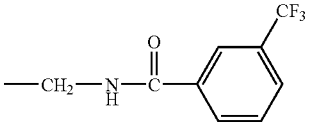 |
| 321 | 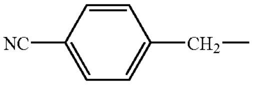 | 1 | 2 | 0 | R | H | 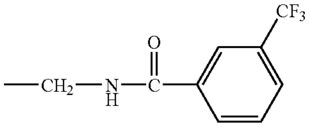 |
| 322 | 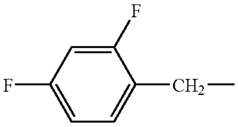 | 1 | 2 | 0 | R | H | 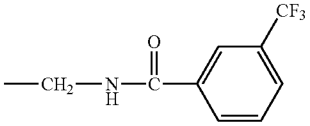 |
| 323 | 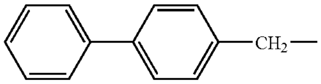 | 1 | 2 | 0 | R | H | 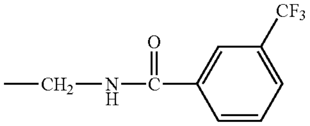 |

TABLE 1.30-continued
| Compd. No. | 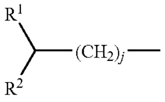 | k | m | n | chirality | $R^3$ | 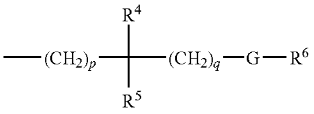 |
|---|---|---|---|---|---|---|---|
| 324 | 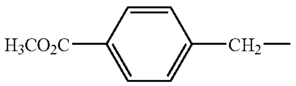 | 1 | 2 | 0 | R | H | 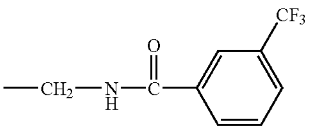 |
| 325 | 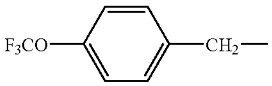 | 1 | 2 | 0 | R | H | 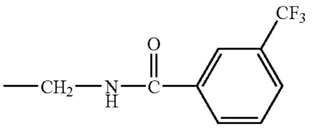 |
| 326 | 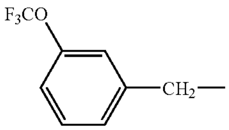 | 1 | 2 | 0 | R | H | 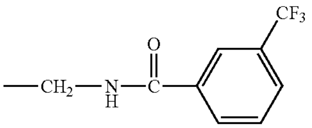 |
| 327 | 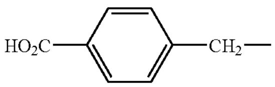 | 1 | 2 | 0 | R | H | 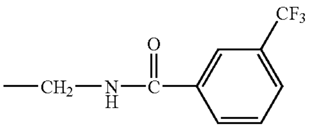 |
| 328 | 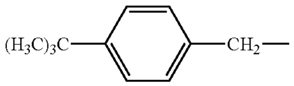 | 1 | 2 | 0 | R | H | 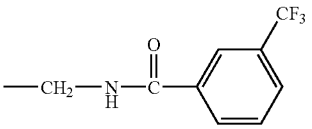 |
| 329 | 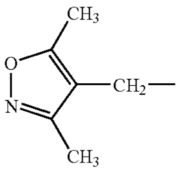 | 1 | 2 | 0 | R | H | 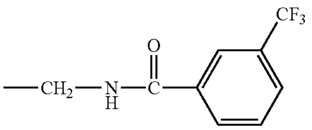 |
| 330 | 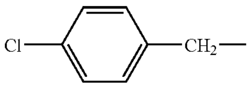 | 0 | 3 | 1 | — | H | 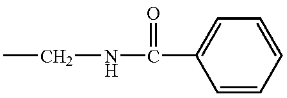 |
TABLE 1.31
| Compd. No. | 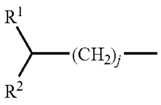 | k | m | n | chirality | $R^3$ | 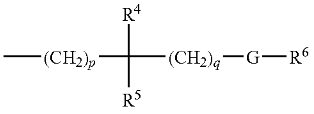 |
|---|---|---|---|---|---|---|---|
| 331 | 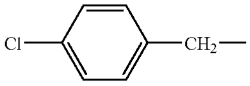 | 0 | 3 | 1 | — | H | 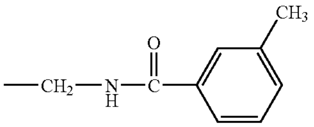 |

TABLE 1.31-continued
| Compd. No. | 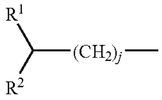 | k | m | n | chirality | $R^3$ | 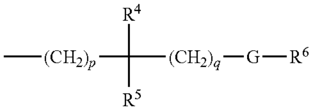 |
|---|---|---|---|---|---|---|---|
| 332 | 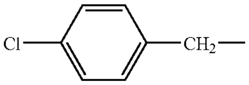 | 0 | 3 | 1 | — | H | 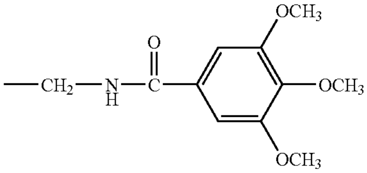 |
| 333 | 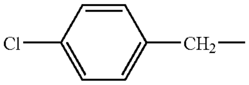 | 0 | 3 | 1 | — | H | 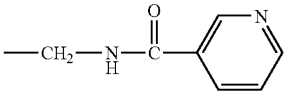 |
| 334 | 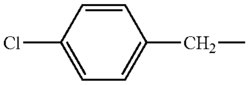 | 0 | 3 | 1 | — | H | 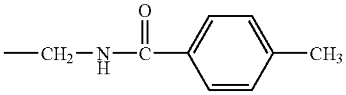 |
| 335 | 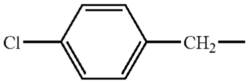 | 0 | 3 | 1 | — | H | 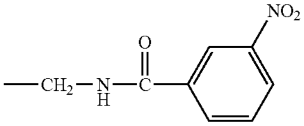 |
| 336 | 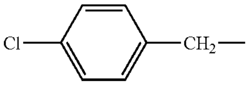 | 0 | 3 | 1 | — | H | 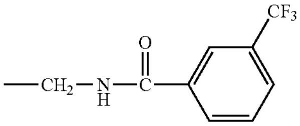 |
| 337 | 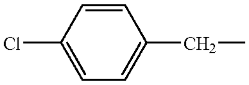 | 0 | 3 | 1 | — | H | 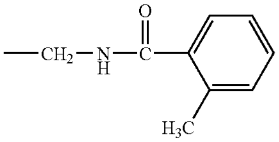 |
| 338 | 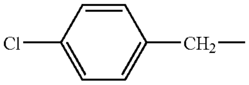 | 0 | 3 | 1 | — | H | 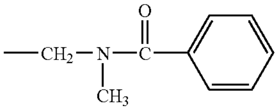 |
| 339 | 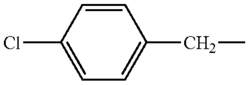 | 0 | 3 | 1 | R | H | 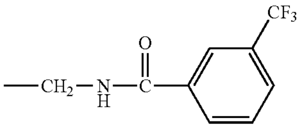 |
| 340 | 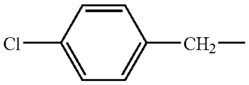 | 0 | 3 | 1 | S | H | 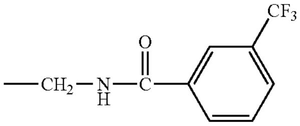 |
| 341 | 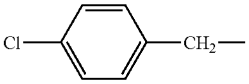 | 0 | 3 | 1 | — | H | 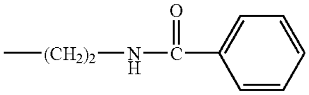 |

TABLE 1.32
| Compd. No. | 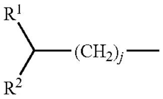 | k | m | n | chirality | $R^3$ | 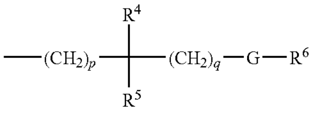 |
|---|---|---|---|---|---|---|---|
| 342 | 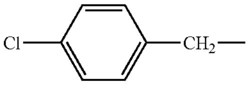 | 0 | 3 | 1 | — | H | 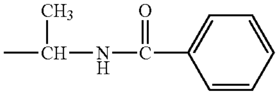 |
| 343 | 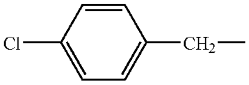 | 0 | 3 | 1 | — | H | 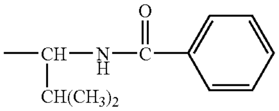 |
| 344 | 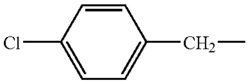 | 0 | 3 | 1 | — | H | 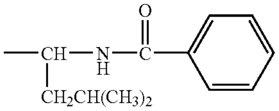 |
| 345 | 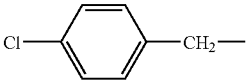 | 0 | 3 | 1 | — | H | 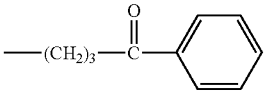 |
| 346 | 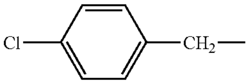 | 0 | 3 | 1 | — | H | 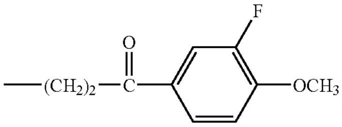 |
| 347 | 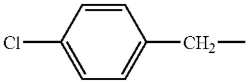 | 0 | 3 | 1 | — | H | 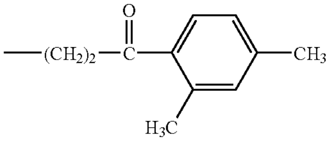 |
| 348 | 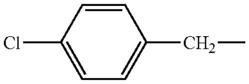 | 0 | 3 | 1 | — | H | 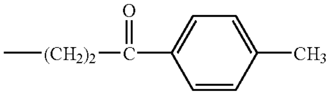 |
| 349 | 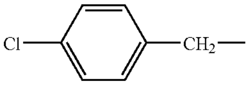 | 0 | 3 | 1 | — | H | 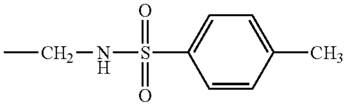 |
| 350 | 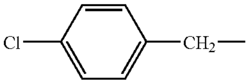 | 0 | 3 | 1 | — | H | 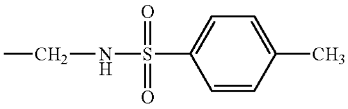 |
| 351 | 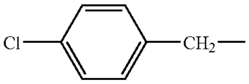 | 0 | 3 | 1 | — | H | 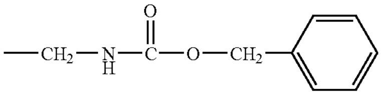 |
| 352 | 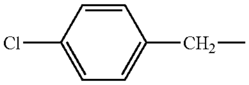 | 0 | 3 | 1 | — | H | 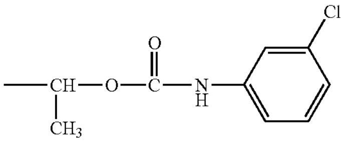 |

TABLE 1.33
| Compd. No. | 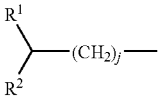 | k | m | n | chirality | $R^3$ | 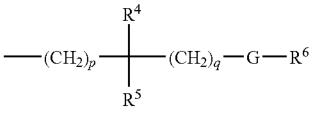 |
|---|---|---|---|---|---|---|---|
| 353 | 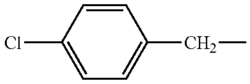 | 1 | 2 | 1 | — | H | 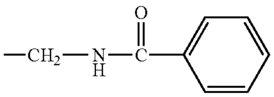 |
| 354 | 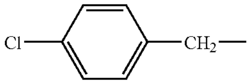 | 1 | 3 | 0 | — | H | 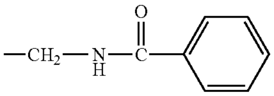 |
| 355 | 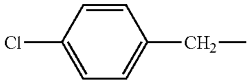 | 1 | 3 | 0 | — | H | 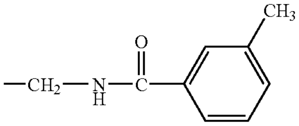 |
| 356 | 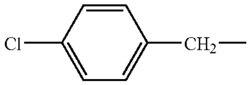 | 1 | 3 | 0 | — | H | 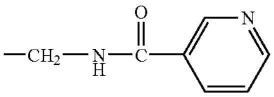 |
| 357 | 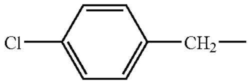 | 1 | 3 | 0 | — | H | 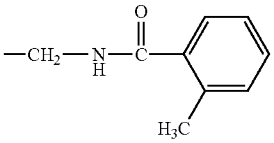 |
| 358 | 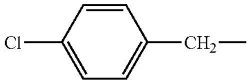 | 1 | 3 | 0 | — | H | 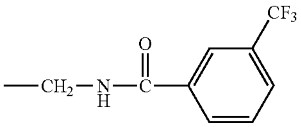 |
| 359 | 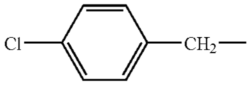 | 1 | 3 | 0 | — | H | 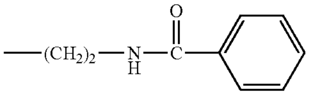 |
| 360 | 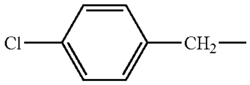 | 1 | 3 | 0 | — | H | 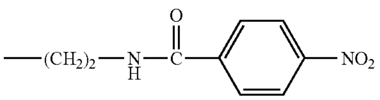 |
| 361 | 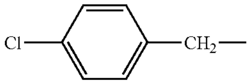 | 1 | 3 | 0 | — | H | 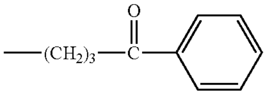 |
| 362 | 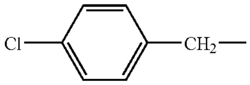 | 1 | 3 | 0 | — | H | 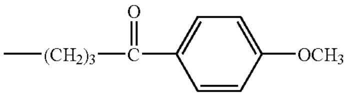 |
| 363 | 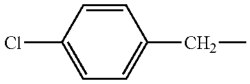 | 1 | 3 | 0 | — | H | 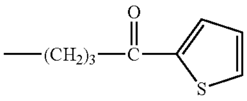 |

TABLE 1.34
| Compd. No. | 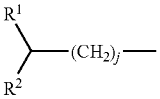 | k | m | n | chirality | $R^3$ | 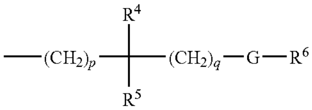 |
|---|---|---|---|---|---|---|---|
| 364 | 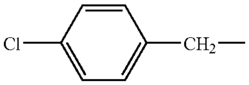 | 1 | 3 | 0 | — | H | 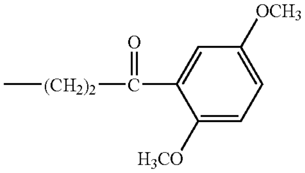 |
| 365 | 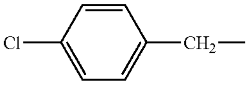 | 1 | 3 | 0 | — | H | 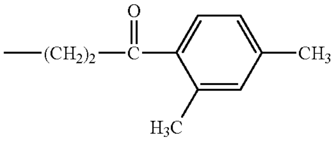 |
| 366 | 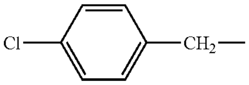 | 1 | 3 | 0 | — | H | 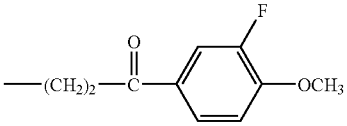 |
| 367 | 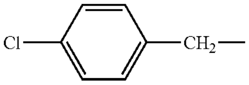 | 1 | 3 | 0 | — | H | 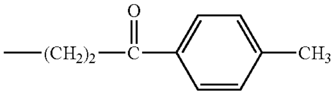 |
| 368 | 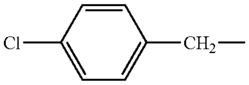 | 1 | 3 | 0 | — | H | 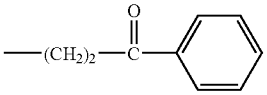 |
| 369 | 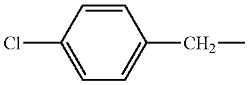 | 1 | 3 | 0 | — | H | 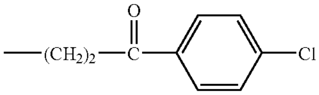 |
| 370 | 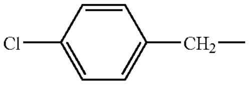 | 1 | 3 | 0 | — | H | 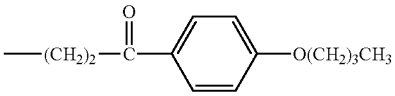 |
| 371 | 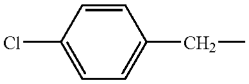 | 1 | 3 | 0 | — | H | 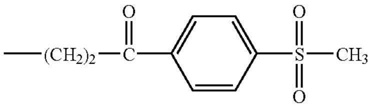 |
| 372 | 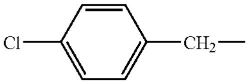 | 1 | 3 | 0 | — | H | 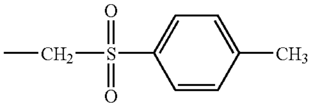 |
| 373 | 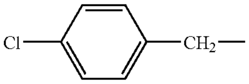 | 1 | 3 | 0 | — | H | 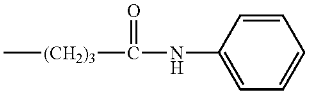 |
| 374 | 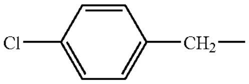 | 1 | 3 | 0 | — | H | 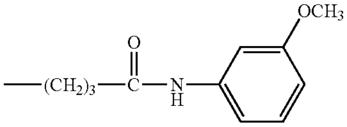 |

TABLE 1.35
| Compd. No. | 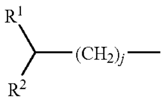 | k | m | n | chirality | $R^3$ | 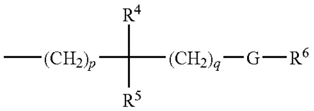 |
|---|---|---|---|---|---|---|---|
| 375 | 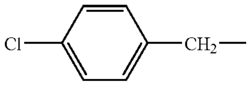 | 1 | 3 | 0 | — | H | 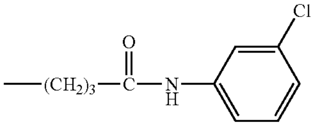 |
| 376 | 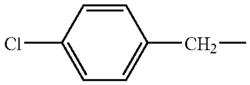 | 1 | 3 | 0 | — | H | 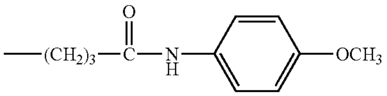 |
| 377 | 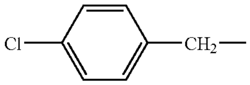 | 1 | 3 | 0 | — | H | 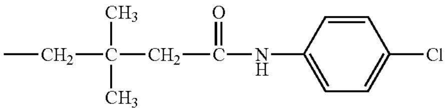 |
| 378 | 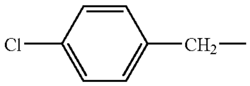 | 1 | 3 | 0 | — | H | 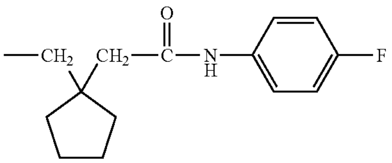 |
| 379 | 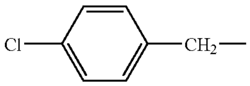 | 1 | 3 | 0 | — | H | 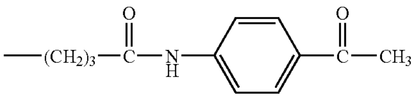 |
| 380 | 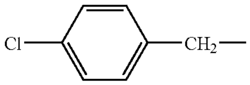 | 1 | 3 | 0 | — | H | 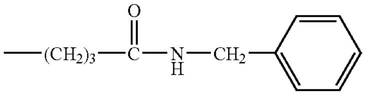 |
| 381 | 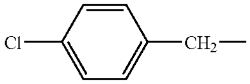 | 1 | 3 | 0 | — | H | 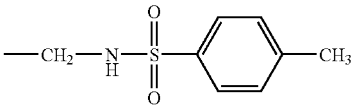 |
| 382 | 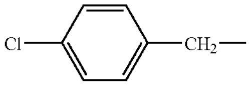 | 1 | 3 | 0 | — | H | 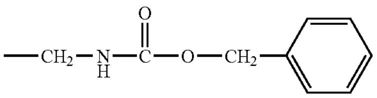 |
| 383 | 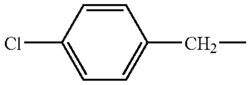 | 1 | 3 | 0 | — | H | 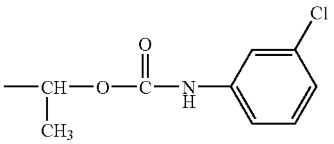 |
| 384 | 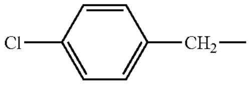 | 2 | 2 | 0 | — | H | 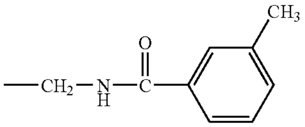 |
| 385 | 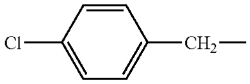 | 2 | 2 | 0 | — | H | 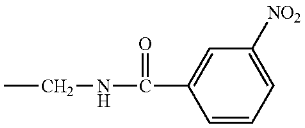 |

TABLE 1.36
| Compd. No. | 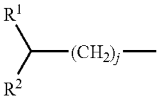 | k | m | n | chirality | $R^3$ | 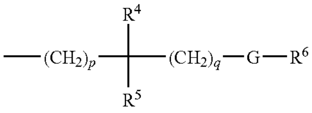 |
|---|---|---|---|---|---|---|---|
| 386 | 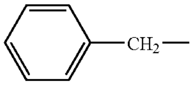 | 2 | 2 | 0 | — | H | 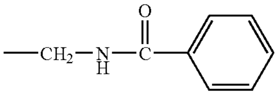 |
| 387 | 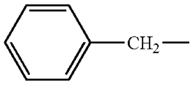 | 2 | 2 | 0 | — | H | 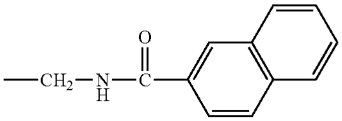 |
| 388 | 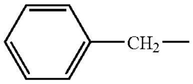 | 2 | 2 | 0 | — | H | 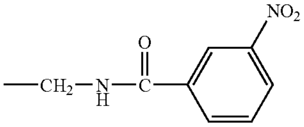 |
| 389 | 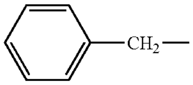 | 2 | 2 | 0 | — | H | 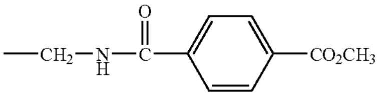 |
| 390 | 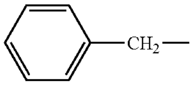 | 2 | 2 | 0 | — | H | 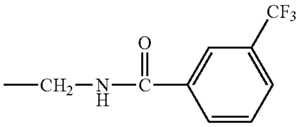 |
| 391 | 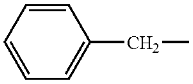 | 2 | 2 | 0 | — | H | 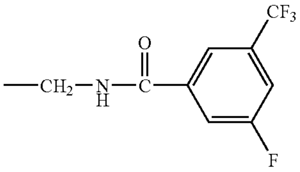 |
| 392 | 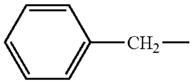 | 2 | 2 | 0 | — | H | 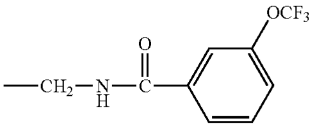 |
| 393 | 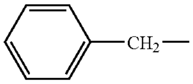 | 2 | 2 | 0 | — | H | 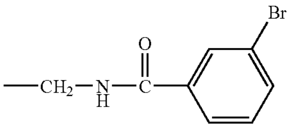 |
| 394 | 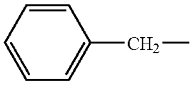 | 2 | 2 | 0 | — | H | 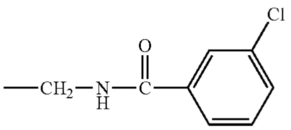 |
| 395 | 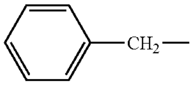 | 2 | 2 | 0 | — | H | 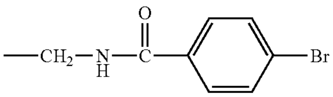 |
| 396 | 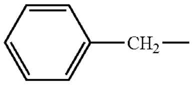 | 2 | 2 | 0 | — | H | 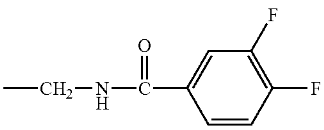 |

TABLE 1.37
| Compd. No. | 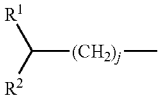 | k | m | n | chirality | $R^3$ | 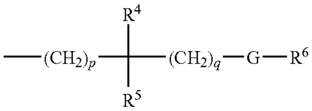 |
|---|---|---|---|---|---|---|---|
| 397 | 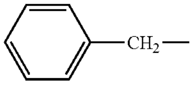 | 2 | 2 | 0 | — | H | 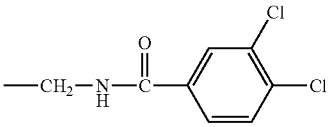 |
| 398 | 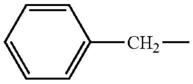 | 2 | 2 | 0 | — | H | 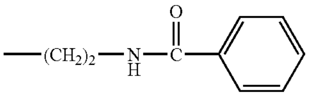 |
| 399 | 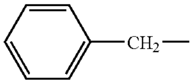 | 2 | 2 | 0 | — | H | 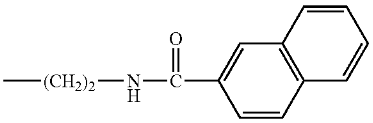 |
| 400 | 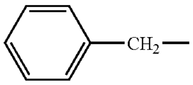 | 2 | 2 | 0 | — | H | 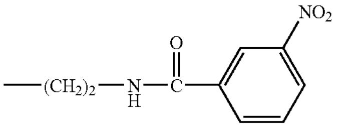 |
| 401 | 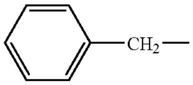 | 2 | 2 | 0 | — | H | 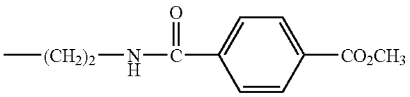 |
| 402 | 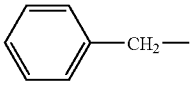 | 2 | 2 | 0 | — | H | 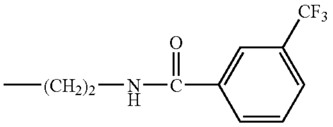 |
| 403 | 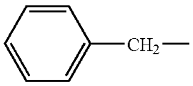 | 2 | 2 | 0 | — | H | 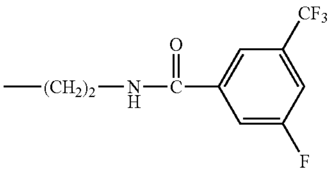 |
| 404 | 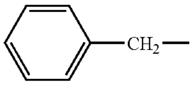 | 2 | 2 | 0 | — | H | 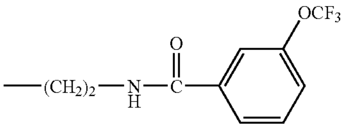 |
| 405 | 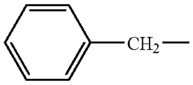 | 2 | 2 | 0 | — | H | 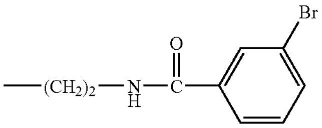 |

TABLE 1.37-continued
| Compd. No. | 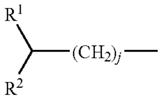 | k | m | n | chirality | $R^3$ | 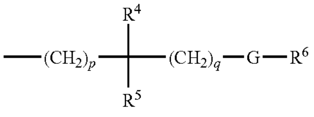 |
|---|---|---|---|---|---|---|---|
| 406 | 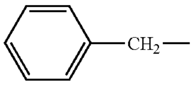 | 2 | 2 | 0 | — | H | 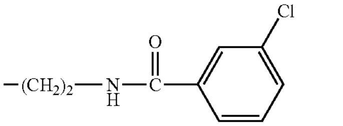 |
| 407 | 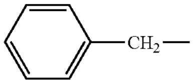 | 2 | 2 | 0 | — | H | 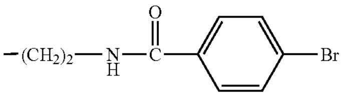 |
TABLE 1.38
| Compd. No. | 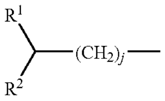 | k | m | n | chirality | $R^3$ | 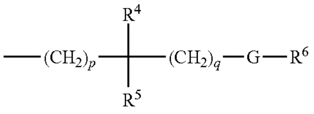 |
|---|---|---|---|---|---|---|---|
| 408 | 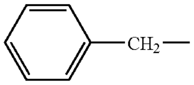 | 2 | 2 | 0 | — | H | 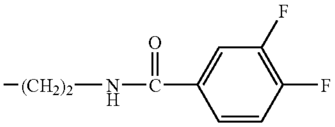 |
| 409 | 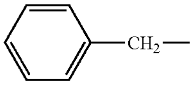 | 2 | 2 | 0 | — | H | 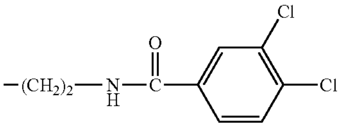 |
| 410 | 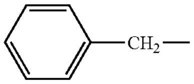 | 2 | 2 | 0 | — | H | 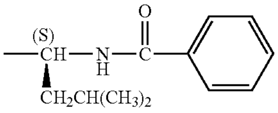 |
| 411 | 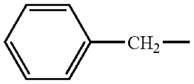 | 2 | 2 | 0 | — | H | 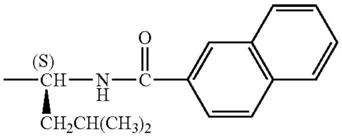 |
| 412 | 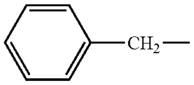 | 2 | 2 | 0 | — | H | 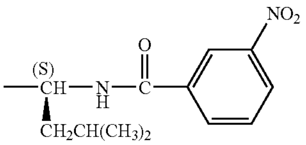 |
| 413 | 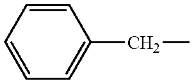 | 2 | 2 | 0 | — | H | 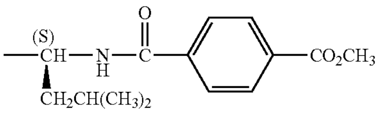 |
| 414 | 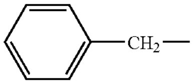 | 2 | 2 | 0 | — | H | 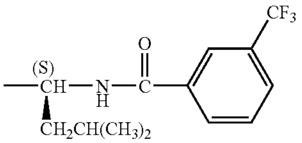 |

TABLE 1.38-continued
| Compd. No. | 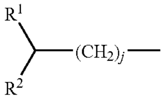 | k | m | n | chirality | $R^3$ | 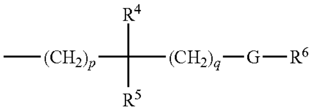 |
|---|---|---|---|---|---|---|---|
| 415 | 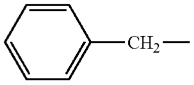 | 2 | 2 | 0 | — | H | 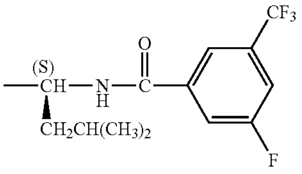 |
| 416 | 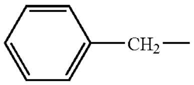 | 2 | 2 | 0 | — | H | 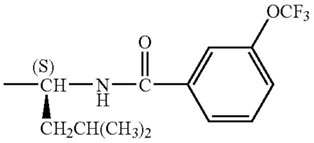 |
| 417 | 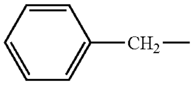 | 2 | 2 | 0 | — | H | 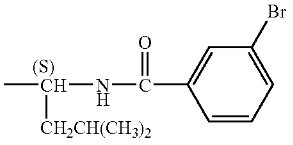 |
| 418 | 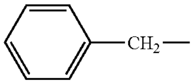 | 2 | 2 | 0 | — | H | 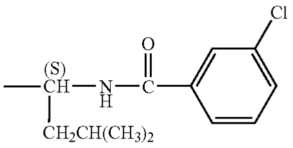 |
TABLE 1.39
| Compd. No. | 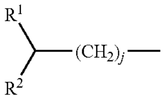 | k | m | n | chirality | $R^3$ | 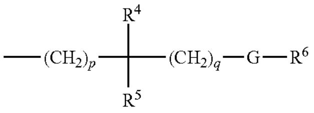 |
|---|---|---|---|---|---|---|---|
| 419 | 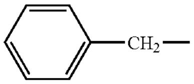 | 2 | 2 | 0 | — | H | 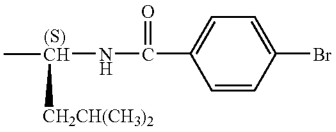 |
| 420 | 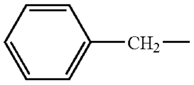 | 2 | 2 | 0 | — | H | 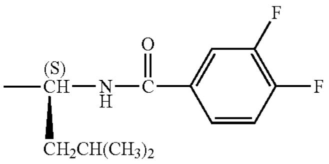 |
| 421 | 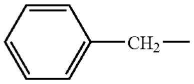 | 2 | 2 | 0 | — | H | 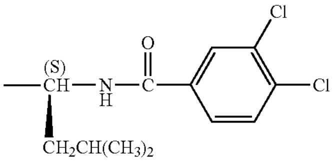 |

TABLE 1.39-continued
| Compd. No. | 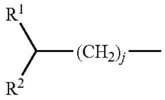 | k | m | n | chirality | $R^3$ | 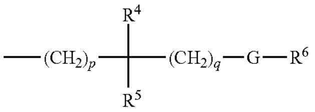 |
|---|---|---|---|---|---|---|---|
| 422 | 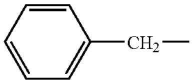 | 2 | 2 | 0 | — | H | 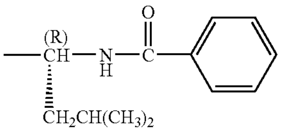 |
| 423 | 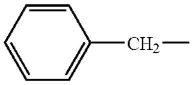 | 2 | 2 | 0 | — | H | 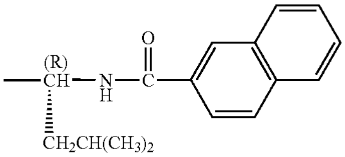 |
| 424 | 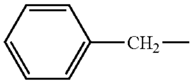 | 2 | 2 | 0 | — | H | 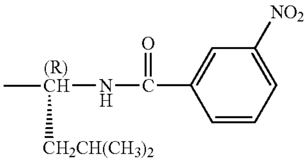 |
| 425 | 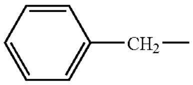 | 2 | 2 | 0 | — | H | 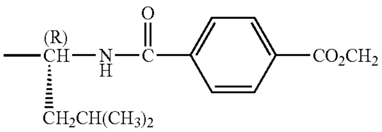 |
| 426 | 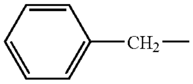 | 2 | 2 | 0 | — | H | 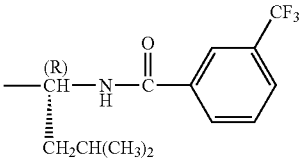 |
| 427 | 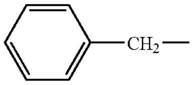 | 2 | 2 | 0 | — | H | 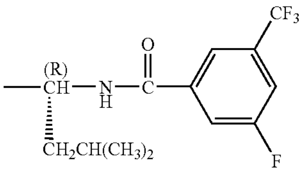 |
| 428 | 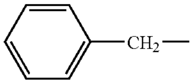 | 2 | 2 | 0 | — | H | 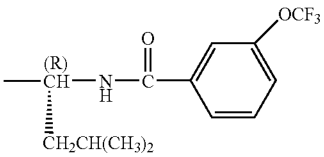 |
| 429 | 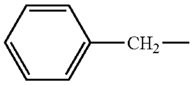 | 2 | 2 | 0 | — | H | 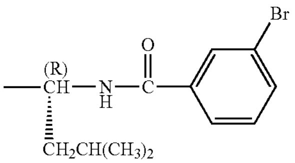 |

TABLE 1.40
| Compd. No. | 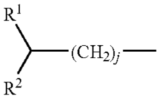 | k | m | n | chirality | $R^3$ | 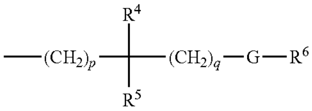 |
|---|---|---|---|---|---|---|---|
| 430 | 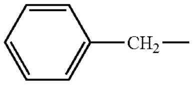 | 2 | 2 | 0 | — | H | 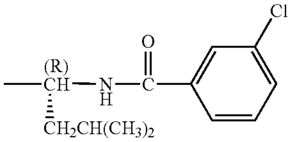 |
| 431 | 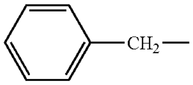 | 2 | 2 | 0 | — | H | 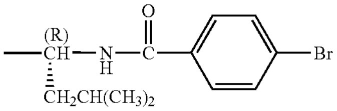 |
| 432 | 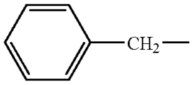 | 2 | 2 | 0 | — | H | 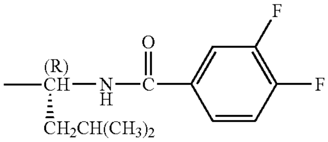 |
| 433 | 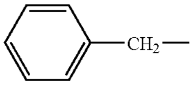 | 2 | 2 | 0 | — | H | 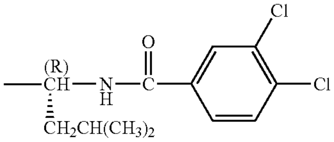 |
| 434 | 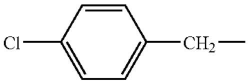 | 1 | 3 | 1 | — | H | 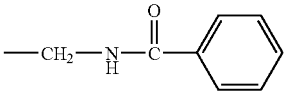 |
| 435 | 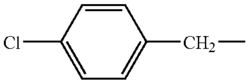 | 1 | 3 | 1 | — | H | 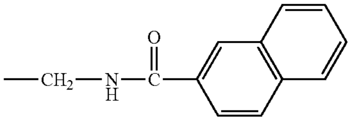 |
| 436 | 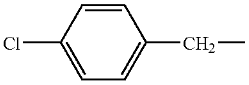 | 1 | 3 | 1 | — | H | 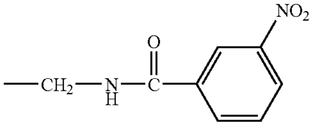 |
| 437 | 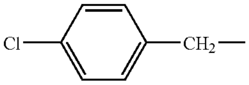 | 1 | 3 | 1 | — | H | 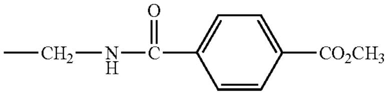 |
| 438 | 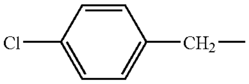 | 1 | 3 | 1 | — | H | 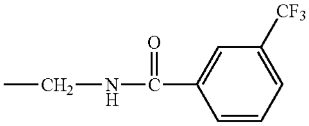 |
| 439 | 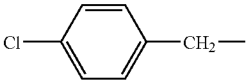 | 1 | 3 | 1 | — | H | 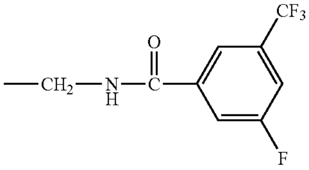 |

TABLE 1.40-continued
| Compd. No. | 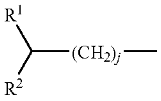 | k | m | n | chirality | $R^3$ | 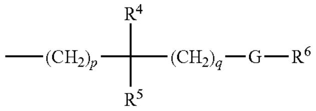 |
|---|---|---|---|---|---|---|---|
| 440 | 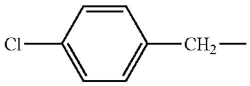 | 1 | 3 | 1 | — | H | 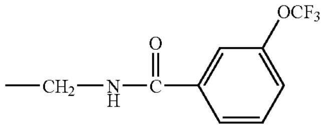 |
TABLE 1.41
| Compd. No. | 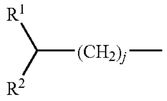 | k | m | n | chirality | $R^3$ | 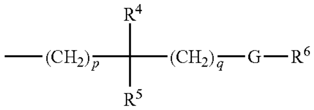 |
|---|---|---|---|---|---|---|---|
| 441 | 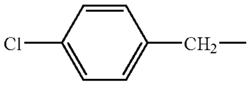 | 1 | 3 | 1 | — | H | 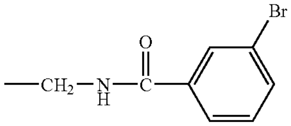 |
| 442 | 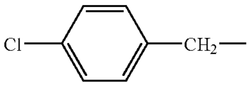 | 1 | 3 | 1 | — | H | 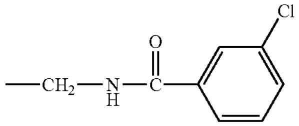 |
| 443 | 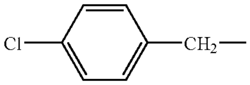 | 1 | 3 | 1 | — | H | 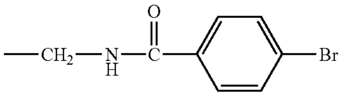 |
| 444 | 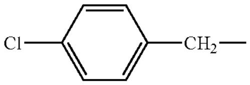 | 1 | 3 | 1 | — | H | 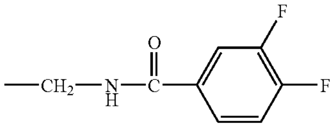 |
| 445 | 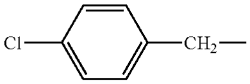 | 1 | 3 | 1 | — | H | 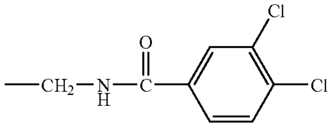 |
| 446 | 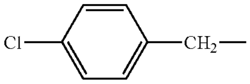 | 1 | 3 | 1 | — | H | 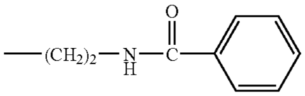 |
| 447 | 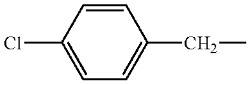 | 1 | 3 | 1 | — | H | 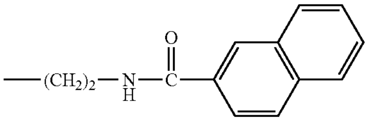 |
| 448 | 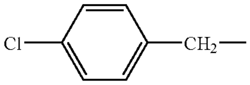 | 1 | 3 | 1 | — | H | 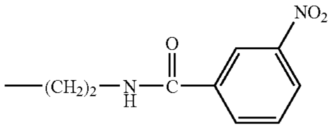 |

TABLE 1.41-continued
| Compd. No. | 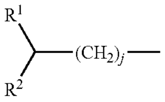 | k | m | n | chirality | $R^3$ | 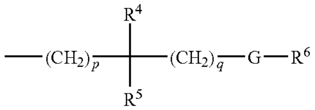 |
|---|---|---|---|---|---|---|---|
| 449 | 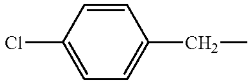 | 1 | 3 | 1 | — | H | 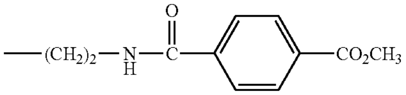 |
| 450 | 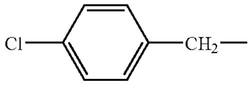 | 1 | 3 | 1 | — | H | 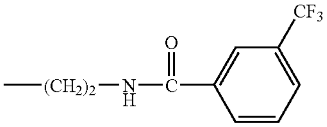 |
| 451 | 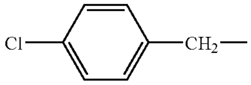 | 1 | 3 | 1 | — | H | 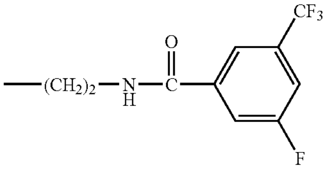 |
TABLE 1.42
| Compd. No. | 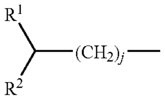 | k | m | n | chirality | $R^3$ | 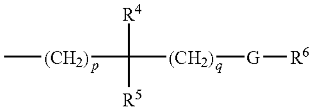 |
|---|---|---|---|---|---|---|---|
| 452 | 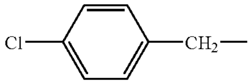 | 1 | 3 | 1 | — | H | 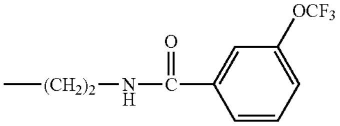 |
| 453 | 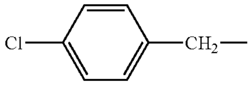 | 1 | 3 | 1 | — | H | 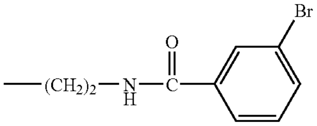 |
| 454 | 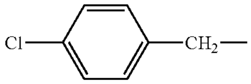 | 1 | 3 | 1 | — | H | 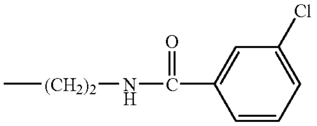 |
| 455 | 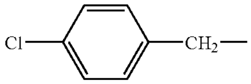 | 1 | 3 | 1 | — | H | 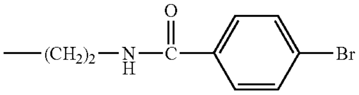 |
| 456 | 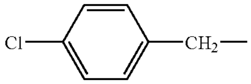 | 1 | 3 | 1 | — | H | 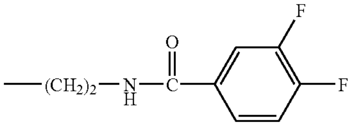 |
| 457 | 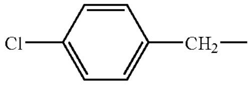 | 1 | 3 | 1 | — | H | 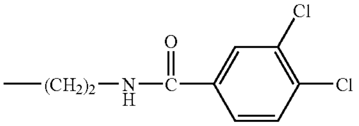 |

TABLE 1.42-continued
| Compd. No. | 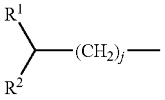 | k | m | n | chirality | $R^3$ | 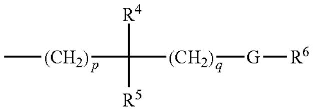 |
|---|---|---|---|---|---|---|---|
| 458 | 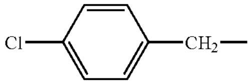 | 2 | 2 | 1 | — | H | 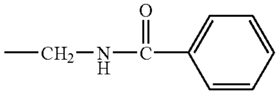 |
| 459 | 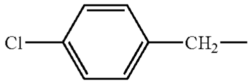 | 2 | 2 | 1 | — | H | 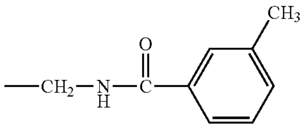 |
| 460 | 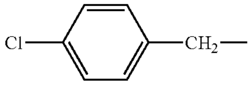 | 2 | 2 | 1 | — | H | 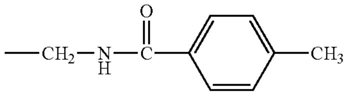 |
| 461 | 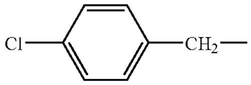 | 2 | 2 | 1 | — | H | 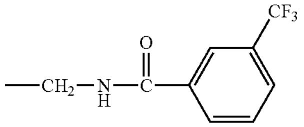 |
| 462 | 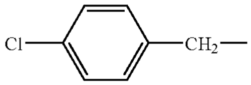 | 2 | 2 | 1 | — | H | 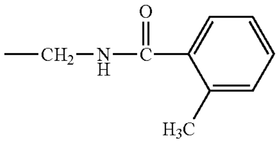 |
TABLE 1.43
| Compd. No. | 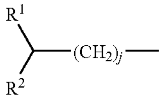 | k | m | n | chirality | $R^3$ | 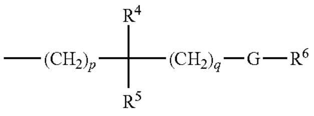 |
|---|---|---|---|---|---|---|---|
| 463 | 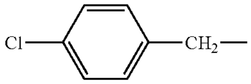 | 2 | 2 | 1 | — | H | 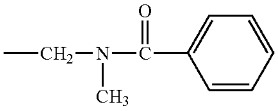 |
| 464 | 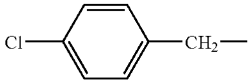 | 2 | 2 | 1 | — | H | 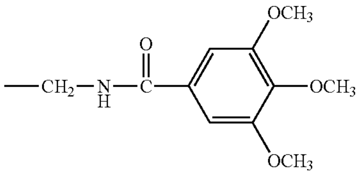 |
| 465 | 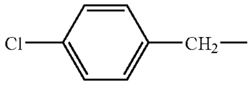 | 2 | 2 | 1 | — | H | 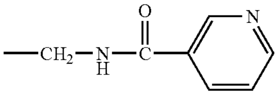 |
| 466 | 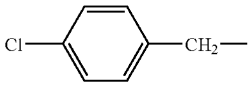 | 2 | 2 | 1 | — | H | 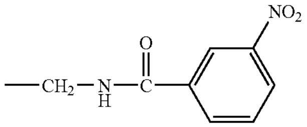 |

TABLE 1.43-continued
| Compd. No. | 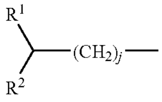 | k | m | n | chirality | $R^3$ | 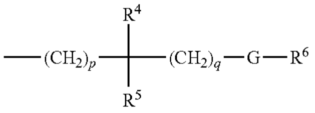 |
|---|---|---|---|---|---|---|---|
| 467 | 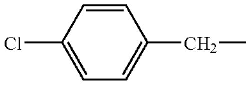 | 2 | 2 | 1 | — | H | 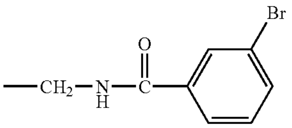 |
| 468 | 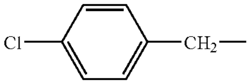 | 2 | 2 | 1 | — | H | 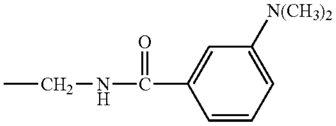 |
| 469 | 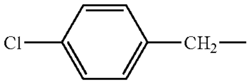 | 2 | 2 | 1 | — | H | 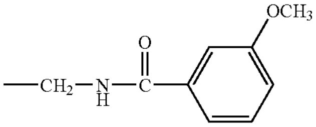 |
| 470 | 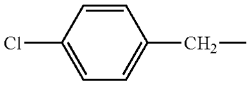 | 2 | 2 | 1 | — | H | 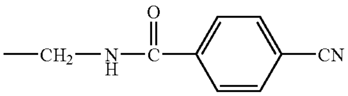 |
| 471 | 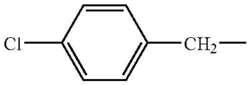 | 2 | 2 | 1 | — | H | 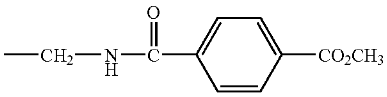 |
| 472 | 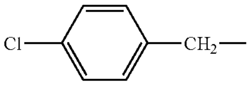 | 2 | 2 | 1 | — | H | 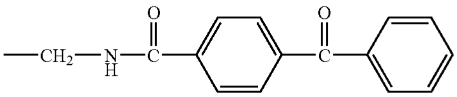 |
| 473 | 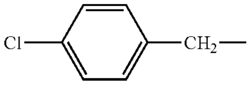 | 2 | 2 | 1 | — | H | 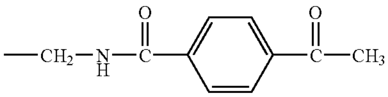 |
TABLE 1.44
| Compd. No. | 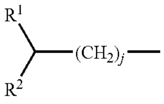 | k | m | n | chirality | $R^3$ | 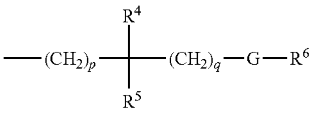 |
|---|---|---|---|---|---|---|---|
| 474 | 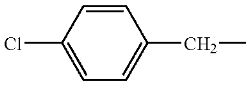 | 2 | 2 | 1 | — | H | 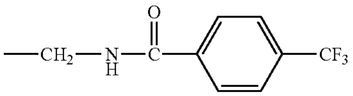 |
| 475 | 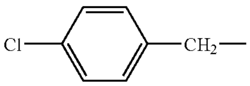 | 2 | 2 | 1 | — | H | 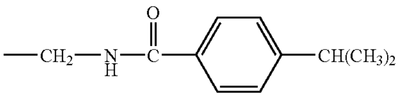 |
| 476 | 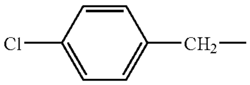 | 2 | 2 | 1 | — | H | 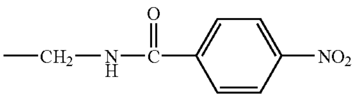 |

TABLE 1.44-continued
| Compd. No. | 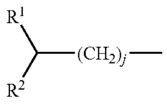 | k | m | n | chirality | $R^3$ | 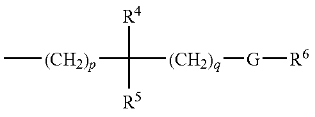 |
|---|---|---|---|---|---|---|---|
| 477 | 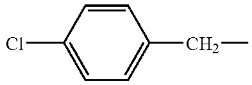 | 2 | 2 | 1 | — | H | 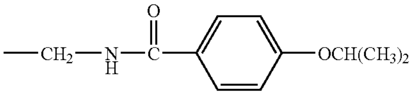 |
| 478 | 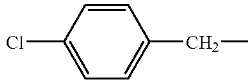 | 2 | 2 | 1 | — | H | 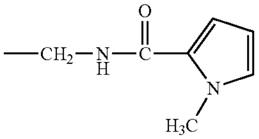 |
| 479 | 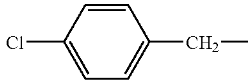 | 2 | 2 | 1 | — | H | 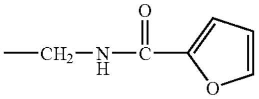 |
| 480 | 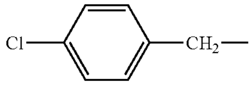 | 2 | 2 | 1 | — | H | 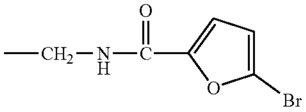 |
| 481 | 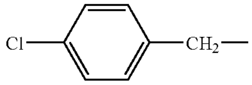 | 2 | 2 | 1 | — | H | 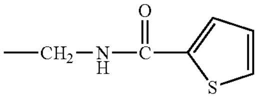 |
| 482 | 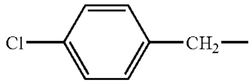 | 2 | 2 | 1 | — | H | 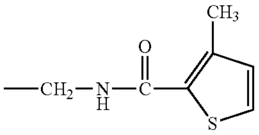 |
| 483 | 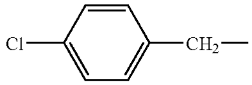 | 2 | 2 | 1 | — | H | 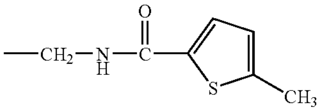 |
| 484 | 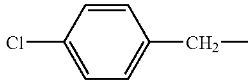 | 2 | 2 | 1 | — | H | 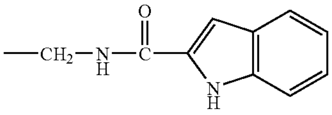 |
TABLE 1.45
| Compd. No. | 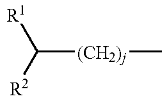 | k | m | n | chirality | $R^3$ | 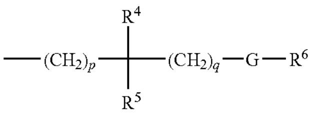 |
|---|---|---|---|---|---|---|---|
| 485 | 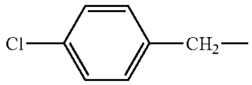 | 2 | 2 | 1 | — | H | 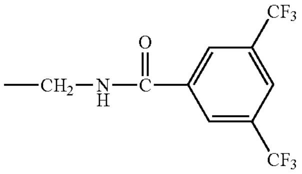 |

TABLE 1.45-continued
| Compd. No. | 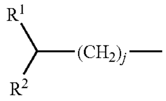 | k | m | n | chirality | $R^3$ | 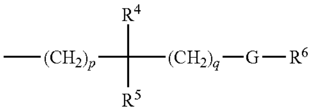 |
|---|---|---|---|---|---|---|---|
| 486 | 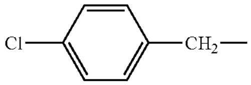 | 2 | 2 | 1 | — | H | 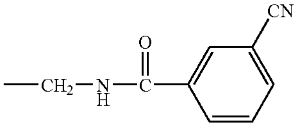 |
| 487 | 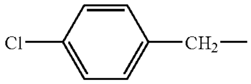 | 2 | 2 | 1 | — | H | 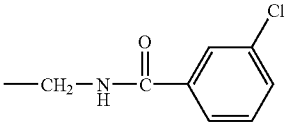 |
| 488 | 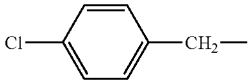 | 2 | 2 | 1 | — | H | 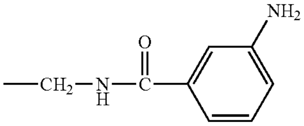 |
| 489 | 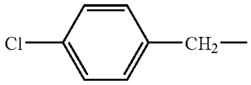 | 2 | 2 | 1 | — | H | 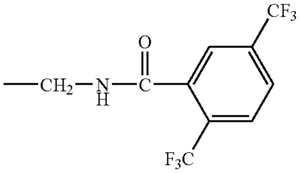 |
| 490 | 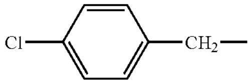 | 2 | 2 | 1 | — | H | 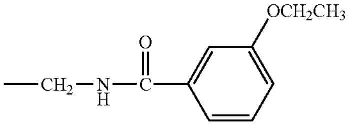 |
| 491 | 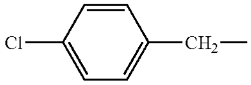 | 2 | 2 | 1 | — | H | 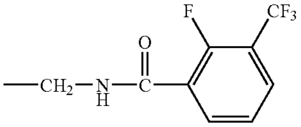 |
| 492 | 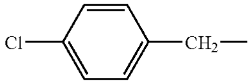 | 2 | 2 | 1 | — | H | 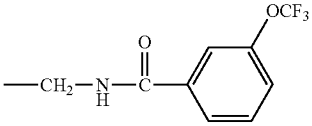 |
| 493 | 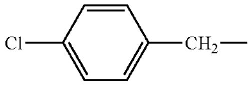 | 2 | 2 | 1 | — | H | 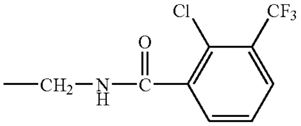 |
| 494 | 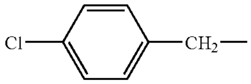 | 2 | 2 | 1 | — | H | 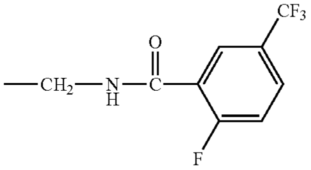 |

TABLE 1.45-continued
| Compd. No. | 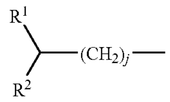 | k | m | n | chirality | $R^3$ | 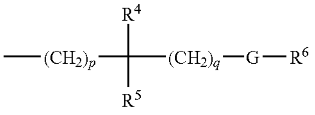 |
|---|---|---|---|---|---|---|---|
| 495 | 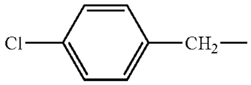 | 2 | 2 | 1 | — | H | 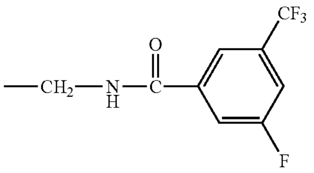 |
TABLE 1.46
| Compd. No. | 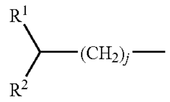 | k | m | n | chirality | $R^3$ | 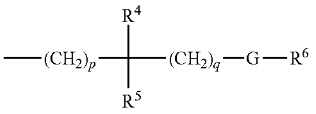 |
|---|---|---|---|---|---|---|---|
| 496 | 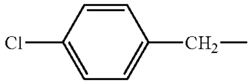 | 2 | 2 | 1 | — | H | 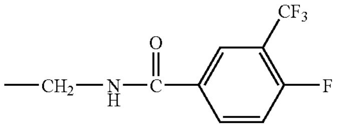 |
| 497 | 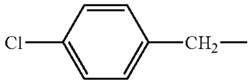 | 2 | 2 | 1 | — | H | 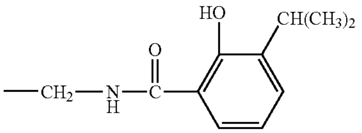 |
| 498 | 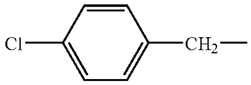 | 2 | 2 | 1 | — | H | 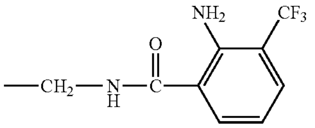 |
| 499 | 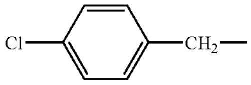 | 2 | 2 | 1 | — | H | 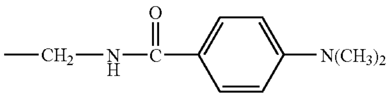 |
| 500 | 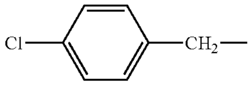 | 2 | 2 | 1 | — | H | 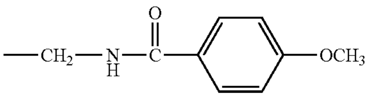 |
| 501 | 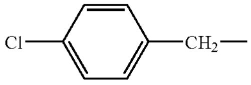 | 2 | 2 | 1 | — | H | 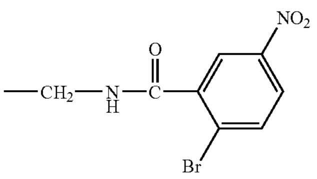 |
| 502 | 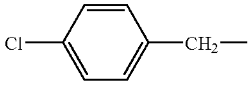 | 2 | 2 | 1 | — | H | 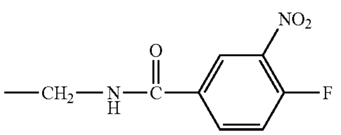 |

TABLE 1.46-continued
| Compd. No. | 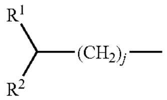 | k | m | n | chirality | $R^3$ | 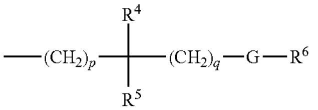 |
|---|---|---|---|---|---|---|---|
| 503 | 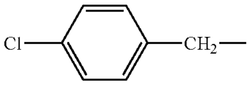 | 2 | 2 | 1 | — | H | 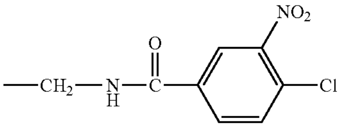 |
| 504 | 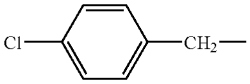 | 2 | 2 | 1 | — | H | 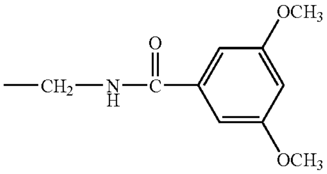 |
| 505 | 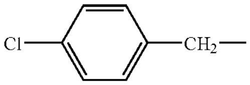 | 2 | 2 | 1 | — | H | 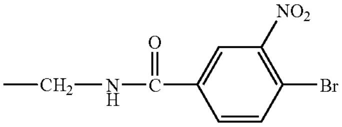 |
| 506 | 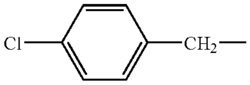 | 2 | 2 | 1 | — | H | 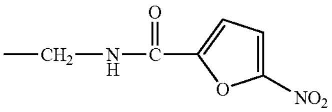 |
TABLE 1.47
| Compd. No. | 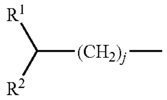 | k | m | n | chirality | $R^3$ | 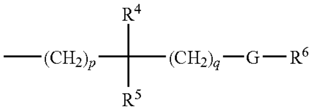 |
|---|---|---|---|---|---|---|---|
| 507 | 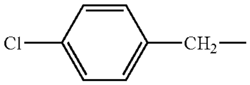 | 2 | 2 | 1 | — | H | 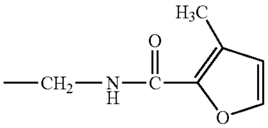 |
| 508 | 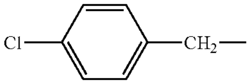 | 2 | 2 | 1 | — | H | 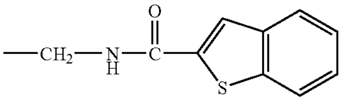 |
| 509 | 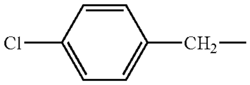 | 2 | 2 | 1 | — | H | 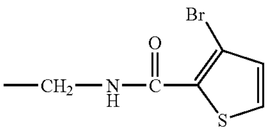 |
| 510 | 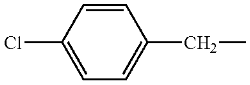 | 2 | 2 | 1 | — | H | 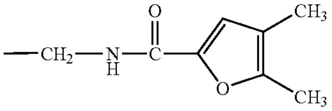 |
| 511 | 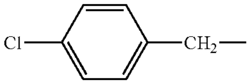 | 2 | 2 | 1 | — | H | 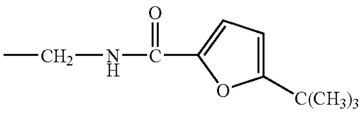 |

TABLE 1.47-continued
| Compd. No. | 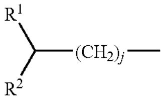 | k | m | n | chirality | $R^3$ | 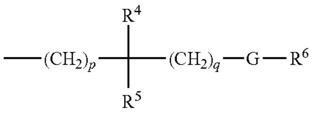 |
|---|---|---|---|---|---|---|---|
| 512 | 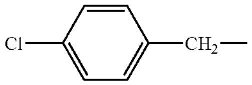 | 2 | 2 | 1 | — | H | 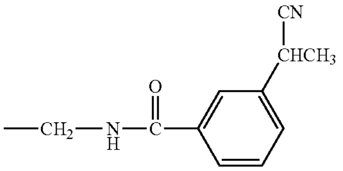 |
| 513 | 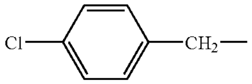 | 2 | 2 | 1 | — | H | 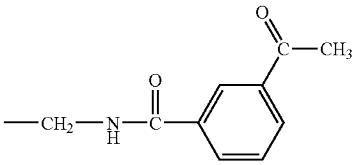 |
| 514 | 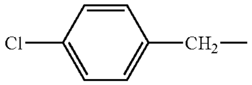 | 2 | 2 | 1 | — | H | 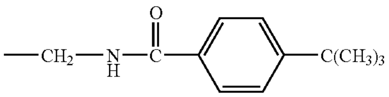 |
| 515 | 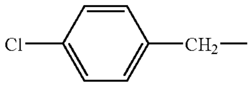 | 2 | 2 | 1 | — | H | 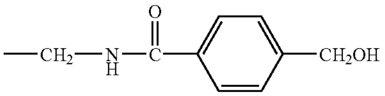 |
| 516 | 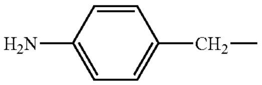 | 2 | 2 | 1 | — | H | 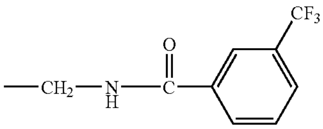 |
| 517 | 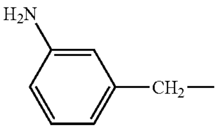 | 2 | 2 | 1 | — | H | 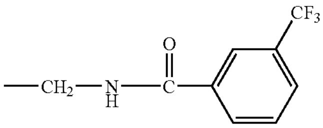 |
TABLE 1.48
| Compd. No. | 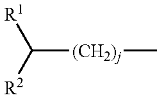 | k | m | n | chirality |
|---|---|---|---|---|---|
| 518 | 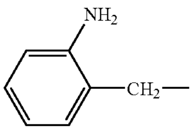 | 2 | 2 | 1 | — |
| 519 | 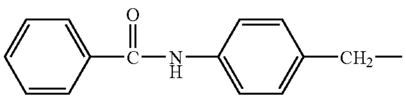 | 2 | 2 | 1 | — |
| 520 | 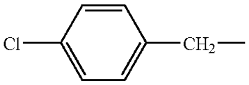 | 2 | 2 | 1 | — |

TABLE 1.48-continued
| | | | | | |
|---|---|---|---|---|---|
| 521 | 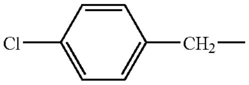 | 2 | 2 | 1 | — |
| 522 | 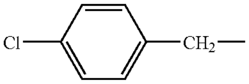 | 2 | 2 | 1 | — |
| 523 | 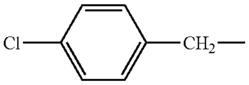 | 2 | 2 | 1 | — |
| 524 | 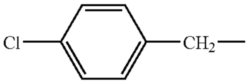 | 2 | 2 | 1 | — |
| 525 | 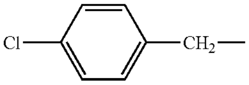 | 2 | 2 | 1 | — |
| 526 | 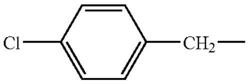 | 2 | 2 | 1 | — |
| 527 | 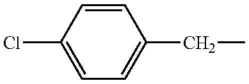 | 2 | 2 | 1 | — |
| 528 | 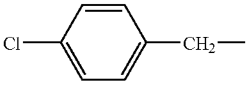 | 2 | 2 | 1 | — |
| Compd. No. | $R^3$ | 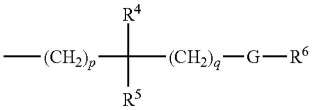 |
|---|---|---|
| 518 | H | 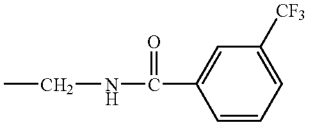 |
| 519 | H | 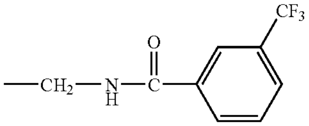 |
| 520 | $-CH_3$ | 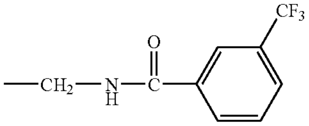 |
| 521 | 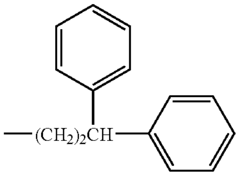 | 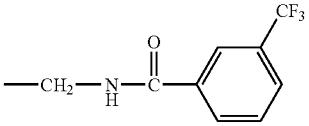 |

TABLE 1.48-continued
| | | |
|---|---|---|
| 522 | 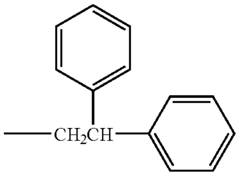 | 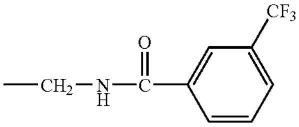 |
| 523 | 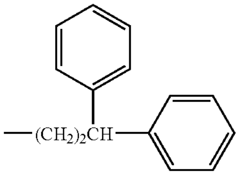 | 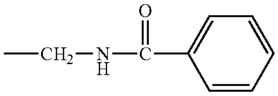 |
| 524 | 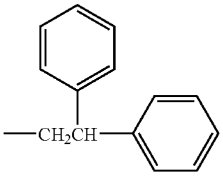 | 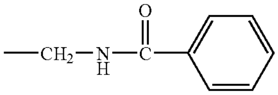 |
| 525 | H | 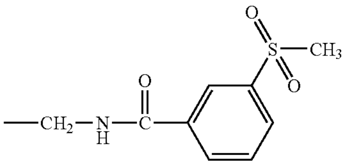 |
| 526 | H | 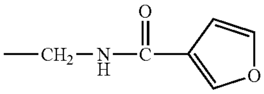 |
| 527 | H | 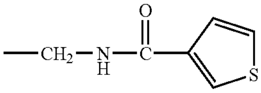 |
| 528 | H | 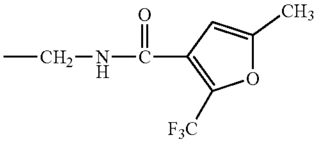 |
TABLE 1.49
| Compd. No. | 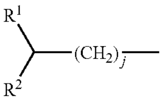 | k | m | n | chirality | $R^3$ | 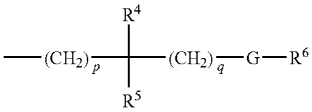 |
|---|---|---|---|---|---|---|---|
| 529 | 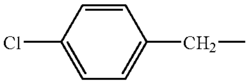 | 2 | 2 | 1 | — | H | 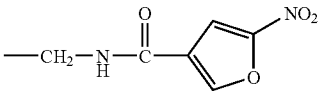 |
| 530 | 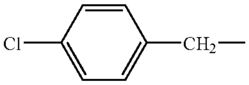 | 2 | 2 | 1 | — | H | 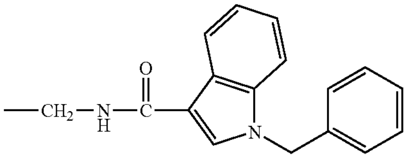 |

TABLE 1.49-continued
| Compd. No. | 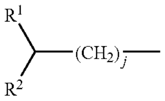 | k | m | n | chirality | $R^3$ | 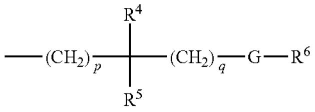 |
|---|---|---|---|---|---|---|---|
| 531 | 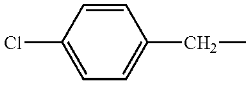 | 2 | 2 | 1 | — | H | 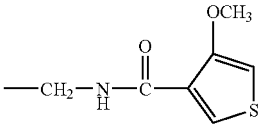 |
| 532 | 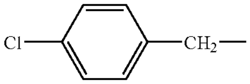 | 2 | 2 | 1 | — | H | 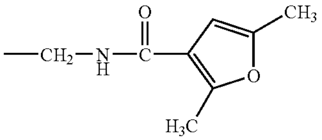 |
| 533 | 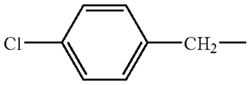 | 2 | 2 | 1 | — | H | 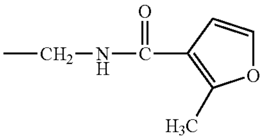 |
| 534 | 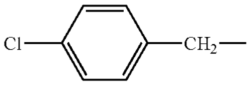 | 2 | 2 | 1 | — | H | 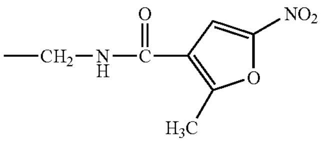 |
| 535 | 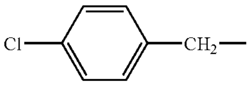 | 2 | 2 | 1 | — | H | 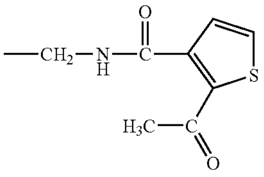 |
| 536 | 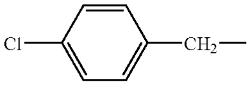 | 2 | 2 | 1 | — | H | 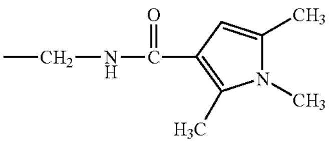 |
| 537 | 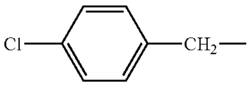 | 2 | 2 | 1 | — | H | 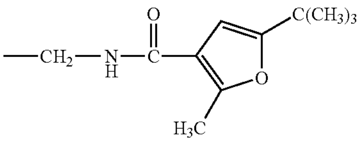 |
| 538 | 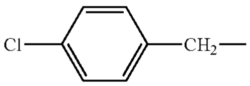 | 2 | 2 | 1 | — | H | 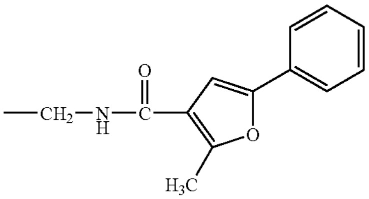 |
| 539 | 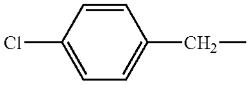 | 2 | 2 | 1 | — | H | 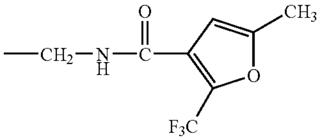 |

TABLE 1.50
| Compd. No. | 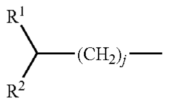 | k | m | n | chirality | $R^3$ | 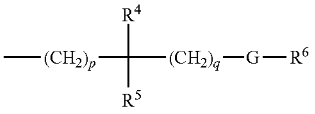 |
|---|---|---|---|---|---|---|---|
| 540 | 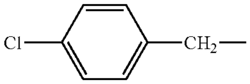 | 2 | 2 | 1 | — | H | 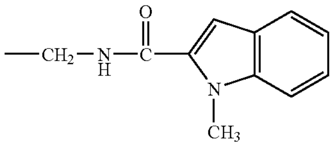 |
| 541 | 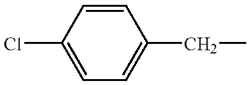 | 2 | 2 | 1 | — | H | 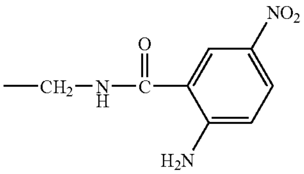 |
| 542 | 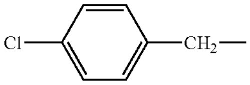 | 2 | 2 | 1 | — | H | 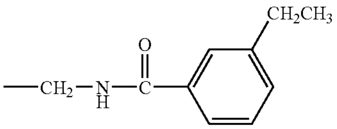 |
| 543 | 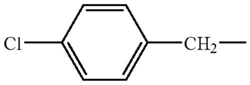 | 2 | 2 | 1 | — | H | 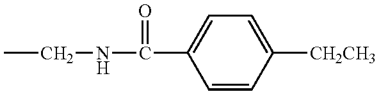 |
| 544 | 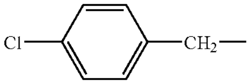 | 2 | 2 | 1 | — | H | 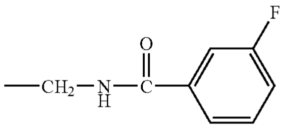 |
| 545 | 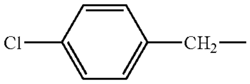 | 2 | 2 | 1 | — | H | 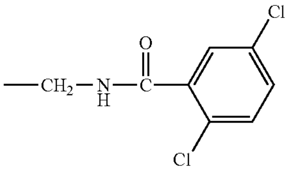 |
| 546 | 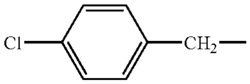 | 2 | 2 | 1 | — | H | 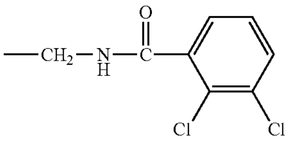 |
| 547 | 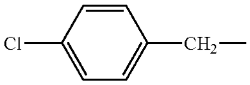 | 2 | 2 | 1 | — | H | 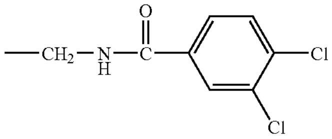 |
| 548 | 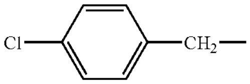 | 2 | 2 | 1 | — | H | 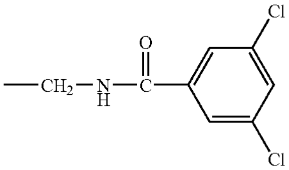 |

TABLE 1.50-continued
| Compd. No. | 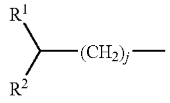 | k | m | n | chirality | R3 | 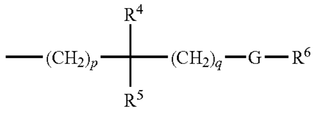 |
|---|---|---|---|---|---|---|---|
| 549 | 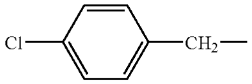 | 2 | 2 | 1 | — | H | 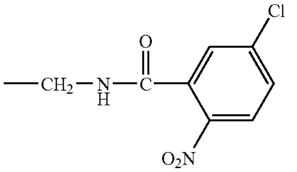 |
| 550 | 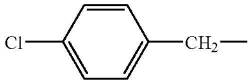 | 2 | 2 | 1 | — | H | 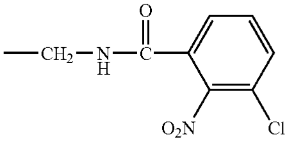 |
TABLE 1.51
| Compd. No. | 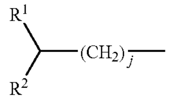 | k | m | n | chirality | R3 | 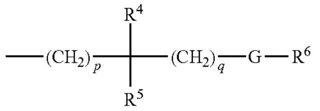 |
|---|---|---|---|---|---|---|---|
| 551 | 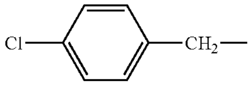 | 2 | 2 | 1 | — | H | 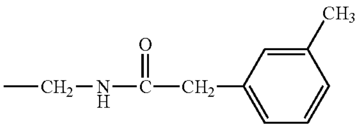 |
| 552 | 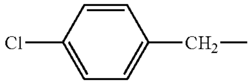 | 2 | 2 | 1 | — | H | 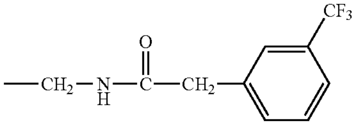 |
| 553 | 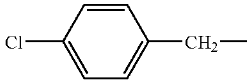 | 2 | 2 | 1 | — | H | 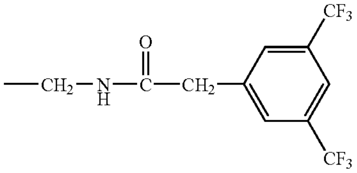 |
| 554 | 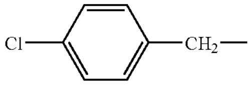 | 2 | 2 | 1 | — | H | 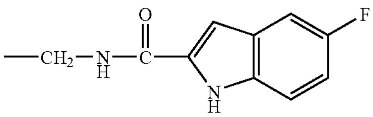 |
| 555 | 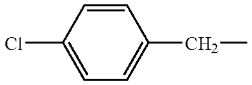 | 2 | 2 | 1 | — | H | 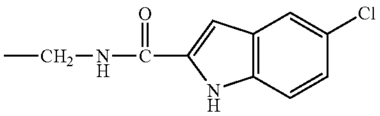 |
| 556 | 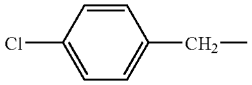 | 2 | 2 | 1 | — | H | 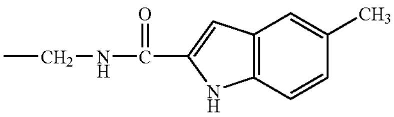 |

TABLE 1.51-continued
| Compd. No. | 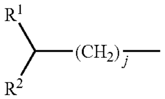 | k | m | n | chirality | $R^3$ | 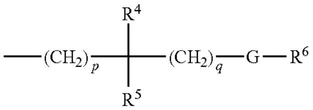 |
|---|---|---|---|---|---|---|---|
| 557 | 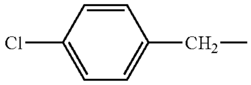 | 2 | 2 | 1 | — | H | 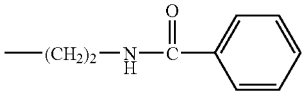 |
| 558 | 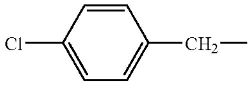 | 2 | 2 | 1 | — | H | 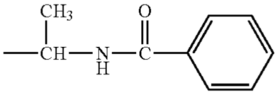 |
| 559 | 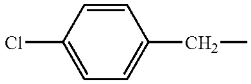 | 2 | 2 | 1 | — | H | 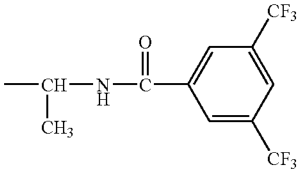 |
| 560 | 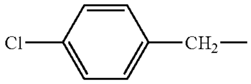 | 2 | 2 | 1 | — | H | 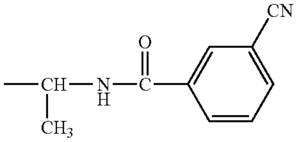 |
| 561 | 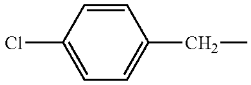 | 2 | 2 | 1 | — | H | 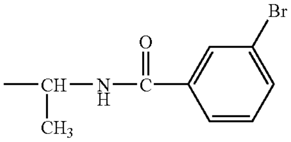 |
TABLE 1.52
| Compd. No. | 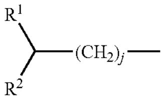 | k | m | n | chirality | $R^3$ | 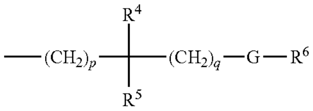 |
|---|---|---|---|---|---|---|---|
| 562 | 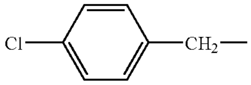 | 2 | 2 | 1 | — | H | 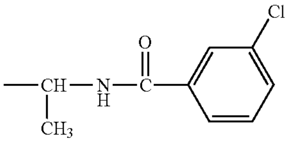 |
| 563 | 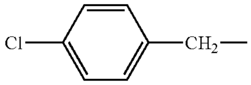 | 2 | 2 | 1 | — | H | 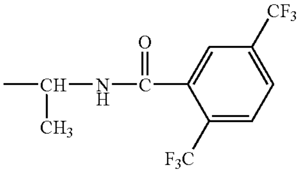 |
| 564 | 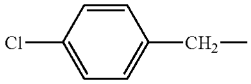 | 2 | 2 | 1 | — | H | 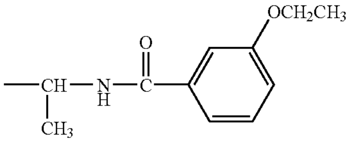 |

TABLE 1.52-continued
| Compd. No. | 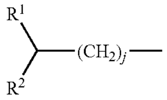 | k | m | n | chirality | $R^3$ | 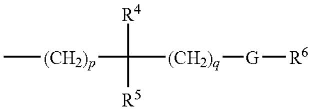 |
|---|---|---|---|---|---|---|---|
| 565 | 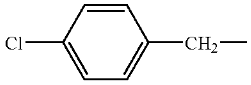 | 2 | 2 | 1 | — | H | 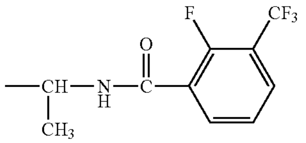 |
| 566 | 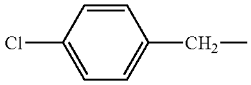 | 2 | 2 | 1 | — | H | 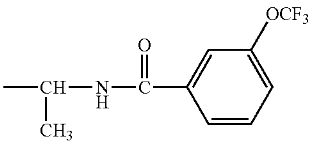 |
| 567 | 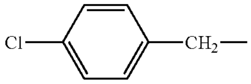 | 2 | 2 | 1 | — | H | 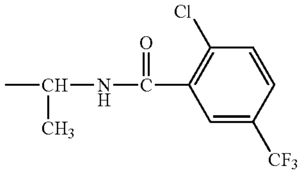 |
| 566 | 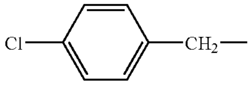 | 2 | 2 | 1 | — | H | 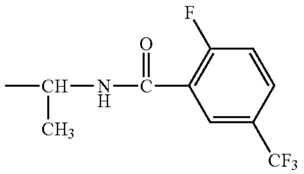 |
| 569 | 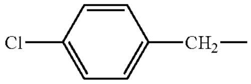 | 2 | 2 | 1 | — | H | 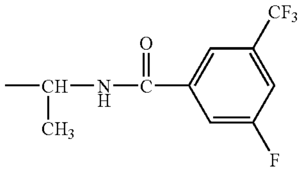 |
| 570 | 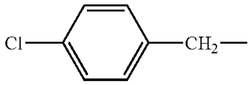 | 2 | 2 | 1 | — | H | 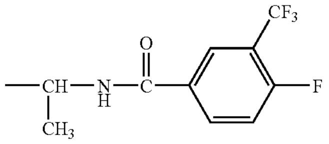 |
| 571 | 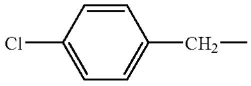 | 2 | 2 | 1 | — | H | 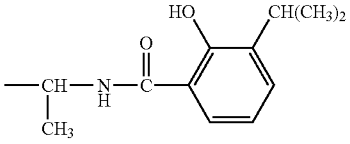 |
| 572 | 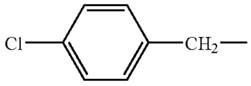 | 2 | 2 | 1 | — | H | 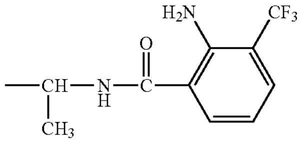 |

TABLE 1.53
| Compd. No. | 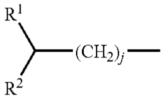 | k | m | n | chirality | $R^3$ | 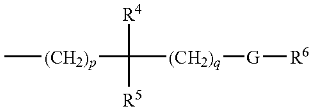 |
|---|---|---|---|---|---|---|---|
| 573 | 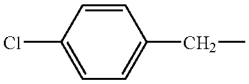 | 2 | 2 | 1 | — | H | 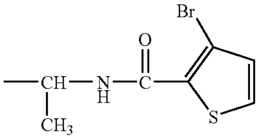 |
| 574 | 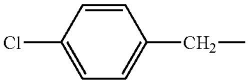 | 2 | 2 | 1 | — | H | 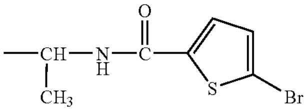 |
| 575 | 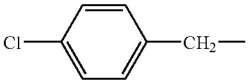 | 2 | 2 | 1 | — | H | 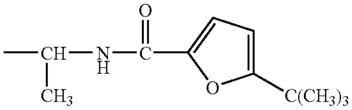 |
| 576 | 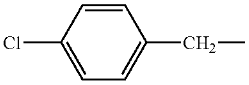 | 2 | 2 | 1 | — | H | 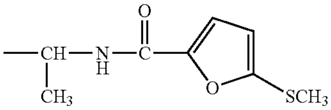 |
| 577 | 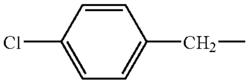 | 2 | 2 | 1 | — | H | 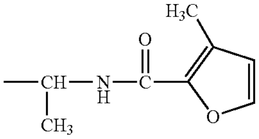 |
| 578 | 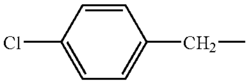 | 2 | 2 | 1 | — | H | 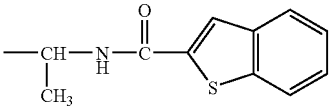 |
| 579 | 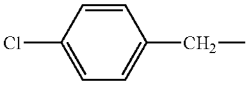 | 2 | 2 | 1 | — | H | 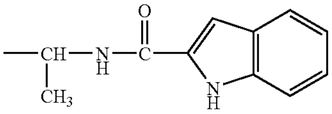 |
| 580 | 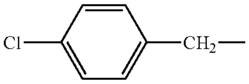 | 2 | 2 | 1 | — | H | 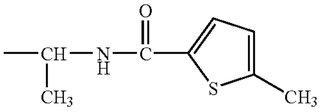 |
| 581 | 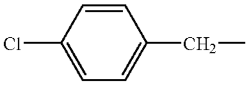 | 2 | 2 | 1 | — | H | 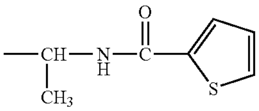 |
| 582 | 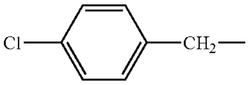 | 2 | 2 | 1 | — | H | 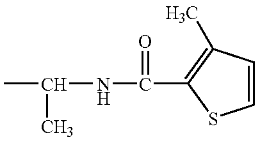 |

TABLE 1.53-continued
| Compd. No. | 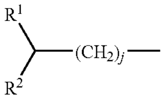 | k | m | n | chirality | $R^3$ | 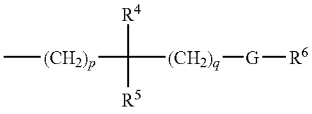 |
|---|---|---|---|---|---|---|---|
| 583 | 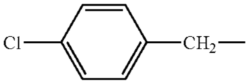 | 2 | 2 | 1 | — | H | 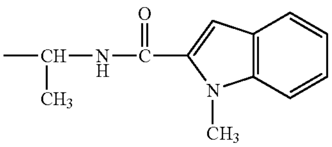 |
TABLE 1.54
| Compd. No. | 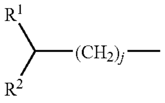 | k | m | n | chirality | $R^3$ | 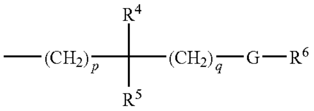 |
|---|---|---|---|---|---|---|---|
| 584 | 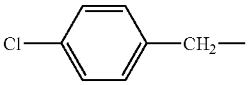 | 2 | 2 | 1 | — | H | 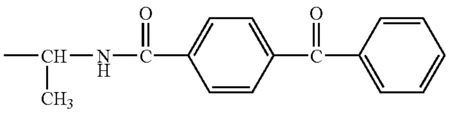 |
| 585 | 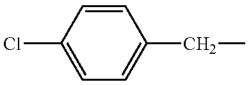 | 2 | 2 | 1 | — | H | 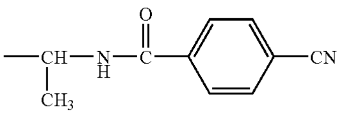 |
| 586 | 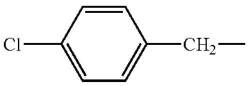 | 2 | 2 | 1 | — | H | 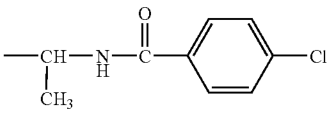 |
| 587 | 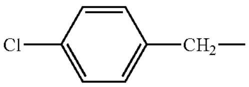 | 2 | 2 | 1 | — | H | 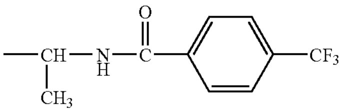 |
| 588 | 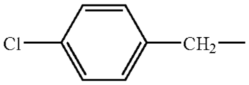 | 2 | 2 | 1 | — | H | 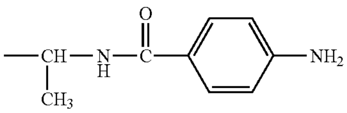 |
| 589 | 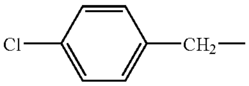 | 2 | 2 | 1 | — | H | 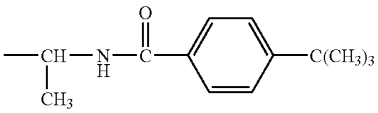 |
| 590 | 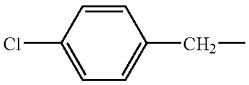 | 2 | 2 | 1 | — | H | 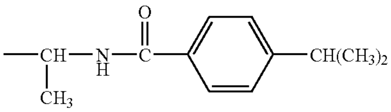 |
| 591 | 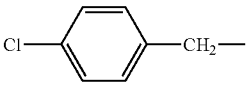 | 2 | 2 | 1 | — | H | 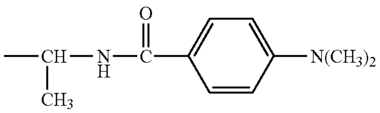 |

TABLE 1.54-continued
| Compd. No. | 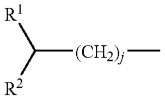 | k | m | n | chirality | $R^3$ | 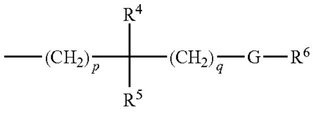 |
|---|---|---|---|---|---|---|---|
| 592 | 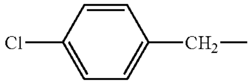 | 2 | 2 | 1 | — | H | 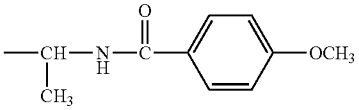 |
| 593 | 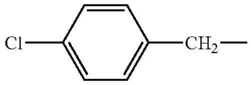 | 2 | 2 | 1 | — | H | 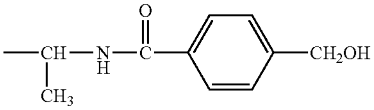 |
| 594 | 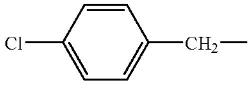 | 2 | 2 | 1 | — | H | 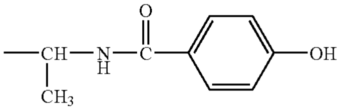 |
TABLE 1.55
| Compd. No. | 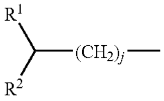 | k | m | n | chirality | $R^3$ | 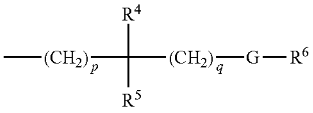 |
|---|---|---|---|---|---|---|---|
| 595 | 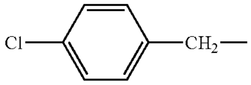 | 2 | 2 | 1 | — | H | 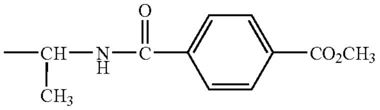 |
| 596 | 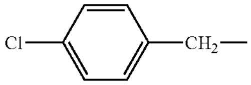 | 2 | 2 | 1 | — | H | 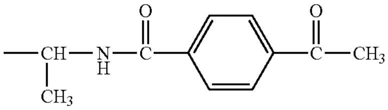 |
| 597 | 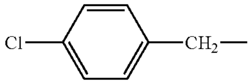 | 2 | 2 | 1 | — | H | 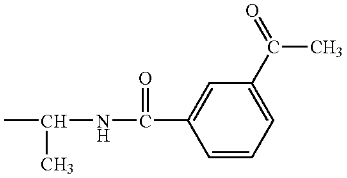 |
| 598 | 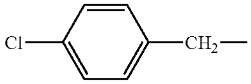 | 2 | 2 | 1 | — | H | 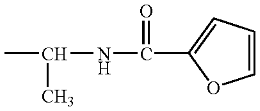 |
| 599 | 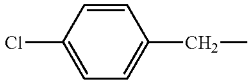 | 2 | 2 | 1 | — | H | 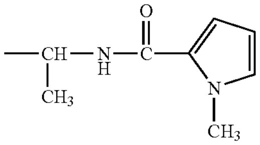 |
| 600 | 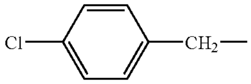 | 2 | 2 | 1 | — | H | 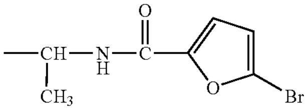 |

TABLE 1.55-continued
| Compd. No. | 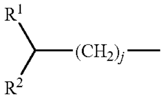 | k | m | n | chirality | $R^3$ | 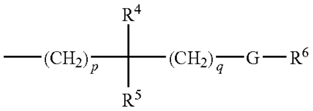 |
|---|---|---|---|---|---|---|---|
| 601 | 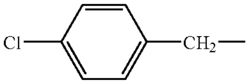 | 2 | 2 | 1 | — | H | 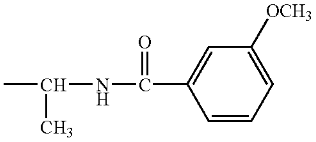 |
| 602 | 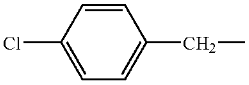 | 2 | 2 | 1 | — | H | 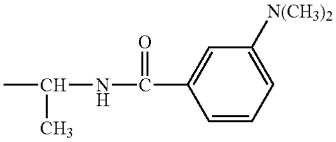 |
| 603 | 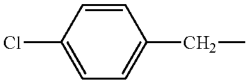 | 2 | 2 | 1 | — | H | 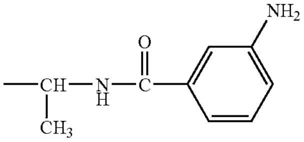 |
| 604 | 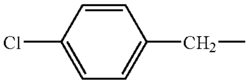 | 2 | 2 | 1 | — | H | 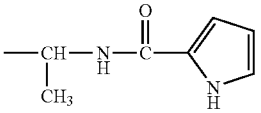 |
| 605 | 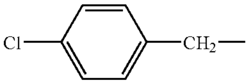 | 2 | 2 | 1 | — | H | 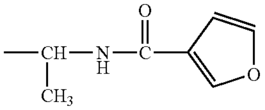 |
TABLE 1.56
| Compd. No. | 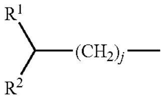 | k | m | n | chirality | $R^3$ | 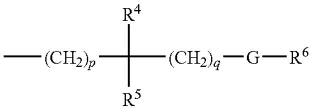 |
|---|---|---|---|---|---|---|---|
| 606 | 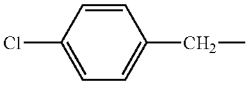 | 2 | 2 | 1 | — | H | 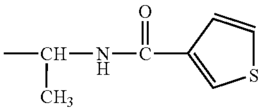 |
| 607 | 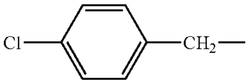 | 2 | 2 | 1 | — | H | 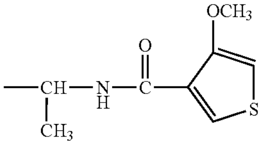 |
| 608 | 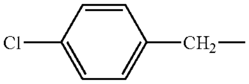 | 2 | 2 | 1 | — | H | 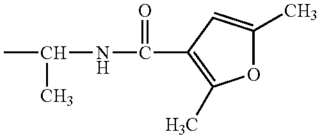 |

TABLE 1.56-continued
| Compd. No. | 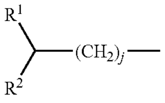 | k | m | n | chirality | $R^3$ | 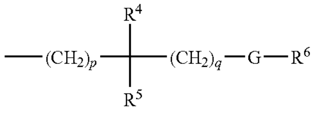 |
|---|---|---|---|---|---|---|---|
| 609 | 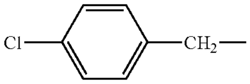 | 2 | 2 | 1 | — | H | 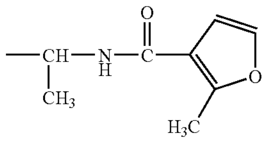 |
| 610 | 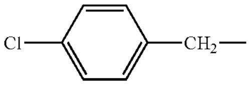 | 2 | 2 | 1 | — | H | 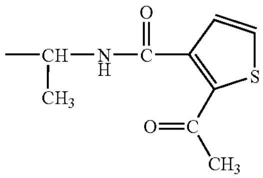 |
| 611 | 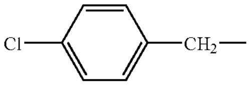 | 2 | 2 | 1 | — | H | 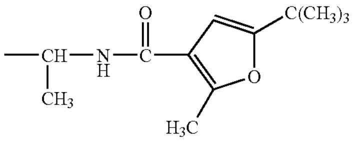 |
| 612 | 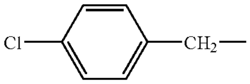 | 2 | 2 | 1 | — | H | 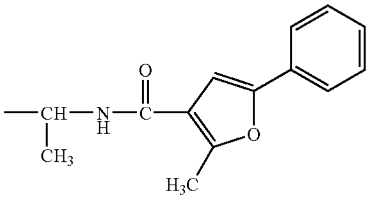 |
| 613 | 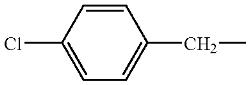 | 2 | 2 | 1 | — | H | 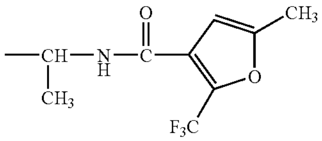 |
| 614 | 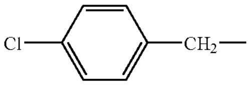 | 2 | 2 | 1 | — | H | 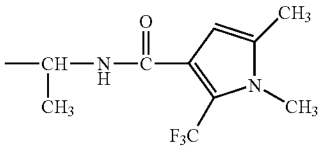 |
| 615 | 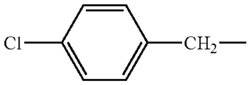 | 2 | 2 | 1 | — | H | 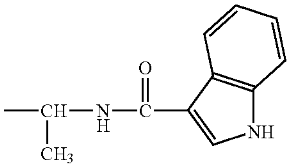 |
| 616 | 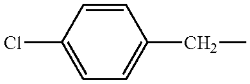 | 2 | 2 | 1 | — | H | 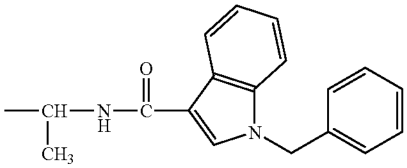 |

TABLE 1.57
| Compd. No. | 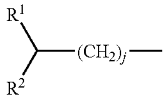 | k | m | n | chirality | $R^3$ | 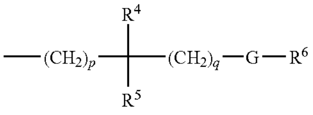 |
|---|---|---|---|---|---|---|---|
| 617 | 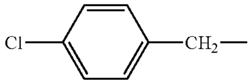 | 2 | 2 | 1 | — | H | 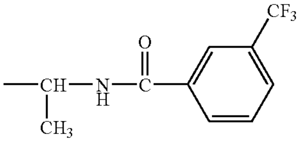 |
| 618 | 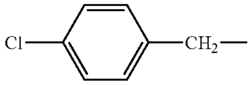 | 2 | 2 | 1 | — | H | 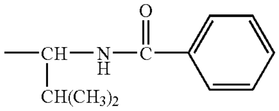 |
| 619 | 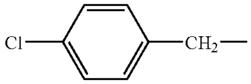 | 2 | 2 | 1 | — | H | 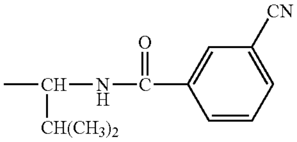 |
| 620 | 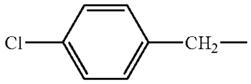 | 2 | 2 | 1 | — | H | 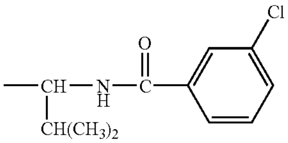 |
| 621 | 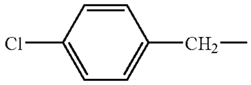 | 2 | 2 | 1 | — | H | 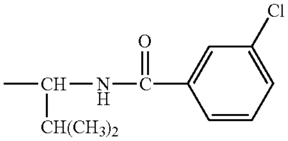 |
| 622 | 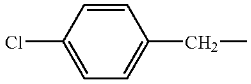 | 2 | 2 | 1 | — | H | 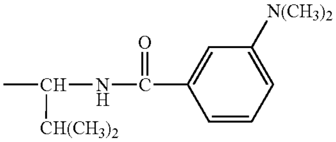 |
| 623 | 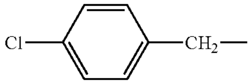 | 2 | 2 | 1 | — | H | 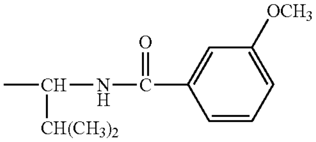 |
| 624 | 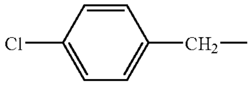 | 2 | 2 | 1 | — | H | 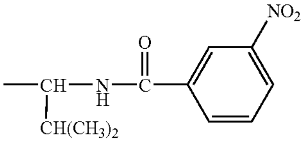 |
| 625 | 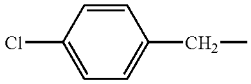 | 2 | 2 | 1 | — | H | 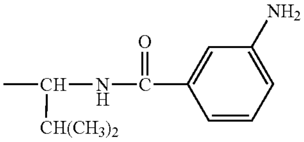 |

TABLE 1.57-continued
| Compd. No. | 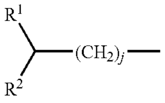 | k | m | n | chirality | $R^3$ | 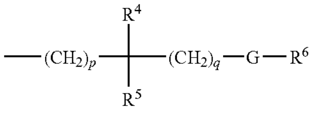 |
|---|---|---|---|---|---|---|---|
| 626 | 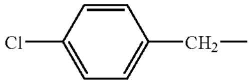 | 2 | 2 | 1 | — | H | 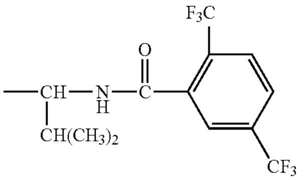 |
| 627 | 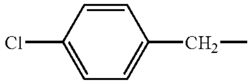 | 2 | 2 | 1 | — | H | 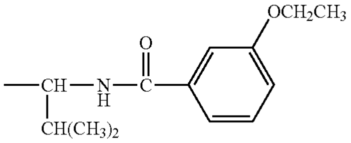 |
TABLE 1.58
| Compd. No. | 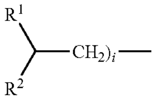 | k | m | n | chirality | $R^3$ | 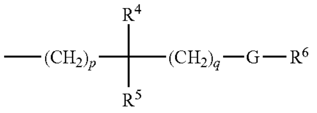 |
|---|---|---|---|---|---|---|---|
| 628 | 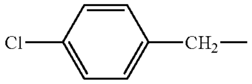 | 2 | 2 | 1 | — | H | 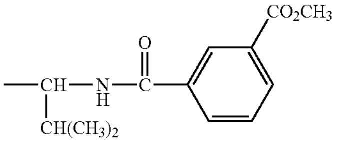 |
| 629 | 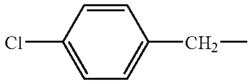 | 2 | 2 | 1 | — | H | 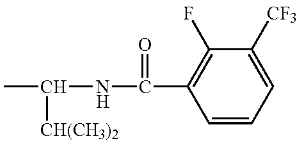 |
| 630 | 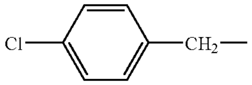 | 2 | 2 | 1 | — | H | 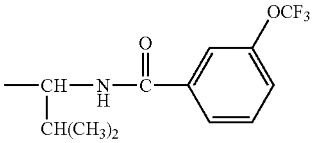 |
| 631 | 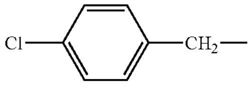 | 2 | 2 | 1 | — | H | 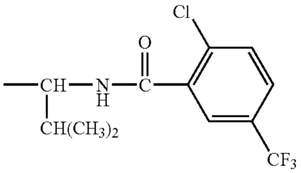 |
| 632 | 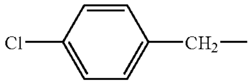 | 2 | 2 | 1 | — | H | 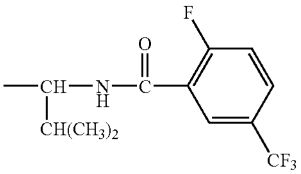 |

TABLE 1.58-continued
| Compd. No. | 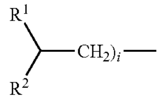 | k | m | n | chirality | $R^3$ | 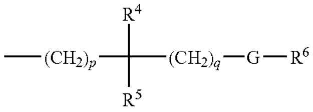 |
|---|---|---|---|---|---|---|---|
| 633 | 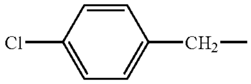 | 2 | 2 | 1 | — | H | 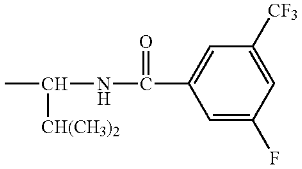 |
| 634 | 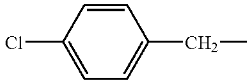 | 2 | 2 | 1 | — | H | 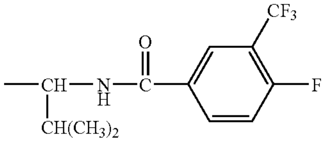 |
| 635 | 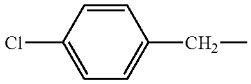 | 2 | 2 | 1 | — | H | 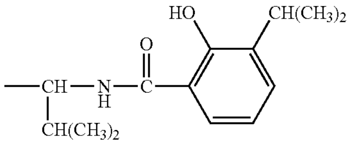 |
| 636 | 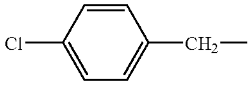 | 2 | 2 | 1 | — | H | 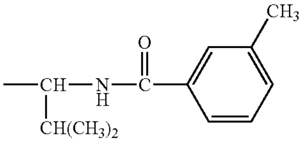 |
| 637 | 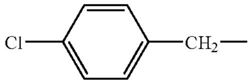 | 2 | 2 | 1 | — | H | 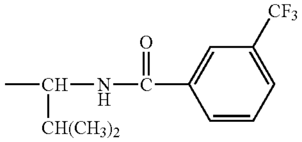 |
| 638 | 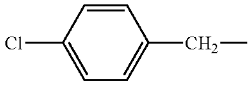 | 2 | 2 | 1 | — | H | 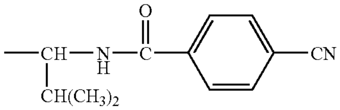 |
TABLE 1.59
| Compd. No. | 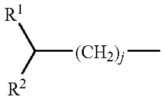 | k | m | n | chirality | $R^3$ | 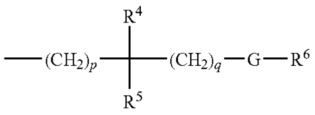 |
|---|---|---|---|---|---|---|---|
| 639 | 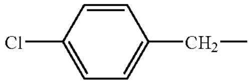 | 2 | 2 | 1 | — | H | 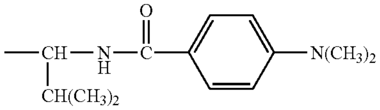 |
| 640 | 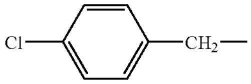 | 2 | 2 | 1 | — | H | 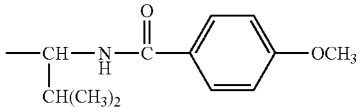 |

TABLE 1.59-continued
| Compd. No. | 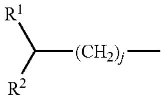 | k | m | n | chirality | $R^3$ | 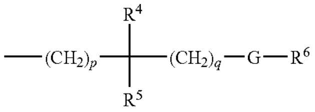 |
|---|---|---|---|---|---|---|---|
| 641 | 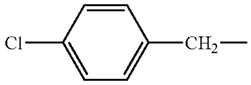 | 2 | 2 | 1 | — | H | 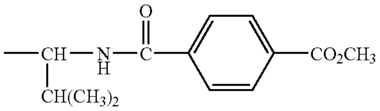 |
| 642 | 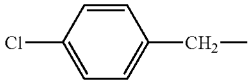 | 2 | 2 | 1 | — | H | 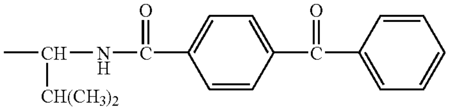 |
| 643 | 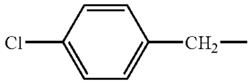 | 2 | 2 | 1 | — | H | 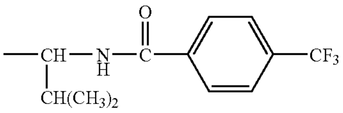 |
| 644 | 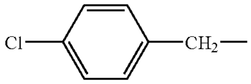 | 2 | 2 | 1 | — | H | 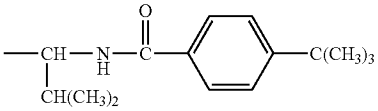 |
| 645 | 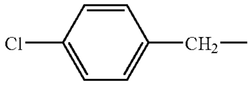 | 2 | 2 | 1 | — | H | 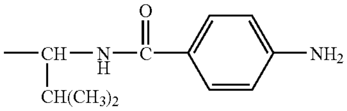 |
| 646 | 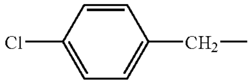 | 2 | 2 | 1 | — | H | 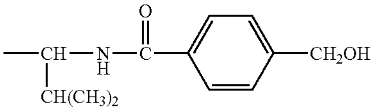 |
| 647 | 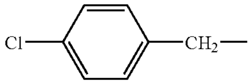 | 2 | 2 | 1 | — | H | 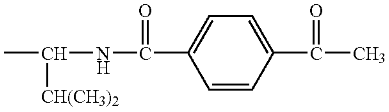 |
| 648 | 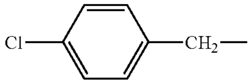 | 2 | 2 | 1 | — | H | 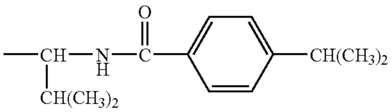 |
| 649 | 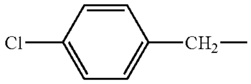 | 2 | 2 | 1 | — | H | 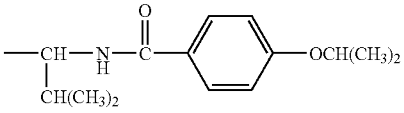 |

TABLE 1.60
| Compd. No. | 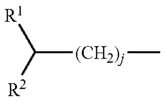 | k | m | n | chirality | $R^3$ | 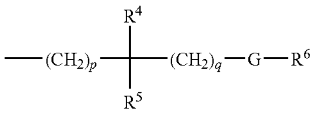 |
|---|---|---|---|---|---|---|---|
| 650 | 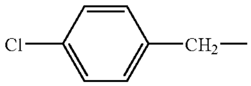 | 2 | 2 | 1 | — | H | 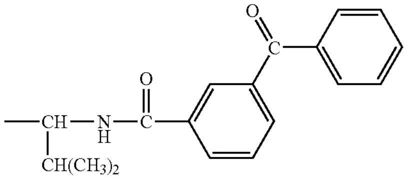 |
| 651 | 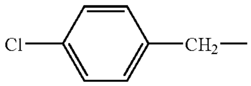 | 2 | 2 | 1 | — | H | 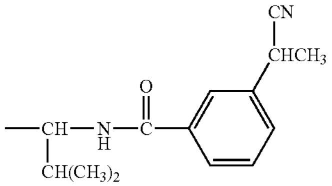 |
| 652 | 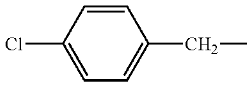 | 2 | 2 | 1 | — | H | 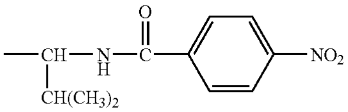 |
| 653 | 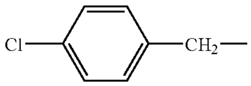 | 2 | 2 | 1 | — | H | 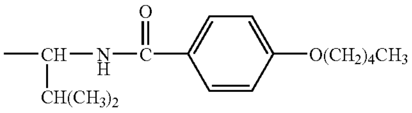 |
| 654 | 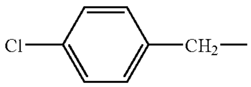 | 2 | 2 | 1 | — | H | 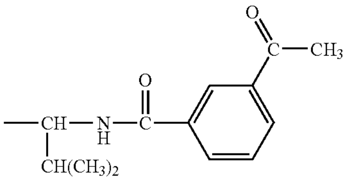 |
| 655 | 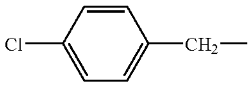 | 2 | 2 | 1 | — | H | 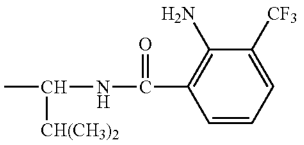 |
| 656 | 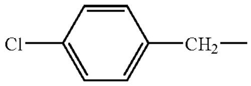 | 2 | 2 | 1 | — | H | 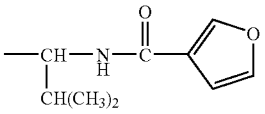 |
| 657 | 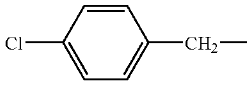 | 2 | 2 | 1 | — | H | 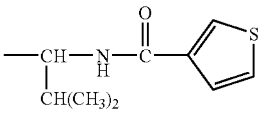 |
| 658 | 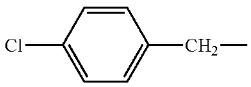 | 2 | 2 | 1 | — | H | 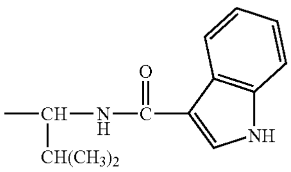 |

TABLE 1.60-continued
| Compd. No. | 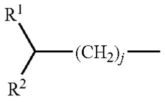 | k | m | n | chirality | $R^3$ | 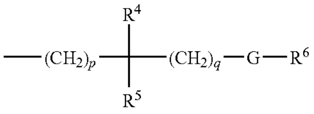 |
|---|---|---|---|---|---|---|---|
| 659 | 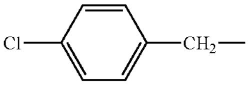 | 2 | 2 | 1 | — | H | 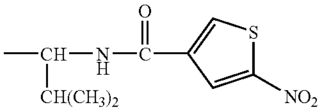 |
| 660 | 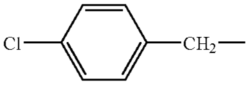 | 2 | 2 | 1 | — | H | 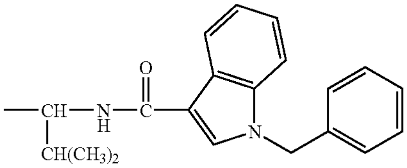 |
TABLE 1.61
| Compd. No. | 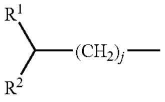 | k | m | n | chirality | $R^3$ | 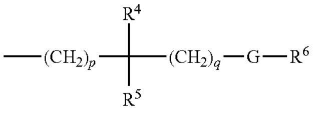 |
|---|---|---|---|---|---|---|---|
| 661 | 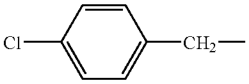 | 2 | 2 | 1 | — | H | 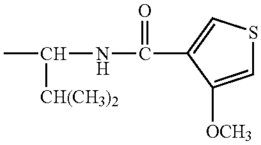 |
| 662 | 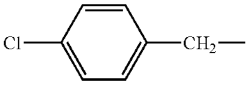 | 2 | 2 | 1 | — | H | 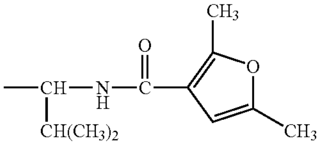 |
| 663 | 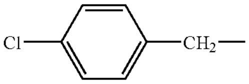 | 2 | 2 | 1 | — | H | 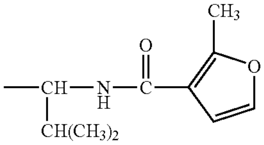 |
| 664 | 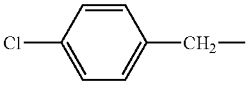 | 2 | 2 | 1 | — | H | 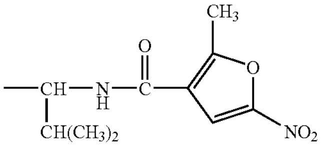 |
| 665 | 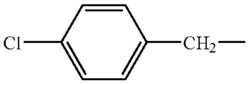 | 2 | 2 | 1 | — | H | 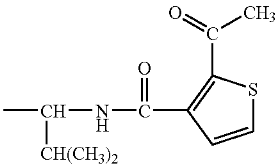 |

TABLE 1.61-continued
| Compd. No. | 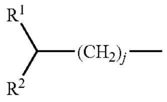 | k | m | n | chirality | $R^3$ | 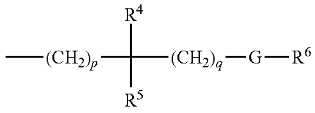 |
|---|---|---|---|---|---|---|---|
| 666 | 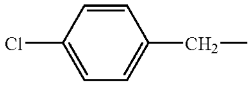 | 2 | 2 | 1 | — | H | 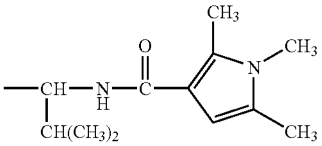 |
| 667 | 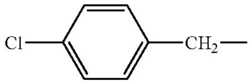 | 2 | 2 | 1 | — | H | 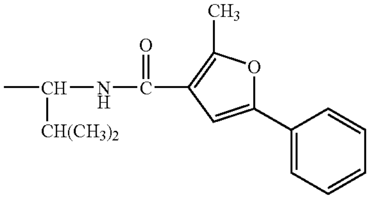 |
| 668 | 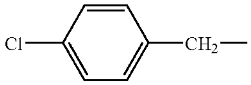 | 2 | 2 | 1 | — | H | 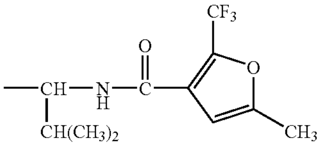 |
| 669 | 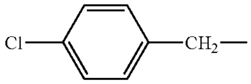 | 2 | 2 | 1 | — | H | 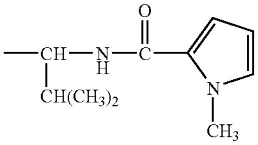 |
| 670 | 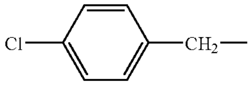 | 2 | 2 | 1 | — | H | 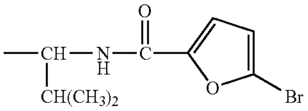 |
| 671 | 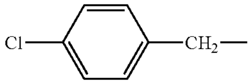 | 2 | 2 | 1 | — | H | 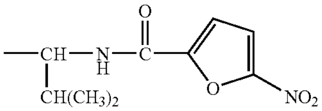 |
TABLE 1.62
| Compd. No. | 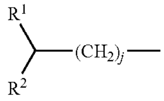 | k | m | n | chirality | $R^3$ | 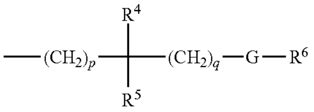 |
|---|---|---|---|---|---|---|---|
| 672 | 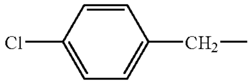 | 2 | 2 | 1 | — | H | 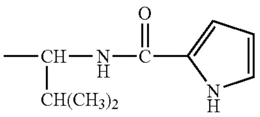 |
| 673 | 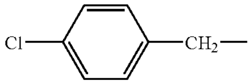 | 2 | 2 | 1 | — | H | 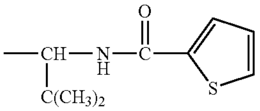 |

TABLE 1.62-continued
| Compd. No. | 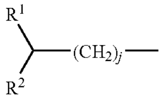 | k | m | n | chirality | $R^3$ | 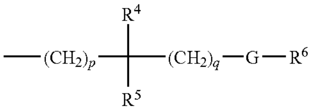 |
|---|---|---|---|---|---|---|---|
| 674 | 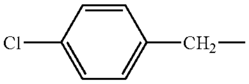 | 2 | 2 | 1 | — | H | 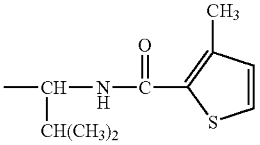 |
| 675 | 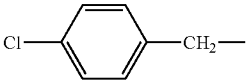 | 2 | 2 | 1 | — | H | 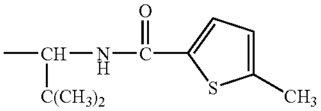 |
| 676 | 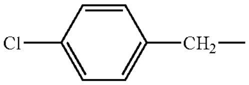 | 2 | 2 | 1 | — | H | 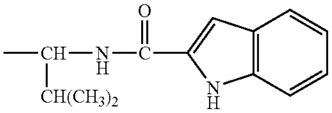 |
| 677 | 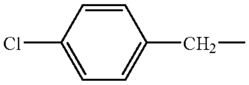 | 2 | 2 | 1 | — | H | 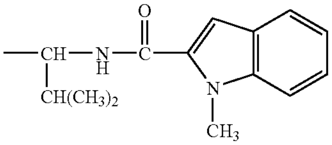 |
| 678 | 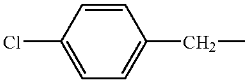 | 2 | 2 | 1 | — | H | 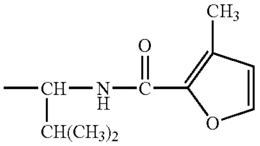 |
| 679 | 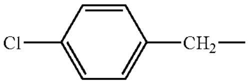 | 2 | 2 | 1 | — | H | 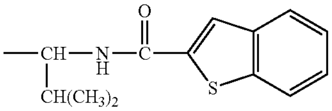 |
| 680 | 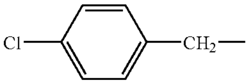 | 2 | 2 | 1 | — | H | 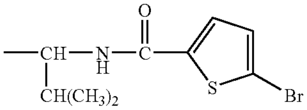 |
| 681 | 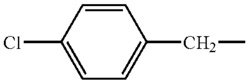 | 2 | 2 | 1 | — | H | 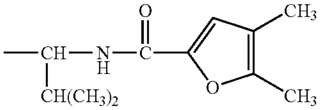 |
| 682 | 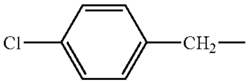 | 2 | 2 | 1 | — | H | 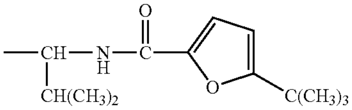 |

TABLE 1.63
| Compd. No. | 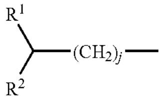 | k | m | n | chirality | $R^3$ | 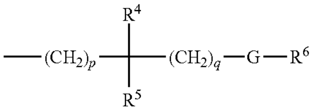 |
|---|---|---|---|---|---|---|---|
| 683 | 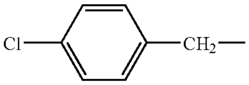 | 2 | 2 | 1 | — | H | 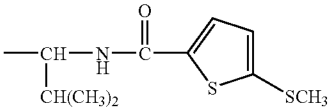 |
| 684 | 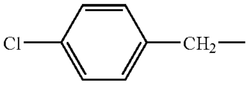 | 2 | 2 | 1 | — | H | 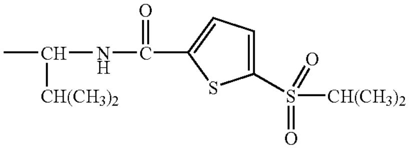 |
| 685 | 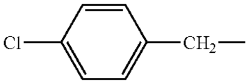 | 2 | 2 | 1 | — | H | 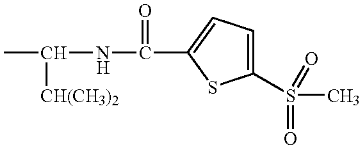 |
| 686 | 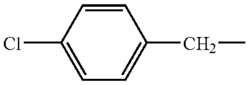 | 2 | 2 | 1 | — | H | 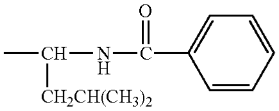 |
| 687 | 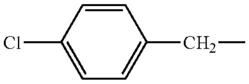 | 2 | 2 | 1 | — | H | 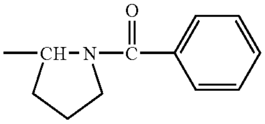 |
| 688 | 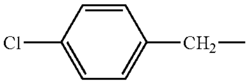 | 2 | 2 | 1 | — | H | 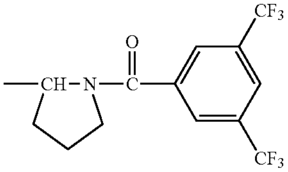 |
| 689 | 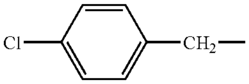 | 2 | 2 | 1 | — | H | 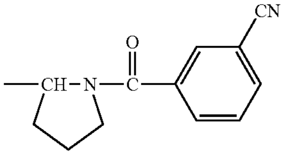 |
| 690 | 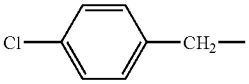 | 2 | 2 | 1 | — | H | 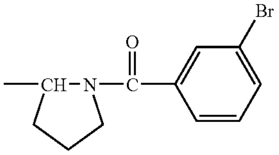 |
| 691 | 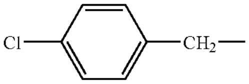 | 2 | 2 | 1 | — | H | 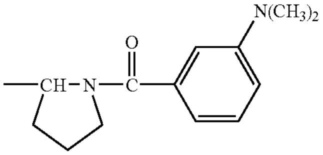 |

TABLE 1.63-continued
| Compd. No. | 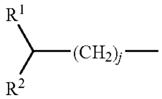 | k | m | n | chirality | $R^3$ | 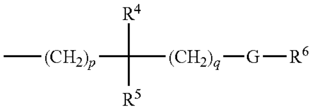 |
| --- | --- | --- | --- | --- | --- | --- | --- |
| 692 | 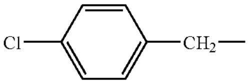 | 2 | 2 | 1 | — | H | 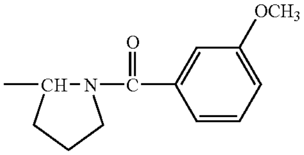 |
| 693 | 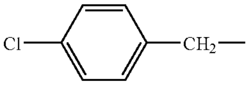 | 2 | 2 | 1 | — | H | 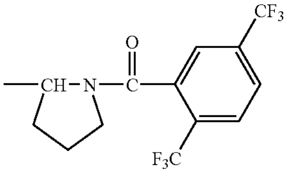 |
TABLE 1.64
| Compd. No. | 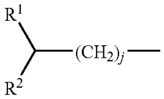 | k | m | n | chirality | $R^3$ | 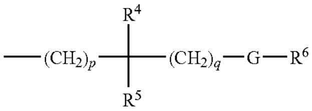 |
| --- | --- | --- | --- | --- | --- | --- | --- |
| 694 | 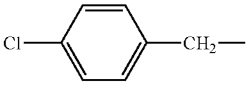 | 2 | 2 | 1 | — | H | 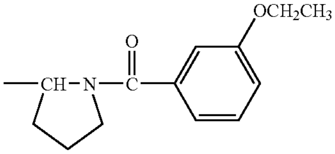 |
| 695 | 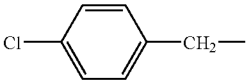 | 2 | 2 | 1 | — | H | 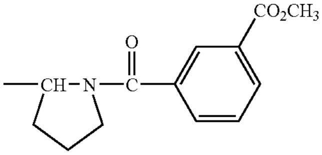 |
| 696 | 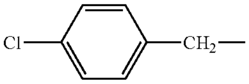 | 2 | 2 | 1 | — | H | 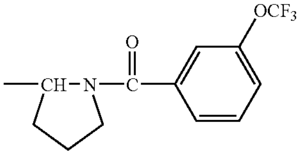 |
| 697 | 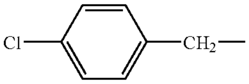 | 2 | 2 | 1 | — | H | 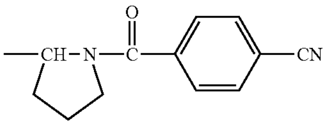 |
| 698 | 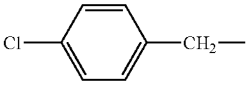 | 2 | 2 | 1 | — | H | 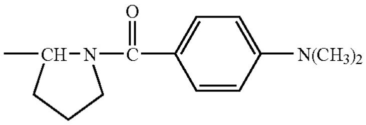 |
| 699 | 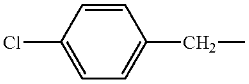 | 2 | 2 | 1 | — | H | 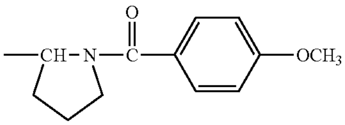 |

TABLE 1.64-continued
| Compd. No. | 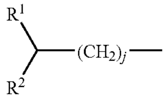 | k | m | n | chirality | $R^3$ | 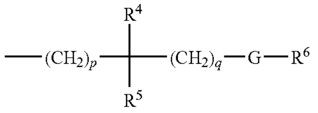 |
|---|---|---|---|---|---|---|---|
| 700 | 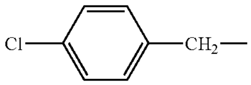 | 2 | 2 | 1 | — | H | 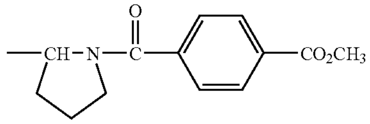 |
| 701 | 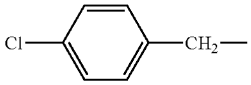 | 2 | 2 | 1 | — | H | 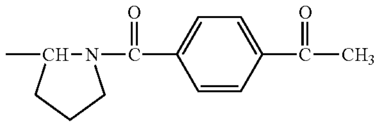 |
| 702 | 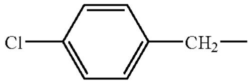 | 2 | 2 | 1 | — | H | 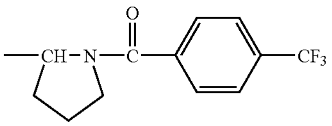 |
| 703 | 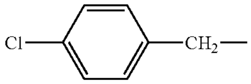 | 2 | 2 | 1 | — | H | 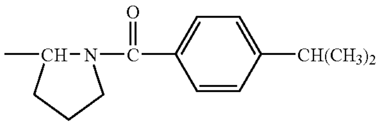 |
| 704 | 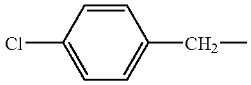 | 2 | 2 | 1 | — | H | 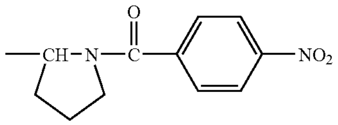 |
TABLE 1.65
| Compd. No. | 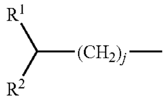 | k | m | n | chirality | $R^3$ | 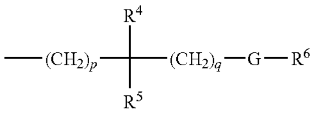 |
|---|---|---|---|---|---|---|---|
| 705 | 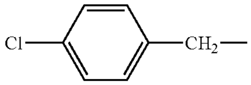 | 2 | 2 | 1 | — | H | 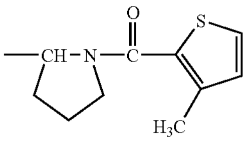 |
| 706 | 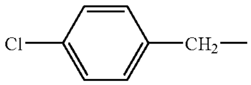 | 2 | 2 | 1 | — | H | 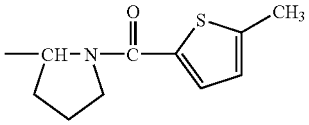 |
| 707 | 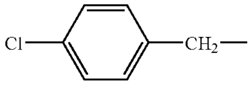 | 2 | 2 | 1 | — | H | 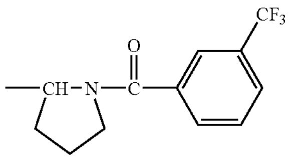 |

TABLE 1.65-continued
| Compd. No. | 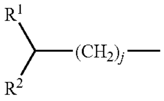 | k | m | n | chirality | $R^3$ | 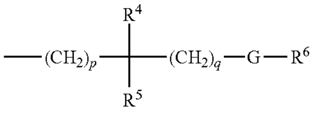 |
|---|---|---|---|---|---|---|---|
| 708 | 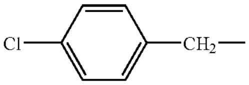 | 2 | 2 | 1 | — | H | 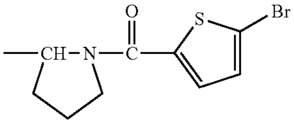 |
| 709 | 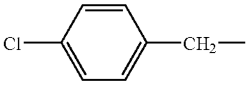 | 2 | 2 | 1 | — | H | 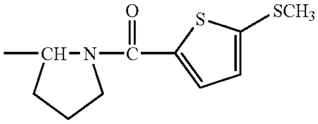 |
| 710 | 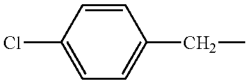 | 2 | 2 | 1 | — | H | 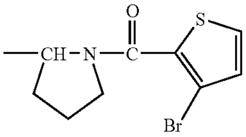 |
| 711 | 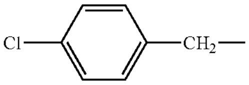 | 2 | 2 | 1 | — | H | 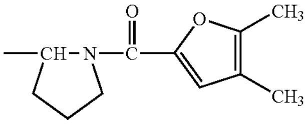 |
| 712 | 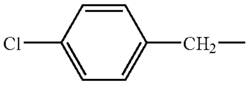 | 2 | 2 | 1 | — | H | 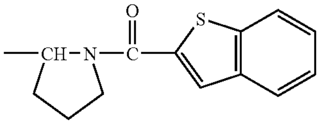 |
| 713 | 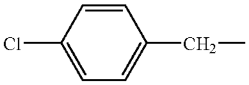 | 2 | 2 | 1 | — | H | 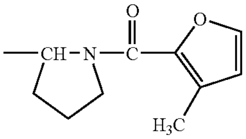 |
| 714 | 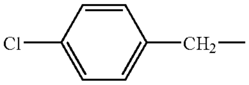 | 2 | 2 | 1 | — | H | 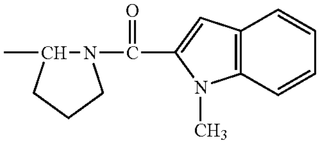 |
| 715 | 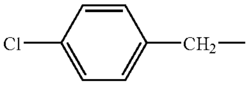 | 2 | 2 | 1 | — | H | 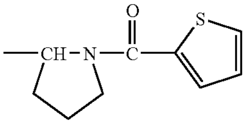 |

TABLE 1.66
| Compd. No. | 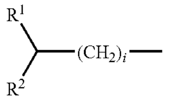 | k | m | n | chirality | $R^3$ | 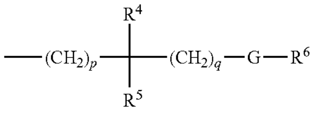 |
|---|---|---|---|---|---|---|---|
| 716 | 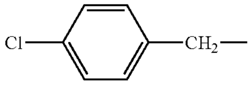 | 2 | 2 | 1 | — | H | 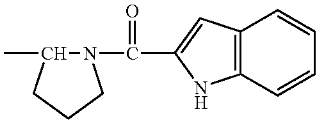 |
| 717 | 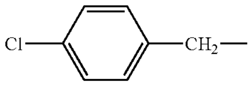 | 2 | 2 | 1 | — | H | 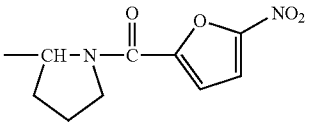 |
| 718 | 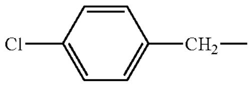 | 2 | 2 | 1 | — | H | 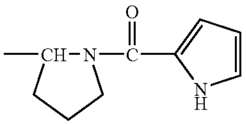 |
| 719 | 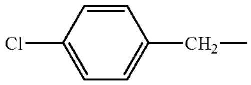 | 2 | 2 | 1 | — | H | 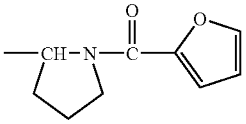 |
| 720 | 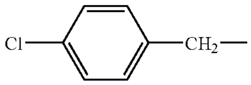 | 2 | 2 | 1 | — | H | 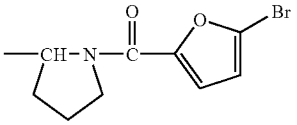 |
| 721 | 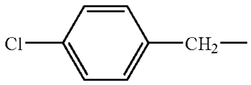 | 2 | 2 | 1 | — | H | 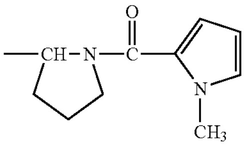 |
| 722 | 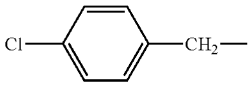 | 2 | 2 | 1 | — | H | 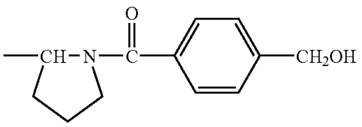 |
| 723 | 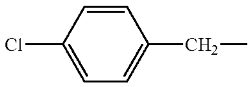 | 2 | 2 | 1 | — | H | 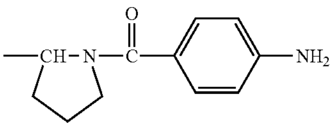 |
| 724 | 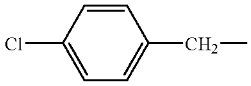 | 2 | 2 | 1 | — | H | 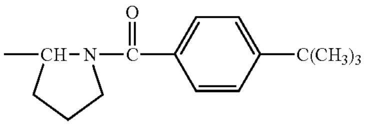 |
| 725 | 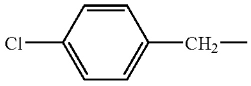 | 2 | 2 | 1 | — | H | 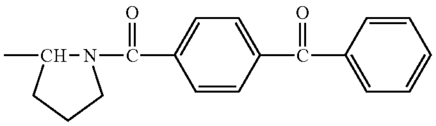 |

TABLE 1.66-continued
| Compd. No. | 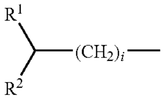 | k | m | n | chirality | $R^3$ | 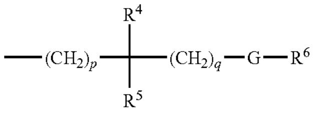 |
|---|---|---|---|---|---|---|---|
| 726 | 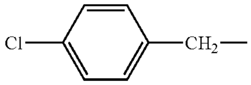 | 2 | 2 | 1 | — | H | 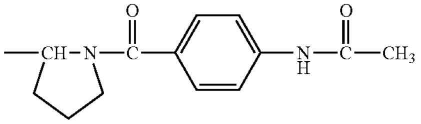 |
TABLE 1.67
| Compd. No. | 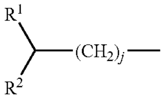 | k | m | n | chirality | $R^3$ | 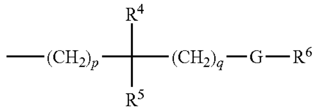 |
|---|---|---|---|---|---|---|---|
| 727 | 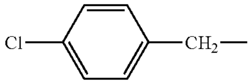 | 2 | 2 | 1 | — | H | 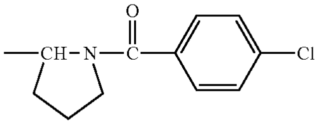 |
| 728 | 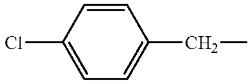 | 2 | 2 | 1 | — | H | 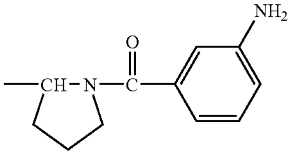 |
| 729 | 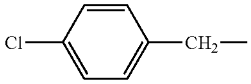 | 2 | 2 | 1 | — | H | 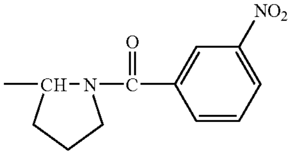 |
| 730 | 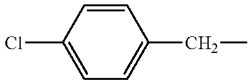 | 2 | 2 | 1 | — | H | 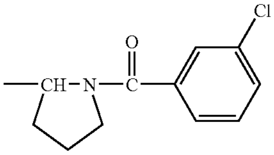 |
| 731 | 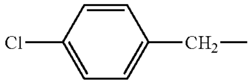 | 2 | 2 | 1 | — | H | 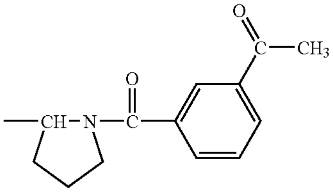 |
| 732 | 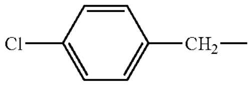 | 2 | 2 | 1 | — | H | 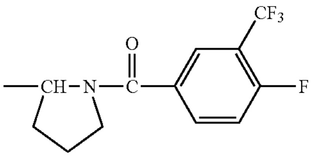 |

TABLE 1.67-continued
| Compd. No. | 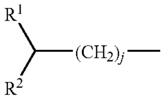 | k | m | n | chirality | R3 | 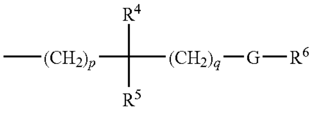 |
|---|---|---|---|---|---|---|---|
| 733 | 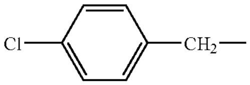 | 2 | 2 | 1 | — | H | 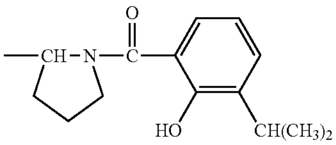 |
| 734 | 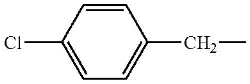 | 2 | 2 | 1 | — | H | 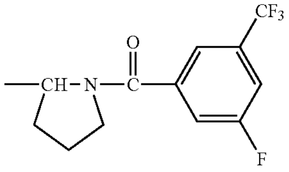 |
| 735 | 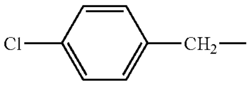 | 2 | 2 | 1 | — | H | 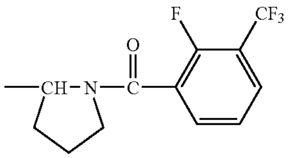 |
| 736 | 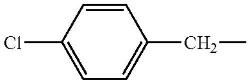 | 2 | 2 | 1 | — | H | 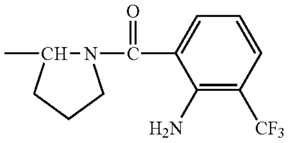 |
| 737 | 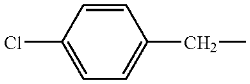 | 2 | 2 | 1 | — | H | 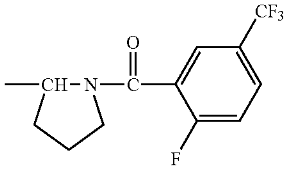 |
TABLE 1.68
| Compd. No. | 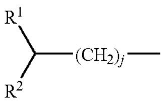 | k | m | n | chirality | R3 | 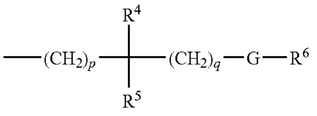 |
|---|---|---|---|---|---|---|---|
| 738 | 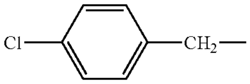 | 2 | 2 | 1 | — | H | 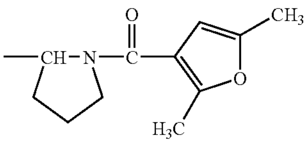 |
| 739 | 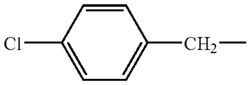 | 2 | 2 | 1 | — | H | 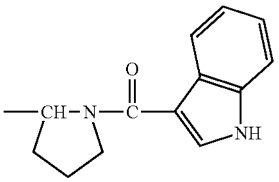 |

TABLE 1.68-continued
| Compd. No. | 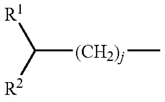 | k | m | n | chirality | $R^3$ | 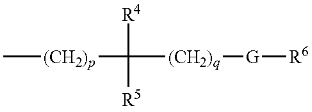 |
|---|---|---|---|---|---|---|---|
| 740 | 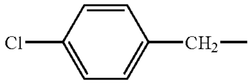 | 2 | 2 | 1 | — | H | 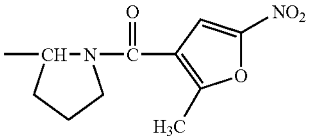 |
| 741 | 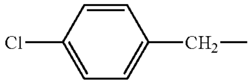 | 2 | 2 | 1 | — | H | 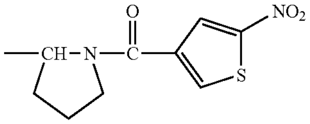 |
| 742 | 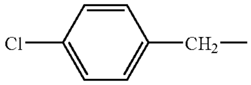 | 2 | 2 | 1 | — | H | 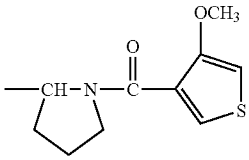 |
| 743 | 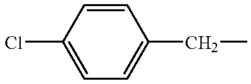 | 2 | 2 | 1 | — | H | 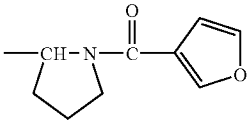 |
| 744 | 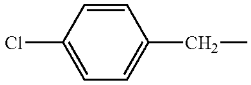 | 2 | 2 | 1 | — | H | 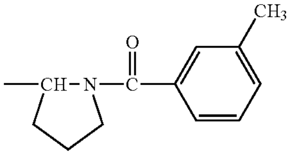 |
| 745 | 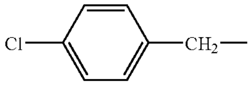 | 2 | 2 | 1 | — | H | 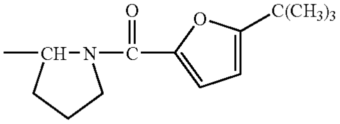 |
| 746 | 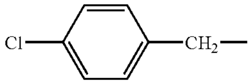 | 2 | 2 | 1 | — | H | 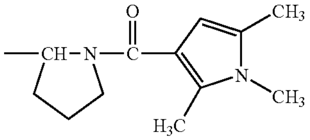 |
| 747 | 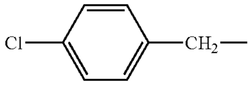 | 2 | 2 | 1 | — | H | 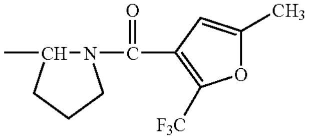 |
| 748 | 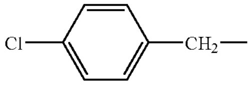 | 2 | 2 | 1 | — | H | 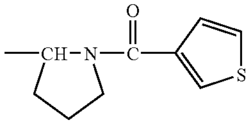 |

TABLE 1.69
| Compd. No. | 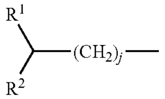 | k | m | n | chirality | $R^3$ | 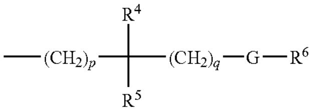 |
|---|---|---|---|---|---|---|---|
| 749 | 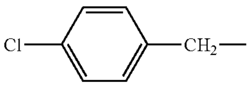 | 2 | 2 | 1 | — | H | 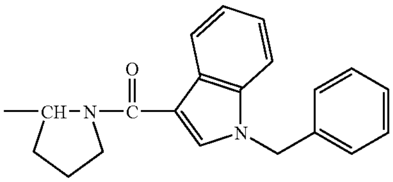 |
| 750 | 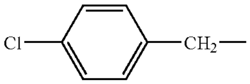 | 2 | 2 | 1 | — | H | 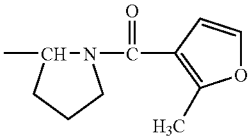 |
| 751 | 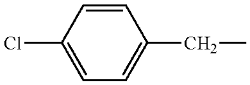 | 2 | 2 | 1 | — | H | 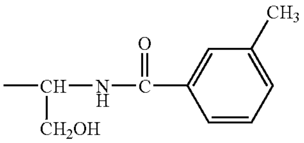 |
| 752 | 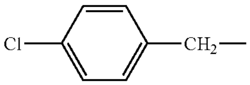 | 2 | 2 | 1 | — | H | 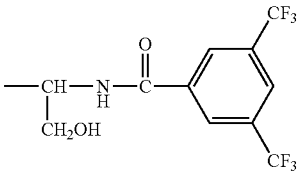 |
| 753 | 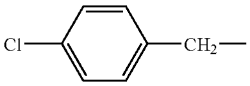 | 2 | 2 | 1 | — | H | 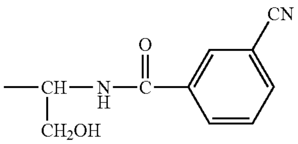 |
| 754 | 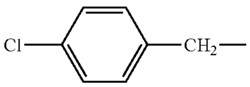 | 2 | 2 | 1 | — | H | 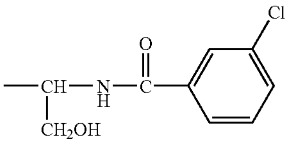 |
| 755 | 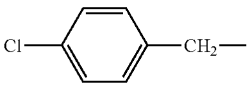 | 2 | 2 | 1 | — | H | 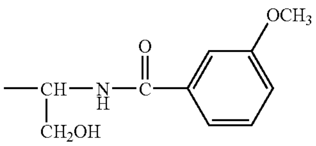 |
| 756 | 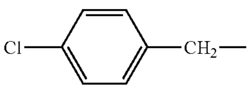 | 2 | 2 | 1 | — | H | 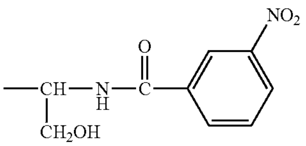 |
| 757 | 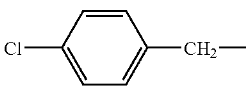 | 2 | 2 | 1 | — | H | 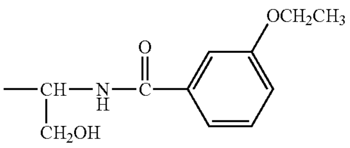 |

TABLE 1.69-continued
| Compd. No. | 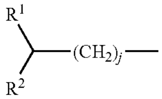 | k | m | n | chirality | $R^3$ | 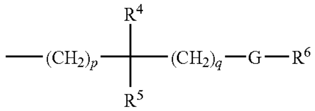 |
| --- | --- | --- | --- | --- | --- | --- | --- |
| 758 | 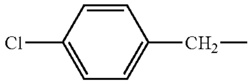 | 2 | 2 | 1 | — | H | 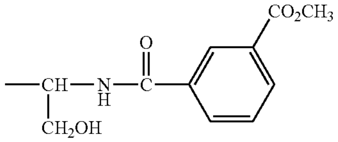 |
| 759 | 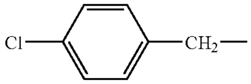 | 2 | 2 | 1 | — | H | 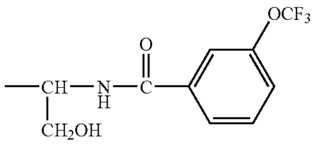 |
TABLE 1.70
| Compd. No. | 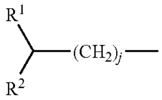 | k | m | n | chirality | $R^3$ | 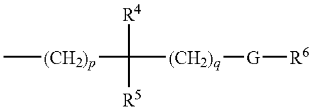 |
| --- | --- | --- | --- | --- | --- | --- | --- |
| 760 | 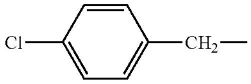 | 2 | 2 | 1 | — | H | 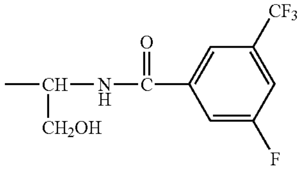 |
| 761 | 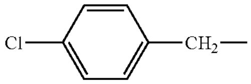 | 2 | 2 | 1 | — | H | 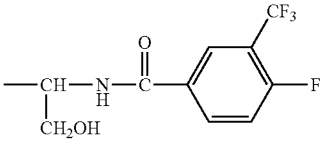 |
| 762 | 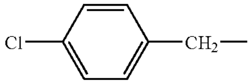 | 2 | 2 | 1 | — | H | 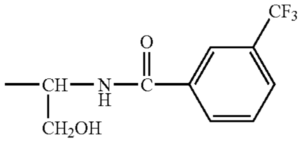 |
| 763 | 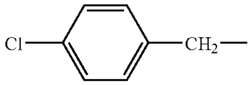 | 2 | 2 | 1 | — | H | 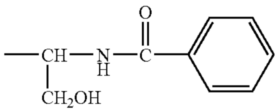 |
| 764 | 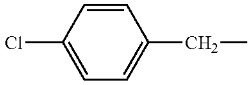 | 2 | 2 | 1 | — | H | 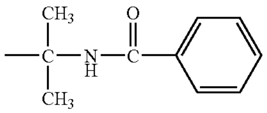 |
| 765 | 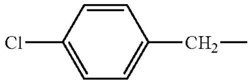 | 2 | 2 | 1 | — | H | 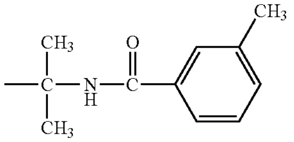 |

TABLE 1.70-continued
| Compd. No. | 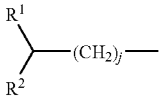 | k | m | n | chirality | $R^3$ | 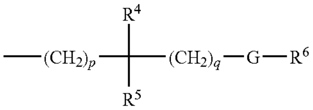 |
|---|---|---|---|---|---|---|---|
| 766 | 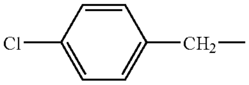 | 2 | 2 | 1 | — | H | 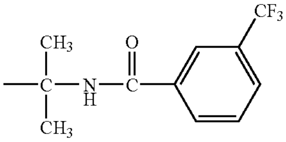 |
| 767 | 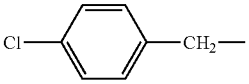 | 2 | 2 | 1 | — | H | 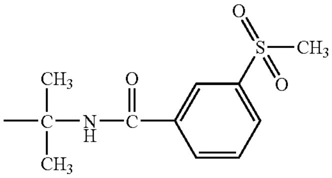 |
| 768 | 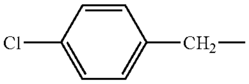 | 2 | 2 | 1 | — | H | 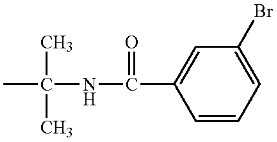 |
| 769 | 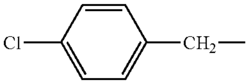 | 2 | 2 | 1 | — | H | 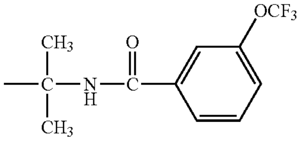 |
| 770 | 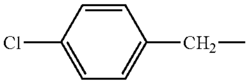 | 2 | 2 | 1 | — | H | 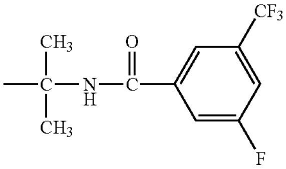 |
TABLE 1.71
| Compd. No. | 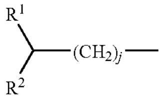 | k | m | n | chirality | $R^3$ | 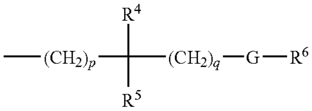 |
|---|---|---|---|---|---|---|---|
| 771 | 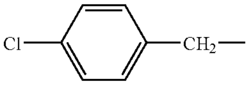 | 2 | 2 | 1 | — | H | 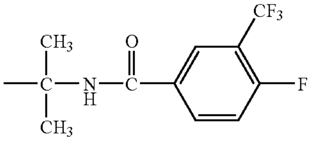 |
| 772 | 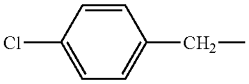 | 2 | 2 | 1 | — | H | 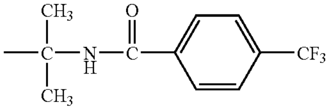 |
| 773 | 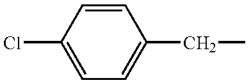 | 2 | 2 | 1 | — | H | 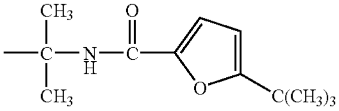 |

TABLE 1.71-continued
| Compd. No. | 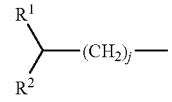 | k | m | n | chirality | $R^3$ | 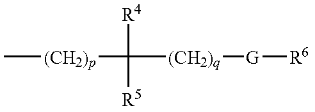 |
|---|---|---|---|---|---|---|---|
| 774 | 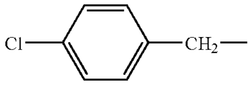 | 2 | 2 | 1 | — | H | 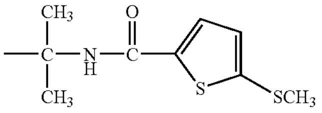 |
| 775 | 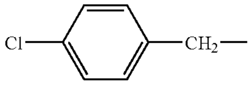 | 2 | 2 | 1 | — | H | 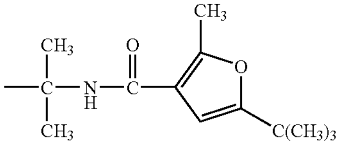 |
| 776 | 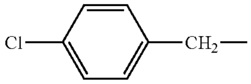 | 2 | 2 | 1 | — | H | 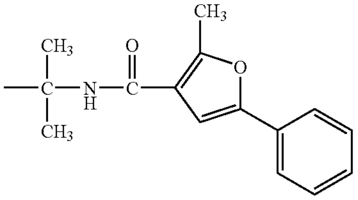 |
| 777 | 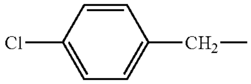 | 2 | 2 | 1 | — | H | 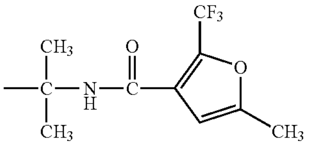 |
| 778 | 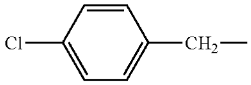 | 2 | 2 | 1 | — | H | 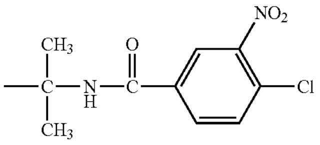 |
| 779 | 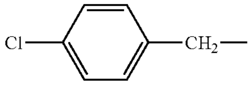 | 2 | 2 | 1 | — | H | 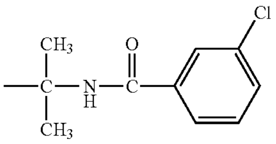 |
| 780 | 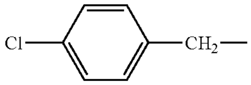 | 2 | 2 | 1 | — | H | 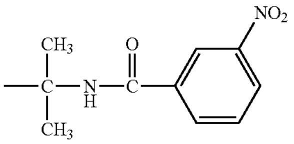 |
| 781 | 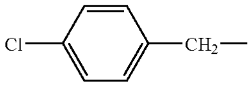 | 2 | 2 | 1 | — | H | 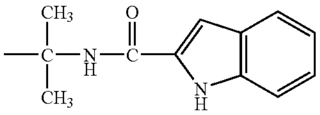 |

TABLE 1.72
| Compd. No. | 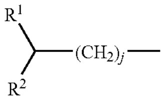 | k | m | n | chirality | $R^3$ | 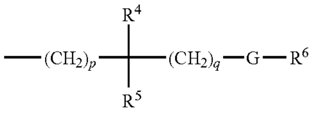 |
|---|---|---|---|---|---|---|---|
| 782 | 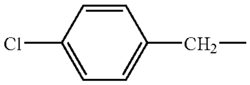 | 2 | 2 | 1 | — | H | 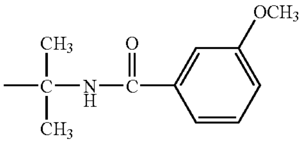 |
| 783 | 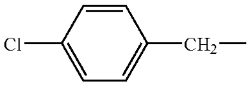 | 2 | 2 | 1 | — | H | 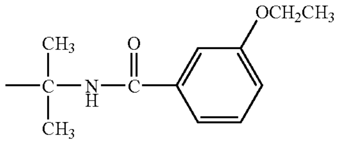 |
| 784 | 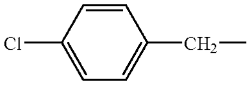 | 2 | 2 | 1 | — | H | 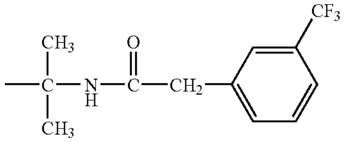 |
| 785 | 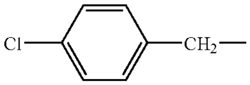 | 2 | 2 | 1 | — | H | 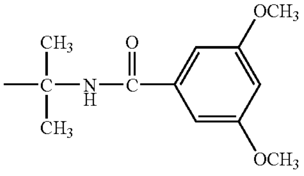 |
| 786 | 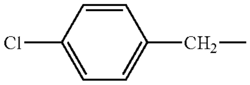 | 2 | 2 | 1 | — | H | 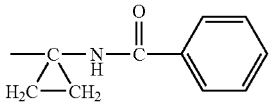 |
| 787 | 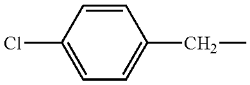 | 2 | 2 | 1 | — | H | 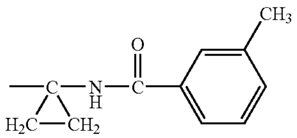 |
| 788 | 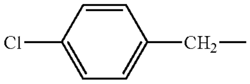 | 2 | 2 | 1 | — | H | 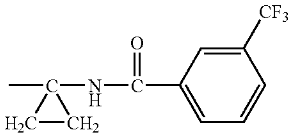 |
| 789 | 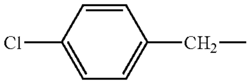 | 2 | 2 | 1 | — | H | 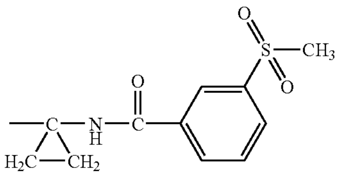 |
| 790 | 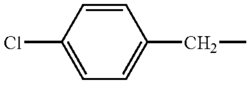 | 2 | 2 | 1 | — | H | 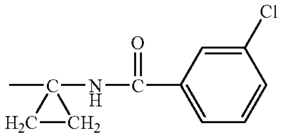 |

TABLE 1.72-continued
| Compd. No. | 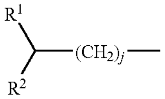 | k | m | n | chirality | $R^3$ | 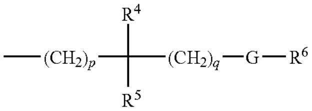 |
|---|---|---|---|---|---|---|---|
| 791 | 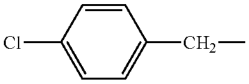 | 2 | 2 | 1 | — | H | 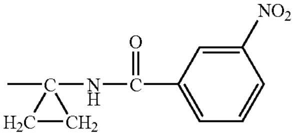 |
| 792 | 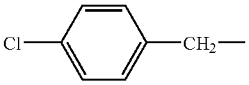 | 2 | 2 | 1 | — | H | 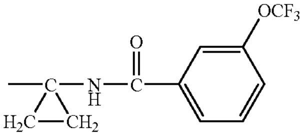 |
TABLE 1.73
| Compd. No. | 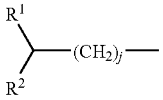 | k | m | n | chirality | $R^3$ | 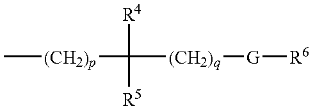 |
|---|---|---|---|---|---|---|---|
| 793 | 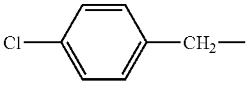 | 2 | 2 | 1 | — | H | 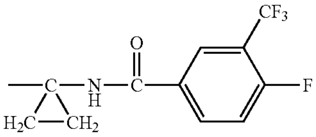 |
| 794 | 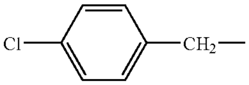 | 2 | 2 | 1 | — | H | 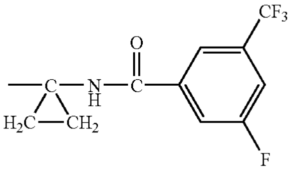 |
| 795 | 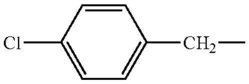 | 2 | 2 | 1 | — | H | 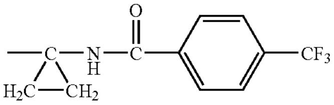 |
| 796 | 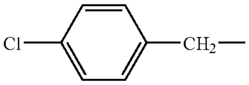 | 2 | 2 | 1 | — | H | 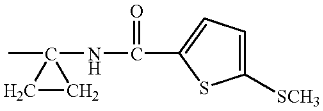 |
| 797 | 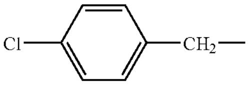 | 2 | 2 | 1 | — | H | 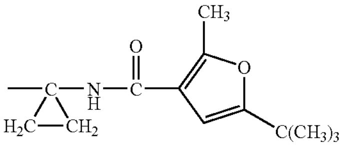 |
| 798 | 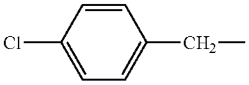 | 2 | 2 | 1 | — | H | 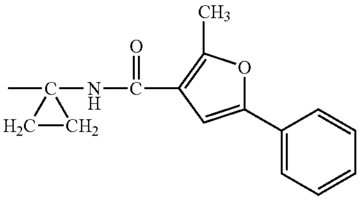 |

TABLE 1.73-continued
| Compd. No. | 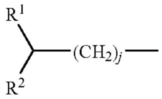 | k | m | n | chirality | $R^3$ | 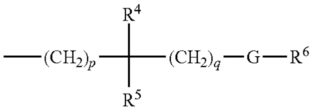 |
|---|---|---|---|---|---|---|---|
| 799 | 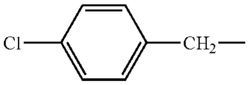 | 2 | 2 | 1 | — | H | 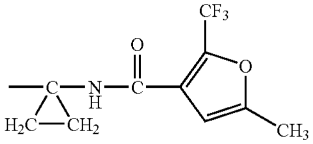 |
| 800 | 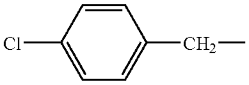 | 2 | 2 | 1 | — | H | 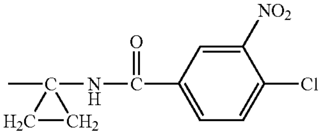 |
| 801 | 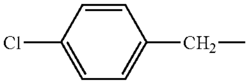 | 2 | 2 | 1 | — | H | 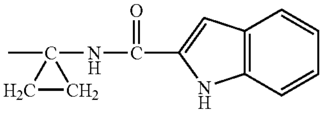 |
| 802 | 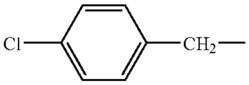 | 2 | 2 | 1 | — | H | 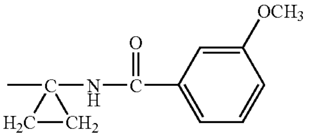 |
| 803 | 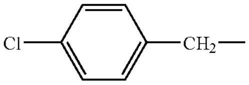 | 2 | 2 | 1 | — | H | 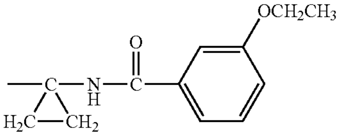 |
TABLE 1.74
| Compd. No. | 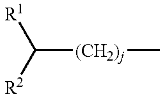 | k | m | n | chirality | $R^3$ | 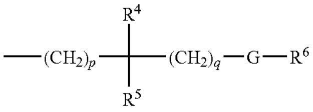 |
|---|---|---|---|---|---|---|---|
| 804 | 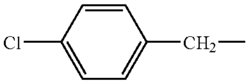 | 2 | 2 | 1 | — | H | 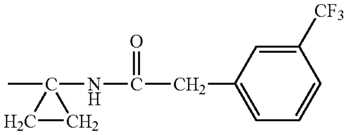 |
| 805 | 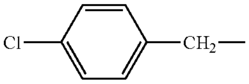 | 2 | 2 | 1 | — | H | 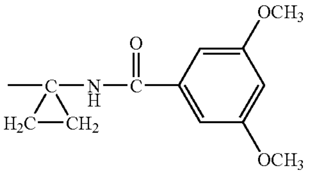 |
| 806 | 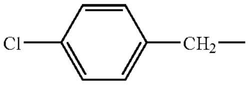 | 2 | 2 | 1 | — | H | 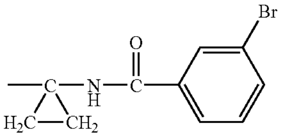 |

TABLE 1.74-continued
| Compd. No. | 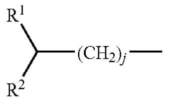 | k | m | n | chirality | $R^3$ | 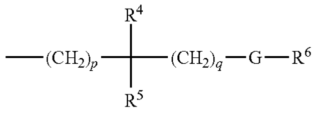 |
|---|---|---|---|---|---|---|---|
| 807 | 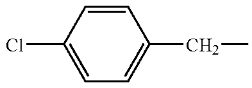 | 2 | 2 | 1 | — | H | 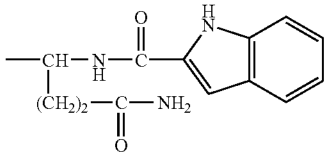 |
| 808 | 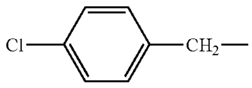 | 2 | 2 | 1 | — | H | 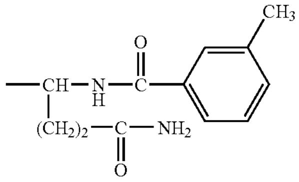 |
| 809 | 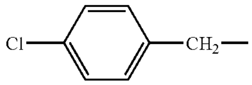 | 2 | 2 | 1 | — | H | 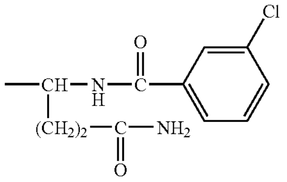 |
| 810 | 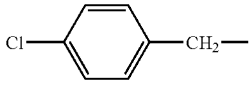 | 2 | 2 | 1 | — | H | 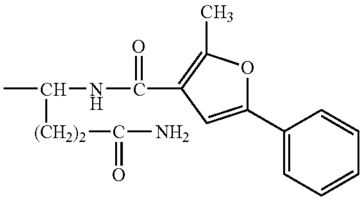 |
| 811 | 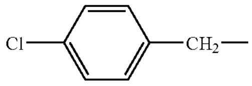 | 2 | 2 | 1 | — | H | 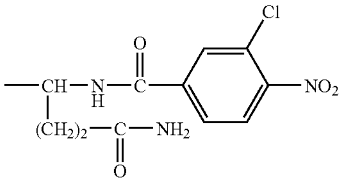 |
| 812 | 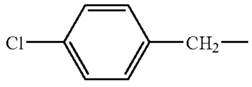 | 2 | 2 | 1 | — | H | 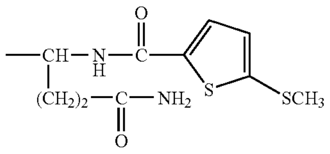 |
| 813 | 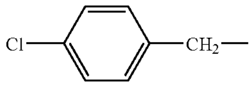 | 2 | 2 | 1 | — | H | 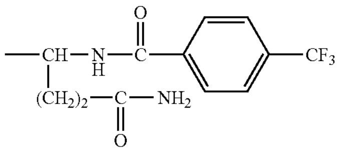 |
| 814 | 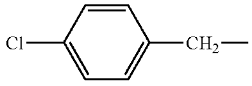 | 2 | 2 | 1 | — | H | 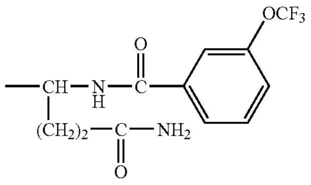 |

TABLE 1.75
| Compd. No. | 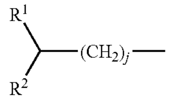 | k | m | n | chirality | $R^3$ | 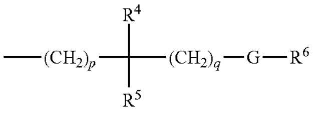 |
|---|---|---|---|---|---|---|---|
| 815 | 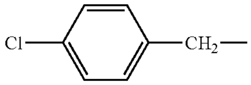 | 2 | 2 | 1 | — | H | 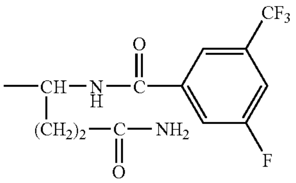 |
| 816 | 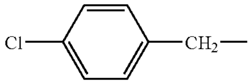 | 2 | 2 | 1 | — | H | 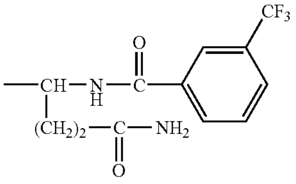 |
| 817 | 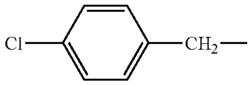 | 2 | 2 | 1 | — | H | 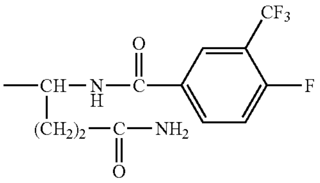 |
| 818 | 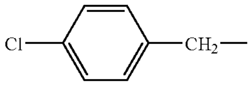 | 2 | 2 | 1 | — | H | 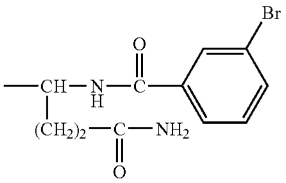 |
| 819 | 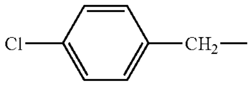 | 2 | 2 | 1 | — | H | 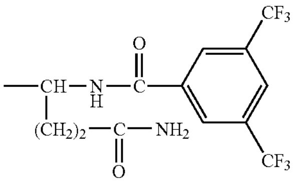 |
| 820 | 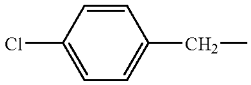 | 2 | 2 | 1 | — | H | 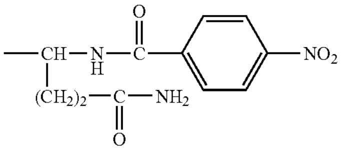 |
| 821 | 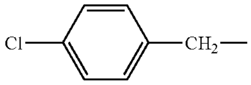 | 2 | 2 | 1 | — | H | 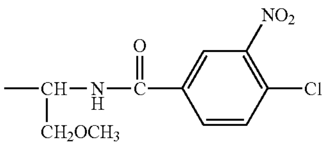 |
| 822 | 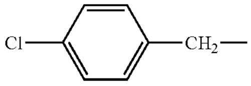 | 2 | 2 | 1 | — | H | 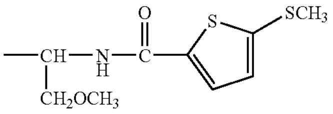 |

TABLE 1.75-continued
| Compd. No. | 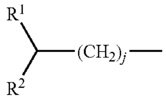 | k | m | n | chirality | $R^3$ | 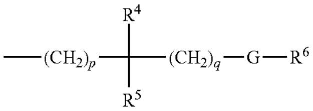 |
|---|---|---|---|---|---|---|---|
| 823 | 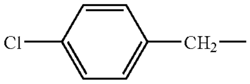 | 2 | 2 | 1 | — | H | 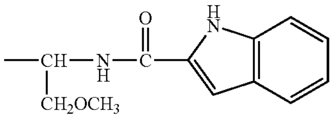 |
| 824 | 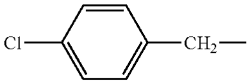 | 2 | 2 | 1 | — | H | 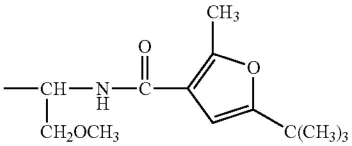 |
| 825 | 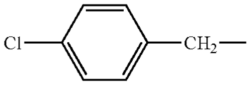 | 2 | 2 | 1 | — | H | 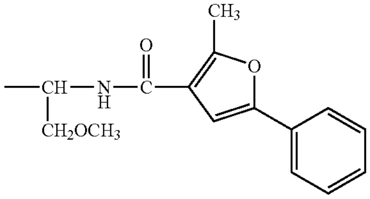 |
TABLE 1.76
| Compd. No. | 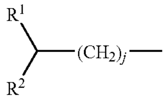 | k | m | n | chirality | $R^3$ | 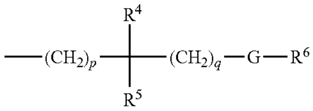 |
|---|---|---|---|---|---|---|---|
| 826 | 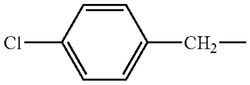 | 2 | 2 | 1 | — | H | 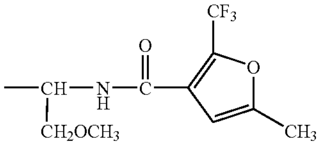 |
| 827 | 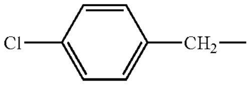 | 2 | 2 | 1 | — | H | 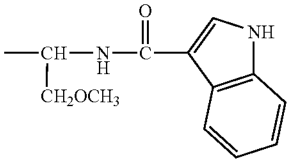 |
| 828 | 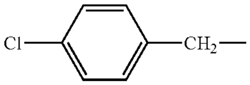 | 2 | 2 | 1 | — | H | 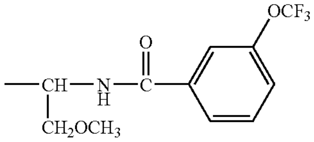 |
| 829 | 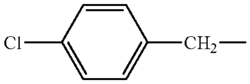 | 2 | 2 | 1 | — | H | 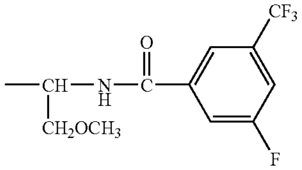 |

TABLE 1.76-continued
| Compd. No. | 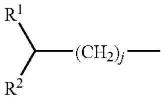 | k | m | n | chirality | $R^3$ | 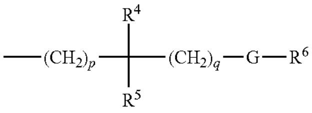 |
|---|---|---|---|---|---|---|---|
| 830 | 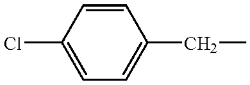 | 2 | 2 | 1 | — | H | 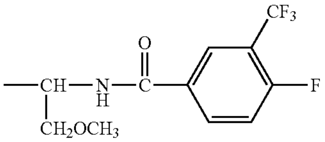 |
| 831 | 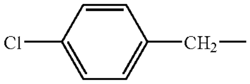 | 2 | 2 | 1 | — | H | 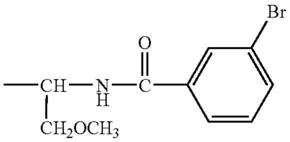 |
| 832 | 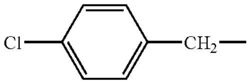 | 2 | 2 | 1 | — | H | 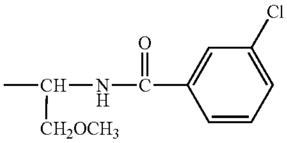 |
| 833 | 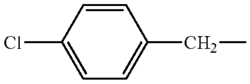 | 2 | 2 | 1 | — | H | 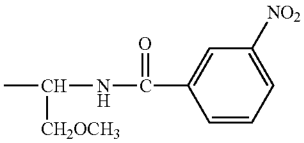 |
| 834 | 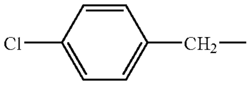 | 2 | 2 | 1 | — | H | 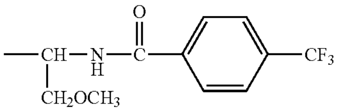 |
| 835 | 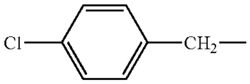 | 2 | 2 | 1 | — | H | 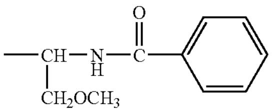 |
| 836 | 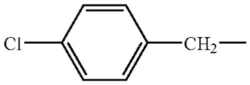 | 2 | 2 | 1 | — | H | 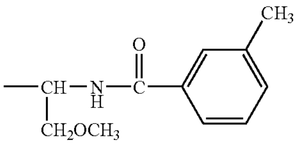 |
TABLE 1.77
| Compd. No. | 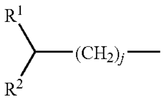 | k | m | n | chirality | $R^3$ | 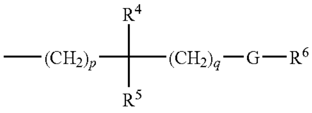 |
|---|---|---|---|---|---|---|---|
| 837 | 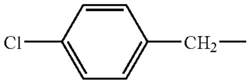 | 2 | 2 | 1 | — | H | 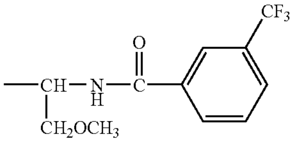 |

TABLE 1.77-continued
| Compd. No. | 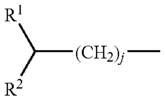 | k | m | n | chirality | $R^3$ | 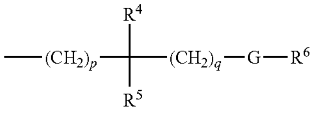 |
|---|---|---|---|---|---|---|---|
| 838 | 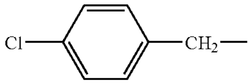 | 2 | 2 | 1 | — | H | 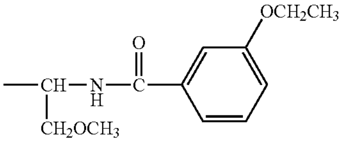 |
| 839 | 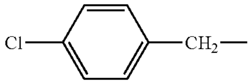 | 2 | 2 | 1 | — | H | 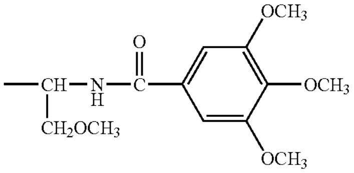 |
| 840 | 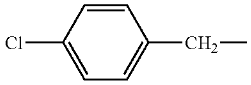 | 2 | 2 | 1 | — | H | 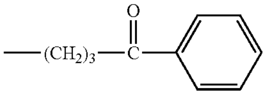 |
| 841 | 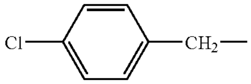 | 2 | 2 | 1 | — | H | 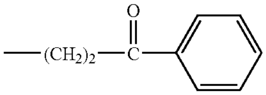 |
| 842 | 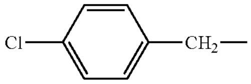 | 2 | 2 | 1 | — | H | 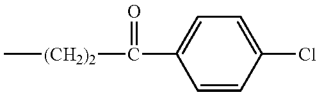 |
| 843 | 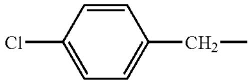 | 2 | 2 | 1 | — | H | 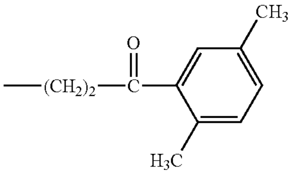 |
| 844 | 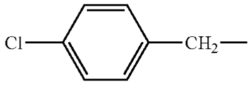 | 2 | 2 | 1 | — | H | 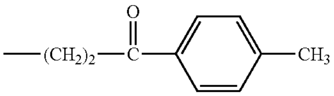 |
| 845 | 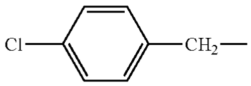 | 2 | 2 | 1 | — | H | 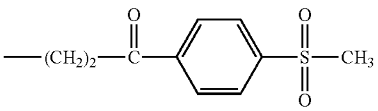 |
| 846 | 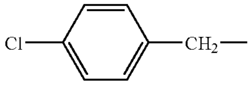 | 2 | 2 | 1 | — | H | 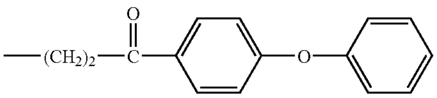 |
| 847 | 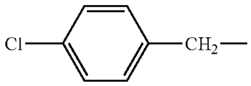 | 2 | 2 | 1 | — | H | 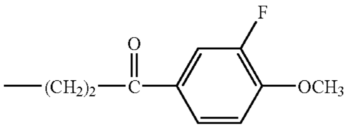 |

TABLE 1.78
| Compd. No. | 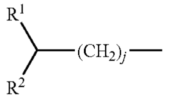 | k | m | n | chirality | $R^3$ | 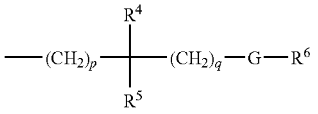 |
|---|---|---|---|---|---|---|---|
| 848 | 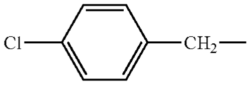 | 2 | 2 | 1 | — | H | 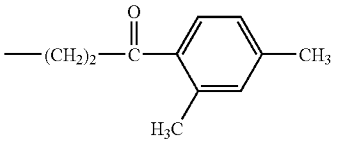 |
| 849 | 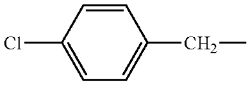 | 2 | 2 | 1 | — | H | 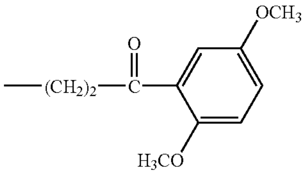 |
| 850 | 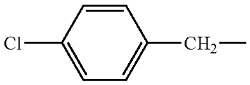 | 2 | 2 | 1 | — | H | 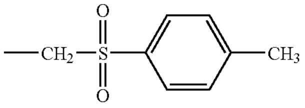 |
| 851 | 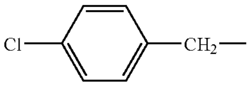 | 2 | 2 | 1 | — | H | 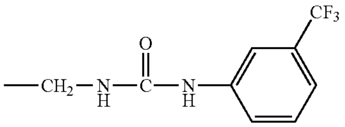 |
| 852 | 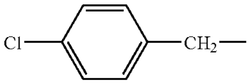 | 2 | 2 | 1 | — | H | 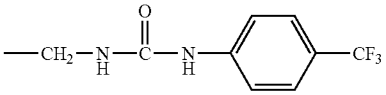 |
| 853 | 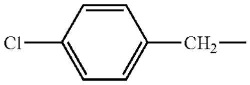 | 2 | 2 | 1 | — | H | 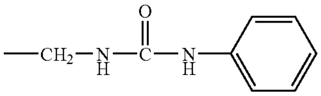 |
| 854 | 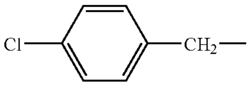 | 2 | 2 | 1 | — | H | 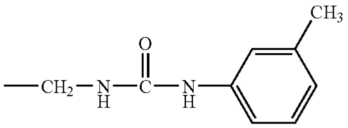 |
| 855 | 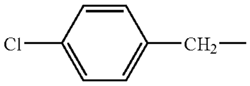 | 2 | 2 | 1 | — | H | 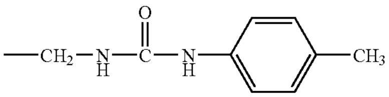 |
| 856 | 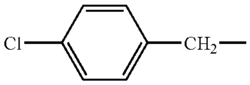 | 2 | 2 | 1 | — | H | 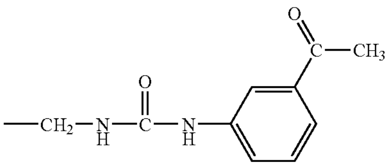 |
| 857 | 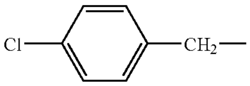 | 2 | 2 | 1 | — | H | 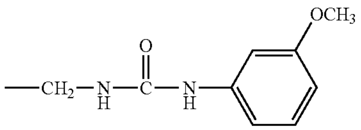 |

TABLE 1.78-continued
| Compd. No. | 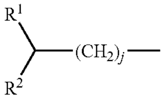 | k | m | n | chirality | R³ | 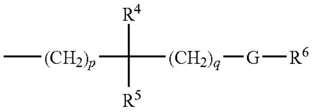 |
|---|---|---|---|---|---|---|---|
| 858 | 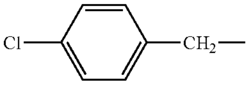 | 2 | 2 | 1 | — | H | 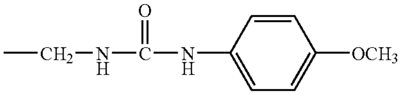 |
TABLE 1.79
| Compd. No. | 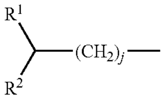 | k | m | n | chirality | R³ | 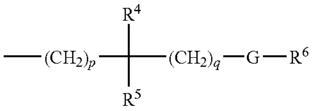 |
|---|---|---|---|---|---|---|---|
| 859 | 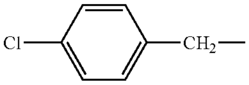 | 2 | 2 | 1 | — | H | 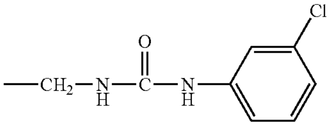 |
| 860 | 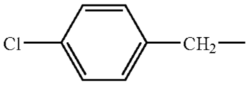 | 2 | 2 | 1 | — | H | 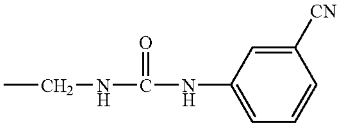 |
| 861 | 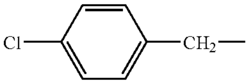 | 2 | 2 | 1 | — | H | 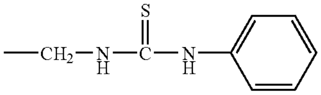 |
| 862 | 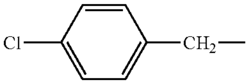 | 2 | 2 | 1 | — | H | 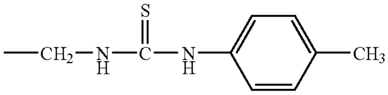 |
| 863 | 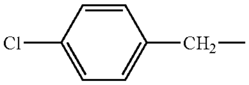 | 2 | 2 | 1 | — | H | 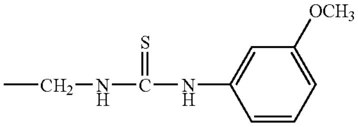 |
| 864 | 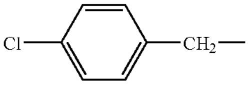 | 2 | 2 | 1 | — | H | 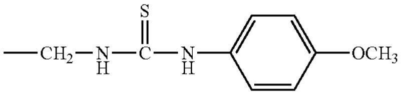 |
| 865 | 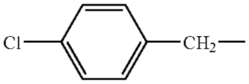 | 2 | 2 | 1 | — | H | 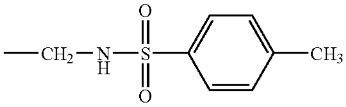 |
| 866 | 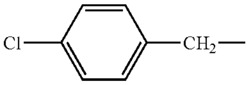 | 2 | 2 | 1 | — | H | 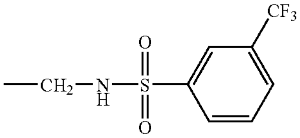 |

TABLE 1.79-continued
| Compd. No. | 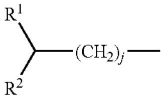 | k | m | n | chirality | R3 | 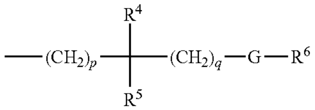 |
|---|---|---|---|---|---|---|---|
| 867 | 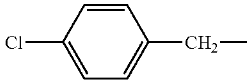 | 2 | 2 | 1 | — | H | 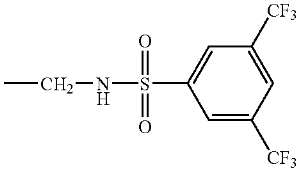 |
| 868 | 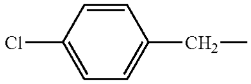 | 2 | 2 | 1 | — | H | 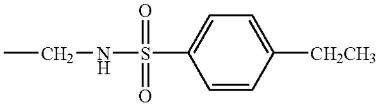 |
| 869 | 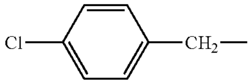 | 2 | 2 | 1 | — | H | 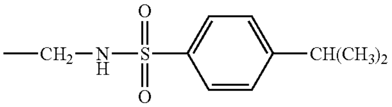 |
TABLE 1.80
| Compd. No. | 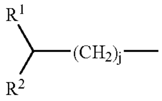 | k | m | n | chirality | R3 | 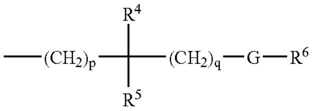 |
|---|---|---|---|---|---|---|---|
| 870 | 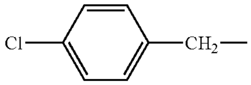 | 2 | 2 | 1 | — | H | 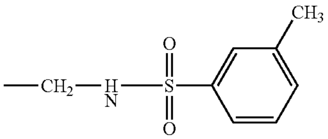 |
| 871 | 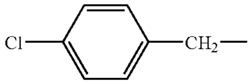 | 2 | 2 | 1 | — | H | 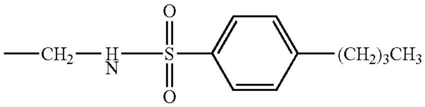 |
| 872 | 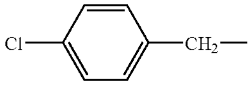 | 2 | 2 | 1 | — | H | 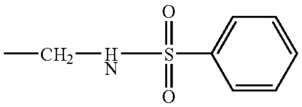 |
| 873 | 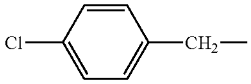 | 2 | 2 | 1 | — | H | 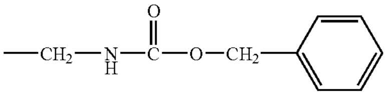 |
| 874 | 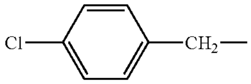 | 2 | 2 | 1 | — | H | 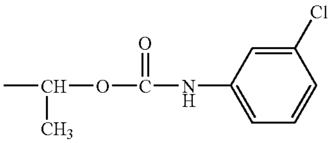 |
| 875 | 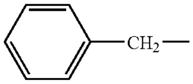 | 2 | 2 | 1 | — | H | 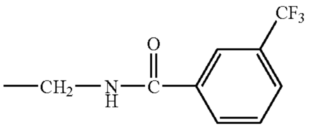 |

TABLE 1.80-continued
| Compd. No. | 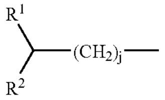 | k | m | n | chirality | $R^3$ | 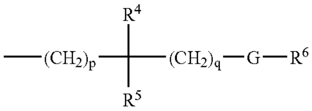 |
|---|---|---|---|---|---|---|---|
| 876 | 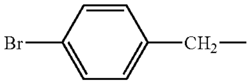 | 2 | 2 | 1 | — | H | 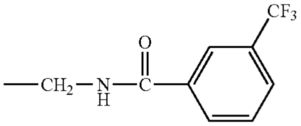 |
| 877 | 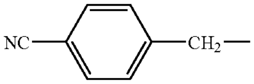 | 2 | 2 | 1 | — | H | 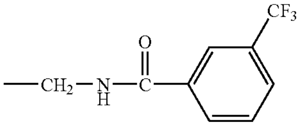 |
| 878 | 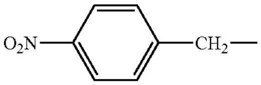 | 2 | 2 | 1 | — | H | 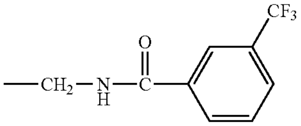 |
| 879 | 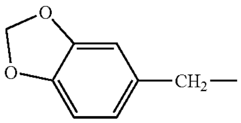 | 2 | 2 | 1 | — | H | 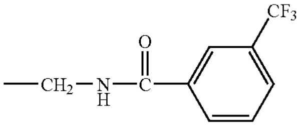 |
| 880 | 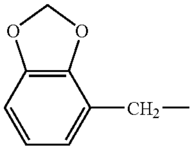 | 2 | 2 | 1 | — | H | 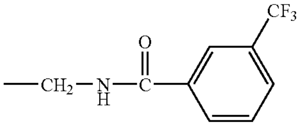 |
TABLE 1.81
| Compd. No. | 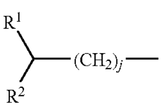 | k | m | n | chirality | $R^3$ | 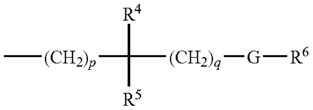 |
|---|---|---|---|---|---|---|---|
| 881 | 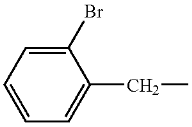 | 2 | 2 | 1 | — | H | 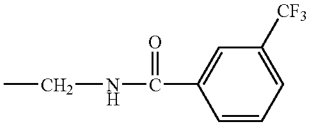 |
| 882 | 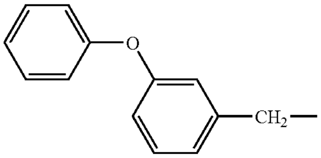 | 2 | 2 | 1 | — | H | 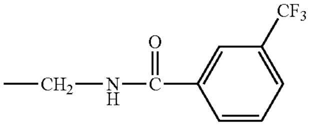 |
| 883 | 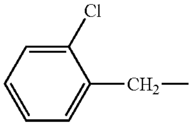 | 2 | 2 | 1 | — | H | 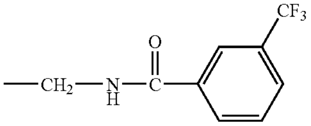 |

TABLE 1.81-continued
| Compd. No. | 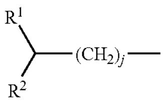 | k | m | n | chirality | $R^3$ | 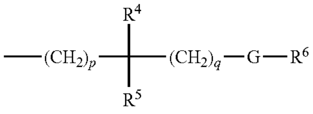 |
|---|---|---|---|---|---|---|---|
| 884 | 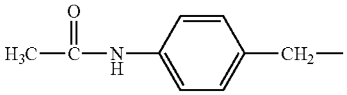 | 2 | 2 | 1 | — | H | 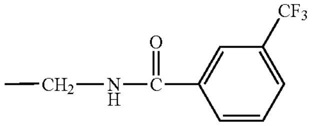 |
| 885 | 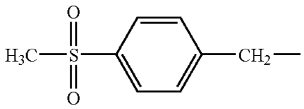 | 2 | 2 | 1 | — | H | 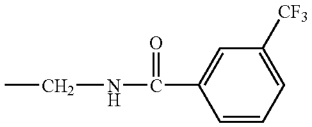 |
| 886 | 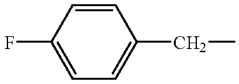 | 2 | 2 | 1 | — | H | 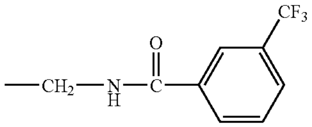 |
| 887 | 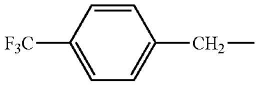 | 2 | 2 | 1 | — | H | 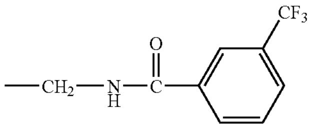 |
| 888 | 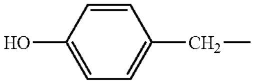 | 2 | 2 | 1 | — | H | 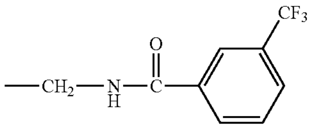 |
| 889 | 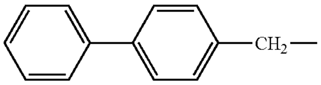 | 2 | 2 | 1 | — | H | 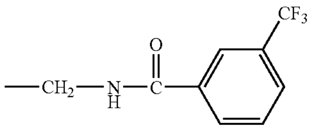 |
| 890 | 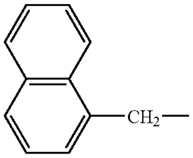 | 2 | 2 | 1 | — | H | 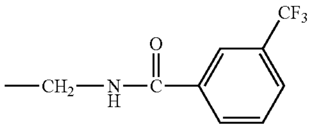 |
| 891 | 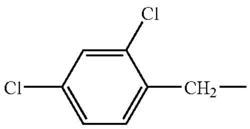 | 2 | 2 | 1 | — | H | 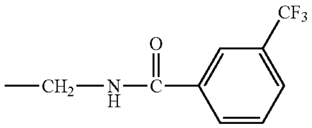 |

TABLE 1.82
| Compd. No. | 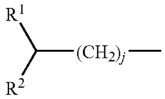 | k | m | n | chirality | $R^3$ | 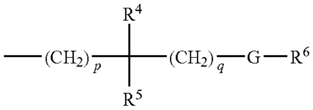 |
|---|---|---|---|---|---|---|---|
| 892 | 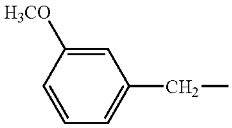 | 2 | 2 | 1 | — | H | 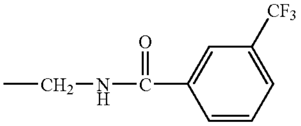 |
| 893 | 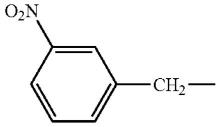 | 2 | 2 | 1 | — | H | 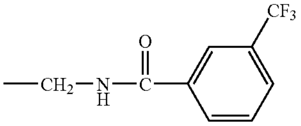 |
| 894 | 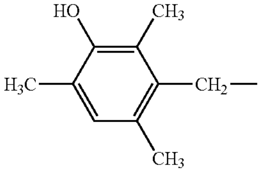 | 2 | 2 | 1 | — | H | 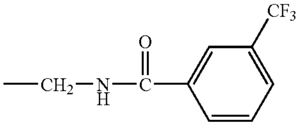 |
| 895 | 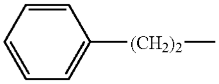 | 2 | 2 | 1 | — | H | 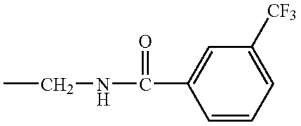 |
| 896 | 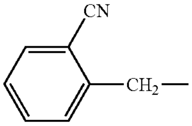 | 2 | 2 | 1 | — | H | 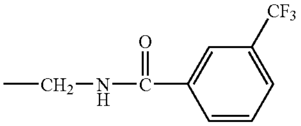 |
| 897 | 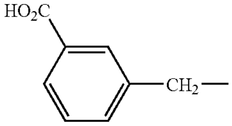 | 2 | 2 | 1 | — | H | 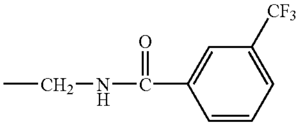 |
| 898 | 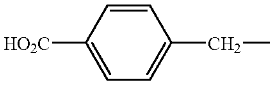 | 2 | 2 | 1 | — | H | 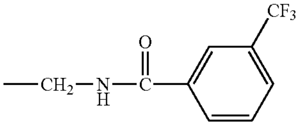 |
| 899 | 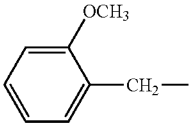 | 2 | 2 | 1 | — | H | 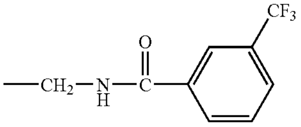 |
| 900 | 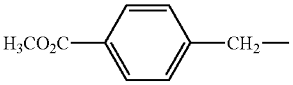 | 2 | 2 | 1 | — | H | 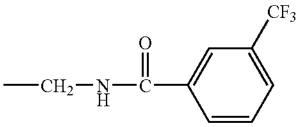 |

TABLE 1.82-continued
| Compd. No. | 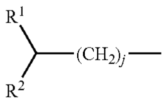 | k | m | n | chirality | $R^3$ | 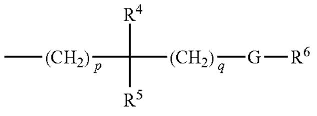 |
|---|---|---|---|---|---|---|---|
| 901 | 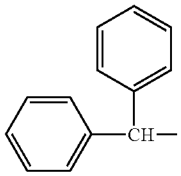 | 2 | 2 | 1 | — | H | 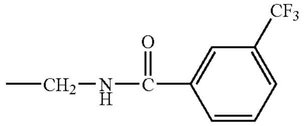 |
| 902 | 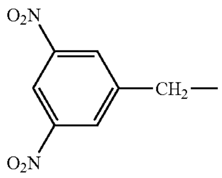 | 2 | 2 | 1 | — | H | 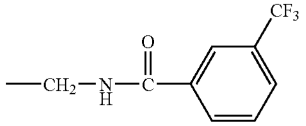 |
TABLE 1.83
| Compd. No. | 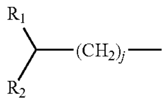 | k | m | n | chirality | $R^3$ | 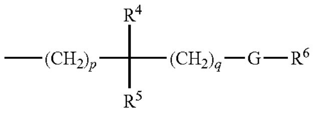 |
|---|---|---|---|---|---|---|---|
| 903 | 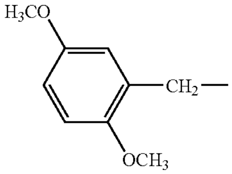 | 2 | 2 | 1 | — | H | 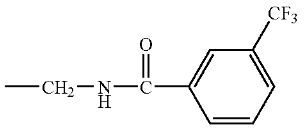 |
| 904 | 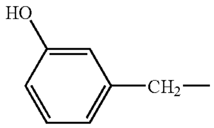 | 2 | 2 | 1 | — | H | 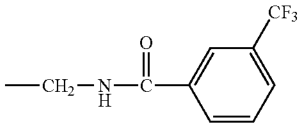 |
| 905 | 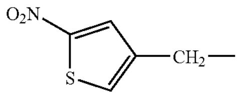 | 2 | 2 | 1 | — | H | 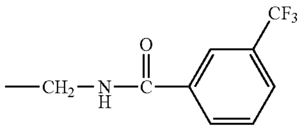 |
| 906 | 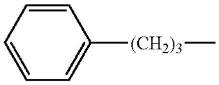 | 2 | 2 | 1 | — | H | 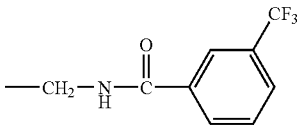 |
| 907 | 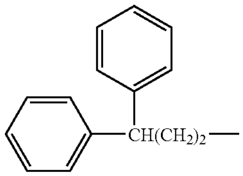 | 2 | 2 | 1 | — | H | 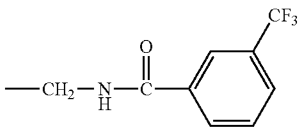 |

TABLE 1.83-continued
| Compd. No. | 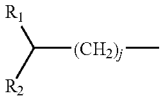 | k | m | n | chirality | $R^3$ | 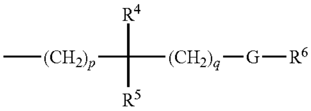 |
|---|---|---|---|---|---|---|---|
| 908 | 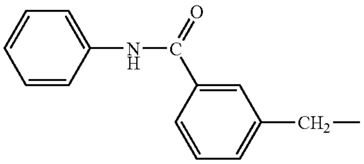 | 2 | 2 | 1 | — | H | 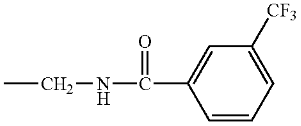 |
| 909 | 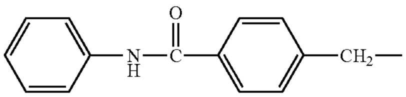 | 2 | 2 | 1 | — | H | 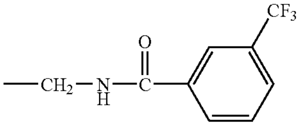 |
| 910 | 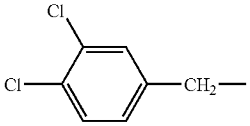 | 2 | 2 | 1 | — | H | 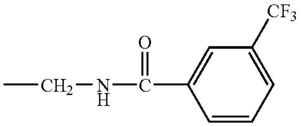 |
| 911 | 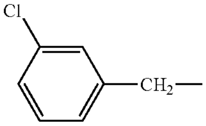 | 2 | 2 | 1 | — | H | 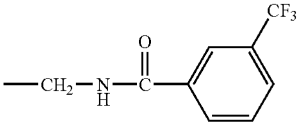 |
| 912 | 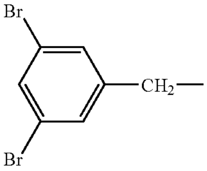 | 2 | 2 | 1 | — | H | 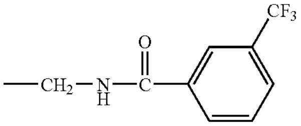 |
| 913 | 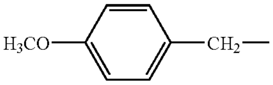 | 2 | 2 | 1 | — | H | 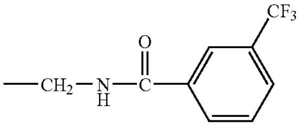 |
TABLE 1.84
| Compd. No. | 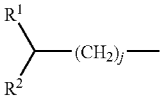 | k | m | n | chirality | $R^3$ | 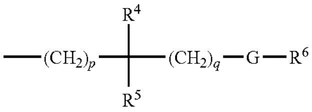 |
|---|---|---|---|---|---|---|---|
| 914 | 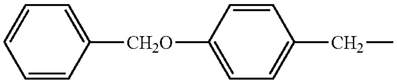 | 2 | 2 | 1 | — | H | 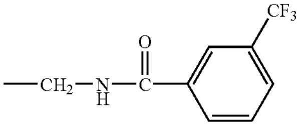 |
| 915 | 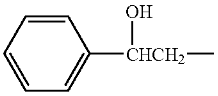 | 2 | 2 | 1 | — | H | 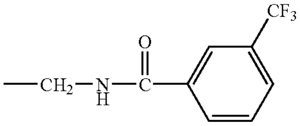 |

TABLE 1.84-continued
| Compd. No. | 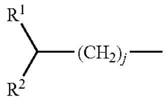 | k | m | n | chirality | $R^3$ | 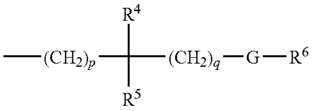 |
|---|---|---|---|---|---|---|---|
| 916 | 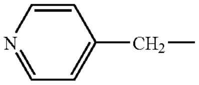 | 2 | 2 | 1 | — | H | 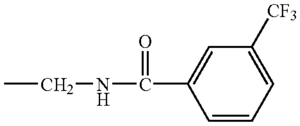 |
| 917 | 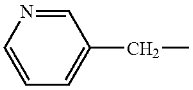 | 2 | 2 | 1 | — | H | 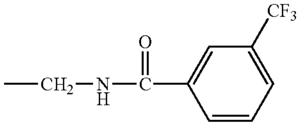 |
| 918 | 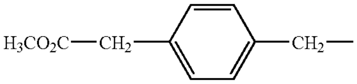 | 2 | 2 | 1 | — | H | 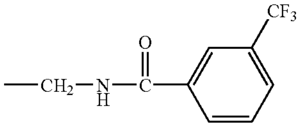 |
| 919 | 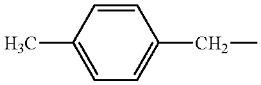 | 2 | 2 | 1 | — | H | 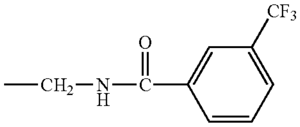 |
| 920 | 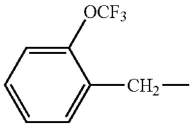 | 2 | 2 | 1 | — | H | 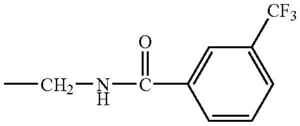 |
| 921 | 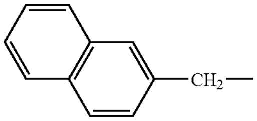 | 2 | 2 | 1 | — | H | 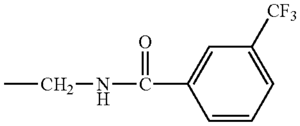 |
| 922 | 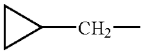 | 2 | 2 | 1 | — | H | 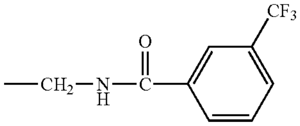 |
| 923 | 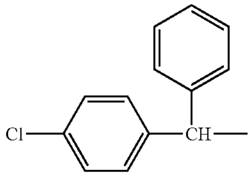 | 2 | 2 | 1 | — | H | 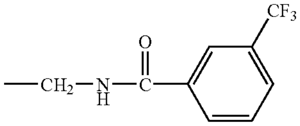 |
| 924 | 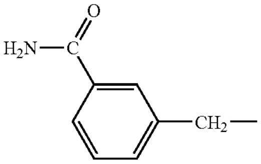 | 2 | 2 | 1 | — | H | 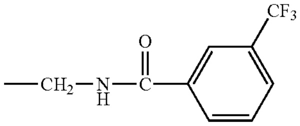 |

TABLE 1.85
| Compd. No. | 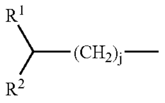 | k | m | n | chirality | $R^3$ | 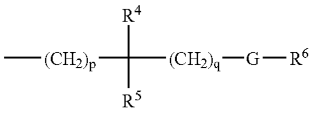 |
|---|---|---|---|---|---|---|---|
| 925 | 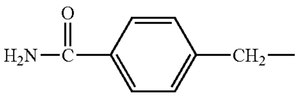 | 2 | 2 | 1 | — | H | 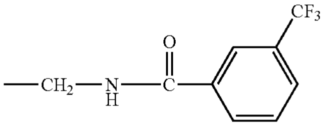 |
| 926 | 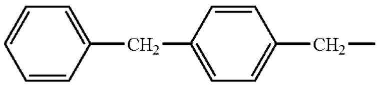 | 2 | 2 | 1 | — | H | 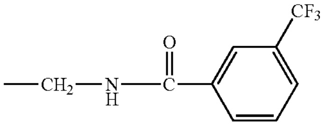 |
| 927 | 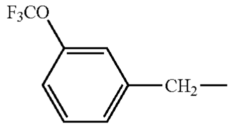 | 2 | 2 | 1 | — | H | 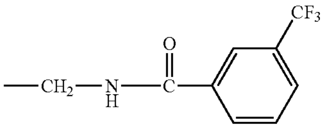 |
| 928 | 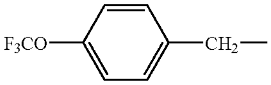 | 2 | 2 | 1 | — | H | 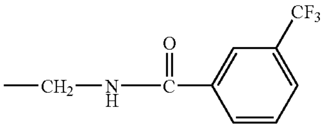 |
| 929 | 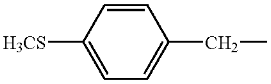 | 2 | 2 | 1 | — | H | 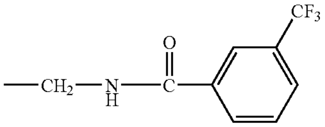 |
| 930 | 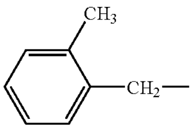 | 2 | 2 | 1 | — | H | 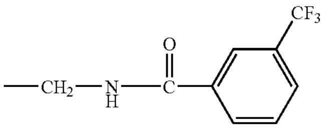 |
| 931 | 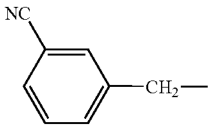 | 2 | 2 | 1 | — | H | 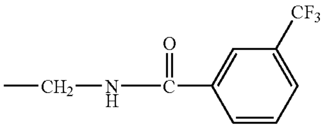 |
| 932 | 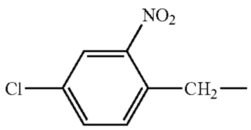 | 2 | 2 | 1 | — | H | 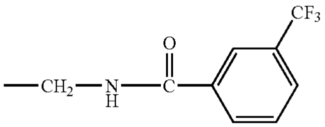 |
| 933 | 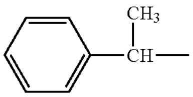 | 2 | 2 | 1 | — | H | 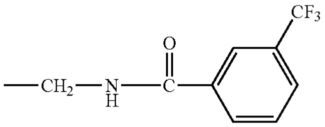 |
| 934 | 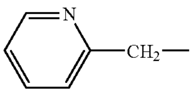 | 2 | 2 | 1 | — | H | 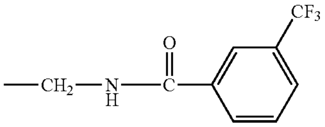 |

TABLE 1.85-continued
| Compd. No. | 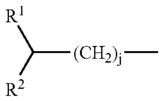 | k | m | n | chirality | $R^3$ | 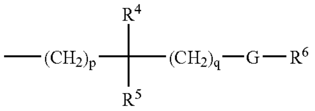 |
|---|---|---|---|---|---|---|---|
| 935 | 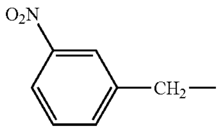 | 2 | 2 | 1 | — | H | 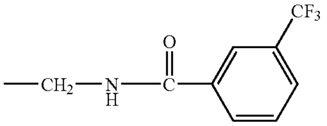 |
TABLE 1.86
| Compd. No. | 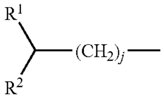 | k | m | n | chirality | $R^3$ | 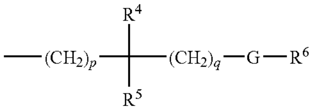 |
|---|---|---|---|---|---|---|---|
| 936 | 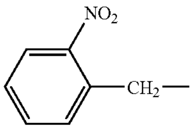 | 2 | 2 | 1 | — | H | 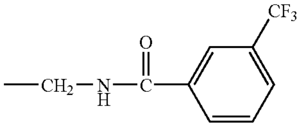 |
| 937 | 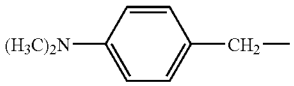 | 2 | 2 | 1 | — | H | 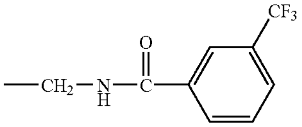 |
| 938 | 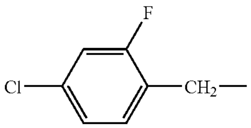 | 2 | 2 | 1 | — | H | 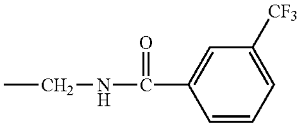 |
| 939 | 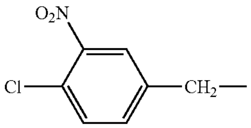 | 2 | 2 | 1 | — | H | 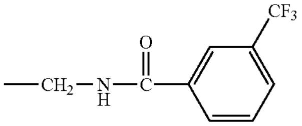 |
| 940 | 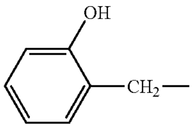 | 2 | 2 | 1 | — | H | 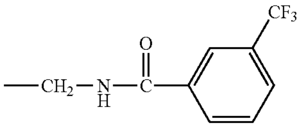 |
| 941 | 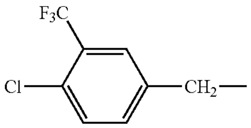 | 2 | 2 | 1 | — | H | 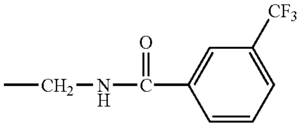 |
| 942 | 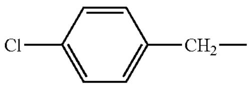 | 2 | 2 | 1 | — | H | 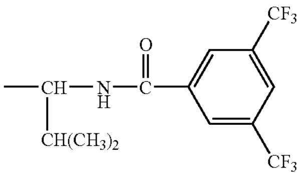 |

TABLE 1.86-continued
| Compd. No. | 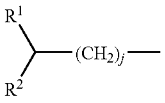 | k | m | n | chirality | $R^3$ | 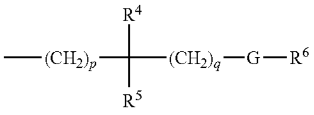 |
|---|---|---|---|---|---|---|---|
| 943 | 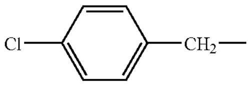 | 1 | 4 | 0 | — | H | 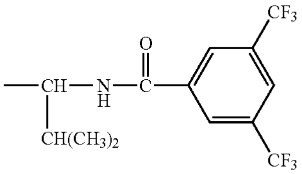 |
| 944 | 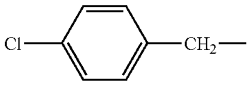 | 1 | 4 | 0 | — | H | 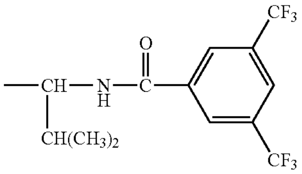 |
| 945 | 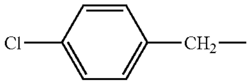 | 1 | 4 | 0 | — | H | 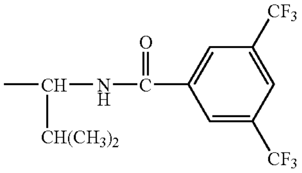 |
| 946 | 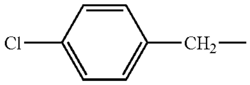 | 1 | 4 | 0 | — | H | 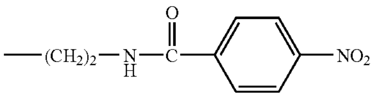 |
TABLE 1.87
| Compd. No. | 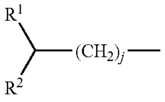 | k | m | n | chirality | $R^3$ | 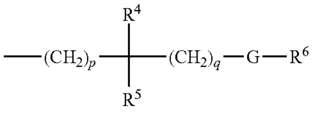 |
|---|---|---|---|---|---|---|---|
| 947 | 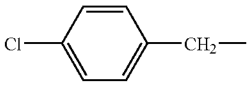 | 1 | 4 | 0 | — | H | 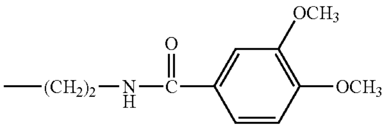 |
| 948 | 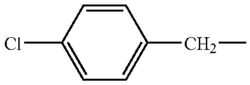 | 1 | 4 | 0 | — | H | 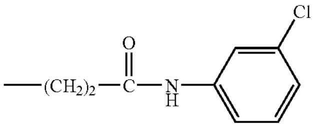 |
| 949 | 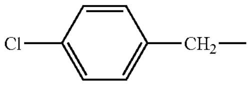 | 1 | 4 | 0 | — | H | 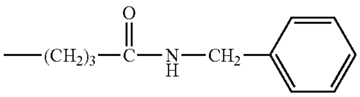 |
| 950 | 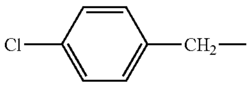 | 0 | 4 | 1 | — | H | 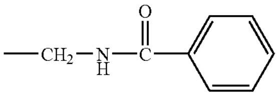 |

TABLE 1.87-continued
| Compd. No. | 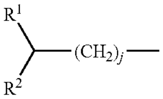 | k | m | n | chirality | $R^3$ | 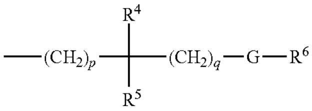 |
|---|---|---|---|---|---|---|---|
| 951 | 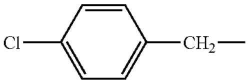 | 1 | 2 | 0 | R | H | 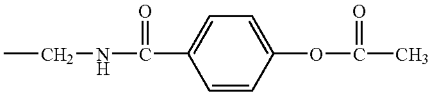 |
| 952 | 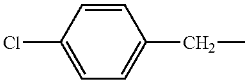 | 1 | 2 | 0 | R | H | 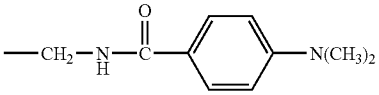 |
| 953 | 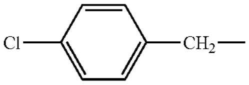 | 1 | 2 | 0 | R | H | 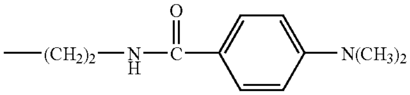 |
| 954 | 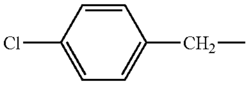 | 1 | 2 | 0 | R | H | 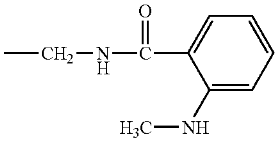 |
| 955 | 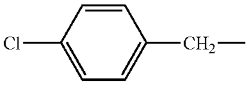 | 1 | 2 | 0 | R | H | 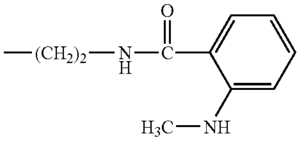 |
| 956 | 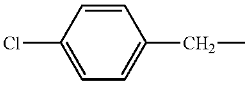 | 1 | 2 | 0 | R | H | 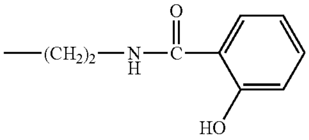 |
| 957 | 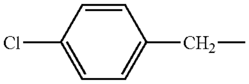 | 1 | 2 | 0 | R | H | 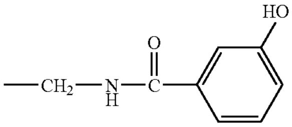 |
TABLE 1.88
| Compd. No. | 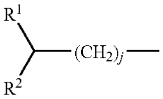 | k | m | n | chirality | $R^3$ | 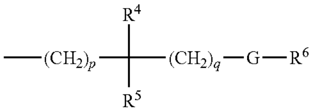 |
|---|---|---|---|---|---|---|---|
| 958 | 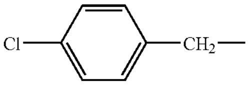 | 1 | 2 | 0 | R | H | 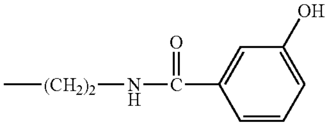 |
| 959 | 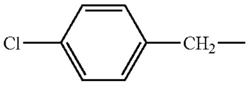 | 1 | 2 | 0 | R | H | 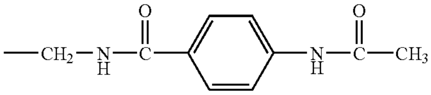 |

TABLE 1.88-continued
| Compd. No. | 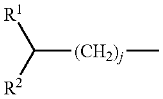 | k | m | n | chirality | $R^3$ | 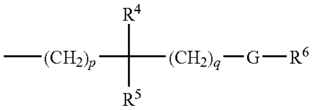 |
|---|---|---|---|---|---|---|---|
| 960 | 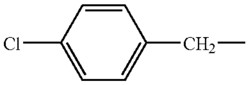 | 1 | 2 | 0 | R | H | 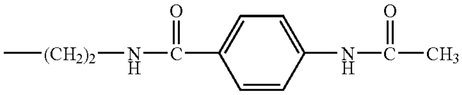 |
| 961 | 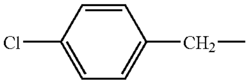 | 1 | 2 | 0 | R | H | 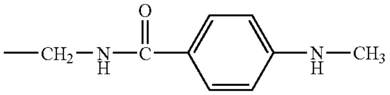 |
| 962 | 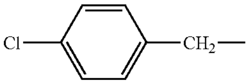 | 1 | 2 | 0 | R | H | 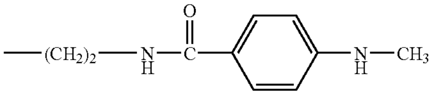 |
| 963 | 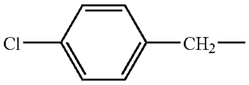 | 1 | 2 | 0 | R | H | 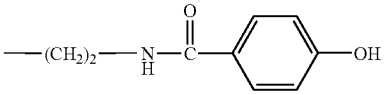 |
| 964 | 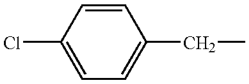 | 1 | 2 | 0 | R | H | 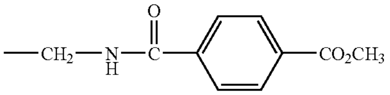 |
| 965 | 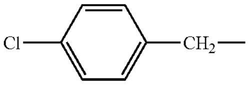 | 1 | 4 | 0 | R | H | 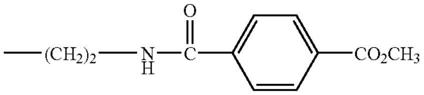 |
| 966 | 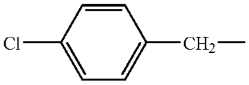 | 1 | 4 | 0 | R | H | 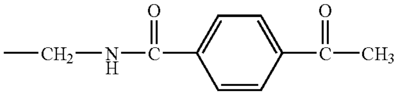 |
| 967 | 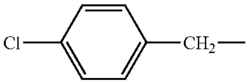 | 1 | 4 | 0 | R | H | 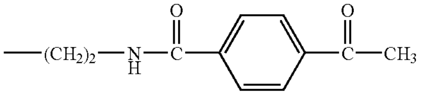 |
| 968 | 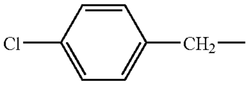 | 1 | 4 | 0 | R | H | 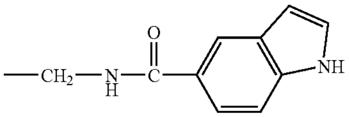 |
TABLE 1.89
| Compd. No. | 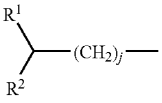 | k | m | n | chirality | $R^3$ | 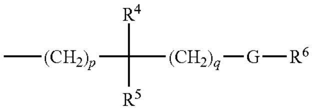 |
|---|---|---|---|---|---|---|---|
| 969 | 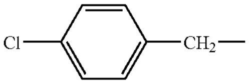 | 1 | 2 | 0 | R | H | 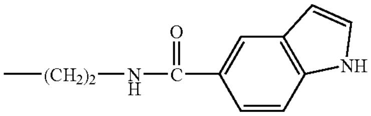 |

TABLE 1.89-continued
| Compd. No. | 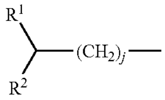 | k | m | n | chirality | $R^3$ | 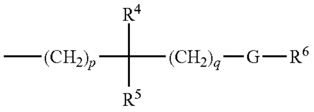 |
|---|---|---|---|---|---|---|---|
| 970 | 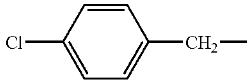 | 1 | 2 | 0 | R | H | 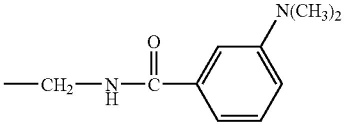 |
| 971 | 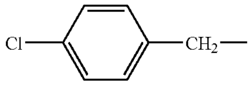 | 1 | 2 | 0 | R | H | 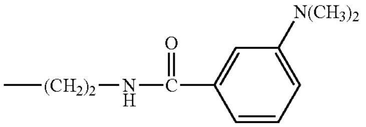 |
| 972 | 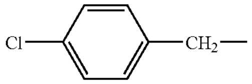 | 1 | 2 | 0 | R | H | 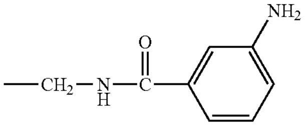 |
| 973 | 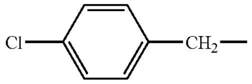 | 1 | 2 | 0 | R | H | 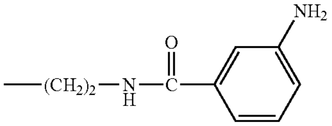 |
| 974 | 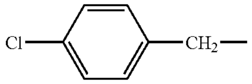 | 1 | 2 | 0 | R | H | 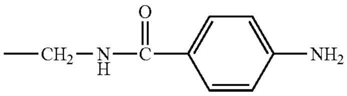 |
| 975 | 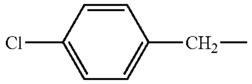 | 1 | 2 | 0 | R | H | 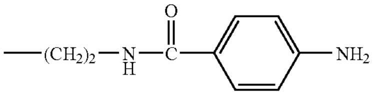 |
| 976 | 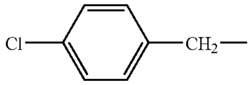 | 1 | 4 | 0 | R | H | 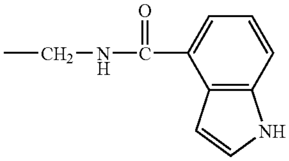 |
| 977 | 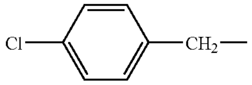 | 1 | 4 | 0 | R | H | 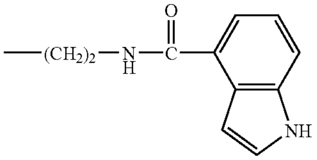 |
| 978 | 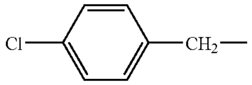 | 1 | 4 | 0 | R | H | 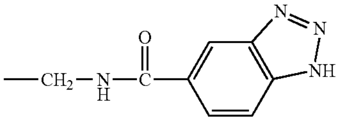 |
| 979 | 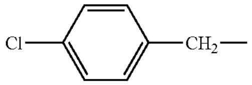 | 1 | 4 | 0 | R | H | 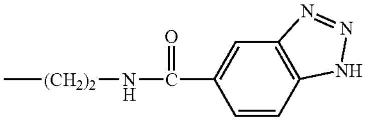 |

TABLE 1.90
| Compd. No. | 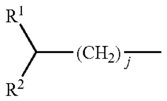 | k | m | n | chirality | $R^3$ | 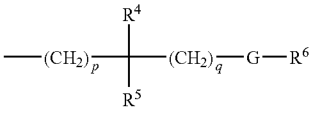 |
|---|---|---|---|---|---|---|---|
| 980 | 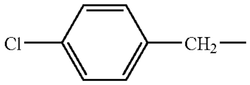 | 1 | 2 | 0 | R | H | 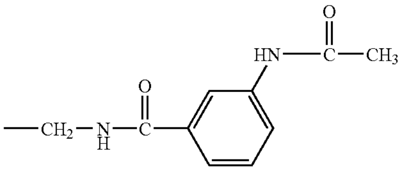 |
| 981 | 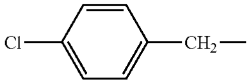 | 1 | 2 | 0 | R | H | 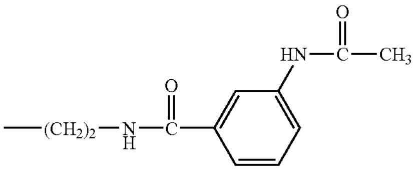 |
| 982 | 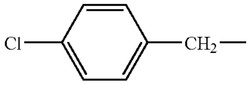 | 1 | 2 | 0 | R | H | 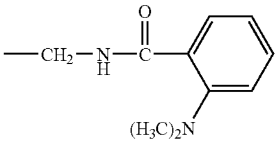 |
| 983 | 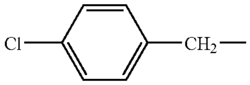 | 1 | 2 | 0 | R | H | 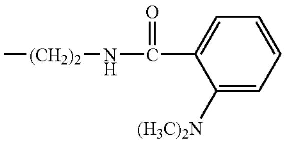 |
| 984 | 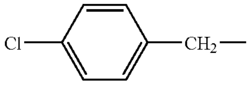 | 1 | 2 | 0 | R | H | 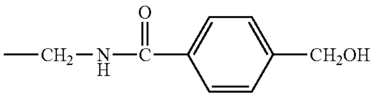 |
| 985 | 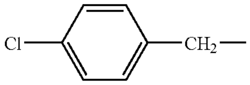 | 1 | 2 | 0 | R | H | 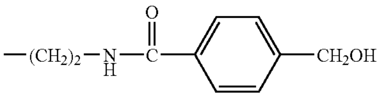 |
| 986 | 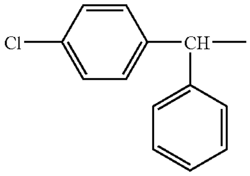 | 1 | 2 | 0 | R | H | 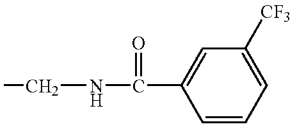 |
| 987 | 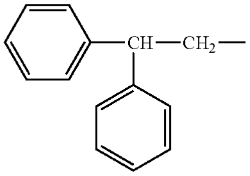 | 2 | 2 | 1 | — | H | 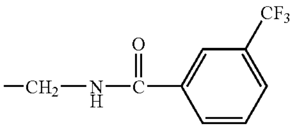 |
| 988 | 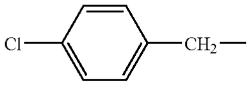 | 1 | 4 | 0 | — | H | 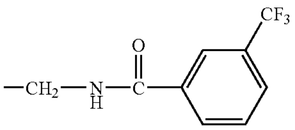 |

TABLE 1.90-continued
| Compd. No. | 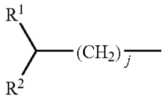 | k | m | n | chirality | $R^3$ | 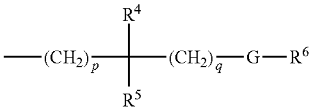 |
|---|---|---|---|---|---|---|---|
| 989 | 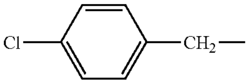 | 1 | 4 | 0 | — | H | 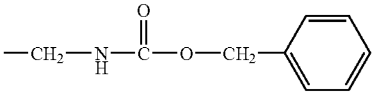 |
| 990 | 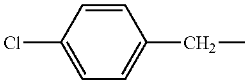 | 1 | 4 | 0 | — | H | 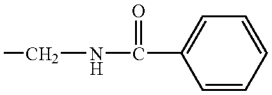 |
TABLE 1.91
| Compd. No. | 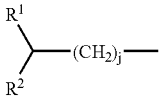 | k | m | n | chirality | $R^3$ | 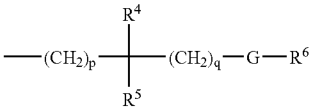 |
|---|---|---|---|---|---|---|---|
| 991 | 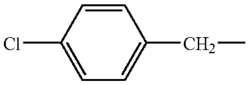 | 1 | 4 | 0 | — | H | 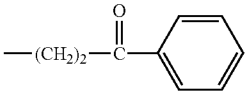 |
| 992 | 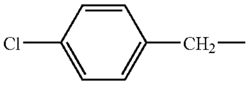 | 1 | 4 | 0 | — | H | 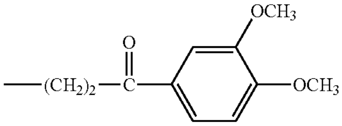 |
| 993 | 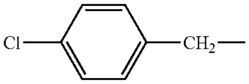 | 1 | 4 | 0 | — | H | 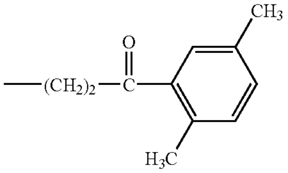 |
| 994 | 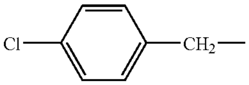 | 1 | 4 | 0 | — | H | 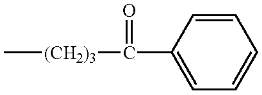 |
| 995 | 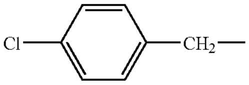 | 1 | 4 | 0 | — | H | 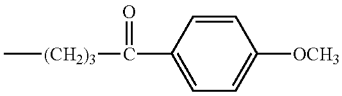 |
| 996 | 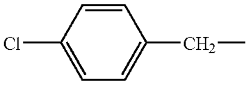 | 1 | 4 | 0 | — | H | 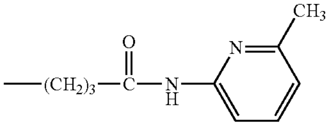 |
| 997 | 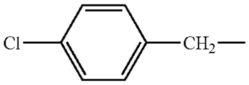 | 2 | 2 | 1 | — | H | 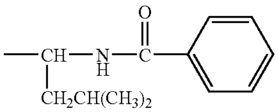 |

TABLE 1.91-continued
| Compd. No. | 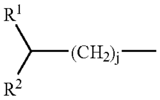 | k | m | n | chirality | $R^3$ | 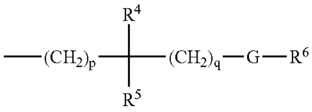 |
|---|---|---|---|---|---|---|---|
| 998 | 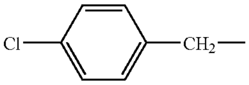 | 2 | 2 | 1 | — | H | 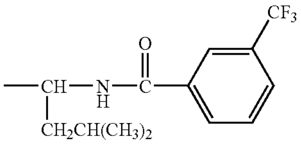 |
| 999 | 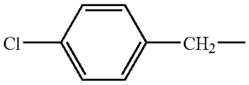 | 2 | 2 | 1 | — | H | 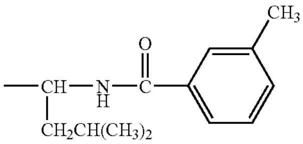 |
| 1000 | 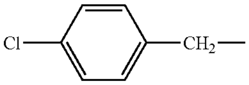 | 2 | 2 | 1 | — | H | 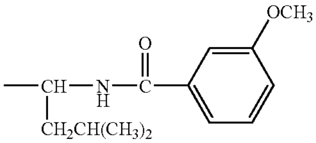 |
| 1001 | 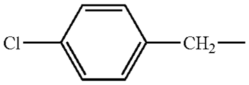 | 2 | 2 | 1 | — | H | 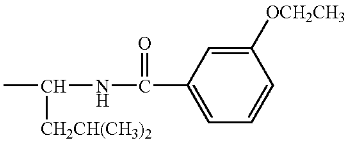 |
TABLE 1.92
| Compd. No. | 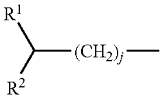 | k | m | n | chirality | $R^3$ | 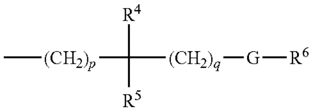 |
|---|---|---|---|---|---|---|---|
| 1002 | 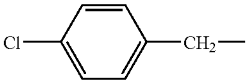 | 2 | 2 | 1 | — | H | 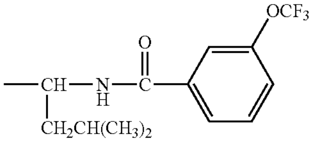 |
| 1003 | 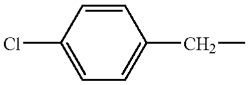 | 2 | 2 | 1 | — | H | 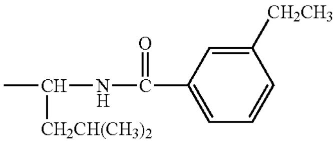 |
| 1004 | 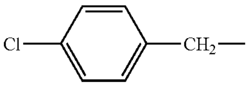 | 2 | 2 | 1 | — | H | 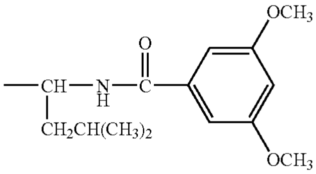 |

TABLE 1.92-continued
| Compd. No. | 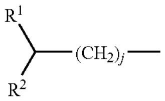 | k | m | n | chirality | $R^3$ | 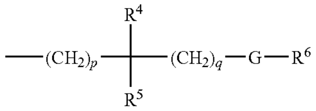 |
|---|---|---|---|---|---|---|---|
| 1005 | 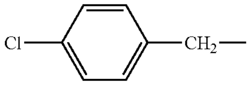 | 2 | 2 | 1 | — | H | 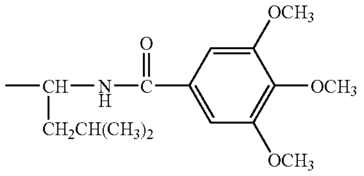 |
| 1006 | 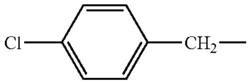 | 2 | 2 | 1 | — | H | 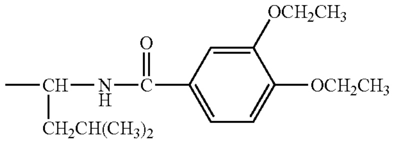 |
| 1007 | 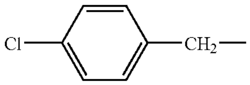 | 2 | 2 | 1 | — | H | 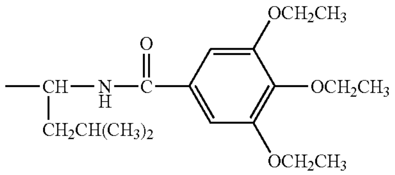 |
| 1008 | 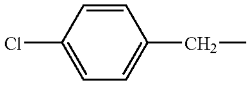 | 2 | 2 | 1 | — | H | 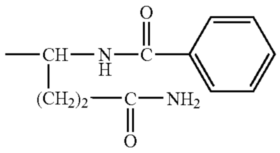 |
| 1009 | 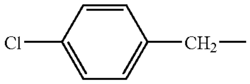 | 2 | 2 | 1 | — | H | 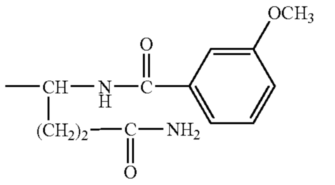 |
| 1010 | 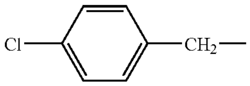 | 2 | 2 | 1 | — | H | 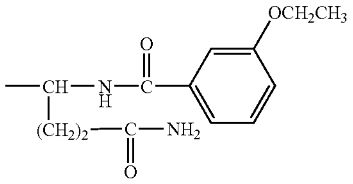 |
| 1011 | 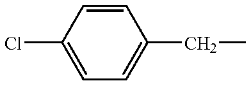 | 2 | 2 | 1 | — | H | 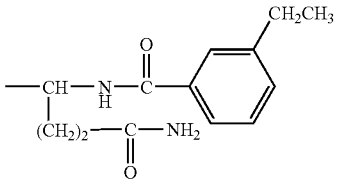 |
| 1012 | 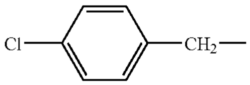 | 2 | 2 | 1 | — | H | 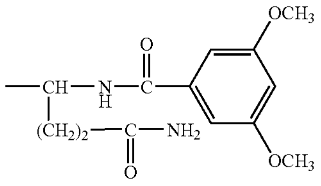 |

TABLE 1.93
| Compd. No. | 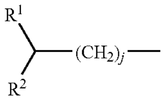 | k | m | n | chirality | $R^3$ | 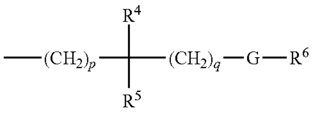 |
|---|---|---|---|---|---|---|---|
| 1013 | 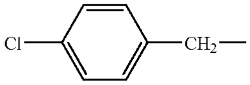 | 2 | 2 | 1 | — | H | 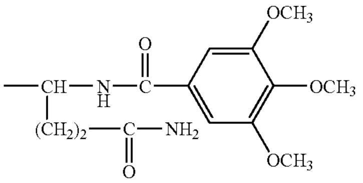 |
| 1014 | 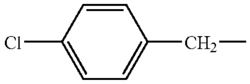 | 2 | 2 | 1 | — | H | 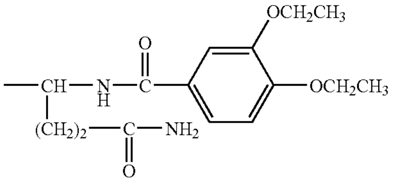 |
| 1015 | 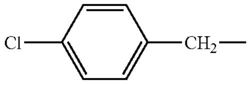 | 2 | 2 | 1 | — | H | 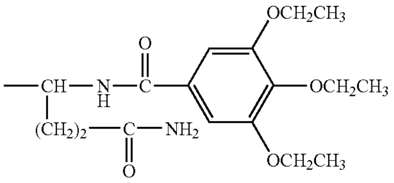 |
| 1016 | 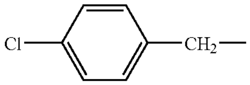 | 2 | 2 | 0 | — | H | 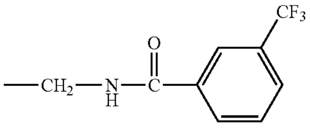 |
| 1017 | 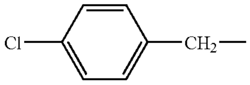 | 2 | 2 | 0 | — | H | 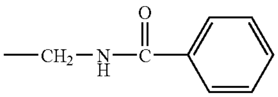 |
| 1018 | 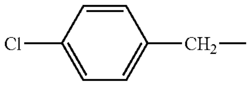 | 2 | 2 | 1 | — | H | 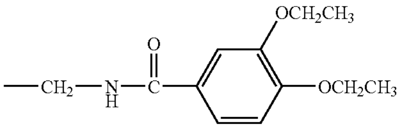 |
| 1019 | 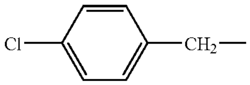 | 2 | 2 | 1 | — | H | 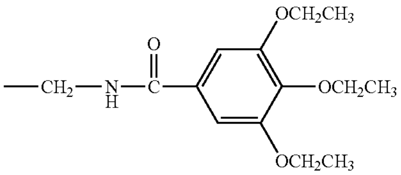 |

TABLE 1.93-continued
| Compd. No. | 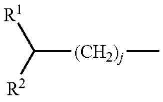 | k | m | n | chirality | $R^3$ | 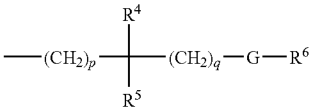 |
|---|---|---|---|---|---|---|---|
| 1020 | 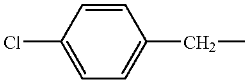 | 2 | 2 | 1 | — | H | 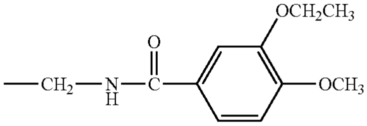 |
| 1021 | 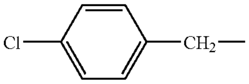 | 2 | 2 | 1 | — | H | 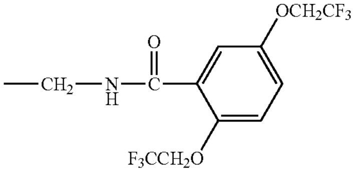 |
| 1022 | 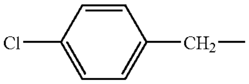 | 2 | 2 | 1 | — | H | 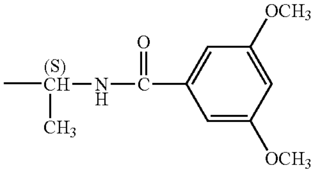 |
| 1023 | 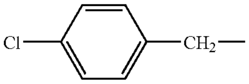 | 2 | 2 | 1 | — | H | 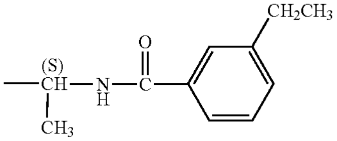 |
TABLE 1.94
| Compd. No. | 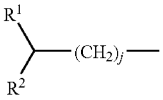 | k | m | n | chirality | $R^3$ | 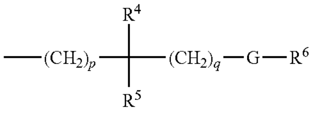 |
|---|---|---|---|---|---|---|---|
| 1024 | 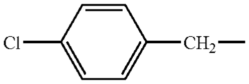 | 2 | 2 | 1 | — | H | 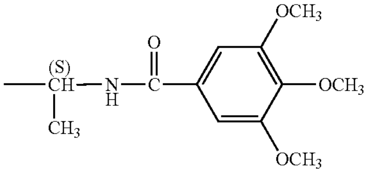 |
| 1025 | 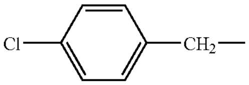 | 2 | 2 | 1 | — | H | 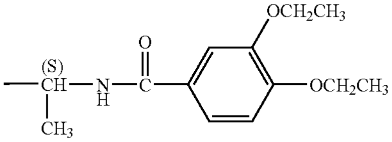 |
| 1026 | 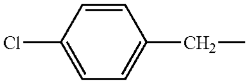 | 2 | 2 | 1 | — | H | 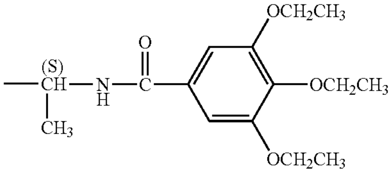 |

TABLE 1.94-continued
| Compd. No. | 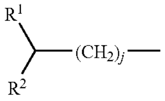 | k | m | n | chirality | $R^3$ | 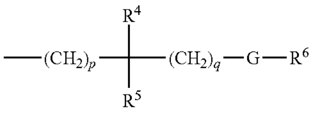 |
|---|---|---|---|---|---|---|---|
| 1027 | 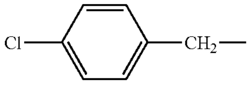 | 2 | 2 | 1 | — | H | 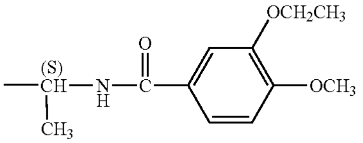 |
| 1028 | 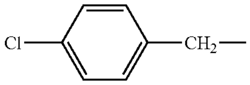 | 2 | 2 | 1 | — | H | 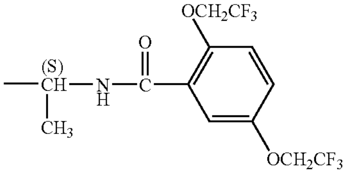 |
| 1029 | 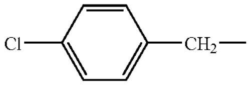 | 2 | 2 | 1 | — | H | 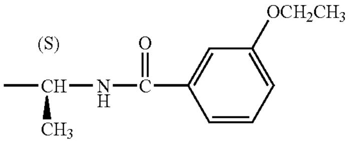 |
| 1030 | 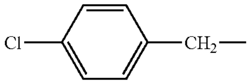 | 2 | 2 | 1 | — | H | 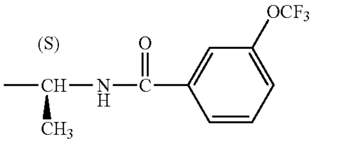 |
| 1031 | 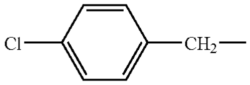 | 2 | 2 | 1 | — | H | 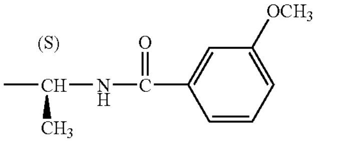 |
| 1032 | 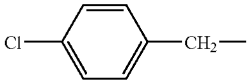 | 2 | 2 | 1 | — | H | 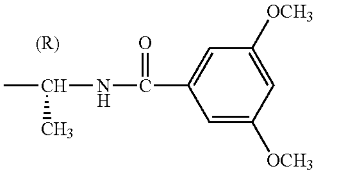 |
| 1033 | 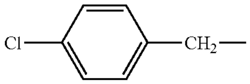 | 2 | 2 | 1 | — | H | 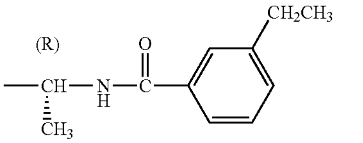 |
| 1034 | 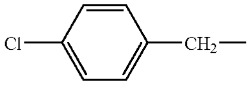 | 2 | 2 | 1 | — | H | 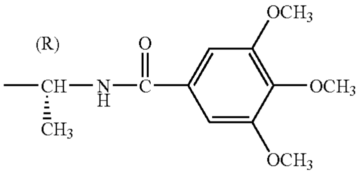 |

TABLE 1.95
| Compd. No. | 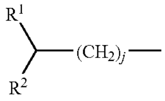 | k | m | n | chirality | $R^3$ | 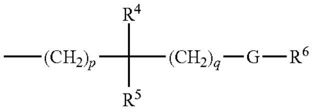 |
|---|---|---|---|---|---|---|---|
| 1035 | 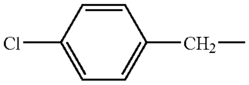 | 2 | 2 | 1 | — | H | 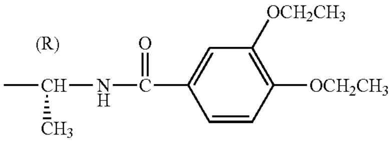 |
| 1036 | 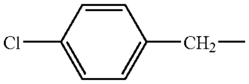 | 2 | 2 | 1 | — | H | 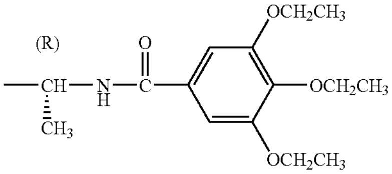 |
| 1037 | 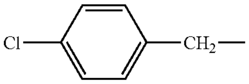 | 2 | 2 | 1 | — | H | 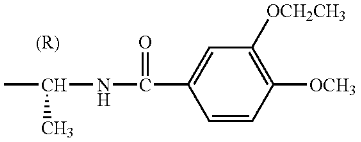 |
| 1038 | 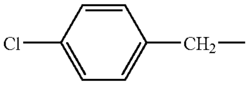 | 2 | 2 | 1 | — | H | 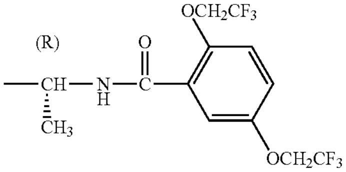 |
| 1039 | 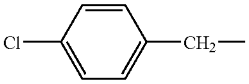 | 2 | 2 | 1 | — | H | 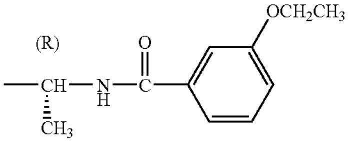 |
| 1040 | 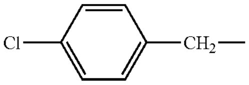 | 2 | 2 | 1 | — | H | 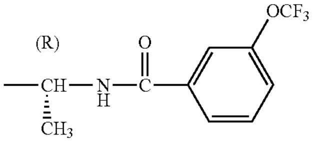 |
| 1041 | 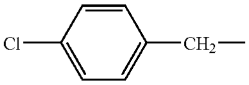 | 2 | 2 | 1 | — | H | 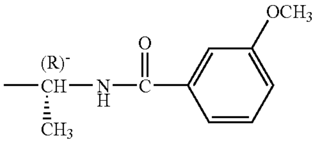 |
| 1042 | 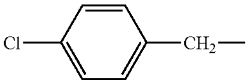 | 2 | 2 | 1 | — | H | 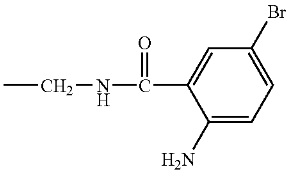 |

TABLE 1.95-continued
| Compd. No. | 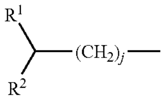 | k | m | n | chirality | $R^3$ | 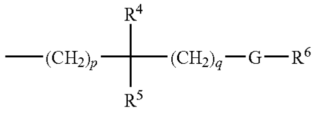 |
|---|---|---|---|---|---|---|---|
| 1043 | 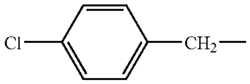 | 2 | 2 | 1 | — | H | 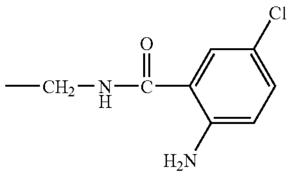 |
| 1044 | 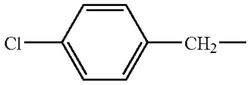 | 2 | 2 | 1 | — | H | 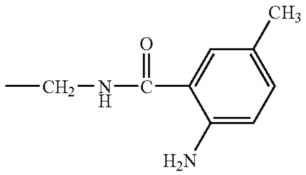 |
| 1045 | 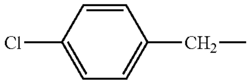 | 2 | 2 | 1 | — | H | 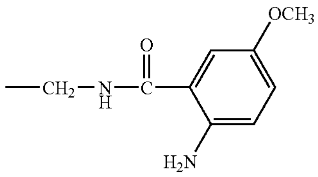 |
TABLE 1.96
| Compd. No. | 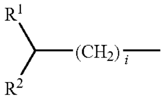 | k | m | n | chirality | $R^3$ | 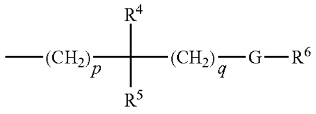 |
|---|---|---|---|---|---|---|---|
| 1046 | 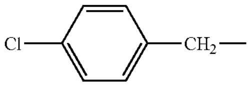 | 2 | 2 | 1 | — | H | 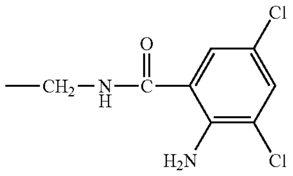 |
| 1047 | 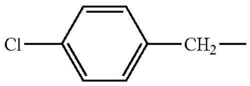 | 2 | 2 | 1 | — | H | 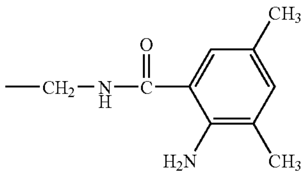 |
| 1048 | 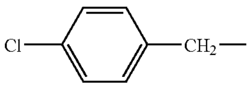 | 2 | 2 | 1 | — | H | 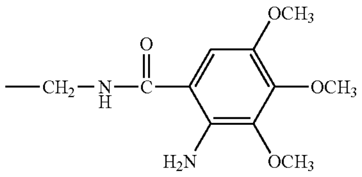 |

TABLE 1.96-continued
| Compd. No. | 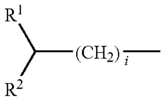 | k | m | n | chirality | $R^3$ | 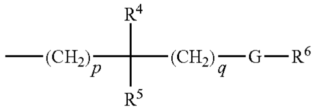 |
| --- | --- | --- | --- | --- | --- | --- | --- |
| 1049 | 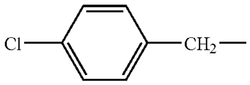 | 2 | 2 | 1 | — | H | 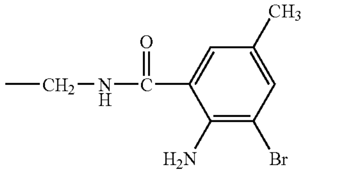 |
| 1050 | 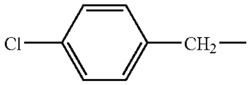 | 2 | 2 | 1 | — | H | 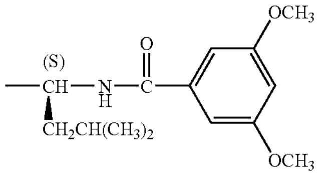 |
| 1051 | 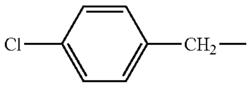 | 2 | 2 | 1 | — | H | 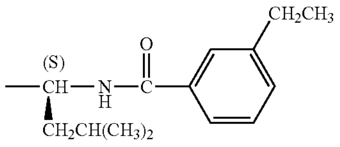 |
| 1052 | 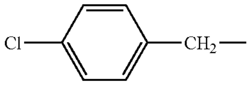 | 2 | 2 | 1 | — | H | 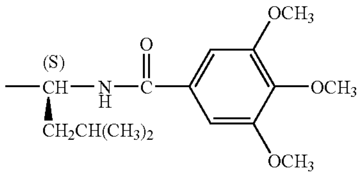 |
| 1053 | 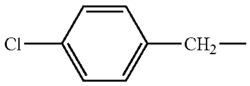 | 2 | 2 | 1 | — | H | 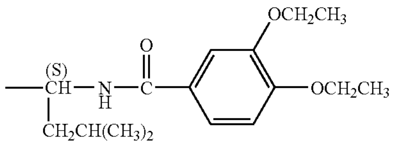 |
| 1054 | 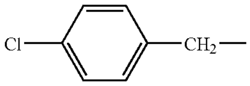 | 2 | 2 | 1 | — | H | 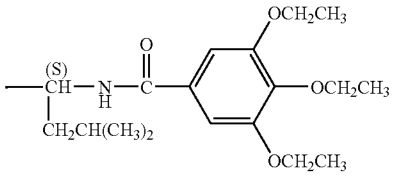 |
| 1055 | 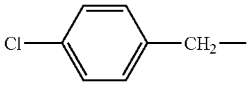 | 2 | 2 | 1 | — | H | 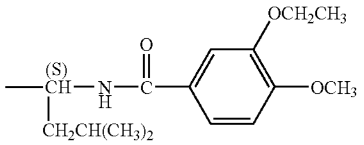 |
| 1056 | 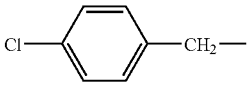 | 2 | 2 | 1 | — | H | 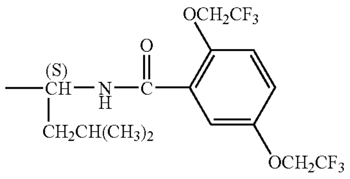 |

TABLE 1.97
| Compd. No. | 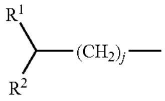 | k | m | n | chirality | $R^3$ | 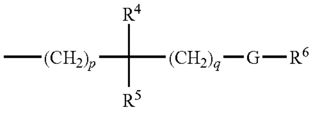 |
|---|---|---|---|---|---|---|---|
| 1057 | 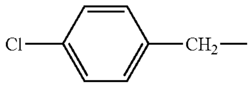 | 2 | 2 | 1 | — | H | 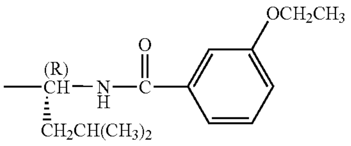 |
| 1058 | 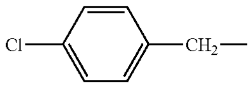 | 2 | 2 | 1 | — | H | 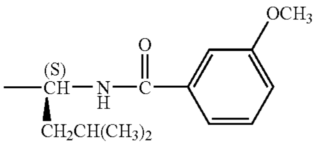 |
| 1059 | 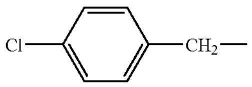 | 2 | 2 | 1 | — | H | 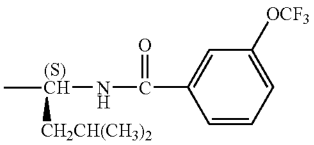 |
| 1060 | 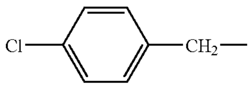 | 2 | 2 | 1 | — | H | 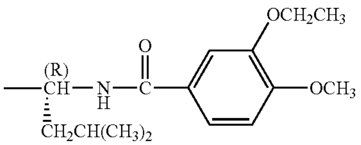 |
| 1061 | 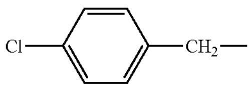 | 2 | 2 | 1 | — | H | 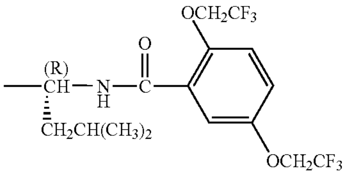 |
| 1062 | 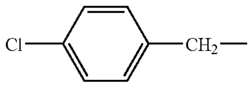 | 2 | 2 | 1 | — | H | 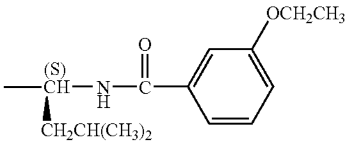 |
| 1063 | 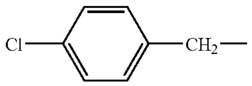 | 2 | 2 | 1 | — | H | 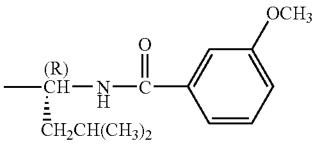 |
| 1064 | 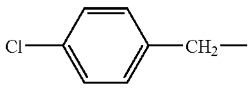 | 2 | 2 | 1 | — | H | 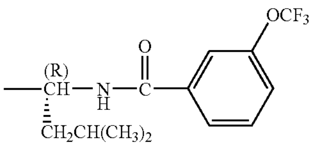 |
| 1065 | 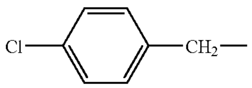 | 2 | 2 | 1 | — | H | 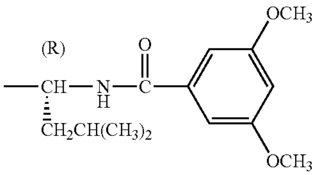 |

TABLE 1.97-continued
| Compd. No. | 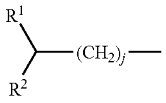 | k | m | n | chirality | $R^3$ | 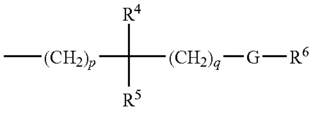 |
|---|---|---|---|---|---|---|---|
| 1066 | 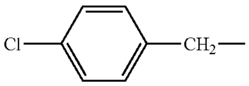 | 2 | 2 | 1 | — | H | 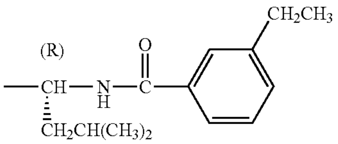 |
| 1067 | 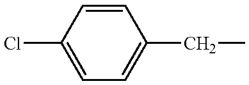 | 2 | 2 | 1 | — | H | 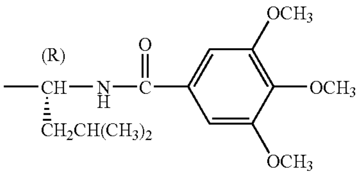 |
TABLE 1.98
| Compd. No. | 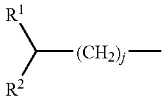 | k | m | n | chirality | $R^3$ | 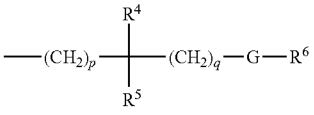 |
|---|---|---|---|---|---|---|---|
| 1068 | 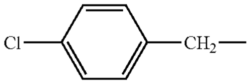 | 2 | 2 | 1 | — | H | 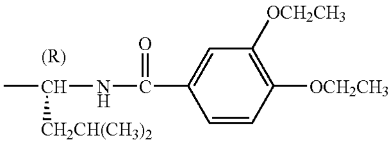 |
| 1069 | 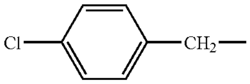 | 2 | 2 | 1 | — | H | 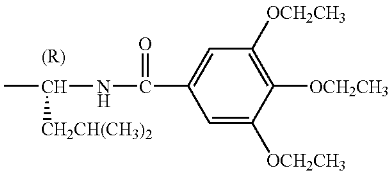 |
| 1070 | 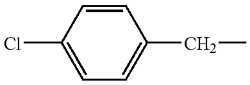 | 2 | 2 | 1 | — | H | 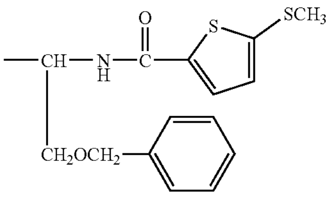 |
| 1071 | 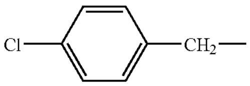 | 2 | 2 | 1 | — | H | 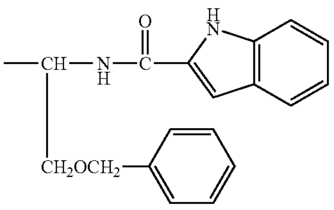 |

TABLE 1.98-continued
| Compd. No. | 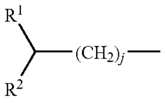 | k | m | n | chirality | $R^3$ | 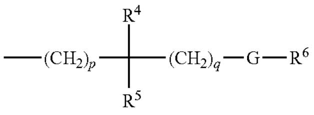 |
| --- | --- | --- | --- | --- | --- | --- | --- |
| 1072 | 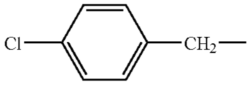 | 2 | 2 | 1 | — | H | 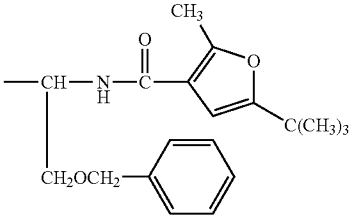 |
| 1073 | 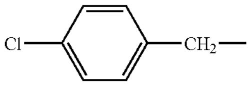 | 2 | 2 | 1 | — | H | 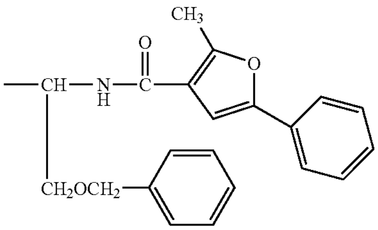 |
| 1074 | 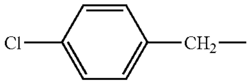 | 2 | 2 | 1 | — | H | 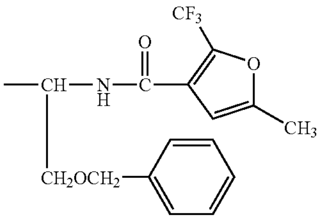 |
| 1075 | 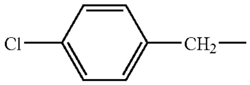 | 2 | 2 | 1 | — | H | 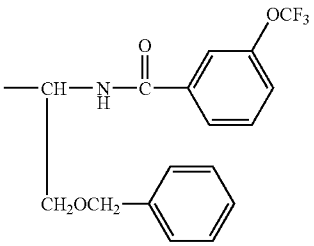 |
| 1076 | 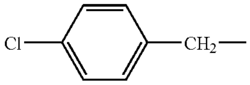 | 2 | 2 | 1 | — | H | 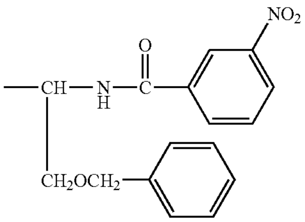 |
| 1077 | 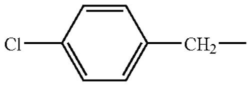 | 2 | 2 | 1 | — | H | 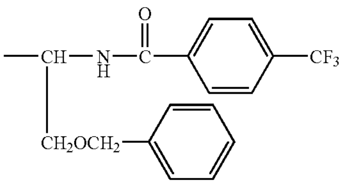 |

TABLE 1.98-continued
| Compd. No. | 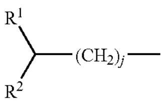 | k | m | n | chirality | $R^3$ | 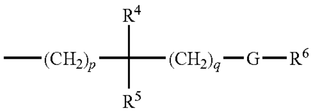 |
| --- | --- | --- | --- | --- | --- | --- | --- |
| 1078 | 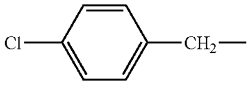 | 2 | 2 | 1 | — | H | 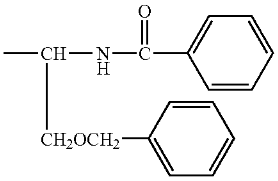 |
TABLE 1.99
| Compd. No. | 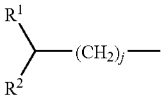 | k | m | n | chirality | $R^3$ | 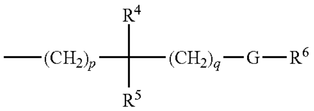 |
| --- | --- | --- | --- | --- | --- | --- | --- |
| 1079 | 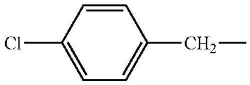 | 2 | 2 | 1 | — | H | 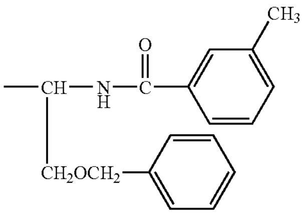 |
| 1080 | 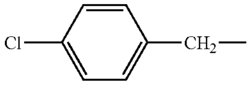 | 2 | 2 | 1 | — | H | 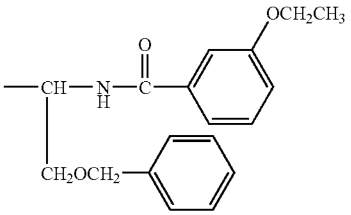 |
| 1081 | 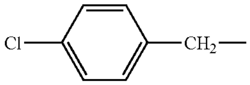 | 2 | 2 | 1 | — | H | 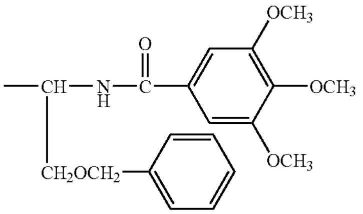 |
| 1082 | 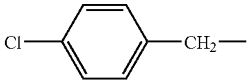 | 2 | 2 | 1 | — | H | 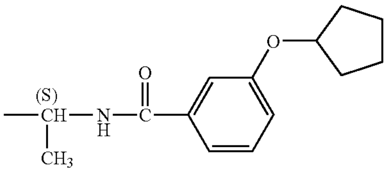 |
| 1083 | 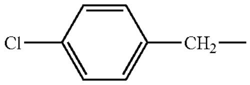 | 2 | 2 | 1 | — | H | 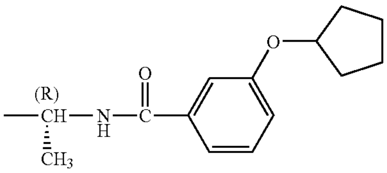 |

TABLE 1.99-continued
| Compd. No. | 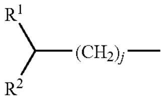 | k | m | n | chirality | $R^3$ | 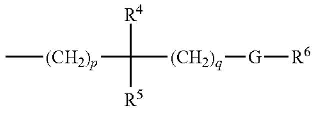 |
|---|---|---|---|---|---|---|---|
| 1084 | 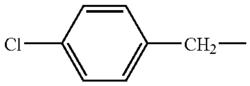 | 1 | 2 | 0 | R | H | 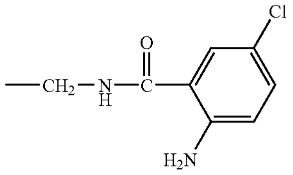 |
| 1085 | 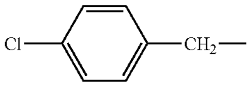 | 1 | 2 | 0 | R | H | 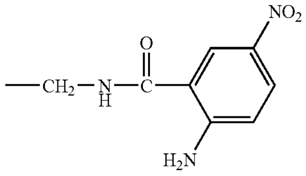 |
| 1086 | 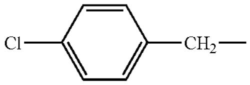 | 1 | 2 | 0 | R | H | 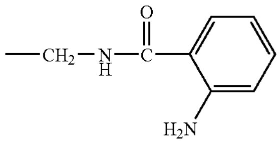 |
| 1087 | 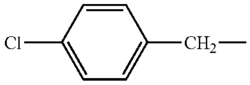 | 1 | 2 | 0 | R | H | 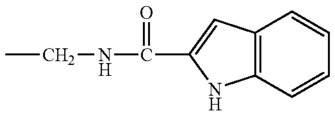 |
| 1088 | 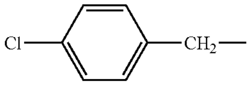 | 1 | 2 | 0 | R | H | 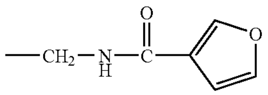 |
| 1089 | 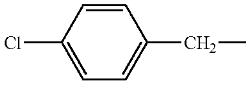 | 1 | 2 | 0 | R | H | 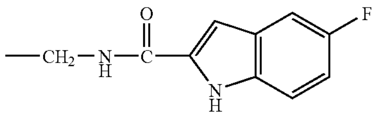 |
TABLE 1.100
| Compd. No. | 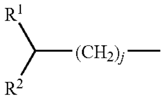 | k | m | n | chirality | $R^3$ | 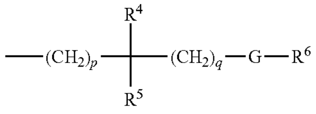 |
|---|---|---|---|---|---|---|---|
| 1090 | 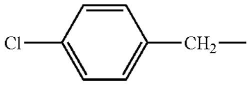 | 2 | 2 | 1 | — | H | 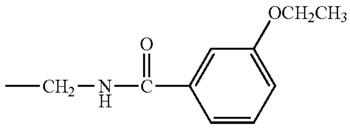 |

TABLE 1.100-continued
| Compd. No. | 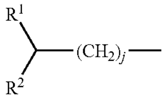 | k | m | n | chirality | $R^3$ | 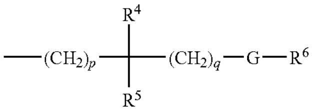 |
|---|---|---|---|---|---|---|---|
| 1091 | 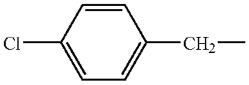 | 2 | 2 | 1 | — | H | 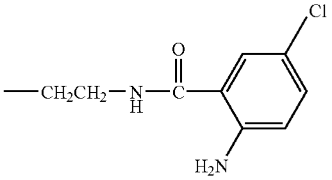 |
| 1092 | 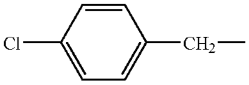 | 2 | 2 | 1 | — | H | 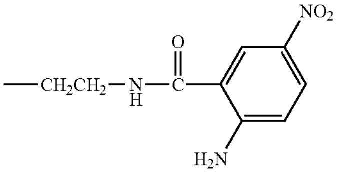 |
| 1093 | 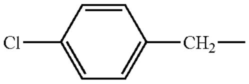 | 2 | 2 | 0 | — | H | 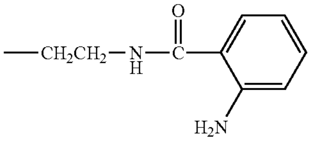 |
| 1094 | 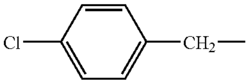 | 2 | 2 | 0 | — | H | 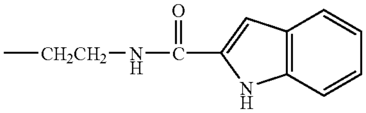 |
| 1095 | 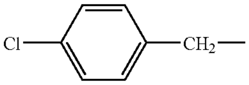 | 2 | 2 | 1 | — | H | 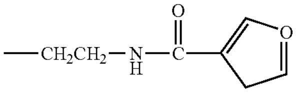 |
| 1096 | 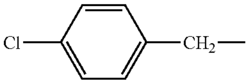 | 2 | 2 | 1 | — | H | 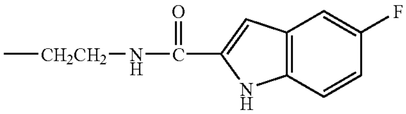 |
| 1097 | 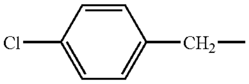 | 2 | 2 | 1 | — | H | 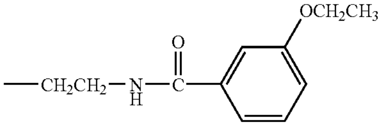 |
| 1098 | 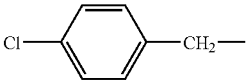 | 2 | 2 | 1 | — | H | 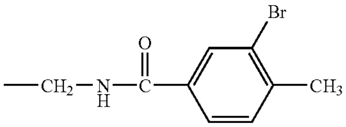 |
| 1099 | 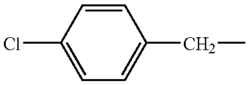 | 2 | 2 | 1 | — | H | 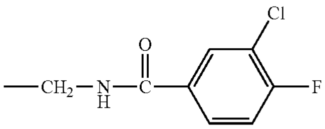 |

TABLE 1.100-continued
| Compd. No. | 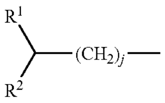 | k | m | n | chirality | $R^3$ | 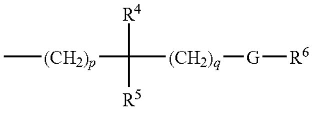 |
|---|---|---|---|---|---|---|---|
| 1100 | 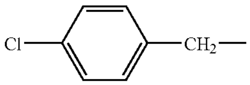 | 2 | 2 | 1 | — | H | 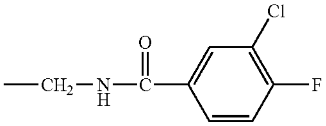 |
TABLE 1.101
| Compd. No. | 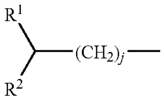 | k | m | n | chirality | $R^3$ | 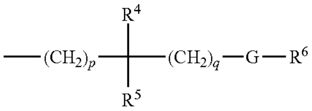 |
|---|---|---|---|---|---|---|---|
| 1101 | 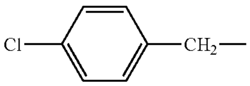 | 1 | 2 | 0 | R | H | 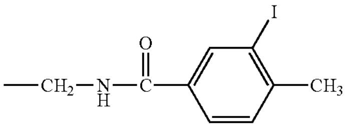 |
| 1102 | 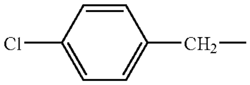 | 1 | 2 | 0 | R | H | 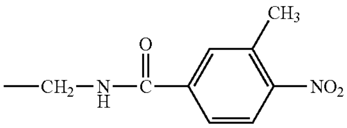 |
| 1103 | 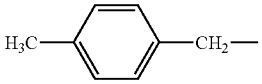 | 1 | 2 | 0 | R | H | 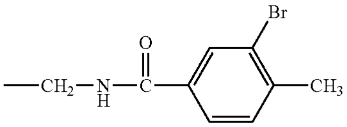 |
| 1104 | 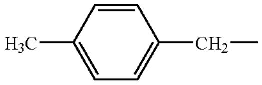 | 1 | 2 | 0 | R | H | 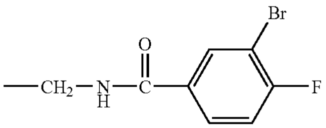 |
| 1105 | 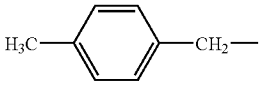 | 1 | 2 | 0 | R | H | 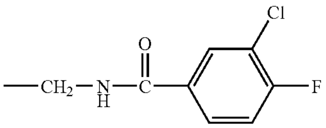 |
| 1106 | 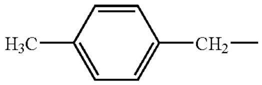 | 1 | 2 | 0 | R | H | 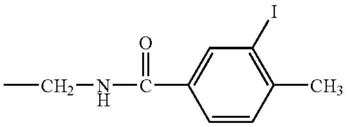 |
| 1107 | 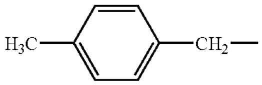 | 1 | 2 | 0 | R | H | 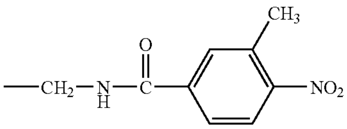 |

TABLE 1.101-continued
| Compd. No. | 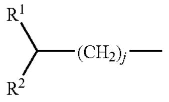 | k | m | n | chirality | $R^3$ | 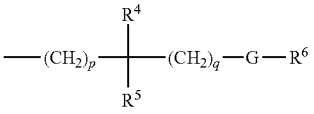 |
|---|---|---|---|---|---|---|---|
| 1108 | 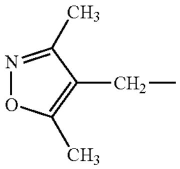 | 1 | 2 | 0 | R | H | 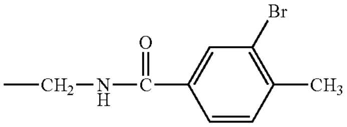 |
| 1109 | 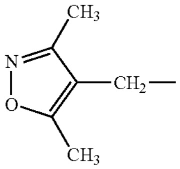 | 1 | 2 | 0 | R | H | 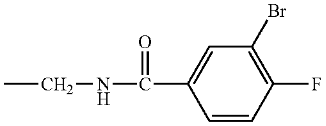 |
| 1110 | 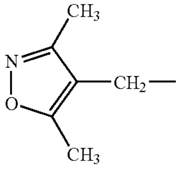 | 1 | 2 | 0 | R | H | 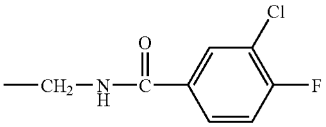 |
| 1111 | 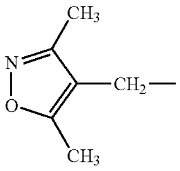 | 1 | 2 | 0 | R | H | 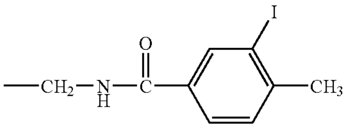 |
TABLE 1.102
| Compd. No. | 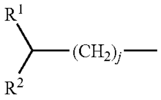 | k | m | n | chirality | $R^3$ | 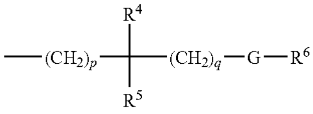 |
|---|---|---|---|---|---|---|---|
| 1112 | 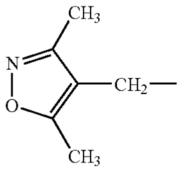 | 1 | 2 | 0 | R | H | 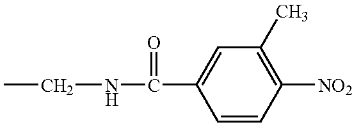 |
| 1113 | 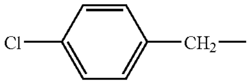 | 2 | 2 | 1 | — | H | 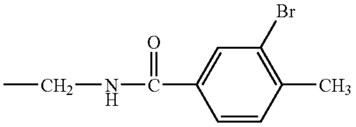 |
| 1114 | 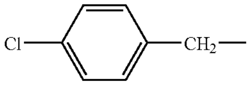 | 2 | 2 | 1 | — | H | 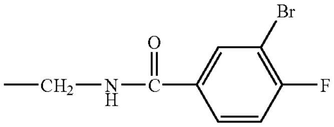 |

TABLE 1.102-continued
| Compd. No. | 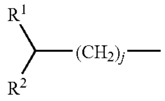 | k | m | n | chirality | $R^3$ | 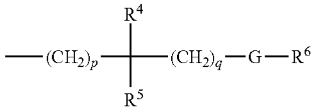 |
|---|---|---|---|---|---|---|---|
| 1115 | 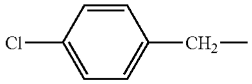 | 2 | 2 | 1 | — | H | 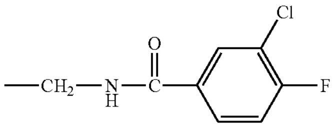 |
| 1116 | 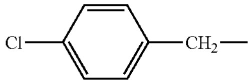 | 2 | 2 | 1 | — | H | 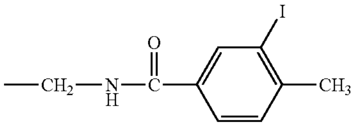 |
| 1117 | 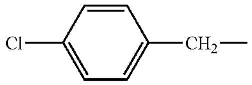 | 2 | 2 | 1 | — | H | 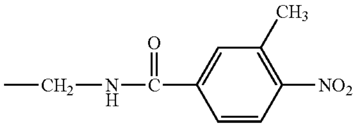 |
| 1118 | 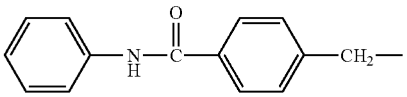 | 1 | 2 | 0 | R | H | 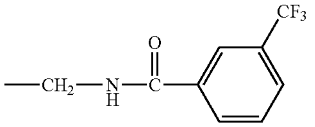 |
| 1119 | 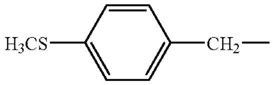 | 1 | 2 | 0 | R | H | 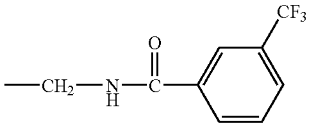 |
| 1120 | 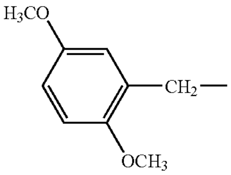 | 1 | 2 | 0 | R | H | 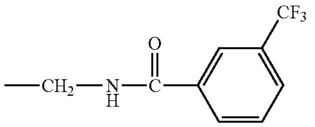 |
| 1121 | 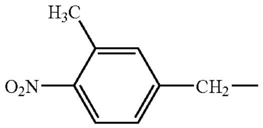 | 1 | 2 | 0 | R | H | 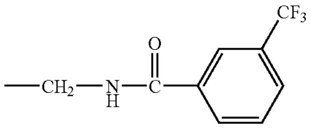 |
| 1122 | 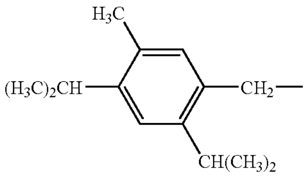 | 1 | 2 | 0 | R | H | 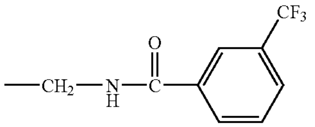 |

TABLE 1.103
| Compd. No. | 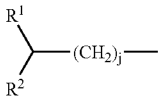 | k | m | n | chirality | $R^3$ | 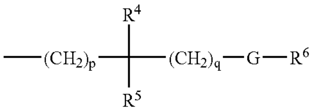 |
|---|---|---|---|---|---|---|---|
| 1123 | 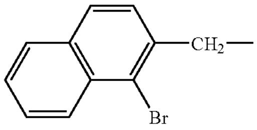 | 1 | 2 | 0 | R | H | 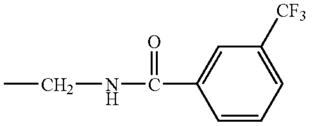 |
| 1124 | 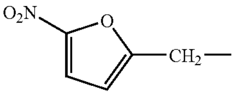 | 1 | 2 | 0 | R | H | 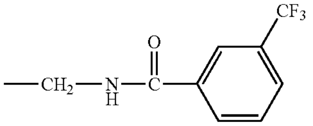 |
| 1125 | 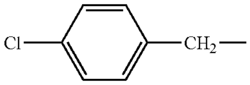 | 2 | 2 | 1 | — | H | 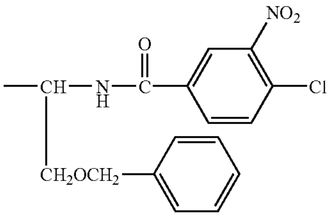 |
| 1126 | 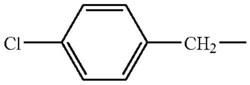 | 2 | 2 | 1 | — | H | 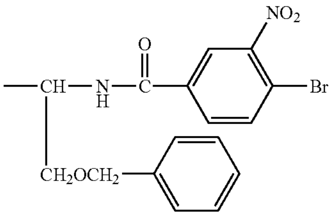 |
| 1127 | 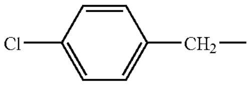 | 2 | 2 | 1 | — | H | 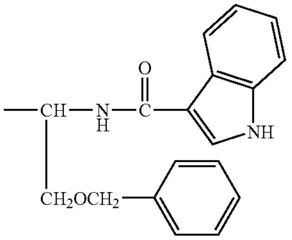 |
| 1128 | 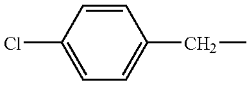 | 2 | 2 | 1 | — | H | 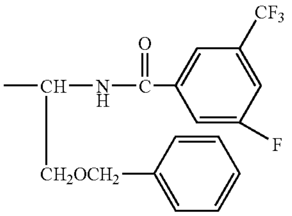 |
| 1129 | 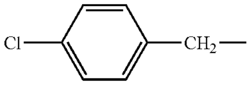 | 2 | 2 | 1 | — | H | 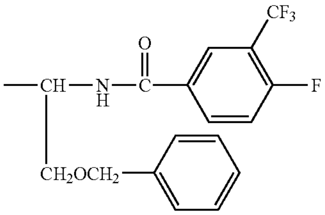 |

TABLE 1.103-continued
| Compd. No. | 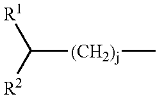 | k | m | n | chirality | $R^3$ | 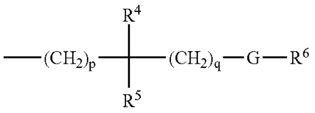 |
|---|---|---|---|---|---|---|---|
| 1130 | 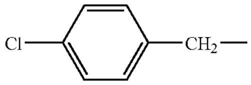 | 2 | 2 | 1 | — | H | 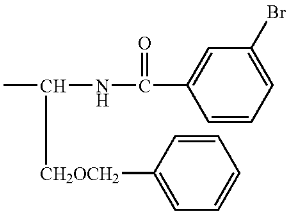 |
| 1131 | 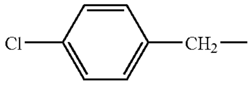 | 2 | 2 | 1 | — | H | 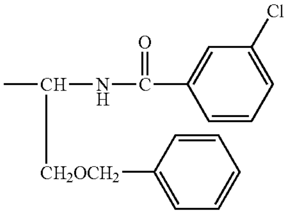 |
| 1132 | 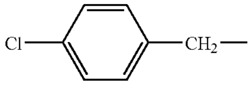 | 2 | 2 | 1 | — | H | 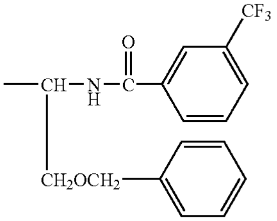 |
| 1133 | 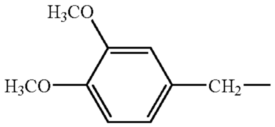 | 1 | 2 | 0 | R | H | 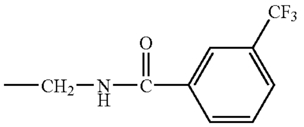 |
TABLE 1.104
| Compd. No. | 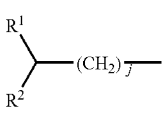 | k | m | n | chirality | $R^3$ | 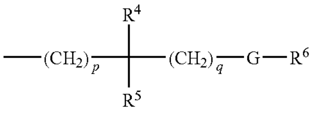 |
|---|---|---|---|---|---|---|---|
| 1134 | 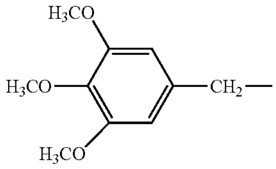 | 1 | 2 | 0 | R | H | 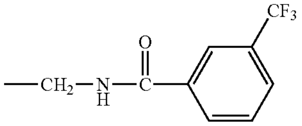 |
| 1135 | 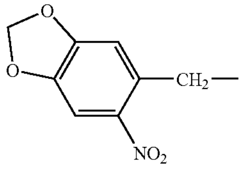 | 1 | 2 | 0 | R | H | 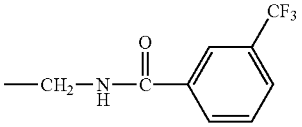 |

TABLE 1.104-continued
| Compd. No. | 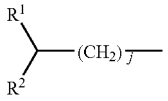 | k | m | n | chirality | $R^3$ | 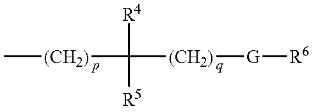 |
|---|---|---|---|---|---|---|---|
| 1136 | 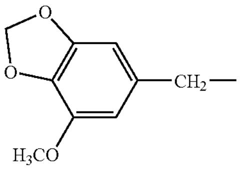 | 1 | 2 | 0 | R | H | 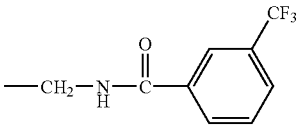 |
| 1137 | 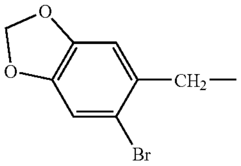 | 1 | 2 | 0 | R | H | 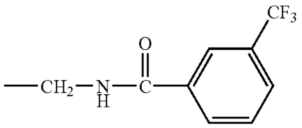 |
| 1138 | 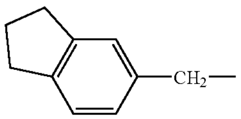 | 1 | 2 | 0 | R | H | 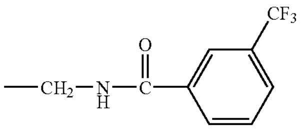 |
| 1139 | 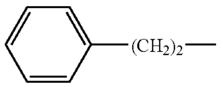 | 1 | 2 | 0 | R | H | 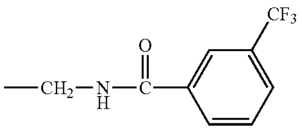 |
| 1140 | 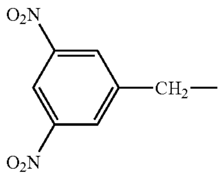 | 1 | 2 | 0 | R | H | 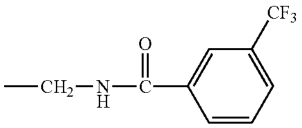 |
| 1141 | 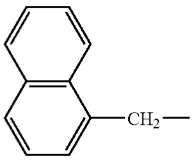 | 1 | 2 | 0 | R | H | 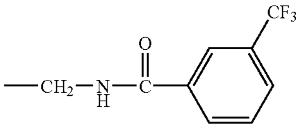 |
| 1142 | 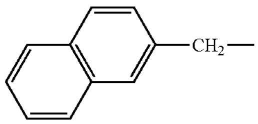 | 1 | 2 | 0 | R | H | 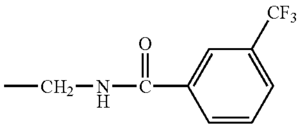 |
| 1143 | 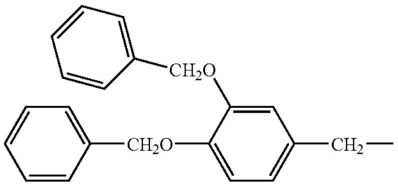 | 1 | 2 | 0 | R | H | 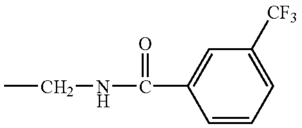 |

TABLE 1.104-continued
| Compd. No. | 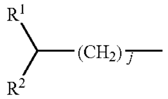 | k | m | n | chirality | $R^3$ | 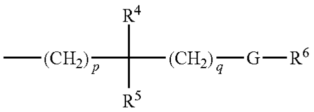 |
|---|---|---|---|---|---|---|---|
| 1144 | 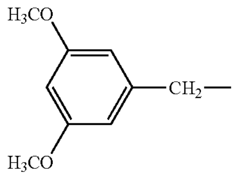 | 1 | 2 | 0 | R | H | 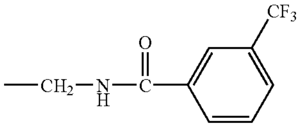 |
TABLE 1.105
| Compd. No. | 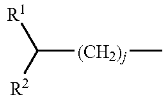 | k | m | n | chirality | $R^3$ | 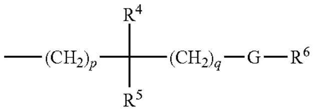 |
|---|---|---|---|---|---|---|---|
| 1145 | 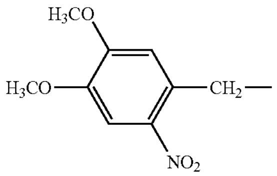 | 1 | 2 | 0 | R | H | 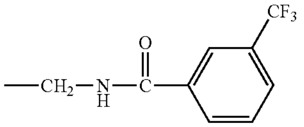 |
| 1146 | 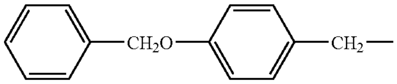 | 1 | 2 | 0 | R | H | 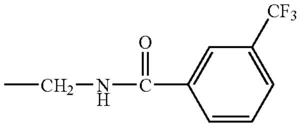 |
| 1147 | 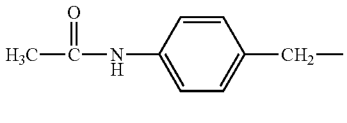 | 1 | 2 | 0 | R | H | 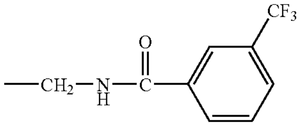 |
| 1148 | 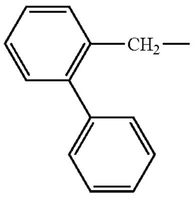 | 1 | 2 | 0 | R | H | 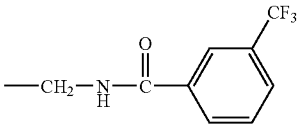 |
| 1149 | 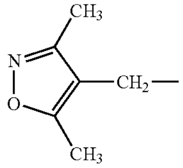 | 1 | 2 | 0 | R | H | 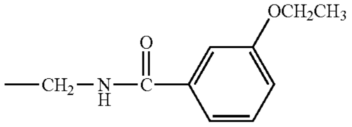 |
| 1150 | 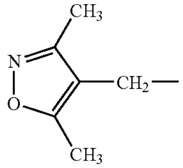 | 1 | 2 | 0 | R | H | 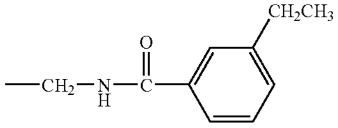 |

TABLE 1.105-continued
| Compd. No. | 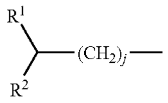 | k | m | n | chirality | $R^3$ | 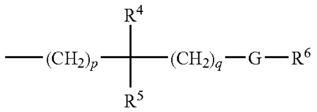 |
|---|---|---|---|---|---|---|---|
| 1151 | 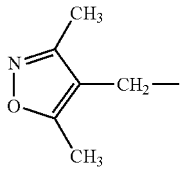 | 1 | 2 | 0 | R | H | 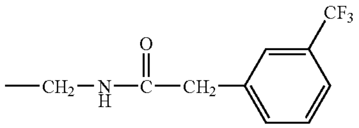 |
| 1152 | 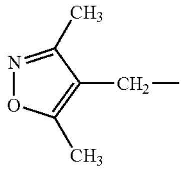 | 1 | 2 | 0 | R | H | 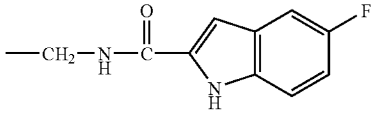 |
| 1153 | 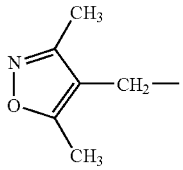 | 1 | 2 | 0 | R | H | 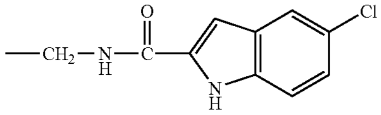 |
| 1154 | 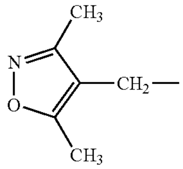 | 1 | 2 | 0 | R | H | 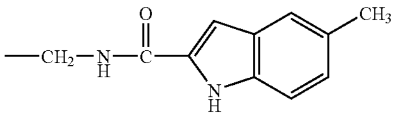 |
| 1155 | 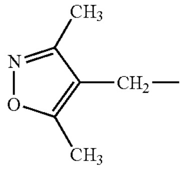 | 1 | 2 | 0 | R | H | 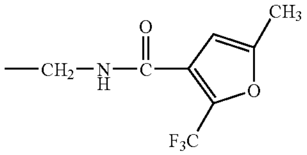 |
TABLE 1.106
| Compd. No. | 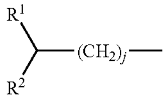 | k | m | n | chirality | $R^3$ | 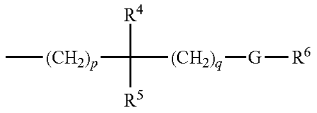 |
|---|---|---|---|---|---|---|---|
| 1156 | 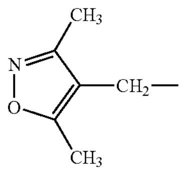 | 1 | 2 | 0 | R | H | 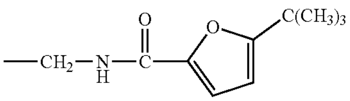 |
| 1157 | 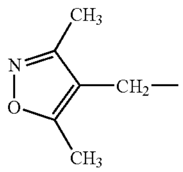 | 1 | 2 | 0 | R | H | 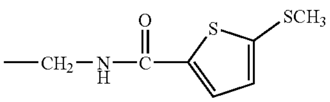 |

TABLE 1.106-continued
| Compd. No. | 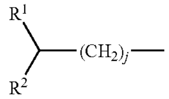 | k | m | n | chirality | $R^3$ | 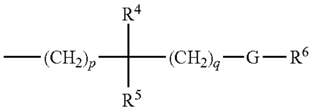 |
|---|---|---|---|---|---|---|---|
| 1158 | 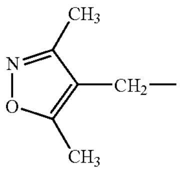 | 1 | 2 | 0 | R | H | 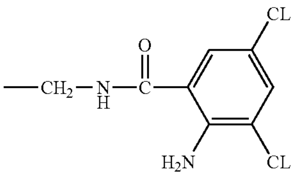 |
| 1159 | 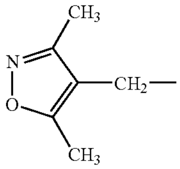 | 1 | 2 | 0 | R | H | 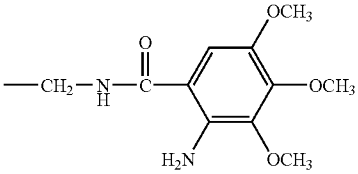 |
| 1160 | 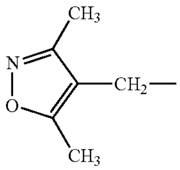 | 1 | 2 | 0 | R | H | 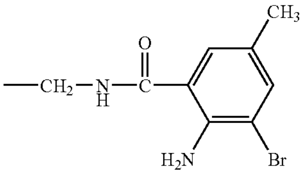 |
| 1161 | 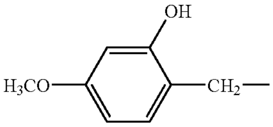 | 1 | 2 | 0 | R | H | 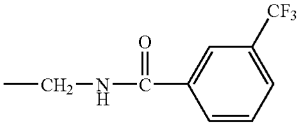 |
| 1162 | 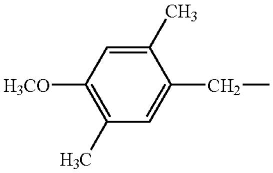 | 1 | 2 | 0 | R | H | 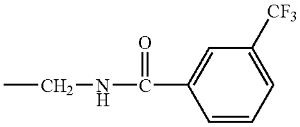 |
| 1163 | 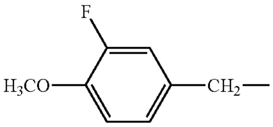 | 1 | 2 | 0 | R | H | 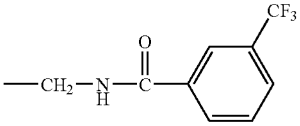 |
| 1164 | 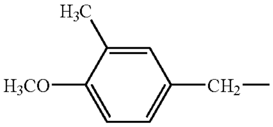 | 1 | 2 | 0 | R | H | 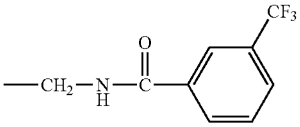 |
| 1165 | 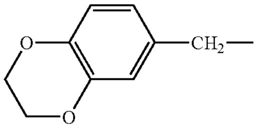 | 1 | 2 | 0 | R | H | 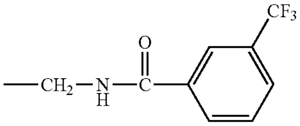 |
| 1166 | 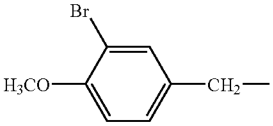 | 1 | 2 | 0 | R | H | 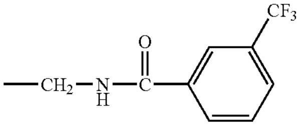 |

TABLE 1.107
| Compd. No. | 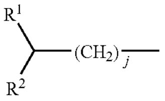 | k | m | n | chirality | $R^3$ | 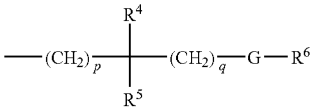 |
|---|---|---|---|---|---|---|---|
| 1167 | 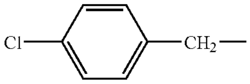 | 2 | 2 | 1 | — | H | 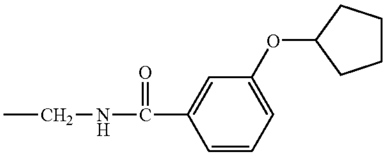 |
| 1168 | 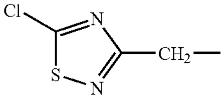 | 1 | 2 | 0 | R | H | 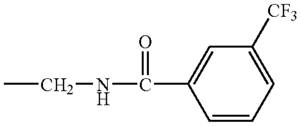 |
| 1169 | 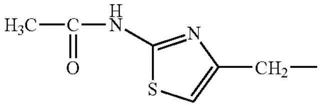 | 1 | 2 | 0 | R | H | 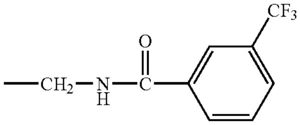 |
| 1170 | 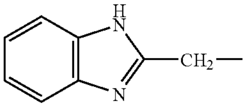 | 1 | 2 | 0 | R | H | 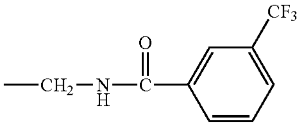 |
| 1171 | 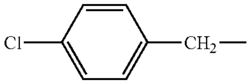 | 1 | 2 | 0 | R | H | 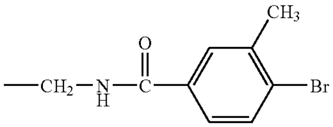 |
| 1172 | 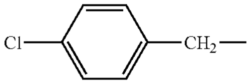 | 1 | 2 | 0 | R | H | 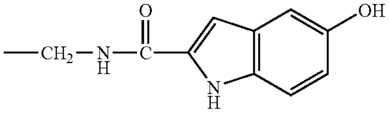 |
| 1173 | 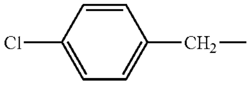 | 1 | 2 | 0 | R | H | 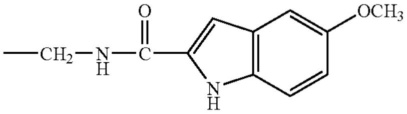 |
| 1174 | 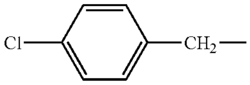 | 1 | 2 | 0 | R | H | 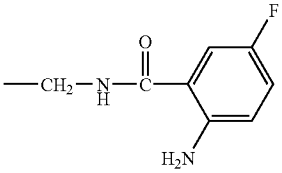 |
| 1175 | 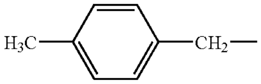 | 1 | 2 | 0 | R | H | 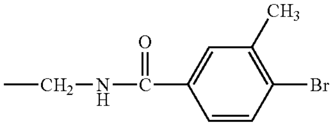 |
| 1176 | 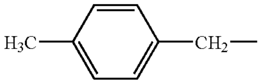 | 1 | 2 | 0 | R | H | 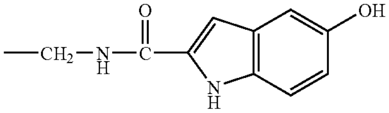 |

TABLE 1.107-continued
| Compd. No. | 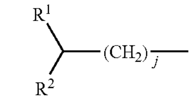 | k | m | n | chirality | $R^3$ | 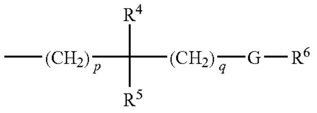 |
|---|---|---|---|---|---|---|---|
| 1177 | 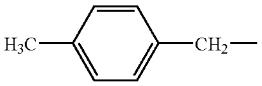 | 1 | 2 | 0 | R | H | 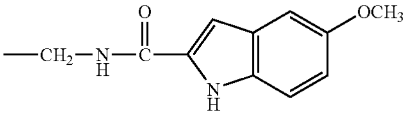 |
TABLE 1.108
| Compd. No. | 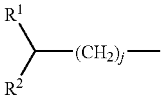 | k | m | n | chirality | $R^3$ | 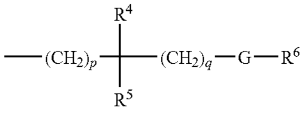 |
|---|---|---|---|---|---|---|---|
| 1178 | 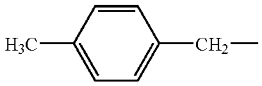 | 1 | 2 | 0 | R | H | 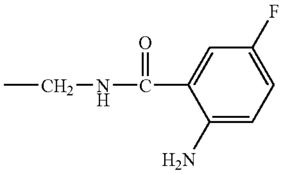 |
| 1179 | 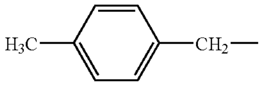 | 1 | 2 | 0 | R | H | 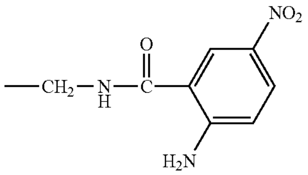 |
| 1180 | 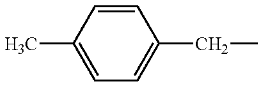 | 1 | 2 | 0 | R | H | 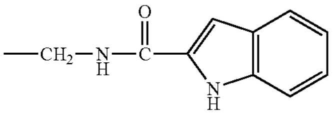 |
| 1181 | 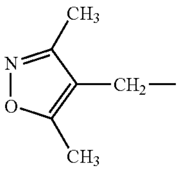 | 1 | 2 | 0 | R | H | 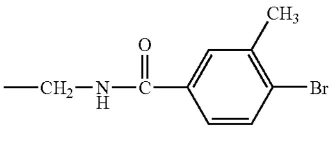 |
| 1182 | 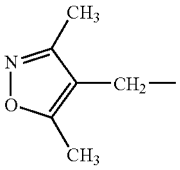 | 1 | 2 | 0 | R | H | 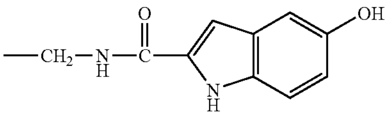 |
| 1183 | 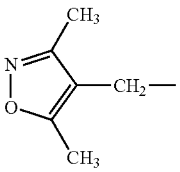 | 1 | 2 | 0 | R | H | 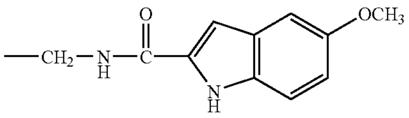 |

TABLE 1.108-continued
| Compd. No. | 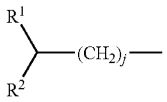 | k | m | n | chirality | $R^3$ | 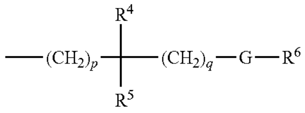 |
|---|---|---|---|---|---|---|---|
| 1184 | 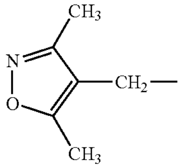 | 1 | 2 | 0 | R | H | 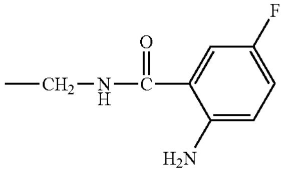 |
| 1185 | 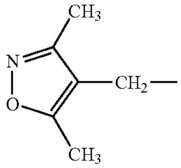 | 1 | 2 | 0 | R | H | 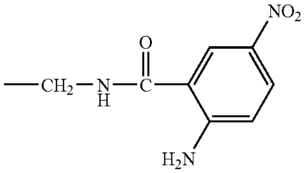 |
| 1186 | 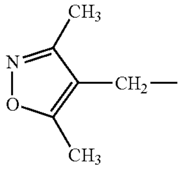 | 1 | 2 | 0 | R | H | 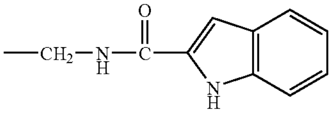 |
| 1187 | 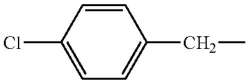 | 2 | 2 | 1 | — | H | 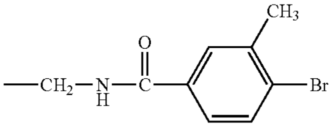 |
| 1188 | 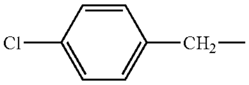 | 2 | 2 | 1 | — | H | 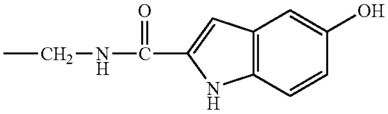 |
TABLE 1.109
| Compd. No. | 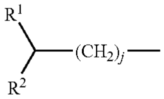 | k | m | n | chirality | $R^3$ | 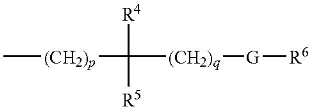 |
|---|---|---|---|---|---|---|---|
| 1189 | 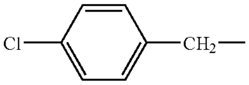 | 2 | 2 | 1 | — | H | 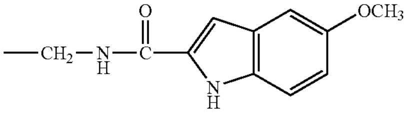 |
| 1190 | 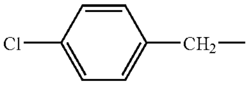 | 2 | 2 | 1 | — | H | 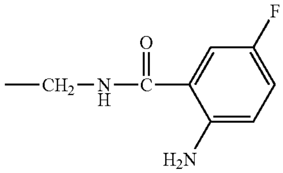 |

TABLE 1.109-continued
| Compd. No. | 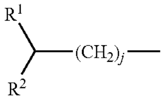 | k | m | n | chirality | $R^3$ | 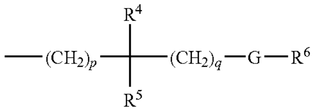 |
|---|---|---|---|---|---|---|---|
| 1191 | 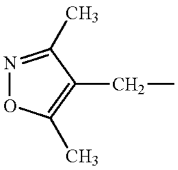 | 1 | 2 | 0 | R | H | 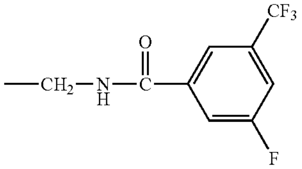 |
| 1192 | 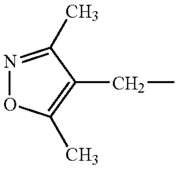 | 1 | 2 | 0 | R | H | 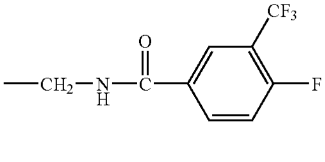 |
| 1193 | 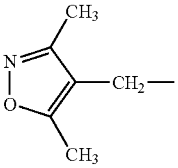 | 1 | 2 | 0 | R | H | 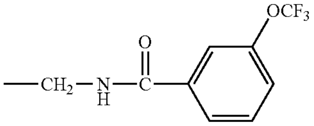 |
| 1194 | 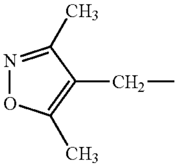 | 1 | 2 | 0 | R | H | 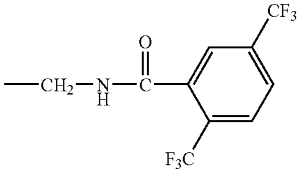 |
| 1195 | 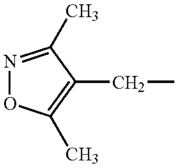 | 1 | 2 | 0 | R | H | 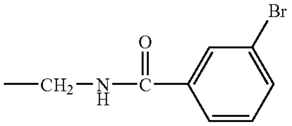 |
| 1196 | 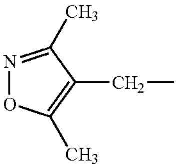 | 1 | 2 | 0 | R | H | 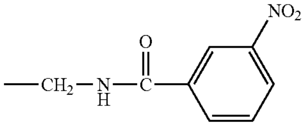 |
| 1197 | 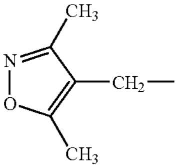 | 1 | 2 | 0 | R | H | 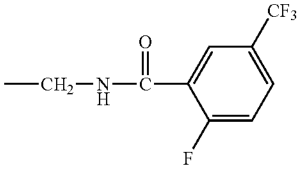 |
| 1198 | 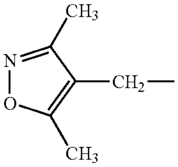 | 1 | 2 | 0 | R | H | 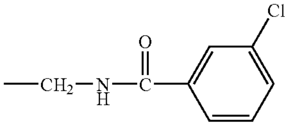 |

TABLE 1.109-continued
| Compd. No. | 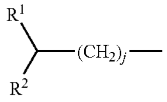 | k | m | n | chirality | $R^3$ | 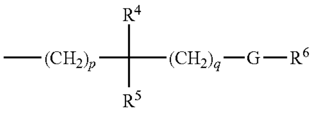 |
|---|---|---|---|---|---|---|---|
| 1199 | 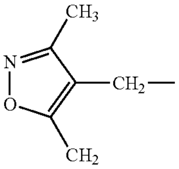 | 1 | 2 | 0 | R | H | 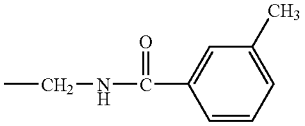 |
TABLE 1.110
| Compd. No. | 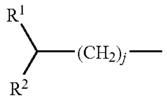 | k | m | n | chirality | $R^3$ | 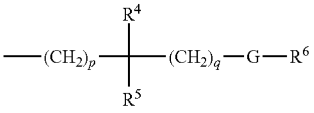 |
|---|---|---|---|---|---|---|---|
| 1200 | 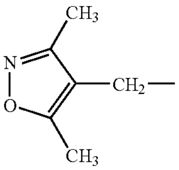 | 1 | 2 | 0 | R | H | 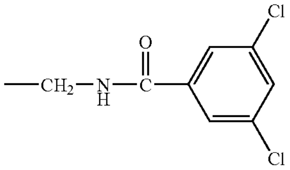 |
| 1201 | 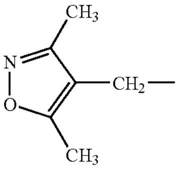 | 1 | 2 | 0 | R | H | 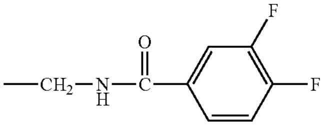 |
| 1202 | 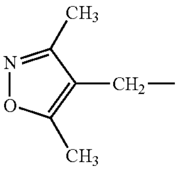 | 1 | 2 | 0 | R | H | 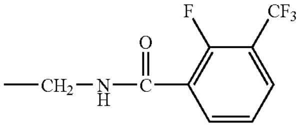 |
| 1203 | 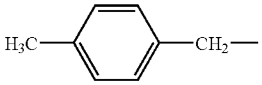 | 1 | 2 | 0 | R | H | 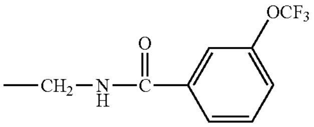 |
| 1204 | 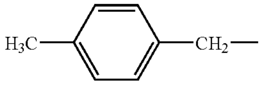 | 1 | 2 | 0 | R | H | 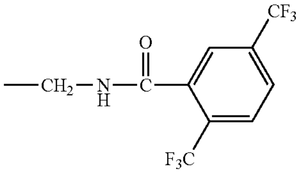 |
| 1205 | 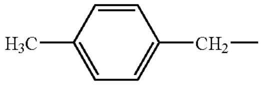 | 1 | 2 | 0 | R | H | 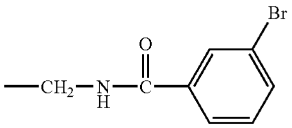 |

TABLE 1.110-continued
| Compd. No. | 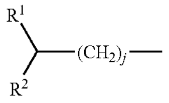 | k | m | n | chirality | $R^3$ | 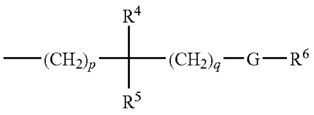 |
|---|---|---|---|---|---|---|---|
| 1206 | 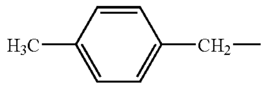 | 1 | 2 | 0 | R | H | 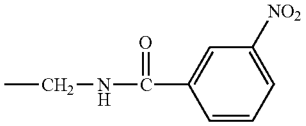 |
| 1207 | 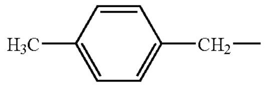 | 1 | 2 | 0 | R | H | 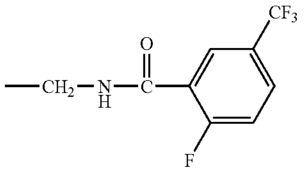 |
| 1208 | 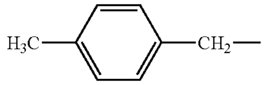 | 1 | 2 | 0 | R | H | 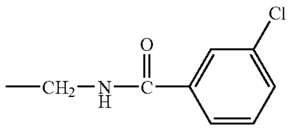 |
| 1209 | 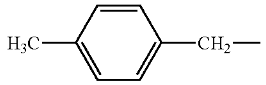 | 1 | 2 | 0 | R | H | 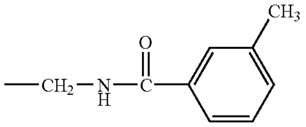 |
| 1210 | 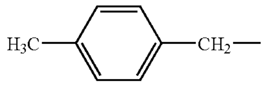 | 1 | 2 | 0 | R | H | 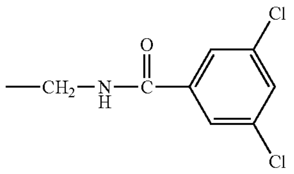 |
TABLE 1.111
| Compd. No. | 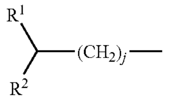 | k | m | n | chirality | $R^3$ | 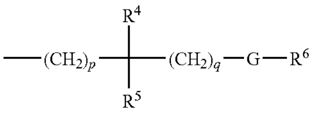 |
|---|---|---|---|---|---|---|---|
| 1211 | 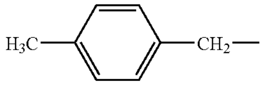 | 1 | 2 | 0 | R | H | 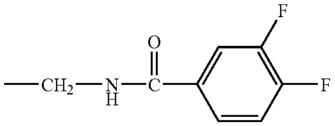 |
| 1212 | 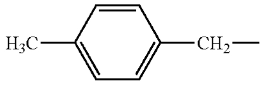 | 1 | 2 | 0 | R | H | 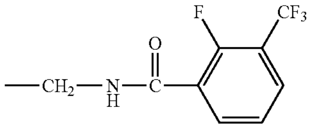 |
| 1213 | 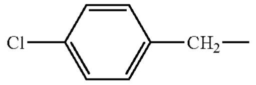 | 2 | 2 | 1 | — | H | 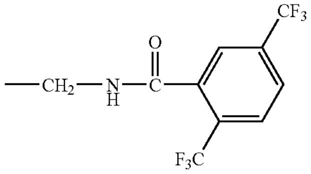 |

TABLE 1.111-continued
| Compd. No. | 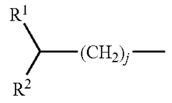 | k | m | n | chirality | $R^3$ | 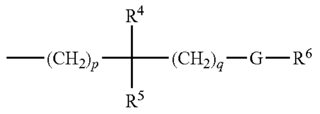 |
|---|---|---|---|---|---|---|---|
| 1214 | 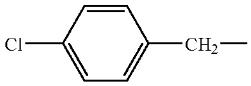 | 2 | 2 | 1 | — | H | 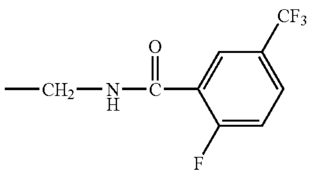 |
| 1215 | 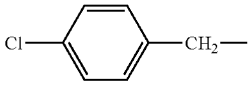 | 2 | 2 | 1 | — | H | 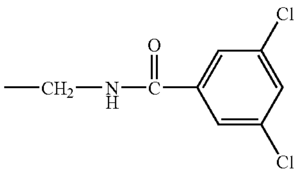 |
| 1216 | 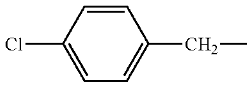 | 2 | 2 | 1 | — | H | 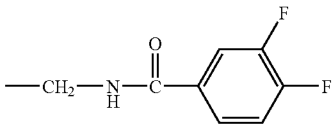 |
| 1217 | 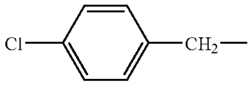 | 1 | 2 | 0 | R | H | 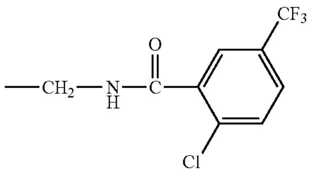 |
| 1218 | 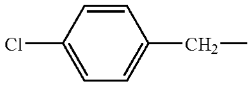 | 1 | 2 | 0 | R | H | 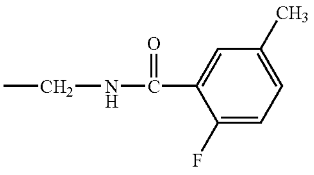 |
| 1219 | 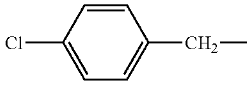 | 1 | 2 | 0 | R | H | 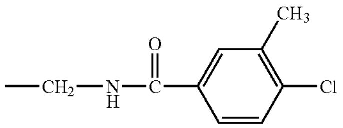 |
| 1220 | 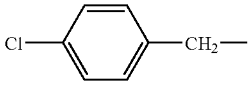 | 1 | 2 | 0 | R | H | 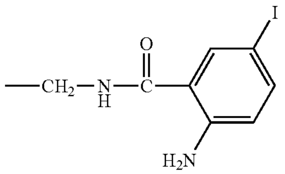 |
| 1221 | 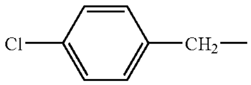 | 1 | 2 | 0 | R | H | 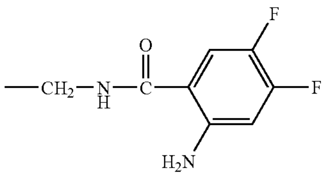 |

TABLE 1.112
| Compd. No. | 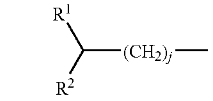 | k | m | n | chirality | $R^3$ | 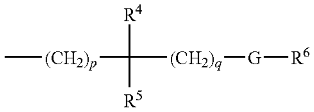 |
|---|---|---|---|---|---|---|---|
| 1222 | 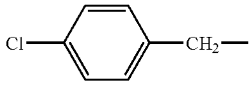 | 1 | 2 | 0 | R | H | 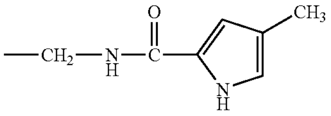 |
| 1223 | 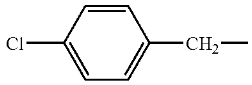 | 1 | 2 | 0 | R | H | 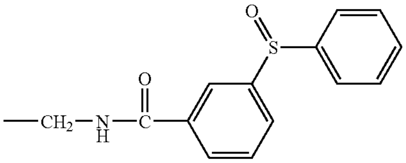 |
| 1224 | 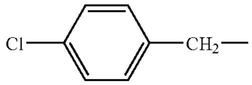 | 1 | 2 | 0 | R | H | 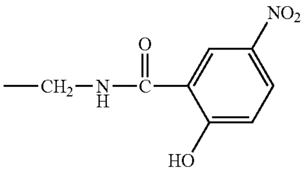 |
| 1225 | 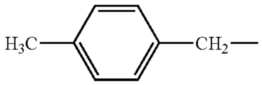 | 1 | 2 | 0 | R | H | 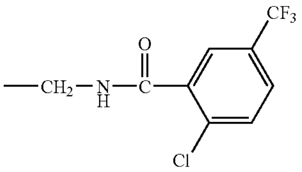 |
| 1226 | 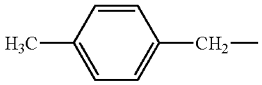 | 1 | 2 | 0 | R | H | 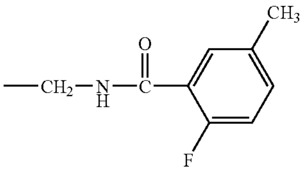 |
| 1227 | 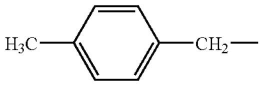 | 1 | 2 | 0 | R | H | 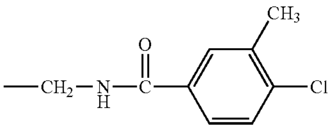 |
| 1228 | 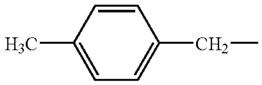 | 1 | 2 | 0 | R | H | 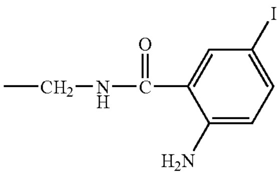 |
| 1229 | 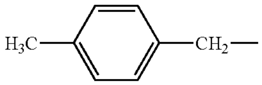 | 1 | 2 | 0 | R | H | 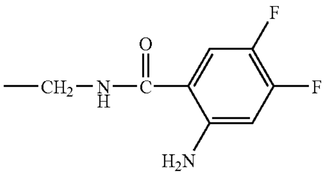 |
| 1230 | 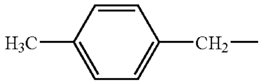 | 1 | 2 | 0 | R | H | 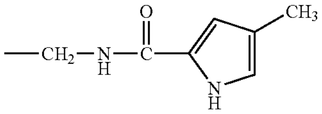 |

TABLE 1.112-continued
| Compd. No. | 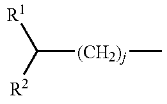 | k | m | n | chirality | $R^3$ | 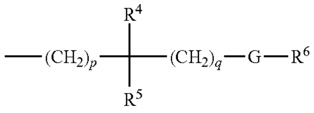 |
|---|---|---|---|---|---|---|---|
| 1231 | 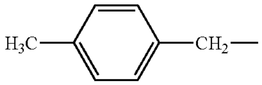 | 1 | 2 | 0 | R | H | 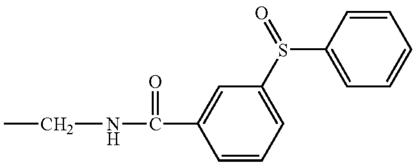 |
| 1232 | 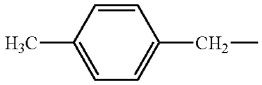 | 1 | 2 | 0 | R | H | 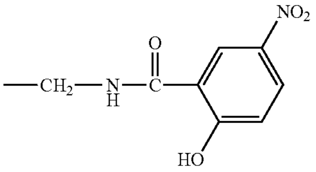 |
TABLE 1.113
| Compd. No. | 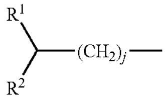 | k | m | n | chirality | $R^3$ | 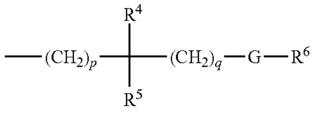 |
|---|---|---|---|---|---|---|---|
| 1233 | 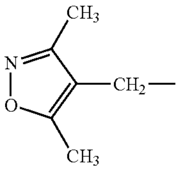 | 1 | 2 | 0 | R | H | 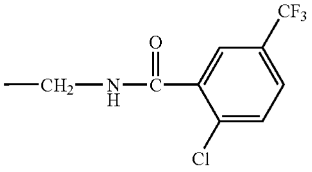 |
| 1234 | 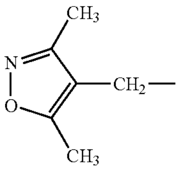 | 1 | 2 | 0 | R | H | 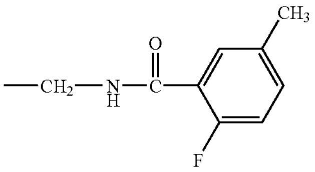 |
| 1235 | 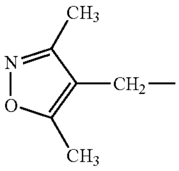 | 1 | 2 | 0 | R | H | 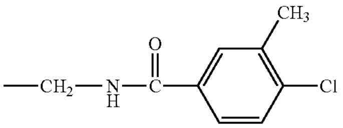 |
| 1236 | 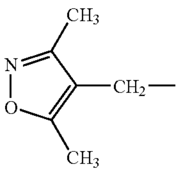 | 1 | 2 | 0 | R | H | 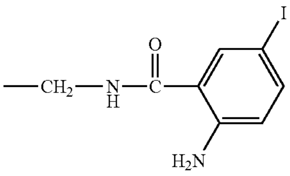 |

TABLE 1.113-continued
| Compd. No. | 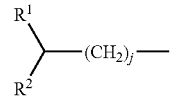 | k | m | n | chirality | $R^3$ | 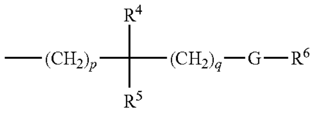 |
|---|---|---|---|---|---|---|---|
| 1237 | 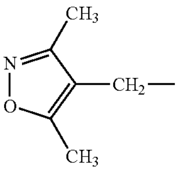 | 1 | 2 | 0 | R | H | 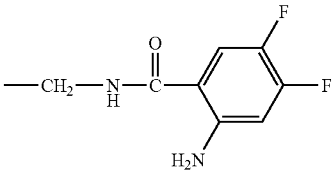 |
| 1238 | 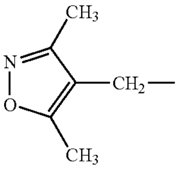 | 1 | 2 | 0 | R | H | 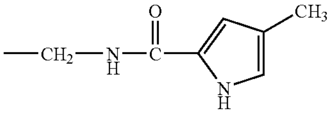 |
| 1239 | 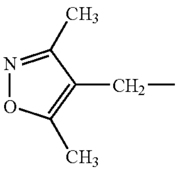 | 1 | 2 | 0 | R | H | 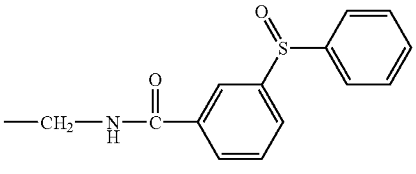 |
| 1240 | 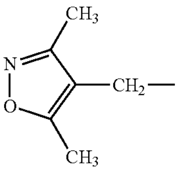 | 1 | 2 | 0 | R | H | 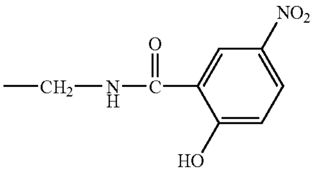 |
| 1241 | 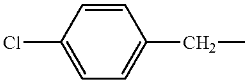 | 2 | 2 | 1 | — | H | 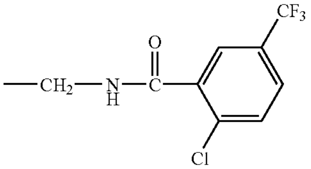 |
| 1242 | 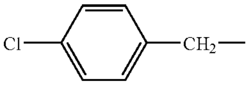 | 2 | 2 | 1 | — | H | 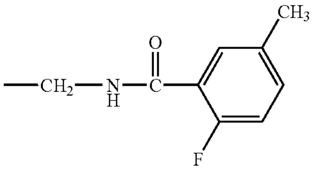 |
| 1243 | 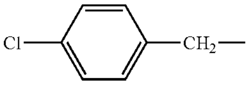 | 2 | 2 | 1 | — | H | 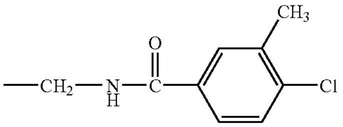 |

TABLE 1.114
| Compd. No. | 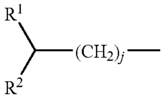 | k | m | n | chirality | $R^3$ | 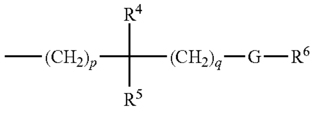 |
|---|---|---|---|---|---|---|---|
| 1244 | 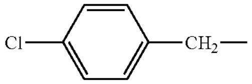 | 2 | 2 | 1 | — | H | 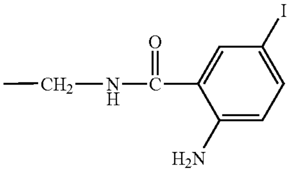 |
| 1245 | 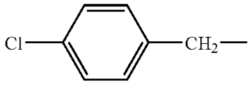 | 2 | 2 | 1 | — | H | 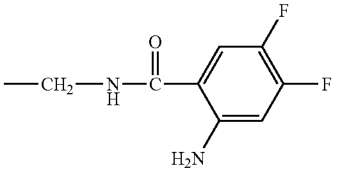 |
| 1246 | 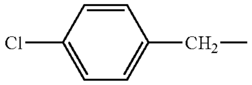 | 2 | 2 | 1 | — | H | 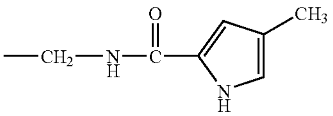 |
| 1247 | 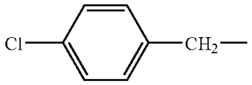 | 2 | 2 | 1 | — | H | 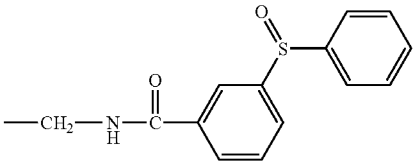 |
| 1248 | 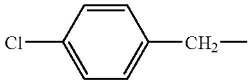 | 2 | 2 | 1 | — | H | 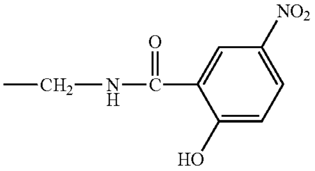 |
| 1249 | 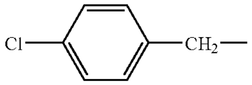 | 1 | 2 | 0 | R | H | 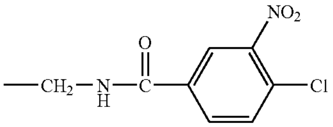 |
| 1250 | 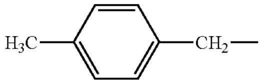 | 1 | 2 | 0 | R | H | 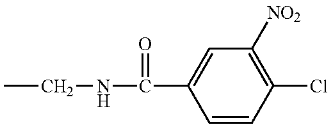 |
| 1251 | 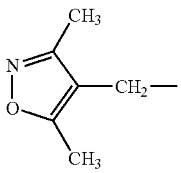 | 1 | 2 | 0 | R | H | 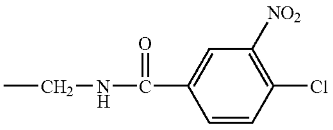 |
| 1252 | 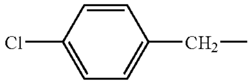 | 1 | 2 | 0 | R | H | 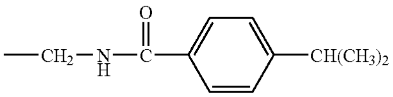 |

TABLE 1.114-continued
| Compd. No. | 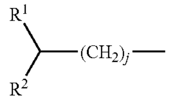 | k | m | n | chirality | $R^3$ | 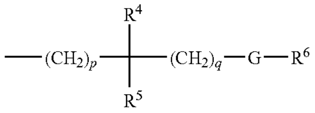 |
|---|---|---|---|---|---|---|---|
| 1253 | 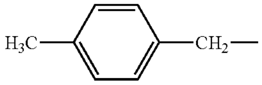 | 1 | 2 | 0 | R | H | 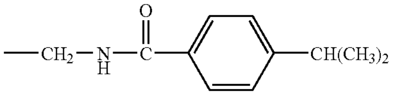 |
| 1254 | 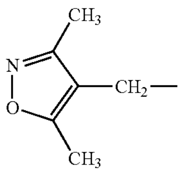 | 1 | 2 | 0 | R | H | 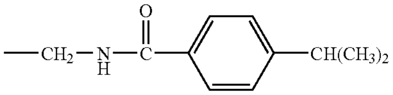 |
TABLE 1.115
| Compd. No. | 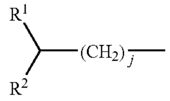 | k | m | n | chirality | $R^3$ | 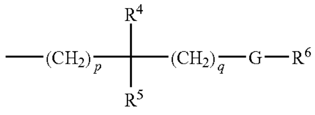 |
|---|---|---|---|---|---|---|---|
| 1255 | 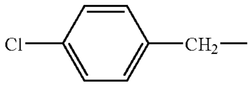 | 1 | 2 | 0 | R | H | 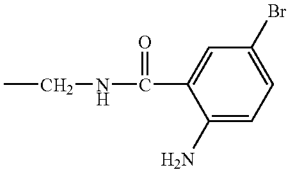 |
| 1256 | 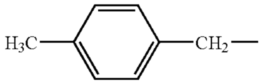 | 1 | 2 | 0 | R | H | 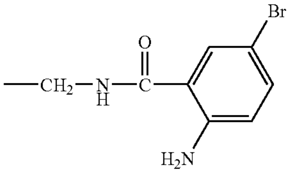 |
| 1257 | 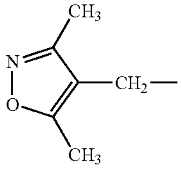 | 1 | 2 | 0 | R | H | 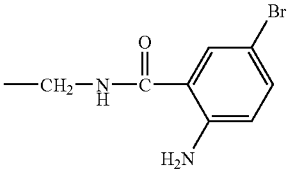 |
| 1258 | 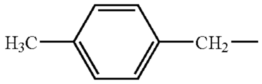 | 1 | 2 | 0 | R | H | 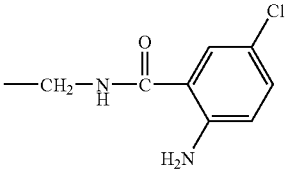 |
| 1259 | 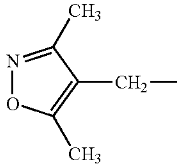 | 1 | 2 | 0 | R | H | 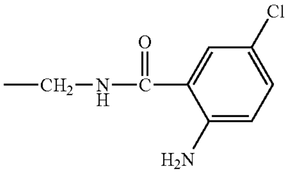 |

TABLE 1.115-continued
| Compd. No. | 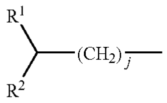 | k | m | n | chirality | $R^3$ | 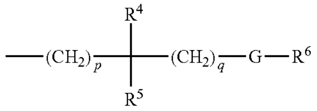 |
|---|---|---|---|---|---|---|---|
| 1260 | 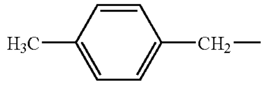 | 1 | 2 | 0 | R | H | 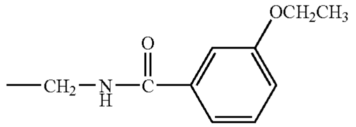 |
| 1261 | 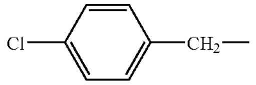 | 1 | 2 | 0 | R | H | 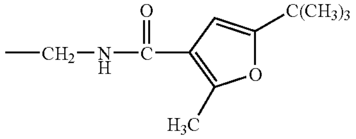 |
| 1262 | 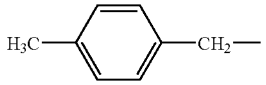 | 1 | 2 | 0 | R | H | 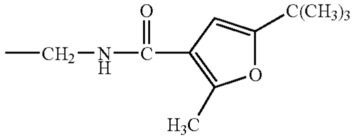 |
| 1263 | 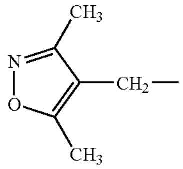 | 1 | 2 | 0 | R | H | 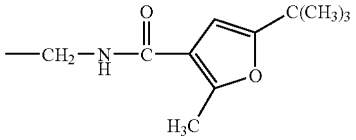 |
| 1264 | 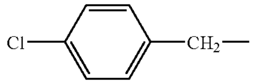 | 1 | 2 | 0 | R | H | 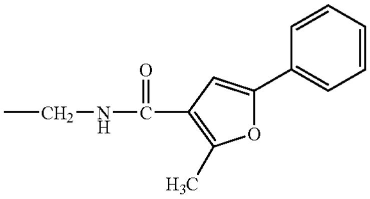 |
| 1265 | 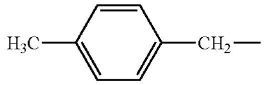 | 1 | 2 | 0 | R | H | 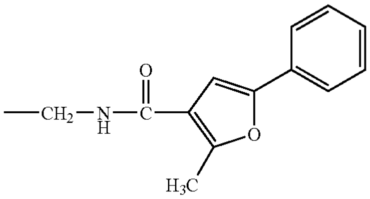 |
TABLE 1.116
| Compd. No. | 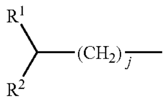 | k | m | n | chirality | $R^3$ | 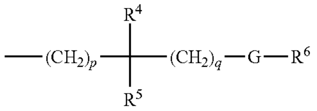 |
|---|---|---|---|---|---|---|---|
| 1266 | 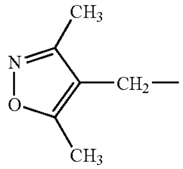 | 1 | 2 | 0 | R | H | 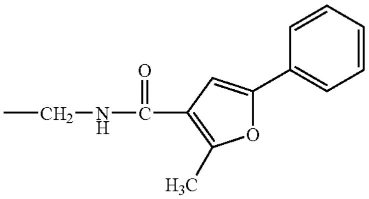 |

TABLE 1.116-continued
| Compd. No. | 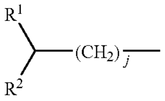 | k | m | n | chirality | $R^3$ | 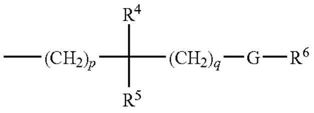 |
|---|---|---|---|---|---|---|---|
| 1267 | 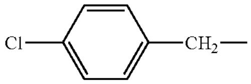 | 1 | 2 | 0 | R | H | 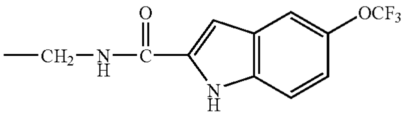 |
| 1268 | 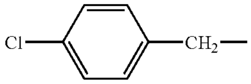 | 1 | 2 | 0 | R | H | 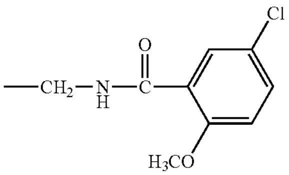 |
| 1269 | 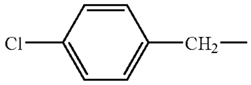 | 1 | 2 | 0 | R | H | 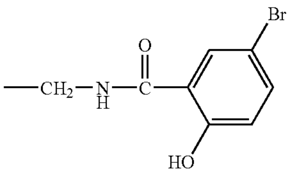 |
| 1270 | 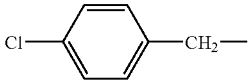 | 1 | 2 | 0 | R | H | 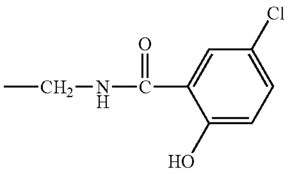 |
| 1271 | 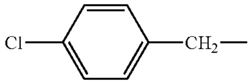 | 1 | 2 | 0 | R | H | 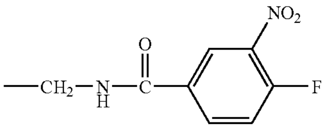 |
| 1272 | 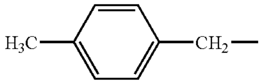 | 1 | 2 | 0 | R | H | 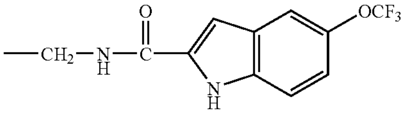 |
| 1273 | 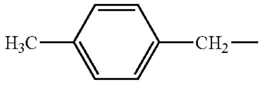 | 1 | 2 | 0 | R | H | 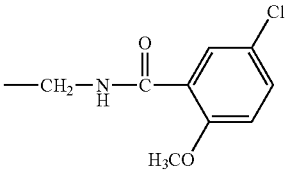 |
| 1274 | 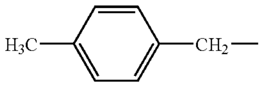 | 1 | 2 | 0 | R | H | 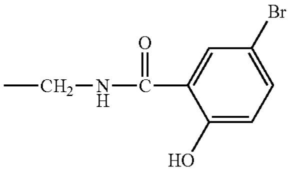 |

TABLE 1.116-continued
| Compd. No. | 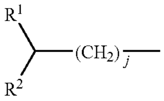 | k | m | n | chirality | $R^3$ | 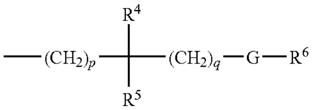 |
|---|---|---|---|---|---|---|---|
| 1275 | 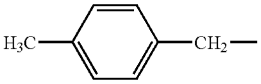 | 1 | 2 | 0 | R | H | 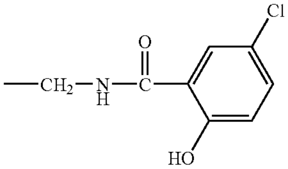 |
| 1276 | 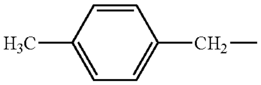 | 1 | 2 | 0 | R | H | 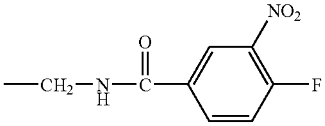 |
TABLE 1.117
| Compd. No. | 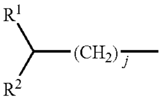 | k | m | n | chirality | $R^3$ | 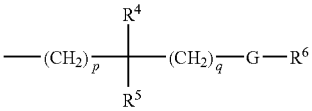 |
|---|---|---|---|---|---|---|---|
| 1277 | 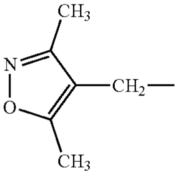 | 1 | 2 | 0 | R | H | 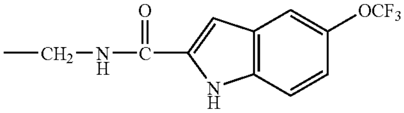 |
| 1278 | 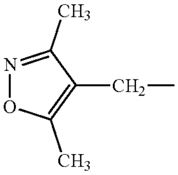 | 1 | 2 | 0 | R | H | 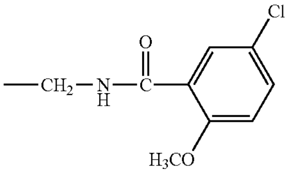 |
| 1279 | 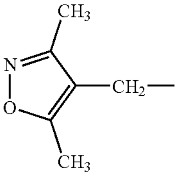 | 1 | 2 | 0 | R | H | 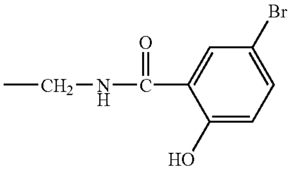 |
| 1280 | 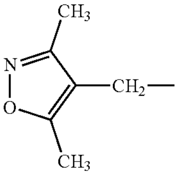 | 1 | 2 | 0 | R | H | 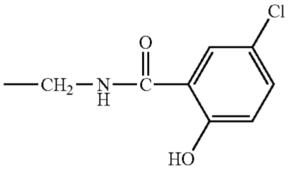 |
| 1281 | 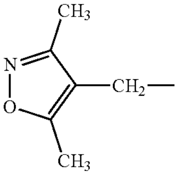 | 1 | 2 | 0 | R | H | 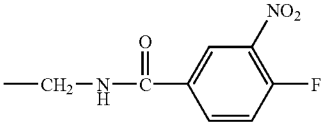 |

TABLE 1.117-continued
| Compd. No. | 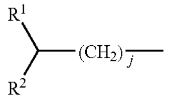 | k | m | n | chirality | $R^3$ | 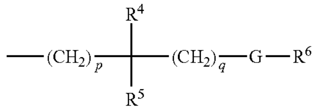 |
|---|---|---|---|---|---|---|---|
| 1282 | 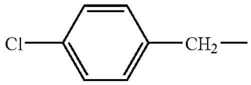 | 2 | 2 | 1 | — | H | 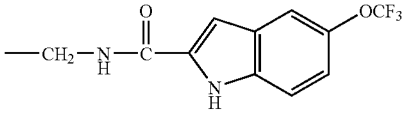 |
| 1283 | 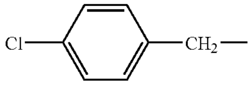 | 2 | 2 | 1 | — | H | 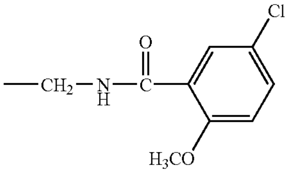 |
| 1284 | 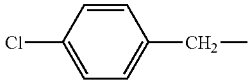 | 2 | 2 | 1 | — | H | 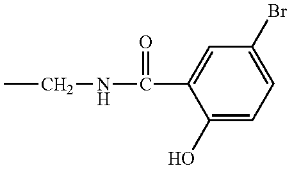 |
| 1285 | 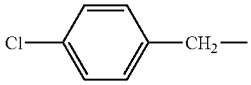 | 2 | 2 | 1 | — | H | 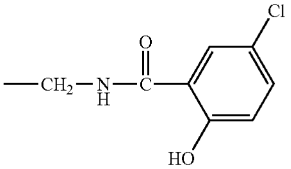 |
| 1286 | 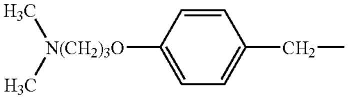 | 1 | 2 | 0 | R | H | 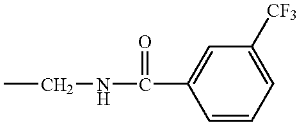 |
| 1287 | 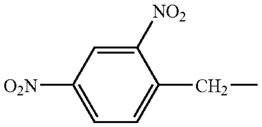 | 1 | 2 | 0 | R | H | 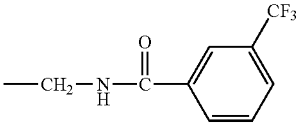 |
TABLE 1.118
| Compd. No. | 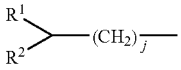 | k | m | n | chirality | $R^3$ | 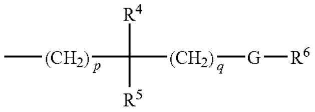 |
|---|---|---|---|---|---|---|---|
| 1288 | 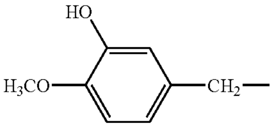 | 1 | 2 | 0 | R | H | 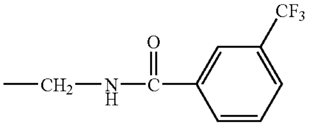 |
| 1289 | 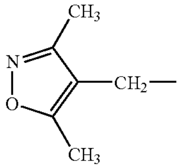 | 1 | 2 | 0 | R | H | 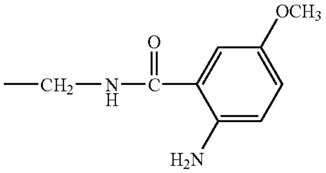 |

TABLE 1.118-continued
| Compd. No. | 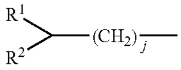 | k | m | n | chirality | $R^3$ | 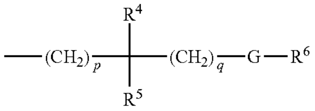 |
|---|---|---|---|---|---|---|---|
| 1290 | 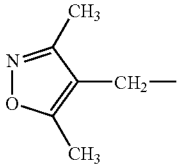 | 1 | 2 | 0 | R | H | 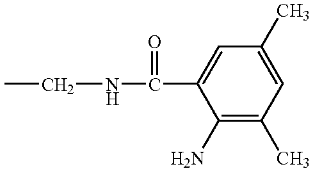 |
| 1291 | 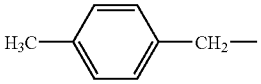 | 1 | 2 | 0 | R | H | 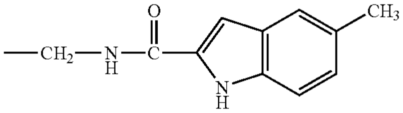 |
| 1292 | 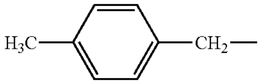 | 1 | 2 | 0 | R | H | 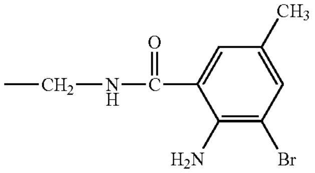 |
| 1293 | 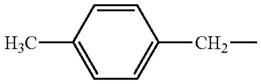 | 1 | 2 | 0 | R | H | 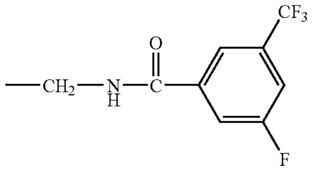 |
| 1294 | 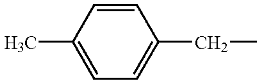 | 1 | 2 | 0 | R | H | 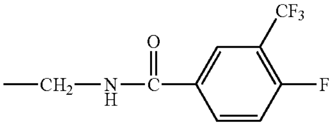 |
| 1295 | 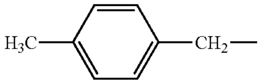 | 1 | 2 | 0 | R | H | 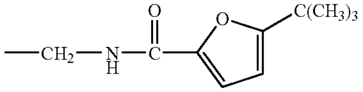 |
| 1296 | 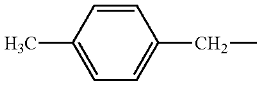 | 1 | 2 | 0 | R | H | 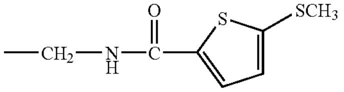 |
| 1297 | 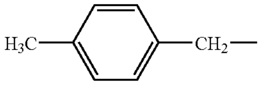 | 1 | 2 | 0 | R | H | 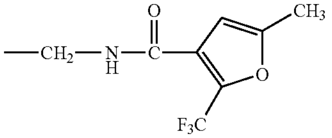 |
| 1298 | 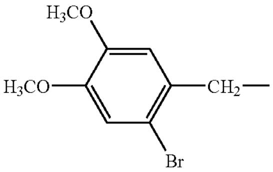 | 1 | 2 | 0 | R | H | 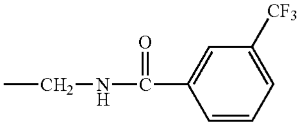 |

TABLE 1.119
| Compd. No. | 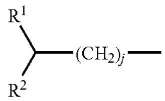 | k | m | n | chirality | $R^3$ | 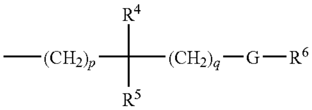 |
|---|---|---|---|---|---|---|---|
| 1299 | 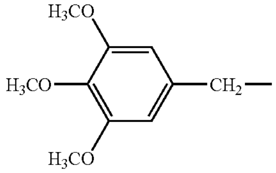 | 1 | 2 | 0 | R | H | 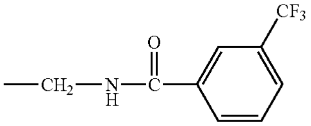 |
| 1300 | 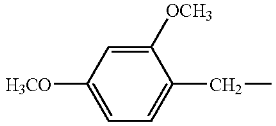 | 1 | 2 | 0 | R | H | 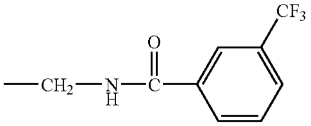 |
| 1301 | 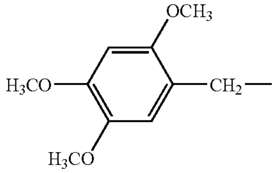 | 1 | 2 | 0 | R | H | 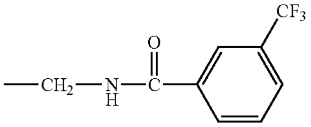 |
| 1302 | 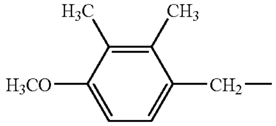 | 1 | 2 | 0 | R | H | 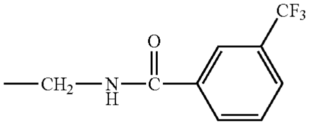 |
| 1303 | 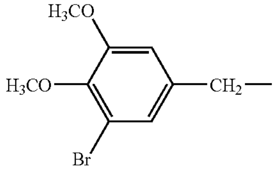 | 1 | 2 | 0 | R | H | 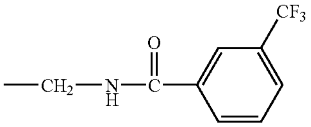 |
| 1304 | 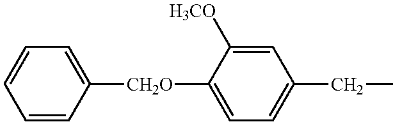 | 1 | 2 | 0 | R | H | 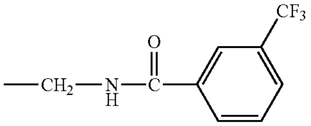 |
| 1305 | 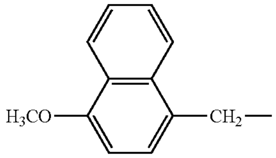 | 1 | 2 | 0 | R | H | 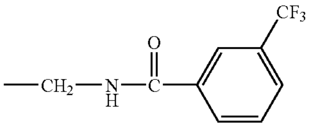 |
| 1306 | 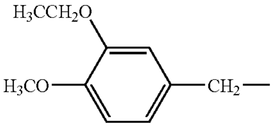 | 1 | 2 | 0 | R | H | 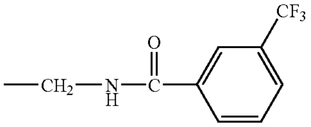 |
| 1307 | 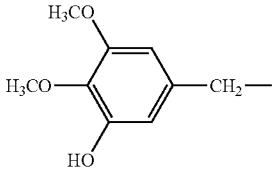 | 1 | 2 | 0 | R | H | 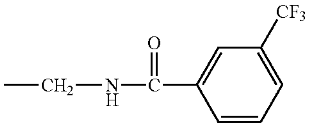 |

TABLE 1.119-continued
| Compd. No. | 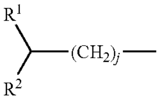 | k | m | n | chirality | $R^3$ | 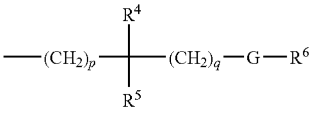 |
|---|---|---|---|---|---|---|---|
| 1308 | 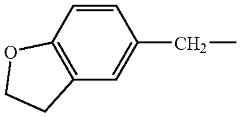 | 1 | 2 | 0 | R | H | 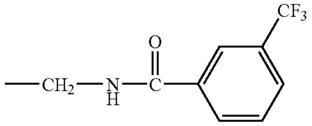 |
| 1309 | 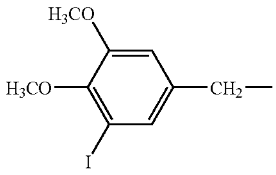 | 1 | 2 | 0 | R | H | 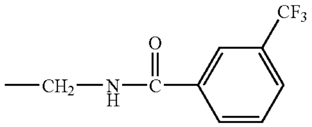 |
TABLE 1.120
| Compd. No. | 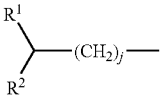 | k | m | n | chirality | $R^3$ | 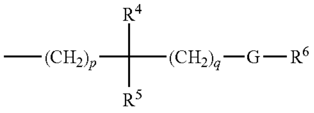 |
|---|---|---|---|---|---|---|---|
| 1310 | 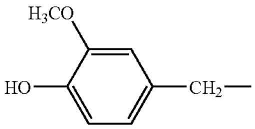 | 1 | 2 | 0 | R | H | 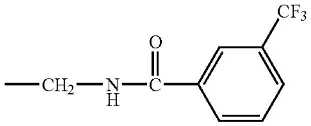 |
| 1311 | 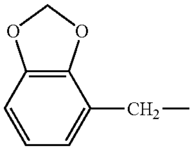 | 1 | 2 | 0 | R | H | 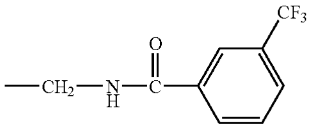 |
| 1312 | 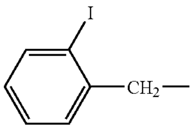 | 1 | 2 | 0 | R | H | 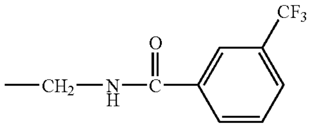 |
| 1313 | 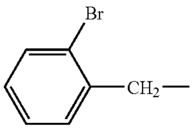 | 1 | 2 | 0 | R | H | 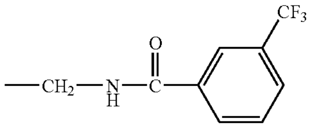 |
| 1314 | 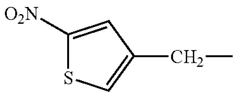 | 1 | 2 | 0 | R | H | 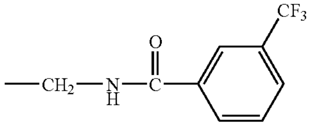 |
| 1315 | 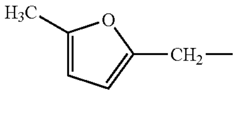 | 1 | 2 | 0 | R | H | 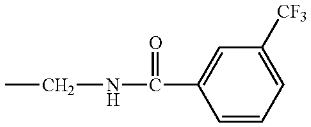 |

TABLE 1.120-continued
| Compd. No. | 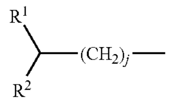 | k | m | n | chirality | $R^3$ | 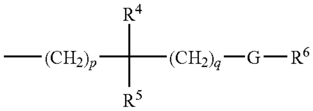 |
|---|---|---|---|---|---|---|---|
| 1316 | 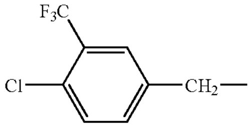 | 1 | 2 | 0 | R | H | 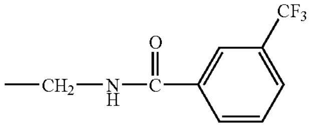 |
| 1317 | 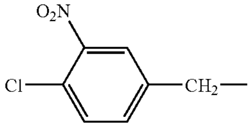 | 1 | 2 | 0 | R | H | 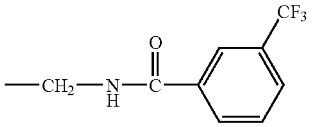 |
| 1318 | 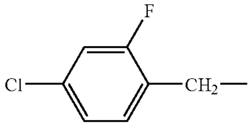 | 1 | 2 | 0 | R | H | 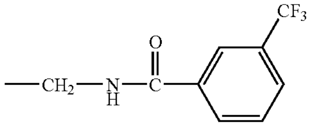 |
| 1319 | 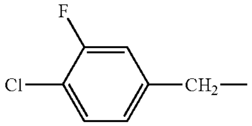 | 1 | 2 | 0 | R | H | 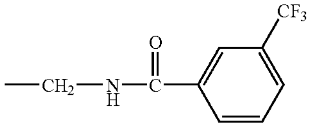 |
| 1320 | 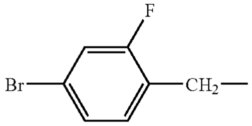 | 1 | 2 | 0 | R | H | 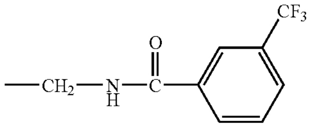 |
TABLE 1.121
| Compd. No. | 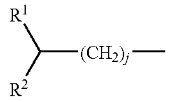 | k | m | n | chirality | $R^3$ | 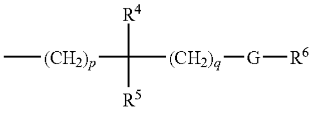 |
|---|---|---|---|---|---|---|---|
| 1321 | 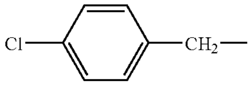 | 1 | 2 | 0 | R | H | 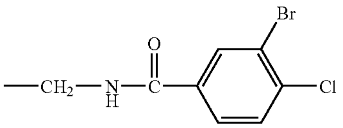 |
| 1322 | 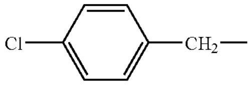 | 1 | 2 | 0 | R | H | 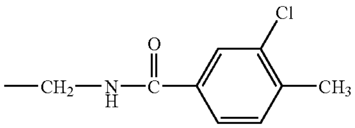 |
| 1323 | 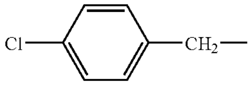 | 1 | 2 | 0 | R | H | 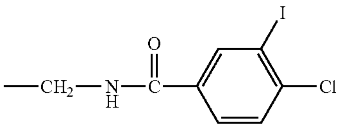 |

TABLE 1.121-continued
| Compd. No. | 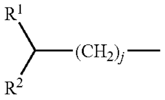 | k | m | n | chirality | $R^3$ | 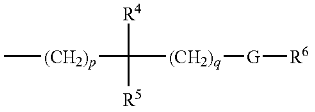 |
|---|---|---|---|---|---|---|---|
| 1324 | 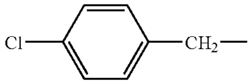 | 1 | 2 | 0 | R | H | 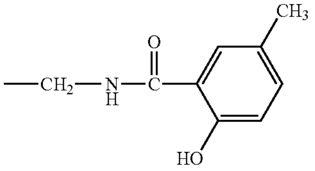 |
| 1325 | 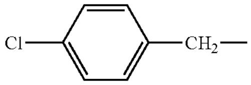 | 1 | 2 | 0 | R | H | 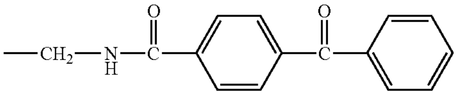 |
| 1326 | 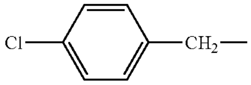 | 1 | 2 | 0 | R | H | 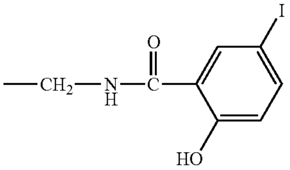 |
| 1327 | 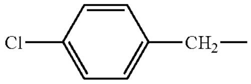 | 1 | 2 | 0 | R | H | 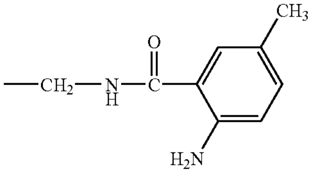 |
| 1328 | 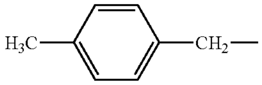 | 1 | 2 | 0 | R | H | 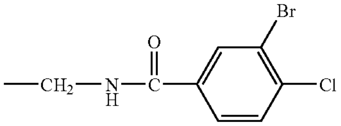 |
| 1329 | 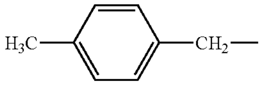 | 1 | 2 | 0 | R | H | 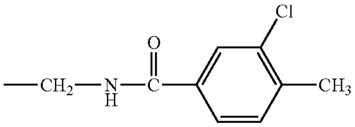 |
| 1330 | 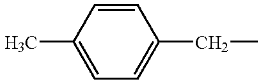 | 1 | 2 | 0 | R | H | 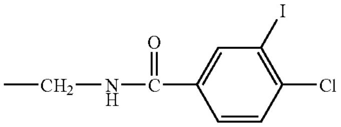 |
| 1331 | 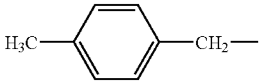 | 1 | 2 | 0 | R | H | 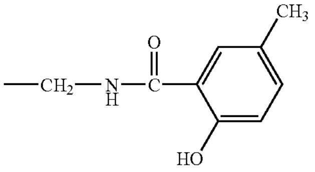 |

TABLE 1.122
| Compd. No. | 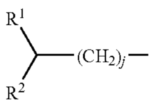 | k | m | n | chirality | $R^3$ | 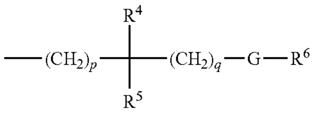 |
|---|---|---|---|---|---|---|---|
| 1332 | 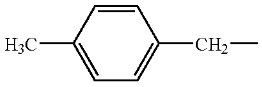 | 1 | 2 | 0 | R | H | 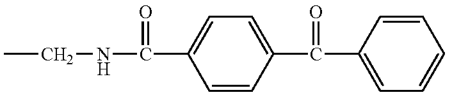 |
| 1333 | 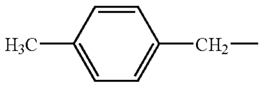 | 1 | 2 | 0 | R | H | 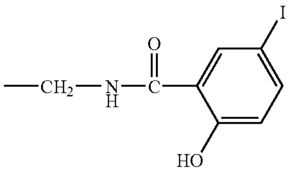 |
| 1334 | 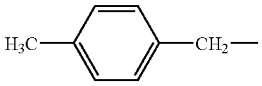 | 1 | 2 | 0 | R | H | 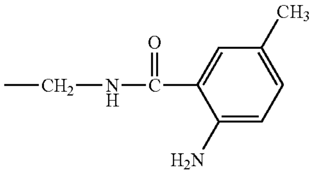 |
| 1335 | 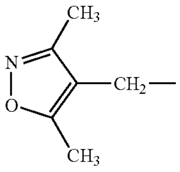 | 1 | 2 | 0 | R | H | 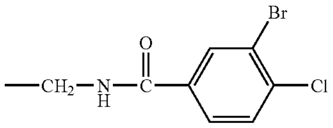 |
| 1336 | 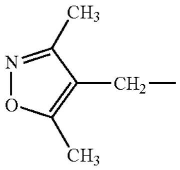 | 1 | 2 | 0 | R | H | 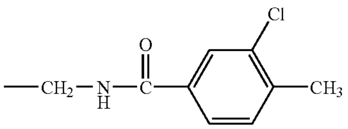 |
| 1337 | 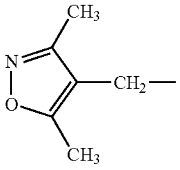 | 1 | 2 | 0 | R | H | 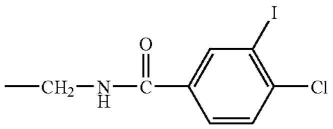 |
| 1338 | 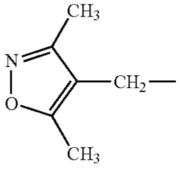 | 1 | 2 | 0 | R | H | 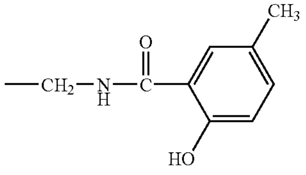 |
| 1339 | 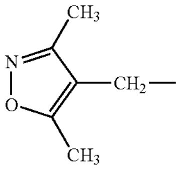 | 1 | 2 | 0 | R | H | 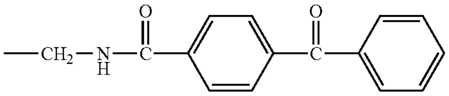 |

TABLE 1.122-continued
| Compd. No. | 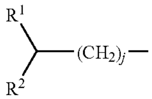 | k | m | n | chirality | $R^3$ | 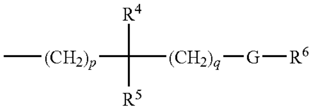 |
|---|---|---|---|---|---|---|---|
| 1340 | 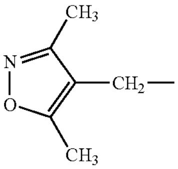 | 1 | 2 | 0 | R | H | 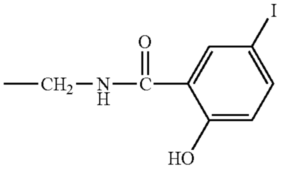 |
| 1341 | 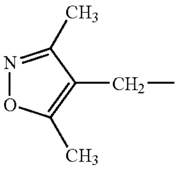 | 1 | 2 | 0 | R | H | 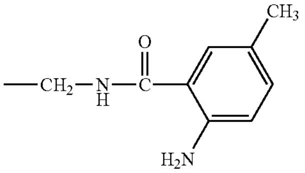 |
| 1342 | 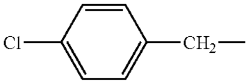 | 2 | 2 | 1 | — | H | 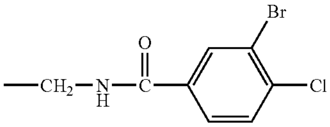 |
TABLE 1.123
| Compd. No. | 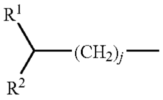 | k | m | n | chirality | $R^3$ | 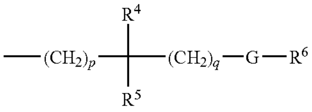 |
|---|---|---|---|---|---|---|---|
| 1343 | 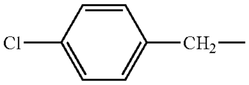 | 2 | 2 | 1 | — | H | 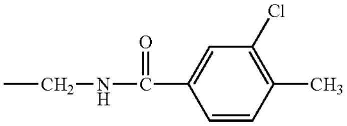 |
| 1344 | 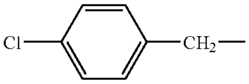 | 2 | 2 | 1 | — | H | 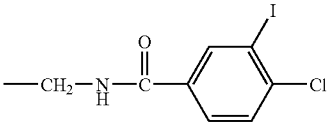 |
| 1345 | 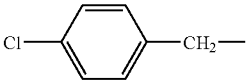 | 2 | 2 | 1 | — | H | 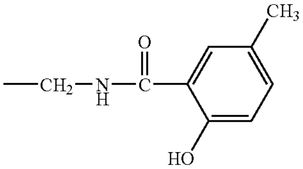 |
| 1346 | 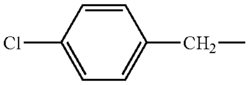 | 2 | 2 | 1 | — | H | 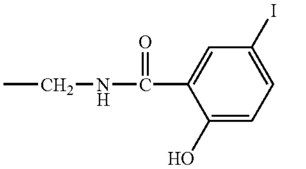 |
| 1347 | 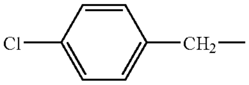 | 1 | 2 | 0 | R | H | 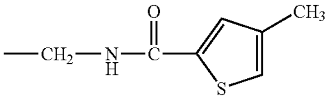 |

TABLE 1.123-continued
| Compd. No. | 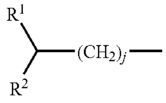 | k | m | n | chirality | $R^3$ | 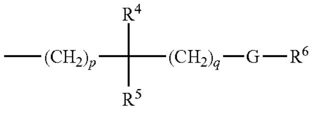 |
|---|---|---|---|---|---|---|---|
| 1348 | 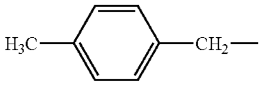 | 1 | 2 | 0 | R | H | 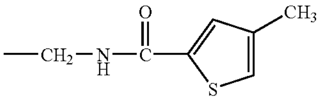 |
| 1349 | 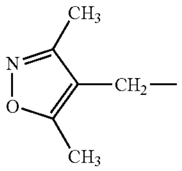 | 1 | 2 | 0 | R | H | 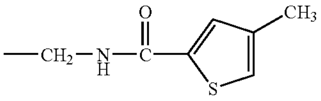 |
| 1350 | 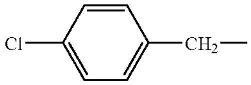 | 2 | 2 | 1 | — | H | 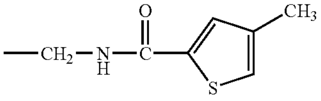 |
| 1351 | 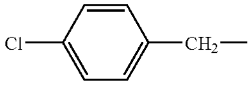 | 1 | 2 | 0 | R | H | 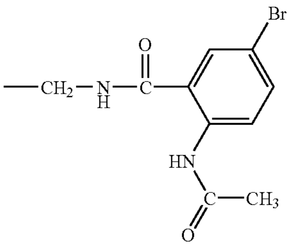 |
| 1352 | 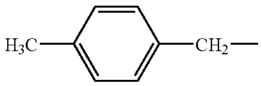 | 1 | 2 | 0 | R | H | 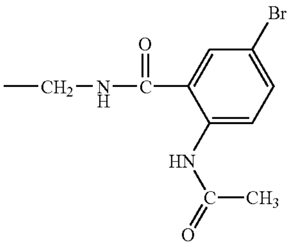 |
| 1353 | 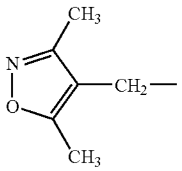 | 1 | 2 | 0 | R | H | 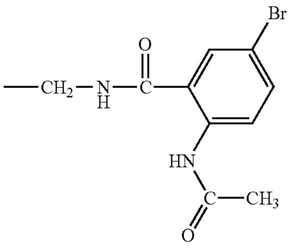 |

TABLE 1.124
| Compd. No. | 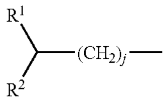 | k | m | n | chirality | $R^3$ | 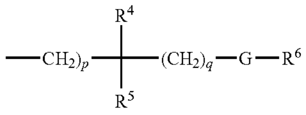 |
|---|---|---|---|---|---|---|---|
| 1354 | 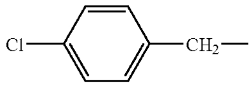 | 2 | 2 | 1 | — | H | 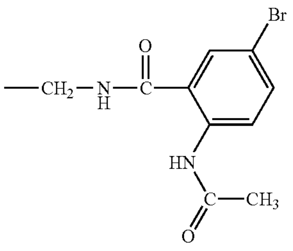 |
| 1355 | 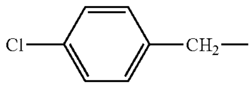 | 1 | 2 | 0 | R | H | 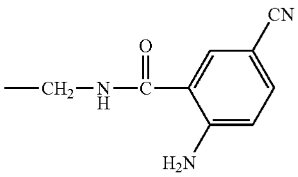 |
| 1356 | 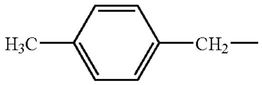 | 1 | 2 | 0 | R | H | 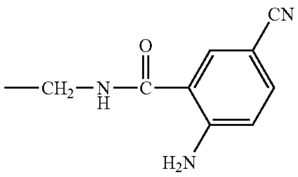 |
| 1357 | 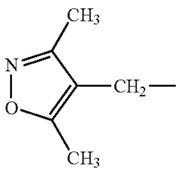 | 1 | 2 | 0 | R | H | 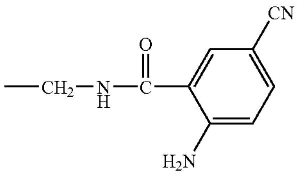 |
| 1358 | 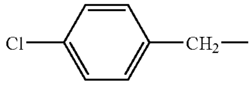 | 2 | 2 | 1 | — | H | 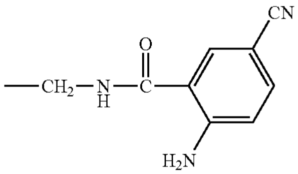 |
| 1359 | 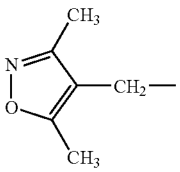 | 1 | 2 | 0 | R | H | 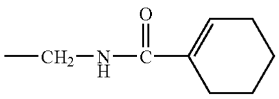 |
| 1360 | 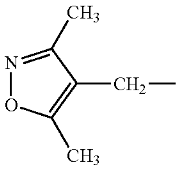 | 1 | 2 | 0 | R | H | 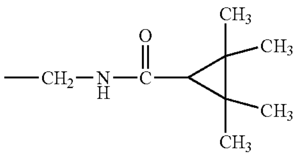 |
| 1361 | 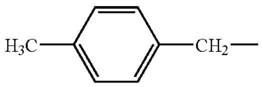 | 1 | 2 | 0 | R | H | 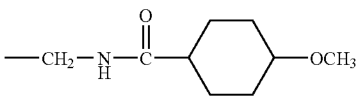 |

TABLE 1.124-continued
| Compd. No. | 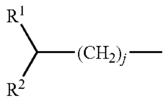 | k | m | n | chirality | R³ | 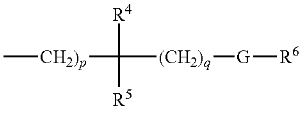 |
|---|---|---|---|---|---|---|---|
| 1362 | 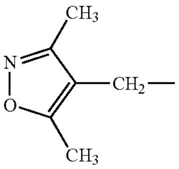 | 1 | 2 | 0 | R | H | 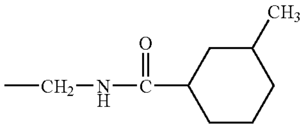 |
| 1363 | 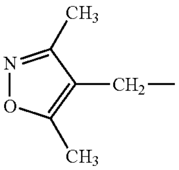 | 1 | 2 | 0 | R | H | 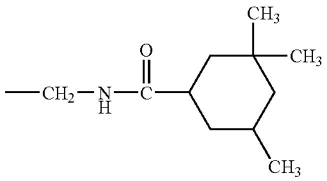 |
| 1364 | 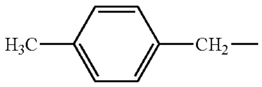 | 1 | 2 | 0 | R | H | 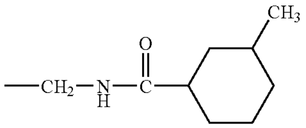 |
TABLE 1.125
| Compd. No. | 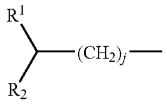 | k | m | n | chirality | R³ | 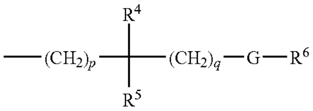 |
|---|---|---|---|---|---|---|---|
| 1365 | 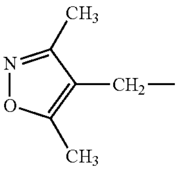 | 1 | 2 | 0 | R | H | 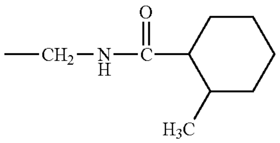 |
| 1366 | 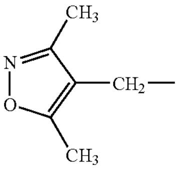 | 1 | 2 | 0 | R | H | 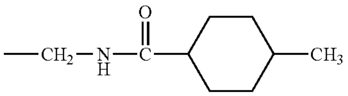 |
| 1367 | 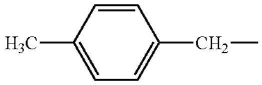 | 1 | 2 | 0 | R | H | 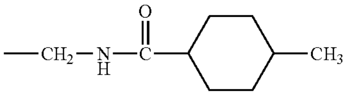 |
| 1368 | 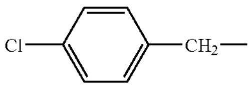 | 1 | 2 | 0 | R | H | 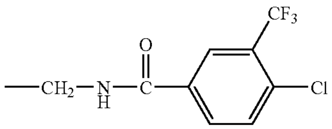 |

TABLE 1.125-continued
| Compd. No. | 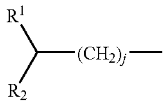 | k | m | n | chirality | $R^3$ | 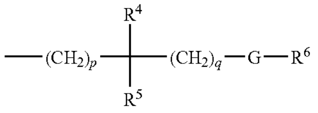 |
| --- | --- | --- | --- | --- | --- | --- | --- |
| 1369 | 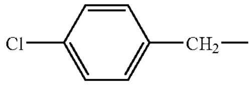 | 1 | 2 | 0 | R | H | 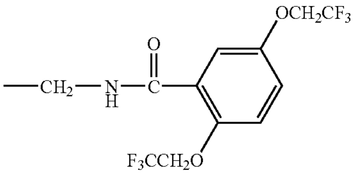 |
| 1370 | 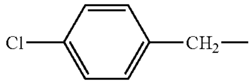 | 1 | 2 | 0 | R | H | 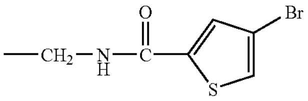 |
| 1371 | 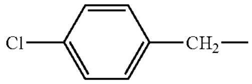 | 1 | 2 | 0 | R | H | 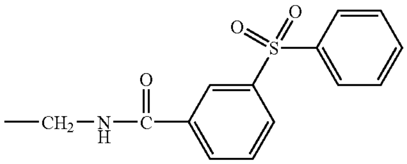 |
| 1372 | 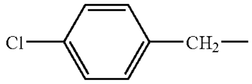 | 1 | 2 | 0 | R | H | 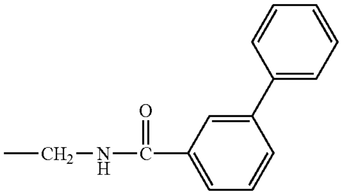 |
| 1373 | 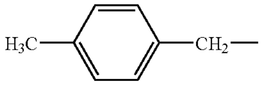 | 1 | 2 | 0 | R | H | 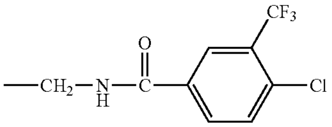 |
| 1374 | 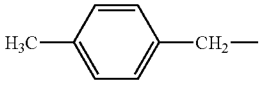 | 1 | 2 | 0 | R | H | 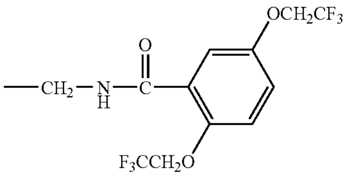 |
| 1375 | 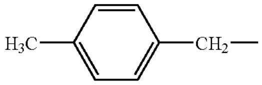 | 1 | 2 | 0 | R | H | 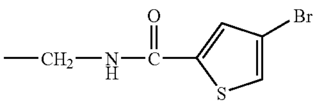 |

TABLE 1.126
| Compd. No. | 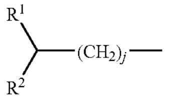 | k | m | n | chirality | $R^3$ | 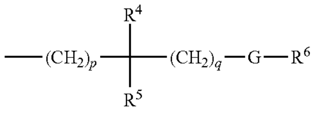 |
|---|---|---|---|---|---|---|---|
| 1376 | 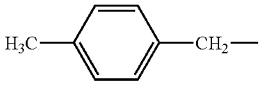 | 1 | 2 | 0 | R | H | 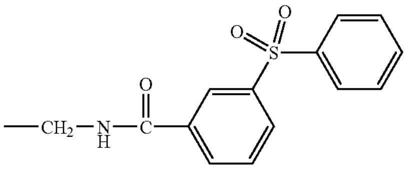 |
| 1377 | 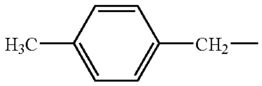 | 1 | 2 | 0 | R | H | 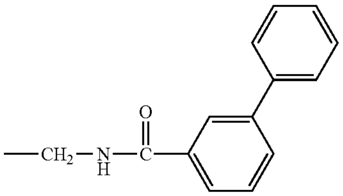 |
| 1378 | 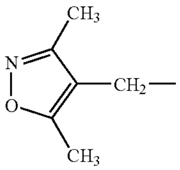 | 1 | 2 | 0 | R | H | 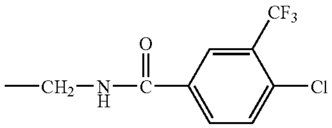 |
| 1379 | 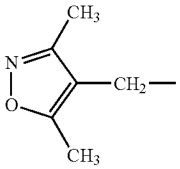 | 1 | 2 | 0 | R | H | 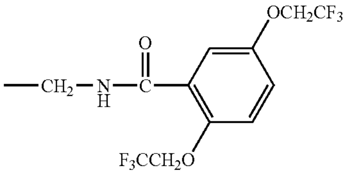 |
| 1380 | 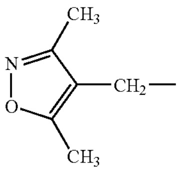 | 1 | 2 | 0 | R | H | 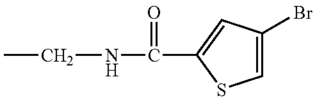 |
| 1381 | 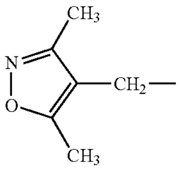 | 1 | 2 | 0 | R | H | 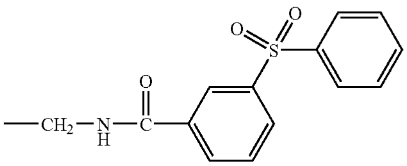 |
| 1382 | 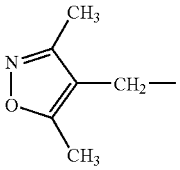 | 1 | 2 | 0 | R | H | 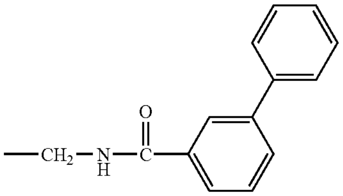 |
| 1383 | 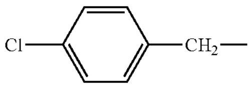 | 2 | 2 | 1 | — | H | 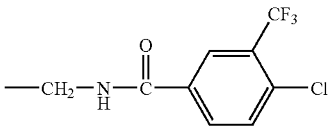 |

TABLE 1.126-continued
| Compd. No. | 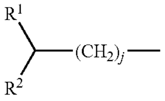 | k | m | n | chirality | $R^3$ | 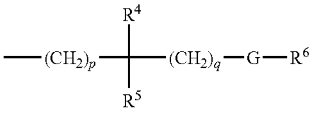 |
|---|---|---|---|---|---|---|---|
| 1384 | 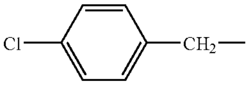 | 2 | 2 | 1 | — | H | 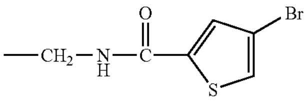 |
| 1385 | 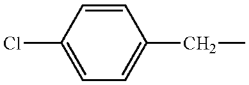 | 2 | 2 | 1 | — | H | 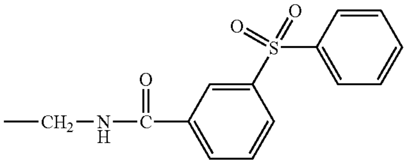 |
| 1386 | 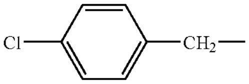 | 2 | 2 | 1 | — | H | 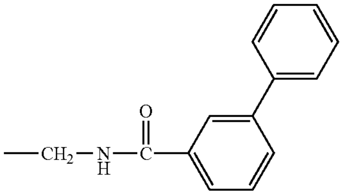 |
TABLE 1.127
| Compd. No. | 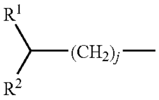 | k | m | n | chirality | $R^3$ | 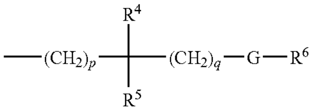 |
|---|---|---|---|---|---|---|---|
| 1387 | 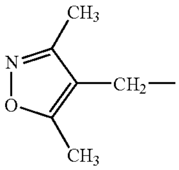 | 1 | 2 | 0 | R | H | 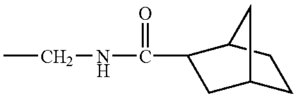 |
| 1388 | 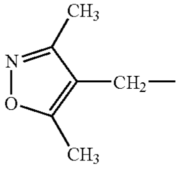 | 1 | 2 | 0 | R | H | 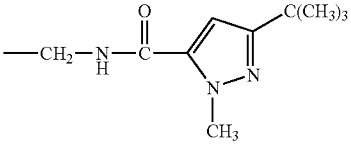 |
| 1389 | 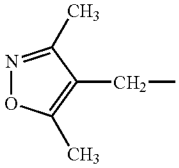 | 1 | 2 | 0 | R | H | 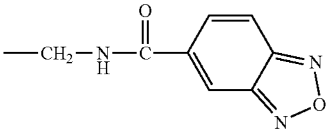 |
| 1390 | 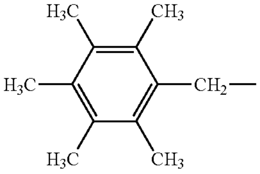 | 1 | 2 | 0 | R | H | 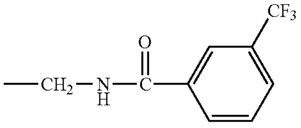 |

TABLE 1.127-continued
| Compd. No. | 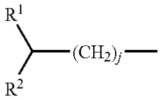 | k | m | n | chirality | $R^3$ | 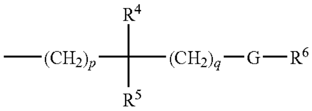 |
|---|---|---|---|---|---|---|---|
| 1391 | 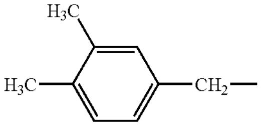 | 1 | 2 | 0 | R | H | 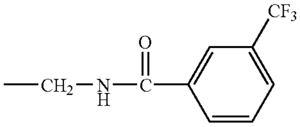 |
| 1392 | 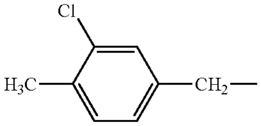 | 1 | 2 | 0 | R | H | 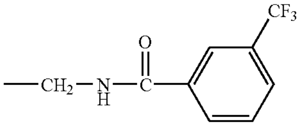 |
| 1393 | 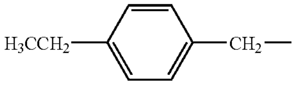 | 1 | 2 | 0 | R | H | 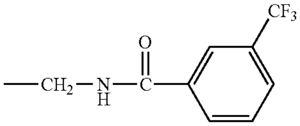 |
| 1394 | 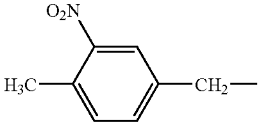 | 1 | 2 | 0 | R | H | 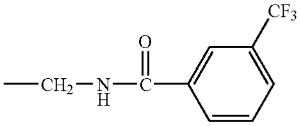 |
| 1395 | 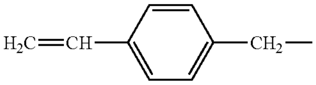 | 1 | 2 | 0 | R | H | 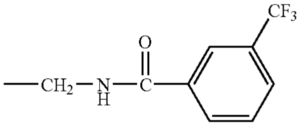 |
| 1396 | 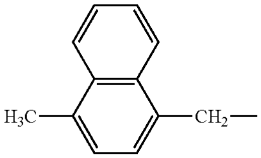 | 1 | 2 | 0 | R | H | 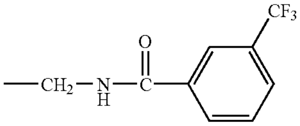 |
| 1397 | 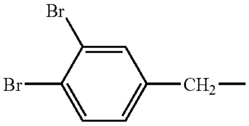 | 1 | 2 | 0 | R | H | 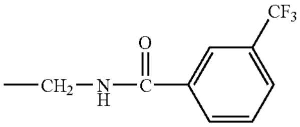 |
TABLE 1.128
| Compd. No. | 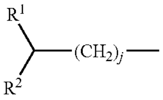 | k | m | n | chirality | $R^3$ | 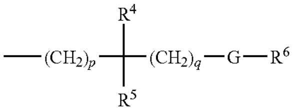 |
|---|---|---|---|---|---|---|---|
| 1398 | 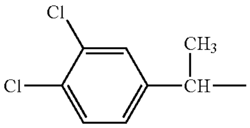 | 1 | 2 | 0 | R | H | 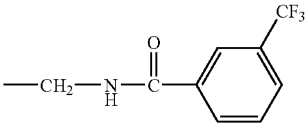 |

TABLE 1.128-continued
| Compd. No. | 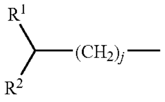 | k | m | n | chirality | $R^3$ | 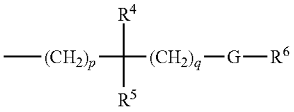 |
|---|---|---|---|---|---|---|---|
| 1399 | 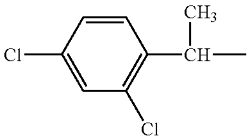 | 1 | 2 | 0 | R | H | 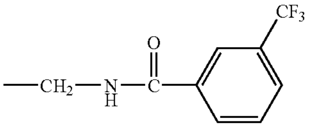 |
| 1400 | 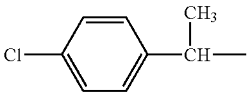 | 1 | 2 | 0 | R | H | 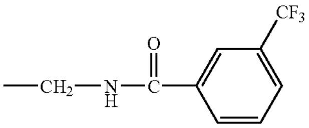 |
| 1401 | 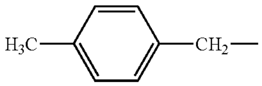 | 1 | 2 | 0 | R | H | 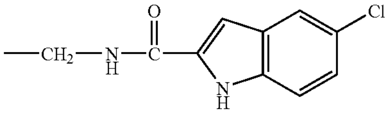 |
| 1402 | 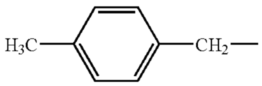 | 1 | 2 | 0 | R | H | 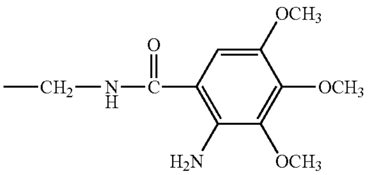 |
| 1403 | 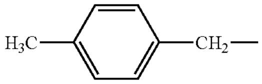 | 1 | 2 | 0 | R | H | 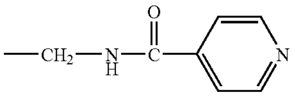 |
| 1404 | 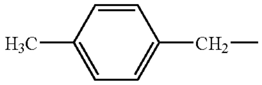 | 1 | 2 | 0 | R | H | 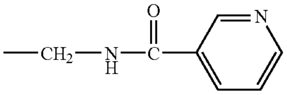 |
| 1405 | 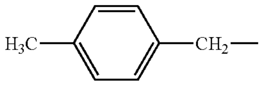 | 1 | 2 | 0 | R | H | 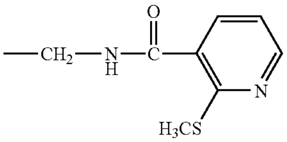 |
| 1406 | 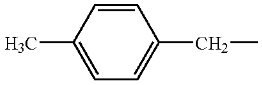 | 1 | 2 | 0 | R | H | 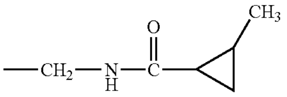 |
| 1407 | 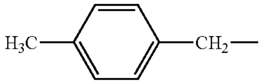 | 1 | 2 | 0 | R | H | 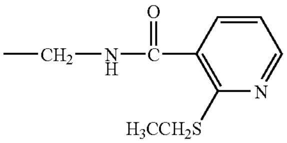 |
| 1408 | 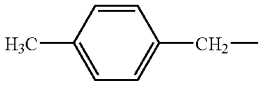 | 1 | 2 | 0 | R | H | 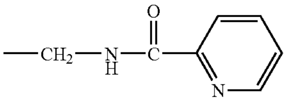 |

TABLE 1.129
| Compd. No. | 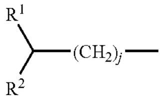 | k | m | n | chirality | $R^3$ | 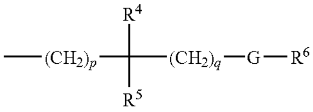 |
|---|---|---|---|---|---|---|---|
| 1409 | 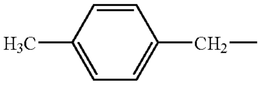 | 1 | 2 | 0 | R | H | 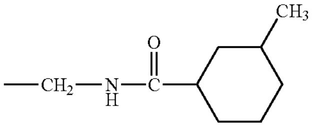 |
| 1410 | 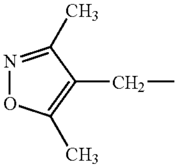 | 1 | 2 | 0 | R | H | 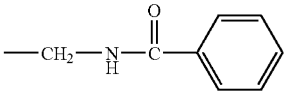 |
| 1411 | 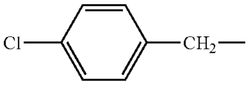 | 1 | 2 | 0 | R | H | 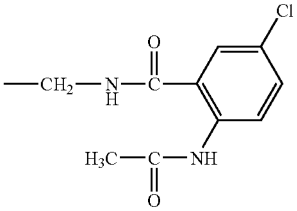 |
| 1412 | 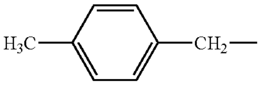 | 1 | 2 | 0 | R | H | 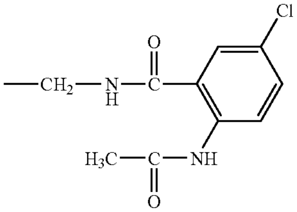 |
| 1413 | 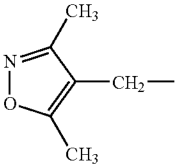 | 1 | 2 | 0 | R | H | 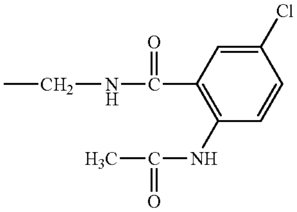 |
| 1414 | 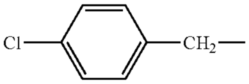 | 2 | 2 | 1 | — | H | 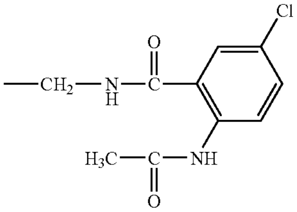 |
| 1415 | 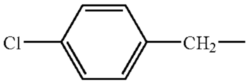 | 1 | 2 | 0 | R | H | 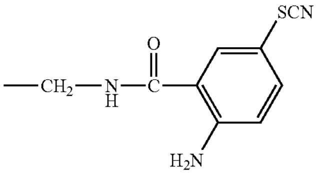 |

TABLE 1.129-continued
| Compd. No. | 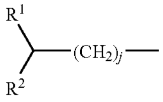 | k | m | n | chirality | $R^3$ | 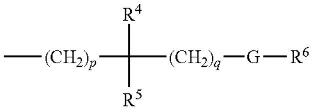 |
|---|---|---|---|---|---|---|---|
| 1416 | 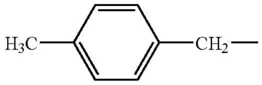 | 1 | 2 | 0 | R | H | 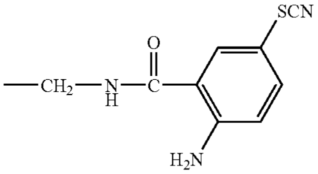 |
| 1417 | 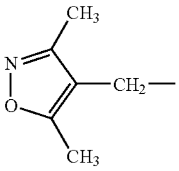 | 1 | 2 | 0 | R | H | 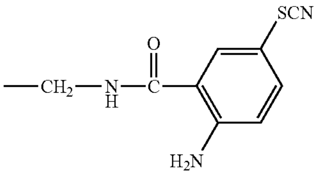 |
| 1418 | 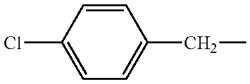 | 2 | 2 | 1 | — | H | 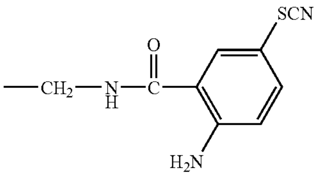 |
| 1419 | 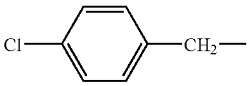 | 1 | 2 | 0 | R | H | 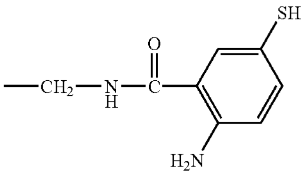 |
TABLE 1.130
| Compd. No. | 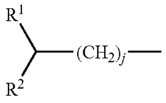 | k | m | n | chirality | $R^3$ | 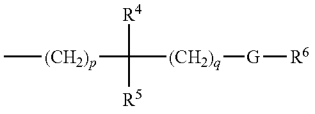 |
|---|---|---|---|---|---|---|---|
| 1420 | 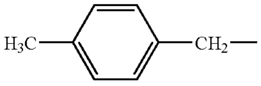 | 1 | 2 | 0 | R | H | 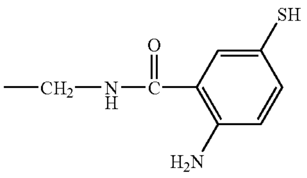 |
| 1421 | 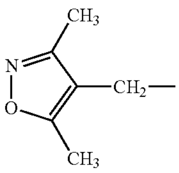 | 1 | 2 | 0 | R | H | 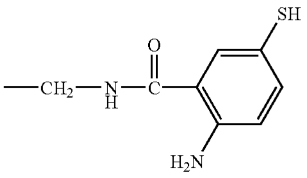 |

TABLE 1.130-continued
| Compd. No. | 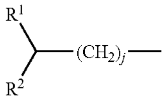 | k | m | n | chirality | $R^3$ | 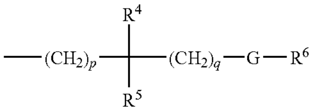 |
|---|---|---|---|---|---|---|---|
| 1422 | 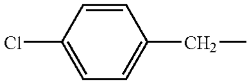 | 2 | 2 | 1 | — | H | 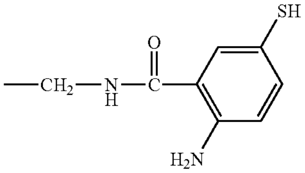 |
| 1423 | 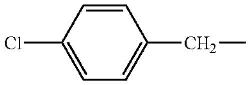 | 1 | 2 | 0 | R | H | 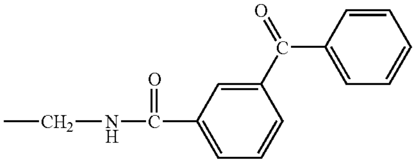 |
| 1424 | 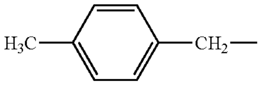 | 1 | 2 | 0 | R | H | 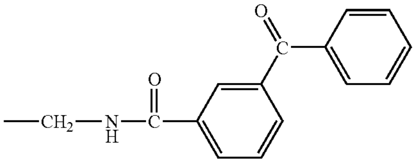 |
| 1425 | 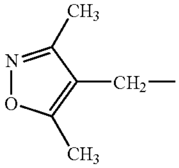 | 1 | 2 | 0 | R | H | 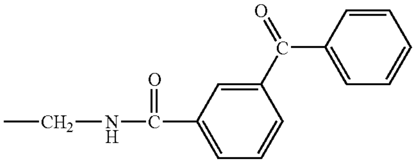 |
| 1426 | 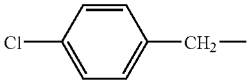 | 2 | 2 | 1 | — | H | 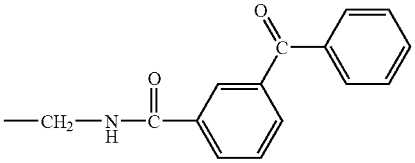 |
| 1427 | 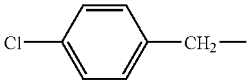 | 2 | 2 | 1 | — | H | 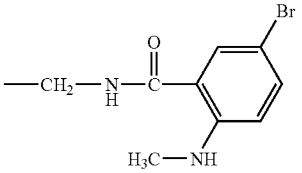 |
| 1428 | 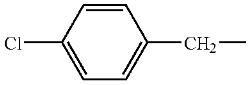 | 2 | 2 | 1 | — | H | 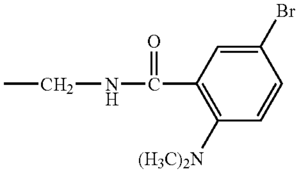 |
| 1429 | 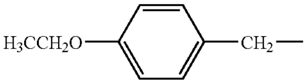 | 2 | 2 | 1 | — | H | 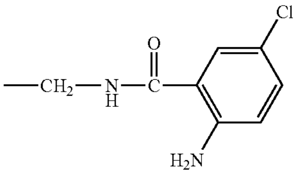 |

TABLE 1.130-continued
| Compd. No. | 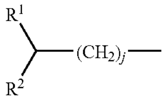 | k | m | n | chirality | $R^3$ | 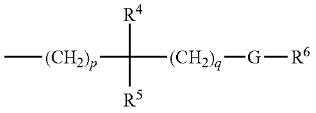 |
|---|---|---|---|---|---|---|---|
| 1430 | 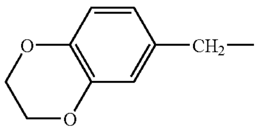 | 2 | 2 | 1 | — | H | 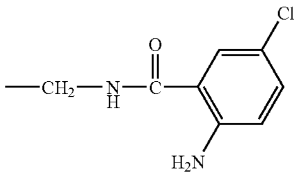 |
TABLE 1.131
| Compd. No. | 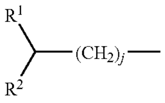 | k | m | n | chirality | $R^3$ | 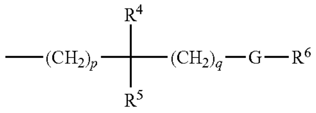 |
|---|---|---|---|---|---|---|---|
| 1431 | 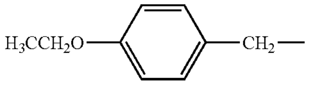 | 2 | 2 | 1 | — | H | 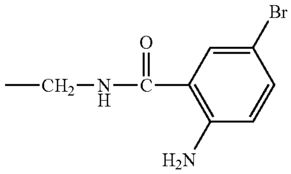 |
| 1432 | 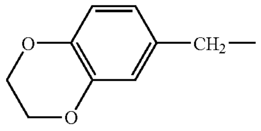 | 2 | 2 | 1 | — | H | 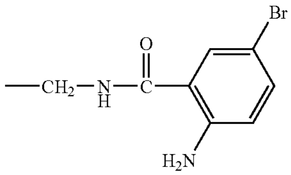 |
| 1433 | 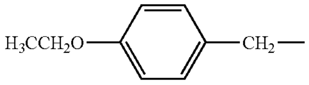 | 2 | 2 | 1 | — | H | 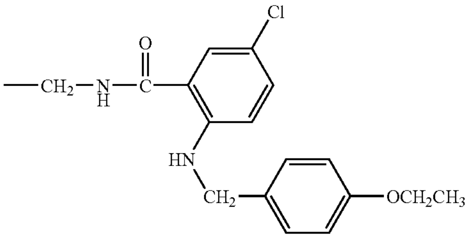 |
| 1434 | 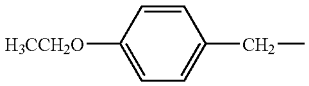 | 2 | 2 | 1 | — | H | 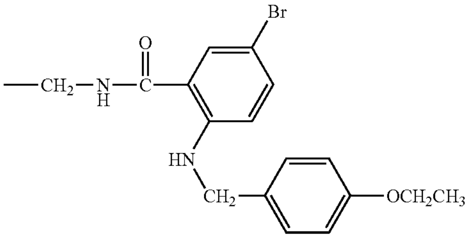 |
| 1435 | 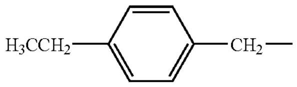 | 2 | 2 | 1 | — | H | 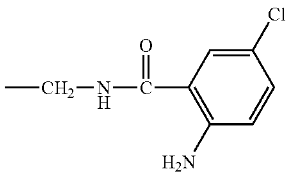 |

TABLE 1.131-continued
| Compd. No. | 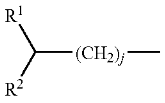 | k | m | n | chirality | $R^3$ | 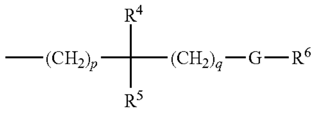 |
|---|---|---|---|---|---|---|---|
| 1436 | 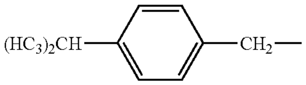 | 2 | 2 | 1 | — | H | 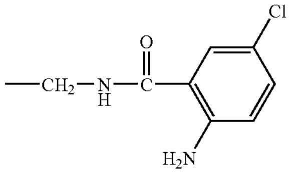 |
| 1437 | 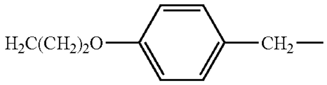 | 2 | 2 | 1 | — | H | 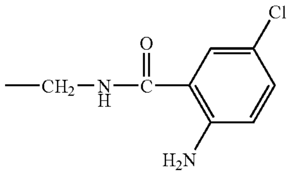 |
| 1438 | 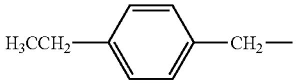 | 2 | 2 | 1 | — | H | 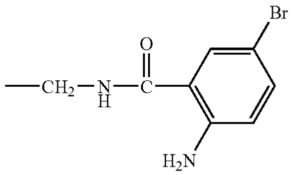 |
| 1439 | 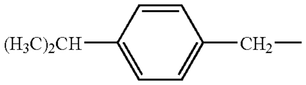 | 2 | 2 | 1 | — | H | 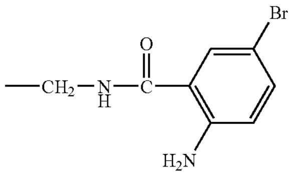 |
| 1440 | 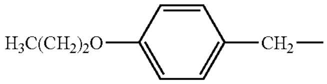 | 2 | 2 | 1 | — | H | 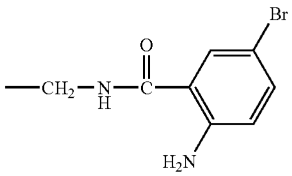 |
| 1441 | 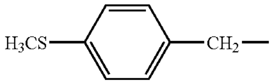 | 2 | 2 | 1 | — | H | 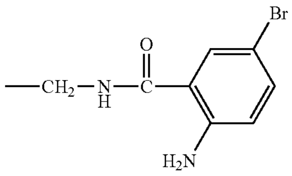 |

TABLE 1.132
| Compd. No. | 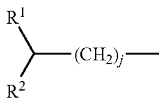 | k | m | n | chirality | $R^3$ | 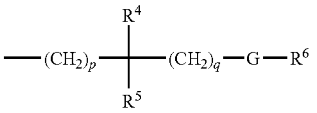 |
|---|---|---|---|---|---|---|---|
| 1442 | 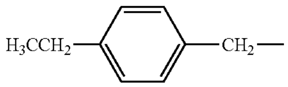 | 2 | 2 | 1 | — | H | 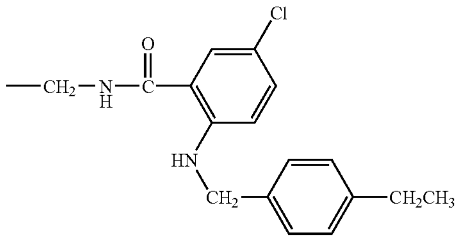 |
| 1443 | 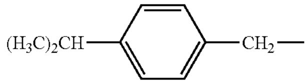 | 2 | 2 | 1 | — | H | 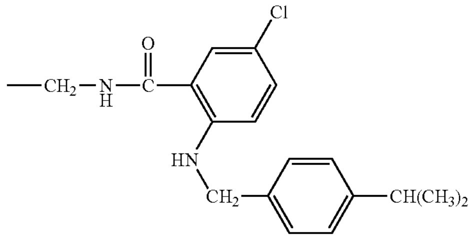 |
| 1444 | 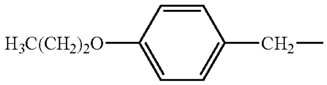 | 2 | 2 | 1 | — | H | 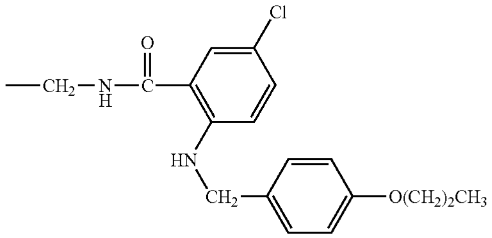 |
| 1445 | 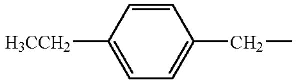 | 2 | 2 | 1 | — | H | 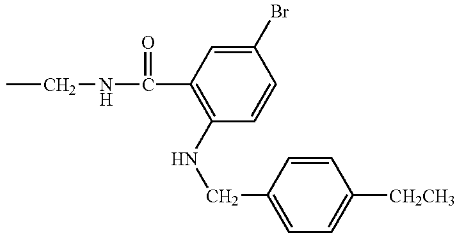 |
| 1446 | 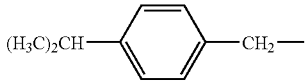 | 2 | 2 | 1 | — | H | 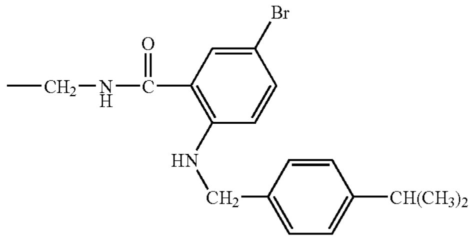 |
| 1447 | 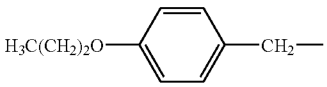 | 2 | 2 | 1 | — | H | 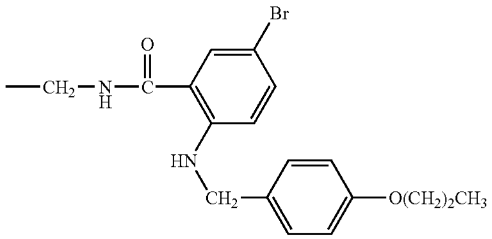 |

TABLE 1.132-continued
| Compd. No. | 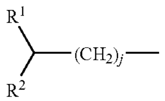 | k | m | n | chirality | $R^3$ | 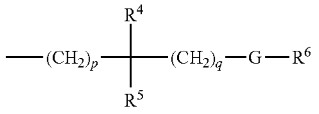 |
|---|---|---|---|---|---|---|---|
| 1448 | 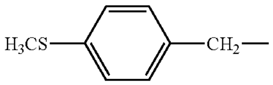 | 2 | 2 | 1 | — | H | 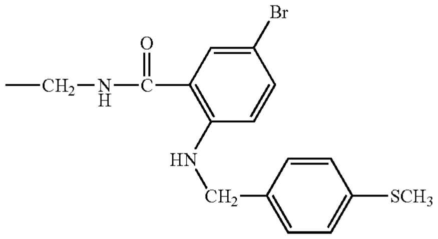 |
| 1449 | 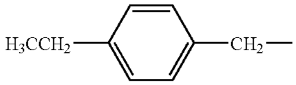 | 2 | 2 | 1 | — | H | 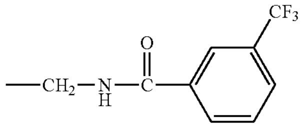 |
| 1450 | 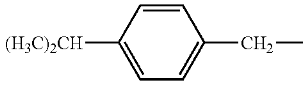 | 2 | 2 | 1 | — | H | 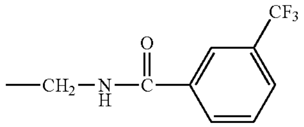 |
| 1451 | 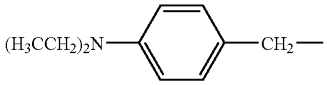 | 2 | 2 | 1 | — | H | 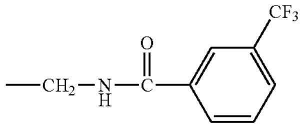 |
| 1452 | 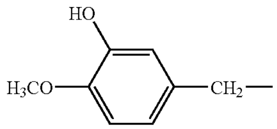 | 2 | 2 | 1 | — | H | 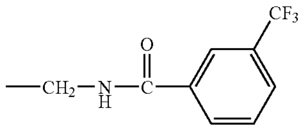 |
TABLE 1.133
| Compd. No. | 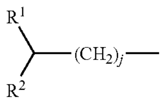 | k | m | n | chirality | $R^3$ | 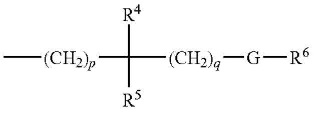 |
|---|---|---|---|---|---|---|---|
| 1453 | 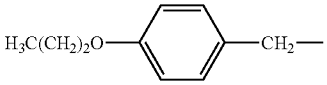 | 2 | 2 | 1 | — | H | 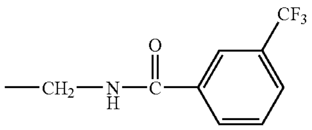 |
| 1454 | 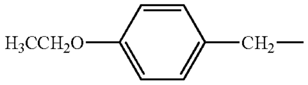 | 2 | 2 | 1 | — | H | 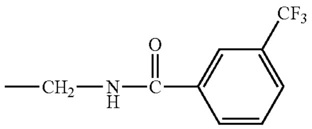 |
| 1455 | 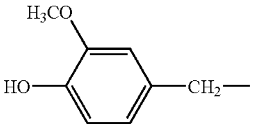 | 2 | 2 | 1 | — | H | 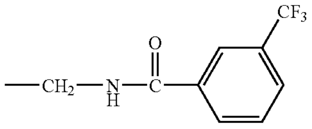 |

TABLE 1.133-continued
| Compd. No. | 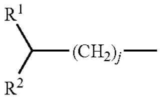 | k | m | n | chirality | $R^3$ | 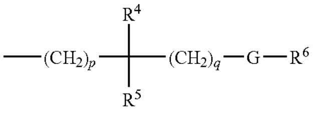 |
|---|---|---|---|---|---|---|---|
| 1456 | 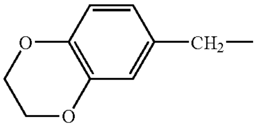 | 2 | 2 | 1 | — | H | 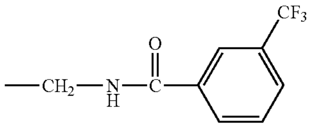 |
| 1457 | 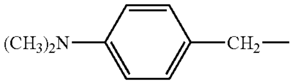 | 2 | 2 | 1 | — | H | 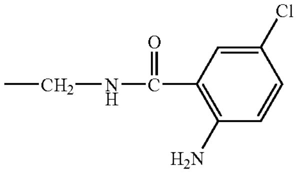 |
| 1458 | 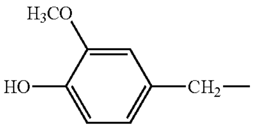 | 2 | 2 | 1 | — | H | 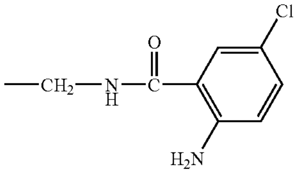 |
| 1459 | 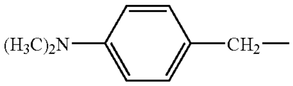 | 2 | 2 | 1 | — | H | 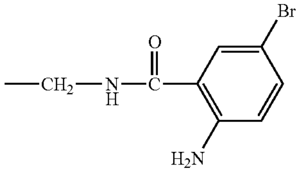 |
| 1460 | 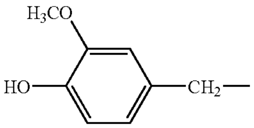 | 2 | 2 | 1 | — | H | 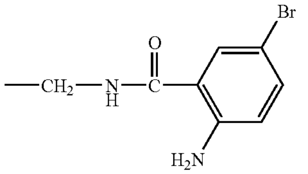 |
| 1461 | 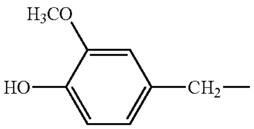 | 2 | 2 | 1 | — | H | 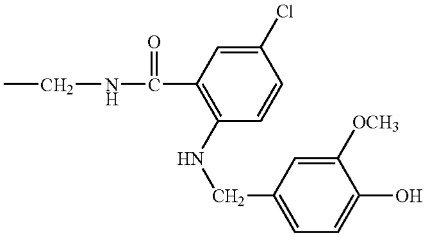 |
| 1462 | 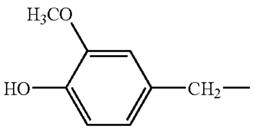 | 2 | 2 | 1 | — | H | 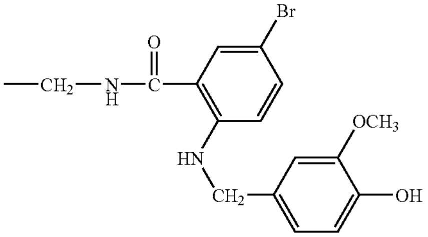 |

TABLE 1.133-continued
| Compd. No. | 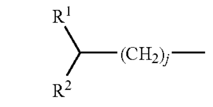 | k | m | n | chirality | $R^3$ | 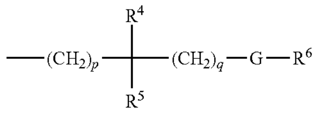 |
|---|---|---|---|---|---|---|---|
| 1463 | 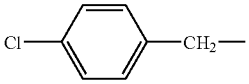 | 2 | 1 | 1 | — | H | 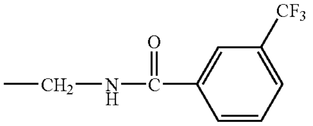 |
TABLE 1.134
| Compd. No. | 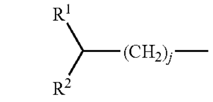 | k | m | n | chirality | $R^3$ | 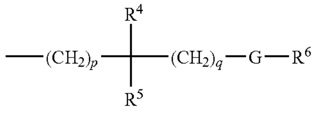 |
|---|---|---|---|---|---|---|---|
| 1464 | 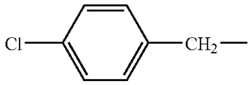 | 2 | 1 | 1 | — | H | 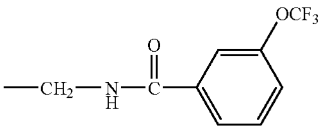 |
| 1465 | 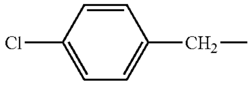 | 2 | 1 | 1 | — | H | 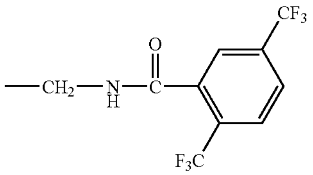 |
| 1466 | 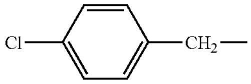 | 2 | 1 | 1 | — | H | 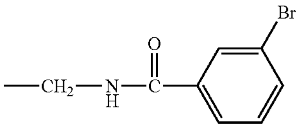 |
| 1467 | 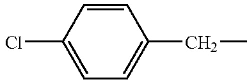 | 2 | 1 | 1 | — | H | 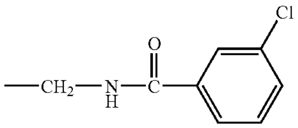 |
| 1468 | 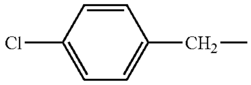 | 2 | 1 | 1 | — | H | 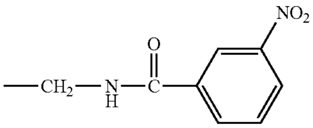 |
| 1469 | 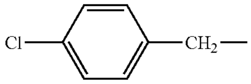 | 2 | 1 | 1 | — | H | 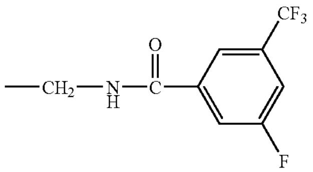 |
| 1470 | 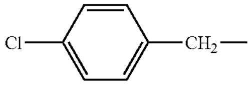 | 2 | 1 | 1 | — | H | 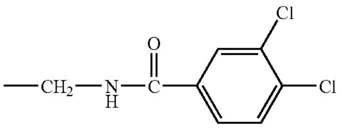 |

TABLE 1.134-continued
| Compd. No. | 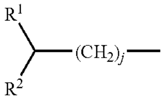 | k | m | n | chirality | $R^3$ | 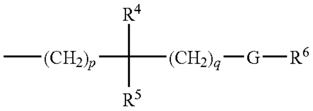 |
|---|---|---|---|---|---|---|---|
| 1471 | 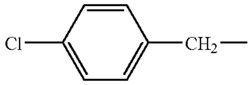 | 2 | 1 | 1 | — | H | 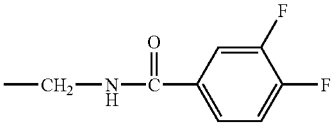 |
| 1472 | 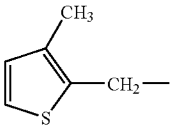 | 1 | 2 | 0 | R | H | 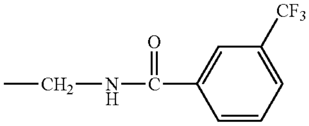 |
| 1473 | 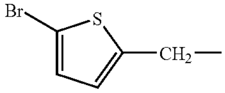 | 1 | 2 | 0 | R | H | 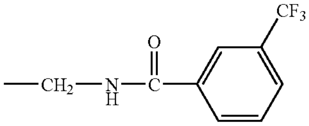 |
| 1474 | 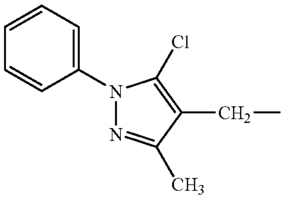 | 1 | 2 | 0 | R | H | 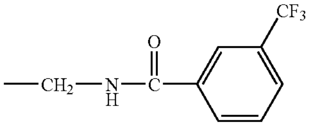 |
TABLE 1.135
| Compd. No. | 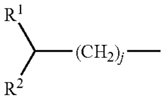 | k | m | n | chirality | $R^3$ | 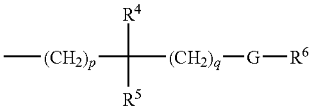 |
|---|---|---|---|---|---|---|---|
| 1475 | 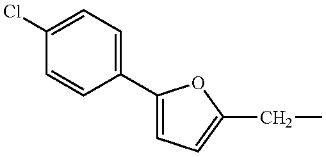 | 1 | 2 | 0 | R | H | 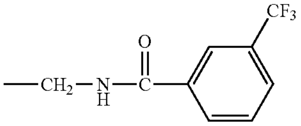 |
| 1476 | 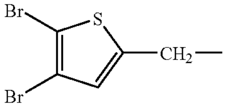 | 1 | 2 | 0 | R | H | 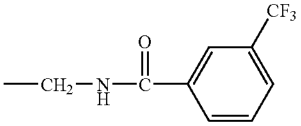 |
| 1477 | 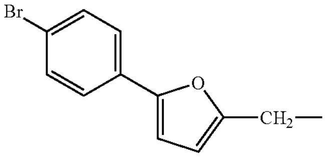 | 1 | 2 | 0 | R | H | 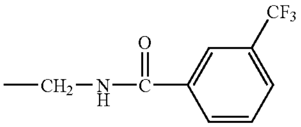 |
| 1478 | 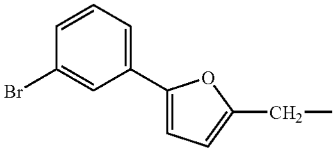 | 1 | 2 | 0 | R | H | 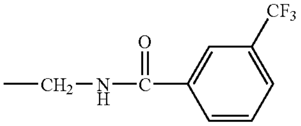 |

TABLE 1.135-continued
| Compd. No. | 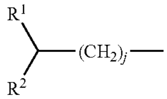 | k | m | n | chirality | $R^3$ | 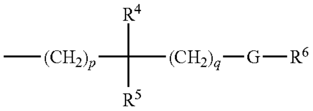 |
|---|---|---|---|---|---|---|---|
| 1479 | 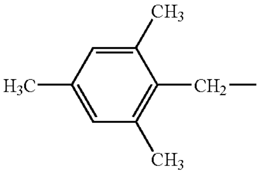 | 1 | 2 | 0 | R | H | 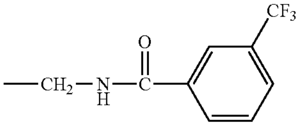 |
| 1480 | 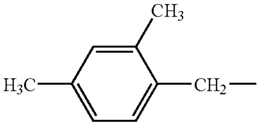 | 1 | 2 | 0 | R | H | 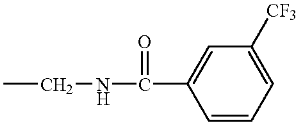 |
| 1481 | 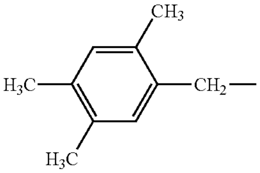 | 1 | 2 | 0 | R | H | 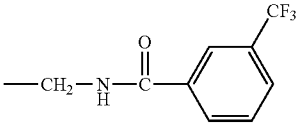 |
| 1482 | 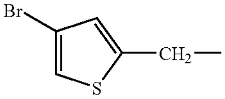 | 1 | 2 | 0 | R | H | 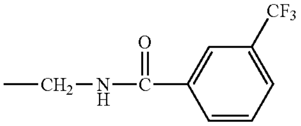 |
| 1483 | 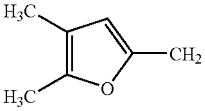 | 1 | 2 | 0 | R | H | 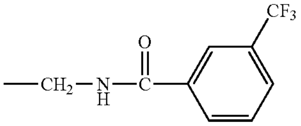 |
| 1484 | 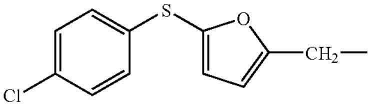 | 1 | 2 | 0 | R | H | 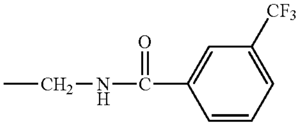 |
| 1485 | 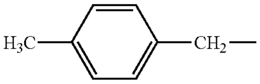 | 1 | 2 | 0 | R | H | 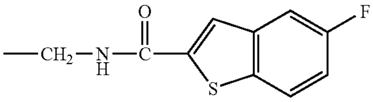 |
TABLE 1.136
| Compd. No. | 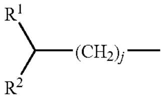 | k | m | n | chirality | $R^3$ | 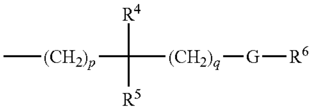 |
|---|---|---|---|---|---|---|---|
| 1486 | 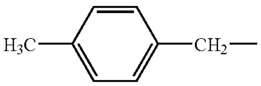 | 1 | 2 | 0 | R | H | 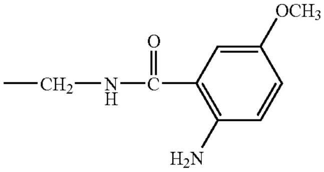 |

TABLE 1.136-continued
| Compd. No. | 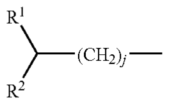 | k | m | n | chirality | $R^3$ | 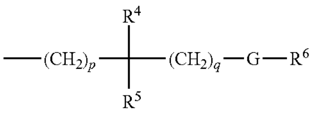 |
|---|---|---|---|---|---|---|---|
| 1487 | 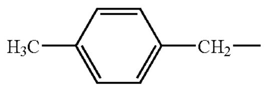 | 1 | 2 | 0 | R | H | 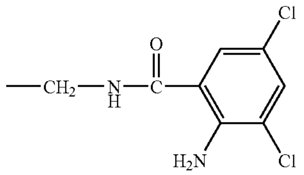 |
| 1488 | 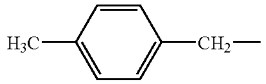 | 1 | 2 | 0 | R | H | 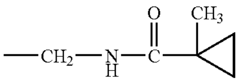 |
| 1489 | 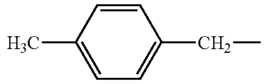 | 1 | 2 | 0 | R | H | 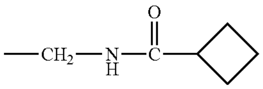 |
| 1490 | 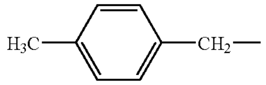 | 1 | 2 | 0 | R | H | 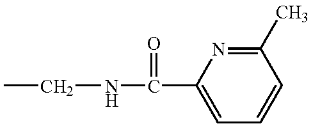 |
| 1491 | 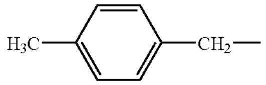 | 1 | 2 | 0 | R | H | 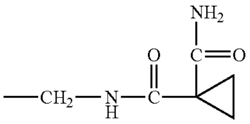 |
| 1492 | 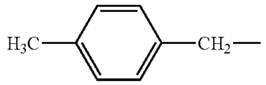 | 1 | 2 | 0 | R | H | 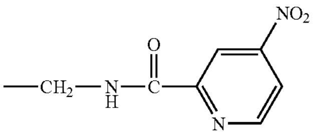 |
| 1493 | 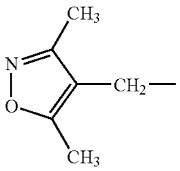 | 1 | 2 | 0 | R | H | 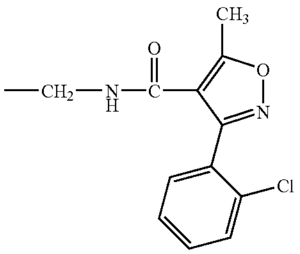 |
| 1494 | 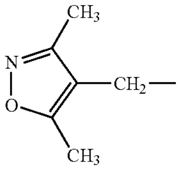 | 1 | 2 | 0 | R | H | 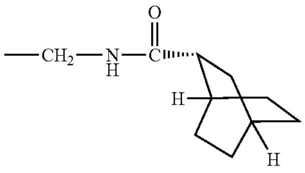 |
| 1495 | 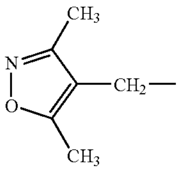 | 1 | 2 | 0 | R | H | 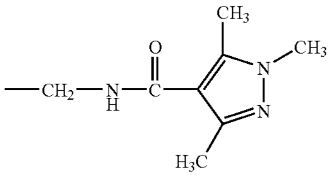 |

TABLE 1.136-continued
| Compd. No. | 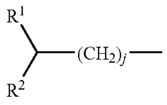 | k | m | n | chirality | $R^3$ | 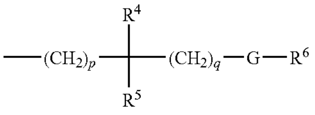 |
|---|---|---|---|---|---|---|---|
| 1496 | 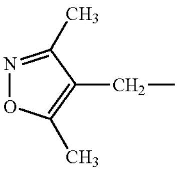 | 1 | 2 | 0 | R | H | 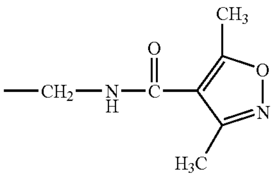 |
TABLE 1.137
| Compd. No. | 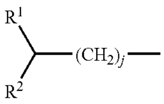 | k | m | n | chirality | $R^3$ | 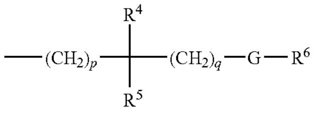 |
|---|---|---|---|---|---|---|---|
| 1497 | 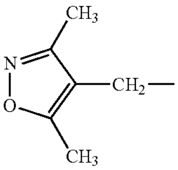 | 1 | 2 | 0 | R | H | 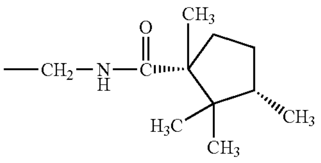 |
| 1498 | 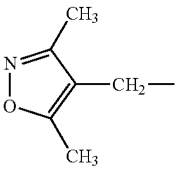 | 1 | 2 | 0 | R | H | 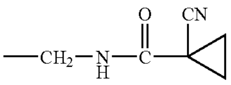 |
| 1499 | 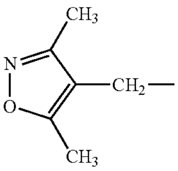 | 1 | 2 | 0 | R | H | 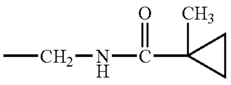 |
| 1500 | 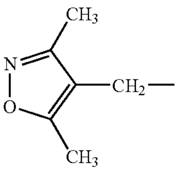 | 1 | 2 | 0 | R | H | 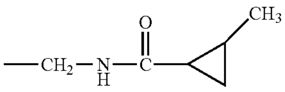 |
| 1501 | 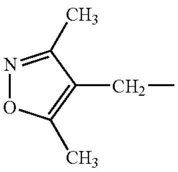 | 1 | 2 | 0 | R | H | 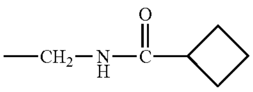 |
| 1502 | 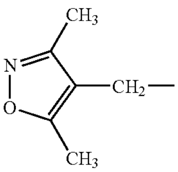 | 1 | 2 | 0 | R | H | 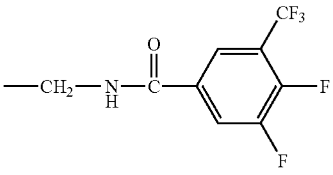 |

TABLE 1.137-continued
| Compd. No. | 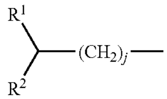 | k | m | n | chirality | $R^3$ | 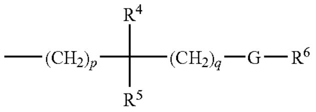 |
|---|---|---|---|---|---|---|---|
| 1503 | 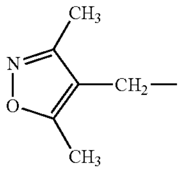 | 1 | 2 | 0 | R | H | 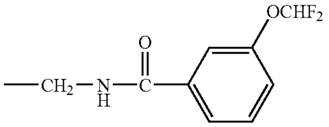 |
| 1504 | 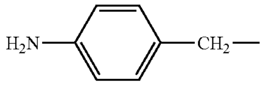 | 1 | 2 | 0 | R | H | 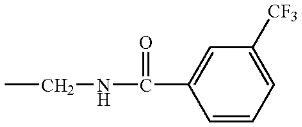 |
| 1505 | 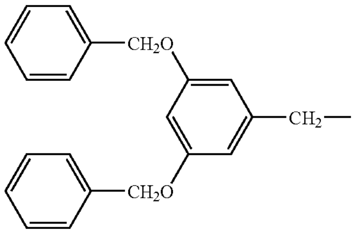 | 1 | 2 | 0 | R | H | 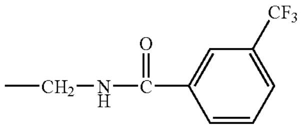 |
| 1506 | 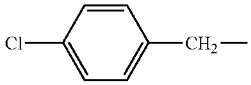 | 2 | 1 | 1 | — | H | 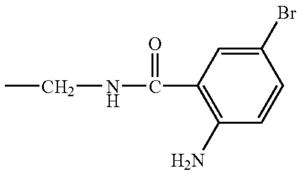 |
| 1507 | 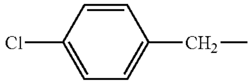 | 2 | 1 | 1 | — | H | 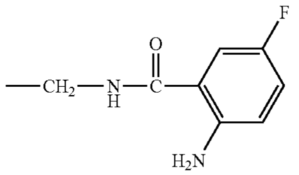 |
TABLE 1.138
| Compd. No. | 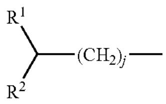 | k | m | n | chirality | $R^3$ | 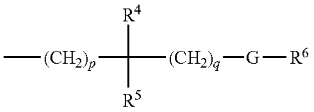 |
|---|---|---|---|---|---|---|---|
| 1508 | 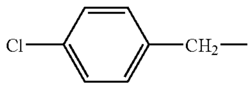 | 2 | 1 | 1 | — | H | 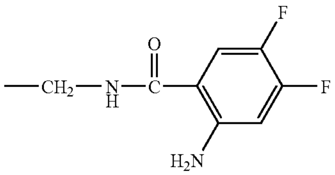 |

TABLE 1.138-continued
| Compd. No. | 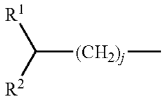 | k | m | n | chirality | $R^3$ | 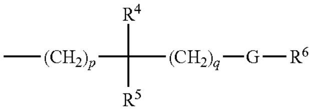 |
|---|---|---|---|---|---|---|---|
| 1509 | 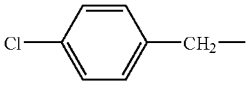 | 2 | 1 | 1 | — | H | 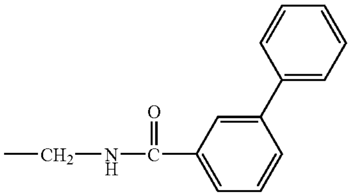 |
| 1510 | 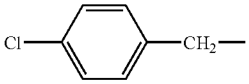 | 2 | 1 | 1 | — | H | 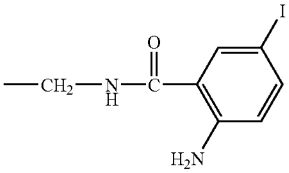 |
| 1511 | 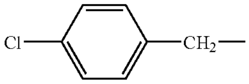 | 2 | 1 | 1 | — | H | 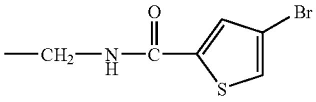 |
| 1512 | 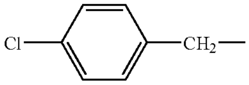 | 2 | 1 | 1 | — | H | 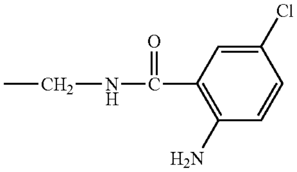 |
| 1513 | 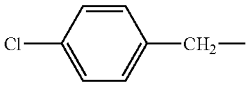 | 2 | 1 | 1 | — | H | 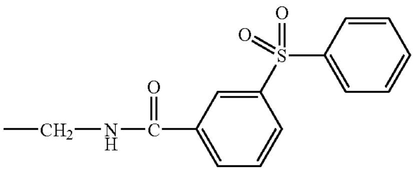 |
| 1514 | 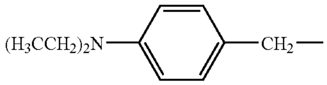 | 2 | 2 | 1 | — | H | 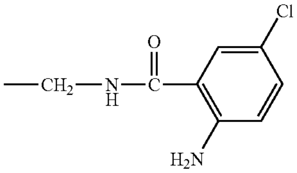 |
| 1515 | 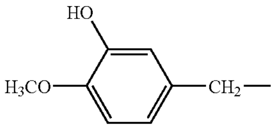 | 2 | 2 | 1 | — | H | 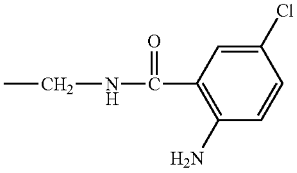 |
| 1516 | 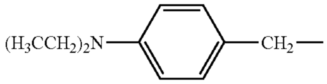 | 2 | 2 | 1 | — | H | 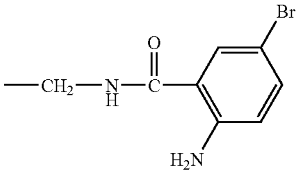 |

TABLE 1.138-continued
| Compd. No. | 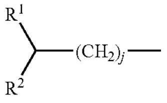 | k | m | n | chirality | $R^3$ | 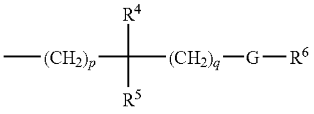 |
|---|---|---|---|---|---|---|---|
| 1517 | 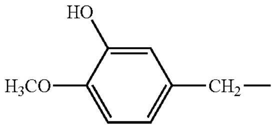 | 2 | 2 | 1 | — | H | 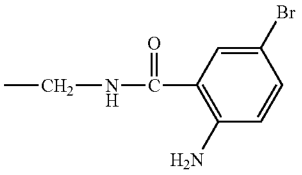 |
| 1518 | 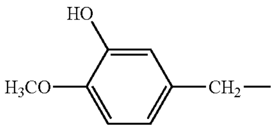 | 2 | 2 | 1 | — | H | 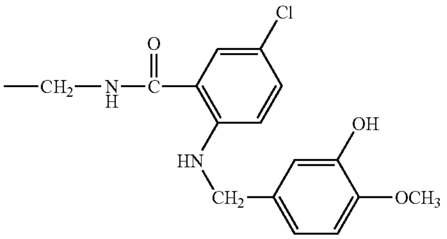 |
TABLE 1.139
| Compd. No. | 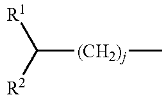 | k | m | n | chirality | $R^3$ | 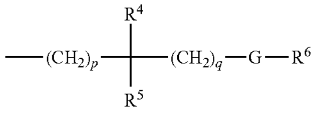 |
|---|---|---|---|---|---|---|---|
| 1519 | 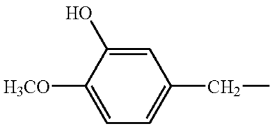 | 2 | 2 | 1 | — | H | 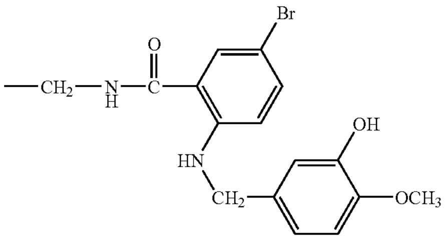 |
| 1520 | 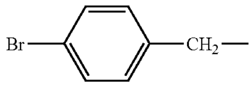 | 1 | 2 | 0 | R | H | 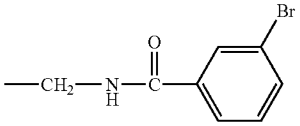 |
| 1521 | 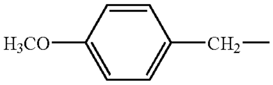 | 1 | 2 | 0 | R | H | 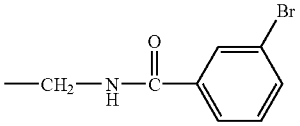 |
| 1522 | 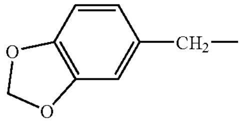 | 1 | 2 | 0 | R | H | 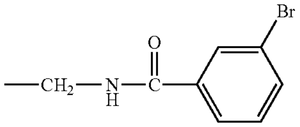 |
| 1523 | 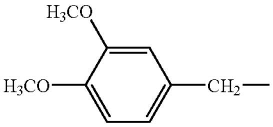 | 1 | 2 | 0 | R | H | 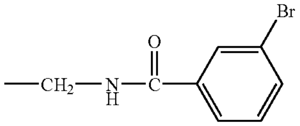 |

TABLE 1.139-continued
| Compd. No. | 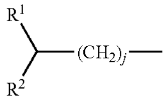 | k | m | n | chirality | $R^3$ | 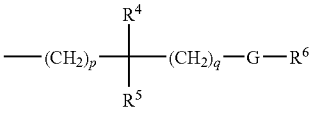 |
|---|---|---|---|---|---|---|---|
| 1524 | 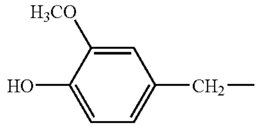 | 1 | 2 | 0 | R | H | 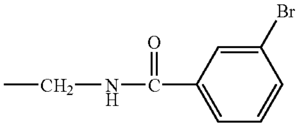 |
| 1525 | 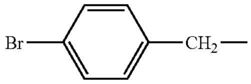 | 1 | 2 | 0 | R | H | 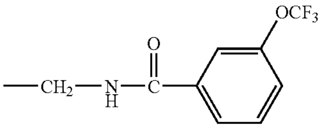 |
| 1526 | 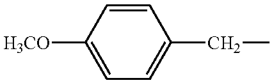 | 1 | 2 | 0 | R | H | 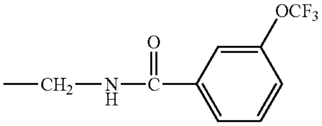 |
| 1527 | 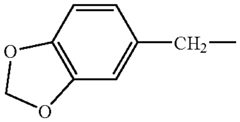 | 1 | 2 | 0 | R | H | 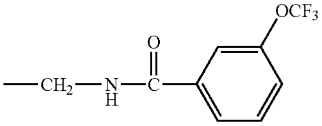 |
| 1528 | 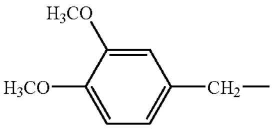 | 1 | 2 | 0 | R | H | 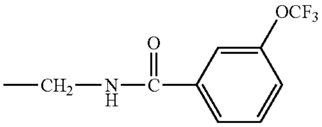 |
| 1529 | 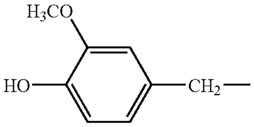 | 1 | 2 | 0 | R | H | 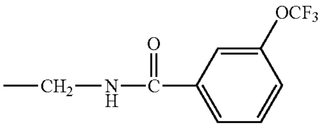 |
TABLE 1.140
| Compd. No. | 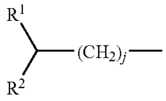 | k | m | n | chirality | $R^3$ | 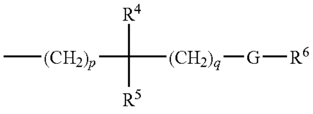 |
|---|---|---|---|---|---|---|---|
| 1530 | 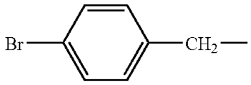 | 1 | 2 | 0 | R | H | 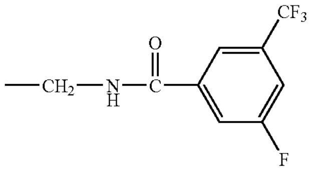 |
| 1531 | 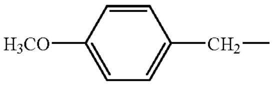 | 1 | 2 | 0 | R | H | 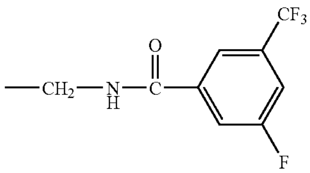 |

TABLE 1.140-continued
| Compd. No. | 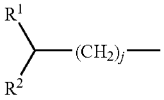 | k | m | n | chirality | $R^3$ | 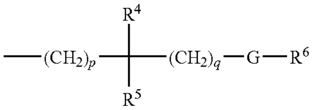 |
|---|---|---|---|---|---|---|---|
| 1532 | 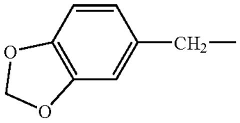 | 1 | 2 | 0 | R | H | 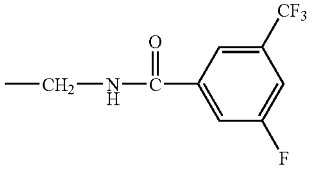 |
| 1533 | 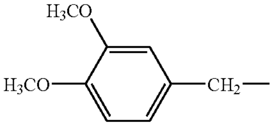 | 1 | 2 | 0 | R | H | 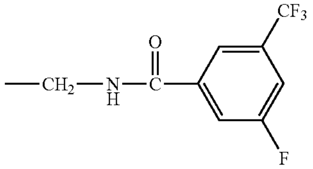 |
| 1534 | 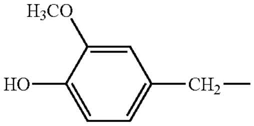 | 1 | 2 | 0 | R | H | 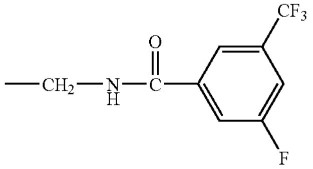 |
| 1535 | 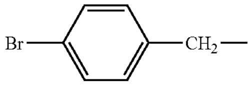 | 1 | 2 | 0 | R | H | 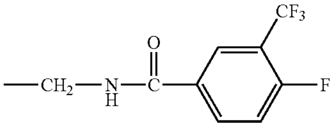 |
| 1536 | 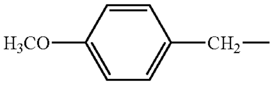 | 1 | 2 | 0 | R | H | 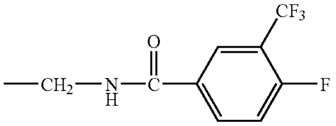 |
| 1537 | 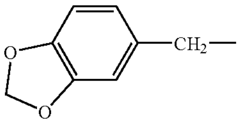 | 1 | 2 | 0 | R | H | 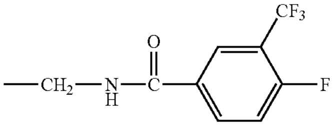 |
| 1538 | 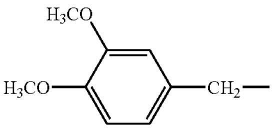 | 1 | 2 | 0 | R | H | 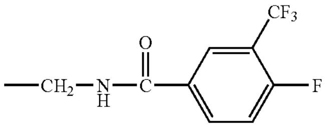 |
| 1539 | 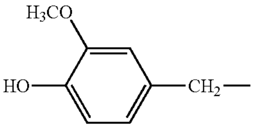 | 1 | 2 | 0 | R | H | 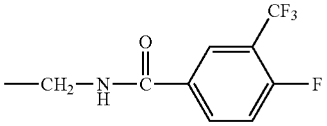 |
| 1540 | 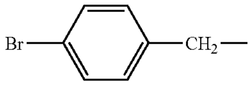 | 1 | 2 | 0 | R | H | 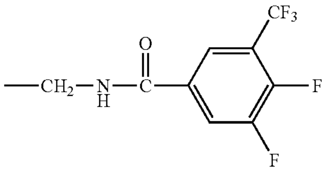 |

TABLE 1.141
| Compd. No. | 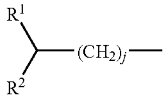 | k | m | n | chirality | $R^3$ | 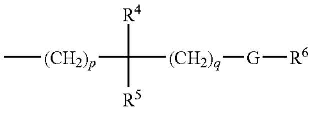 |
|---|---|---|---|---|---|---|---|
| 1541 | 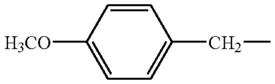 | 1 | 2 | 0 | R | H | 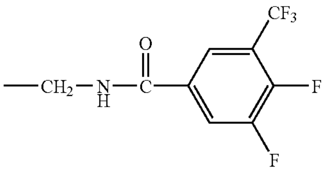 |
| 1542 | 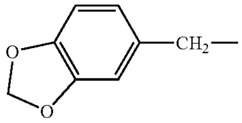 | 1 | 2 | 0 | R | H | 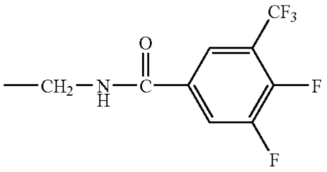 |
| 1543 | 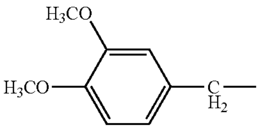 | 1 | 2 | 0 | R | H | 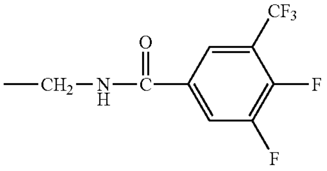 |
| 1544 | 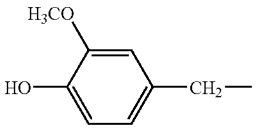 | 1 | 2 | 0 | R | H | 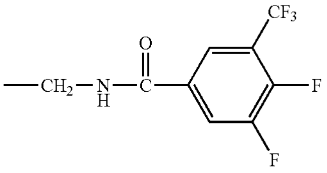 |
| 1545 | 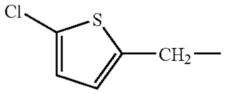 | 1 | 2 | 0 | R | H | 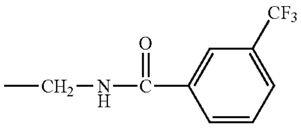 |
| 1546 | 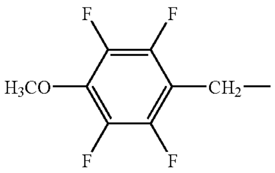 | 1 | 2 | 0 | R | H | 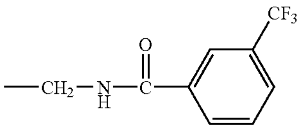 |
| 1547 | 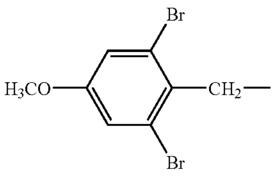 | 1 | 2 | 0 | R | H | 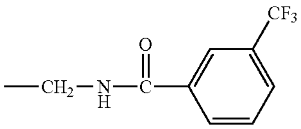 |
| 1548 | 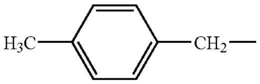 | 1 | 2 | 0 | R | H | 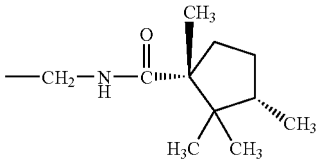 |

TABLE 1.141-continued
| Compd. No. | 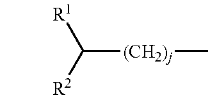 | k | m | n | chirality | $R^3$ | 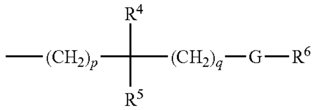 |
|---|---|---|---|---|---|---|---|
| 1549 | 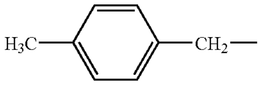 | 1 | 2 | 0 | R | H | 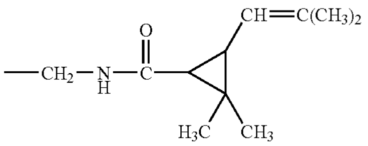 |
| 1550 | 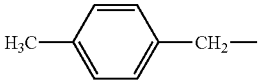 | 1 | 2 | 0 | R | H | 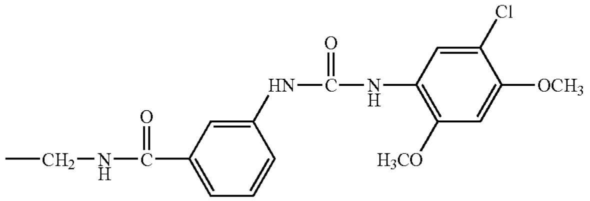 |
| 1551 | 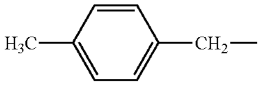 | 1 | 2 | 0 | R | H | 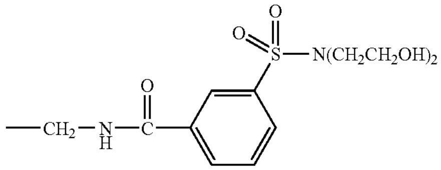 |
TABLE 1.142
| Compd. No. | 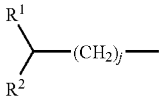 | k | m | n | chirality | $R^3$ | 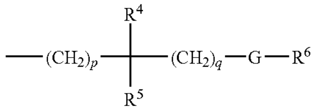 |
|---|---|---|---|---|---|---|---|
| 1552 | 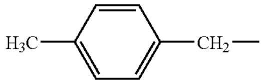 | 1 | 2 | 0 | R | H | 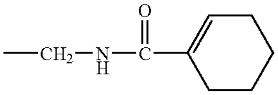 |
| 1553 | 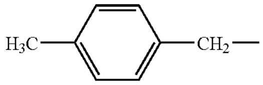 | 1 | 2 | 0 | R | H | 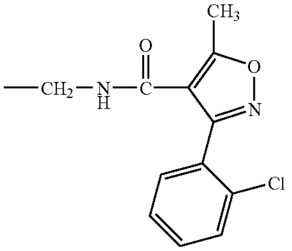 |
| 1554 | 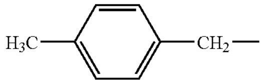 | 1 | 2 | 0 | R | H | 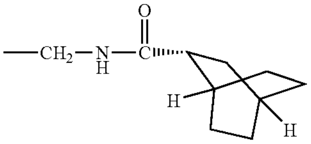 |
| 1555 | 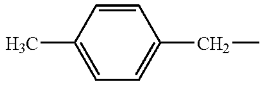 | 1 | 2 | 0 | R | H | 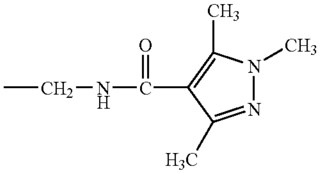 |

TABLE 1.142-continued
| Compd. No. | 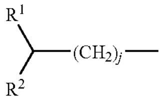 | k | m | n | chirality | $R^3$ | 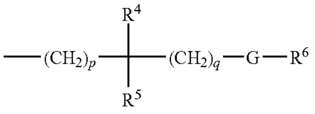 |
|---|---|---|---|---|---|---|---|
| 1556 | 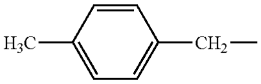 | 1 | 2 | 0 | R | H | 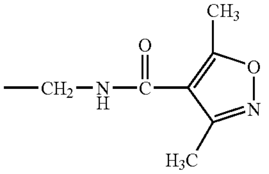 |
| 1557 | 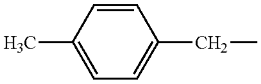 | 1 | 2 | 0 | R | H | 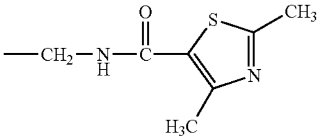 |
| 1558 | 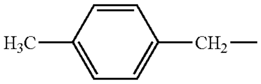 | 1 | 2 | 0 | R | H | 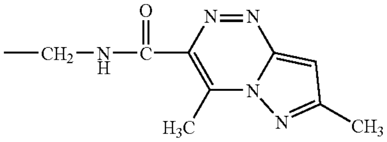 |
| 1559 | 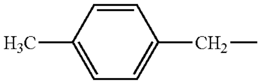 | 1 | 2 | 0 | R | H | 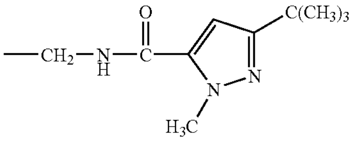 |
| 1560 | 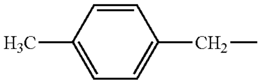 | 1 | 2 | 0 | R | H | 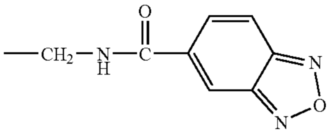 |
| 1561 | 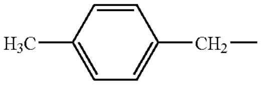 | 1 | 2 | 0 | R | H | 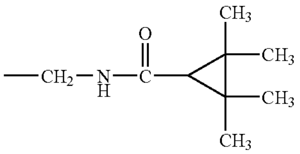 |
| 1562 | 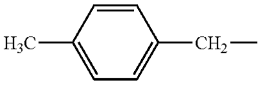 | 1 | 2 | 0 | R | H | 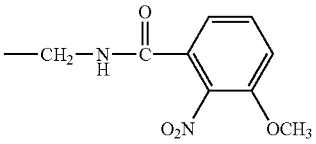 |
TABLE 1.143
| Compd. No. | 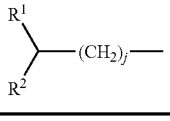 | k | m | n |
|---|---|---|---|---|
| 1563 | 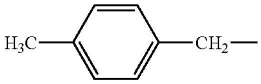 | 1 | 2 | 0 |

TABLE 1.143-continued
| | | | | |
|---|---|---|---|---|
| 1564 | 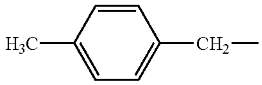 | 1 | 2 | 0 |
| 1565 | 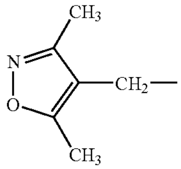 | 1 | 2 | 0 |
| 1566 | 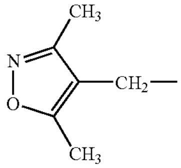 | 1 | 2 | 0 |
| 1567 | 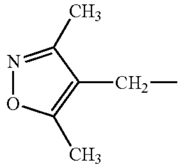 | 1 | 2 | 0 |
| 1568 | 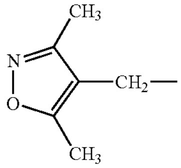 | 1 | 2 | 0 |
| 1569 | 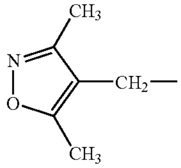 | 1 | 2 | 0 |
| 1570 | 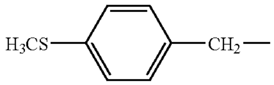 | 2 | 2 | 1 |
| 1571 | 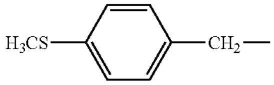 | 2 | 2 | 1 |
| 1572 | 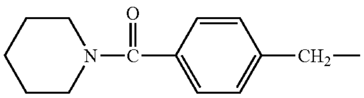 | 2 | 2 | 1 |
| 1573 | 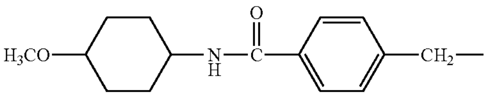 | 2 | 2 | 1 |

TABLE 1.143-continued
| Compd. No. | chirality | $R^3$ | 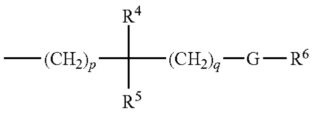 |
|---|---|---|---|
| 1563 | R | H | 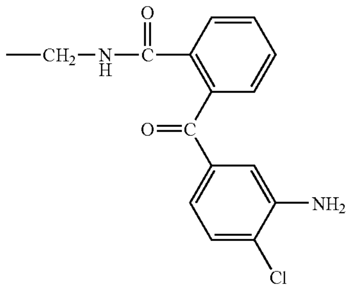 |
| 1564 | R | H | 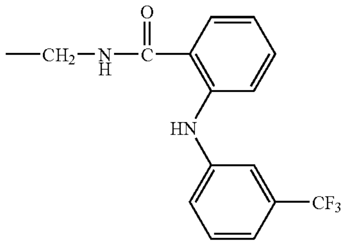 |
| 1565 | R | H | 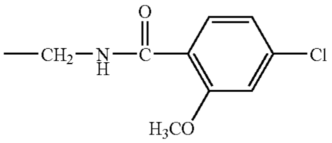 |
| 1566 | R | H | 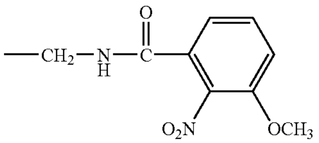 |
| 1567 | R | H | 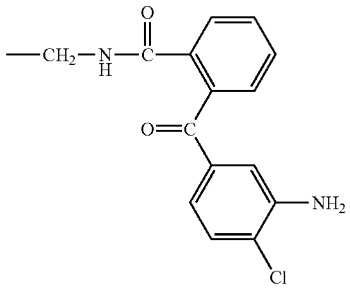 |
| 1568 | R | H | 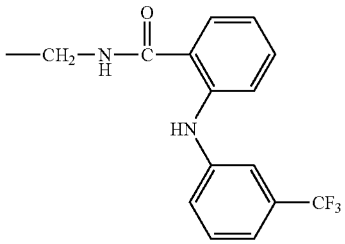 |

TABLE 1.143-continued
| | | | |
|---|---|---|---|
| 1569 | R | H | 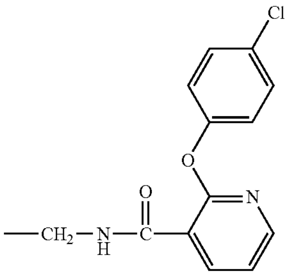 |
| 1570 | — | H | 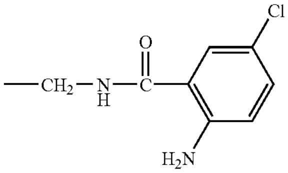 |
| 1571 | — | H | 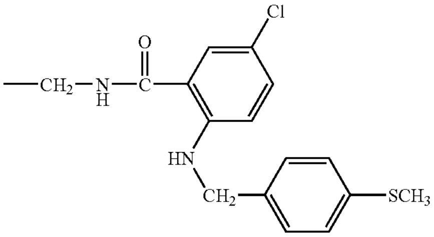 |
| 1572 | — | H | 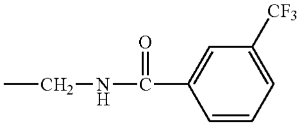 |
| 1573 | — | H | 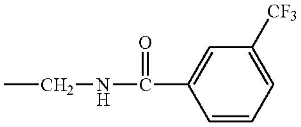 |
TABLE 1.144
| Compd. No. | 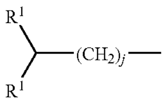 | k | m | n | chirality | $R^3$ | 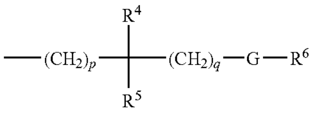 |
|---|---|---|---|---|---|---|---|
| 1574 | 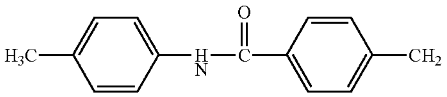 | 2 | 2 | 1 | — | H | 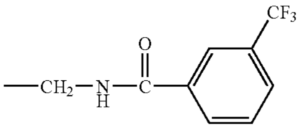 |
| 1575 | 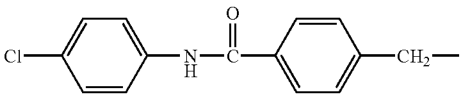 | 2 | 2 | 1 | — | H | 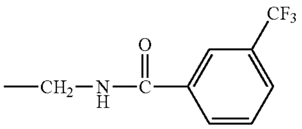 |

TABLE 1.144-continued
| Compd. No. | 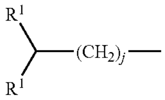 | k | m | n | chirality | $R^3$ | 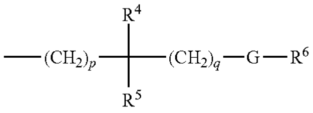 |
|---|---|---|---|---|---|---|---|
| 1576 | 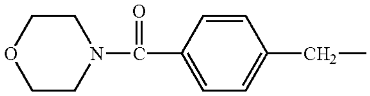 | 2 | 2 | 1 | — | H | 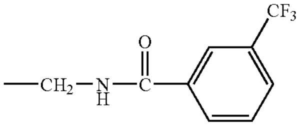 |
| 1577 | 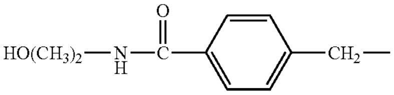 | 2 | 2 | 1 | — | H | 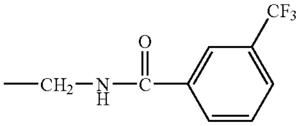 |
| 1578 | 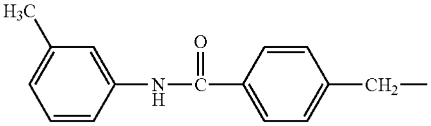 | 2 | 2 | 1 | — | H | 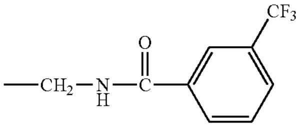 |
| 1579 | 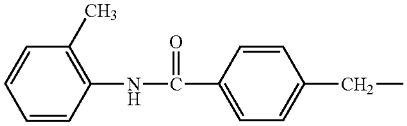 | 2 | 2 | 1 | — | H | 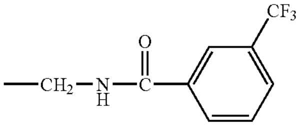 |
| 1580 | 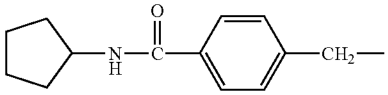 | 2 | 2 | 1 | — | H | 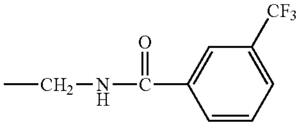 |
| 1581 | 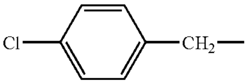 | 2 | 2 | 1 | — | H | 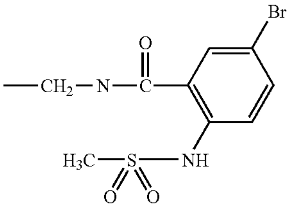 |
| 1582 | 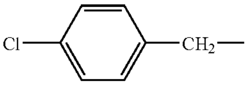 | 2 | 2 | 1 | — | H | 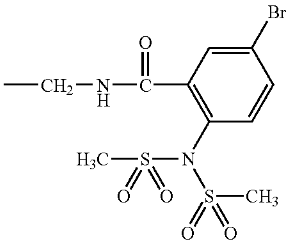 |
| 1583 | 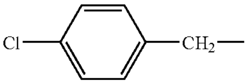 | 1 | 2 | 0 | R | H | 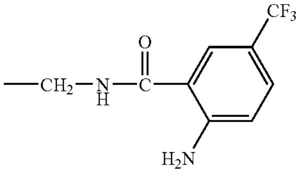 |

TABLE 1.144-continued
| Compd. No. | 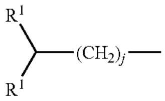 | k | m | n | chirality | $R^3$ | 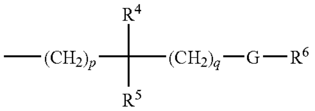 |
|---|---|---|---|---|---|---|---|
| 1584 | 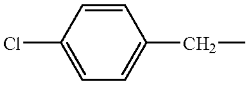 | 1 | 2 | 0 | R | H | 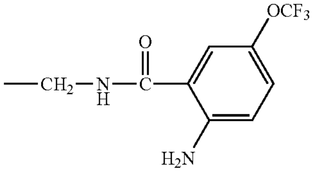 |
TABLE 1.145
| Compd. No. | 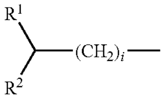 | k | m | n | chirality | $R^3$ | 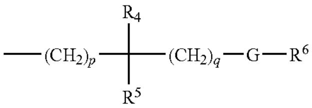 |
|---|---|---|---|---|---|---|---|
| 1585 | 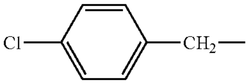 | 1 | 2 | 0 | R | H | 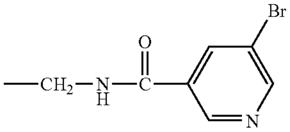 |
| 1586 | 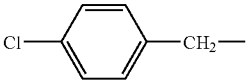 | 1 | 2 | 0 | R | H | 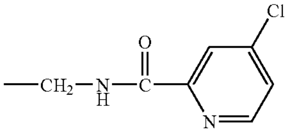 |
| 1587 | 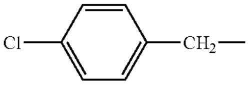 | 1 | 2 | 0 | R | H | 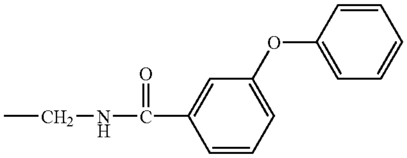 |
| 1588 | 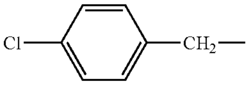 | 1 | 2 | 0 | R | H | 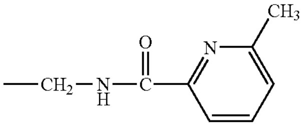 |
| 1589 | 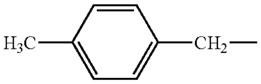 | 1 | 2 | 0 | R | H | 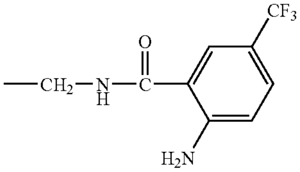 |
| 1590 | 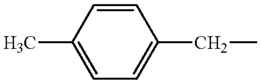 | 1 | 2 | 0 | R | H | 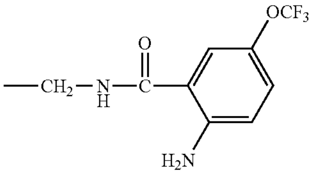 |

TABLE 1.145-continued
| Compd. No. | 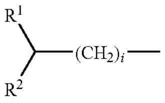 | k | m | n | chirality | $R^3$ | 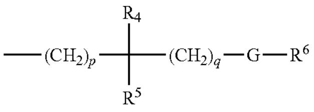 |
|---|---|---|---|---|---|---|---|
| 1591 | 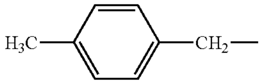 | 1 | 2 | 0 | R | H | 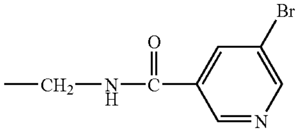 |
| 1592 | 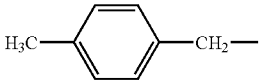 | 1 | 2 | 0 | R | H | 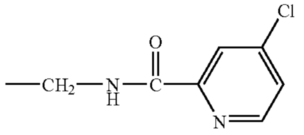 |
| 1593 | 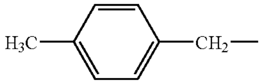 | 1 | 2 | 0 | R | H | 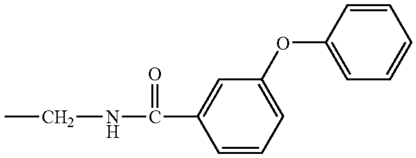 |
| 1594 | 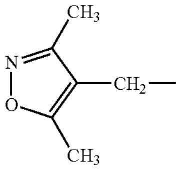 | 1 | 2 | 0 | R | H | 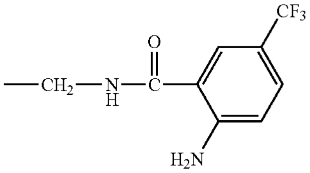 |
| 1595 | 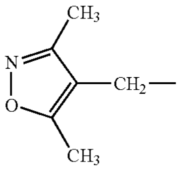 | 1 | 2 | 0 | R | H | 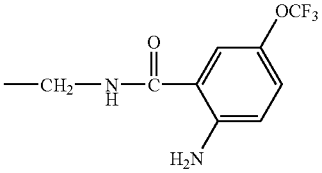 |
TABLE 1.146
| Compd. No. | 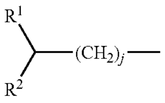 | k | m | n | chirality | $R^3$ | 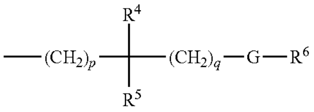 |
|---|---|---|---|---|---|---|---|
| 1596 | 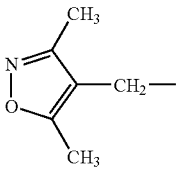 | 1 | 2 | 0 | R | H | 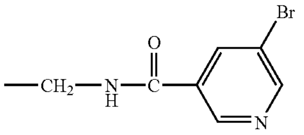 |
| 1597 | 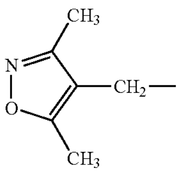 | 1 | 2 | 0 | R | H | 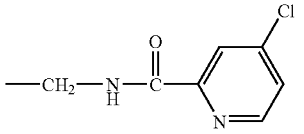 |

TABLE 1.146-continued
| Compd. No. | 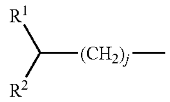 | k | m | n | chirality | $R^3$ | 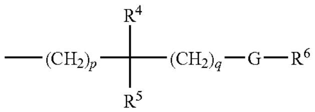 |
|---|---|---|---|---|---|---|---|
| 1598 | 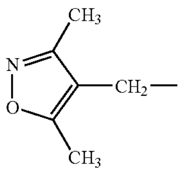 | 1 | 2 | 0 | R | H | 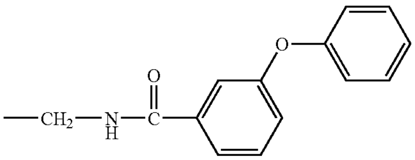 |
| 1599 | 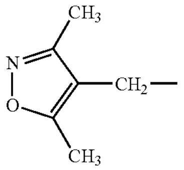 | 1 | 2 | 0 | R | H | 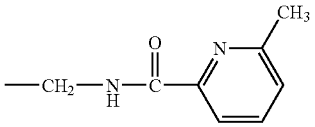 |
| 1600 | 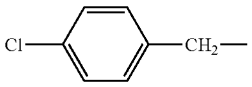 | 2 | 2 | 1 | — | H | 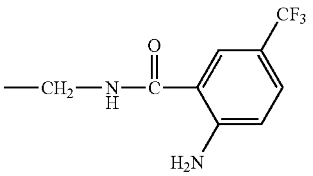 |
| 1601 | 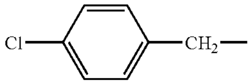 | 2 | 2 | 1 | — | H | 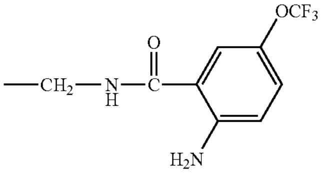 |
| 1602 | 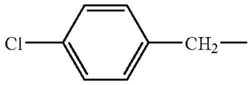 | 2 | 2 | 1 | — | H | 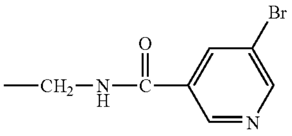 |
| 1603 | 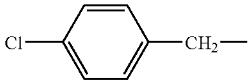 | 2 | 2 | 1 | — | H | 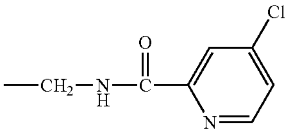 |
| 1604 | 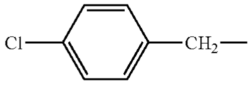 | 2 | 2 | 1 | — | H | 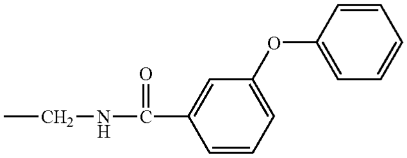 |
| 1605 | 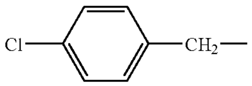 | 2 | 2 | 1 | — | H | 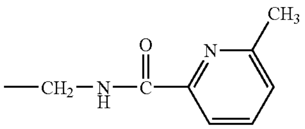 |

TABLE 1.146-continued
| Compd. No. | 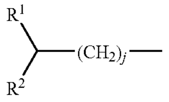 | k | m | n | chirality | $R^3$ | 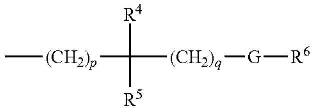 |
|---|---|---|---|---|---|---|---|
| 1606 | 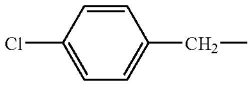 | 1 | 2 | 0 | R | H | 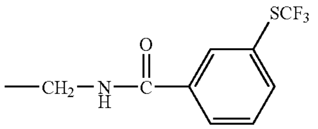 |
TABLE 1.147
| Compd. No. | 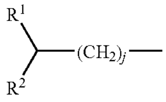 | k | m | n | chirality | $R^3$ | 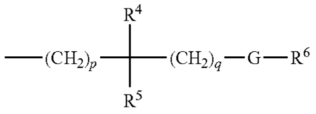 |
|---|---|---|---|---|---|---|---|
| 1607 | 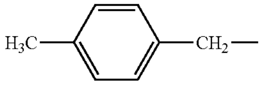 | 1 | 2 | 0 | R | H | 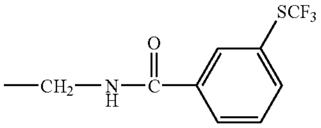 |
| 1608 | 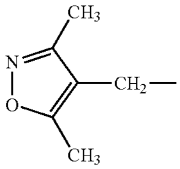 | 1 | 2 | 0 | R | H | 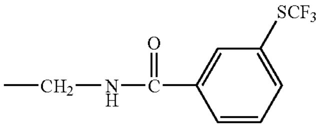 |
| 1609 | 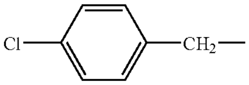 | 2 | 2 | 1 | — | H | 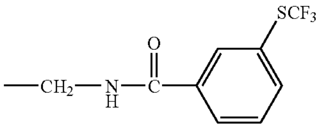 |
| 1610 | 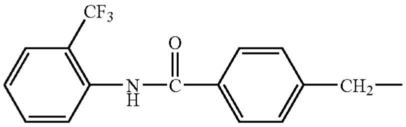 | 2 | 2 | 1 | — | H | 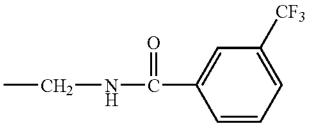 |
| 1611 | 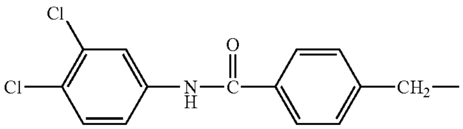 | 2 | 2 | 1 | — | H | 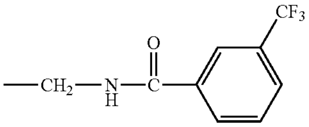 |
| 1612 | 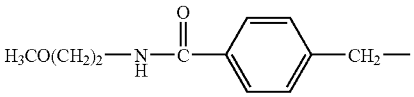 | 2 | 2 | 1 | — | H | 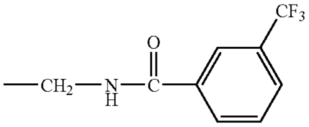 |
| 1613 | 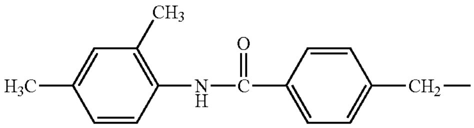 | 2 | 2 | 1 | — | H | 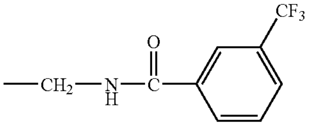 |

TABLE 1.147-continued
| Compd. No. | 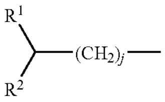 | k | m | n | chirality | $R^3$ | 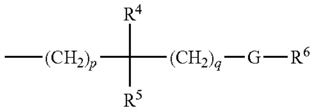 |
|---|---|---|---|---|---|---|---|
| 1614 | 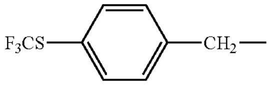 | 1 | 2 | 0 | R | H | 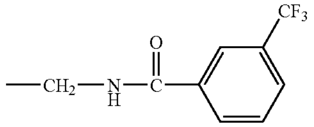 |
| 1615 | 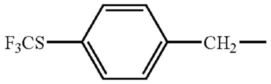 | 2 | 2 | 1 | — | H | 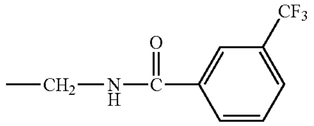 |
| 1616 | 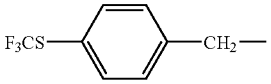 | 2 | 2 | 1 | — | H | 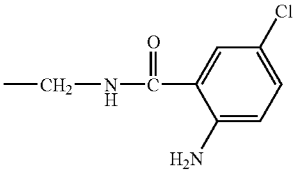 |
| 1617 | 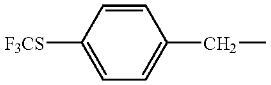 | 2 | 2 | 1 | — | H | 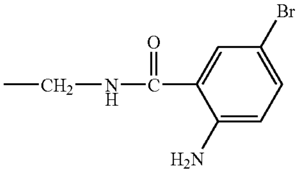 |
TABLE 1.148
| Compd. No. | 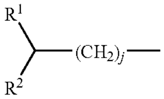 | k | m | n | chirality | $R^3$ | 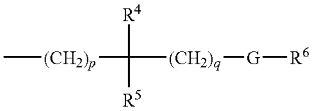 |
|---|---|---|---|---|---|---|---|
| 1618 | 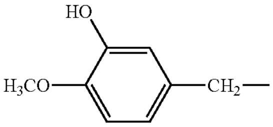 | 1 | 2 | 0 | R | H | 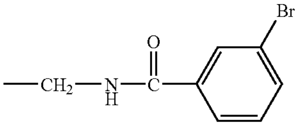 |
| 1619 | 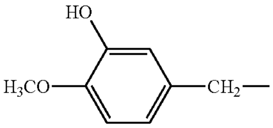 | 1 | 2 | 0 | R | H | 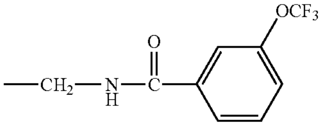 |
| 1620 | 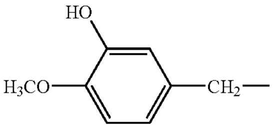 | 1 | 2 | 0 | R | H | 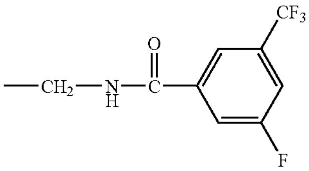 |
| 1621 | 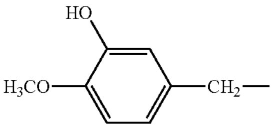 | 1 | 2 | 0 | R | H | 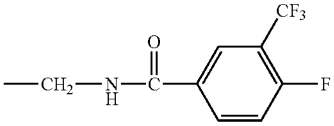 |

TABLE 1.148-continued
| Compd. No. | 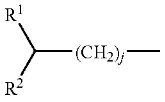 | k | m | n | chirality | $R^3$ | 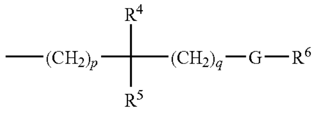 |
|---|---|---|---|---|---|---|---|
| 1622 | 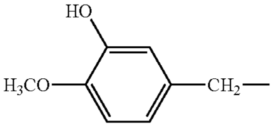 | 1 | 2 | 0 | R | H | 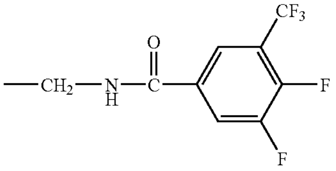 |
| 1623 | 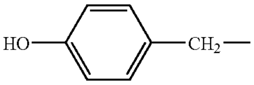 | 1 | 2 | 0 | R | H | 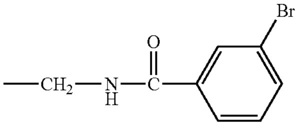 |
| 1624 | 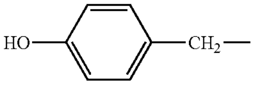 | 1 | 2 | 0 | R | H | 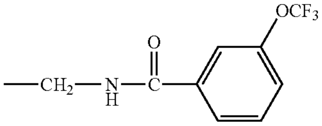 |
| 1625 | 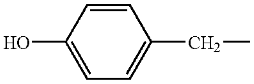 | 1 | 2 | 0 | R | H | 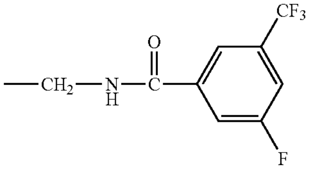 |
| 1626 | 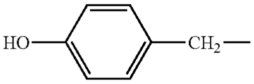 | 1 | 2 | 0 | R | H | 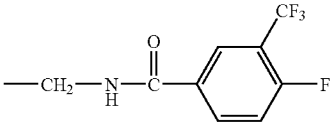 |
| 1627 | 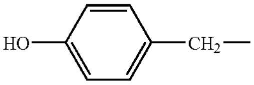 | 1 | 2 | 0 | R | H | 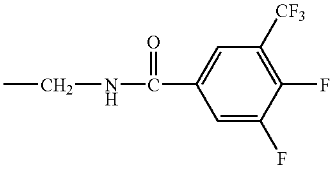 |
| 1628 | 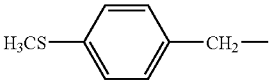 | 1 | 2 | 0 | R | H | 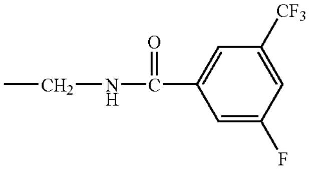 |

TABLE 1.149
| Compd. No. | 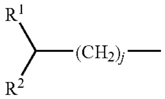 | k | m | n | chirality | $R^3$ | 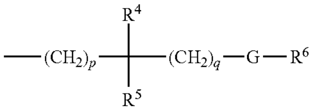 |
| --- | --- | --- | --- | --- | --- | --- | --- |
| 1629 | 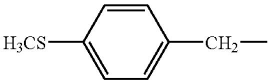 | 1 | 2 | 0 | R | H | 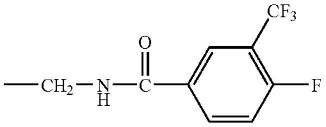 |
| 1630 | 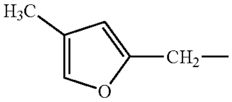 | 1 | 2 | 0 | R | H | 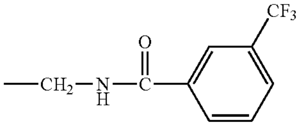 |
| 1631 | 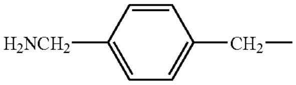 | 1 | 2 | 0 | R | H | 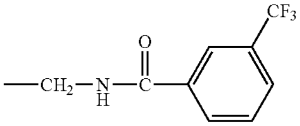 |
| 1632 | 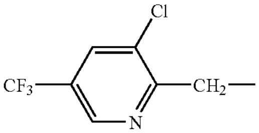 | 1 | 2 | 0 | R | H | 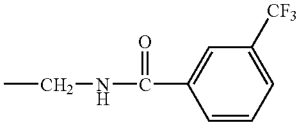 |
| 1633 | 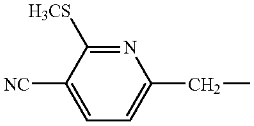 | 1 | 2 | 0 | R | H | 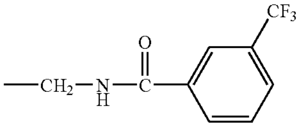 |
| 1634 | 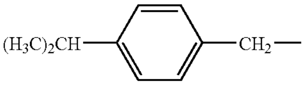 | 1 | 2 | 0 | R | H | 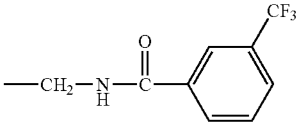 |
| 1635 | 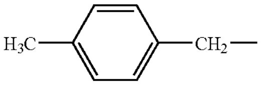 | 1 | 2 | 0 | R | H | 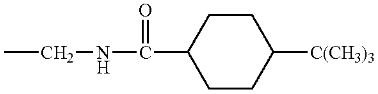 |
| 1636 | 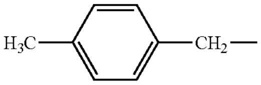 | 1 | 2 | 0 | R | H | 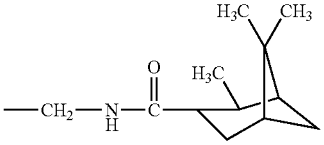 |
| 1637 | 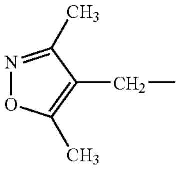 | 1 | 2 | 0 | R | H | 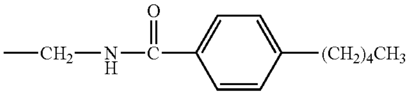 |
| 1638 | 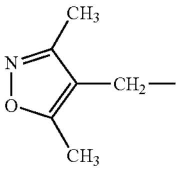 | 1 | 2 | 0 | R | H | 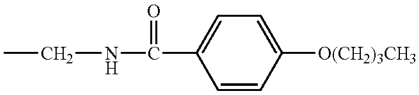 |

TABLE 1.149-continued
| Compd. No. | 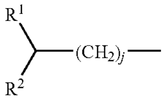 | k | m | n | chirality | $R^3$ | 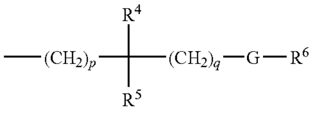 |
|---|---|---|---|---|---|---|---|
| 1639 | 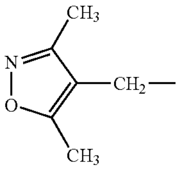 | 1 | 2 | 0 | R | H | 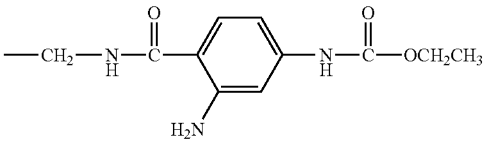 |
TABLE 1.150
| Compd. No. | 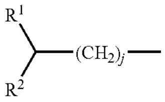 | k | m | n | chirality | $R^3$ | 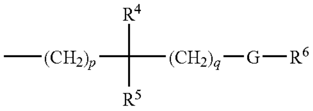 |
|---|---|---|---|---|---|---|---|
| 1640 | 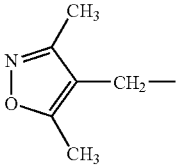 | 1 | 2 | 0 | R | H | 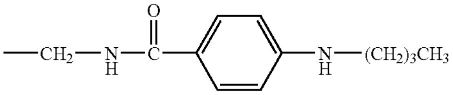 |
| 1641 | 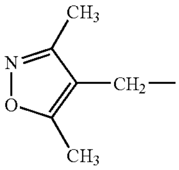 | 1 | 2 | 0 | R | H | 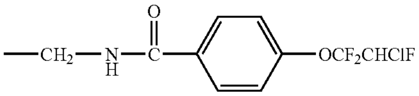 |
| 1642 | 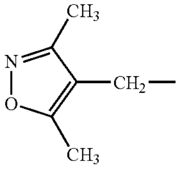 | 1 | 2 | 0 | R | H | 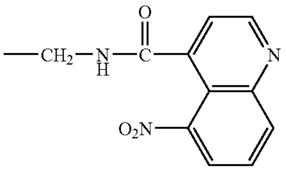 |
| 1643 | 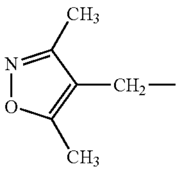 | 1 | 2 | 0 | R | H | 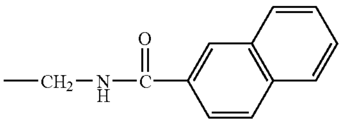 |
| 1644 | 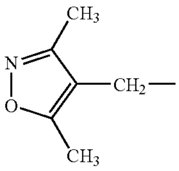 | 1 | 2 | 0 | R | H | 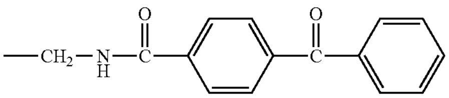 |

TABLE 1.150-continued
| Compd. No. | 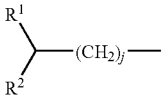 | k | m | n | chirality | $R^3$ | 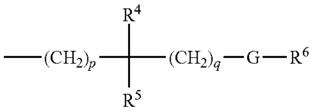 |
|---|---|---|---|---|---|---|---|
| 1645 | 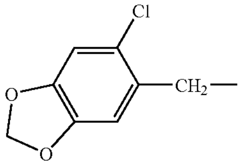 | 1 | 2 | 0 | R | H | 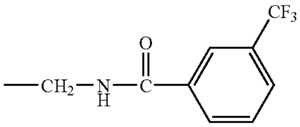 |
| 1646 | 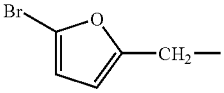 | 1 | 2 | 0 | R | H | 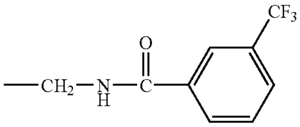 |
| 1647 | 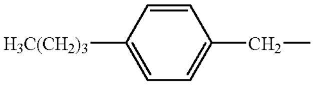 | 2 | 2 | 1 | — | H | 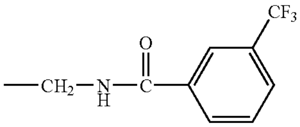 |
| 1648 | 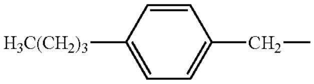 | 1 | 2 | 0 | R | H | 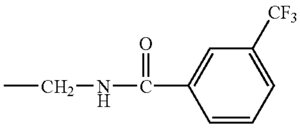 |
| 1649 | 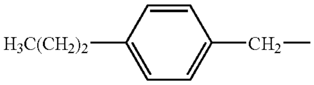 | 2 | 2 | 1 | — | H | 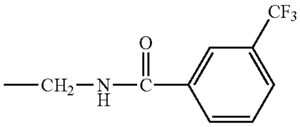 |
| 1650 | 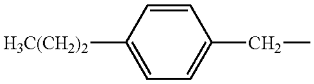 | 1 | 2 | 0 | R | H | 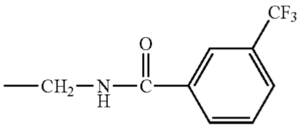 |
TABLE 1.151
| Compd. No. | 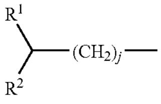 | k | m | n | chirality | $R^3$ | 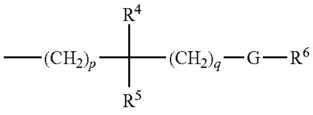 |
|---|---|---|---|---|---|---|---|
| 1651 | 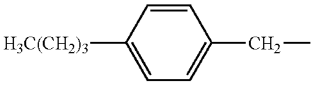 | 2 | 2 | 1 | — | H | 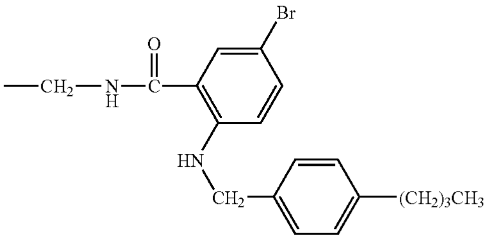 |

TABLE 1.151-continued
| Compd. No. | 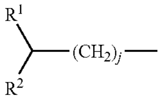 | k | m | n | chirality | $R^3$ | 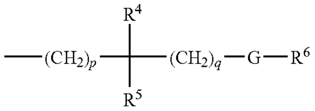 |
|---|---|---|---|---|---|---|---|
| 1652 | 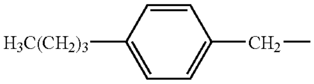 | 2 | 2 | 1 | — | H | 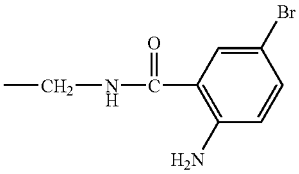 |
| 1653 | 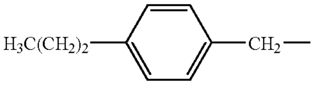 | 2 | 2 | 1 | — | H | 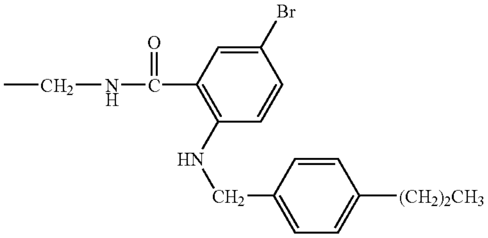 |
| 1654 | 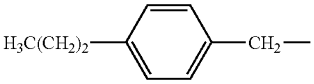 | 2 | 2 | 1 | — | H | 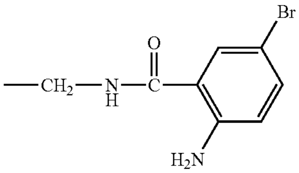 |
| 1655 | 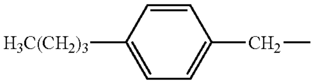 | 2 | 2 | 1 | — | H | 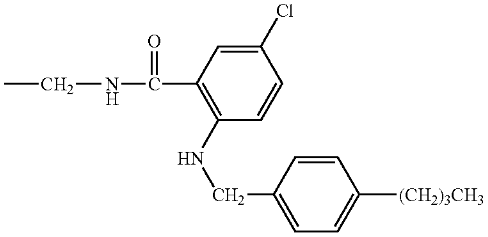 |
| 1656 | 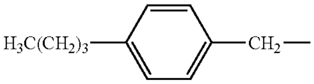 | 2 | 2 | 1 | — | H | 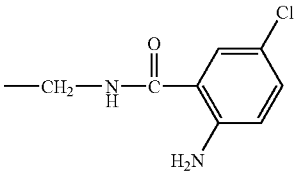 |
| 1657 | 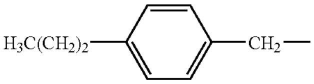 | 2 | 2 | 1 | — | H | 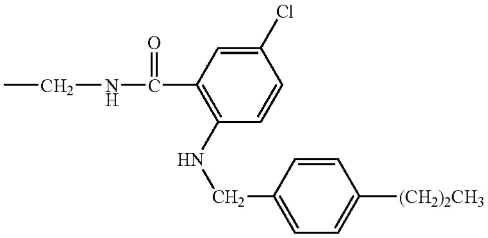 |
| 1658 | 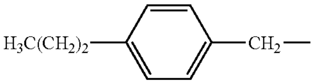 | 2 | 2 | 1 | — | H | 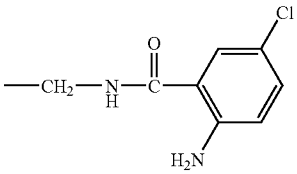 |

TABLE 1.151-continued
| Compd. No. | 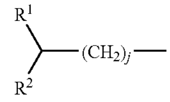 | k | m | n | chirality | $R^3$ | 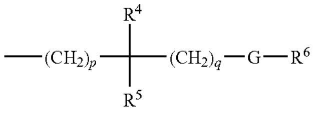 |
|---|---|---|---|---|---|---|---|
| 1659 | 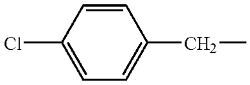 | 2 | 2 | 1 | — | H | 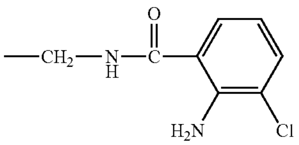 |
| 1660 | 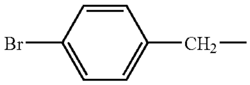 | 1 | 2 | 0 | R | H | 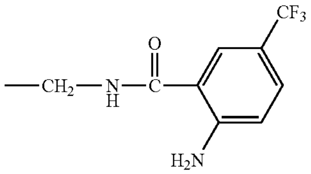 |
| 1661 | 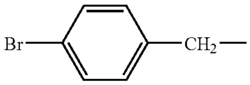 | 1 | 2 | 0 | R | H | 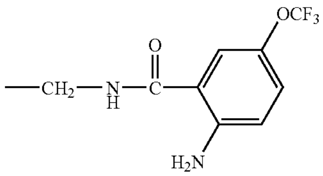 |
TABLE 1.152
| Compd. No. | 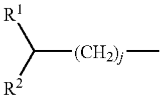 | k | m | n | chirality | $R^3$ | 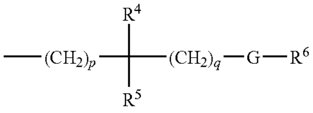 |
|---|---|---|---|---|---|---|---|
| 1662 | 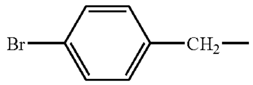 | 1 | 2 | 0 | R | H | 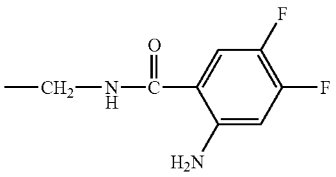 |
| 1663 | 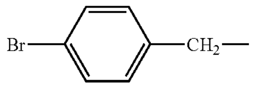 | 1 | 2 | 0 | R | H | 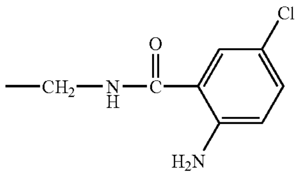 |
| 1664 | 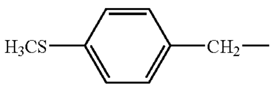 | 2 | 2 | 1 | — | H | 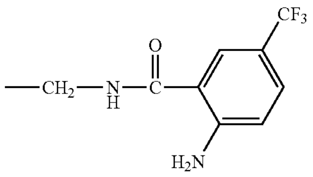 |

TABLE 1.152-continued
| Compd. No. | 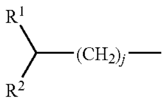 | k | m | n | chirality | $R^3$ | 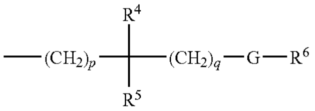 |
|---|---|---|---|---|---|---|---|
| 1665 | 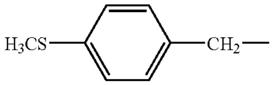 | 2 | 2 | 1 | — | H | 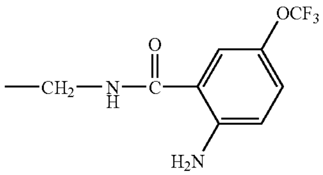 |
| 1666 | 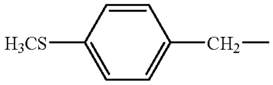 | 2 | 2 | 1 | — | H | 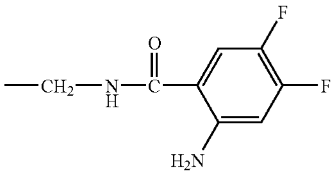 |
| 1667 | 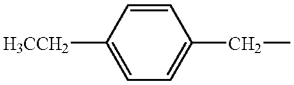 | 2 | 2 | 1 | — | H | 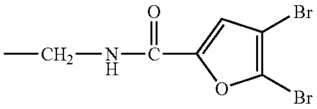 |
| 1668 | 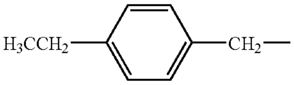 | 2 | 2 | 1 | — | H | 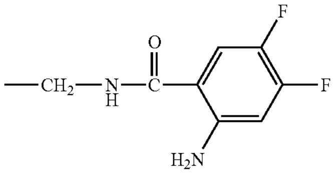 |
| 1669 | 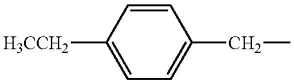 | 2 | 2 | 1 | — | H | 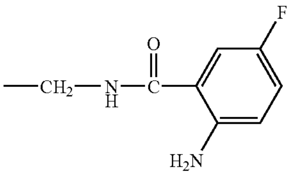 |
| 1670 | 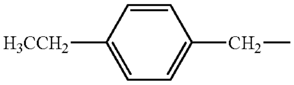 | 2 | 2 | 1 | — | H | 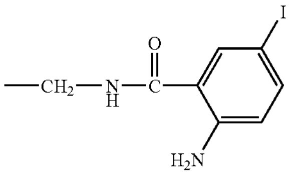 |
| 1671 | 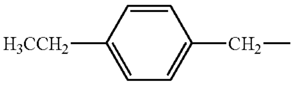 | 2 | 2 | 1 | — | H | 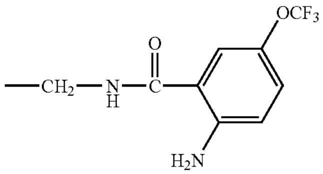 |
| 1672 | 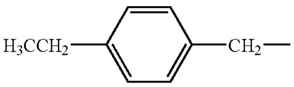 | 2 | 2 | 1 | — | H | 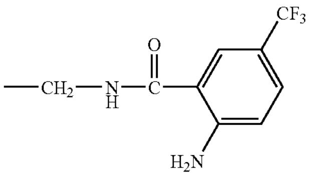 |

TABLE 1.153
| Compd. No. | 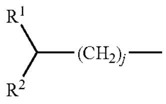 | k | m | n | chirality | $R^3$ | 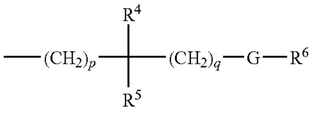 |
|---|---|---|---|---|---|---|---|
| 1673 | 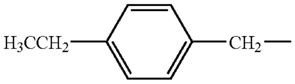 | 2 | 2 | 1 | — | H | 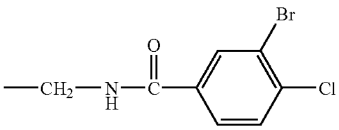 |
| 1674 | 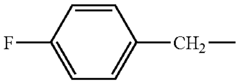 | 2 | 2 | 1 | — | H | 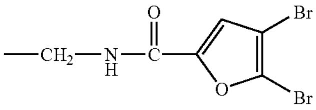 |
| 1675 | 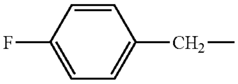 | 2 | 2 | 1 | — | H | 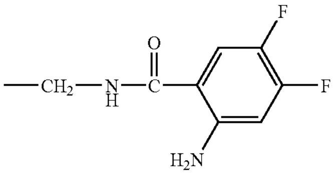 |
| 1676 | 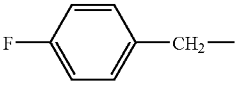 | 2 | 2 | 1 | — | H | 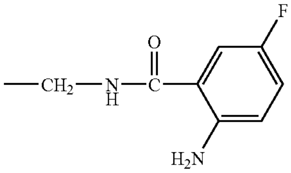 |
| 1677 | 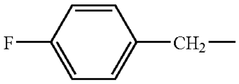 | 2 | 2 | 1 | — | H | 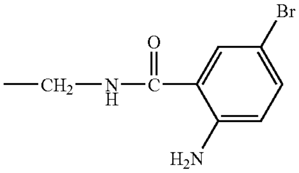 |
| 1678 | 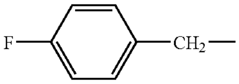 | 2 | 2 | 1 | — | H | 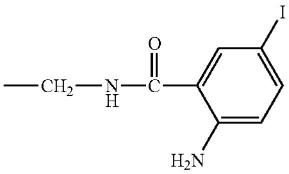 |
| 1679 | 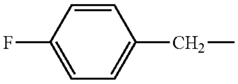 | 2 | 2 | 1 | — | H | 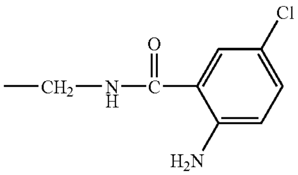 |
| 1680 | 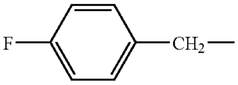 | 2 | 2 | 1 | — | H | 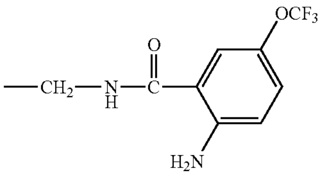 |

TABLE 1.153-continued
| Compd. No. | 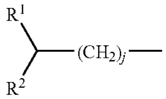 | k | m | n | chirality | $R^3$ | 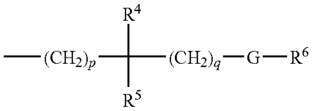 |
|---|---|---|---|---|---|---|---|
| 1681 | 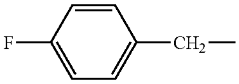 | 2 | 2 | 1 | — | H | 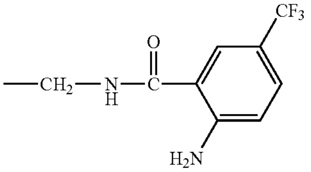 |
| 1682 | 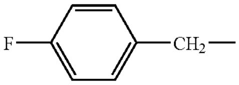 | 2 | 2 | 1 | — | H | 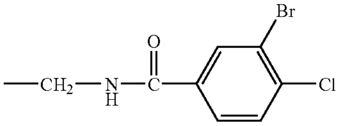 |
| 1683 | 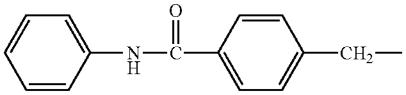 | 2 | 2 | 1 | — | H | 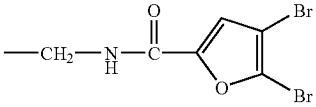 |
TABLE 1.154
| Compd. No. | 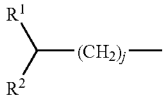 | k | m | n | chirality | $R^3$ | 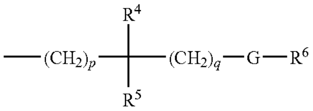 |
|---|---|---|---|---|---|---|---|
| 1684 | 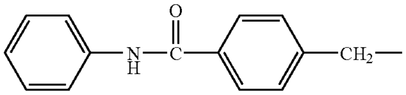 | 2 | 2 | 1 | — | H | 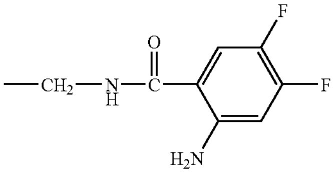 |
| 1685 | 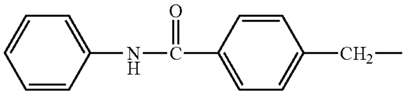 | 2 | 2 | 1 | — | H | 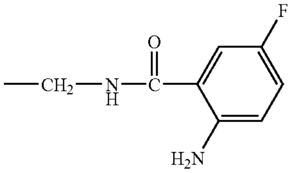 |
| 1686 | 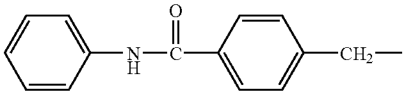 | 2 | 2 | 1 | — | H | 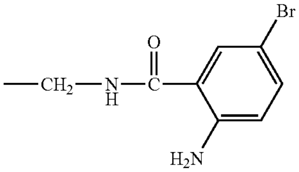 |
| 1687 | 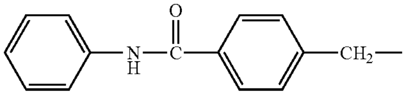 | 2 | 2 | 1 | — | H | 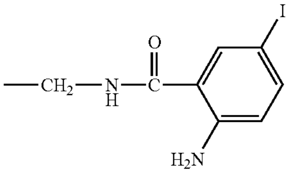 |

TABLE 1.154-continued
| Compd. No. | 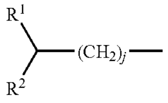 | k | m | n | chirality | $R^3$ | 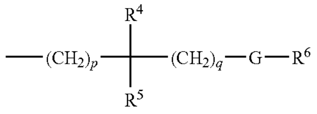 |
|---|---|---|---|---|---|---|---|
| 1688 | 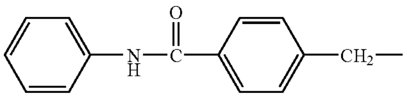 | 2 | 2 | 1 | — | H | 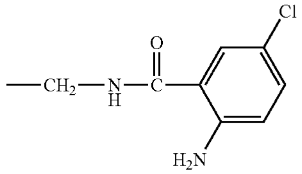 |
| 1689 | 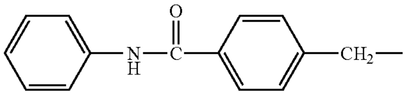 | 2 | 2 | 1 | — | H | 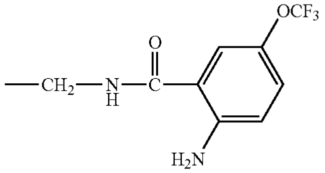 |
| 1690 | 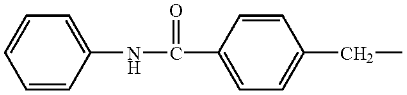 | 2 | 2 | 1 | — | H | 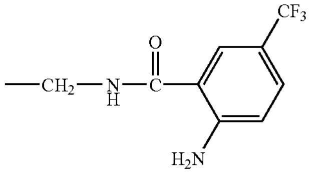 |
| 1691 | 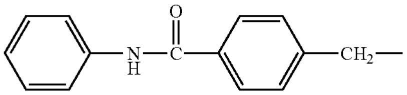 | 2 | 2 | 1 | — | H | 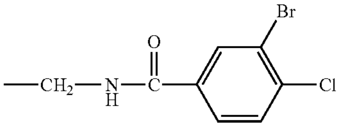 |
| 1692 | 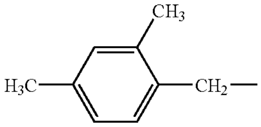 | 1 | 2 | 0 | R | H | 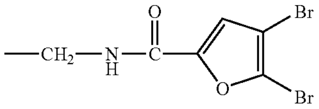 |
| 1693 | 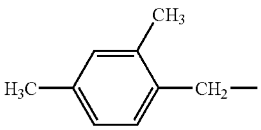 | 1 | 2 | 0 | R | H | 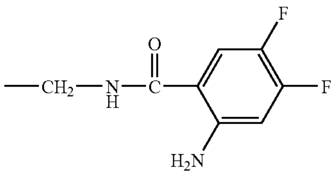 |
| 1694 | 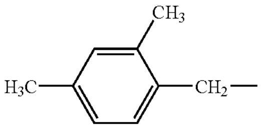 | 1 | 2 | 0 | R | H | 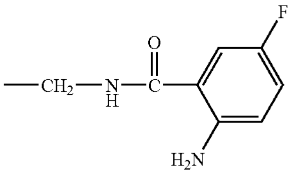 |

TABLE 1.155
| Compd. No. | 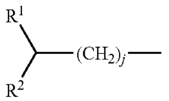 | k | m | n | chirality | $R^3$ | 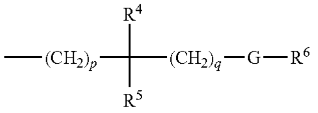 |
|---|---|---|---|---|---|---|---|
| 1695 | 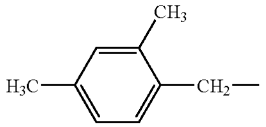 | 1 | 2 | 0 | R | H | 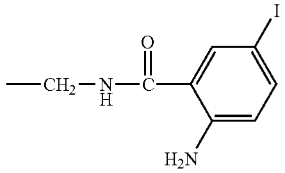 |
| 1696 | 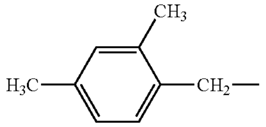 | 1 | 2 | 0 | R | H | 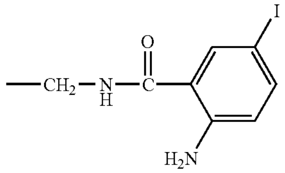 |
| 1697 | 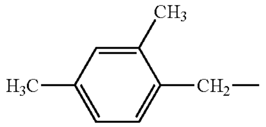 | 1 | 2 | 0 | R | H | 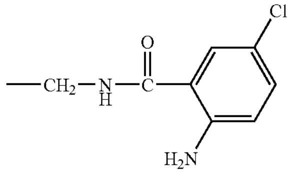 |
| 1698 | 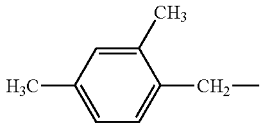 | 1 | 2 | 0 | R | H | 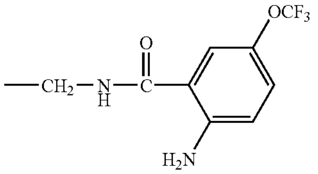 |
| 1699 | 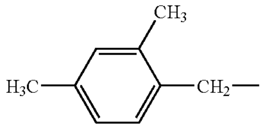 | 1 | 2 | 0 | R | H | 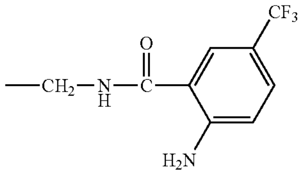 |
| 1700 | 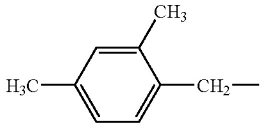 | 1 | 2 | 0 | R | H | 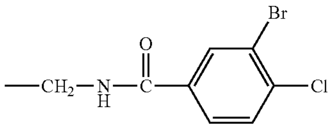 |
| 1701 | 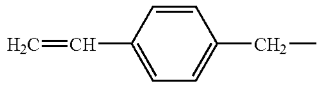 | 1 | 2 | 0 | R | H | 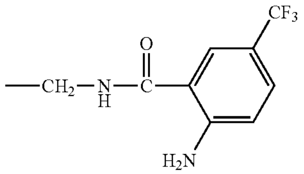 |
| 1702 | 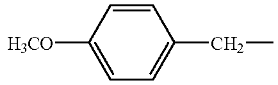 | 1 | 2 | 0 | R | H | 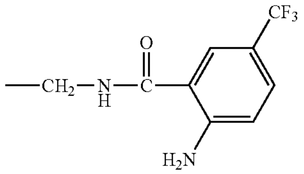 |

TABLE 1.155-continued
| Compd. No. | 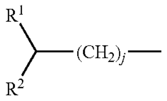 | k | m | n | chirality | $R^3$ | 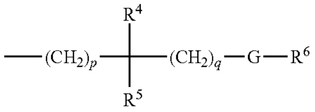 |
|---|---|---|---|---|---|---|---|
| 1703 | 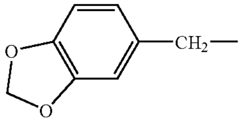 | 1 | 2 | 0 | R | H | 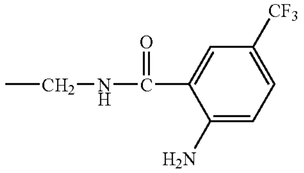 |
| 1704 | 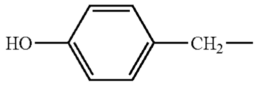 | 1 | 2 | 0 | R | H | 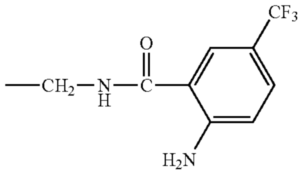 |
| 1705 | 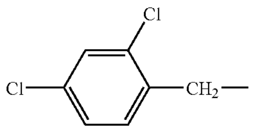 | 1 | 2 | 0 | R | H | 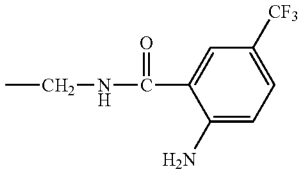 |
TABLE 1.156
| Compd. No. | 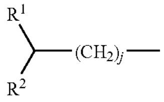 | k | m | n | chirality | $R^3$ | 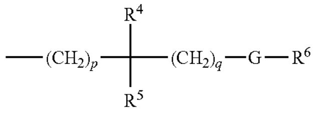 |
|---|---|---|---|---|---|---|---|
| 1706 | 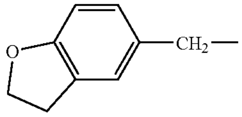 | 1 | 2 | 0 | R | H | 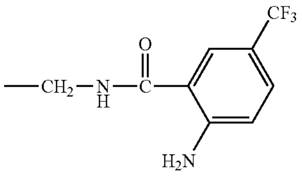 |
| 1707 | 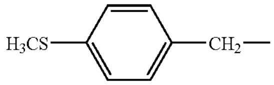 | 1 | 2 | 0 | R | H | 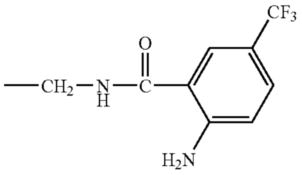 |
| 1708 | 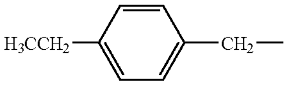 | 1 | 2 | 0 | R | H | 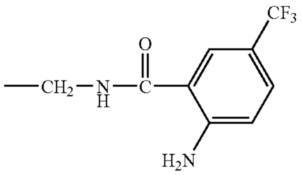 |

TABLE 1.156-continued
| Compd. No. | 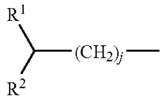 | k | m | n | chirality | $R^3$ | 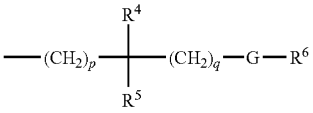 |
|---|---|---|---|---|---|---|---|
| 1709 | 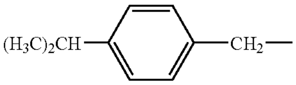 | 1 | 2 | 0 | R | H | 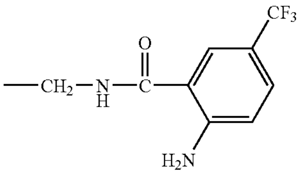 |
| 1710 | 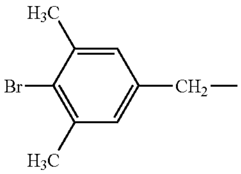 | 1 | 2 | 0 | R | H | 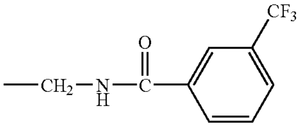 |
| 1711 | 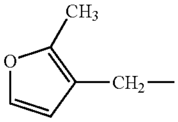 | 1 | 2 | 0 | R | H | 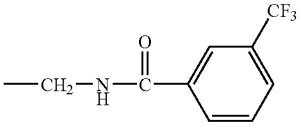 |
| 1712 | 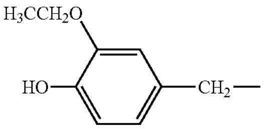 | 1 | 2 | 0 | R | H | 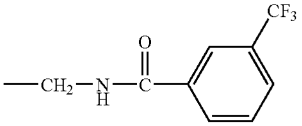 |
| 1713 | 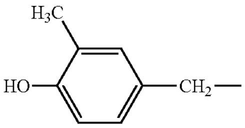 | 1 | 2 | 0 | R | H | 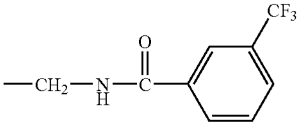 |
| 1714 | 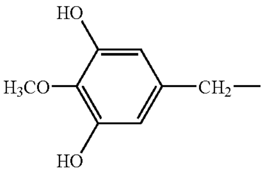 | 1 | 2 | 0 | R | H | 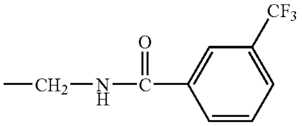 |
| 1715 | 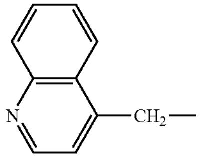 | 1 | 2 | 0 | R | H | 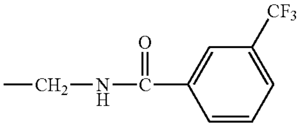 |
| 1716 | 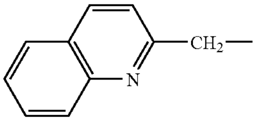 | 1 | 2 | 0 | R | H | 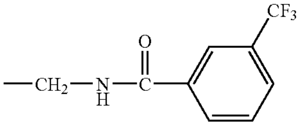 |

TABLE 1.157
| Compd. No. | 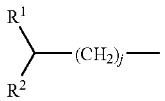 | k | m | n | chirality | $R^3$ | 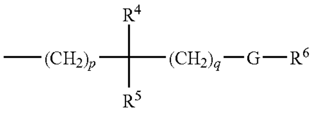 |
|---|---|---|---|---|---|---|---|
| 1717 | 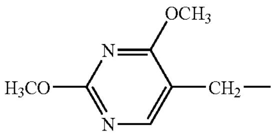 | 1 | 2 | 0 | R | H | 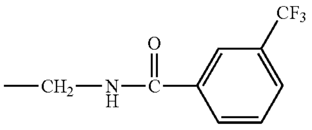 |
| 1718 | 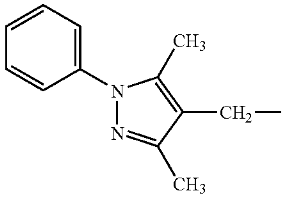 | 1 | 2 | 0 | R | H | 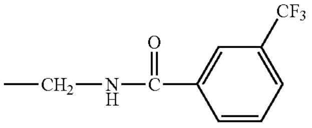 |
| 1719 | 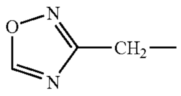 | 1 | 2 | 0 | R | H | 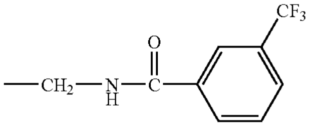 |
| 1720 | 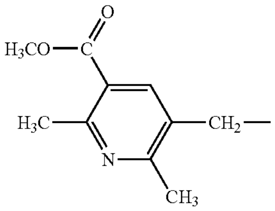 | 1 | 2 | 0 | R | H | 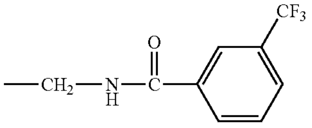 |
| 1721 | 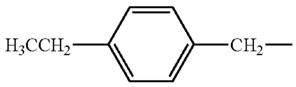 | 1 | 2 | 0 | R | H | 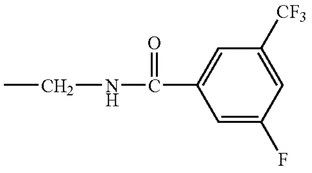 |
| 1722 | 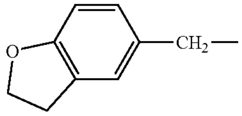 | 1 | 2 | 0 | R | H | 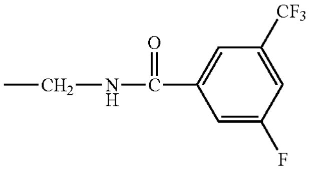 |
| 1723 | 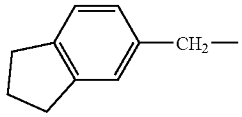 | 1 | 2 | 0 | R | H | 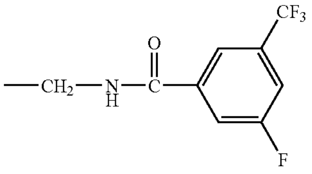 |
| 1724 | 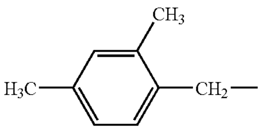 | 1 | 2 | 0 | R | H | 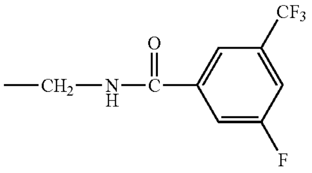 |

TABLE 1.157-continued
| Compd. No. | 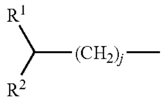 | k | m | n | chirality | $R^3$ | 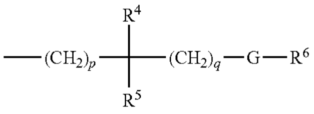 |
|---|---|---|---|---|---|---|---|
| 1725 | 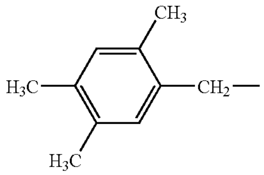 | 1 | 2 | 0 | R | H | 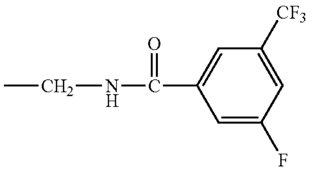 |
| 1726 | 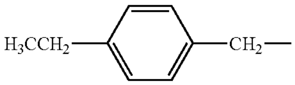 | 1 | 2 | 0 | R | H | 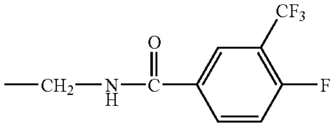 |
| 1727 | 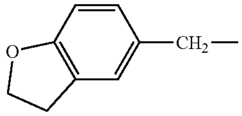 | 1 | 2 | 0 | R | H | 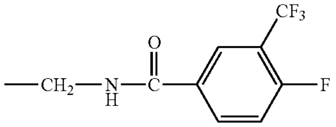 |
TABLE 1.158
| Compd. No. | 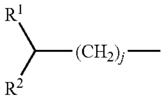 | k | m | n | chirality | $R^3$ | 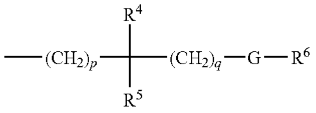 |
|---|---|---|---|---|---|---|---|
| 1728 | 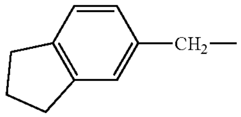 | 1 | 2 | 0 | R | H | 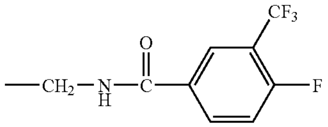 |
| 1729 | 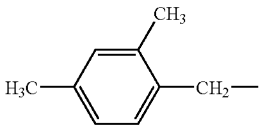 | 1 | 2 | 0 | R | H | 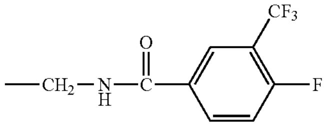 |
| 1730 | 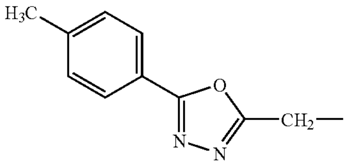 | 1 | 2 | 0 | R | H | 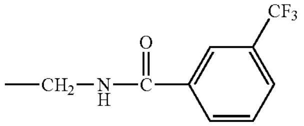 |
| 1731 | 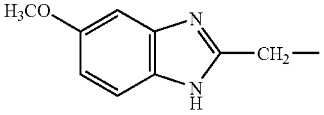 | 1 | 2 | 0 | R | H | 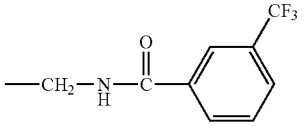 |
| 1732 | 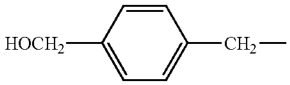 | 1 | 2 | 0 | R | H | 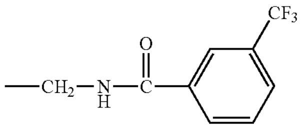 |

TABLE 1.158-continued
| Compd. No. | 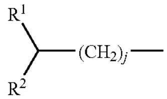 | k | m | n | chirality | $R^3$ | 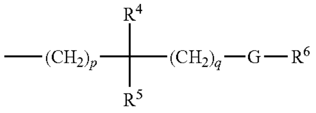 |
|---|---|---|---|---|---|---|---|
| 1733 | 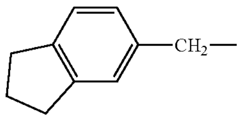 | 1 | 2 | 0 | R | H | 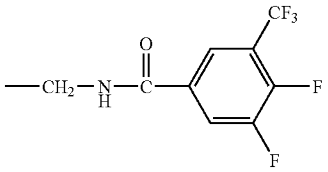 |
| 1734 | 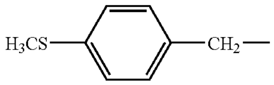 | 1 | 2 | 0 | R | H | 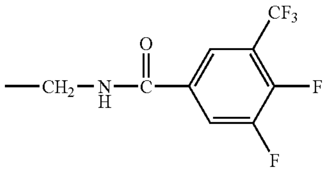 |
| 1735 | 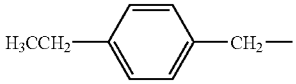 | 1 | 2 | 0 | R | H | 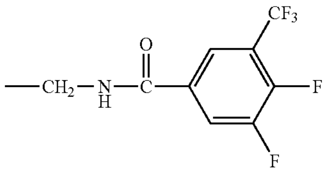 |
| 1736 | 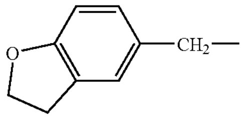 | 1 | 2 | 0 | R | H | 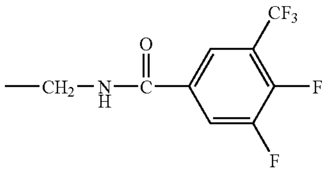 |
| 1737 | 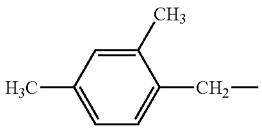 | 1 | 2 | 0 | R | H | 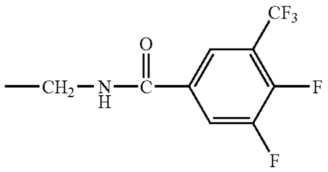 |
| 1738 | 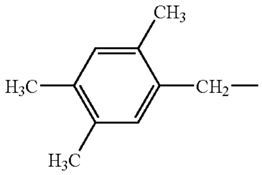 | 1 | 2 | 0 | R | H | 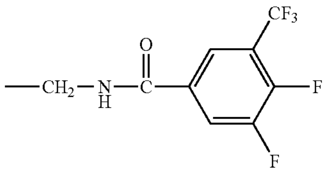 |
TABLE 1.159
| Compd. No. | 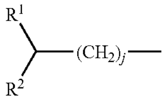 | k | m | n | chirality | $R^3$ | 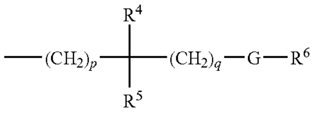 |
|---|---|---|---|---|---|---|---|
| 1739 | 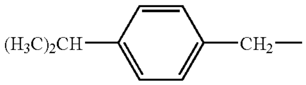 | 1 | 2 | 0 | R | H | 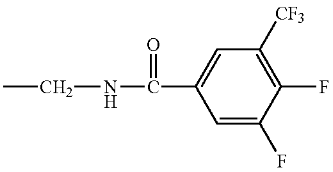 |

TABLE 1.159-continued
| Compd. No. | 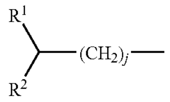 | k | m | n | chirality | $R^3$ | 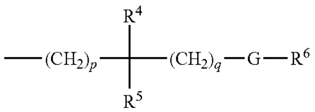 |
|---|---|---|---|---|---|---|---|
| 1740 | 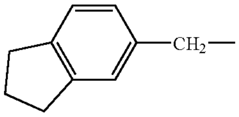 | 1 | 2 | 0 | R | H | 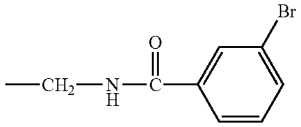 |
| 1741 | 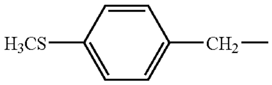 | 1 | 2 | 0 | R | H | 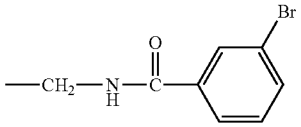 |
| 1742 | 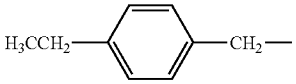 | 1 | 2 | 0 | R | H | 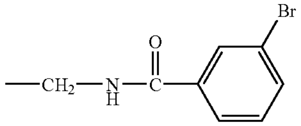 |
| 1743 | 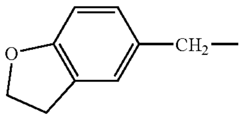 | 1 | 2 | 0 | R | H | 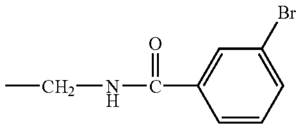 |
| 1744 | 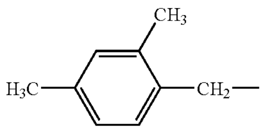 | 1 | 2 | 0 | R | H | 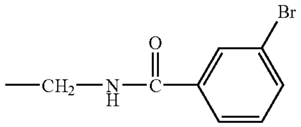 |
| 1745 | 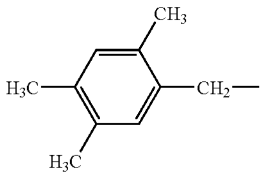 | 1 | 2 | 0 | R | H | 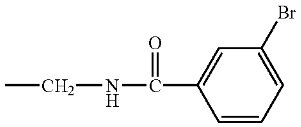 |
| 1746 | 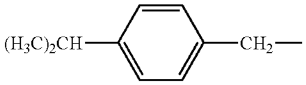 | 1 | 2 | 0 | R | H | 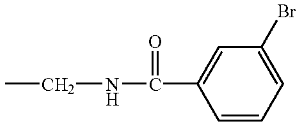 |
| 1747 | 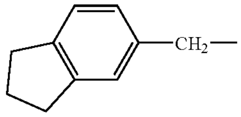 | 1 | 2 | 0 | R | H | 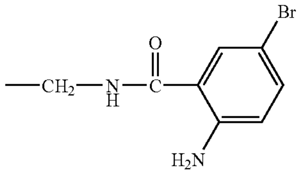 |
| 1748 | 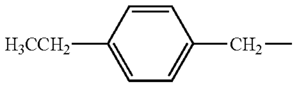 | 1 | 2 | 0 | R | H | 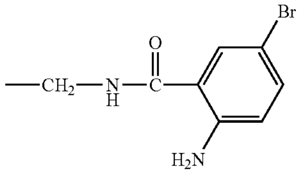 |

TABLE 1.159-continued
| Compd. No. | 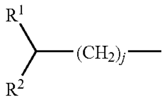 | k | m | n | chirality | $R^3$ | 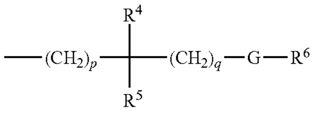 |
|---|---|---|---|---|---|---|---|
| 1749 | 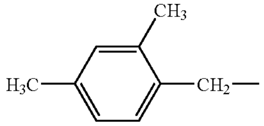 | 1 | 2 | 0 | R | H | 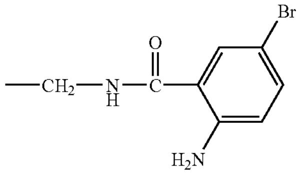 |
TABLE 1.160
| Compd. No. | 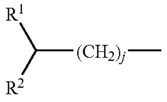 | k | m | n | chirality | $R^3$ | 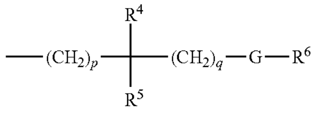 |
|---|---|---|---|---|---|---|---|
| 1750 | 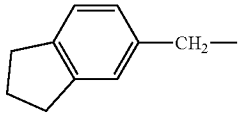 | 1 | 2 | 0 | R | H | 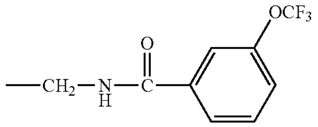 |
| 1751 | 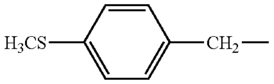 | 1 | 2 | 0 | R | H | 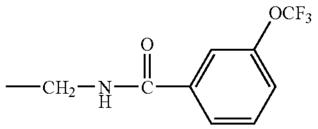 |
| 1752 | 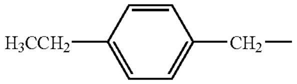 | 1 | 2 | 0 | R | H | 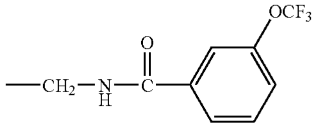 |
| 1753 | 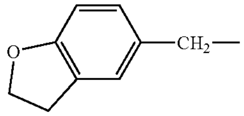 | 1 | 2 | 0 | R | H | 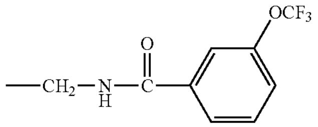 |
| 1754 | 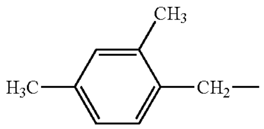 | 1 | 2 | 0 | R | H | 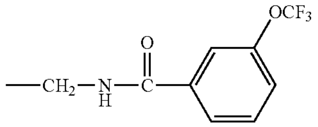 |
| 1755 | 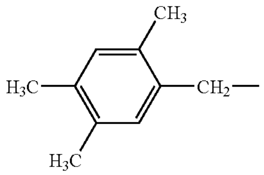 | 1 | 2 | 0 | R | H | 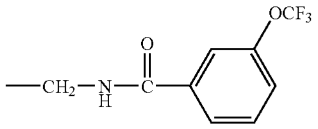 |
| 1756 | 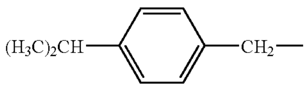 | 1 | 2 | 0 | R | H | 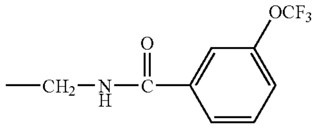 |

TABLE 1.160-continued
| Compd. No. | 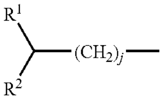 | k | m | n | chirality | $R^3$ | 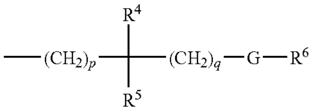 |
|---|---|---|---|---|---|---|---|
| 1757 | 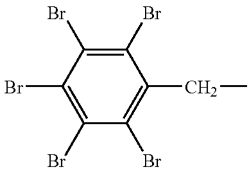 | 1 | 2 | 0 | R | H | 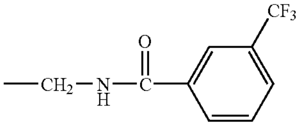 |
| 1758 | 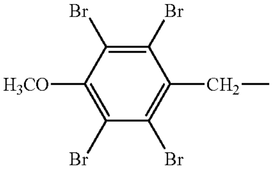 | 1 | 2 | 0 | R | H | 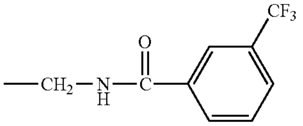 |
| 1759 | 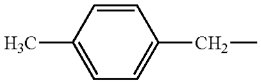 | 1 | 2 | 0 | R | H | 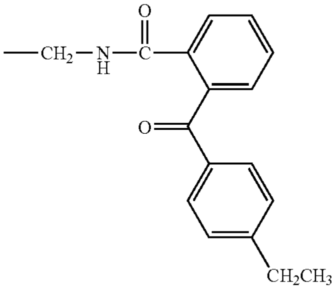 |
| 1760 | 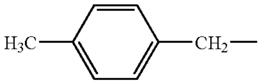 | 1 | 2 | 0 | R | H | 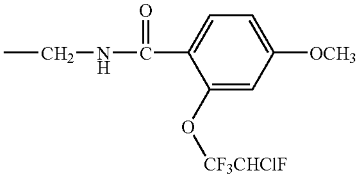 |
TABLE 1.161
| Compd. No. | 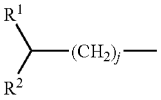 | k | m | n | chirality | $R^3$ | 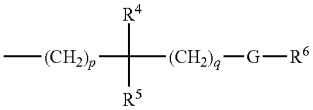 |
|---|---|---|---|---|---|---|---|
| 1761 | 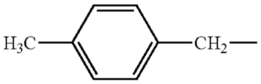 | 1 | 2 | 0 | R | H | 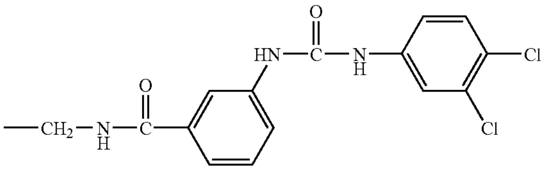 |
| 1762 | 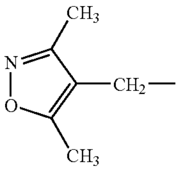 | 1 | 2 | 0 | R | H | 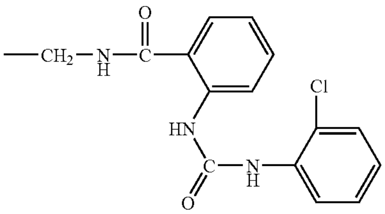 |

TABLE 1.161-continued
| Compd. No. | 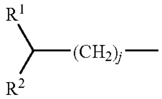 | k | m | n | chirality | $R^3$ | 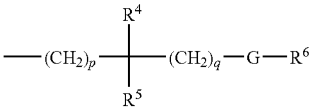 |
|---|---|---|---|---|---|---|---|
| 1763 | 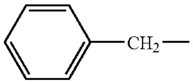 | 2 | 2 | 0 | — | H | 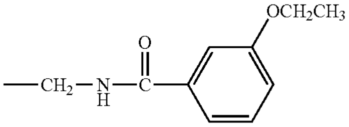 |
| 1764 | 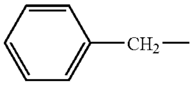 | 2 | 2 | 0 | — | H | 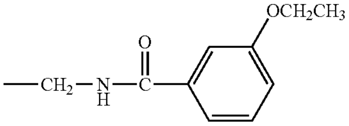 |
| 1765 | 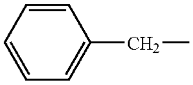 | 2 | 2 | 0 | — | H | 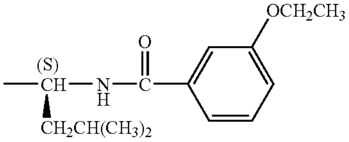 |
| 1766 | 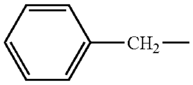 | 2 | 2 | 0 | — | H | 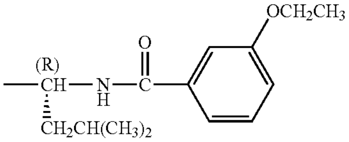 |
| 1767 | 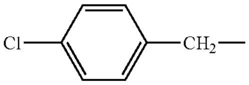 | 1 | 3 | 1 | — | H | 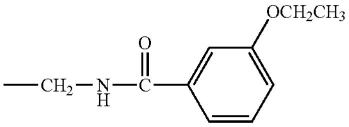 |
| 1768 | 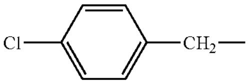 | 1 | 3 | 1 | — | H | 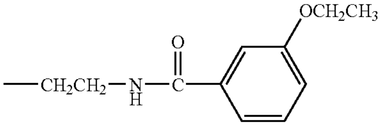 |
| 1769 | 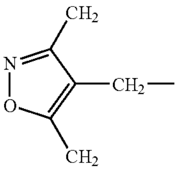 | 1 | 2 | 0 | R | H | 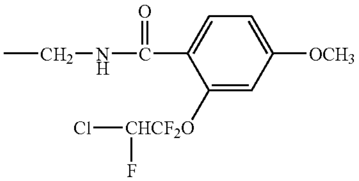 |
| 1770 | 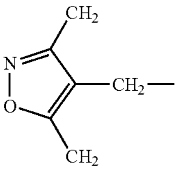 | 1 | 2 | 0 | R | H | 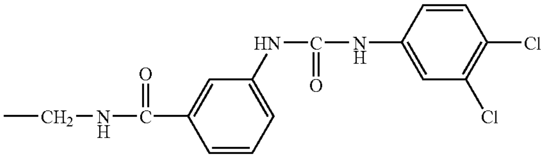 |
| 1771 | 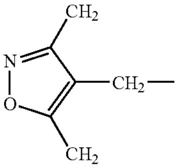 | 1 | 2 | 0 | R | H | 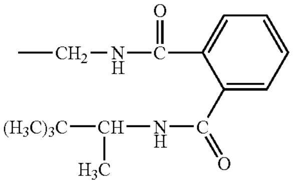 |

TABLE 1.162
| Compd. No. | 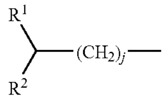 | k | m | n | chirality |
|---|---|---|---|---|---|
| 1772 | 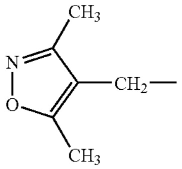 | 1 | 2 | 0 | R |
| 1773 | 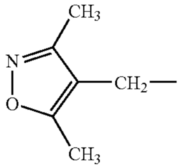 | 1 | 2 | 0 | R |
| 1774 | 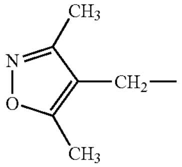 | 1 | 2 | 0 | R |
| 1775 | 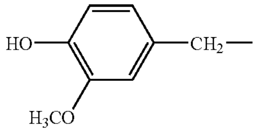 | 1 | 2 | 0 | R |
| 1776 | 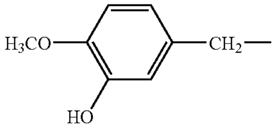 | 1 | 2 | 0 | R |
| 1777 | 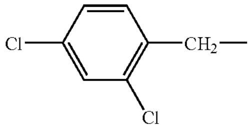 | 2 | 2 | 1 | — |
| 1778 | 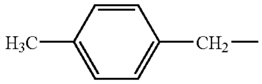 | 2 | 2 | 1 | — |
| 1779 | 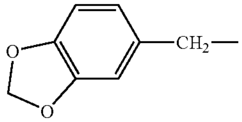 | 2 | 2 | 1 | — |
| 1780 | 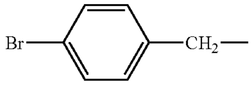 | 2 | 2 | 1 | — |
| 1781 | 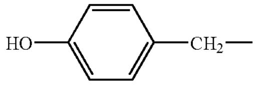 | 2 | 2 | 1 | — |

TABLE 1.162-continued
| | | | | | |
|---|---|---|---|---|---|
| 1782 | 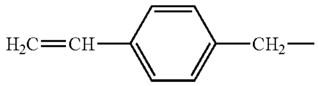 | 2 | 2 | 1 | — |
| Compd. No. | $R^3$ | 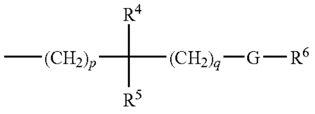 |
|---|---|---|
| 1772 | H | 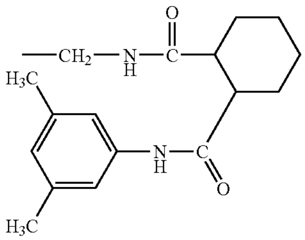 |
| 1773 | H | 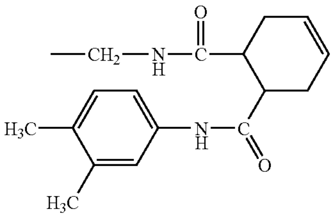 |
| 1774 | H | 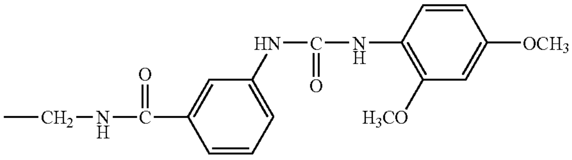 |
| 1775 | H | 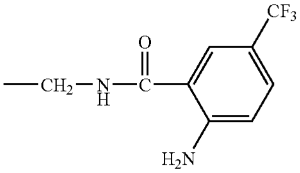 |
| 1776 | H | 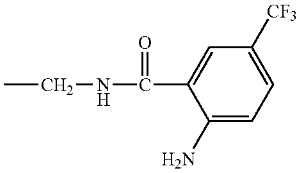 |
| 1777 | H | 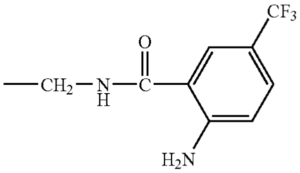 |
| 1778 | H | 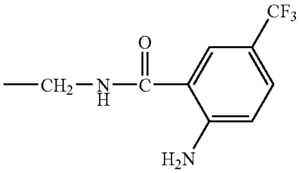 |

TABLE 1.162-continued
| | | |
|---|---|---|
| 1779 | H | 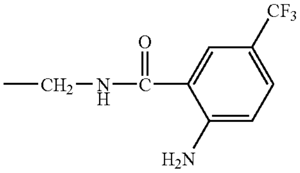 |
| 1780 | H | 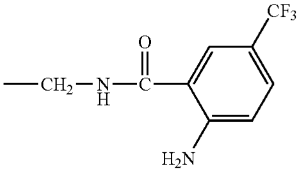 |
| 1781 | H | 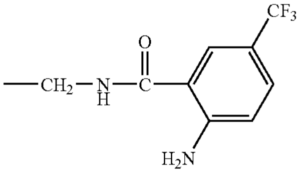 |
| 1782 | H | 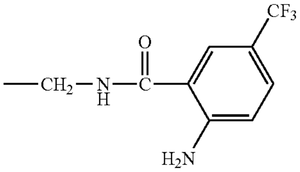 |
TABLE 1.163
| Compd. No. | 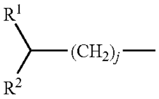 | k | m | n | chirality | $R^3$ | 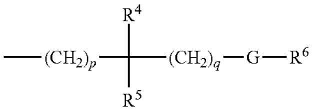 |
|---|---|---|---|---|---|---|---|
| 1783 | 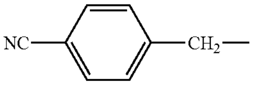 | 2 | 2 | 1 | — | H | 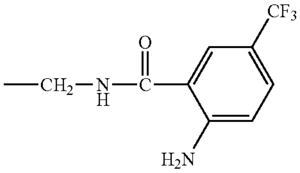 |
| 1784 | 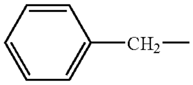 | 2 | 2 | 1 | — | H | 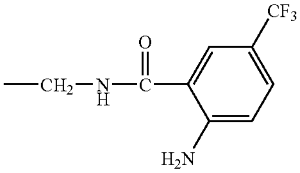 |
| 1785 | 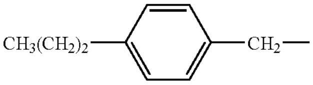 | 2 | 2 | 1 | — | H | 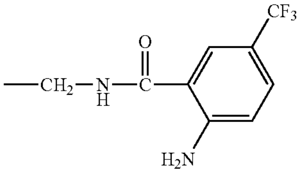 |

TABLE 1.163-continued
| Compd. No. | 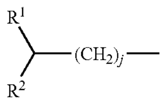 | k | m | n | chirality | $R^3$ | 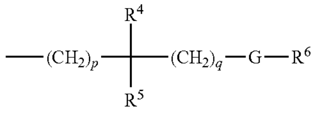 |
|---|---|---|---|---|---|---|---|
| 1786 | 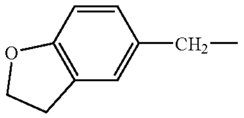 | 2 | 2 | 1 | — | H | 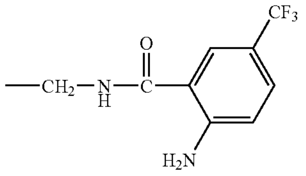 |
| 1787 | 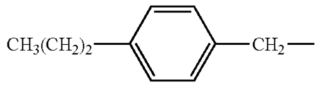 | 1 | 2 | 0 | R | H | 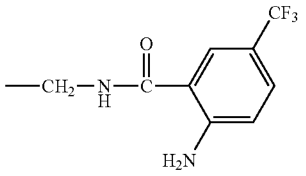 |
| 1788 | 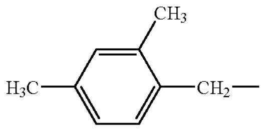 | 2 | 2 | 1 | — | H | 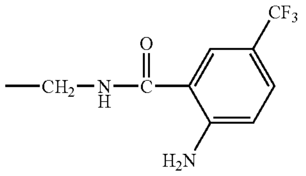 |
| 1789 | 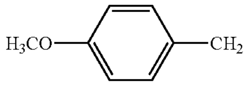 | 2 | 2 | 1 | — | H | 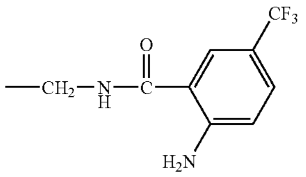 |
| 1790 | 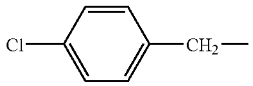 | 1 | 2 | 0 | S | H | 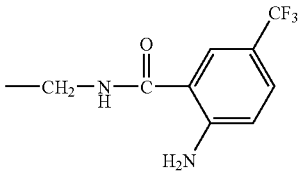 |
| 1791 | 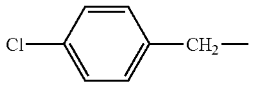 | 1 | 2 | 0 | S | H | 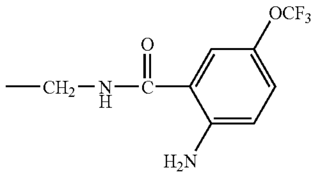 |
| 1792 | 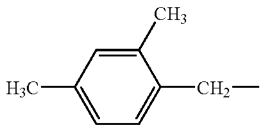 | 2 | 2 | 1 | — | H | 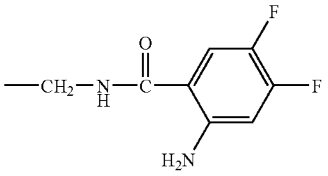 |

TABLE 1.163-continued
| Compd. No. | 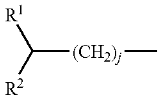 | k | m | n | chirality | $R^3$ | 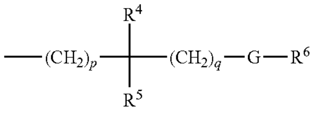 |
|---|---|---|---|---|---|---|---|
| 1793 | 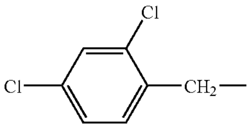 | 2 | 2 | 1 | — | H | 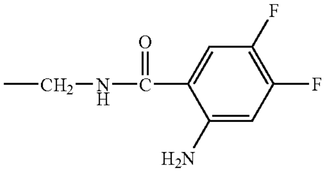 |
TABLE 1.164
| Compd. No. | 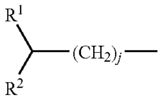 | k | m | n | chirality | $R^3$ | 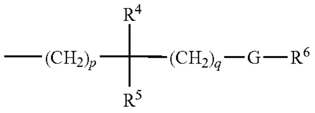 |
|---|---|---|---|---|---|---|---|
| 1794 | 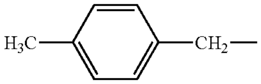 | 2 | 2 | 1 | — | H | 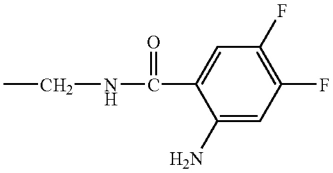 |
| 1795 | 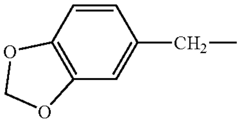 | 2 | 2 | 1 | — | H | 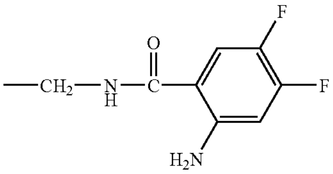 |
| 1798 | 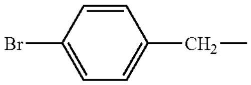 | 2 | 2 | 1 | — | H | 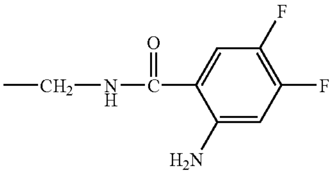 |
| 1797 | 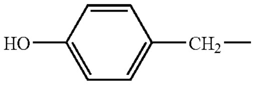 | 2 | 2 | 1 | — | H | 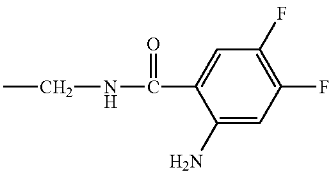 |
| 1798 | 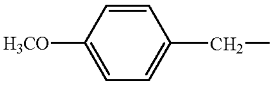 | 2 | 2 | 1 | — | H | 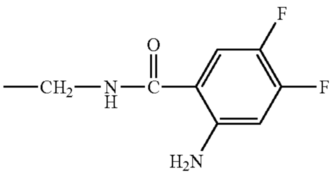 |

TABLE 1.164-continued
| Compd. No. | 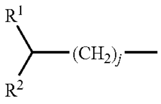 | k | m | n | chirality | $R^3$ | 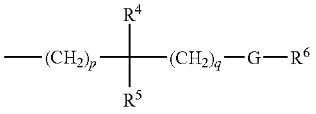 |
|---|---|---|---|---|---|---|---|
| 1799 | 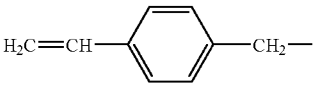 | 2 | 2 | 1 | — | H | 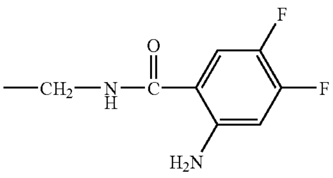 |
| 1800 | 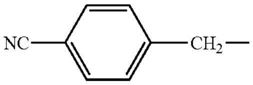 | 2 | 2 | 1 | — | H | 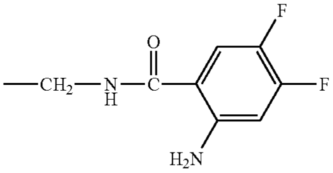 |
| 1801 | 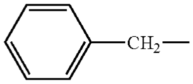 | 2 | 2 | 1 | — | H | 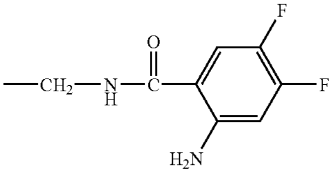 |
| 1802 | 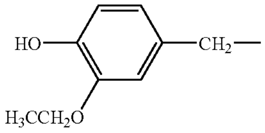 | 1 | 2 | 0 | R | H | 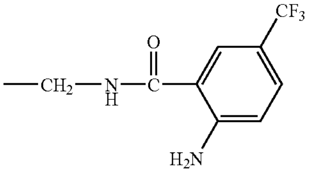 |
| 1803 | 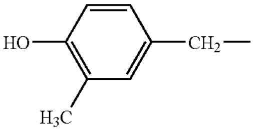 | 1 | 2 | 0 | R | H | 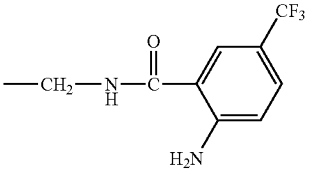 |
| 1804 | 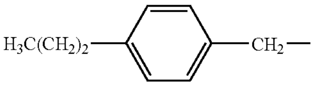 | 2 | 2 | 1 | — | H | 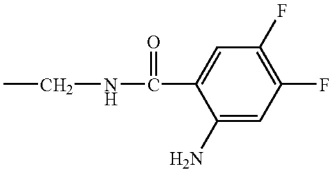 |
TABLE 1.165
| Compd. No. | 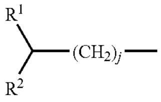 | k | m | n | chirality | $R^3$ | 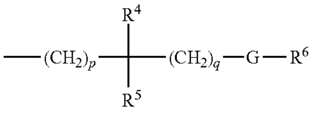 |
|---|---|---|---|---|---|---|---|
| 1805 | 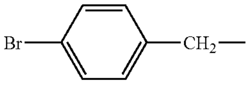 | 1 | 2 | 0 | R | H | 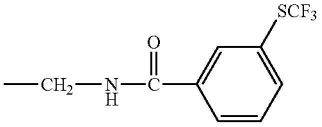 |

TABLE 1.165-continued
| Compd. No. | 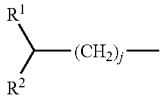 | k | m | n | chirality | $R^3$ | 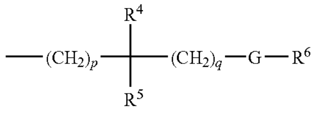 |
|---|---|---|---|---|---|---|---|
| 1806 | 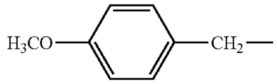 | 1 | 2 | 0 | R | H | 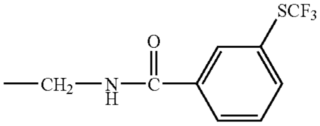 |
| 1807 | 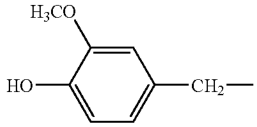 | 1 | 2 | 0 | R | H | 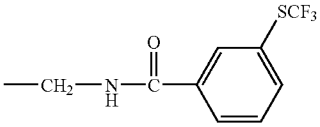 |
| 1808 | 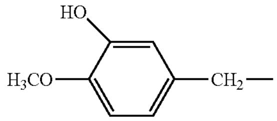 | 1 | 2 | 0 | R | H | 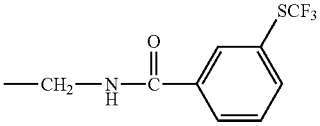 |
| 1809 | 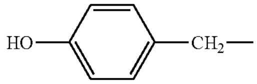 | 1 | 2 | 0 | R | H | 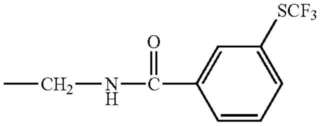 |
| 1810 | 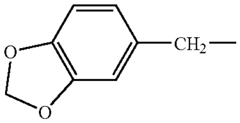 | 1 | 2 | 0 | R | H | 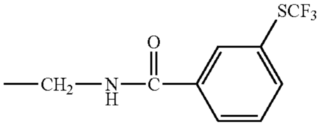 |
| 1811 | 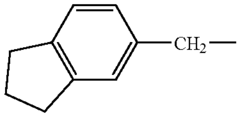 | 1 | 2 | 0 | R | H | 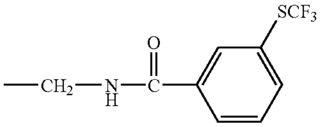 |
| 1812 | 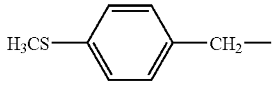 | 1 | 2 | 0 | R | H | 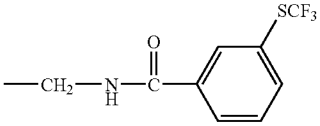 |
| 1813 | 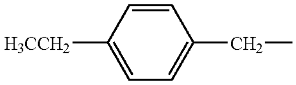 | 1 | 2 | 0 | R | H | 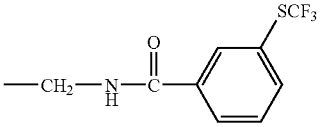 |
| 1814 | 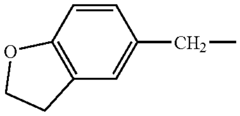 | 1 | 2 | 0 | R | H | 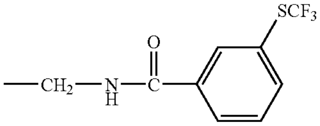 |
| 1815 | 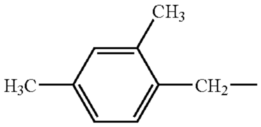 | 1 | 2 | 0 | R | H | 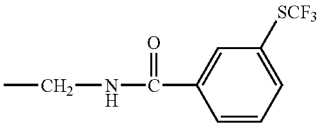 |

TABLE 1.166
| Compd. No. | 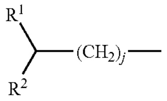 | k | m | n | chirality | $R^3$ | 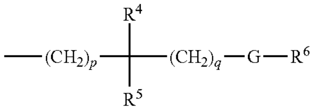 |
|---|---|---|---|---|---|---|---|
| 1816 | 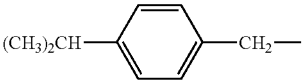 | 1 | 2 | 0 | R | H | 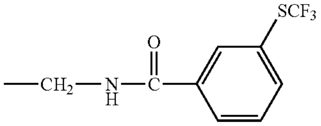 |
| 1817 | 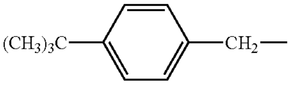 | 1 | 2 | 0 | R | H | 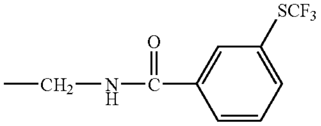 |
| 1818 | 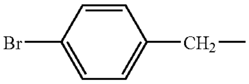 | 1 | 2 | 0 | R | H | 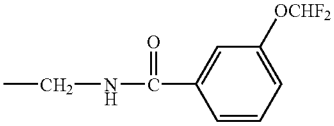 |
| 1819 | 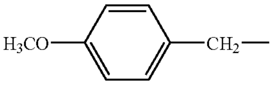 | 1 | 2 | 0 | R | H | 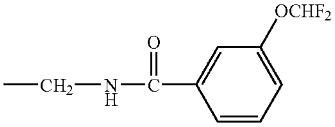 |
| 1820 | 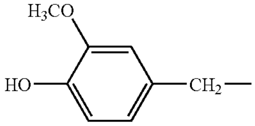 | 1 | 2 | 0 | R | H | 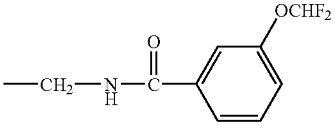 |
| 1821 | 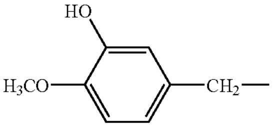 | 1 | 2 | 0 | R | H | 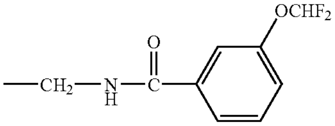 |
| 1822 | 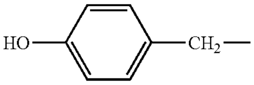 | 1 | 2 | 0 | R | H | 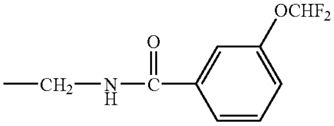 |
| 1823 | 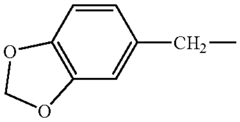 | 1 | 2 | 0 | R | H | 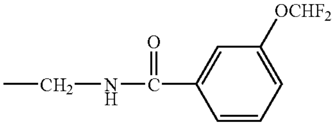 |
| 1824 | 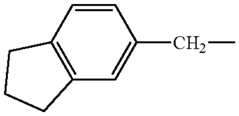 | 1 | 2 | 0 | R | H | 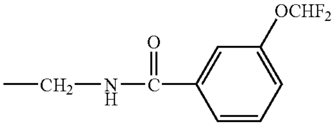 |
| 1825 | 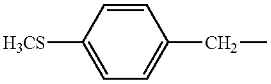 | 1 | 2 | 0 | R | H | 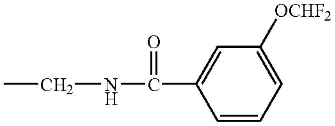 |

TABLE 1.166-continued
| Compd. No. | 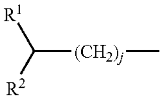 | k | m | n | chirality | $R^3$ | 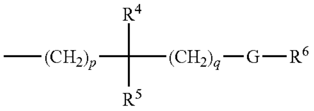 |
|---|---|---|---|---|---|---|---|
| 1826 | 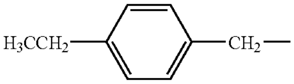 | 1 | 2 | 0 | R | H | 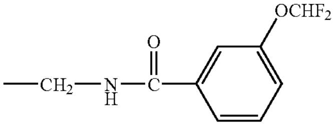 |
TABLE 1.167
| Compd. No. | 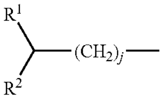 | k | m | n | chirality | $R^3$ | 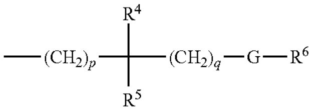 |
|---|---|---|---|---|---|---|---|
| 1327 | 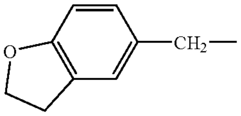 | 1 | 2 | 0 | R | H | 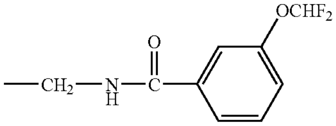 |
| 1328 | 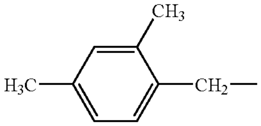 | 1 | 2 | 0 | R | H | 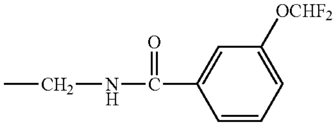 |
| 1829 | 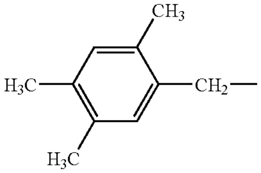 | 1 | 2 | 0 | R | H | 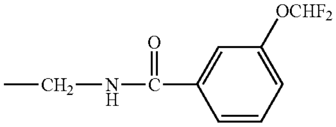 |
| 1330 | 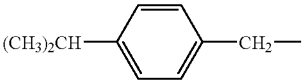 | 1 | 2 | 0 | R | H | 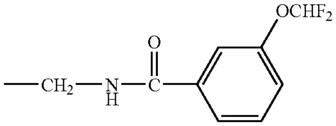 |
| 1831 | 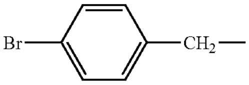 | 1 | 2 | 0 | R | H | 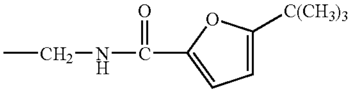 |
| 1832 | 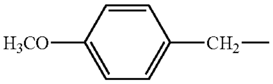 | 1 | 2 | 0 | R | H | 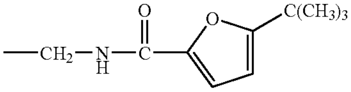 |
| 1833 | 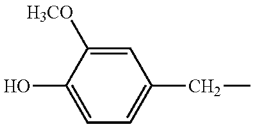 | 1 | 2 | 0 | R | H | 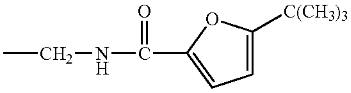 |
| 1834 | 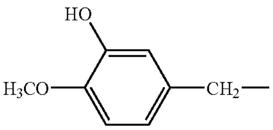 | 1 | 2 | 0 | R | H | 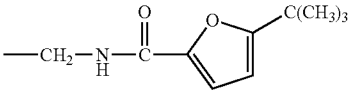 |

TABLE 1.167-continued
| Compd. No. | 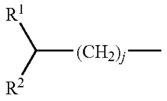 | k | m | n | chirality | $R^3$ | 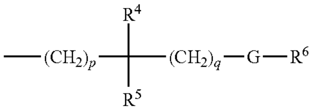 |
|---|---|---|---|---|---|---|---|
| 1835 | 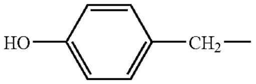 | 1 | 2 | 0 | R | H | 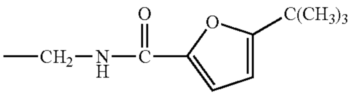 |
| 1836 | 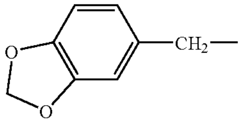 | 1 | 2 | 0 | R | H | 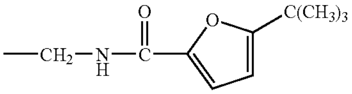 |
| 1837 | 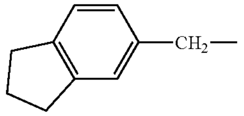 | 1 | 2 | 0 | R | H | 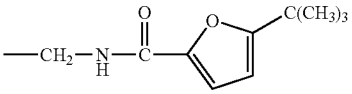 |
TABLE 1.168
| Compd. No. | 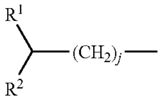 | k | m | n | chirality | $R^3$ | 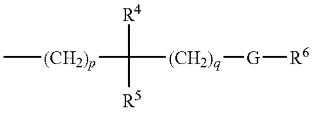 |
|---|---|---|---|---|---|---|---|
| 1838 | 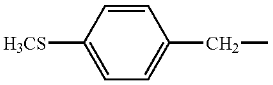 | 1 | 2 | 0 | R | H | 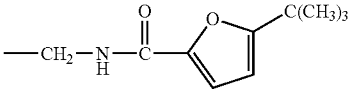 |
| 1839 | 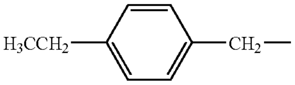 | 1 | 2 | 0 | R | H | 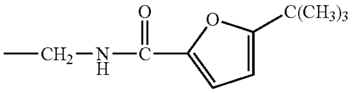 |
| 1840 | 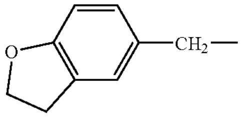 | 1 | 2 | 0 | R | H | 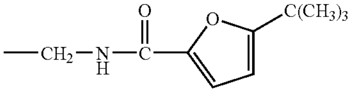 |
| 1841 | 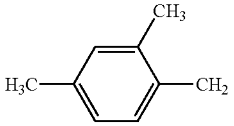 | 1 | 2 | 0 | R | H | 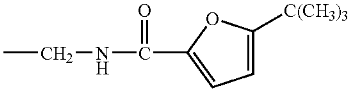 |
| 1842 | 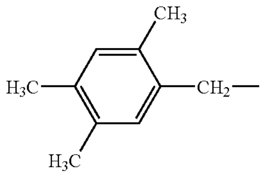 | 1 | 2 | 0 | R | H | 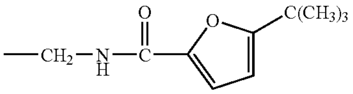 |
| 1843 | 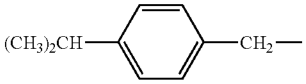 | 1 | 2 | 0 | R | H | 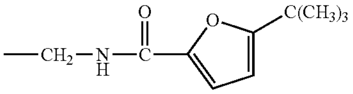 |
| 1844 | 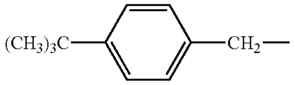 | 1 | 2 | 0 | R | H | 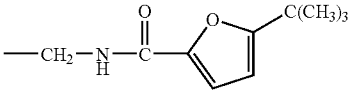 |

TABLE 1.168-continued
| Compd. No. | 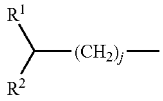 | k | m | n | chirality | $R^3$ | 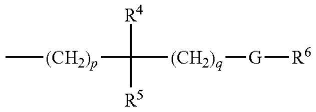 |
|---|---|---|---|---|---|---|---|
| 1845 | 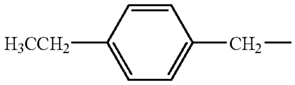 | 1 | 2 | 0 | R | H | 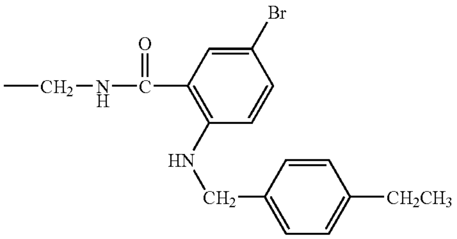 |
| 1846 | 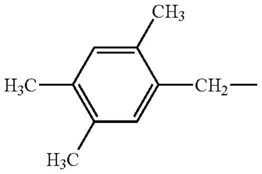 | 1 | 2 | 0 | R | H | 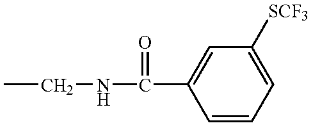 |
| 1847 | 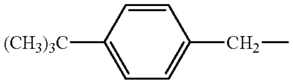 | 1 | 2 | 0 | R | H | 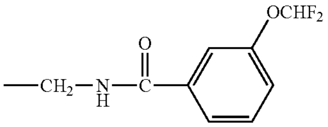 |
| 1848 | 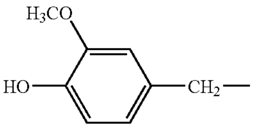 | 1 | 2 | 0 | R | H | 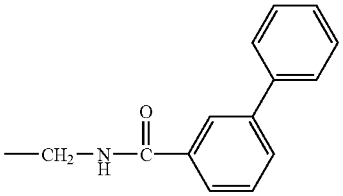 |
TABLE 1.169
| Compd. No. | 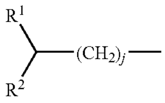 | k | m | n | chirality | $R^3$ | 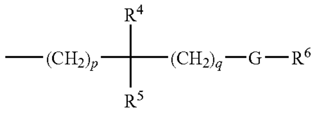 |
|---|---|---|---|---|---|---|---|
| 1849 | 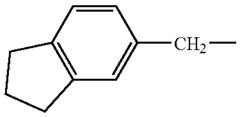 | 1 | 2 | 0 | R | H | 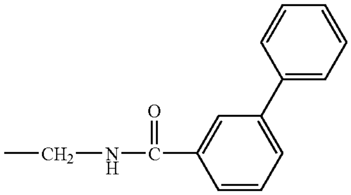 |
| 1850 | 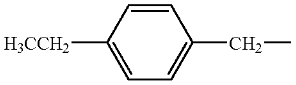 | 1 | 2 | 0 | R | H | 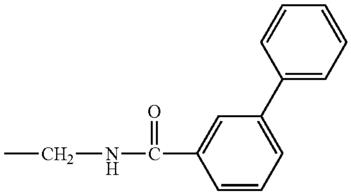 |

TABLE 1.169-continued
| Compd. No. | 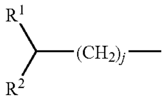 | k | m | n | chirality | $R^3$ | 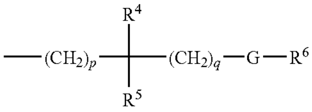 |
|---|---|---|---|---|---|---|---|
| 1851 | 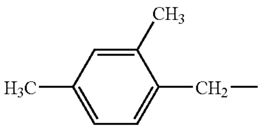 | 1 | 2 | 0 | R | H | 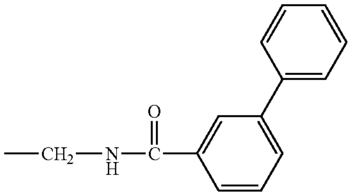 |
| 1852 | 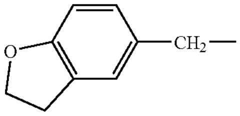 | 1 | 2 | 0 | R | H | 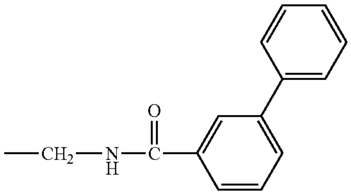 |
| 1853 | 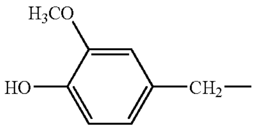 | 1 | 2 | 0 | R | H | 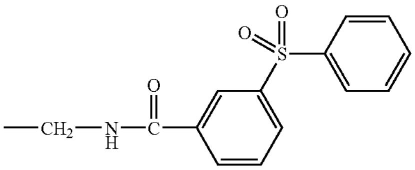 |
| 1854 | 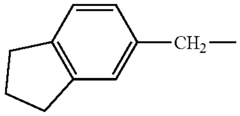 | 1 | 2 | 0 | R | H | 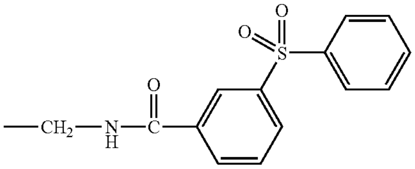 |
| 1855 | 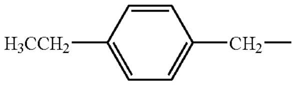 | 1 | 2 | 0 | R | H | 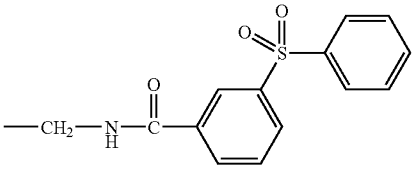 |
| 1856 | 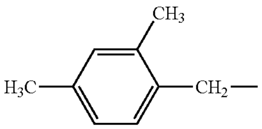 | 1 | 2 | 0 | R | H | 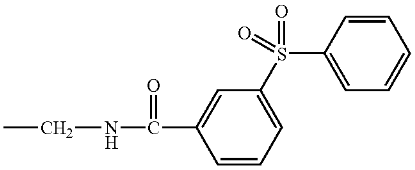 |
| 1857 | 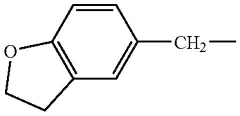 | 1 | 2 | 0 | R | H | 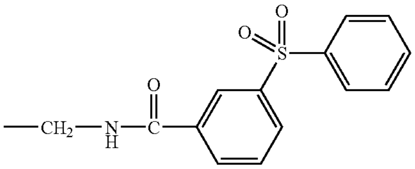 |

TABLE 1.169-continued
| Compd. No. | 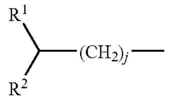 | k | m | n | chirality | $R^3$ | 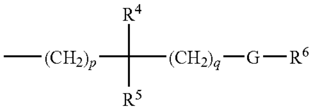 |
|---|---|---|---|---|---|---|---|
| 1858 | 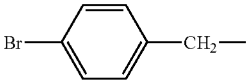 | 1 | 2 | 0 | R | H | 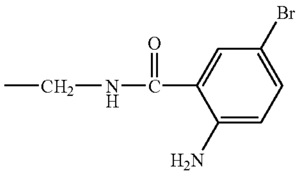 |
| 1859 | 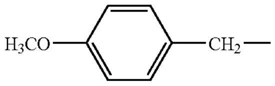 | 1 | 2 | 0 | R | H | 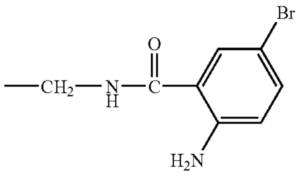 |
TABLE 1.170
| Compd. No. | 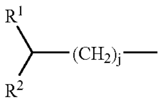 | k | m | n | chirality | $R^3$ | 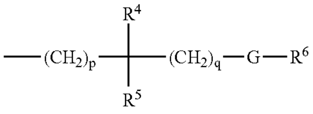 |
|---|---|---|---|---|---|---|---|
| 1860 | 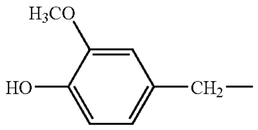 | 1 | 2 | 0 | R | H | 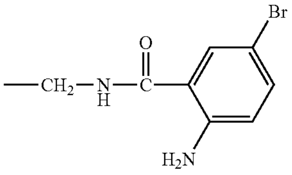 |
| 1861 | 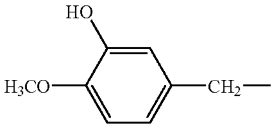 | 1 | 2 | 0 | R | H | 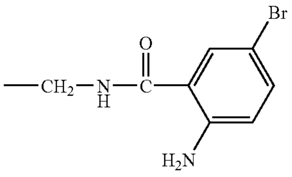 |
| 1662 | 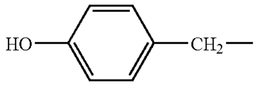 | 1 | 2 | 0 | R | H | 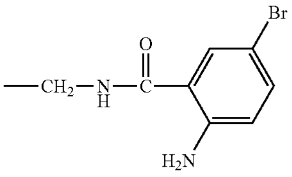 |
| 1863 | 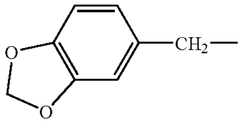 | 1 | 2 | 0 | R | H | 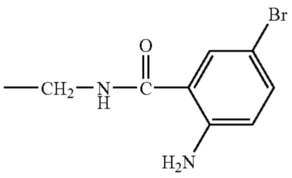 |

TABLE 1.170-continued
| Compd. No. | 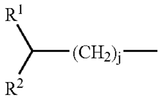 | k | m | n | chirality | $R^3$ | 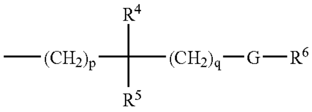 |
|---|---|---|---|---|---|---|---|
| 1864 | 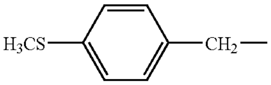 | 1 | 2 | 0 | R | H | 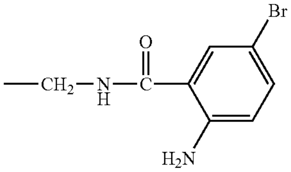 |
| 1865 | 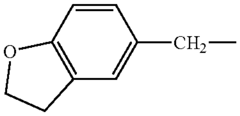 | 1 | 2 | 0 | R | H | 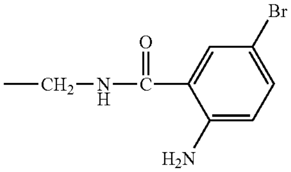 |
| 1866 | 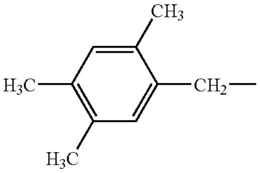 | 1 | 2 | 0 | R | H | 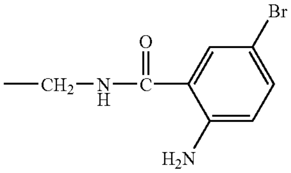 |
| 1867 | 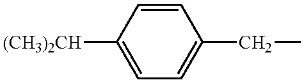 | 1 | 2 | 0 | R | H | 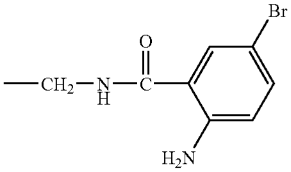 |
| 1868 | 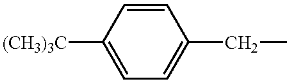 | 1 | 2 | 0 | R | H | 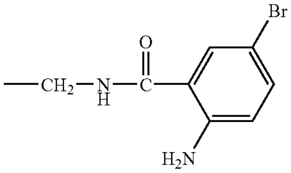 |
| 1869 | 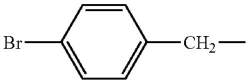 | 1 | 2 | 0 | R | H | 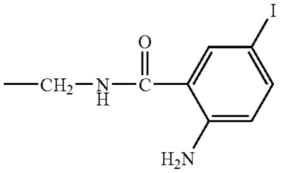 |
| 1870 | 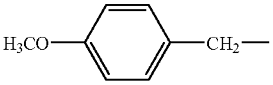 | 1 | 2 | 0 | R | H | 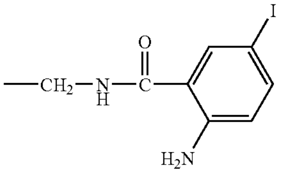 |

TABLE 1.171
| Compd. No. | 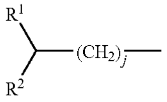 | k | m | n | chirality | $R^3$ | 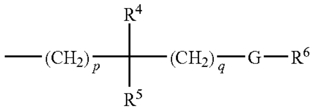 |
|---|---|---|---|---|---|---|---|
| 1871 | 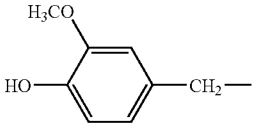 | 1 | 2 | 0 | R | H | 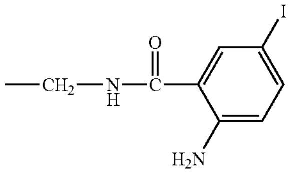 |
| 1872 | 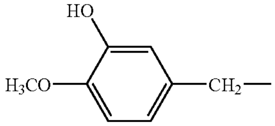 | 1 | 2 | 0 | R | H | 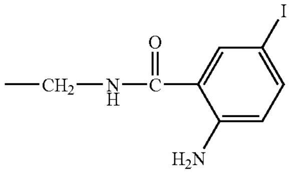 |
| 1873 | 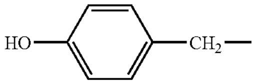 | 1 | 2 | 0 | R | H | 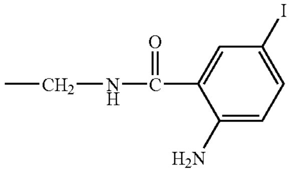 |
| 1874 | 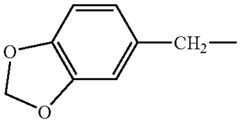 | 1 | 2 | 0 | R | H | 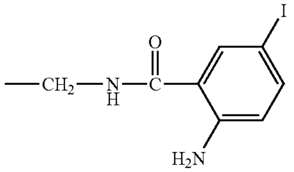 |
| 1875 | 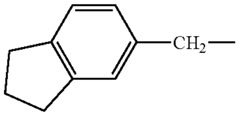 | 1 | 2 | 0 | R | H | 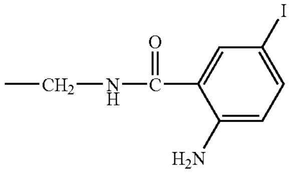 |
| 1876 | 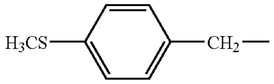 | 1 | 2 | 0 | R | H | 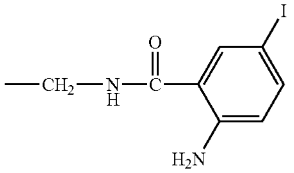 |
| 1877 | 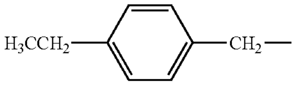 | 1 | 2 | 0 | R | H | 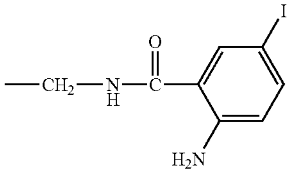 |
| 1878 | 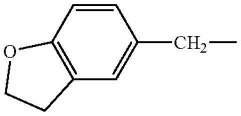 | 1 | 2 | 0 | R | H | 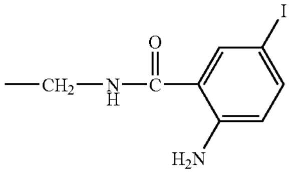 |

TABLE 1.171-continued
| Compd. No. | 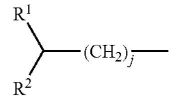 | k | m | n | chirality | $R^3$ | 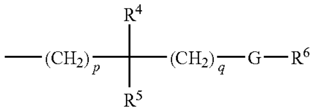 |
|---|---|---|---|---|---|---|---|
| 1879 | 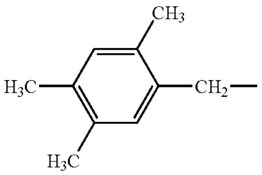 | 1 | 2 | 0 | R | H | 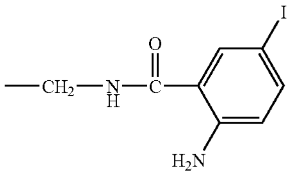 |
| 1880 | 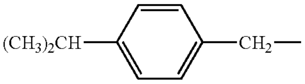 | 1 | 2 | 0 | R | H | 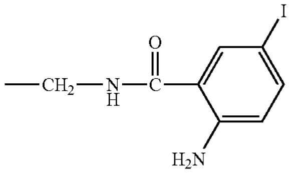 |
| 1881 | 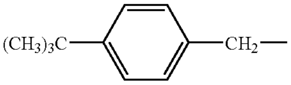 | 1 | 2 | 0 | R | H | 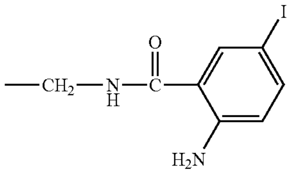 |
TABLE 1.172
| Compd. No. | 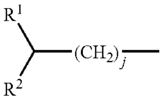 | k | m | n | chirality | $R^3$ | 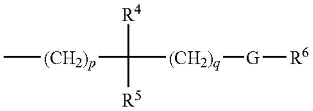 |
|---|---|---|---|---|---|---|---|
| 1882 | 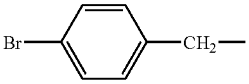 | 1 | 2 | 0 | R | H | 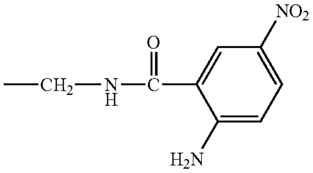 |
| 1883 | 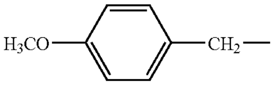 | 1 | 2 | 0 | R | H | 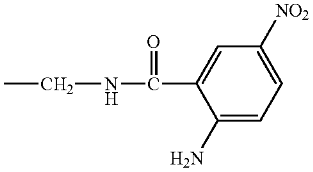 |
| 1884 | 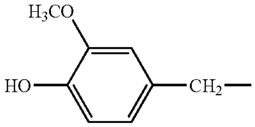 | 1 | 2 | 0 | R | H | 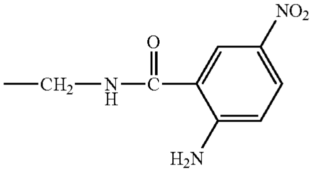 |

TABLE 1.172-continued
| Compd. No. | 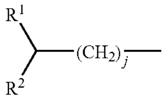 | k | m | n | chirality | $R^3$ | 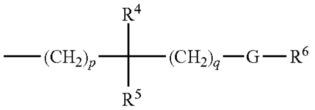 |
|---|---|---|---|---|---|---|---|
| 1885 | 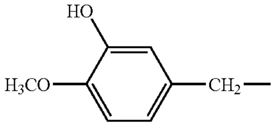 | 1 | 2 | 0 | R | H | 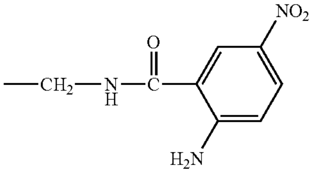 |
| 1886 | 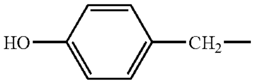 | 1 | 2 | 0 | R | H | 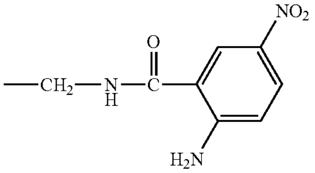 |
| 1887 | 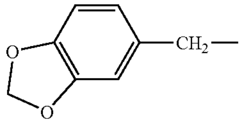 | 1 | 2 | 0 | R | H | 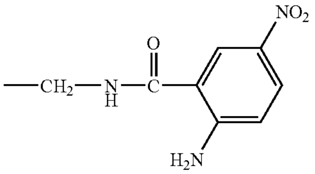 |
| 1888 | 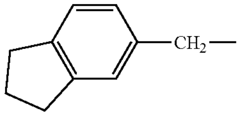 | 1 | 2 | 0 | R | H | 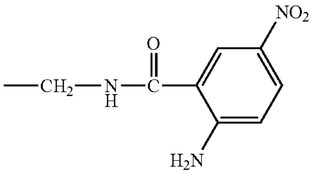 |
| 1889 | 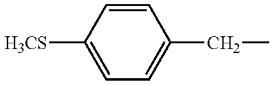 | 1 | 2 | 0 | R | H | 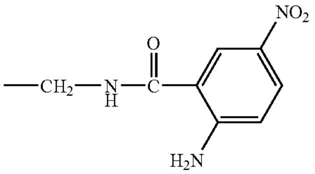 |
| 1890 | 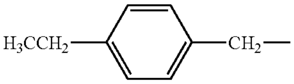 | 1 | 2 | 0 | R | H | 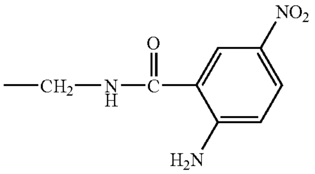 |
| 1891 | 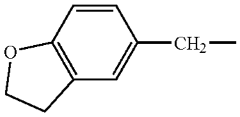 | 1 | 2 | 0 | R | H | 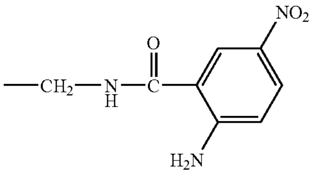 |

TABLE 1.172-continued
| Compd. No. | 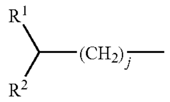 | k | m | n | chirality | $R^3$ | 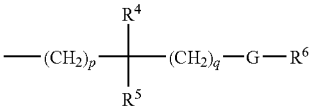 |
|---|---|---|---|---|---|---|---|
| 1892 | 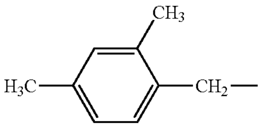 | 1 | 2 | 0 | R | H | 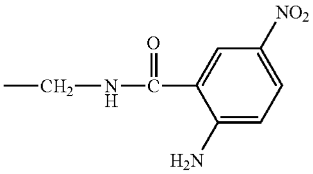 |
TABLE 1.173
| Compd. No. | 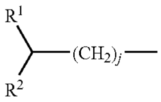 | k | m | n | chirality | $R^3$ | 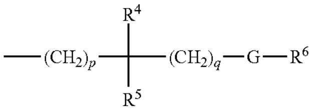 |
|---|---|---|---|---|---|---|---|
| 1893 | 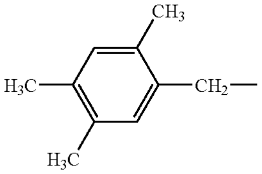 | 1 | 2 | 0 | R | H | 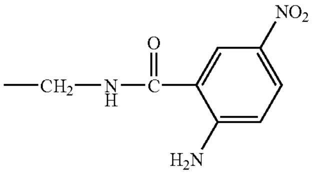 |
| 1894 | 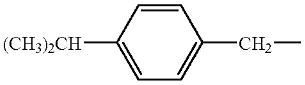 | 1 | 2 | 0 | R | H | 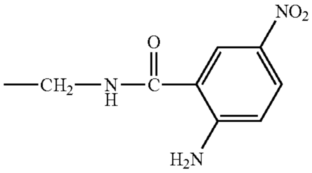 |
| 1895 | 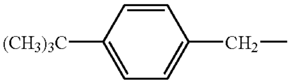 | 1 | 2 | 0 | R | H | 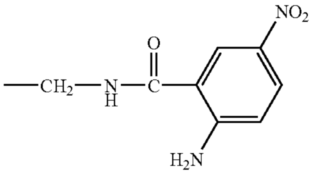 |
| 1896 | 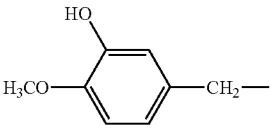 | 1 | 2 | 0 | R | H | 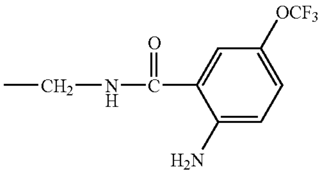 |
| 1897 | 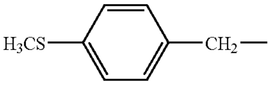 | 1 | 2 | 0 | R | H | 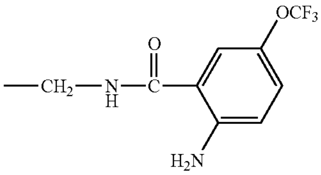 |

TABLE 1.173-continued
| Compd. No. | 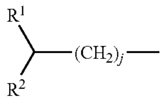 | k | m | n | chirality | $R^3$ | 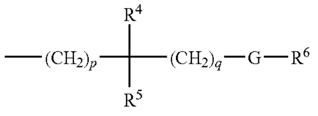 |
|---|---|---|---|---|---|---|---|
| 1898 | 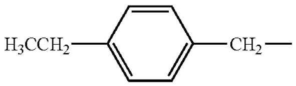 | 1 | 2 | 0 | R | H | 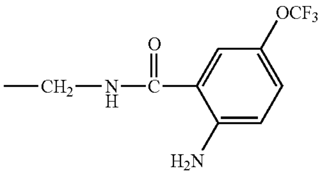 |
| 1899 | 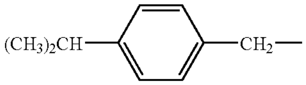 | 1 | 2 | 0 | R | H | 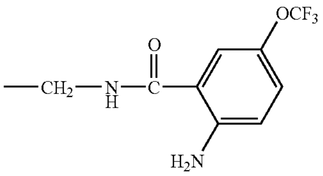 |
| 1900 | 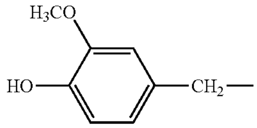 | 1 | 2 | 0 | R | H | 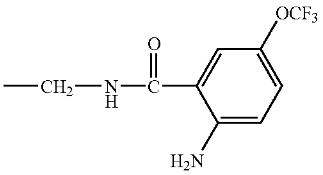 |
| 1901 | 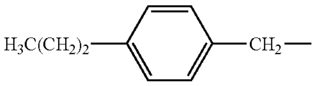 | 1 | 2 | 0 | R | H | 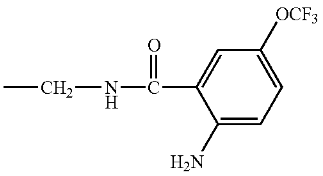 |
| 1902 | 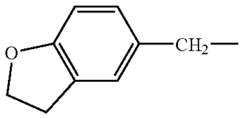 | 1 | 2 | 0 | R | H | 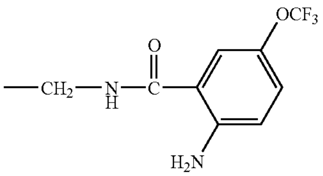 |
| 1903 | 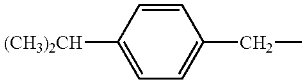 | 2 | 2 | 1 | — | H | 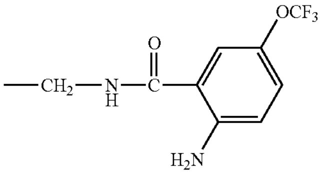 |

TABLE 1.174
| Compd. No. | 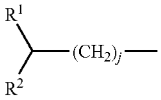 | k | m | n | chirality | $R^3$ | 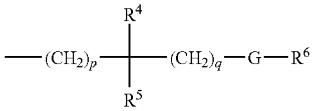 |
|---|---|---|---|---|---|---|---|
| 1904 | 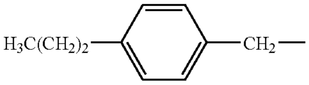 | 2 | 2 | 1 | — | H | 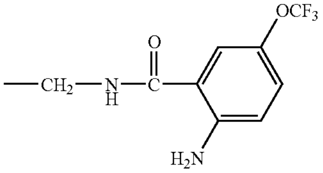 |
| 1905 | 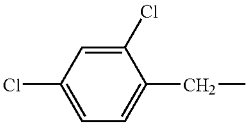 | 1 | 2 | 0 | R | H | 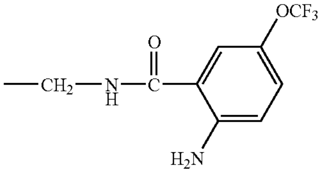 |
| 1906 | 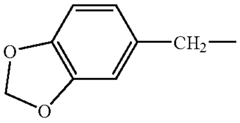 | 1 | 2 | 0 | R | H | 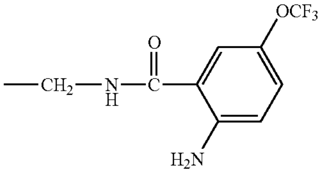 |
| 1907 | 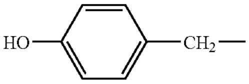 | 1 | 2 | 0 | R | H | 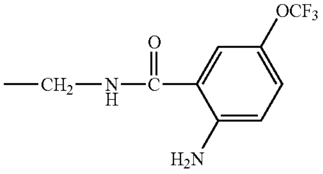 |
| 1908 | 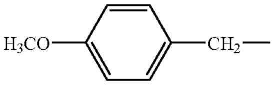 | 1 | 2 | 0 | R | H | 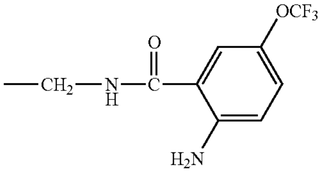 |
| 1909 | 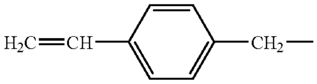 | 1 | 2 | 0 | R | H | 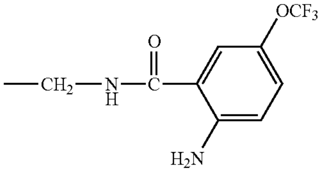 |
| 1910 | 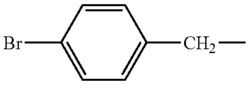 | 2 | 2 | 1 | — | H | 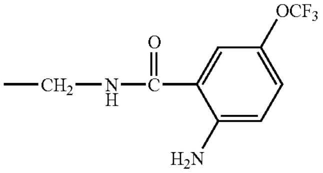 |

TABLE 1.174-continued
| Compd. No. | 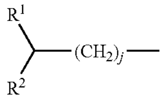 | k | m | n | chirality | $R^3$ | 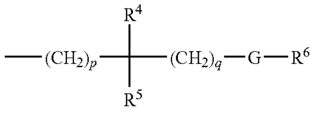 |
|---|---|---|---|---|---|---|---|
| 1911 | 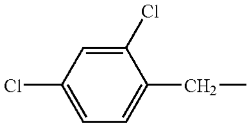 | 2 | 2 | 1 | — | H | 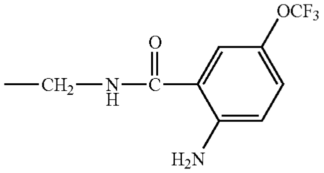 |
| 1912 | 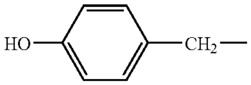 | 2 | 2 | 1 | — | H | 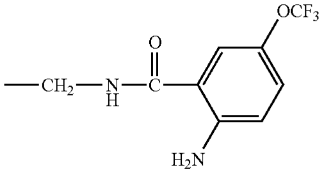 |
| 1913 | 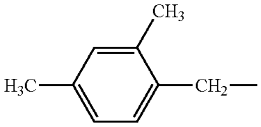 | 2 | 2 | 1 | — | H | 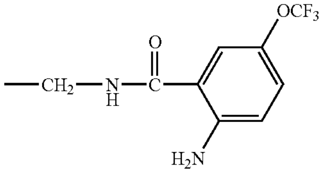 |
| 1914 | 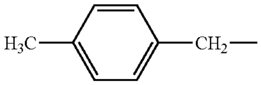 | 2 | 2 | 1 | — | H | 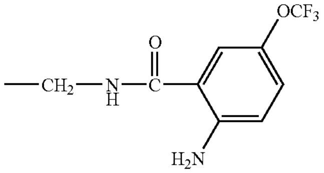 |
TABLE 1.175
| Compd. No. | 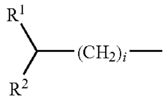 | k | m | n | chirality | $R^3$ | 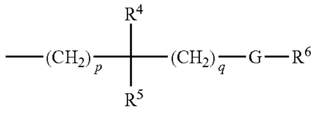 |
|---|---|---|---|---|---|---|---|
| 1915 | 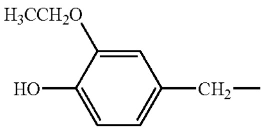 | 1 | 2 | 0 | R | H | 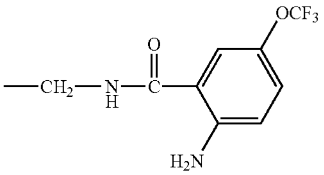 |
| 1916 | 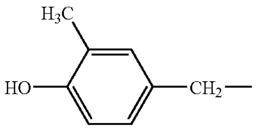 | 1 | 2 | 0 | R | H | 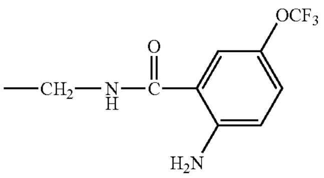 |

TABLE 1.175-continued
| Compd. No. | 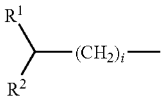 | k | m | n | chirality | $R^3$ | 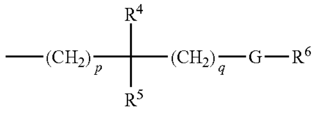 |
|---|---|---|---|---|---|---|---|
| 1917 | 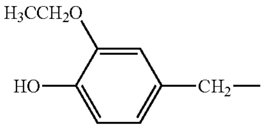 | 2 | 2 | 1 | — | H | 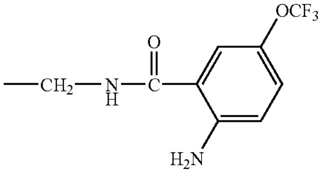 |
| 1918 | 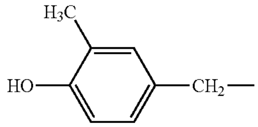 | 2 | 2 | 1 | — | H | 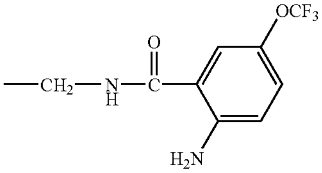 |
| 1919 | 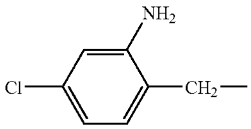 | 2 | 2 | 1 | — | H | 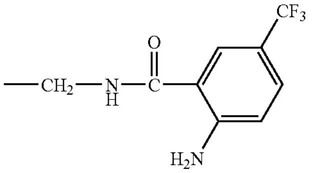 |
| 1920 | 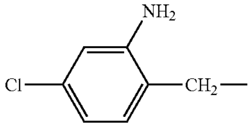 | 2 | 2 | 1 | — | H | 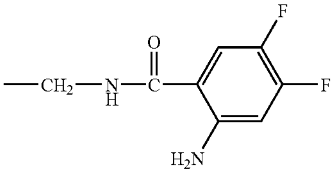 |
| 1921 | 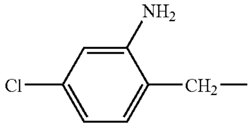 | 1 | 2 | 0 | R | H | 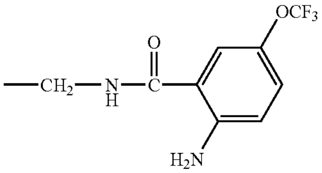 |
| 1922 | 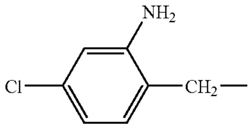 | 2 | 2 | 1 | — | H | 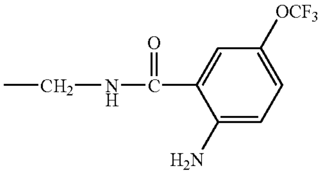 |
| 1923 | 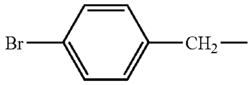 | 2 | 2 | 1 | — | H | 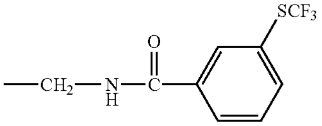 |
| 1924 | 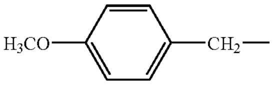 | 2 | 2 | 1 | — | H | 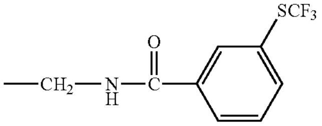 |

TABLE 1.175-continued
| Compd. No. | 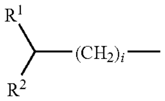 | k | m | n | chirality | $R^3$ | 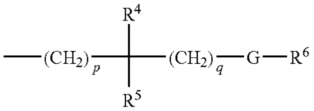 |
|---|---|---|---|---|---|---|---|
| 1925 | 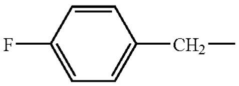 | 2 | 2 | 1 | — | H | 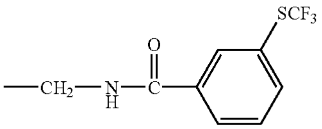 |
TABLE 1.176
| Compd. No. | 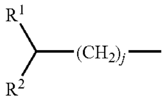 | k | m | n | chirality | $R^3$ | 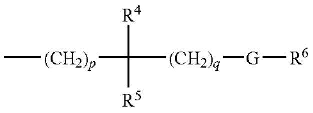 |
|---|---|---|---|---|---|---|---|
| 1926 | 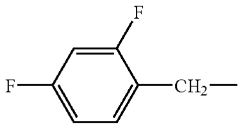 | 2 | 2 | 1 | — | H | 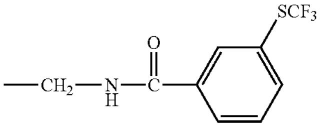 |
| 1927 | 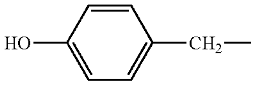 | 2 | 2 | 1 | — | H | 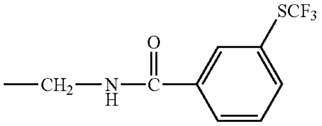 |
| 1928 | 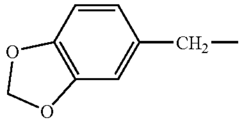 | 2 | 2 | 1 | — | H | 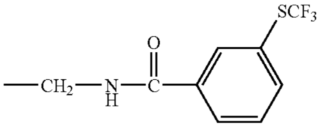 |
| 1929 | 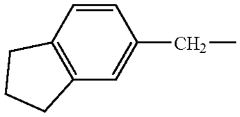 | 2 | 2 | 1 | — | H | 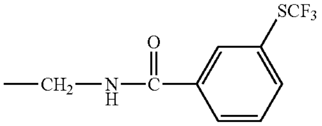 |
| 1930 | 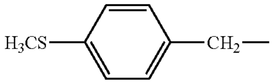 | 2 | 2 | 1 | — | H | 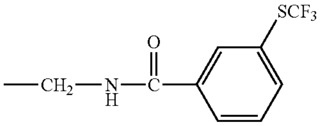 |
| 1931 | 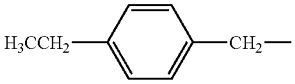 | 2 | 2 | 1 | — | H | 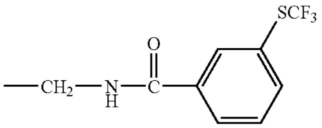 |
| 1932 | 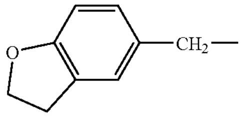 | 2 | 2 | 1 | — | H | 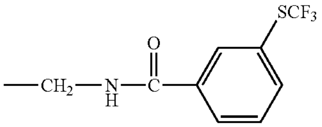 |
| 1933 | 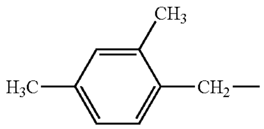 | 2 | 2 | 1 | — | H | 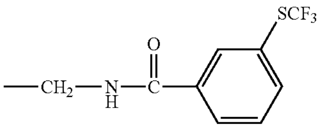 |

TABLE 1.176-continued
| Compd. No. | 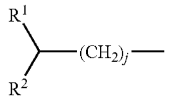 | k | m | n | chirality | $R^3$ | 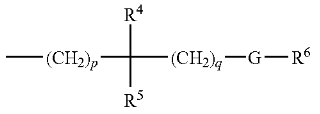 |
|---|---|---|---|---|---|---|---|
| 1934 | 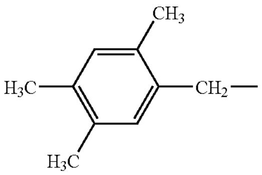 | 2 | 2 | 1 | — | H | 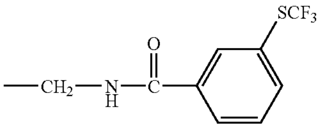 |
| 1935 | 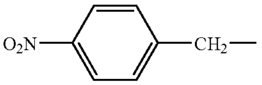 | 2 | 2 | 1 | — | H | 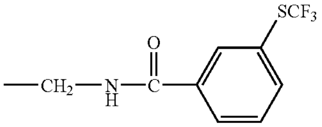 |
| 1936 | 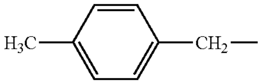 | 2 | 2 | 1 | — | H | 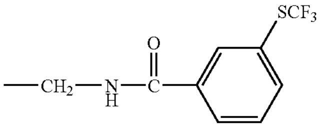 |
TABLE 1.177
| Compd. No. | 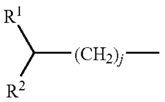 | k | m | n | chirality | $R^3$ | 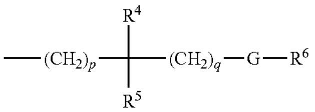 |
|---|---|---|---|---|---|---|---|
| 1937 | 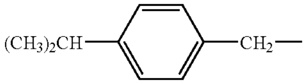 | 2 | 2 | 1 | — | H | 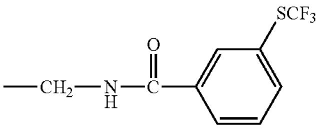 |
| 1938 | 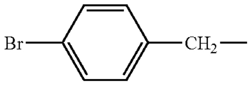 | 2 | 2 | 1 | — | H | 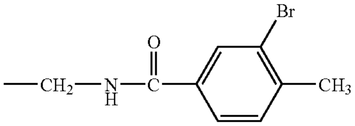 |
| 1939 | 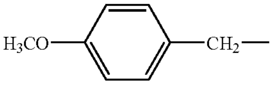 | 2 | 2 | 1 | — | H | 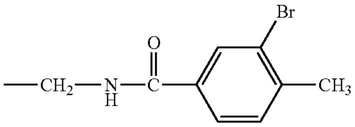 |
| 1940 | 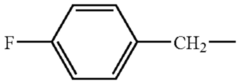 | 2 | 2 | 1 | — | H | 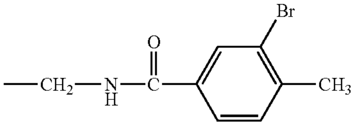 |
| 1941 | 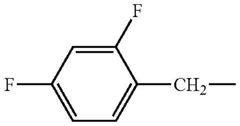 | 2 | 2 | 1 | — | H | 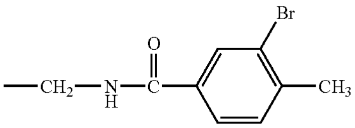 |

TABLE 1.177-continued
| Compd. No. | 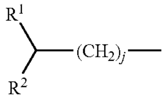 | k | m | n | chirality | $R^3$ | 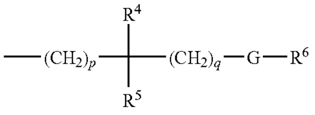 |
|---|---|---|---|---|---|---|---|
| 1942 | 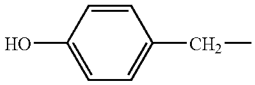 | 2 | 2 | 1 | — | H | 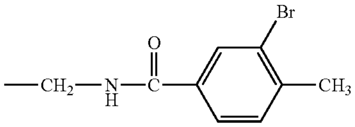 |
| 1943 | 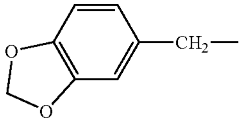 | 2 | 2 | 1 | — | H | 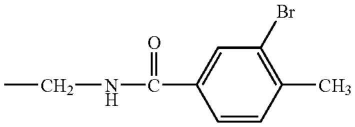 |
| 1944 | 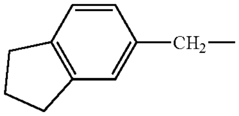 | 2 | 2 | 1 | — | H | 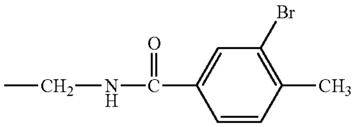 |
| 1945 | 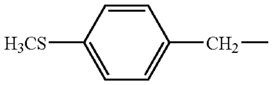 | 2 | 2 | 1 | — | H | 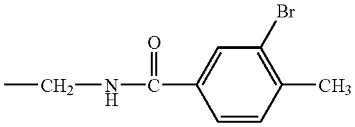 |
| 1946 | 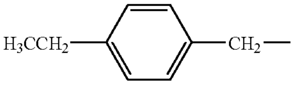 | 2 | 2 | 1 | — | H | 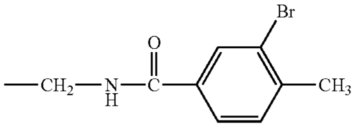 |
| 1947 | 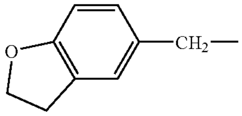 | 2 | 2 | 1 | — | H | 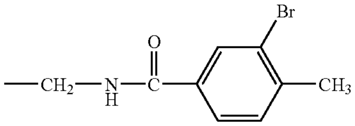 |
TABLE 1.178
| Compd. No. | 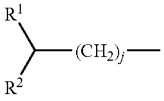 | k | m | n | chirality | $R^3$ | 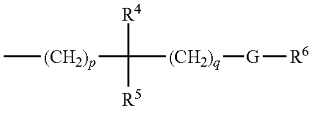 |
|---|---|---|---|---|---|---|---|
| 1948 | 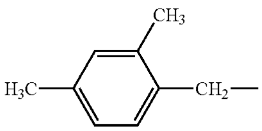 | 2 | 2 | 1 | — | H | 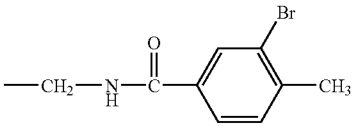 |
| 1949 | 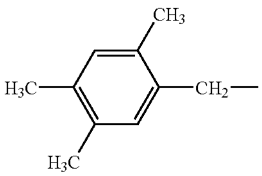 | 2 | 2 | 1 | — | H | 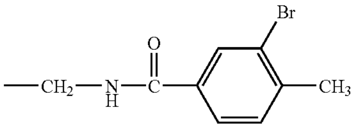 |

TABLE 1.178-continued
| Compd. No. | 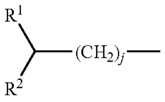 | k | m | n | chirality | $R^3$ | 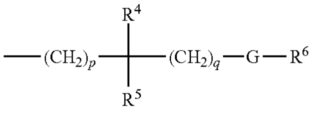 |
|---|---|---|---|---|---|---|---|
| 1950 | 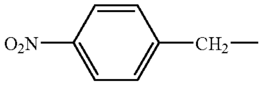 | 2 | 2 | 1 | — | H | 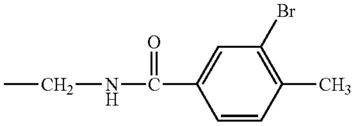 |
| 1951 | 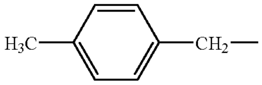 | 2 | 2 | 1 | — | H | 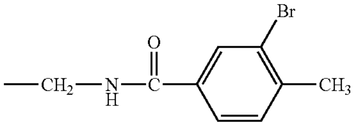 |
| 1952 | 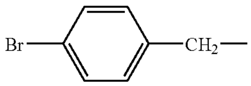 | 2 | 2 | 1 | — | H | 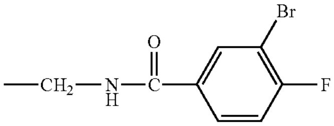 |
| 1953 | 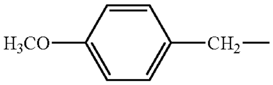 | 2 | 2 | 1 | — | H | 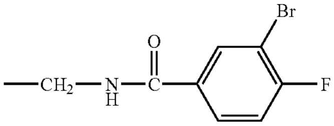 |
| 1954 | 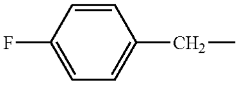 | 2 | 2 | 1 | — | H | 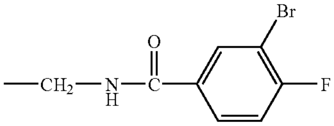 |
| 1955 | 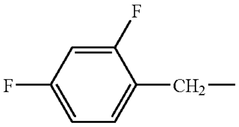 | 2 | 2 | 1 | — | H | 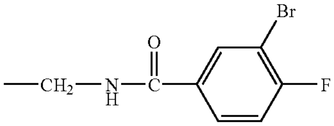 |
| 1956 | 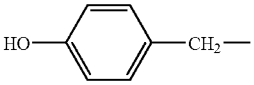 | 2 | 2 | 1 | — | H | 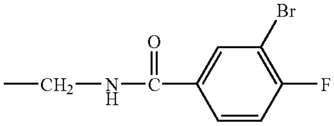 |
| 1957 | 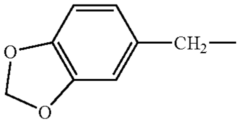 | 2 | 2 | 1 | — | H | 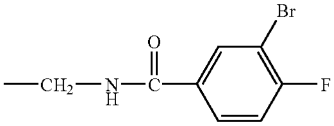 |
| 1958 | 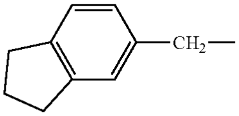 | 2 | 2 | 1 | — | H | 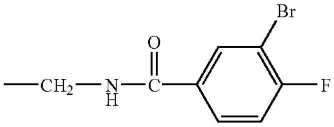 |

TABLE 1.179
| Compd. No. | 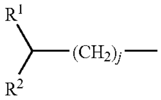 | k | m | n | chirality | $R^3$ | 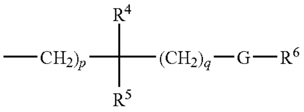 |
|---|---|---|---|---|---|---|---|
| 1959 | 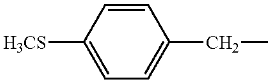 | 2 | 2 | 1 | — | H | 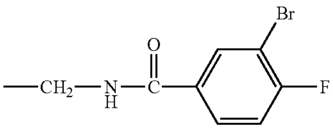 |
| 1960 | 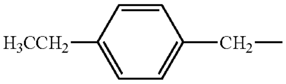 | 2 | 2 | 1 | — | H | 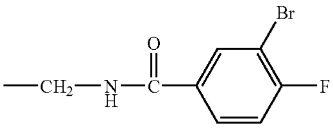 |
| 1961 | 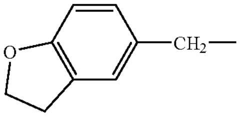 | 2 | 2 | 1 | — | H | 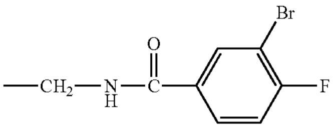 |
| 1962 | 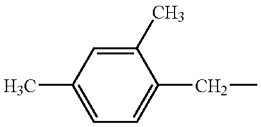 | 2 | 2 | 1 | — | H | 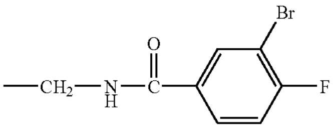 |
| 1963 | 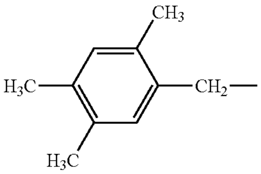 | 2 | 2 | 1 | — | H | 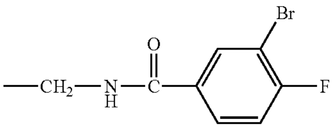 |
| 1964 | 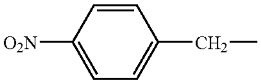 | 2 | 2 | 1 | — | H | 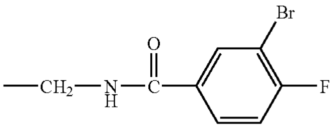 |
| 1965 | 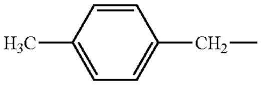 | 2 | 2 | 1 | — | H | 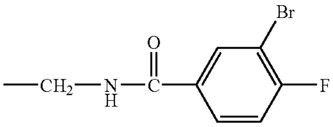 |
| 1966 | 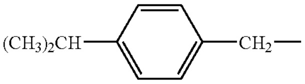 | 2 | 2 | 1 | — | H | 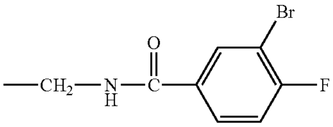 |
| 1967 | 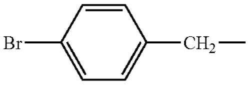 | 2 | 2 | 1 | — | H | 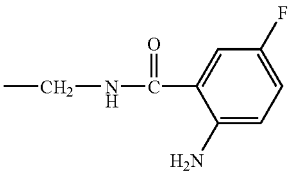 |

TABLE 1.179-continued
| Compd. No. | 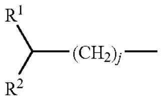 | k | m | n | chirality | $R^3$ | 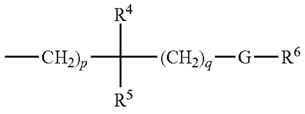 |
|---|---|---|---|---|---|---|---|
| 1968 | 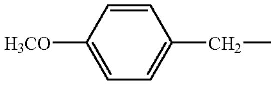 | 2 | 2 | 1 | — | H | 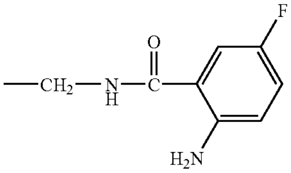 |
| 1969 | 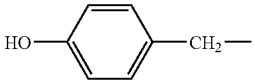 | 2 | 2 | 1 | — | H | 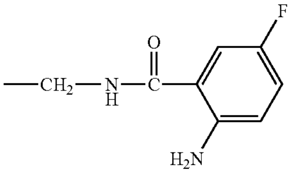 |
TABLE 1.180
| Compd. No. | 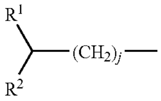 | k | m | n | chirality | $R^3$ | 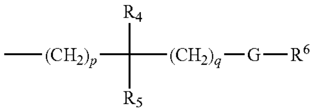 |
|---|---|---|---|---|---|---|---|
| 1970 | 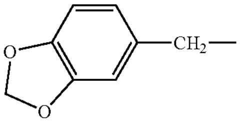 | 2 | 2 | 1 | — | H | 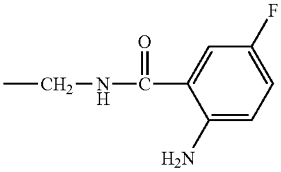 |
| 1971 | 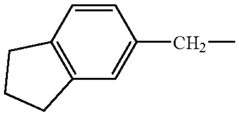 | 2 | 2 | 1 | — | H | 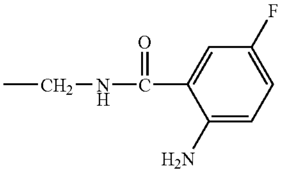 |
| 1972 | 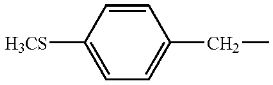 | 2 | 2 | 1 | — | H | 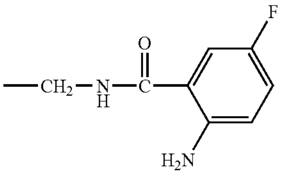 |
| 1973 | 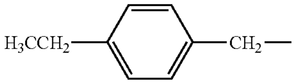 | 2 | 2 | 1 | — | H | 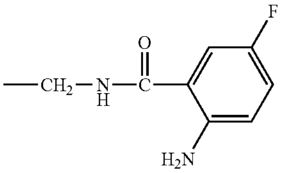 |

TABLE 1.180-continued
| Compd. No. | 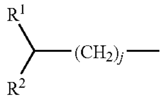 | k | m | n | chirality | $R^3$ | 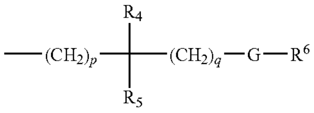 |
|---|---|---|---|---|---|---|---|
| 1974 | 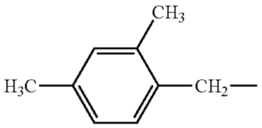 | 2 | 2 | 1 | — | H | 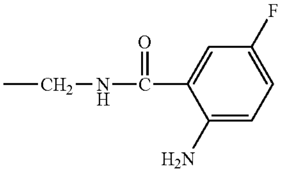 |
| 1975 | 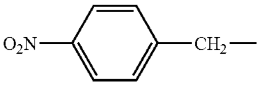 | 2 | 2 | 1 | — | H | 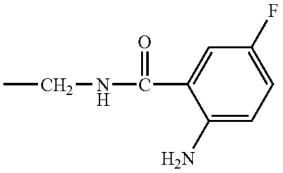 |
| 1976 | 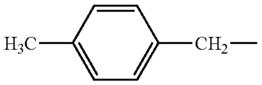 | 2 | 2 | 1 | — | H | 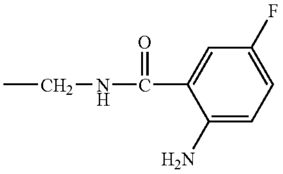 |
| 1977 | 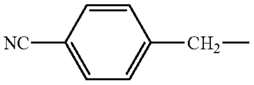 | 2 | 2 | 1 | — | H | 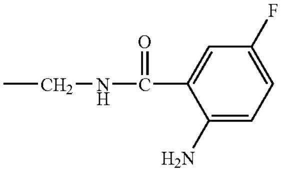 |
| 1978 | 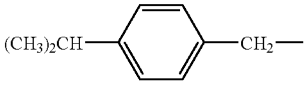 | 2 | 2 | 1 | — | H | 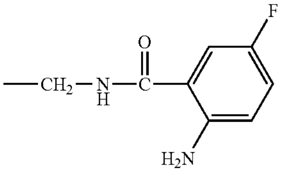 |
| 1979 | 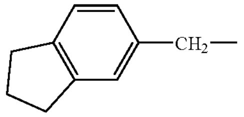 | 2 | 2 | 1 | — | H | 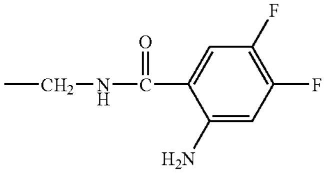 |
| 1980 | 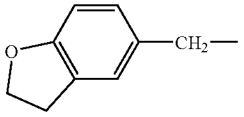 | 2 | 2 | 1 | — | H | 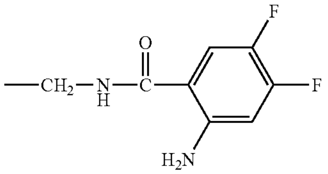 |

TABLE 1.181
| Compd. No. | 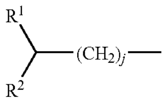 | k | m | n | chirality | $R^3$ | 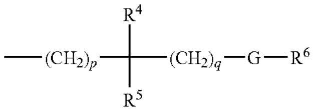 |
|---|---|---|---|---|---|---|---|
| 1981 | 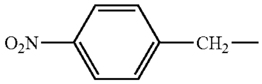 | 2 | 2 | 1 | — | H | 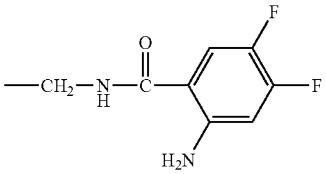 |
| 1982 | 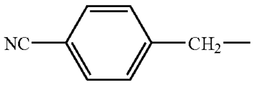 | 2 | 2 | 1 | — | H | 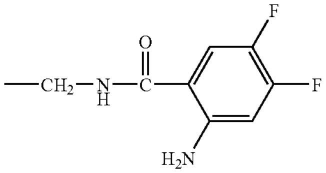 |
| 1983 | 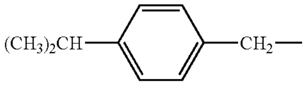 | 2 | 2 | 1 | — | H | 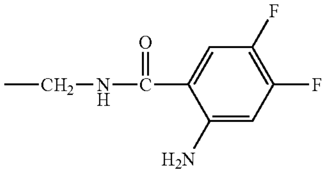 |
| 1984 | 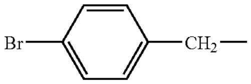 | 2 | 2 | 1 | — | H | 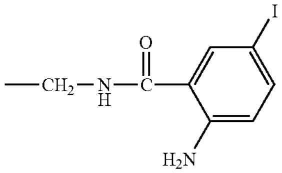 |
| 1985 | 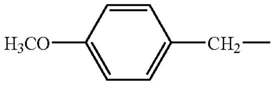 | 2 | 2 | 1 | — | H | 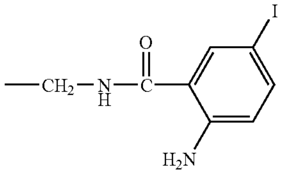 |
| 1986 | 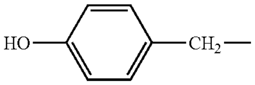 | 2 | 2 | 1 | — | H | 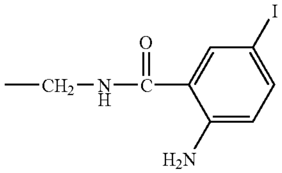 |
| 1987 | 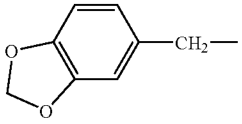 | 2 | 2 | 1 | — | H | 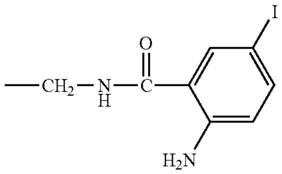 |
| 1988 | 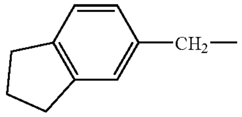 | 2 | 2 | 1 | — | H | 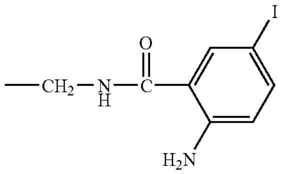 |

TABLE 1.181-continued
| Compd. No. | 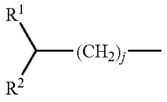 | k | m | n | chirality | $R^3$ | 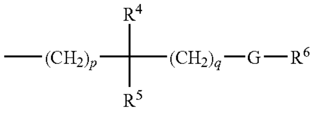 |
|---|---|---|---|---|---|---|---|
| 1989 | 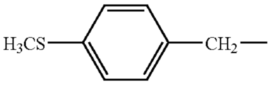 | 2 | 2 | 1 | — | H | 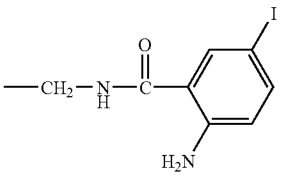 |
| 1990 | 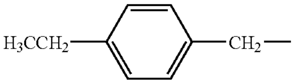 | 2 | 2 | 1 | — | H | 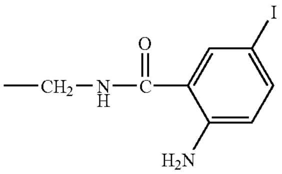 |
| 1991 | 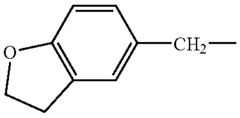 | 2 | 2 | 1 | — | H | 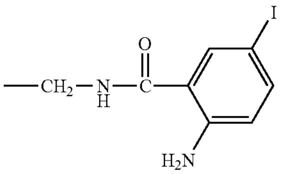 |
TABLE 1.182
| Compd. No. | 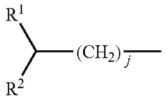 | k | m | n | chirality | $R^3$ | 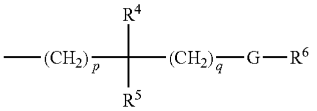 |
|---|---|---|---|---|---|---|---|
| 1992 | 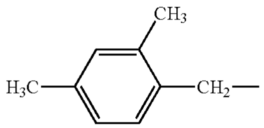 | 2 | 2 | 1 | — | H | 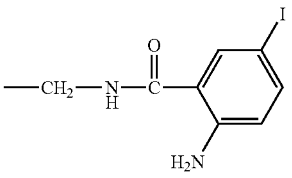 |
| 1993 | 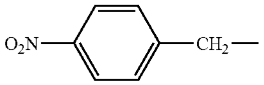 | 2 | 2 | 1 | — | H | 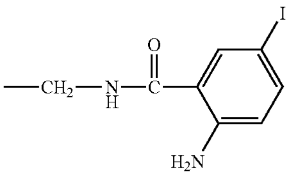 |
| 1994 | 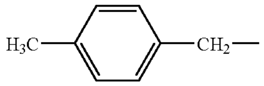 | 2 | 2 | 1 | — | H | 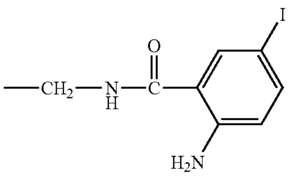 |

TABLE 1.182-continued
| Compd. No. | 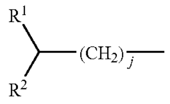 | k | m | n | chirality | $R^3$ | 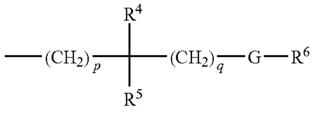 |
|---|---|---|---|---|---|---|---|
| 1995 | 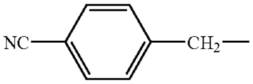 | 2 | 2 | 1 | — | H | 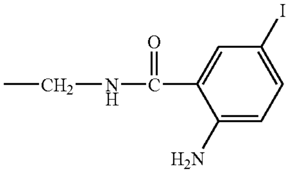 |
| 1996 | 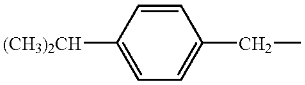 | 2 | 2 | 1 | — | H | 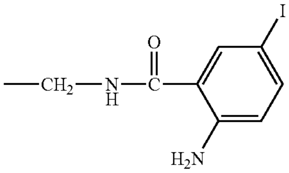 |
| 1997 | 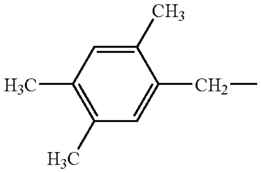 | 2 | 2 | 1 | — | H | 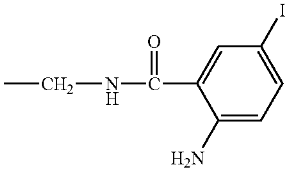 |
| 1998 | 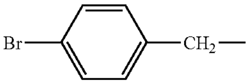 | 2 | 2 | 1 | — | H | 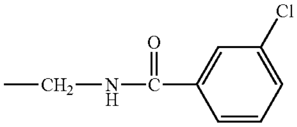 |
| 1999 | 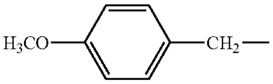 | 2 | 2 | 1 | — | H | 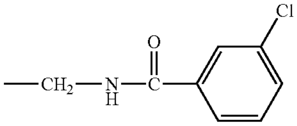 |
| 2000 | 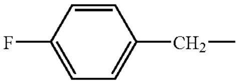 | 2 | 2 | 1 | — | H | 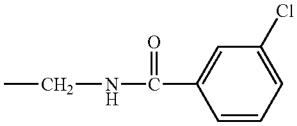 |
| 2001 | 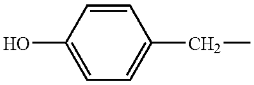 | 2 | 2 | 1 | — | H | 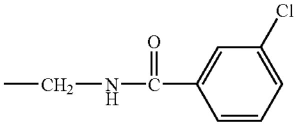 |
| 2002 | 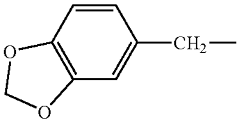 | 2 | 2 | 1 | — | H | 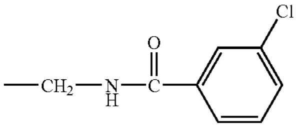 |

TABLE 1.183
| Compd. No. | 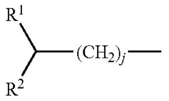 | k | m | n | chirality | $R^3$ | 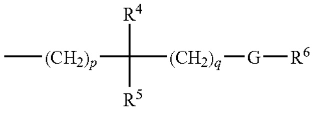 |
|---|---|---|---|---|---|---|---|
| 2003 | 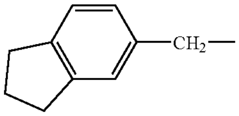 | 2 | 2 | 1 | — | H | 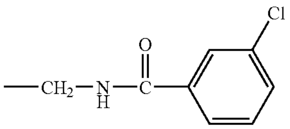 |
| 2004 | 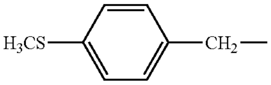 | 2 | 2 | 1 | — | H | 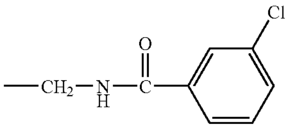 |
| 2005 | 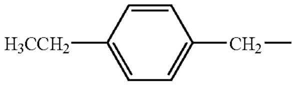 | 2 | 2 | 1 | — | H | 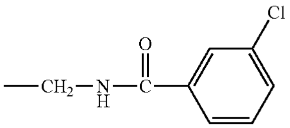 |
| 2006 | 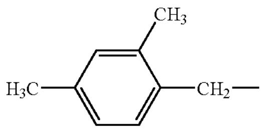 | 2 | 2 | 1 | — | H | 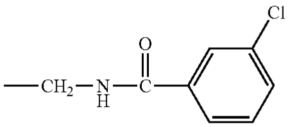 |
| 2007 | 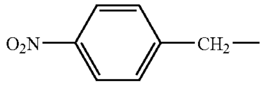 | 2 | 2 | 1 | — | H | 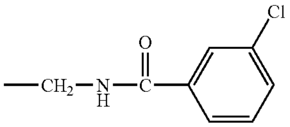 |
| 2008 | 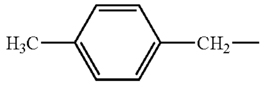 | 2 | 2 | 1 | — | H | 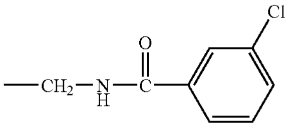 |
| 2009 | 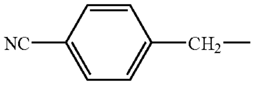 | 2 | 2 | 1 | — | H | 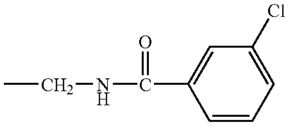 |
| 2010 | 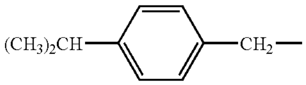 | 2 | 2 | 1 | — | H | 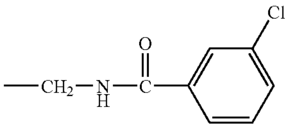 |
| 2011 | 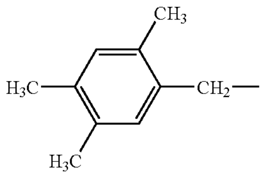 | 2 | 2 | 1 | — | H | 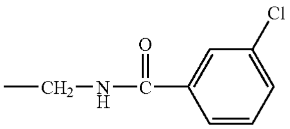 |
| 2012 | 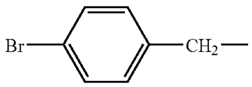 | 2 | 2 | 1 | — | H | 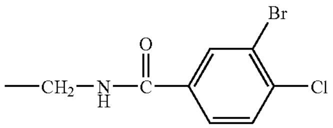 |

TABLE 1.183-continued
| Compd. No. | 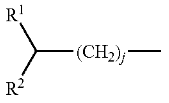 | k | m | n | chirality | $R^3$ | 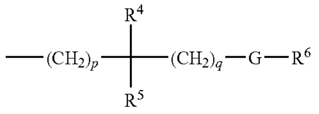 |
|---|---|---|---|---|---|---|---|
| 2013 | 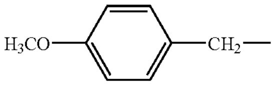 | 2 | 2 | 1 | — | H | 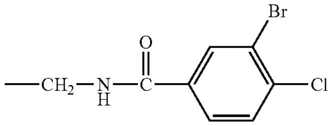 |
TABLE 1.184
| Compd. No. | 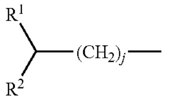 | k | m | n | chirality | $R^3$ | 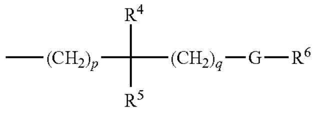 |
|---|---|---|---|---|---|---|---|
| 2014 | 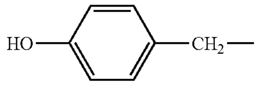 | 2 | 2 | 1 | — | H | 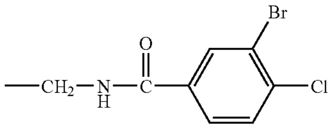 |
| 2015 | 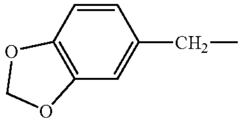 | 2 | 2 | 1 | — | H | 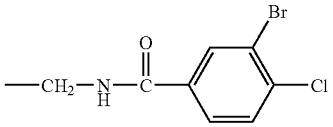 |
| 2016 | 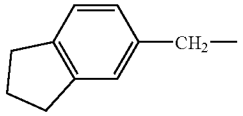 | 2 | 2 | 1 | — | H | 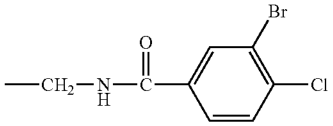 |
| 2017 | 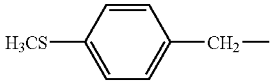 | 2 | 2 | 1 | — | H | 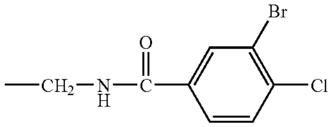 |
| 2018 | 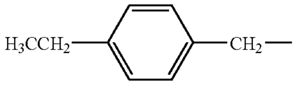 | 2 | 2 | 1 | — | H | 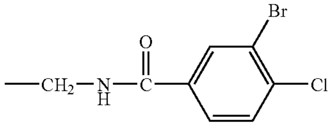 |
| 2019 | 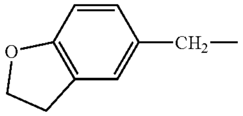 | 2 | 2 | 1 | — | H | 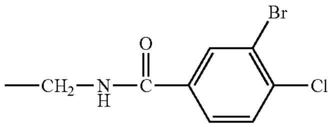 |
| 2020 | 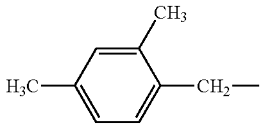 | 2 | 2 | 1 | — | H | 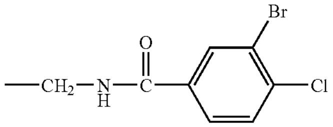 |
| 2021 | 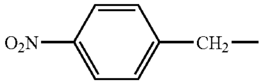 | 2 | 2 | 1 | — | H | 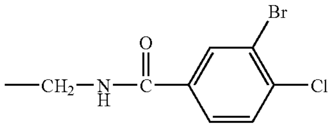 |

TABLE 1.184-continued
| Compd. No. | 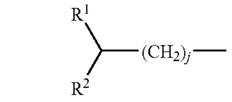 | k | m | n | chirality | $R^3$ | 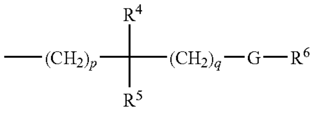 |
|---|---|---|---|---|---|---|---|
| 2022 | 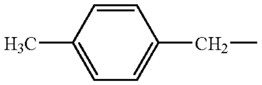 | 2 | 2 | 1 | — | H | 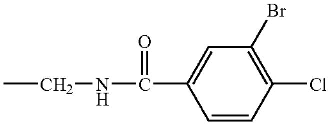 |
| 2023 | 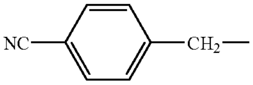 | 2 | 2 | 1 | — | H | 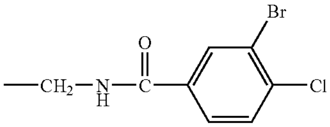 |
| 2024 | 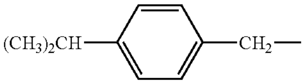 | 2 | 2 | 1 | — | H | 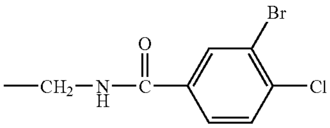 |
TABLE 1.185
| Compd. No. | 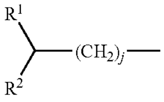 | k | m | n | chirality | $R^3$ | 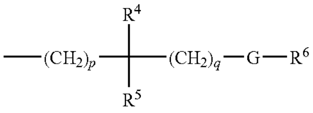 |
|---|---|---|---|---|---|---|---|
| 2025 | 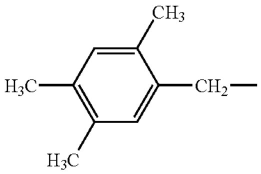 | 2 | 2 | 1 | — | H | 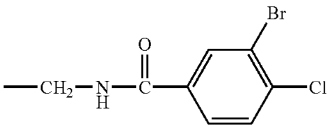 |
| 2026 | 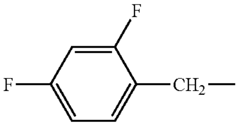 | 2 | 2 | 1 | — | H | 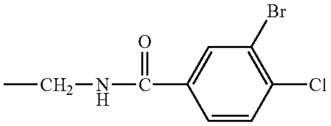 |
| 2027 | 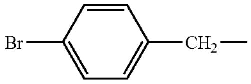 | 2 | 2 | 1 | — | H | 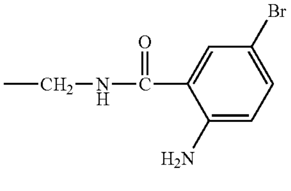 |
| 2028 | 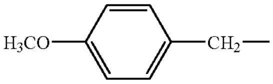 | 2 | 2 | 1 | — | H | 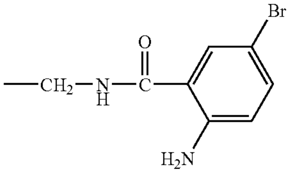 |

TABLE 1.185-continued
| Compd. No. | 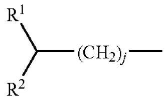 | k | m | n | chirality | $R^3$ | 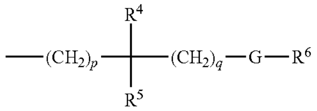 |
| --- | --- | --- | --- | --- | --- | --- | --- |
| 2029 | 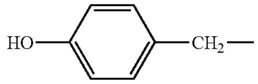 | 2 | 2 | 1 | — | H | 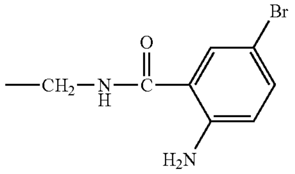 |
| 2030 | 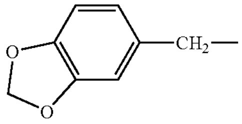 | 2 | 2 | 1 | — | H | 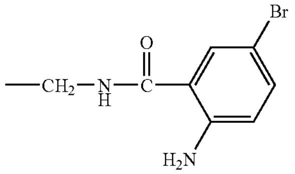 |
| 2031 | 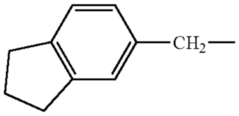 | 2 | 2 | 1 | — | H | 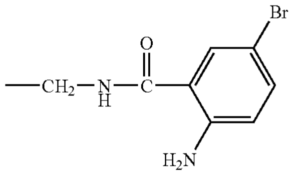 |
| 2032 | 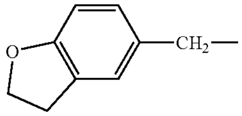 | 2 | 2 | 1 | — | H | 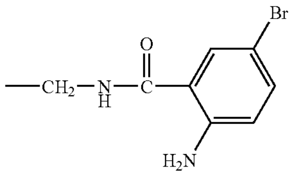 |
| 2033 | 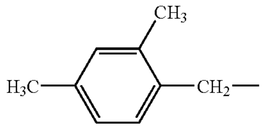 | 2 | 2 | 1 | — | H | 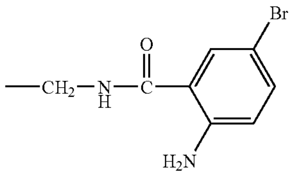 |
| 2034 | 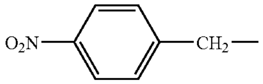 | 2 | 2 | 1 | — | H | 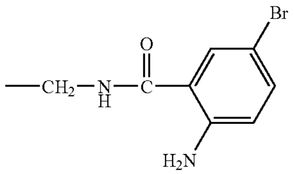 |
| 2035 | 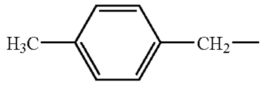 | 2 | 2 | 1 | — | H | 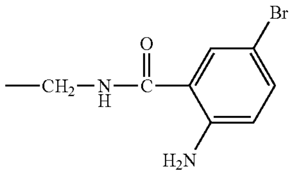 |

TABLE 1.186
| Compd. No. | 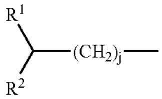 | k | m | n | chirality | $R^3$ | 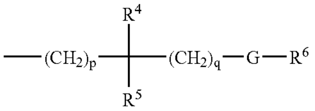 |
|---|---|---|---|---|---|---|---|
| 2036 | 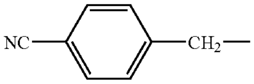 | 2 | 2 | 1 | — | H | 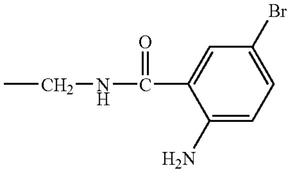 |
| 2037 | 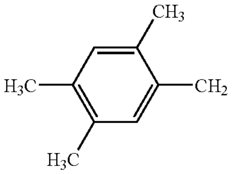 | 2 | 2 | 1 | — | H | 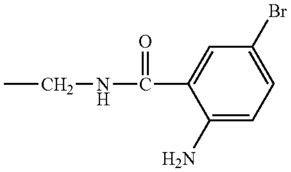 |
| 2033 | 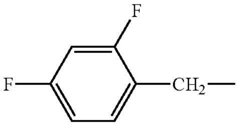 | 2 | 2 | 1 | — | H | 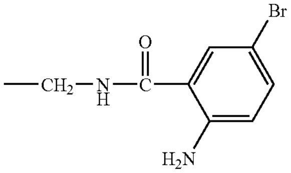 |
| 2039 | 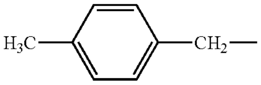 | 2 | 2 | 1 | — | H | 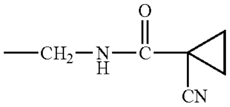 |
| 2040 | 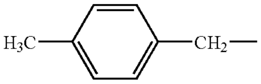 | 1 | 2 | 0 | R | H | 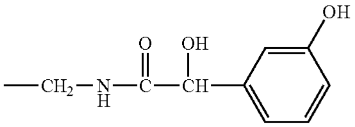 |
| 2041 | 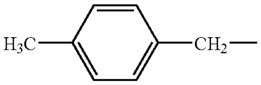 | 1 | 2 | 0 | R | H | 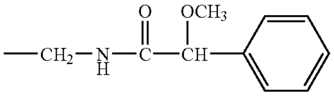 |
| 2042 | 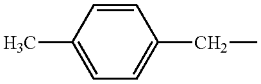 | 1 | 2 | 0 | R | H | 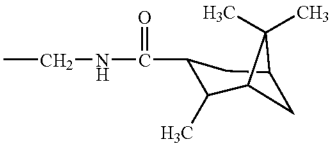 |
| 2043 | 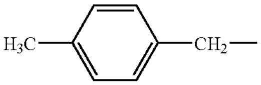 | 1 | 2 | 0 | R | H | 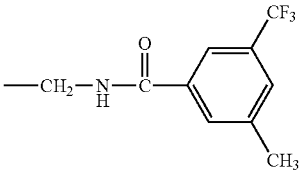 |
| 2044 | 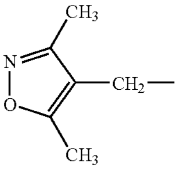 | 1 | 2 | 0 | R | H | 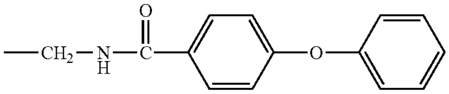 |

TABLE 1.186-continued
| Compd. No. | 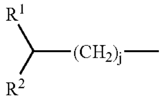 | k | m | n | chirality | $R^3$ | 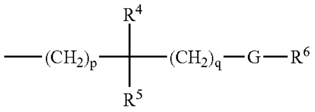 |
|---|---|---|---|---|---|---|---|
| 2045 | 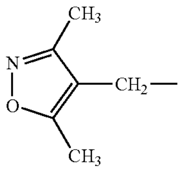 | 1 | 2 | 0 | R | H | 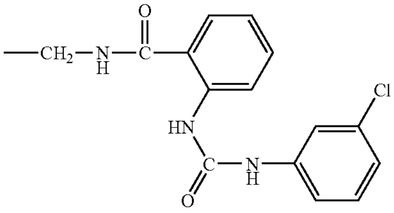 |
| 2046 | 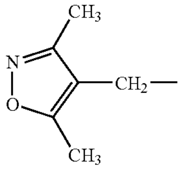 | 1 | 2 | 0 | R | H | 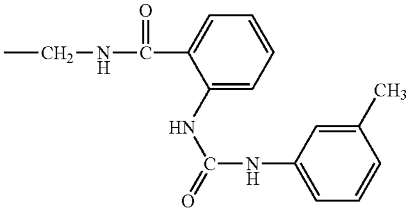 |
TABLE 1.187
| Compd. No. | 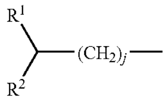 | k | m | n | chirality | $R^3$ | 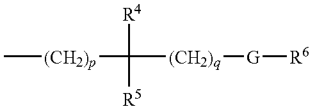 |
|---|---|---|---|---|---|---|---|
| 2047 | 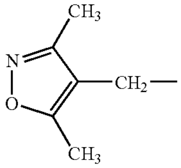 | 1 | 2 | 0 | R | H | 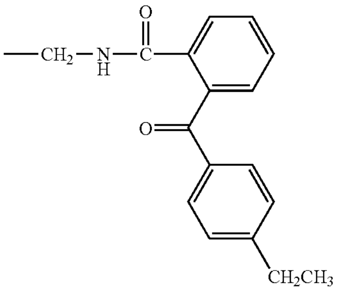 |
| 2048 | 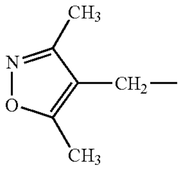 | 1 | 2 | 0 | R | H | 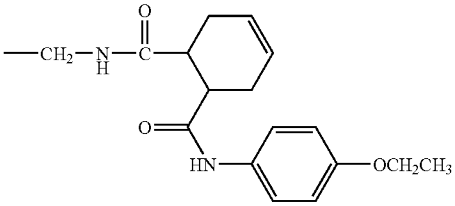 |
| 2049 | 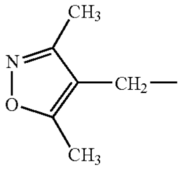 | 1 | 2 | 0 | R | H | 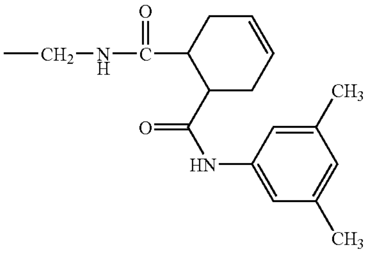 |

TABLE 1.187-continued
| Compd. No. | 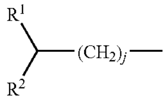 | k | m | n | chirality | $R^3$ | 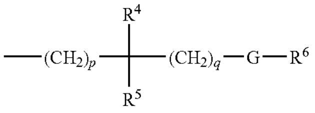 |
|---|---|---|---|---|---|---|---|
| 2050 | 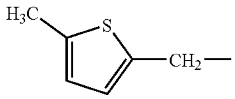 | 1 | 2 | 0 | R | H | 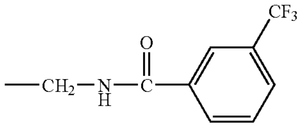 |
| 2051 | 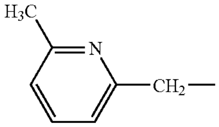 | 1 | 2 | 0 | R | H | 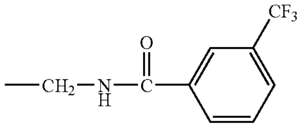 |
| 2052 | 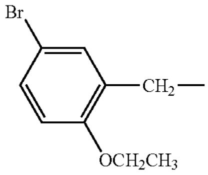 | 2 | 2 | 1 | — | H | 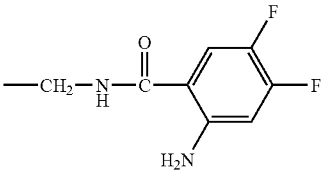 |
| 2053 | 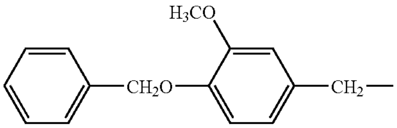 | 2 | 2 | 1 | — | H | 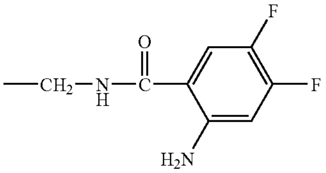 |
| 2054 | 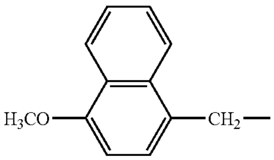 | 2 | 2 | 1 | — | H | 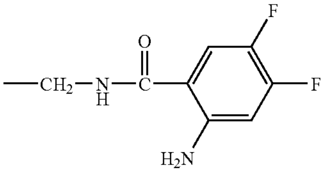 |
| 2055 | 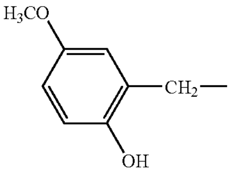 | 2 | 2 | 1 | — | H | 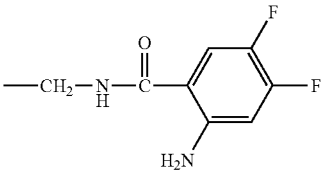 |
| 2056 | 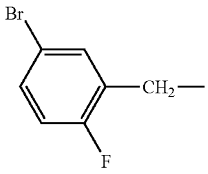 | 2 | 2 | 1 | — | H | 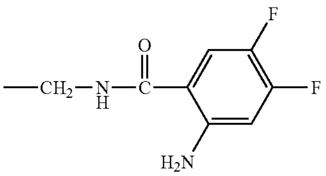 |
| 2057 | 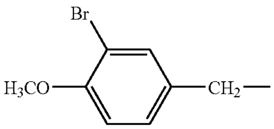 | 2 | 2 | 1 | — | H | 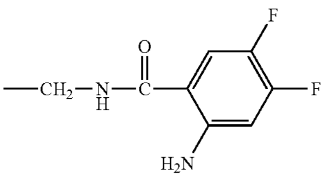 |

TABLE 1.188
| Compd. No. | 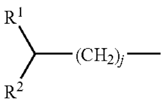 | k | m | n | chirality | $R^3$ | 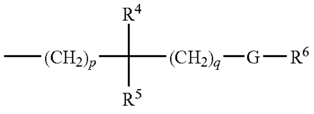 |
|---|---|---|---|---|---|---|---|
| 2058 | 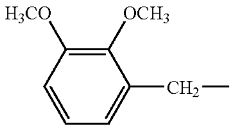 | 2 | 2 | 1 | — | H | 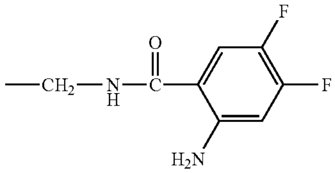 |
| 2059 | 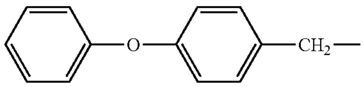 | 2 | 2 | 1 | — | H | 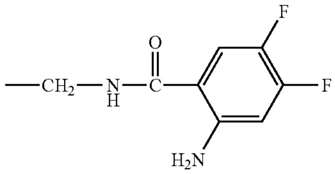 |
| 2060 | 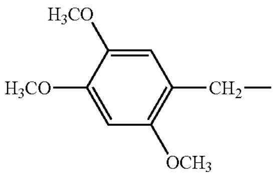 | 2 | 2 | 1 | — | H | 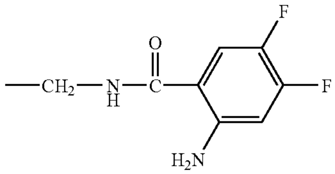 |
| 2061 | 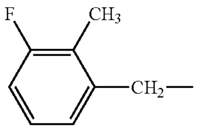 | 2 | 2 | 1 | — | H | 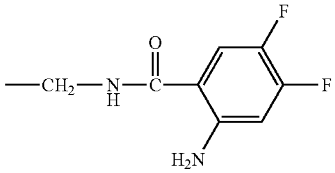 |
| 2062 | 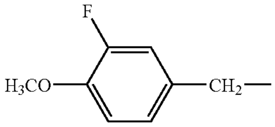 | 2 | 2 | 1 | — | H | 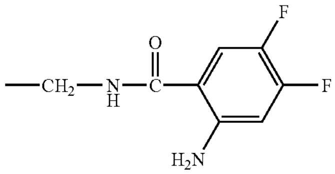 |
| 2063 | 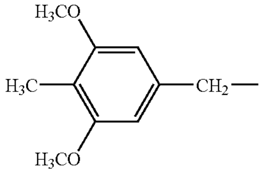 | 2 | 2 | 1 | — | H | 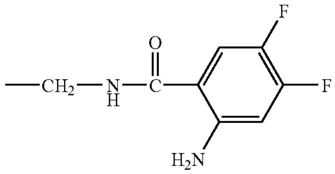 |
| 2064 | 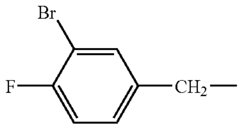 | 2 | 2 | 1 | — | H | 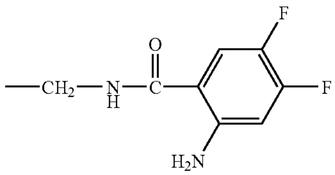 |

TABLE 1.188-continued
| Compd. No. | 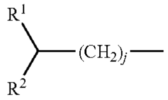 | k | m | n | chirality | $R^3$ | 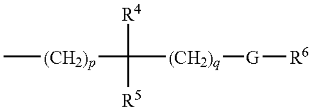 |
|---|---|---|---|---|---|---|---|
| 2065 | 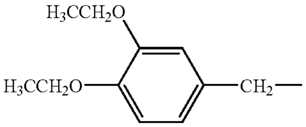 | 2 | 2 | 1 | — | H | 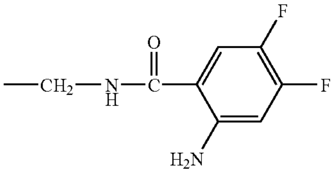 |
| 2066 | 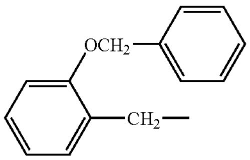 | 2 | 2 | 1 | — | H | 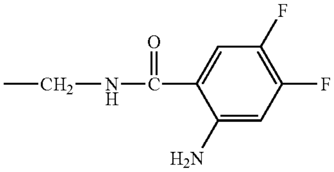 |
| 2067 | 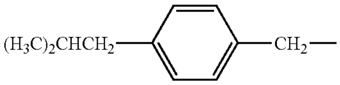 | 2 | 2 | 1 | — | H | 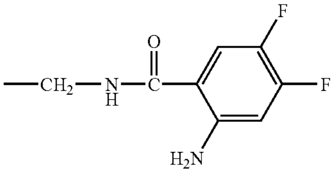 |
| 2068 | 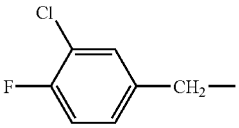 | 2 | 2 | 1 | — | H | 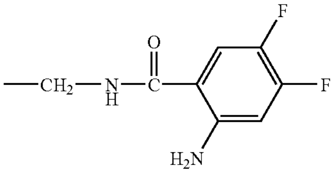 |
TABLE 1.189
| Compd. No. | 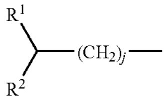 | k | m | n | chirality | $R^3$ | 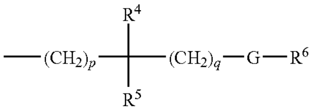 |
|---|---|---|---|---|---|---|---|
| 2069 | 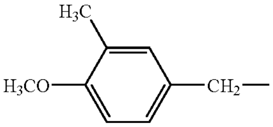 | 2 | 2 | 1 | — | H | 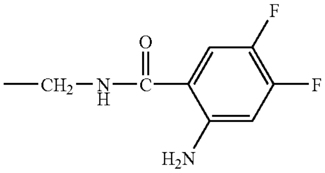 |
| 2070 | 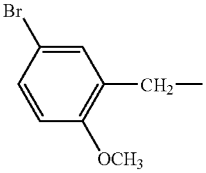 | 2 | 2 | 1 | — | H | 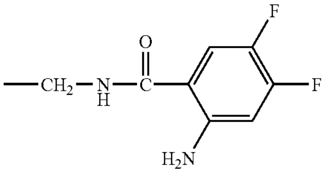 |

TABLE 1.189-continued
| Compd. No. | 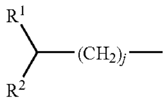 | k | m | n | chirality | $R^3$ | 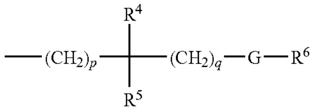 |
|---|---|---|---|---|---|---|---|
| 2071 | 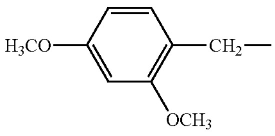 | 2 | 2 | 1 | — | H | 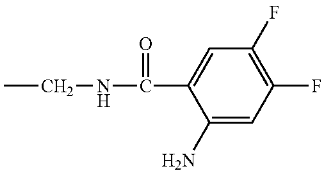 |
| 2072 | 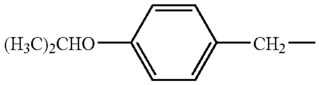 | 2 | 2 | 1 | — | H | 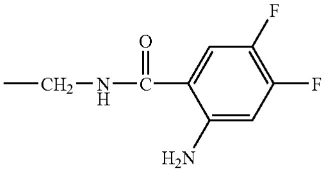 |
| 2073 | 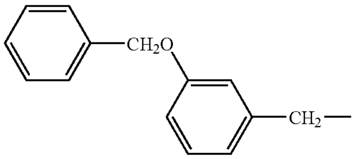 | 2 | 2 | 1 | — | H | 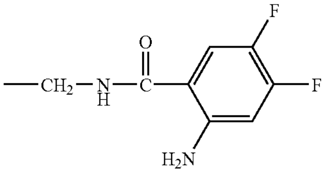 |
| 2074 | 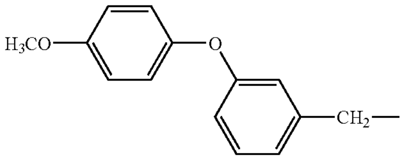 | 2 | 2 | 1 | — | H | 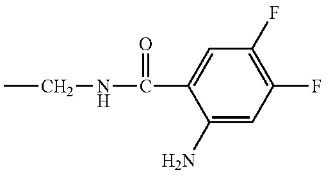 |
| 2075 | 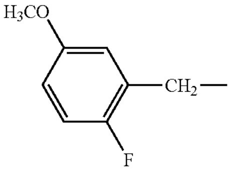 | 2 | 2 | 1 | — | H | 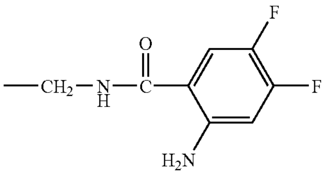 |
| 2076 | 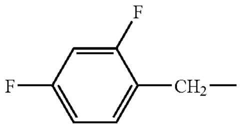 | 2 | 2 | 1 | — | H | 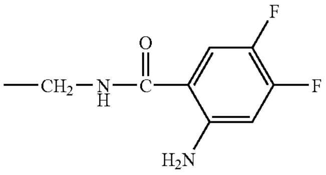 |
| 2077 | 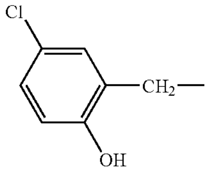 | 2 | 2 | 1 | — | H | 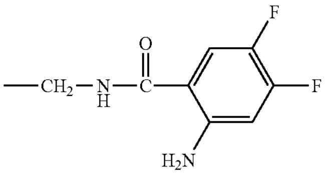 |
| 2078 | 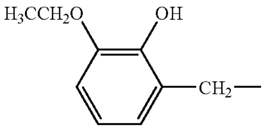 | 2 | 2 | 1 | — | H | 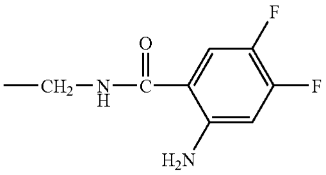 |

TABLE 1.189-continued
| Compd. No. | 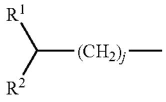 | k | m | n | chirality | $R^3$ | 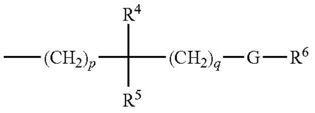 |
|---|---|---|---|---|---|---|---|
| 2079 | 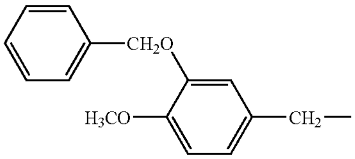 | 2 | 2 | 1 | — | H | 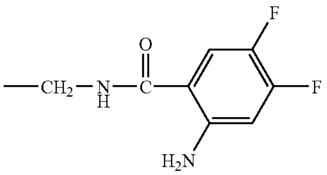 |
TABLE 1.190
| Compd. No. | 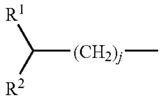 | k | m | n | chirality | $R^3$ | 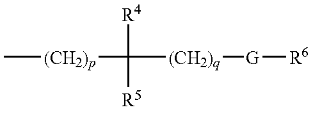 |
|---|---|---|---|---|---|---|---|
| 2080 | 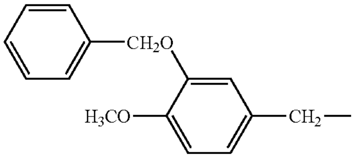 | 2 | 2 | 1 | — | H | 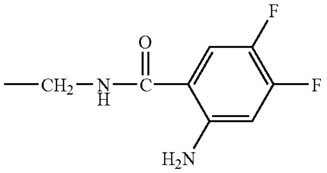 |
| 2081 | 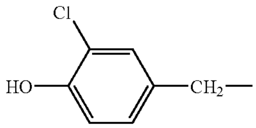 | 2 | 2 | 1 | — | H | 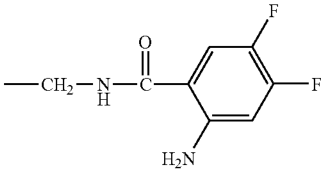 |
| 2082 | 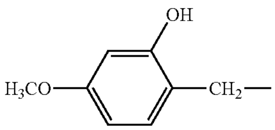 | 2 | 2 | 1 | — | H | 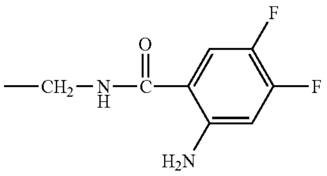 |
| 2083 | 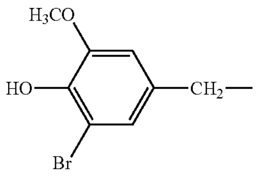 | 1 | 2 | 0 | R | H | 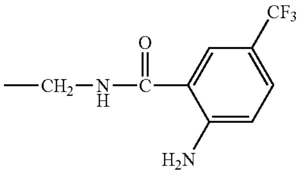 |
| 2084 | 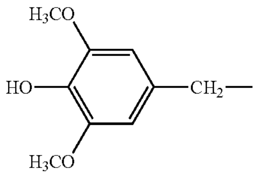 | 1 | 2 | 0 | R | H | 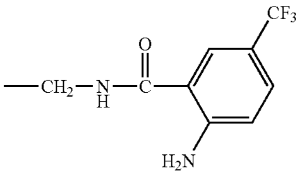 |

TABLE 1.190-continued
| Compd. No. | 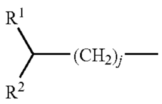 | k | m | n | chirality | $R^3$ | 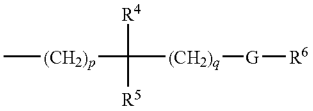 |
|---|---|---|---|---|---|---|---|
| 2085 | 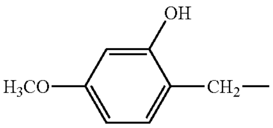 | 1 | 2 | 0 | R | H | 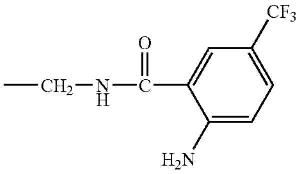 |
| 2086 | 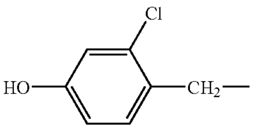 | 1 | 2 | 0 | R | H | 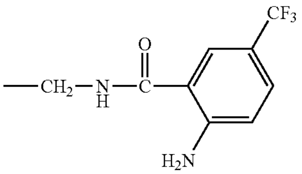 |
| 2087 | 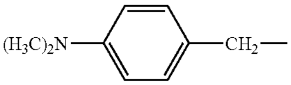 | 1 | 2 | 0 | R | H | 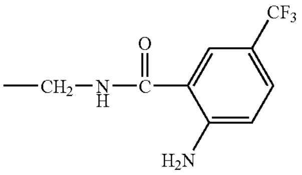 |
| 2088 | 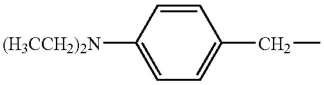 | 1 | 2 | 0 | R | H | 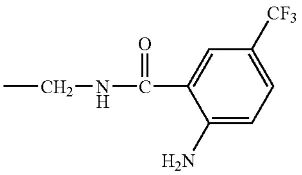 |
| 2089 | 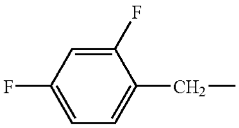 | 1 | 2 | 0 | R | H | 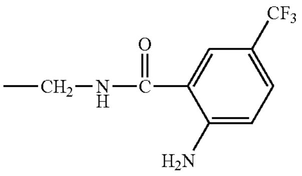 |
| 2090 | 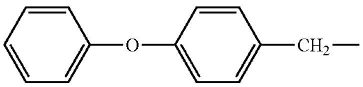 | 1 | 2 | 0 | R | H | 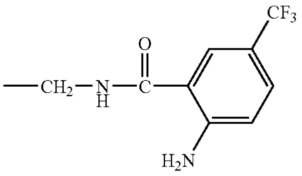 |

TABLE 1.191
| Compd. No. | 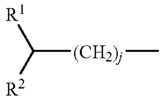 | k | m | n | chirality | $R^3$ | 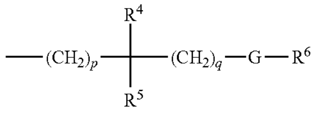 |
|---|---|---|---|---|---|---|---|
| 2091 | 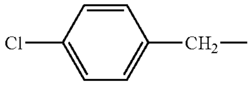 | 2 | 2 | 1 | — | H | 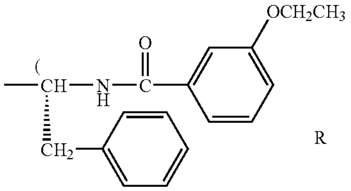 |
| 2092 | 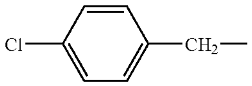 | 2 | 2 | 1 | — | H | 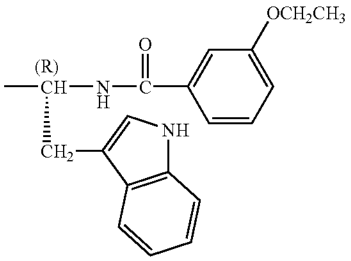 |
| 2093 | 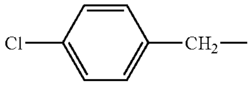 | 2 | 2 | 1 | — | H | 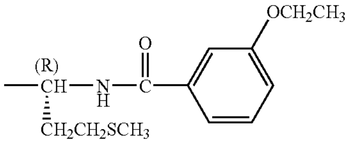 |
| 2094 | 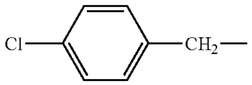 | 2 | 2 | 1 | — | H | 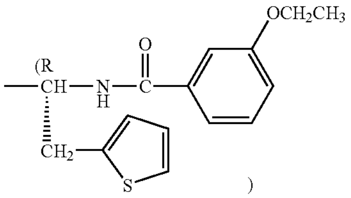 |
| 2095 | 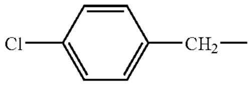 | 2 | 2 | 1 | — | H | 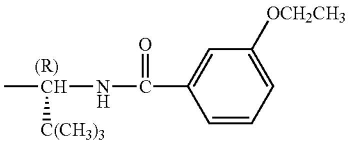 |
| 2096 | 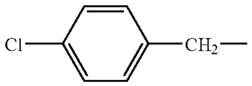 | 2 | 2 | 1 | — | H | 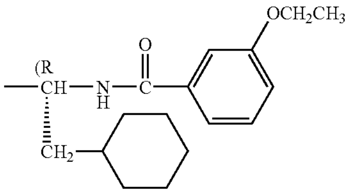 |
| 2097 | 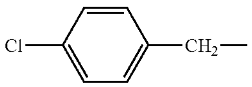 | 2 | 2 | 1 | — | H | 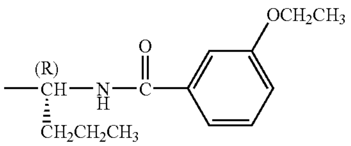 |

TABLE 1.191-continued
| Compd. No. | 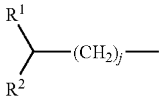 | k | m | n | chirality | $R^3$ | 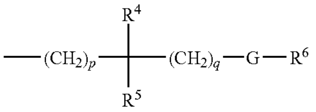 |
|---|---|---|---|---|---|---|---|
| 2098 | 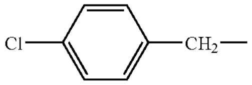 | 2 | 2 | 1 | — | H | 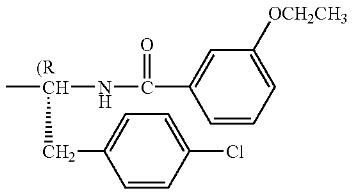 |
| 2099 | 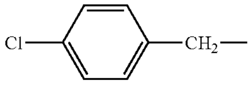 | 2 | 2 | 1 | — | H | 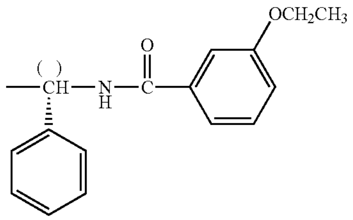 |
| 2100 | 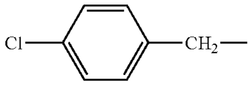 | 2 | 2 | 1 | — | H | 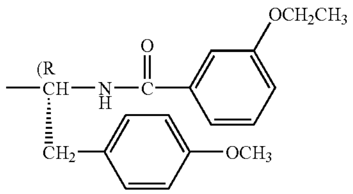 |
| 2101 | 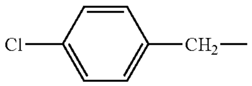 | 2 | 2 | 1 | — | H | 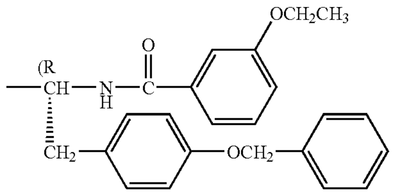 |
TABLE 1.192
| Compd. No. | 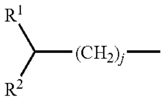 | k | m | n | chirality | $R^3$ | 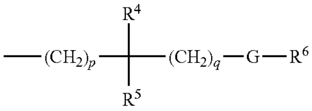 |
|---|---|---|---|---|---|---|---|
| 2102 | 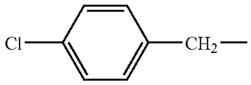 | 2 | 2 | 1 | — | H | 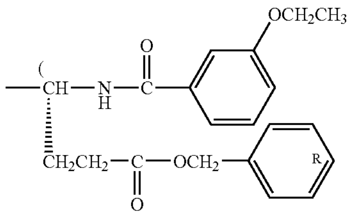 |
| 2103 | 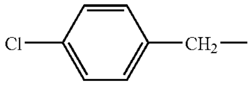 | 2 | 2 | 1 | — | H | 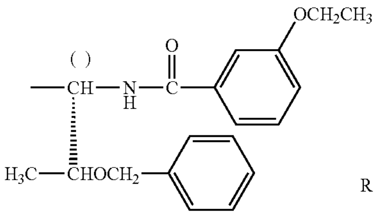 |

TABLE 1.192-continued
| Compd. No. | 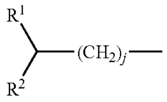 | k | m | n | chirality | $R^3$ | 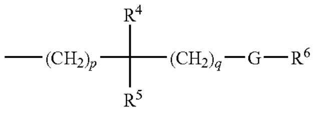 |
|---|---|---|---|---|---|---|---|
| 2104 | 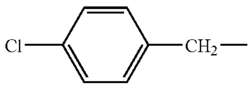 | 2 | 2 | 1 | — | H | 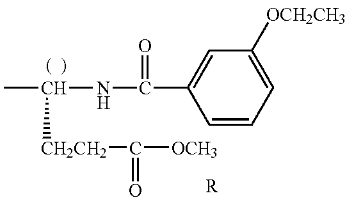 R |
| 2105 | 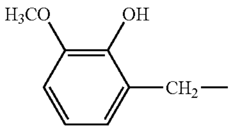 | 2 | 2 | 1 | — | H | 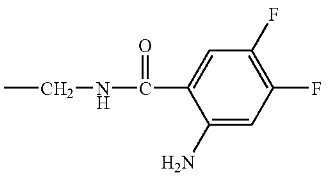 |
| 2106 | 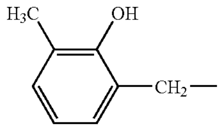 | 2 | 2 | 1 | — | H | 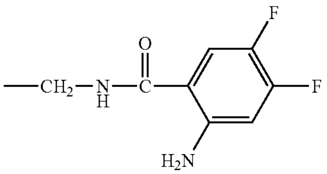 |
| 2107 | 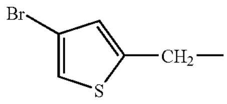 | 2 | 2 | 1 | — | H | 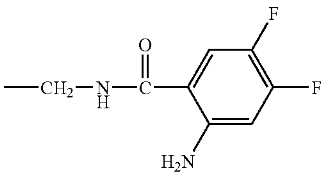 |
| 2108 | 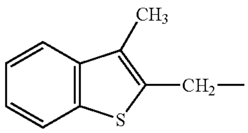 | 2 | 2 | 1 | — | H | 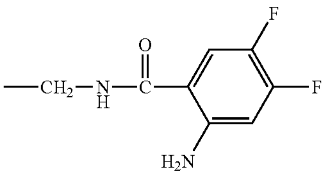 |
| 2109 | 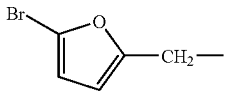 | 2 | 2 | 1 | — | H | 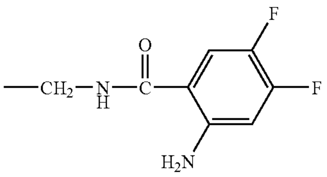 |
| 2110 | 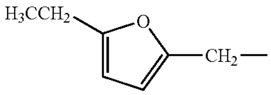 | 2 | 2 | 1 | — | H | 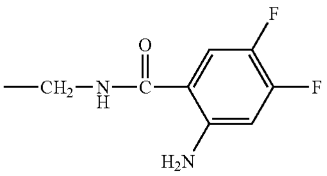 |

TABLE 1.192-continued
| Compd. No. | 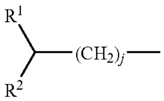 | k | m | n | chirality | $R^3$ | 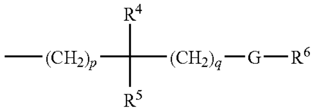 |
|---|---|---|---|---|---|---|---|
| 2111 | 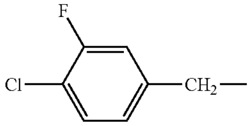 | 2 | 2 | 1 | — | H | 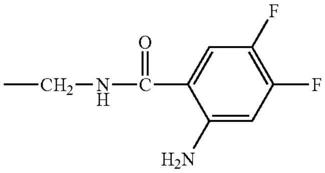 |
| 2112 | 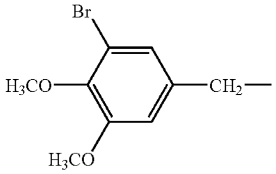 | 2 | 2 | 1 | — | H | 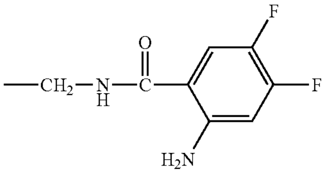 |
TABLE 1.193
| Compd. No. | 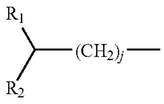 | k | m | n | chirality | $R^3$ | 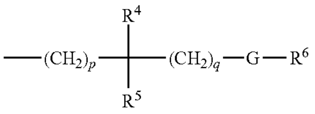 |
|---|---|---|---|---|---|---|---|
| 2113 | 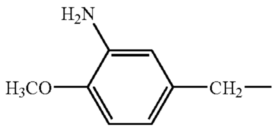 | 2 | 2 | 1 | — | H | 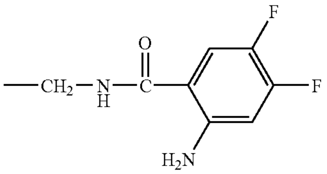 |
| 2114 | 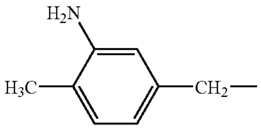 | 2 | 2 | 1 | — | H | 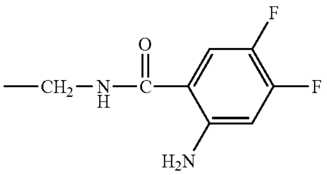 |
| 2115 | 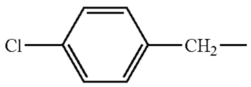 | 2 | 2 | 1 | — | H | 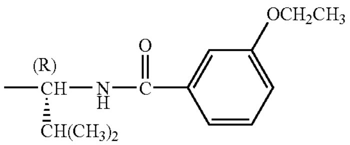 |
| 2116 | 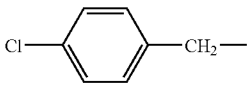 | 2 | 2 | 1 | — | H | 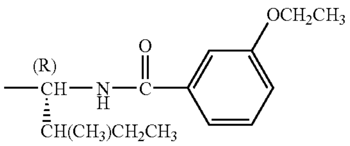 |
| 2117 | 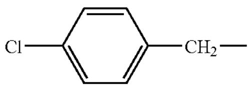 | 2 | 2 | 1 | — | H | 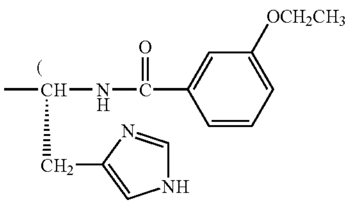 |

TABLE 1.193-continued
| Compd. No. | 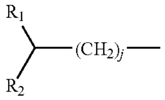 | k | m | n | chirality | $R^3$ | 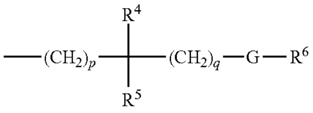 |
|---|---|---|---|---|---|---|---|
| 2118 | 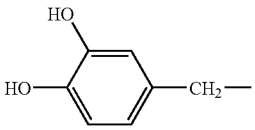 | 1 | 2 | 0 | R | H | 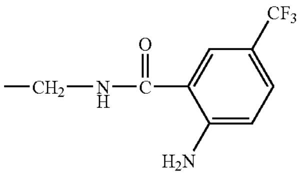 |
| 2119 | 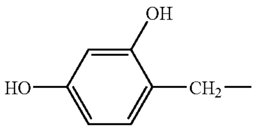 | 1 | 2 | 0 | R | H | 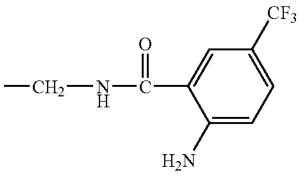 |
| 2120 | 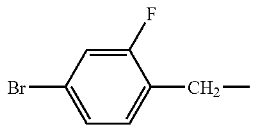 | 1 | 2 | 0 | R | H | 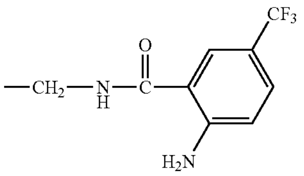 |
| 2121 | 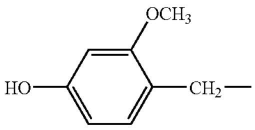 | 1 | 2 | 0 | R | H | 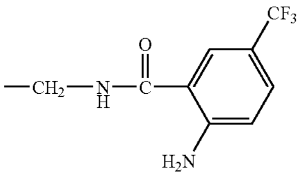 |
| 2122 | 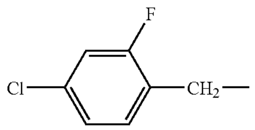 | 1 | 2 | 0 | R | H | 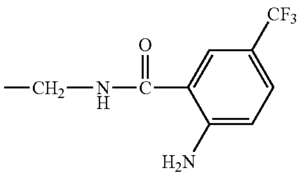 |
| 2123 | 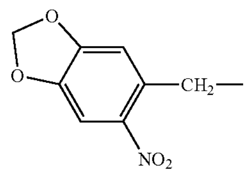 | 1 | 2 | 0 | R | H | 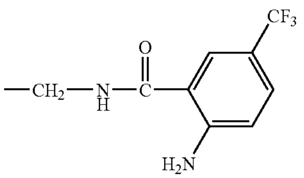 |

TABLE 1.194
| Compd. No. | 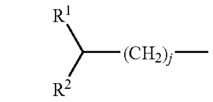 | k | m | n | chirality | $R^3$ | 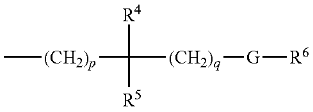 |
|---|---|---|---|---|---|---|---|
| 2124 | 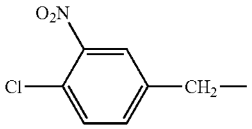 | 1 | 2 | 0 | R | H | 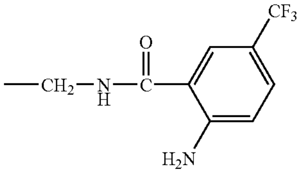 |
| 2125 | 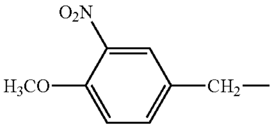 | 1 | 2 | 0 | R | H | 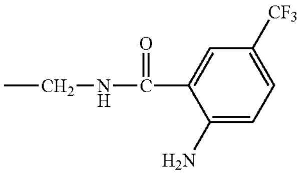 |
| 2126 | 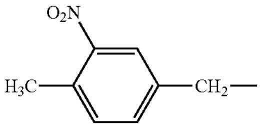 | 1 | 2 | 0 | R | H | 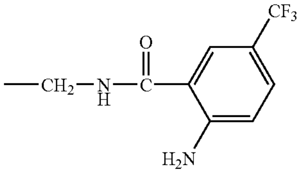 |
| 2127 | 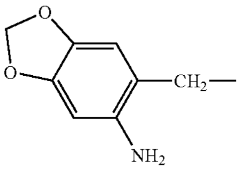 | 1 | 2 | 0 | R | H | 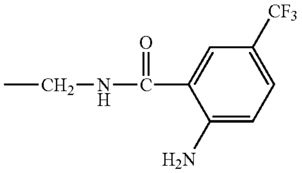 |
| 2128 | 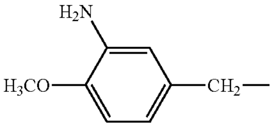 | 1 | 2 | 0 | R | H | 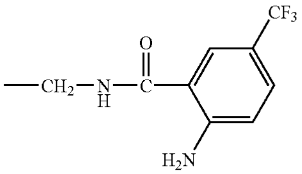 |
| 2129 | 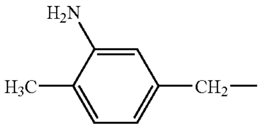 | 1 | 2 | 0 | R | H | 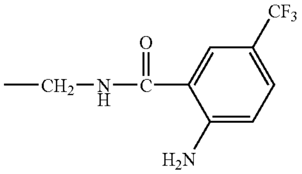 |
| 2130 | 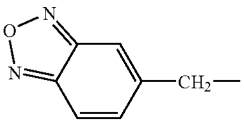 | 2 | 2 | 1 | — | H | 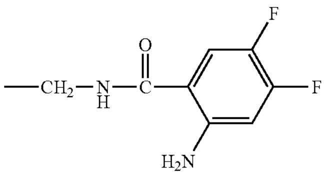 |
| 2131 | 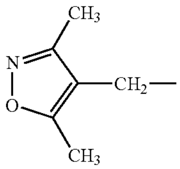 | 2 | 2 | 1 | — | H | 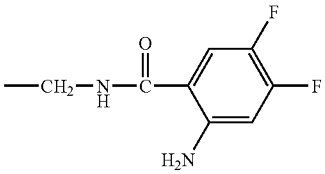 |

TABLE 1.194-continued
| Compd. No. | 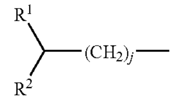 | k | m | n | chirality | $R^3$ | 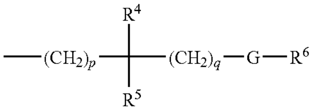 |
|---|---|---|---|---|---|---|---|
| 2132 | 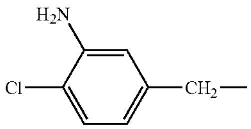 | 1 | 2 | 0 | R | H | 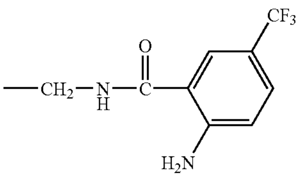 |
| 2133 | 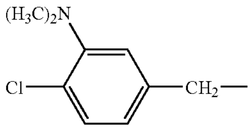 | 1 | 2 | 0 | R | H | 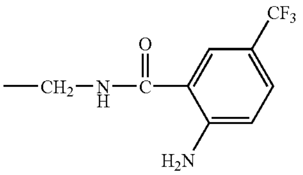 |
| 2134 | 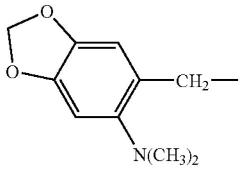 | 1 | 2 | 0 | R | H | 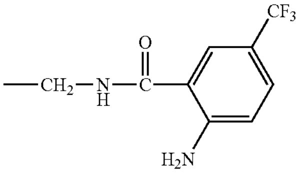 |
TABLE 1.195
| Compd. No. | 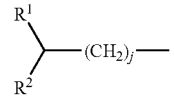 | k | m | n | chirality | $R^3$ | 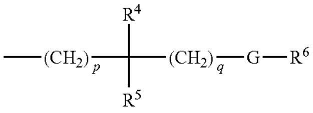 |
|---|---|---|---|---|---|---|---|
| 2135 | 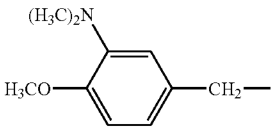 | 1 | 2 | 0 | R | H | 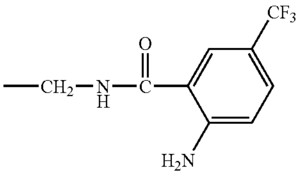 |
| 2136 | 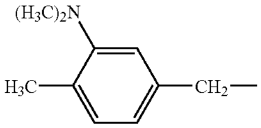 | 1 | 2 | 0 | R | H | 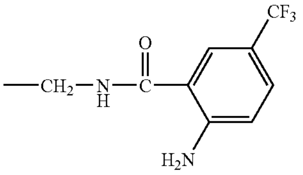 |
| 2137 | 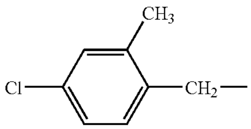 | 1 | 2 | 0 | R | H | 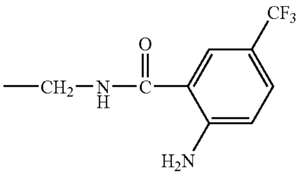 |

TABLE 1.195-continued
| Compd. No. | 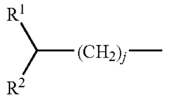 | k | m | n | chirality | $R^3$ | 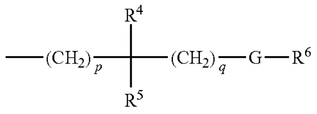 |
|---|---|---|---|---|---|---|---|
| 2138 | 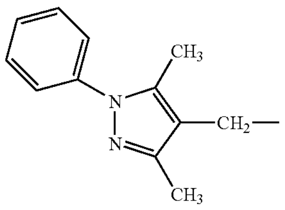 | 1 | 2 | 0 | R | H | 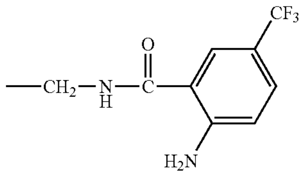 |
| 2139 | 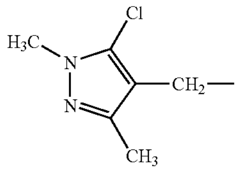 | 1 | 2 | 0 | R | H | 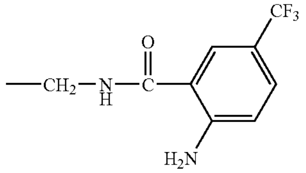 |
| 2140 | 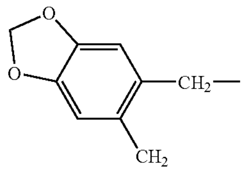 | 2 | 2 | 1 | — | H | 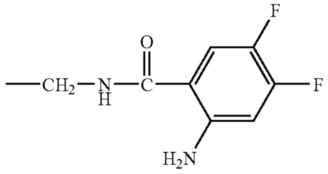 |
| 2141 | 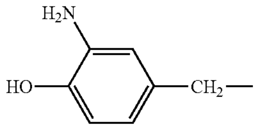 | 2 | 2 | 1 | — | H | 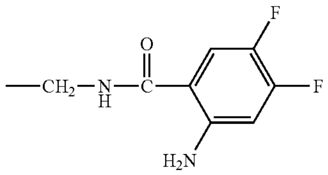 |
| 2142 | 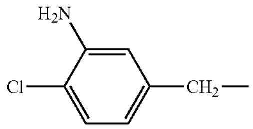 | 2 | 2 | 1 | — | H | 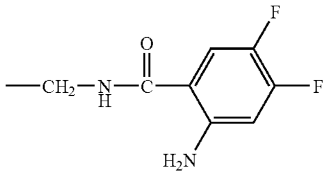 |
| 2143 | 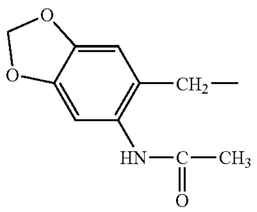 | 2 | 2 | 1 | — | H | 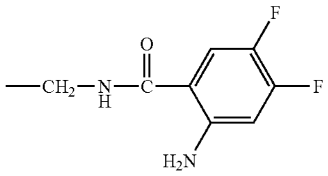 |
| 2144 | 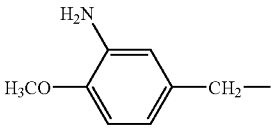 | 2 | 2 | 1 | — | H | 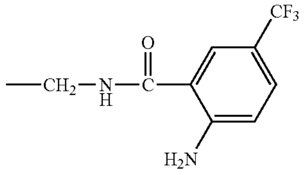 |

TABLE 1.195-continued
| Compd. No. | 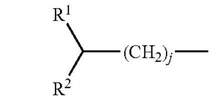 | k | m | n | chirality | $R^3$ | 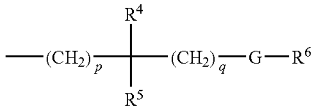 |
|---|---|---|---|---|---|---|---|
| 2145 | 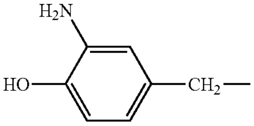 | 2 | 2 | 1 | — | H | 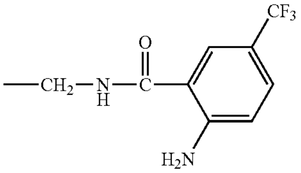 |
TABLE 1.196
| Compd. No. | 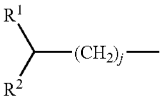 | k | m | n | chirality | $R^3$ | 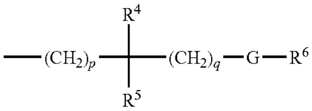 |
|---|---|---|---|---|---|---|---|
| 2146 | 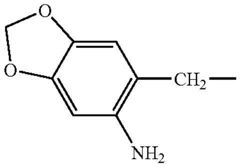 | 2 | 2 | 1 | — | H | 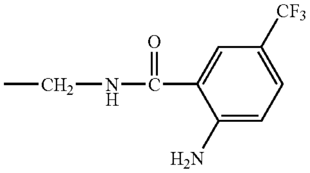 |
| 2147 | 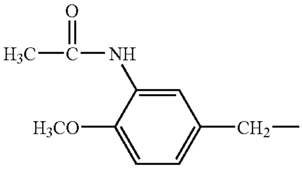 | 2 | 2 | 1 | — | H | 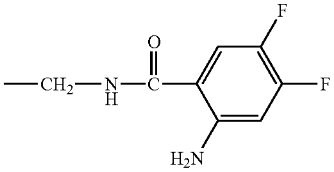 |
| 2148 | 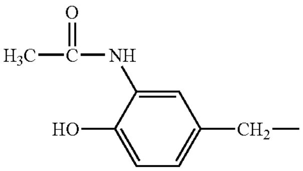 | 2 | 2 | 1 | — | H | 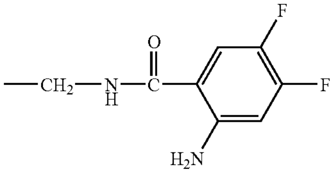 |
| 2149 | 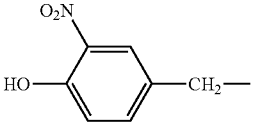 | 1 | 2 | 0 | R | H | 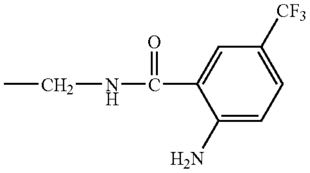 |
| 2150 | 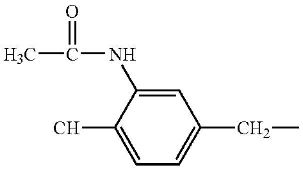 | 1 | 2 | 0 | R | H | 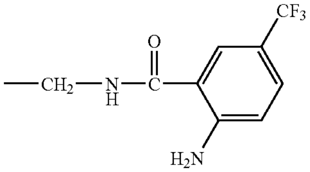 |

TABLE 1.196-continued
| Compd. No. | 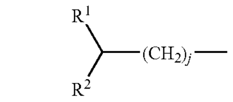 | k | m | n | chirality | $R^3$ | 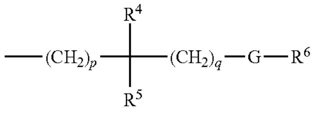 |
|---|---|---|---|---|---|---|---|
| 2151 | 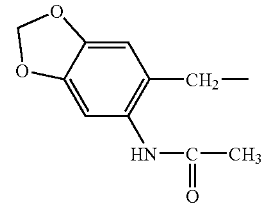 | 1 | 2 | 0 | R | H | 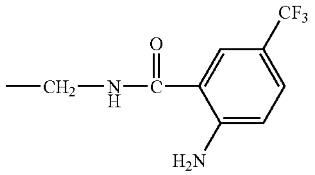 |
| 2152 | 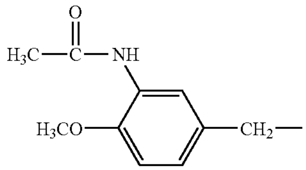 | 1 | 2 | 0 | R | H | 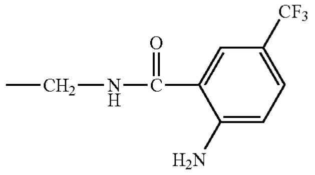 |
| 2153 | 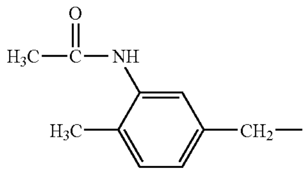 | 1 | 2 | 0 | R | H | 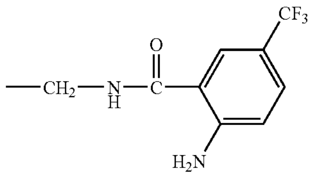 |
| 2154 | 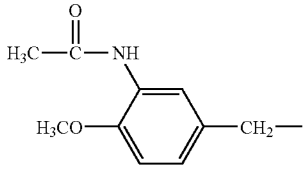 | 2 | 2 | 1 | — | H | 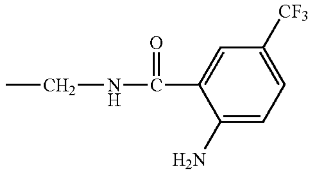 |
| 2155 | 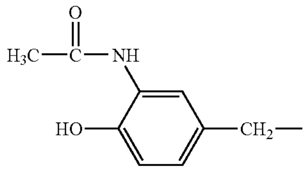 | 2 | 2 | 1 | — | H | 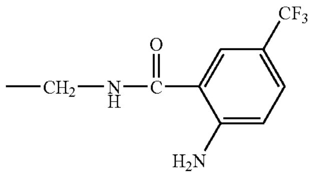 |
| 2156 | 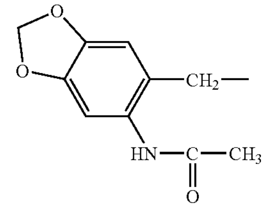 | 2 | 2 | 1 | — | H | 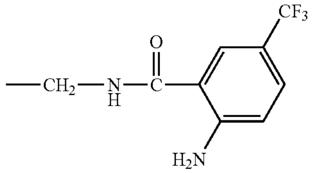 |

TABLE 1.197
| Compd. No. | 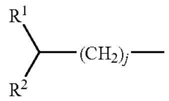 | k | m | n | chirality | $R^3$ | 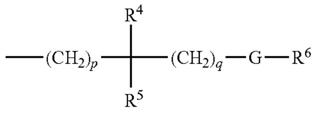 |
|---|---|---|---|---|---|---|---|
| 2157 | 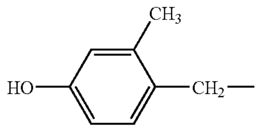 | 1 | 2 | 0 | R | H | 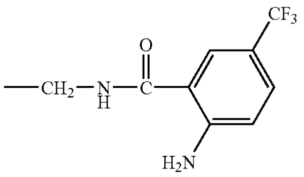 |
| 2158 | 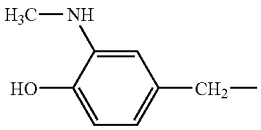 | 1 | 2 | 0 | R | H | 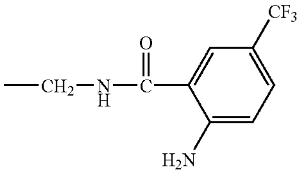 |
| 2159 | 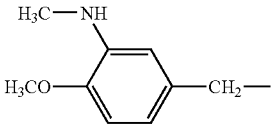 | 2 | 2 | 1 | — | H | 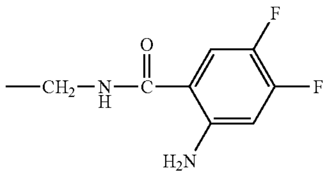 |
| 2160 | 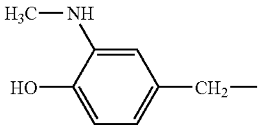 | 2 | 2 | 1 | — | H | 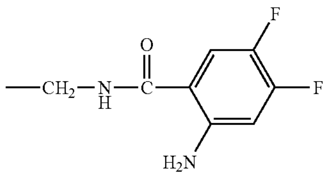 |
| 2161 | 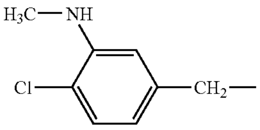 | 2 | 2 | 1 | — | H | 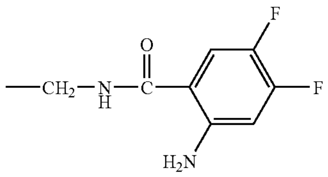 |
| 2162 | 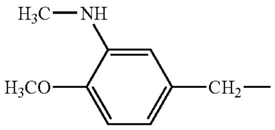 | 2 | 2 | 1 | — | H | 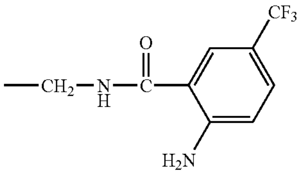 |
| 2163 | 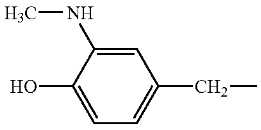 | 2 | 2 | 1 | — | H | 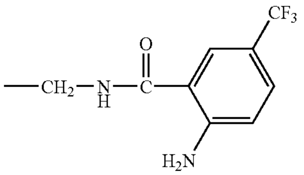 |
| 2164 | 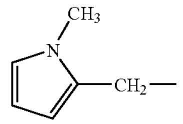 | 1 | 2 | 0 | R | H | 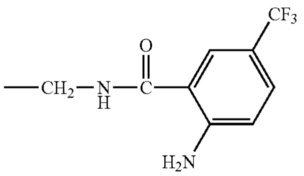 |

TABLE 1.197-continued
| Compd. No. | 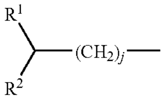 | k | m | n | chirality | $R^3$ | 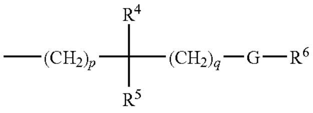 |
|---|---|---|---|---|---|---|---|
| 2165 | 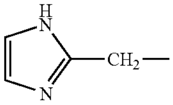 | 1 | 2 | 0 | R | H | 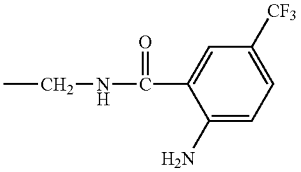 |
| 2166 | 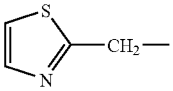 | 1 | 2 | 0 | R | H | 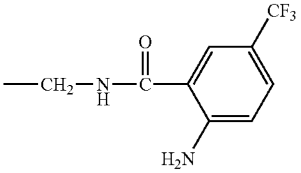 |
| 2167 | 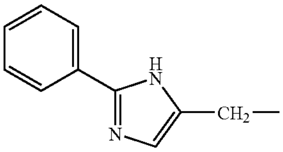 | 1 | 2 | 0 | R | H | 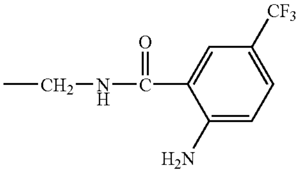 |
TABLE 1.198
| Compd. No. | 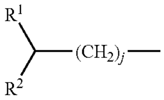 | k | m | n | chirality | $R^3$ | 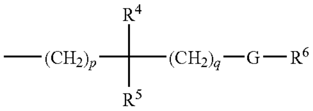 |
|---|---|---|---|---|---|---|---|
| 2168 | 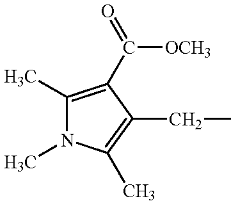 | 1 | 2 | 0 | R | H | 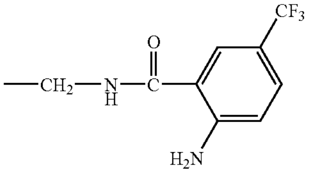 |
| 2169 | 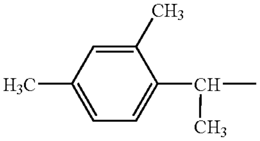 | 1 | 2 | 0 | R | H | 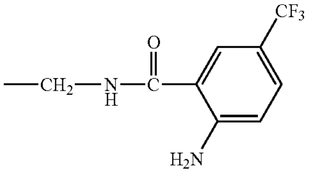 |
| 2170 | 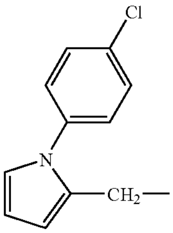 | 1 | 2 | 0 | R | H | 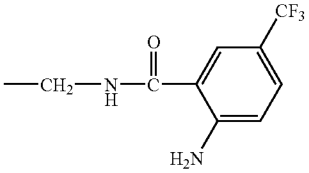 |

TABLE 1.198-continued
| Compd. No. | 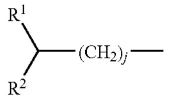 | k | m | n | chirality | $R^3$ | 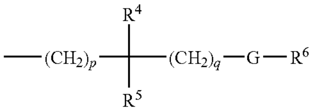 |
|---|---|---|---|---|---|---|---|
| 2171 | 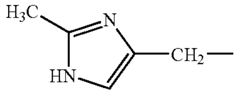 | 1 | 2 | 0 | R | H | 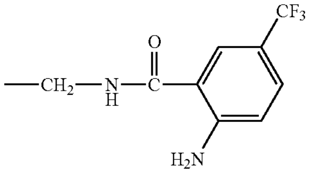 |
| 2172 | 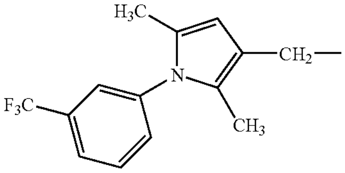 | 1 | 2 | 0 | R | H | 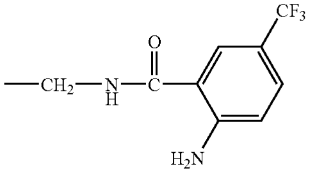 |
| 2173 | 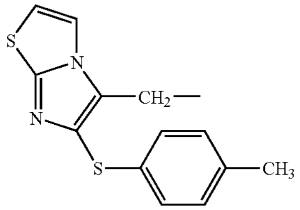 | 1 | 2 | 0 | R | H | 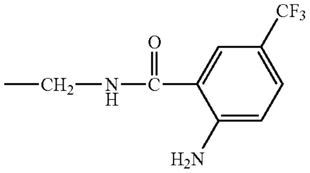 |
| 2174 | 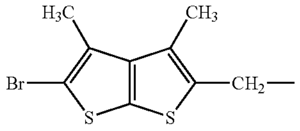 | 1 | 2 | 0 | R | H | 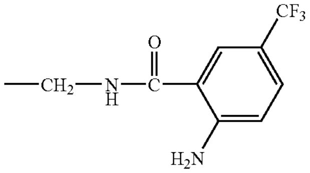 |
| 2175 | 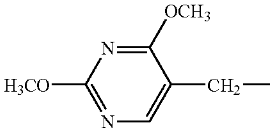 | 1 | 2 | 0 | R | H | 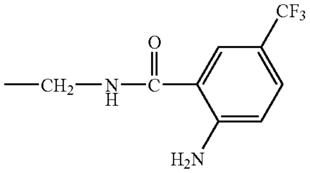 |
| 2176 | 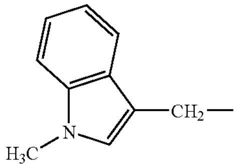 | 1 | 2 | 0 | R | H | 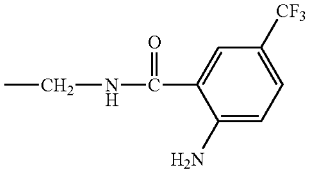 |
| 2177 | 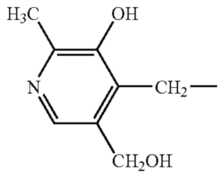 | 1 | 2 | 0 | R | H | 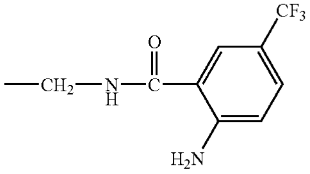 |

TABLE 1.198-continued
| Compd. No. | 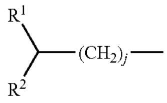 | k | m | n | chirality | $R^3$ | 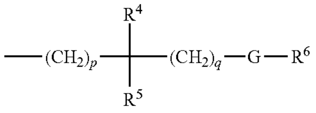 |
|---|---|---|---|---|---|---|---|
| 2178 | 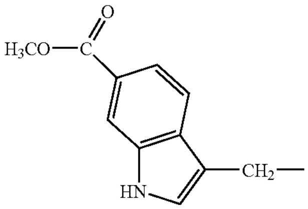 | 1 | 2 | 0 | R | H | 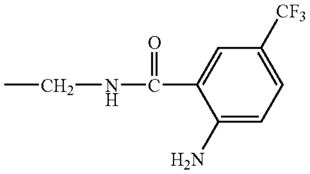 |
TABLE 1.199
| Compd. No. | 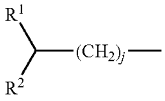 | k | m | n | chirality | $R^3$ | 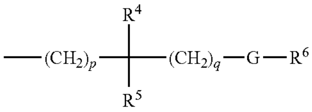 |
|---|---|---|---|---|---|---|---|
| 2179 | 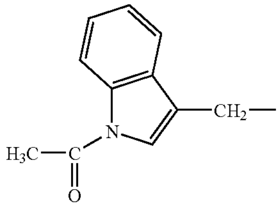 | 1 | 2 | 0 | R | H | 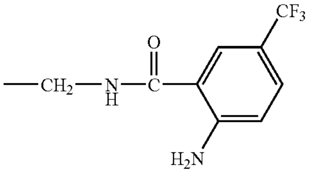 |
| 2180 | 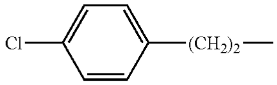 | 1 | 2 | 0 | R | H | 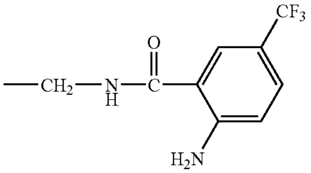 |
| 2181 | 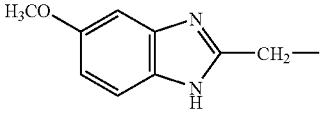 | 1 | 2 | 0 | R | H | 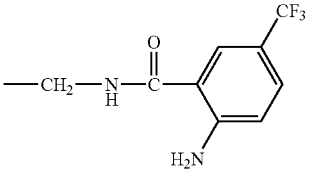 |
| 2182 | 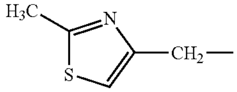 | 1 | 2 | 0 | R | H | 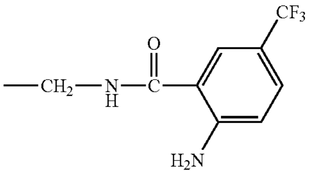 |
| 2183 | 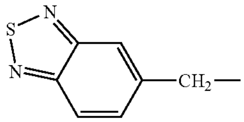 | 1 | 2 | 0 | R | H | 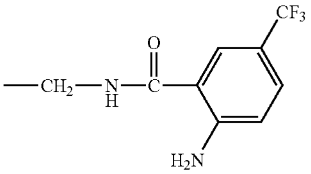 |

TABLE 1.199-continued
| Compd. No. | 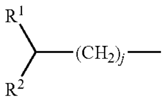 | k | m | n | chirality | $R^3$ | 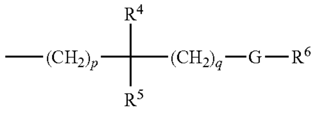 |
|---|---|---|---|---|---|---|---|
| 2184 | 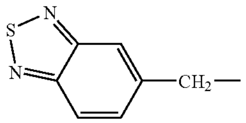 | 2 | 2 | 1 | — | H | 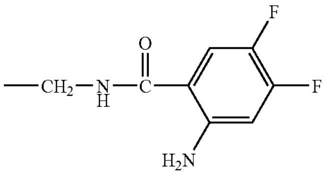 |
| 2185 | 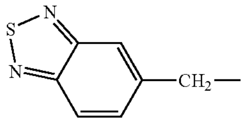 | 2 | 2 | 1 | — | H | 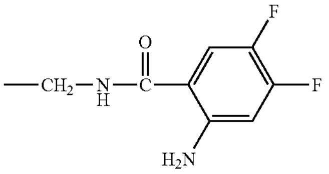 |
| 2186 | 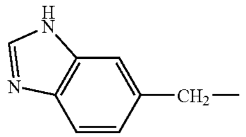 | 2 | 2 | 1 | — | H | 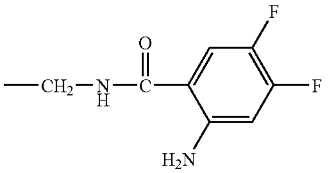 |
| 2187 | 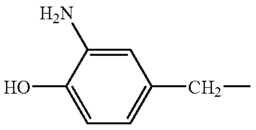 | 1 | 2 | 0 | R | H | 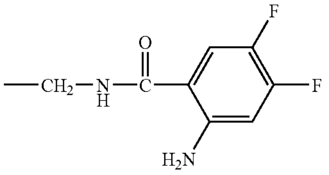 |
| 2188 | 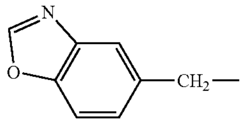 | 2 | 2 | 1 | — | H | 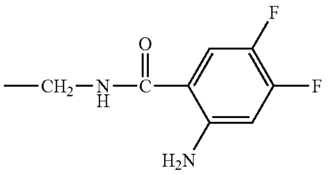 |
| 2189 | 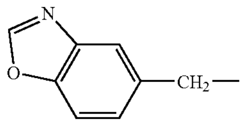 | 1 | 2 | 0 | R | H | 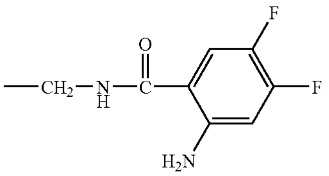 |

TABLE 1.200
| Compd. No. | 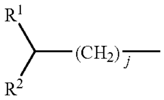 | k | m | n | chirality | $R^3$ | 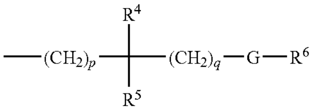 |
|---|---|---|---|---|---|---|---|
| 2190 | 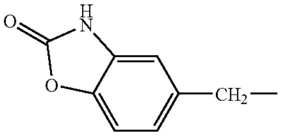 | 2 | 2 | 1 | — | H | 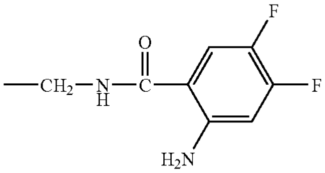 |
| 2191 | 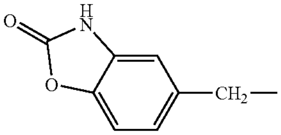 | 2 | 2 | 1 | — | H | 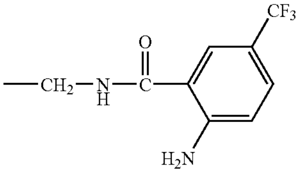 |
| 2192 | 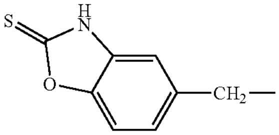 | 2 | 2 | 1 | — | H | 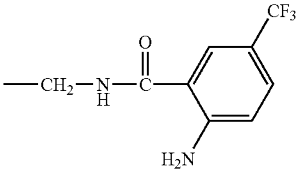 |
| 2193 | 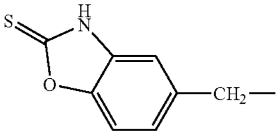 | 2 | 2 | 1 | — | H | 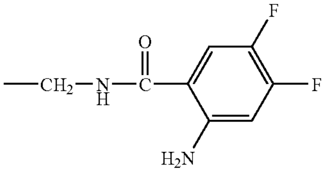 |
| 2194 | 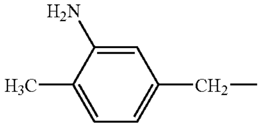 | 2 | 2 | 1 | — | H | 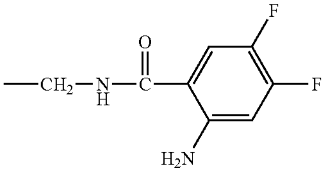 |
| 2195 | 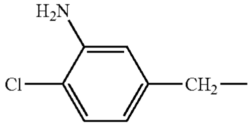 | 2 | 2 | 1 | — | H | 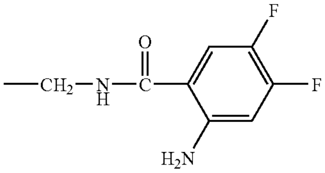 |
| 2196 | 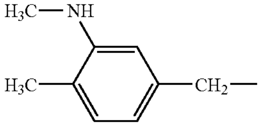 | 1 | 2 | 0 | R | H | 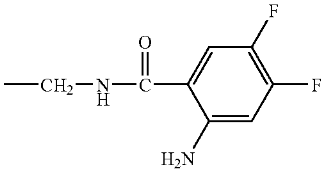 |
| 2197 | 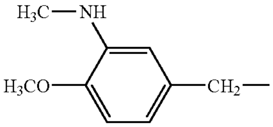 | 1 | 2 | 0 | R | H | 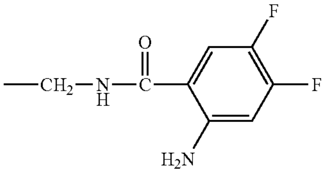 |

TABLE 1.200-continued
| Compd. No. | 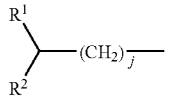 | k | m | n | chirality | $R^3$ | 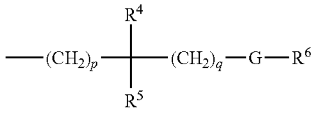 |
|---|---|---|---|---|---|---|---|
| 2198 | 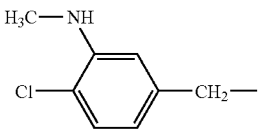 | 1 | 2 | 0 | R | H | 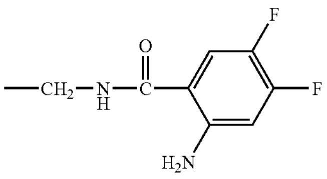 |
| 2199 | 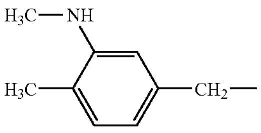 | 2 | 2 | 1 | — | H | 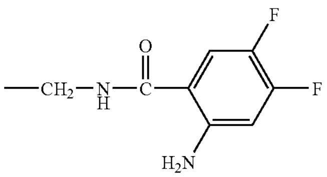 |
| 2200 | 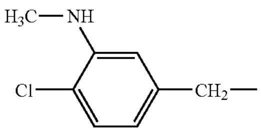 | 2 | 2 | 1 | — | H | 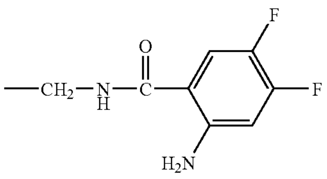 |
TABLE 1.201
| Compd. No. | 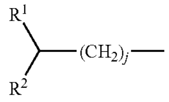 | k | m | n | chirality | $R^3$ | 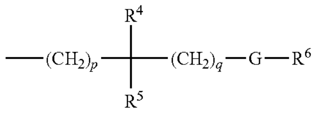 |
|---|---|---|---|---|---|---|---|
| 2201 | 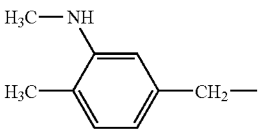 | 2 | 2 | 1 | — | H | 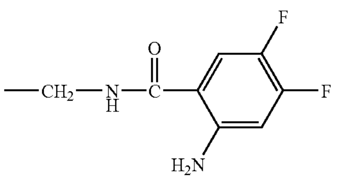 |
| 2202 | 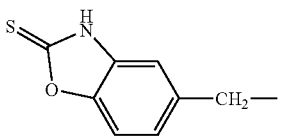 | 1 | 2 | 0 | R | H | 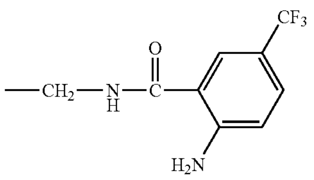 |
| 2203 | 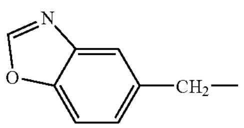 | 2 | 2 | 1 | — | H | 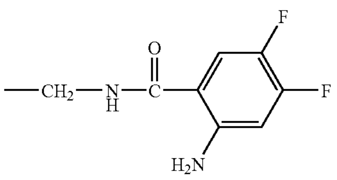 |

TABLE 1.201-continued
| Compd. No. | 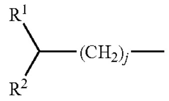 | k | m | n | chirality | $R^3$ | 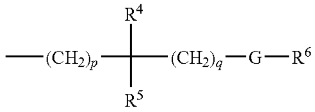 |
|---|---|---|---|---|---|---|---|
| 2204 | 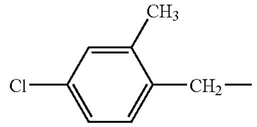 | 2 | 2 | 1 | — | H | 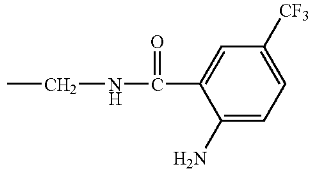 |
| 2205 | 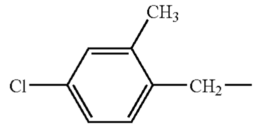 | 2 | 2 | 1 | — | H | 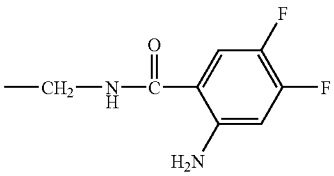 |
| 2206 | 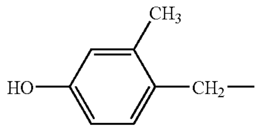 | 2 | 2 | 1 | — | H | 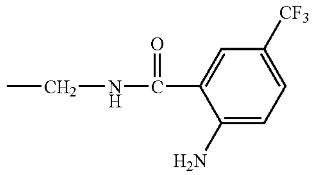 |
| 2207 | 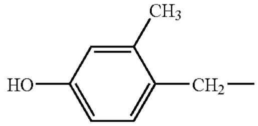 | 2 | 2 | 1 | — | H | 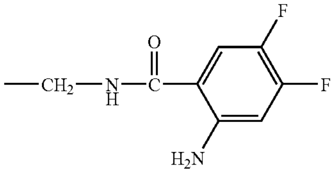 |
| 2208 | 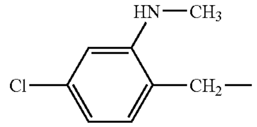 | 2 | 2 | 1 | — | H | 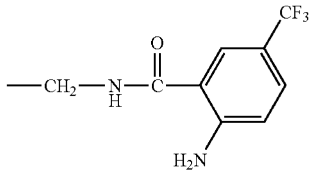 |
| 2209 | 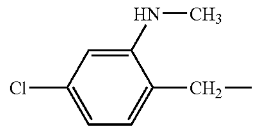 | 2 | 2 | 1 | — | H | 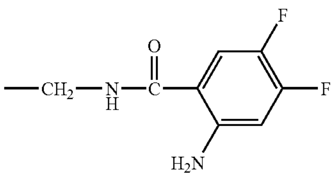 |
| 2210 | 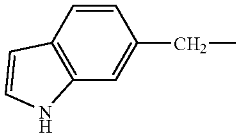 | 1 | 2 | 0 | R | H | 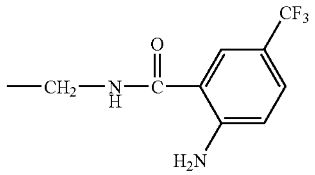 |

TABLE 1.201-continued
| Compd. No. | 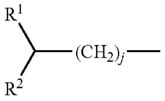 | k | m | n | chirality | $R^3$ | 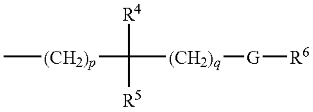 |
|---|---|---|---|---|---|---|---|
| 2211 | 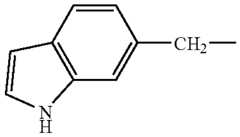 | 2 | 2 | 1 | — | H | 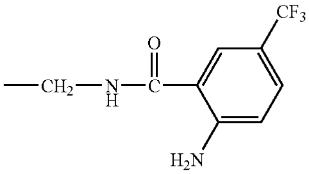 |
TABLE 1.202
| Compd. No. | 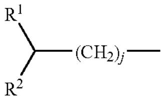 | k | m | n | chirality | $R^3$ | 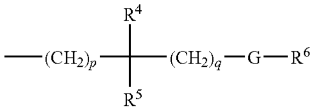 |
|---|---|---|---|---|---|---|---|
| 2212 | 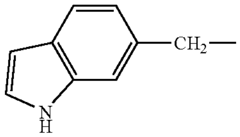 | 2 | 2 | 1 | — | H | 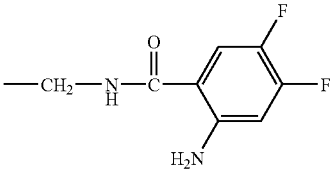 |
| 2213 | 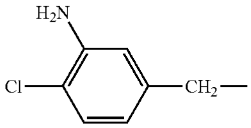 | 2 | 2 | 1 | — | H | 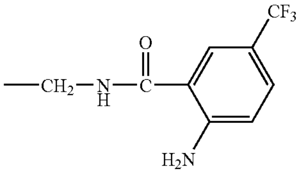 |
| 2214 | 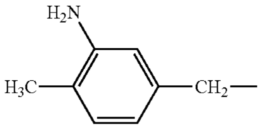 | 2 | 2 | 1 | — | H | 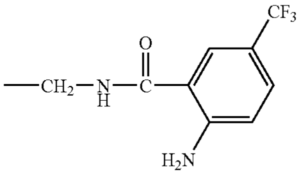 |
| 2215 | 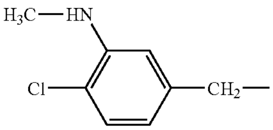 | 1 | 2 | 0 | R | H | 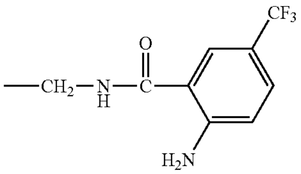 |
| 2216 | 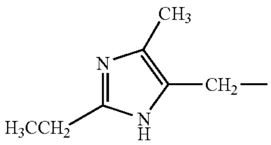 | 1 | 2 | 0 | R | H | 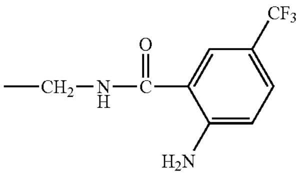 |

TABLE 1.202-continued
| Compd. No. | 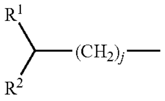 | k | m | n | chirality | $R^3$ | 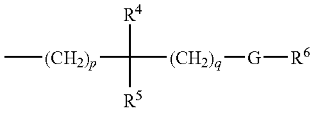 |
|---|---|---|---|---|---|---|---|
| 2217 | 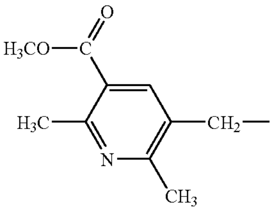 | 1 | 2 | 0 | R | H | 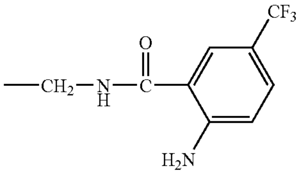 |
| 2218 | 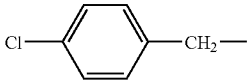 | 1 | 2 | 0 | R | H | 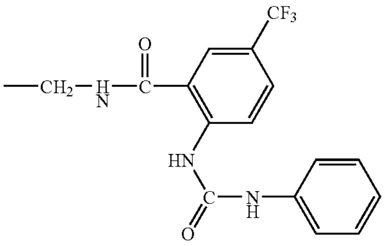 |
| 2219 | 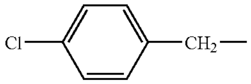 | 1 | 2 | 0 | R | H | 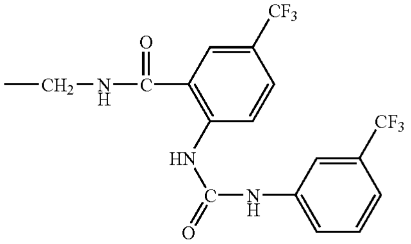 |
| 2220 | 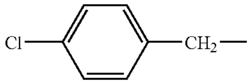 | 1 | 2 | 0 | R | H | 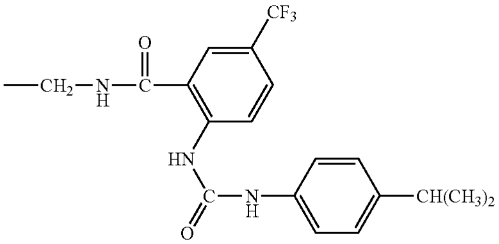 |
| 2221 | 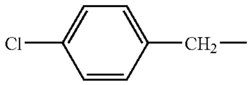 | 1 | 2 | 0 | R | H | 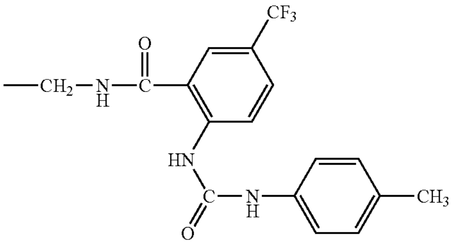 |
| 2222 | 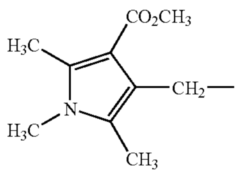 | 1 | 2 | 0 | R | H | 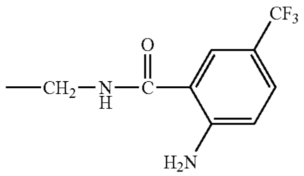 |

TABLE 1.203
| Compd. No. | 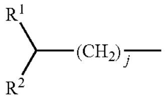 | k | m | n | chirality | $R^3$ | 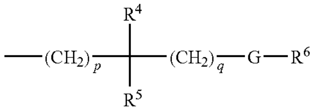 |
|---|---|---|---|---|---|---|---|
| 2223 | 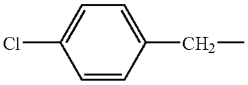 | 1 | 2 | 0 | R | H | 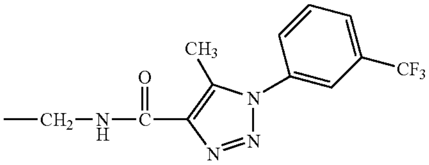 |
| 2224 | 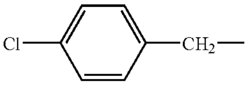 | 1 | 2 | 0 | R | H | 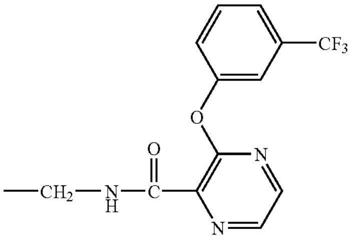 |
| 2225 | 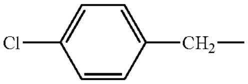 | 1 | 2 | 0 | R | H | 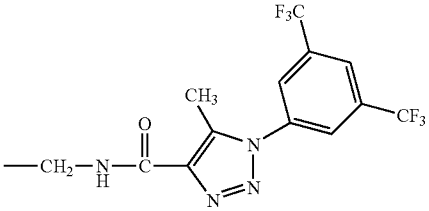 |
| 2226 | 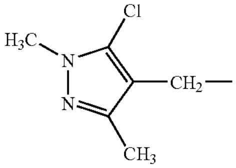 | 1 | 2 | 0 | R | H | 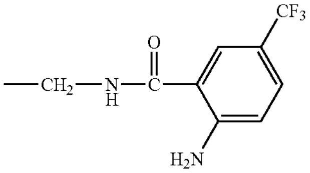 |
| 2227 | 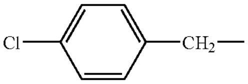 | 1 | 2 | 0 | R | H | 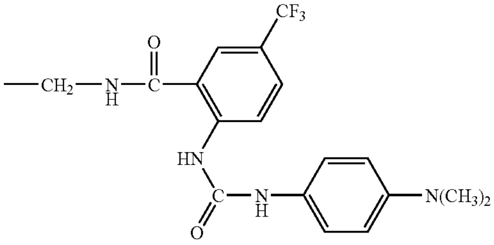 |
| 2228 | 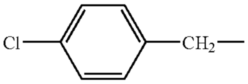 | 1 | 2 | 0 | R | H | 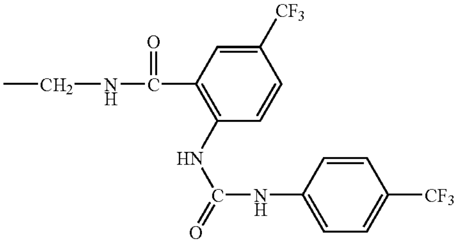 |

TABLE 1.203-continued
| Compd. No. | 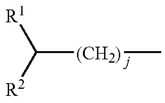 | k | m | n | chirality | $R^3$ | 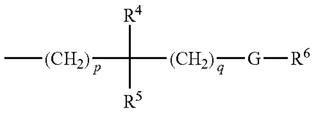 |
|---|---|---|---|---|---|---|---|
| 2229 | 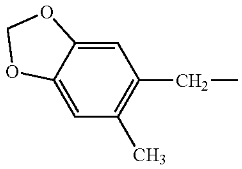 | 1 | 2 | 0 | R | H | 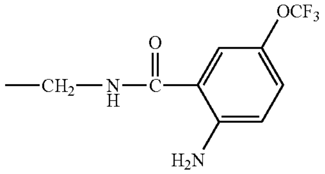 |
| 2230 | 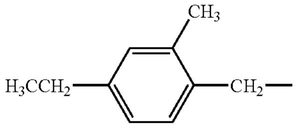 | 1 | 2 | 0 | R | H | 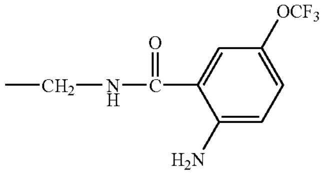 |
| 2231 | 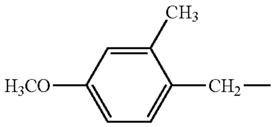 | 1 | 2 | 0 | R | H | 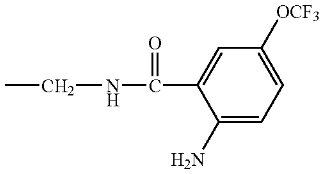 |
| 2232 | 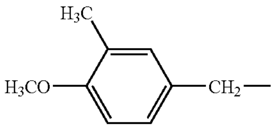 | 1 | 2 | 0 | R | H | 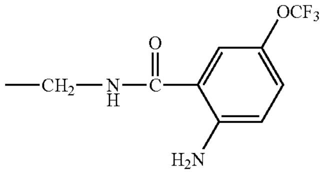 |
| 2233 | 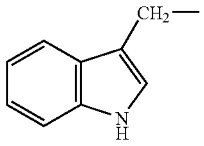 | 1 | 2 | 0 | R | H | 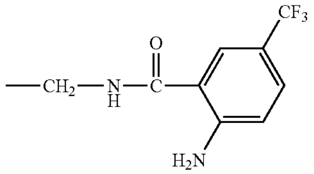 |
TABLE 1.204
| Compd. No. | 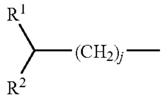 | k | m | n | chirality | $R^3$ | 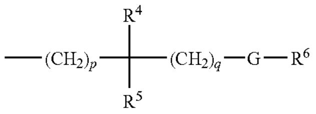 |
|---|---|---|---|---|---|---|---|
| 2234 | 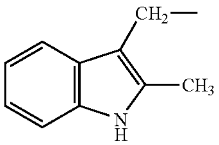 | 1 | 2 | 0 | R | H | 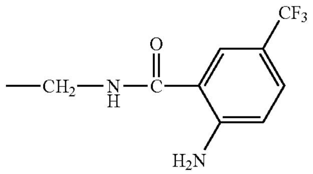 |

TABLE 1.204-continued
| Compd. No. | 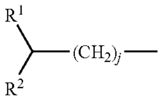 | k | m | n | chirality | $R^3$ | 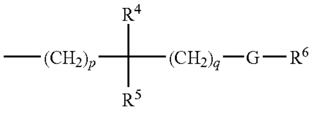 |
|---|---|---|---|---|---|---|---|
| 2235 | 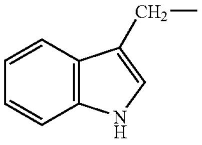 | 1 | 2 | 0 | R | H | 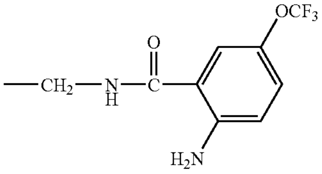 |
| 2236 | 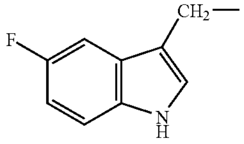 | 1 | 2 | 0 | R | H | 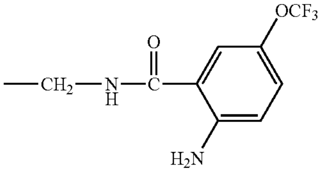 |
| 2237 | 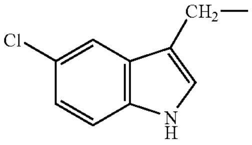 | 1 | 2 | 0 | R | H | 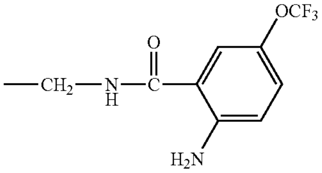 |
| 2238 | 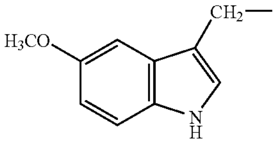 | 1 | 2 | 0 | R | H | 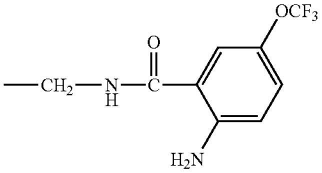 |
| 2239 | 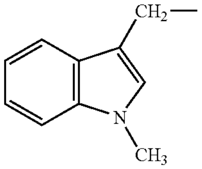 | 1 | 2 | 0 | R | H | 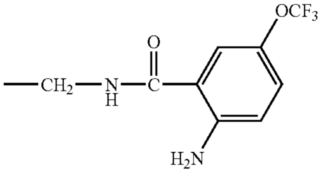 |
| 2240 | 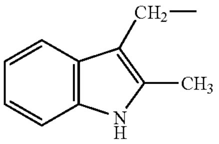 | 1 | 2 | 0 | R | H | 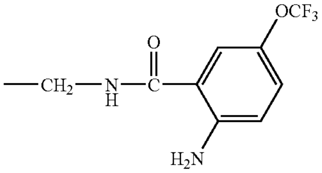 |
| 2241 | 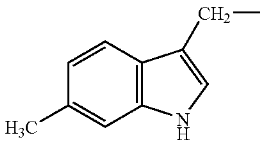 | 1 | 2 | 0 | R | H | 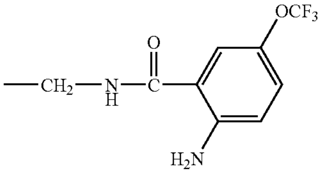 |

TABLE 1.204-continued
| Compd. No. | 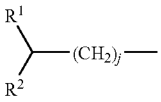 | k | m | n | chirality | $R^3$ | 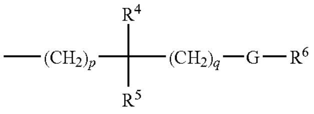 |
|---|---|---|---|---|---|---|---|
| 2242 | 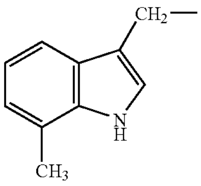 | 1 | 2 | 0 | R | H | 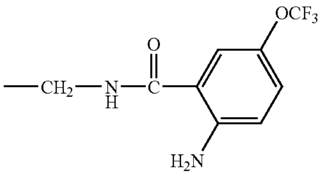 |
| 2243 | 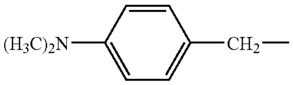 | 1 | 2 | 0 | R | H | 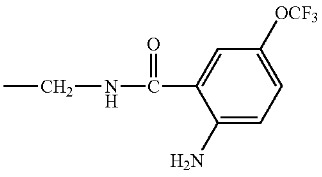 |
| 2244 | 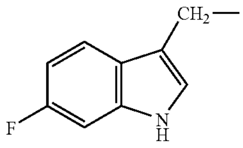 | 1 | 2 | 0 | R | H | 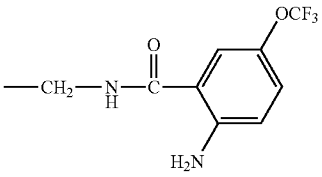 |
TABLE 1.205
| Compd. No. | 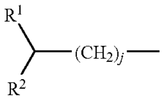 | k | m | n | chirality | $R^3$ | 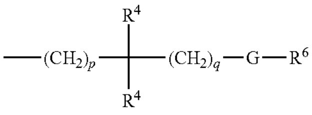 |
|---|---|---|---|---|---|---|---|
| 2245 | 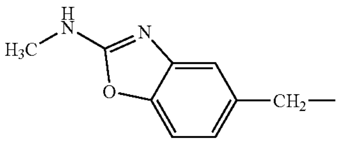 | 1 | 2 | 0 | R | H | 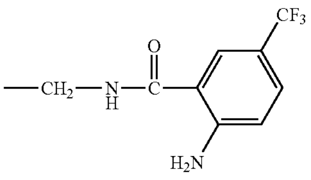 |
| 2246 | 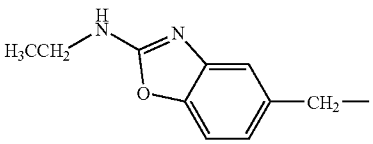 | 1 | 2 | 0 | R | H | 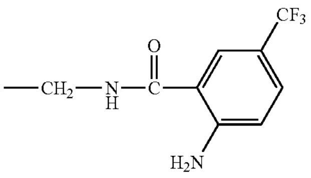 |
| 2247 | 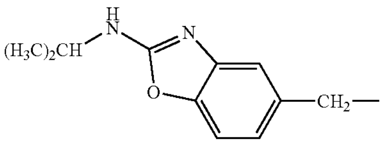 | 1 | 2 | 0 | R | H | 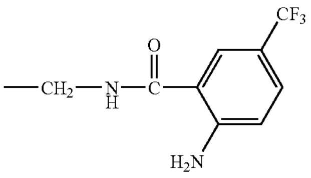 |

TABLE 1.205-continued
| Compd. No. | 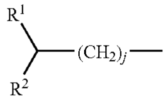 | k | m | n | chirality | $R^3$ | 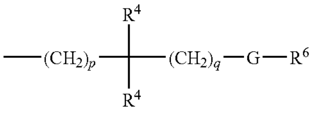 |
|---|---|---|---|---|---|---|---|
| 2248 | 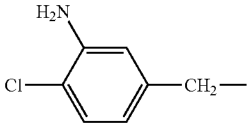 | 1 | 2 | 0 | R | H | 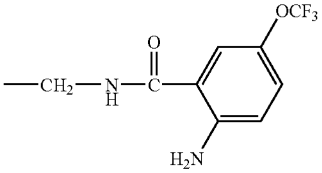 |
| 2249 | 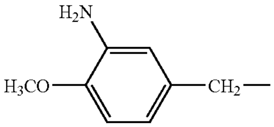 | 1 | 2 | 0 | R | H | 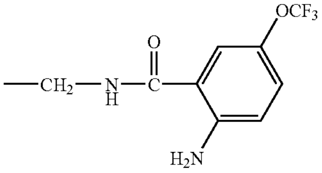 |
| 2250 | 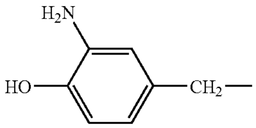 | 1 | 2 | 0 | R | H | 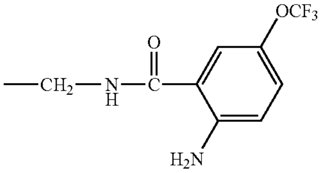 |
| 2251 | 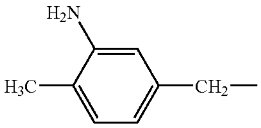 | 1 | 2 | 0 | R | H | 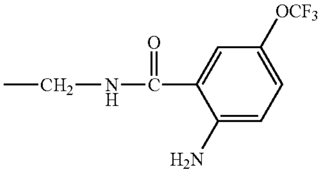 |
| 2252 | 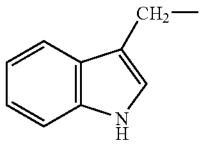 | 2 | 2 | 1 | — | H | 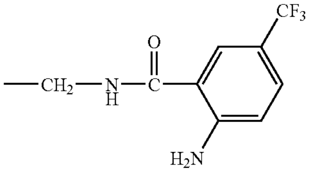 |
| 2253 | 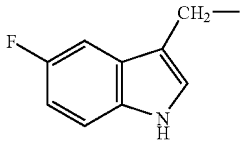 | 2 | 2 | 1 | — | H | 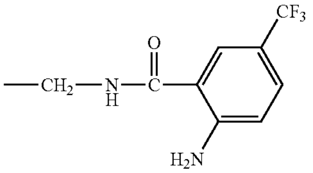 |
| 2254 | 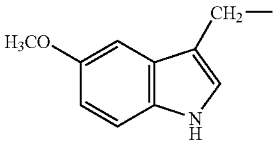 | 2 | 2 | 1 | — | H | 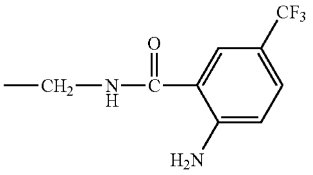 |

TABLE 1.205-continued
| Compd. No. | 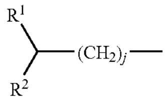 | k | m | n | chirality | $R^3$ | 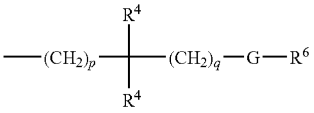 |
|---|---|---|---|---|---|---|---|
| 2255 | 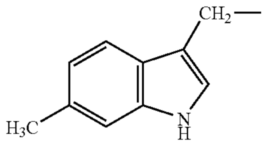 | 2 | 2 | 1 | — | H | 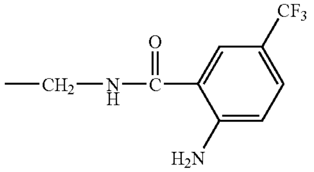 |
TABLE 1.206
| Compd. No. | 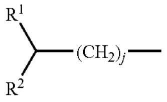 | k | m | n | chirality | $R^3$ | 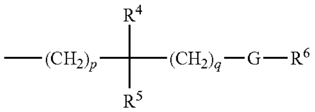 |
|---|---|---|---|---|---|---|---|
| 2256 | 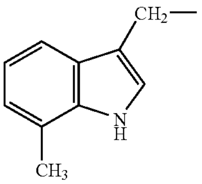 | 2 | 2 | 1 | — | H | 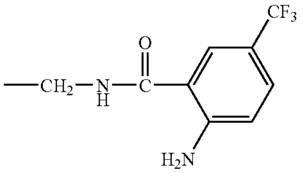 |
| 2257 | 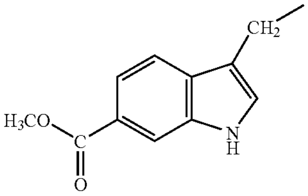 | 2 | 2 | 1 | — | H | 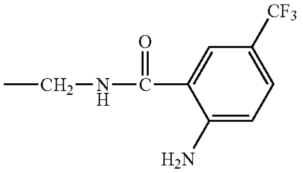 |
| 2258 | 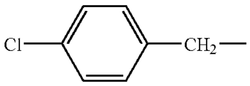 | 1 | 2 | 0 | R | H | 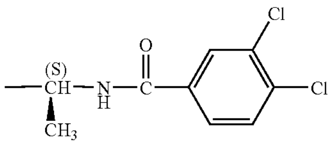 |
| 2259 | 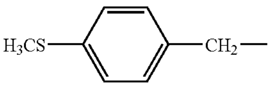 | 1 | 2 | 0 | R | H | 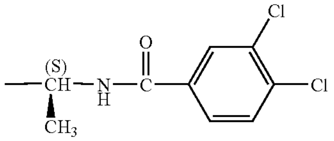 |
| 2260 | 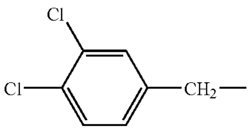 | 1 | 2 | 0 | R | H | 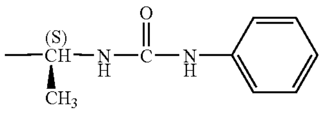 |
| 2261 | 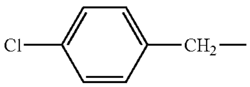 | 1 | 2 | 0 | R | H | 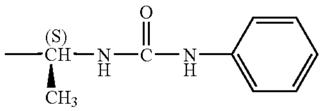 |

TABLE 1.206-continued
| Compd. No. | 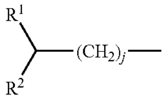 | k | m | n | chirality | $R^3$ | 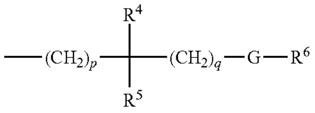 |
| --- | --- | --- | --- | --- | --- | --- | --- |
| 2262 | 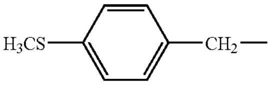 | 1 | 2 | 0 | R | H | 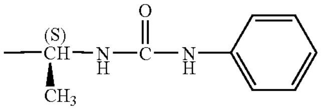 |
| 2263 | 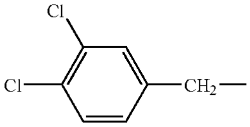 | 1 | 2 | 0 | S | H | 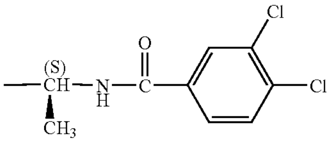 |
| 2264 | 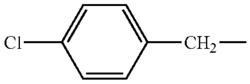 | 1 | 2 | 0 | S | H | 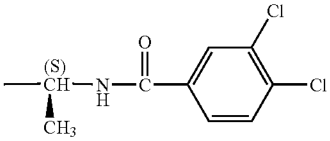 |
| 2265 | 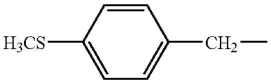 | 1 | 2 | 0 | S | H | 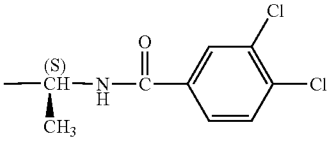 |
| 2266 | 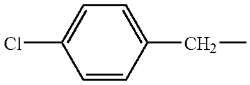 | 1 | 2 | 0 | S | H | 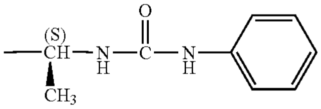 |
TABLE 1.207
| Compd. No. | 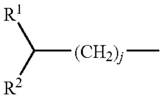 | k | m | n | chirality | $R^3$ | 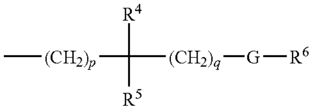 |
| --- | --- | --- | --- | --- | --- | --- | --- |
| 2267 | 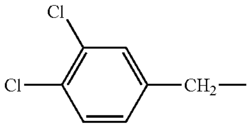 | 2 | 2 | 1 | - | H | 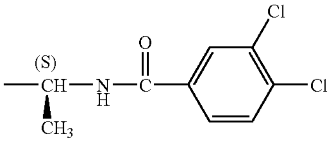 |
| 2268 | 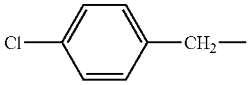 | 2 | 2 | 1 | - | H | 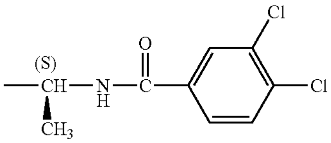 |
| 2269 | 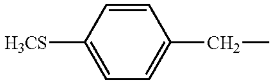 | 2 | 2 | 1 | - | H | 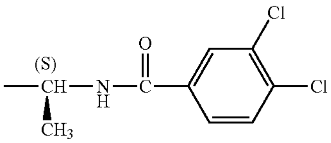 |

TABLE 1.207-continued
| Compd. No. | 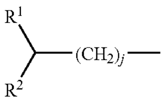 | k | m | n | chirality | $R^3$ | 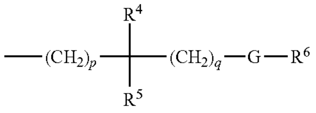 |
|---|---|---|---|---|---|---|---|
| 2270 | 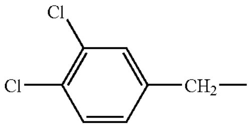 | 2 | 2 | 1 | - | H | 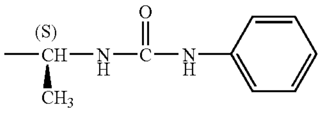 |
| 2271 | 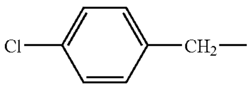 | 2 | 2 | 1 | - | H | 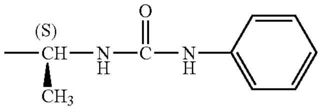 |
| 2272 | 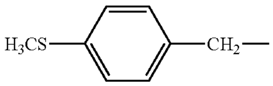 | 2 | 2 | 1 | - | H | 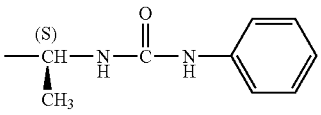 |
| 2273 | 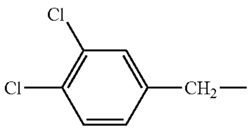 | 2 | 2 | 1 | - | H | 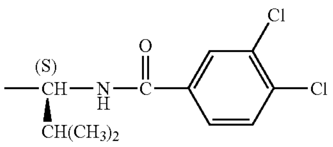 |
| 2274 | 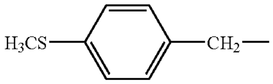 | 2 | 2 | 1 | - | H | 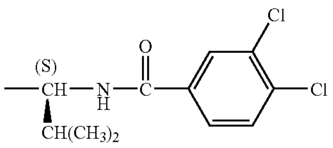 |
| 2275 | 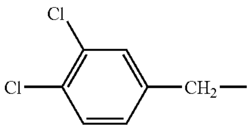 | 2 | 2 | 1 | - | H | 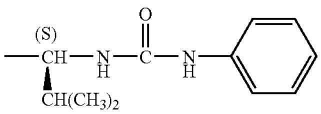 |
| 2276 | 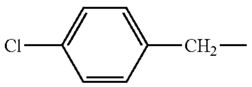 | 2 | 2 | 1 | - | H | 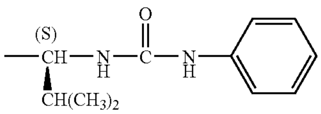 |
| 2277 | 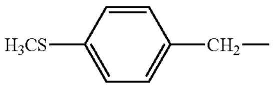 | 2 | 2 | 1 | - | H | 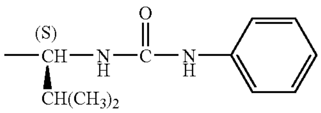 |

TABLE 1.208
| Compd. No. | 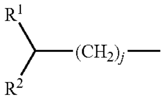 | k | m | n | chirality | $R^3$ | 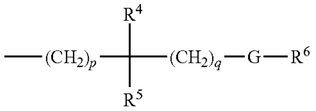 |
|---|---|---|---|---|---|---|---|
| 2278 | 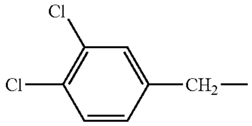 | 1 | 2 | 0 | R | H | 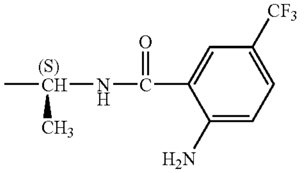 |
| 2279 | 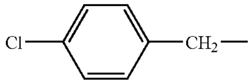 | 1 | 2 | 0 | R | H | 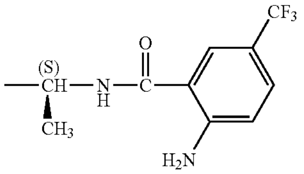 |
| 2280 | 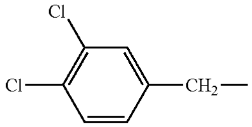 | 1 | 2 | 0 | S | H | 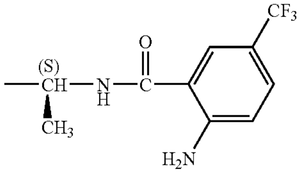 |
| 2281 | 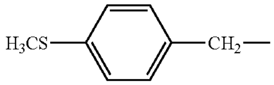 | 1 | 2 | 0 | S | H | 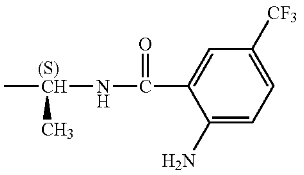 |
| 2282 | 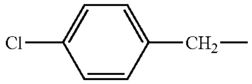 | 2 | 2 | 1 | - | H | 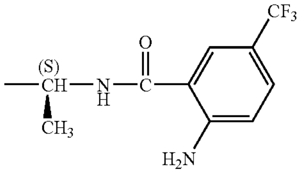 |
| 2283 | 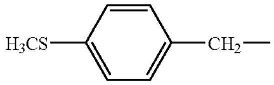 | 2 | 2 | 1 | - | H | 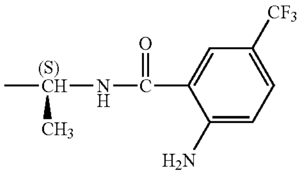 |
| 2284 | 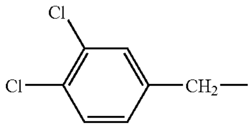 | 2 | 2 | 1 | - | H | 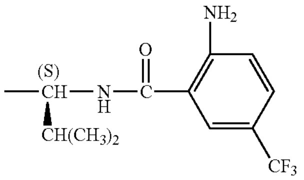 |
| 2285 | 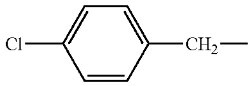 | 2 | 2 | 1 | - | H | 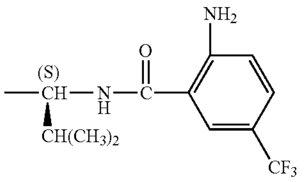 |

TABLE 1.208-continued
| Compd. No. | 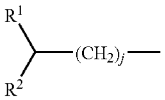 | k | m | n | chirality | $R^3$ | 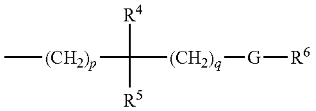 |
|---|---|---|---|---|---|---|---|
| 2286 | 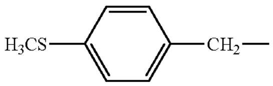 | 2 | 2 | 1 | - | H | 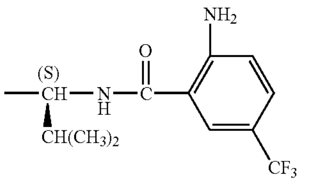 |
| 2287 | 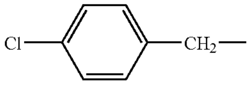 | 2 | 2 | 1 | - | H | 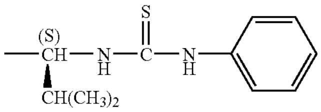 |
| 2288 | 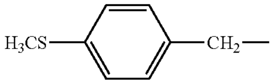 | 2 | 2 | 1 | - | H | 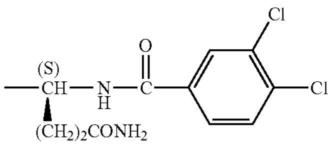 |
TABLE 1.209
| Compd. No. | 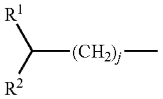 | k | m | n | chirality | $R^3$ | 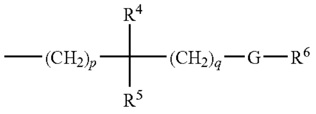 |
|---|---|---|---|---|---|---|---|
| 2289 | 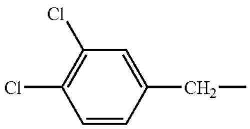 | 2 | 2 | 1 | - | H | 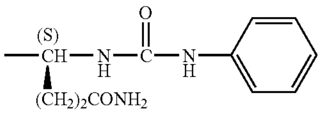 |
| 2290 | 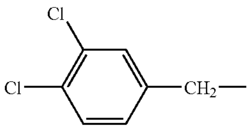 | 2 | 2 | 1 | - | H | 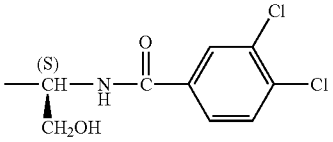 |
| 2291 | 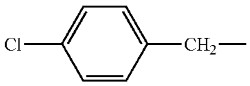 | 2 | 2 | 1 | - | H | 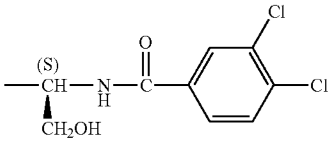 |
| 2292 | 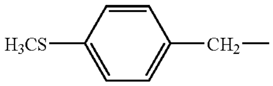 | 2 | 2 | 1 | - | H | 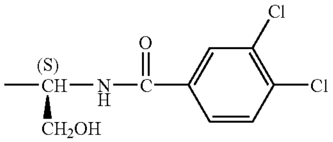 |
| 2293 | 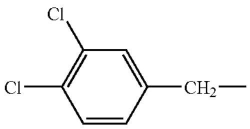 | 2 | 2 | 1 | - | H | 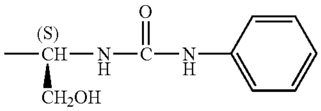 |

TABLE 1.209-continued
| Compd. No. | 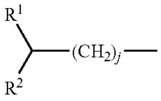 | k | m | n | chirality | $R^3$ | 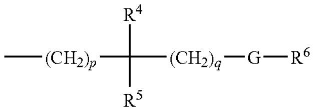 |
|---|---|---|---|---|---|---|---|
| 2294 | 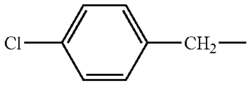 | 2 | 2 | 1 | - | H | 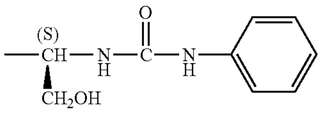 |
| 2295 | 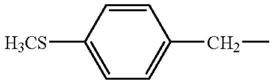 | 2 | 2 | 1 | - | H | 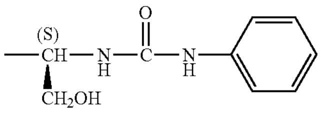 |
| 2296 | 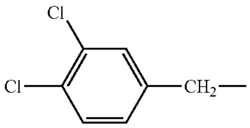 | 1 | 2 | 0 | R | H | 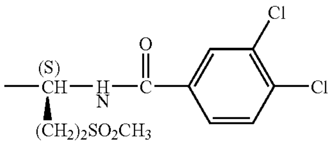 |
| 2297 | 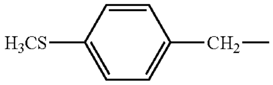 | 1 | 2 | 0 | R | H | 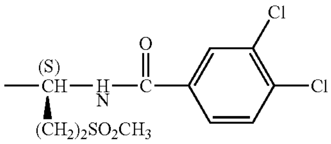 |
| 2298 | 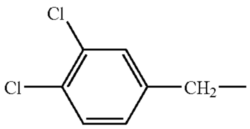 | 1 | 2 | 0 | R | H | 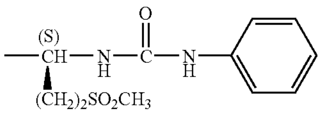 |
| 2299 | 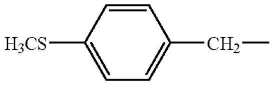 | 1 | 2 | 0 | R | H | 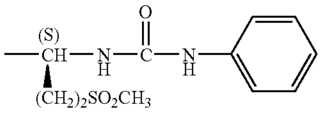 |
TABLE 1.210
| Compd. No. | 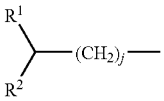 | k | m | n | chirality | $R^3$ | 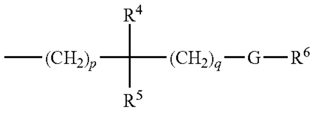 |
|---|---|---|---|---|---|---|---|
| 2300 | 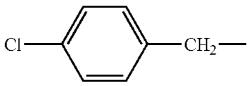 | 1 | 2 | 0 | S | H | 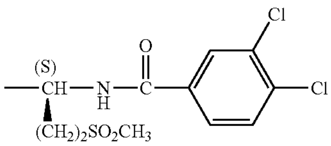 |
| 2301 | 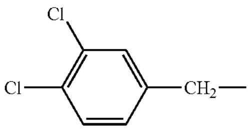 | 1 | 2 | 0 | S | H | 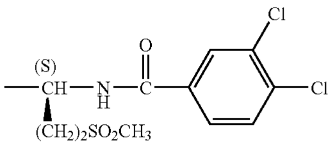 |

TABLE 1.210-continued
| Compd. No. | 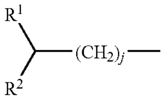 | k | m | n | chirality | $R^3$ | 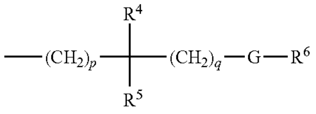 |
|---|---|---|---|---|---|---|---|
| 2302 | 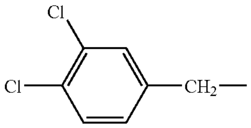 | 1 | 2 | 0 | R | H | 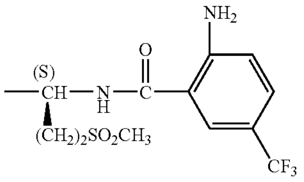 |
| 2303 | 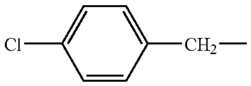 | 1 | 2 | 0 | R | H | 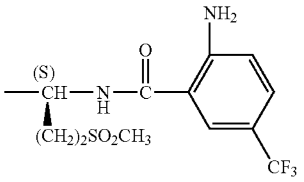 |
| 2304 | 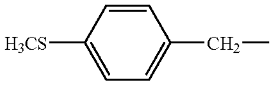 | 1 | 2 | 0 | R | H | 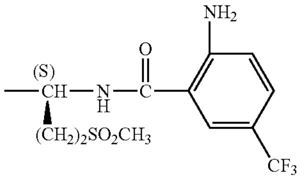 |
| 2305 | 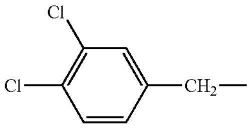 | 1 | 2 | 0 | S | H | 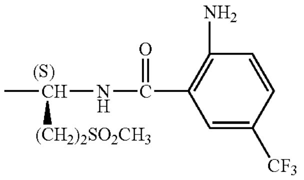 |
| 2306 | 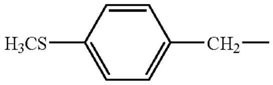 | 1 | 2 | 0 | S | H | 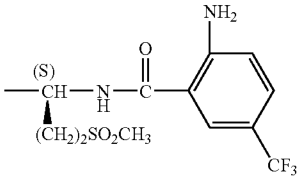 |
| 2307 | 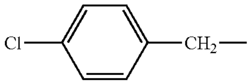 | 1 | 2 | 0 | R | H | 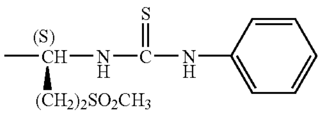 |
| 2308 | 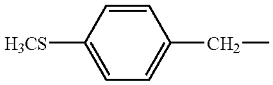 | 1 | 2 | 0 | R | H | 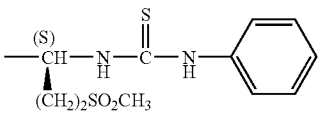 |
| 2309 | 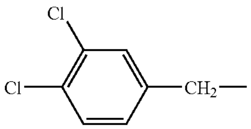 | 1 | 2 | 0 | S | H | 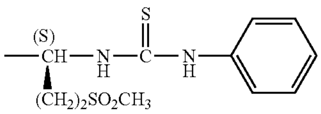 |

TABLE 1.210-continued
| Compd. No. | 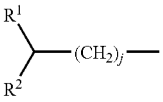 | k | m | n | chirality | $R^3$ | 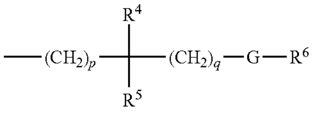 |
|---|---|---|---|---|---|---|---|
| 2310 | 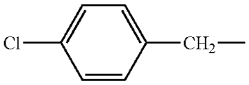 | 1 | 2 | 0 | S | H | 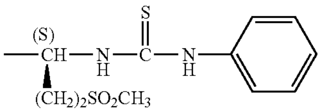 |
TABLE 1.211
| Compd. No. | 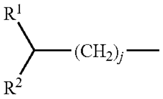 | k | m | n | chirality | $R^3$ | 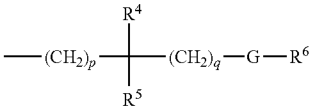 |
|---|---|---|---|---|---|---|---|
| 2311 | 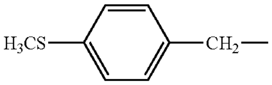 | 1 | 2 | 0 | S | H | 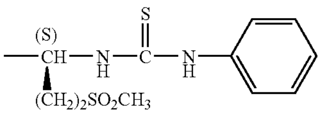 |
| 2312 | 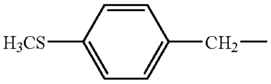 | 1 | 2 | 0 | R | H | 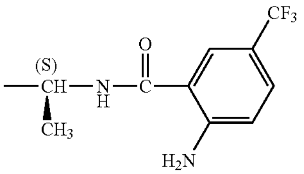 |
| 2313 | 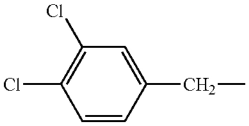 | 1 | 2 | 0 | R | H | 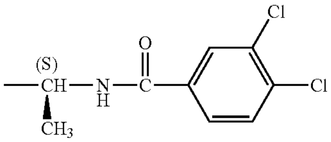 |
| 2314 | 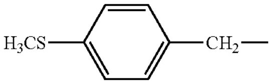 | 1 | 2 | 0 | S | H | 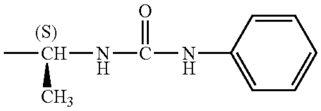 |
| 2315 | 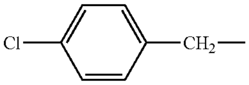 | 2 | 2 | 1 | - | H | 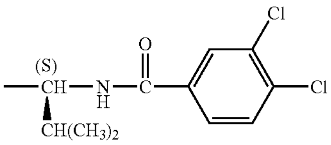 |
| 2316 | 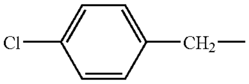 | 1 | 2 | 0 | S | H | 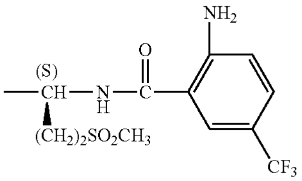 |

TABLE 1.211-continued
| Compd. No. | 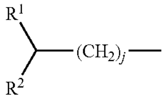 | k | m | n | chirality | $R^3$ | 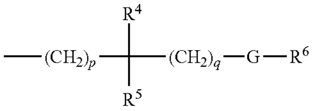 |
|---|---|---|---|---|---|---|---|
| 2317 | 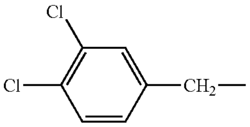 | 2 | 2 | 1 | - | H | 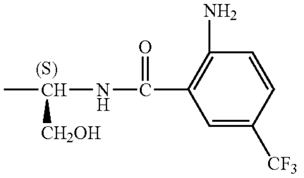 |
| 2318 | 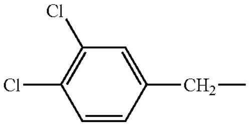 | 1 | 2 | 0 | R | H | 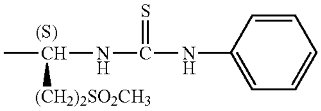 |
| 2319 | 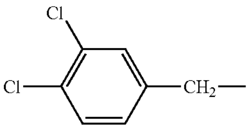 | 2 | 2 | 1 | - | H | 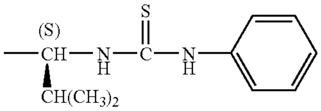 |
| 2320 | 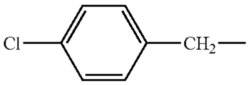 | 2 | 2 | 1 | - | H | 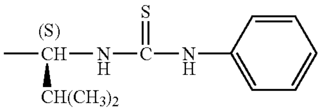 |
| 2321 | 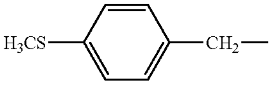 | 2 | 2 | 1 | - | H | 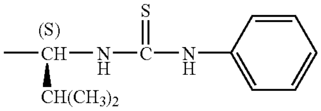 |
TABLE 1.212
| Compd. No. | 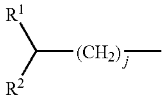 | k | m | n | chirality | $R^3$ | 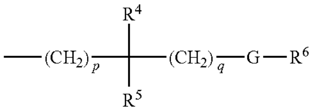 |
|---|---|---|---|---|---|---|---|
| 2322 | 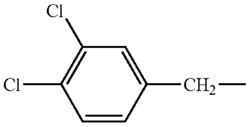 | 2 | 2 | 1 | - | H | 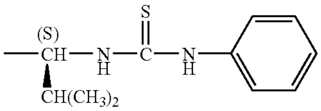 |
| 2323 | 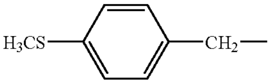 | 2 | 2 | 1 | - | H | 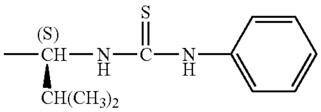 |
| 2324 | 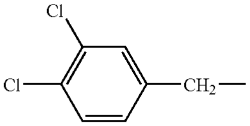 | 2 | 2 | 1 | - | H | 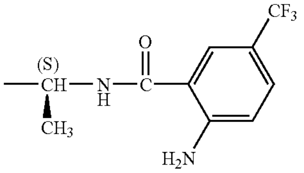 |

TABLE 1.212-continued
| Compd. No. | 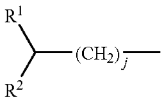 | k | m | n | chirality | $R^3$ | 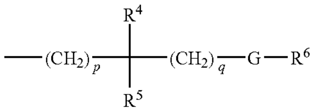 |
|---|---|---|---|---|---|---|---|
| 2325 | 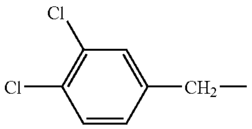 | 1 | 2 | 0 | R | H | 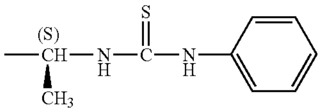 |
| 2326 | 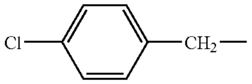 | 1 | 2 | 0 | R | H | 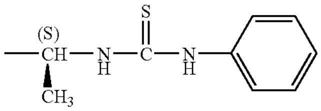 |
| 2327 | 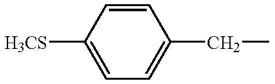 | 1 | 2 | 0 | S | H | 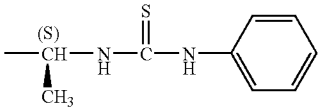 |
| 2328 | 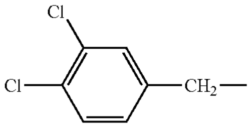 | 1 | 2 | 0 | S | H | 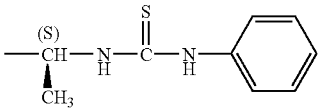 |
| 2329 | 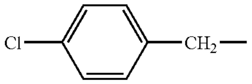 | 1 | 2 | 0 | S | H | 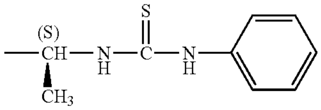 |
| 2330 | 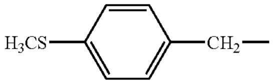 | 1 | 2 | 0 | S | H | 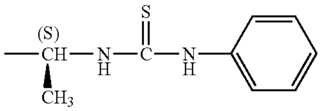 |
| 2331 | 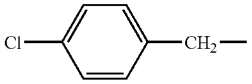 | 1 | 2 | 0 | S | H | 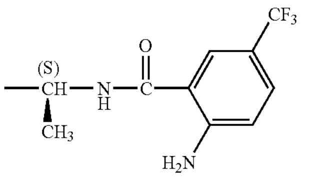 |
| 2332 | 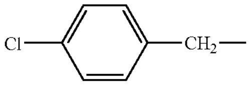 | 1 | 2 | 0 | R | H | 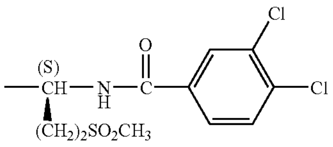 |
TABLE 1.213
| Compd. No. | 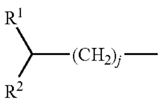 | k | m | n | chirality | $R^3$ | 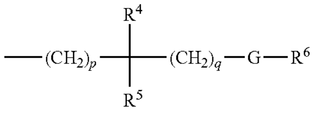 |
|---|---|---|---|---|---|---|---|
| 2333 | 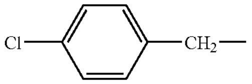 | 1 | 2 | 0 | R | H | 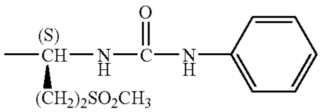 |

TABLE 1.213-continued
| Compd. No. | 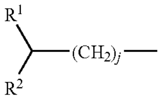 | k | m | n | chirality | $R^3$ | 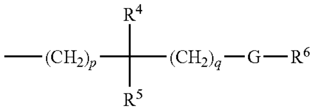 |
|---|---|---|---|---|---|---|---|
| 2334 | 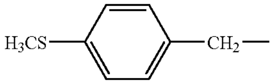 | 1 | 2 | 0 | S | H | 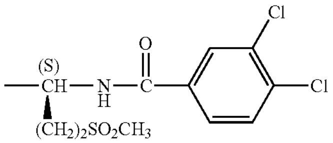 |
| 2335 | 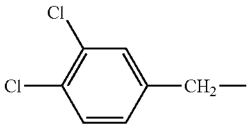 | 1 | 2 | 0 | S | H | 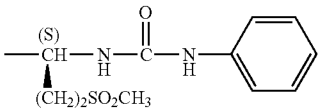 |
| 2336 | 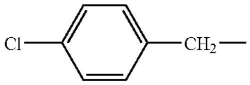 | 1 | 2 | 0 | S | H | 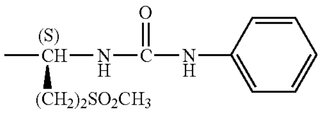 |
| 2337 | 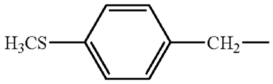 | 1 | 2 | 0 | S | H | 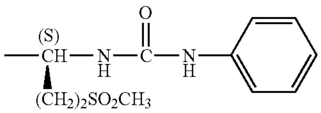 |
| 2338 | 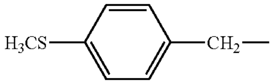 | 2 | 2 | 1 | - | H | 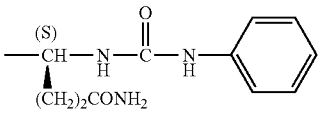 |
| 2339 | 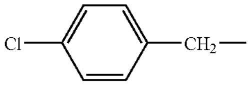 | 2 | 2 | 1 | - | H | 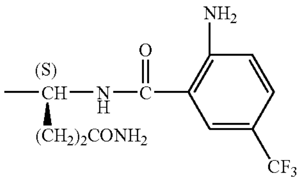 |
| 2340 | 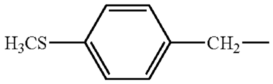 | 2 | 2 | 1 | - | H | 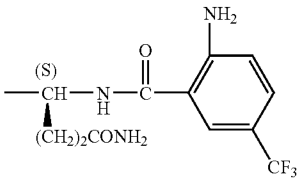 |
| 2341 | 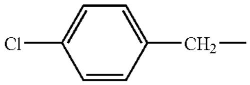 | 2 | 2 | 1 | - | H | 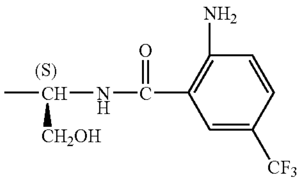 |
| 2342 | 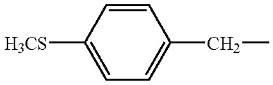 | 2 | 2 | 1 | - | H | 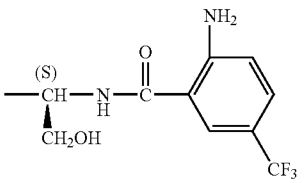 |

TABLE 1.213-continued
| Compd. No. | 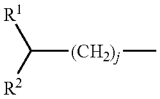 | k | m | n | chirality | $R^3$ | 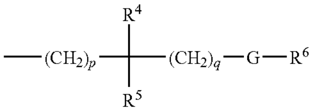 |
|---|---|---|---|---|---|---|---|
| 2343 | 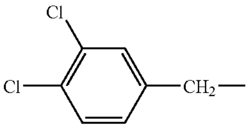 | 2 | 2 | 1 | - | H | 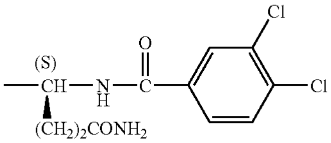 |
TABLE 1.214
| Compd. No. | 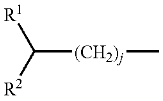 | k | m | n | chirality | $R^3$ | 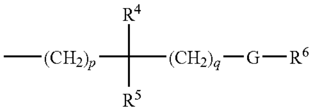 |
|---|---|---|---|---|---|---|---|
| 2344 | 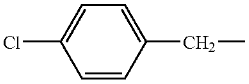 | 2 | 2 | 1 | - | H | 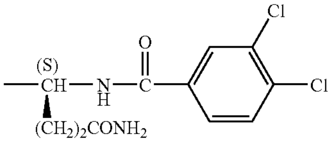 |
| 2345 | 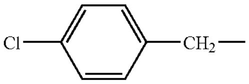 | 2 | 2 | 1 | - | H | 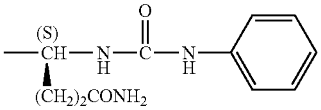 |
| 2346 | 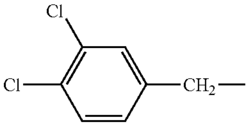 | 2 | 2 | 1 | - | H | 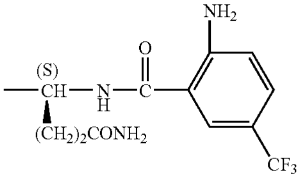 |
| 2347 | 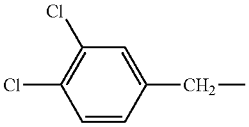 | 1 | 2 | 0 | S | H | 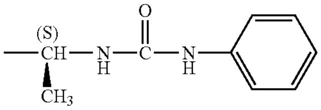 |
| 2348 | 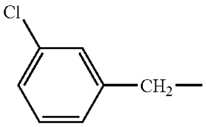 | 1 | 2 | 0 | R | H | 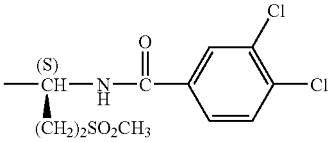 |
| 2349 | 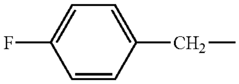 | 1 | 2 | 0 | R | H | 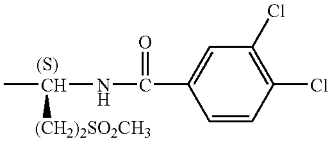 |
| 2350 | 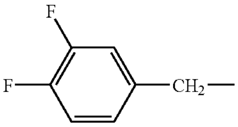 | 1 | 2 | 0 | R | H | 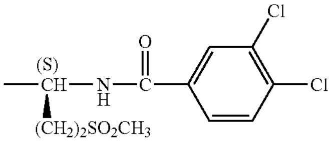 |

TABLE 1.214-continued
| Compd. No. | 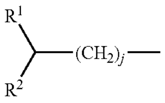 | k | m | n | chirality | $R^3$ | 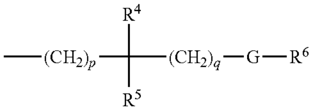 |
|---|---|---|---|---|---|---|---|
| 2351 | 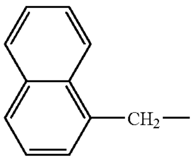 | 1 | 2 | 0 | R | H | 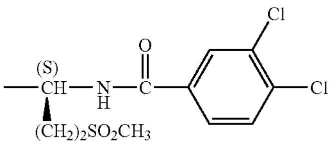 |
| 2352 | 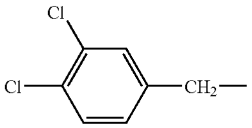 | 2 | 2 | 1 | - | H | 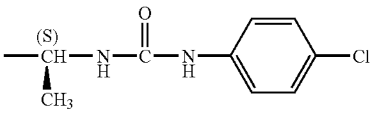 |
| 2353 | 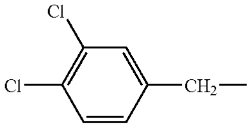 | 2 | 2 | 1 | - | H | 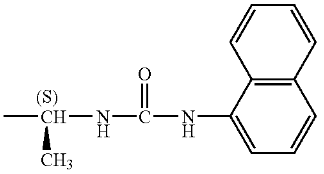 |
| 2354 | 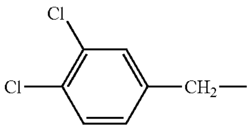 | 1 | 2 | 0 | R | H | 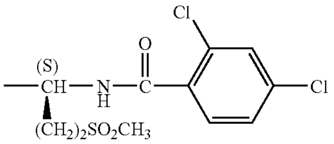 |
TABLE 1.215
| Compd. No. | 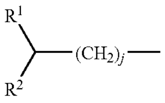 | k | m | n | chirality | $R^3$ | 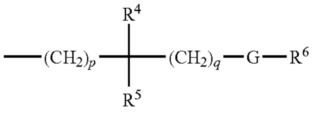 |
|---|---|---|---|---|---|---|---|
| 2344 | 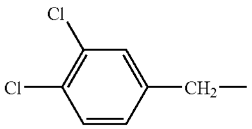 | 1 | 2 | 0 | R | H | 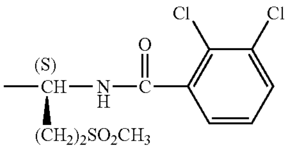 |
| 2345 | 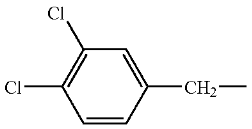 | 1 | 2 | 0 | R | H | 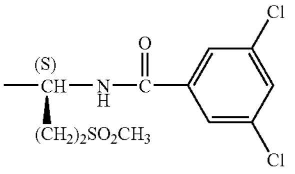 |
| 2346 | 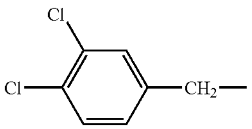 | 1 | 2 | 0 | R | H | 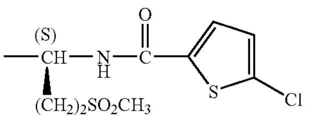 |
| 2347 | 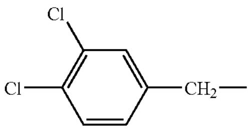 | 1 | 2 | 0 | R | H | 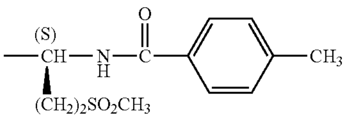 |

TABLE 1.215-continued
| Compd. No. | 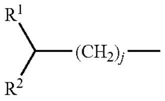 | k | m | n | chirality | $R^3$ | 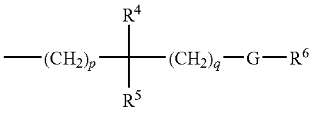 |
|---|---|---|---|---|---|---|---|
| 2348 | 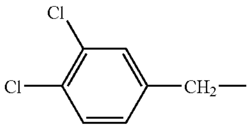 | 1 | 2 | 0 | R | H | 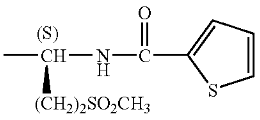 |
| 2349 | 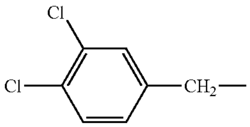 | 1 | 2 | 0 | R | H | 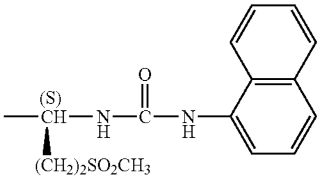 |
| 2350 | 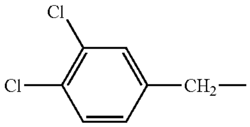 | 1 | 2 | 0 | R | H | 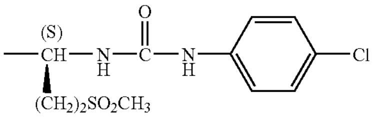 |
| 2351 | 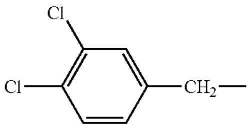 | 1 | 2 | 0 | R | H | 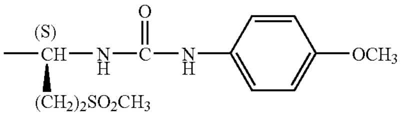 |
| 2352 | 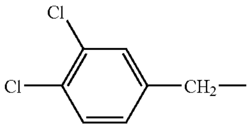 | 2 | 2 | 1 | - | H | 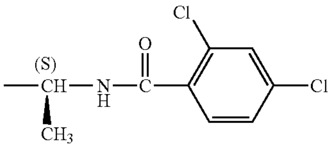 |
| 2353 | 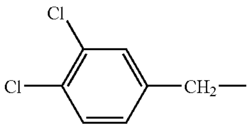 | 2 | 2 | 1 | - | H | 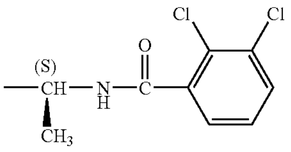 |
| 2354 | 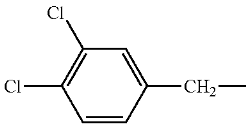 | 2 | 2 | 1 | - | H | 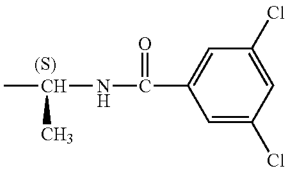 |
TABLE 1.216
| Compd. No. | 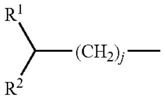 | k | m | n | chirality | $R^3$ | 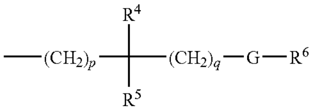 |
|---|---|---|---|---|---|---|---|
| 2366 | 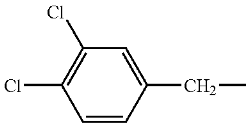 | 2 | 2 | 1 | - | H | 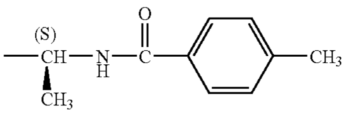 |

TABLE 1.216-continued
| Compd. No. | 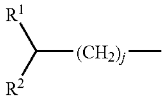 | k | m | n | chirality | $R^3$ | 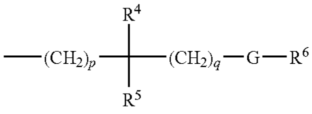 |
|---|---|---|---|---|---|---|---|
| 2367 | 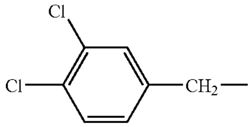 | 2 | 2 | 1 | - | H | 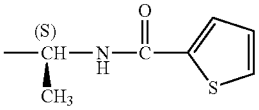 |
| 2368 | 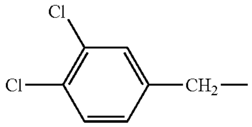 | 2 | 2 | 1 | - | H | 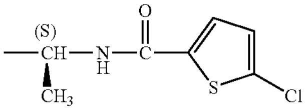 |
| 2369 | 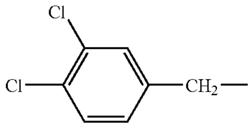 | 2 | 2 | 1 | - | H | 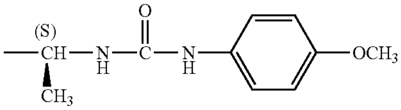 |
| 2370 | 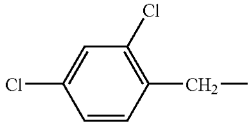 | 2 | 2 | 1 | - | H | 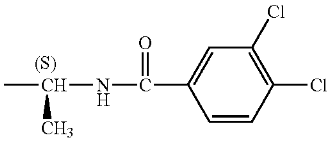 |
| 2371 | 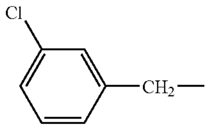 | 2 | 2 | 1 | - | H | 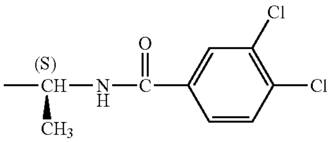 |
| 2372 | 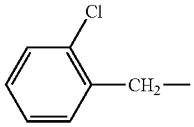 | 2 | 2 | 1 | - | H | 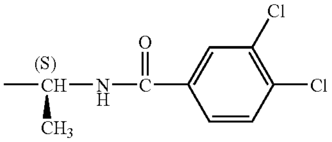 |
| 2373 | 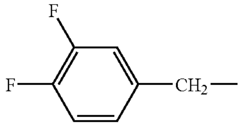 | 2 | 2 | 1 | - | H | 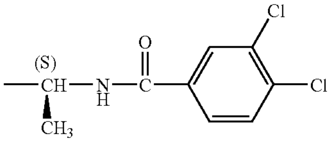 |
| 2374 | 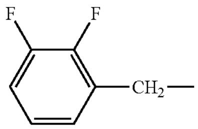 | 2 | 2 | 1 | - | H | 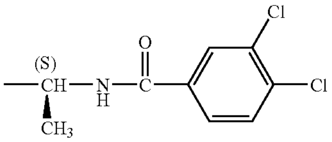 |
| 2375 | 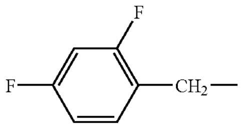 | 2 | 2 | 1 | - | H | 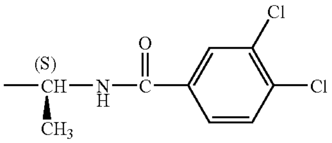 |

TABLE 1.216-continued
| Compd. No. | 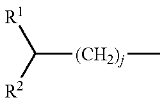 | k | m | n | chirality | $R^3$ | 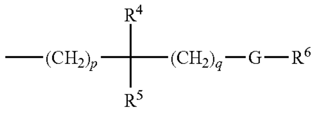 |
| --- | --- | --- | --- | --- | --- | --- | --- |
| 2376 | 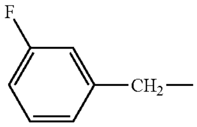 | 2 | 2 | 1 | - | H | 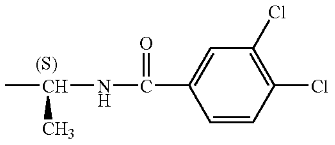 |
TABLE 1.217
| Compd. No. | 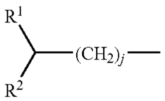 | k | m | n | chirality | $R^3$ | 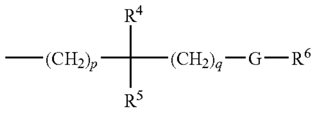 |
| --- | --- | --- | --- | --- | --- | --- | --- |
| 2377 | 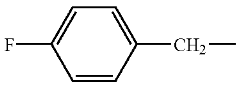 | 2 | 2 | 1 | - | H | 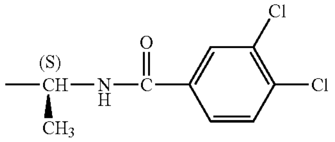 |
| 2378 | 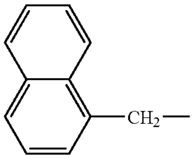 | 2 | 2 | 1 | - | H | 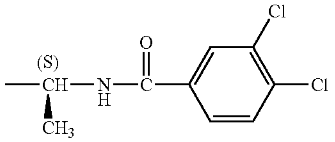 |
| 2379 | 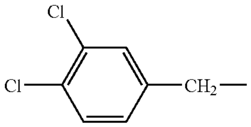 | 2 | 2 | 1 | - | H | 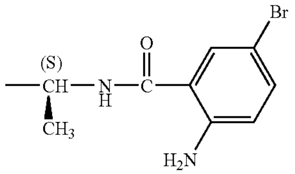 |
| 2380 | 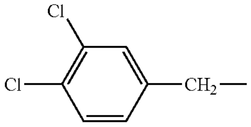 | 2 | 2 | 1 | - | H | 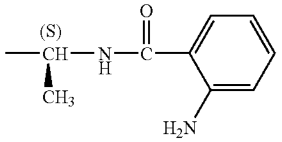 |
| 2381 | 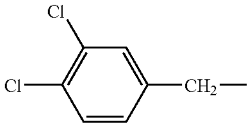 | 2 | 2 | 1 | - | H | 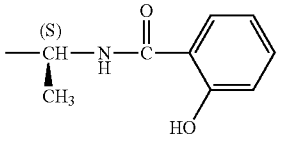 |
| 2382 | 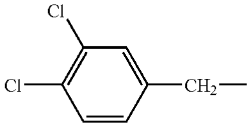 | 2 | 2 | 1 | - | H | 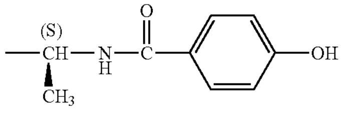 |
| 2383 | 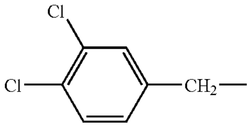 | 2 | 2 | 1 | - | H | 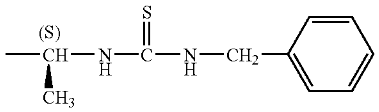 |

TABLE 1.217-continued
| Compd. No. | 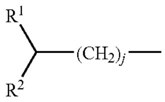 | k | m | n | chirality | $R^3$ | 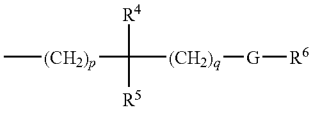 |
|---|---|---|---|---|---|---|---|
| 2384 | 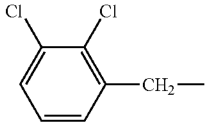 | 1 | 2 | 0 | R | H | 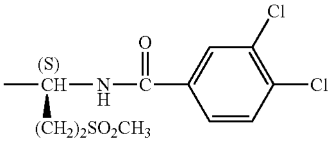 |
| 2385 | 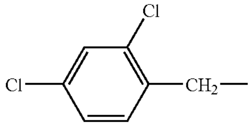 | 1 | 2 | 0 | R | H | 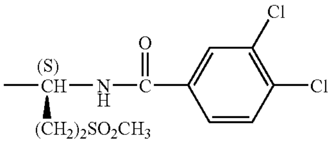 |
| 2386 | 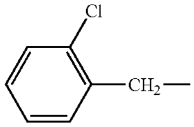 | 1 | 2 | 0 | R | H | 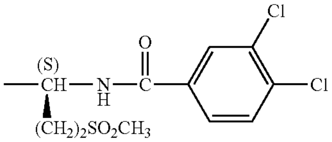 |
| 2387 | 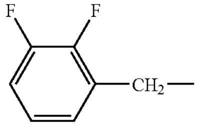 | 1 | 2 | 0 | R | H | 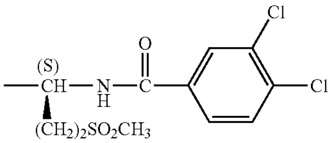 |
TABLE 1.218
| Compd. No. | 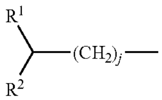 | k | m | n | chirality | $R^3$ | 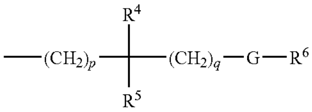 |
|---|---|---|---|---|---|---|---|
| 2388 | 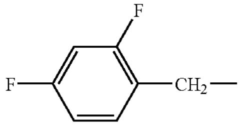 | 1 | 2 | 0 | R | H | 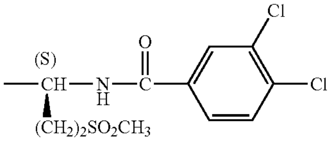 |
| 2389 | 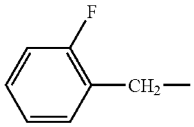 | 1 | 2 | 0 | R | H | 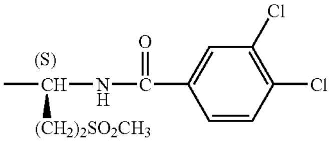 |
| 2390 | 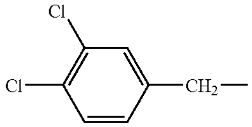 | 1 | 2 | 0 | R | H | 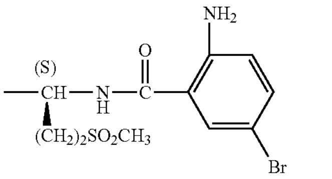 |

TABLE 1.218-continued
| Compd. No. | 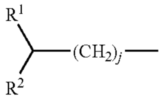 | k | m | n | chirality | $R^3$ | 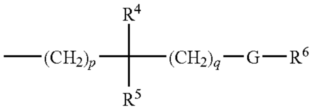 |
|---|---|---|---|---|---|---|---|
| 2391 | 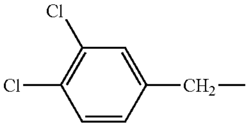 | 1 | 2 | 0 | R | H | 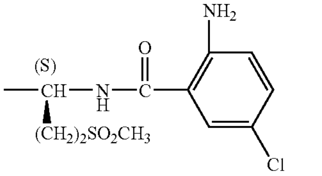 |
| 2392 | 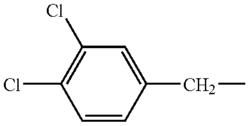 | 1 | 2 | 0 | R | H | 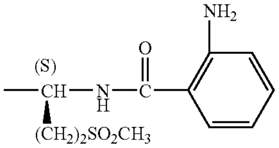 |
| 2393 | 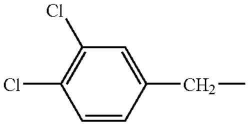 | 1 | 2 | 0 | R | H | 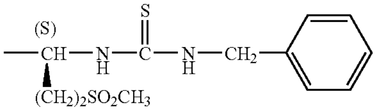 |
| 2394 | 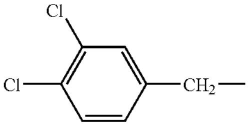 | 2 | 2 | 1 | - | H | 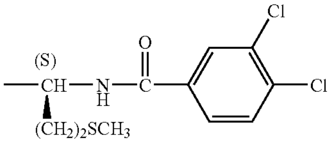 |
| 2395 | 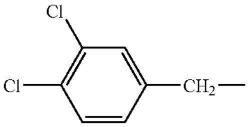 | 2 | 2 | 1 | - | H | 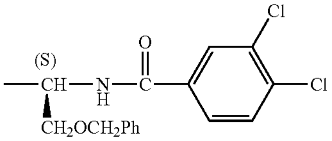 |
| 2396 | 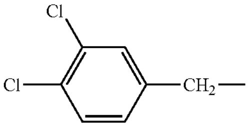 | 2 | 2 | 1 | - | H | 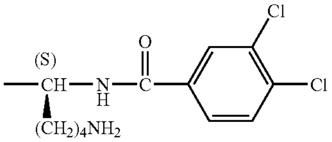 |
| 2397 | 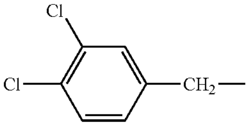 | 2 | 2 | 1 | - | H | 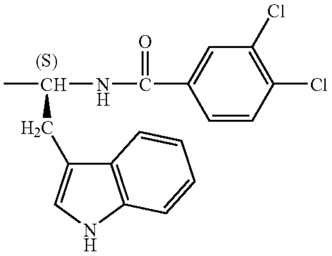 |
| 2398 | 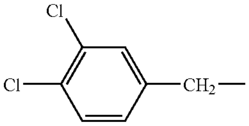 | 2 | 2 | 1 | - | H | 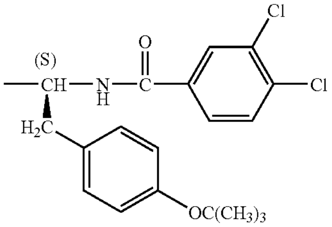 |

TABLE 1.219
| Compd. No. | 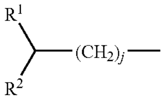 | k | m | n | chirality | $R^3$ | 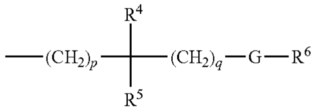 |
|---|---|---|---|---|---|---|---|
| 2399 | 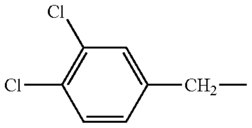 | 2 | 2 | 1 | - | H | 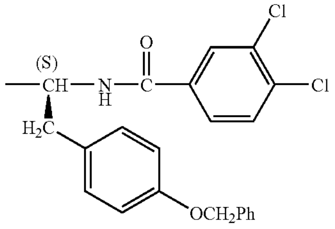 |
| 2400 | 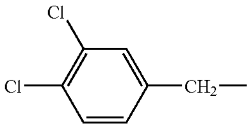 | 2 | 2 | 1 | - | H | 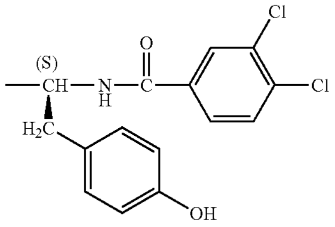 |
| 2401 | 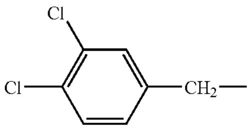 | 2 | 2 | 1 | - | H | 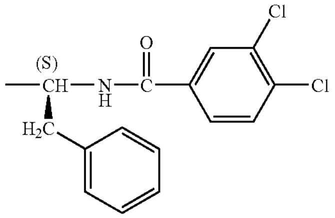 |
| 2402 | 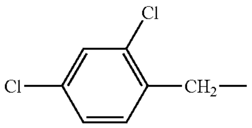 | 2 | 2 | 1 | - | H | 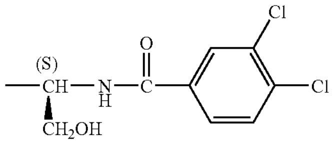 |
| 2403 | 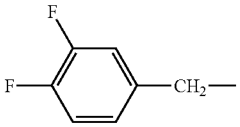 | 2 | 2 | 1 | - | H | 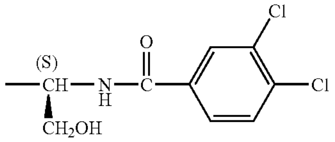 |
| 2404 | 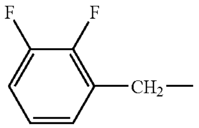 | 2 | 2 | 1 | - | H | 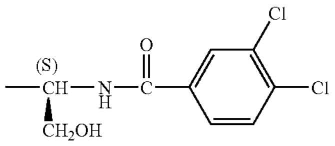 |
| 2405 | 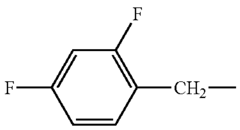 | 2 | 2 | 1 | - | H | 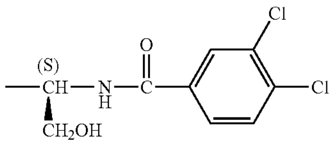 |
| 2406 | 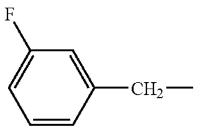 | 2 | 2 | 1 | - | H | 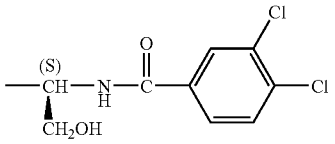 |

TABLE 1.219-continued
| Compd. No. | 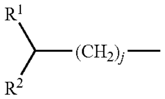 | k | m | n | chirality | $R^3$ | 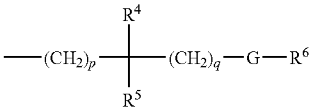 |
|---|---|---|---|---|---|---|---|
| 2407 | 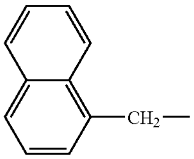 | 2 | 2 | 1 | - | H | 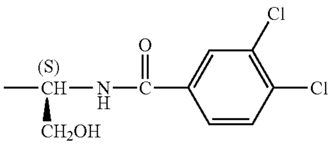 |
| 2408 | 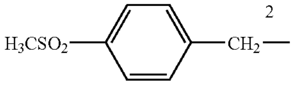 | 2 | 2 | 1 | - | H | 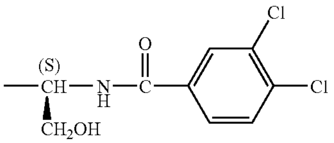 |
| 2409 | 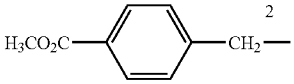 | 2 | 2 | 1 | - | H | 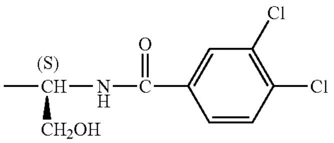 |
TABLE 1.220
| Compd. No. | 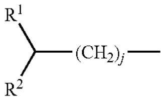 | k | m | n | chirality | $R^3$ | 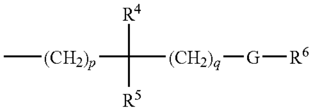 |
|---|---|---|---|---|---|---|---|
| 2410 | 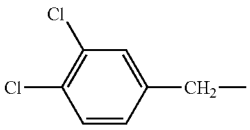 | 2 | 2 | 1 | - | H | 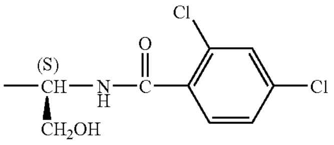 |
| 2411 | 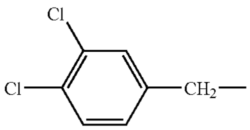 | 2 | 2 | 1 | - | H | 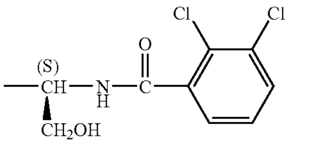 |
| 2412 | 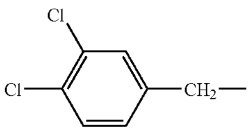 | 2 | 2 | 1 | - | H | 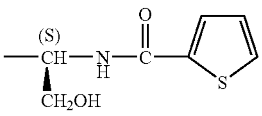 |
| 2413 | 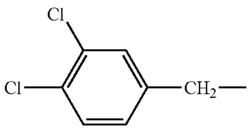 | 2 | 2 | 1 | - | H | 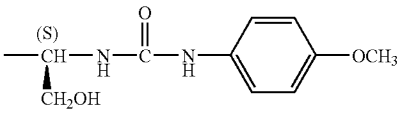 |
| 2414 | 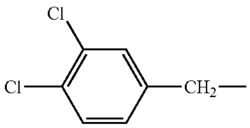 | 2 | 2 | 1 | - | H | 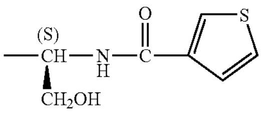 |

TABLE 1.220-continued
| Compd. No. | 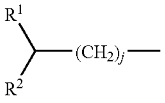 | k | m | n | chirality | $R^3$ | 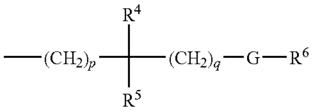 |
|---|---|---|---|---|---|---|---|
| 2415 | 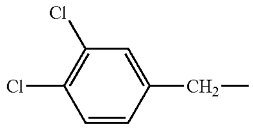 | 2 | 2 | 1 | - | H | 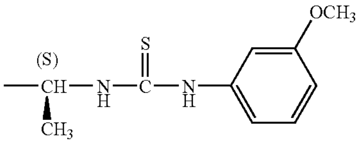 |
| 2416 | 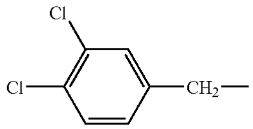 | 2 | 2 | 1 | - | H | 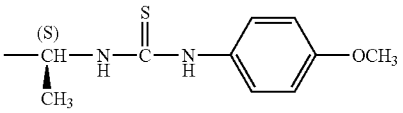 |
| 2417 | 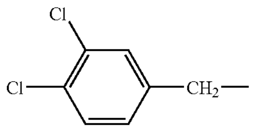 | 2 | 2 | 1 | - | H | 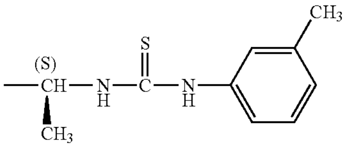 |
| 2418 | 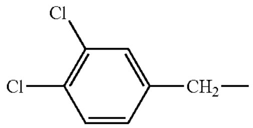 | 2 | 2 | 1 | - | H | 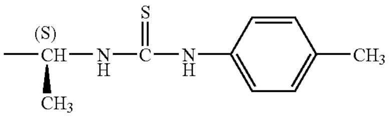 |
| 2419 | 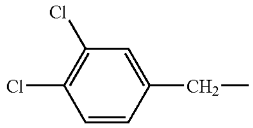 | 2 | 2 | 1 | - | H | 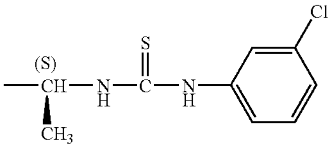 |
| 2420 | 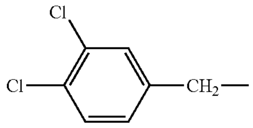 | 2 | 2 | 1 | - | H | 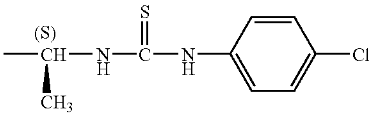 |
TABLE 1.221
| Compd. No. | 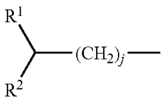 | k | m | n | chirality | $R^3$ | 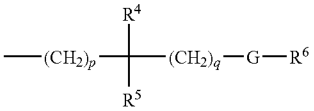 |
|---|---|---|---|---|---|---|---|
| 2421 | 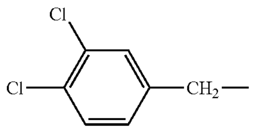 | 2 | 2 | 1 | - | H | 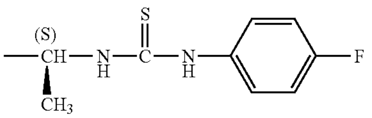 |
| 2422 | 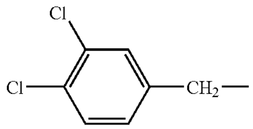 | 1 | 2 | 0 | R | H | 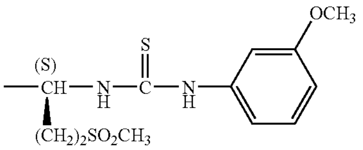 |

TABLE 1.221-continued

| Compd. No. | 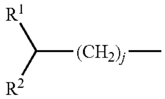 | k | m | n | chirality | $R^3$ | 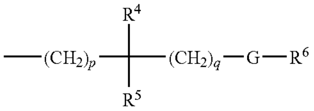 |
|---|---|---|---|---|---|---|---|
| 2423 | 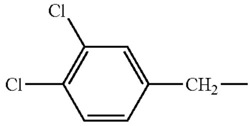 | 1 | 2 | 0 | R | H | 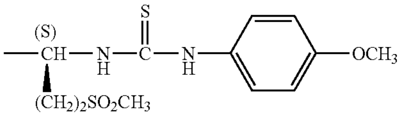 |
| 2424 | 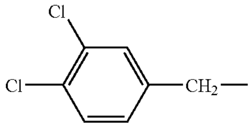 | 1 | 2 | 0 | R | H | 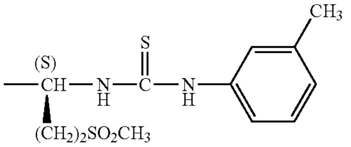 |
| 2425 | 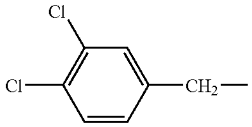 | 1 | 2 | 0 | R | H | 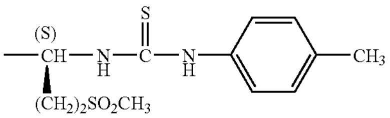 |
| 2426 | 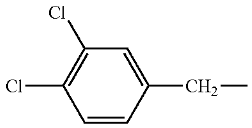 | 1 | 2 | 0 | R | H | 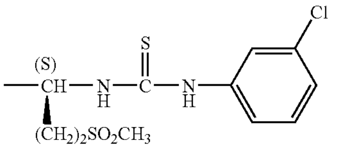 |
| 2427 | 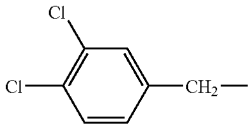 | 1 | 2 | 0 | R | H | 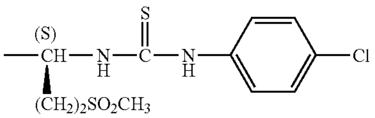 |
| 2428 | 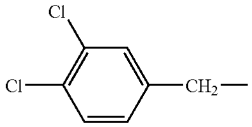 | 1 | 2 | 0 | R | H | 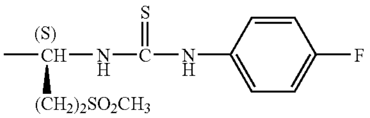 |

In the present invention, the acid addition salt of the cyclic amine compound is also used. The acid includes mineral acids such as hydrochloric acid, hydrobromic acid, sulfuric acid, phosphoric acid, and carbonic acid and organic acids such as maleic acid, citric acid, malic acid, tartaric acid, fumaric acid, methanesulfonic acid, trifluoroacetic acid and formic acid.

Further, the $C_1$ to $C_6$ alkyl addition salt of the cyclic amine compound such as 1-(4-chlorobenzyl)-1-methyl-4-[{N-(3-trifluoromethylbenzoyl)glycyl} aminomethyl]piperidinium iodide is also used in the present invention. The alkyl group includes a methyl group, an ethyl group, an n-propyl group, an n-butyl group, an n-pentyl group, an n-hexyl group, an n-heptyl group, an n-octyl group, an isopropyl group, an isobutyl group, a sec-butyl group, a tert-butyl group, an isopentyl group, a neopentyl group, a tert-pentyl group, a 2-methylpentyl group and a 1-ethylbutyl group as suitable examples, but includes the methyl group and the ethyl group as especially preferable concrete examples. The counter anion of the ammonium cation includes halide anions such as a fluoride ion, a chloride ion, a bromide ion and an iodide ion as suitable concrete examples.

In the present invention, the racemate and all the possible optical isomers of the compound represented by the formula (I) can be used.

The compound represented by the formula (I) can be synthesized by either of the following general preparation methods, as mentioned in WO 99/25686.

(Preparation Method 1)

A preparation method by reacting 1 equivalent of a compound represented by the following formula (II)

(II)

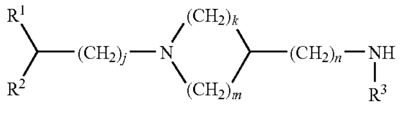

[wherein, $R^1$, $R^2$, $R^3$, j, k, m, and n are the same as the definitions, respectively, in the above-described formula (I)], with 0.1 to 10 equivalents of a carboxylic acid represented by the following formula (III) or a reactive derivative thereof (III)

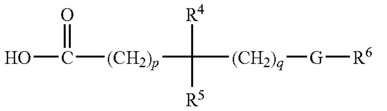

[wherein, $R^4$, $R^5$, $R^6$, G, p, and q are the same as the definitions, respectively, in the above-mentioned formula (I)], in the absence or presence of a solvent.

"The reactive derivative" of the carboxylic acid represented by the above-mentioned formula (III) means a highly reactive carboxylic acid derivative usually used in the field of synthetic organic chemistry, such as an acid halide, an acid anhydride, a mixed acid anhydride or the like.

The reaction can be allowed to smoothly proceed by the suitable use of proper amounts of a dehydrating agent, such as molecular sieve; a coupling reagent such as dicyclohexylcarbodiimide (DCC), N-ethyl-N'-(3-dimethylaminopropyl)carbodiimide (EDCI or WSC), carbonyldiimidazole (CDI), N-hydroxysuccinimide (HOSu), N-hydroxybenzotriazole (HOBt), benzotriazol-1-yloxytris(pyrrolidino)phosphonium hexafluorophosphate (PyBOP), 2-(1H-benzotriazol-1-yl)-1,1,3,3-tetramthyluronium hexafluorophosphate (HBTU), 2-(1H-benzotriazol-1-yl)-1,1,3,3-tetramethyluronium tetrafluoroborate (TBTU), 2-(5-norbornene-2,3-dicarboxyimido)-1,1,3,3-tetramethyluronium tetrafluoroborate (TNTU), O-(N-succinimidyl)-1,1,3,3-tetramethyluronium tetrafluorbborate (TST-U) or bromotris(pyrrolidino)phosphonium hexafluorophosphate (PyBroP); and a base, for example, an inorganic base such as potassium carbonate, calcium carbonate or sodium bicarbonate, an amine such as triethylamine, diisopropylethylamine or pyridine, or a polymer supported base such as (piperidinomethyl)polystyrene, (morpholinomethyl)polystyrene, (dimethylaminomethyl) polystyrene, poly(4-vinylpyridine) or the like.

(Preparation Method 2)

A preparation method by reacting 1 equivalent of an alkylating reagent represented by the following formula (IV)

(IV)

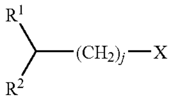

[wherein, $R^1$, $R^2$, and j are the same as the definitions, respectively, in the above-described formula (I); X represents a halogen atom, an alkylsulfonyloxy group, or an arylsulfonyloxy group], with 0.1 to 10 equivalents of a compound represented by the following formula (V)

(V)

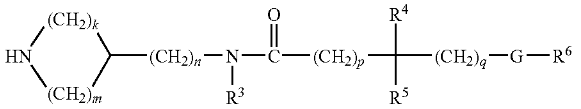

[wherein, $R^3$, $R^4$, $R^5$, $R^6$, G, k, m, n, p, and q are the same as the definitions, respectively, in the above-mentioned formula (I)], in the absence or presence of a solvent.

The reaction can be allowed to smoothly proceed by the suitable use of the same base as that in the above-mentioned preparation method 1. Further, in the present preparation method, the reaction can be accelerated by the coexistence of an iodide compound such as potassium iodide, sodium iodide or the like in some cases.

In the above-mentioned formula (IV), X represents a halogen atom, an alkylsulfonyloxy group or an arylsulfonyloxy group. The suitable examples of the halogen atoms include a chlorine atom, a bromine atom, and an iodine atom. The suitable concrete example of the alkylsulfonyloxy group includes a methylsulfonyloxy group, a trifluoromethylsulfonyloxy group and the like. The suitable concrete example of the arylsulfonyloxy group includes a tosyloxy group.

(Preparation Method 3)

A preparation method by reacting 1 equivalent of an aldehyde represented by the following formula (VI)

(VI)

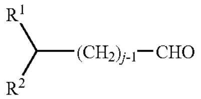

[wherein, $R^1$, and $R^2$ are the same as the definitions, respectively, in the above-mentioned formula (I); j represents 1 or 2], or the following formula (VII)

$R^1$—CHO (VII)

[wherein, $R^1$ is the same as the definition in the above-mentioned formula (I); this compound corresponds to a case that j expresses 0 in the formula (I)] with 0.1 to 10 equivalents of a compound represented by the above-mentioned formula (V), in the absence or presence of a solvent.

The reaction is generally called a reductive amination reaction, and includes, as a reducing condition, a catalytic hydrogenation reaction using a catalyst containing a metal such as palladium, platinum, nickel or rhodium, a hydrogenation reaction using a borane or a complex hydride such as lithium aluminum hydride, sodium borohydride, sodium cyanoborohydride, or sodium triacetoxyborohydride and an electrolytic reduction reaction.

(Preparation Method 4)

A preparation method by reacting 1 equivalent of a compound represented by the following formula (VIII)

(VIII)

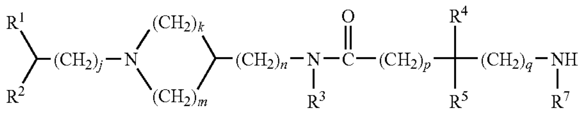

[wherein, $R^1$, $R^2$, $R^3$, $R^4$, $R^5$, $R^7$, j, k, m, n, p, and q are the same as the definitions, respectively, in the above-mentioned formula (I)], with 0.1 to 10 equivalents of a carboxylic acid or sulfonic acid represented by the following formula (IX) or a reactive derivative thereof

HO—A—$R^6$ (IX)

[wherein, $R^6$ is the same as the definition of $R^6$ in the above-mentioned formula (I); "A" represents a carbonyl group or a sulfonyl group], in the absence or presence of a solvent.

The reactive derivative of the carboxylic acid or sulfonic acid represented by the formula (IX) means a highly reactive carboxylic acid or sulfonic acid derivative generally used in the field of synthetic organic chemistry, such as an acid halide, an acid anhydride or a mixed acid anhydride.

The reaction can be allowed to smoothly proceed by the suitable use of the same dehydrating agent, coupling reagent or base as those in the above-mentioned preparation method 1.

(Preparation Method 5)

A preparation method by reacting 1 equivalent of a compound represented by the above-mentioned formula (VIII) with 0.1 to 10 equivalents of an isocyanate or isothiocyanate represented by the following formula (X)

$$Z{=}C{=}N{-}R^6 \quad (X)$$

[wherein, $R^6$ is the same as the definition of $R^6$ in the above-mentioned formula (I); Z represents an oxygen atom or a sulfur atom], in the absence or presence of a solvent.

(Preparation Method 6)

A preparation method by reacting 1 equivalent of a compound represented by the following formula (XI)

(XI)

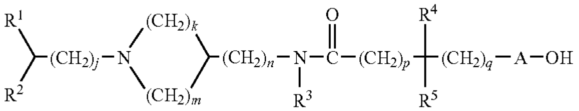

[wherein, $R^1$, $R^2$, $R^3$, $R^4$, $R^5$, j, k, m, n, p, and q are the same as the definitions, respectively, in the above-mentioned formula (I); "A" represents a carbonyl group or a sulfonyl group], with 0.1 to 10 equivalents of an amine represented by the following formula (XII)

$$R^6{-}NH_2 \quad (XII)$$

[wherein, $R^6$ is the same as the definition of $R^6$ in the above-mentioned formula (I)], in the absence or presence of a solvent.

The reaction can be allowed to smoothly proceed by the suitable use of the same dehydrating agent, coupling reagent or base as those in the above-mentioned preparation method 1.

When the substrate supplied for the reaction in each of the above-mentioned preparation methods 1 to 6 has substituents which can be thought to generally react under the reaction conditions of each preparation method in organic synthetic chemistry or affect the reaction, the objective compound can be obtained by protecting the functional groups of the substrate with known proper protecting groups, supplying the protected substrate for the reaction and then removing the protecting groups by a known method.

In addition, the compound used in the present invention can also be obtained by further converting the (single or plural) substituent(s) of the compound prepared by the above-mentioned preparation method 1 to 6 by a known reaction generally used in organic synthetic chemistry, such as an alkylation reaction, an acylation reaction or a reduction reaction.

In each of the above-mentioned preparation methods, a halogenated hydrocarbon such as dichloromethane or chloroform, an aromatic hydrocarbon such as benzene or toluene, an ether such as diethyl ether or tetrahydrofuran, an ester such as ethyl acetate, an aprotic polar solvent such as dimethyl formamide, dimethyl sulfoxide or acetonitrile, or an alcohol such as methanol, ethanol or isopropyl alcohol, is suitably used as a reaction solvent in response to the reaction.

In any preparation method, the reaction temperature is in the range of −78° C. to +150° C., preferably 0° C. to 100° C. After the reaction is completed, the objective cyclic amine compound represented by the above-mentioned formula (I) can be isolated in usual isolating and purifying operations, namely the operations of concentration, filtration, extraction, solid-phase extraction, recrystallization, chromatography, and so on. Further, the isolated compound can be converted into a pharmaceutically acceptable acid addition salt or $C_1$ to $C_6$ alkyl addition salt by usual methods.

EXAMPLES

The present invention will be explained specifically hereafter on the basis of examples. However, the present invention is not limited to the examples. Compound numbers assigned to compounds in the following examples correspond to compound numbers (Compd. No.), respectively, assigned to compounds shown as suitable concrete examples in Tables 1.1 to 1.221.

Reference Example 1

Synthesis of (R)-1-(4-chlorobenzyl)-3-[{N-(3,4-difluorobenzoyl) glycyl}amino]pyrrolidine (Compd. No. 69)

The compounds of the present invention were synthesized by the preparation method mentioned in WO 99/25686, and, for example, (R)-1-(4-chlorobenzyl)-3-[{N-(3,4-difluorobenzoyl)glycyl}amino]pyrrolidine of Compd. No. 69 was synthesized as follows.

1) 3-Amino-1-(4-chlorobenzyl)pyrrolidine-dihydrochloride

4-Chlorobenzyl chloride (4.15 g, 25.8 mmol) and i-$Pr_2NEt$ (6.67 g, 51.6 mmol) were added to the DMF solution (50 mL of 3-{(tert-butoxycarbonyl)amino}pyrrolidine (4.81 g, 25.8 mmol) in DMF (50 ml). The reaction mixture was stirred at 70° C. for 15 hours, and the solvent was then removed under reduced pressure. The residue was recrystallized ($CH_3CN$, 50 mL) to obtain the objective 3-{(tert-butoxycarbonyl)amino}-1-(4-chlorobenzyl)pyrrolidine (6.43 g, 80%) as the yellowish white solid.

$^1$H-NMR ($CDCl_3$, 300 MHz) δ 1.37 (s, 9H), 1.5-1.7 (br, 1H), 2.1-2.4 (m, 2H), 2.5-2.7 (m, 2H), 2.83 (br, 1H), 3.57 (s, 2H), 4.1-4.3 (br, 1H), 4.9-5.1 (br, 1H), 7.15-7.35 (br, 4H); the purity was determined with RPLC/MS (98%); ESI/MS m/e 311.0 ($M^+$+H, $C_{16}H_{24}ClN_2O_2$).

1M HCl-$Et_2O$ (100 mL) was added to the $CH_3OH$ (80 mL) solution of the 3-{(tert-butoxycarbonyl)amino}-1-(4-chlorobenzyl)pyrrolidine (6.38 g, 20.5 mmol) and then stirred at 25° C. for 15 hours. The solvent was removed under reduced pressure to obtain the solid. The solid was recrystallized ($CH_3OH/CH_3CN$=1:2, 130 mL) to obtain the purified 3-amino-1-(4-chlorobenzyl)pyrrolidine·dihydrochloride (4.939 g, 85%) as white powder.

$^1$H-NMR ($d_6$-DMSO, 300 MHz) δ 3.15 (br, 1H), 3.3-3.75 (br-m, 4H), 3.9 (br, 1H), 4.05 (br, 1H), 4.44 (br, 1H), 4.54 (br, 1H), 7.5-7.7 (m, 4H), 8.45 (br, 1H), 8.60 (br, 1H); the purity was determined with RPLC/MS (>99%); ESI/MS m/e 211.0 ($M^+$+H, $C_{11}H_{16}ClN_2$).

Optically active (R)-3-amino-1-(4-chlorobenzyl)pyrrolidine-dihydrochloride and (S)-3-amino-1-(4-chlorobenzyl) pyrrolidine-dihydrochloride were synthesized from the corresponding starting materials, respectively, by the above-mentioned method. The products showed the same $^{1}$H-NMR as that of the above-mentioned racemate.

2) (R)-3-{(N-tert-βutoxycarbonyl)glycyl}amino-1-(4-chlorobenzyl)pyrrolidine

A mixture of (R)-3-amino-1-(4-chlorobenzyl)pyrrolidine-dihydrochloride (4.54 g, 16.0 mmol), a 2M NaOH solution (80 mL), and ethyl acetate (80 mL) was stirred, and the organic layer was then separated. The aqueous layer was extracted with ethyl acetate (80 mL×2). The obtained organic layers were combined, dried over anhydrous sodium sulfate, filtered, and then concentrated to obtain the free (R)-3-amino-1-(4-chlorobenzyl)pyrrolidine (3.35 g, 99%).

$Et_3N$ (2.5 mL, 17.6 mmol), N-tert-butoxycarbonylglycine (2.79 g, 16.0 mmol), EDCI (3.07 g, 16.0 mmol) and HOBt (12.16 g, 16 mmol) were added to the $CH_2Cl_2$ (80 mL) solution of the (R)-3-amino-1-(4-chlorobenzyl)pyrrolidine (3.35 g, 16 mmol). The reaction mixture was stirred at 25° C. for 16 hours, and then mixed with a 2M NaOH solution (80 mL). The organic layer was separated, and the aqueous layer was extracted with dichloromethane (100 mL×3). The obtained organic layers were combined, washed with water (100 mL×2) and aqueous sodium chloride solution (100 mL), dried over anhydrous sodium sulfate, filtered and then concentrated. The objective (R)-3-{N-(tert-butoxycarbonyl) glycyl}amino-1-(4-chlorobenzyl)pyrrolidine (5.40 g, 92%) was obtained by column chromatography ($SiO_2$, ethyl acetate).

3) Synthesis of (R)-1-(4-chlorobenzyl)-3-(glycylamino)pyrrolidine

A 4M HCl dioxane (38 mL) solution was added to the methanol (60 mL) solution of the (R)-3-{N-(tert-butoxycarbonyl)glycyl}amino-1-(4-chlorobenzyl)pyrrolidine (5.39 g, 14.7 mmol). The solution was stirred at room temperature for 2 hours. The reaction mixture was concentrated and then mixed with a 2M NaOH solution (80 mL). The mixture was extracted with dichloromethane (80 mL×3), and the extracts were combined, dried over anhydrous sodium sulfate, and then concentrated. The (R)-3-(glycylamino)-1-(4-chlorobenzyl)pyrrolidine (3.374 g, 86%) was obtained by column chromatography ($SiO_2$, AcOEt/EtOH/$Et_3N$=90/5/5).

$^{1}$H-NMR ($CDCl_3$, 270 MHz) δ 1.77 (dd, J=1.3 and 6.9 Hz, 1H), 2.20-3.39 (m, 2H), 2.53 (dd, J=3.3 and 9.6 Hz, 1H), 2.62 (dd, J=6.6 and 9.6 Hz, 1H), 2.78-2.87 (m, 1H), 3.31 (s, 2H), 3.57 (s, 2H), 4.38-4.53 (br, 1H), 7.18-7.32 (m, 4H), 7.39 (br, s, 1H).

4) (R)-1-(4-Chlorobenzyl)-3-[{N-(3,4-difluorobenzoyl)glycyl}amino]pyrrolidine (Compd. No. 69)

The chloroform (0.4 mL) solution of 3,4-difluorobenzoyl chloride (0.060 mmol) was added to the chloroform (1.0 mL) solution of the (R)-1-(4-chlorobenzyl)-3-(glycylamino)pyrrolidine (0.050 mmol) and triethylamine (0.070 mmol). The reaction mixture was stirred at room temperature for 2.5 hours, and then mixed with a (aminomethyl)polystyrene resin (1.04 mmol/g, 50 mg, 50 mmol). The mixture was stirred at room temperature for 12 hours, and filtered. The resin was washed with dichloromethane (0.5 mL). The filtrate and the washings were combined and mixed with dichloromethane (4 mL). The solution was washed with a 2M NaOH aqueous solution (0.5 mL), and then concentrated to obtain the (R)-1-(4-chlorobenzyl)-3-[{N-(3,4-difluorobenzoyl) glycyl}amino]pyrrolidine (Compd. No. 69) (7.8 mg, 38%): the purity was determined with RPLC/MS (>99%); ESI/MS m/e 408.0 ($M^{+}$+H, $C_{20}H_{20}ClF_2N_3O_2$).

Example 1

Assay of the Inhibitory Potency of a Compound Against the Rise in the Intracellular Calcium Concentration of CCR3 Expressing Cells by Eotaxin The inhibitory potency of the compound of the present invention against the rise in the intracellular calcium concentration was assayed using K562 cells stably expressing a CCR3 receptor by the following method.

A 1 mM Fura 2 acetoxymethyl ester (Dojin Kagaku Co.) was added to a suspension obtained by suspending the CCR3 expressing K562 cells in a 10 mM HEPES-containing HBSS solution, and then incubated at 37° C. for 30 minutes. The suspension was excited with 340 nm and 380 nm light, and the 340/380 ratio was monitored to measure the intracellular calcium concentration. Human eotaxin (0.5 μg/ml) was used as an agonist, and the inhibitory potency of the compound was assayed by treating the CCR3 expressing K562 cells with the compound at five minutes before the stimulation using the eotaxin, assaying the intracellular calcium concentration of the treated CCR3 expressing K562 cells, and then calculating the inhibition potency (%) by the use of the following expression.

$$\text{Inhibition rate } (\%)=\{1-(A-B)/(C-B)\}\times 100$$

(A: an intracellular calcium concentration, when the cells were treated with the compound and then stimulated with the eotaxin; B: an intracellular calcium concentration, when the cells were not stimulated with the eotaxin; C: an intracellular calcium concentration, when the cells were not treated with the compound but stimulated with the eotaxin).

When the inhibitory activities of the cyclic amine derivatives used in the present invention were assayed, for example, the following compounds showed inhibitory activities of 20% to 50%, 50% to 80%, and >80%, respectively, at a concentration of 10 μM.

The compounds which showed the inhibitory activities of 20% to 50% at the concentration of 10 μM:

Compd. Nos. 11, 156, 234, 330, 392, 424, 481, 523, 525, 533, 558, 567, 582, 602, 613, 630, 646, 649, 701, 738, 741, 754, 767, 814, 816, 833, 839, 873, 902, 909, 945, 1002, 1159, 1170, 1258, 1315, 1352, 1357, 1407, 1417, 1448, 1472, 1504, 1508, 1531, 1558, 1562, 1569, 1661, 1670, 1686, 1719, 1751, 1756, 1769, 1775, 1783, 1797, 1802, 1803, 1815, 1834, 1841, 1846, 1883, 1887, 1889, 1892, 1913, 1924, 1928, 1960, 2006, 2013, 2035, 2052, 2083, 2113, 2127, 2136, 2189, 2320, 2321, 2323, 2327, 2330, 2334, 2336, 2338, 2345, 2394, 2394, 2398, 2398, 2400, 2400, 2406, 2406, 2407, 2407, 2409, 2409, 2420, 2420, 2421, 2421

The compounds which showed the inhibitory activities of 50% to 80% at the concentration of 10 μL M:

Compd. Nos. 83, 115, 146, 150, 216, 294, 297, 322, 405, 440, 459, 461, 466, 482, 484, 487, 490, 492, 503, 526, 528, 550, 562, 570, 578, 620, 623, 659, 685, 687, 703, 716, 730, 733, 755, 770, 850, 856, 867, 876, 998, 1015, 1024, 1223, 1259, 1267, 1295, 1377, 1402, 1412, 1420, 1485, 1519, 1550, 1560, 1595, 1601, 1650, 1701, 1725, 1754, 1836, 1856, 1870, 1912, 1923, 1929, 2095, 2120, 2138, 2179, 2258, 2260, 2261, 2267, 2268, 2270, 2275, 2276, 2278, 2287, 2290, 2291, 2294, 2297, 2300, 2301, 2302, 2307, 2309, 2313, 2317, 2322, 2324, 2326, 2328, 2329, 2333, 2335, 2343, 2344, 2346, 2347, 2348, 2350, 2351, 2353, 2358, 2360, 2361, 2364, 2365, 2368, 2369, 2377, 2379, 2381, 2402, 2403, 2404, 2405, 2408, 2410, 2411, 2416, 2417, 2418

The compounds which showed the inhibitory activities of >80% at the concentration of 10 μM:

Compd. Nos. 7, 32, 68, 169, 173, 203, 209, 215, 520, 544, 547, 851, 852, 855, 874, 910, 1003, 1012, 1032, 1038, 1042, 1043, 1046, 1114, 1190, 1244, 1247, 1384, 1441, 1513, 1527, 1545, 1582, 1673, 1687, 1689, 1705, 1850, 1869, 1871, 1876, 1877, 1899, 2027, 2289, 2293, 2296, 2298, 2315, 2318, 2319, 2325, 2332, 2349, 2352, 2354, 2355, 2356, 2357, 2359, 2362, 2363, 2366, 2367, 2370, 2371, 2372, 2373, 2374, 2375, 2376, 2378, 2382, 2383, 2390, 2393, 2396, 2412, 2413, 2414, 2415, 2422, 2423, 2424, 2425, 2426, 2427, 2428

Example 2

Assay of Inhibitory Potency Against the Binding of Eotaxin to a CCR3 Expressing Cells Membrane Fraction A cell membrane fraction prepared from human CCR3 expressing K562 cells was suspended in an assay buffer solution (25 mM HEPES, pH 7.6, 1 mM $CaCl_2$, 5 mM $MgCl_2$, 0.5% BSA) at a concentration of 0.5 mg/mL to prepare the cell membrane fraction suspension. A test compound was diluted with the assay buffer solution to prepare the test compound solution. [$^{125}$I]-labeled human eotaxin (Amasham Co.) was diluted with the assay buffer solution at a concentration of 1 μCi/mL to prepare the labeled ligand solution. 25 μL of the test compound solution, 25 μL of the labeled ligand solution and 50 μL of the cell membrane fraction suspension were sequentially injected into each well of a 96 well microplate coated with 0.5% BSA, stirred (100 μL of the reaction solution), and then incubated at 25° C. for 90 minutes.

After the reaction was finished, the reaction solution was filtered with the 96 well filter plate (Millipore Inc.) in which the filter was previously immersed in a 0.5% polyethylenimine solution, and the filter was washed with 150 μL of a cold washing buffer solution (assay buffer+0.5M NaCl) four times (150 μL of the cold washing buffer solution was added and then filtered). After the filter was dried with air, 25 μL of a liquid scintillator was added to each well, and the radioactivity retained in the membrane fraction on the filter was measured with a TopCounter (Packard Co.).

The inhibitory potency of the test compound against the binding of the human eotaxin to the CCR3 membrane fraction was calculated, wherein a count on the addition of 100 ng of non-labeled human eotaxin in stead of the test compound was subtracted, and a count on the non-addition of the test compound was 100%.

$$\text{Inhibition (\%)}=\{1-(A-B)/(C-B)\}\times 100$$

(A: a count, when the test compound was added; B: a count, when 100 ng of the non-labeled human eotaxin was added; C: a count, when only [$^{125}$I]-labeled human eotaxin was added).

When the inhibitory activities of the cyclic amine derivatives used in the present invention were assayed, the inhibitory activities of typical compounds in the present example were approximately equivalent to the inhibitory activities measured in Example 1.

UTILIZABILITY IN INDUSTRY

The medicine containing as an active ingredient the cyclic amine compound, the pharmaceutically acceptable acid addition salt thereof or the pharmaceutically acceptable $C_1$ to $C_6$ alkyl addition salt thereof, of the present invention, or the medicine for treating or preventing diseases in which CCR3 participates, has an activity for inhibiting the action of the ligand of the CCR3, such as eotaxin, to a target cell as the CCR3 antagonist. Thereby, the medicine is useful as a medicine for treating and/or preventing diseases for whose progress and maintenance the tissue infiltration of eosinophils, basophils, activated T-cells and so on play main rolls, for example, allergic diseases such as bronchial asthma, allergic rhinitis, atopic dermatitis, urticaria, contact dermatitis and allergic conjunctivitis, inflammatory bowel diseases such as ulcerative colitis, Crohn disease and so on. Further, the medicine is useful as a medicine for treating and/or preventing AIDS by the HIV-1 infection-inhibiting activity based on the CCR3 antagonism.

The invention claimed is:

1. A method for treatment of allergic conjunctivitis, eosinophilia, eosinophilic gastroentereitis, eosinophilic enteropathy, eosinophilic fasciitis, eosinophilic granuloma, eosinophilic pustular folliculitis, and eosinophilic leukemia, comprising administering to a subject an effective amount of a compound having CCR3 antagonistic activity, wherein said compound is represented by the following formula (I), a pharmaceutically acceptable acid addition salt thereof, or a pharmaceutically acceptable $C_1$ to $C_6$ alkyl addition salt thereof, (I)

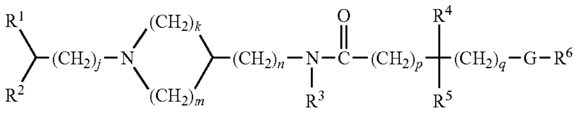

wherein, $R^1$ represents an aromatic heterocyclic group selected from the group consisting of an imidazolyl group, a pyrazolyl group, an oxazolyl group, an isoxazolyl group, a thiazolyl group, an isothiazolyl group, a pyrimidinyl group, a triazinyl group, a triazolyl group, an oxadiazolyl group, a thiadiazolyl group, a thienothienyl group, an indolyl group, a benzofuranyl group a benzothienyl group, a quinolyl group, a benzimidazolyl group, a benzoxazolyl group, a benzotriazolyl group, a benzoxadiazolyl group, a benzothiadiazolyl group, further provided that the naphthyl group or the aromatic heterocyclic group may be substituted by one or more halogen atoms, hydroxy groups, cyano groups, nitro groups, carboxyl groups, carbamoyl groups, $C_1$ to $C_6$ alkyl groups, $C_3$ to $C_8$ cycloalkyl groups, $C_2$ to $C_6$ alkenyl groups, C1 to C6 alkoxy groups, $C_1$ to $C_6$ alkylthio groups, $C_3$ to $C_5$ alkylene groups, $C_2$ to $C_4$ alkylenoxy groups, $C_1$ to $C_3$ alkylenedioxy groups, phenyl groups, phenoxy groups, phenylthio groups, benzyl groups, benzyloxy groups, benzoylamino groups, $C_2$ to $C_7$ alkanoyl groups, $C_2$ to $C_7$ alkoxycarbonyl groups, $C_2$ to $C_7$ alkanoyloxy groups, $C_2$ to $C_7$ alkanoylamino groups, $C_2$ to $C_7$ N-alkylcarbamoyl groups, $C_4$ to $C_9$ N-cycloalkylcarbamoyl groups, $C_1$ to $C_6$ alkylsulfonyl groups, $C_3$ to $C_8$ (alkoxycarbonyl)methyl groups, N-phenylcarbamoyl groups, piperidinocarbonyl groups, morpholinocarbonyl groups, 1-pyrrolidinylcarbonyl groups, divalent groups represented by the formula: —NH(C═O)O—, divalent groups represented by the formula: —NH(C═S)O—, amino groups, mono($C_1$ to $C_6$ alkyl)amino groups or di($C_1$ to $C_6$ alkyl)amino groups, and further provided that the substituents of the phenyl group, the $C_3$ to $C_8$ cycloalkyl group, the aromatic heterocyclic group or the condensed ring may further be substituted by one or more halogen atoms, hydroxy groups, amino groups, trifluoromethyl groups, $C_1$ to $C_6$ alkyl groups or $C_1$ to $C_6$ alkoxy groups;

$R^2$ represents a hydrogen atom, a $C_1$ to $C_6$ alkyl group, a $C_2$ to $C_7$ alkoxycarbonyl group, a hydroxy group or a phenyl group, provided that the $C_1$ to $C_6$ alkyl group or the phenyl group in $R^2$ may be substituted by one or more halogen atoms, hydroxy groups, $C_1$ to $C_6$ alkyl groups or $C_1$ to $C_6$ alkoxy groups, and provided that when j is 0, $R^2$ is not a hydroxy group;

j is 0;

k represents 0 or 1;

m represents an integer of 2 to 3;

n represents 0;

$R^3$ represents a hydrogen atom or a $C_1$ to $C_6$ alkyl group which may be substituted by one or two phenyl groups which may be substituted by the same or different numbers of halogen atoms, hydroxy groups, $C_1$ to $C_6$ alkyl groups or $C_1$ to $C_6$ alkoxy groups;

$R^4$ and $R^5$, which may be the same or different, represent a hydrogen atom, a hydroxy group, a phenyl group or a $C_1$ to $C_6$ alkyl group, and the $C_1$ to $C_6$ alkyl group represented by $R^4$ and/or $R^5$ may be substituted by one or more halogen atoms, hydroxy groups, cyano groups, nitro groups, carboxyl groups, carbamoyl groups, mercapto groups, guanidino groups, $C_3$ to $C_8$ cycloalkyl groups, $C_1$ to $C_6$ alkoxy groups, $C_1$ to $C_6$ alkylthio groups, phenyl groups which may be substituted by one or more halogen atoms, hydroxy groups, $C_1$ to $C_6$ alkyl groups, $C_1$ to $C_6$ alkoxy groups or benzyloxy groups, phenoxy groups, benzyloxy groups, benzyloxycarbonyl groups, $C_2$ to $C_7$ alkanoyl groups, $C_2$ to $C_7$ alkoxycarbonyl groups, $C_2$ to $C_7$ alkanoyloxy groups, $C_2$ to $C_7$ alkanoylamino groups, $C_2$ to $C_7$ N-alkylcarbamoyl groups, $C_1$ to $C_6$ alkylsulfonyl groups, amino groups, mono($C_1$ to $C_6$ alkyl)amino groups, di($C_1$ to $C_6$ alkyl) amino groups or aromatic heterocyclic groups (having one to three atoms of oxygen, sulfur and/or nitrogen as heteroatoms), or condensed rings formed by the condensation of the aromatic heterocyclic group with a benzene ring, or $R^4$ and $R^5$ may together form a three to six-membered cyclic hydrocarbon;

p represents 0 or 1;

q represents 0 or 1;

G represents a group represented by —$NR^7$—CO—, —NH—CO—NH—, or —NH—CS—NH provided that $R^7$ is a hydrogen atom;

$R^6$ represents a phenyl group, a $C_3$ to $C_8$ cycloalkyl group, a $C_3$ to $C_6$ cycloalkenyl group, a benzyl group or an aromatic heterocyclic group having one to three atoms of oxygen, sulfur and/or nitrogen as heteroatoms, provided that the phenyl group, the benzyl group or the aromatic heterocyclic group represented by $R^6$ may be condensed, to make a condensed ring, with a benzene ring or an aromatic heterocyclic group having one or three atoms of oxygen, sulfur and/or nitrogen as heteroatoms, further provided that the phenyl group, the $C_3$ to $C_8$ cycloalkyl group, the $C_3$ to $C_6$ cycloalkenyl group, the benzyl group, the aromatic heterocyclic group or the condensed ring represented by $R^6$ may be substituted by one or more halogen atoms, hydroxy groups, mercapto groups, cyano groups, nitro groups, thiocyanato groups, carboxyl groups, carbamoyl groups, trifluoromethyl groups, $C_1$ to $C_6$ alkyl groups, $C_3$ to $C_6$ cycloalkyl groups, $C_2$ to $C_6$ alkenyl groups, $C_1$ to $C_6$ alkoxy groups, $C_3$ to $C_8$ cycloalkyloxy groups, $C_1$ to $C_6$ alkylthio groups, $C_1$ to $C_3$ alkylenedioxy groups, phenyl groups, phenoxy groups, phenylamino groups, benzyl groups, benzoyl groups, phenylsulfinyl groups, phenylsulfonyl groups, 3-phenylureido groups, $C_2$ to $C_7$ alkanoyl groups, $C_2$ to $C_7$ alkoxycarbonyl groups, $C_2$ to $C_7$ alkanoyloxy groups, $C_2$ to $C_7$ alkanoylamino group, $C_2$ to $C_7$ N-alkylcarbamoyl groups, $C_1$ to $C_6$ alkylsulfonyl groups, phenylcarbamoyl groups, N,N-di($C_1$ to $C_6$ alkyl)sulfamoyl groups, amino groups, mono($C_1$ to $C_6$ alkyl)amino groups, di($C_1$ to $C_6$ alkyl)amino groups, benzylamino groups, $C_2$ to $C_7$ (alkoxycarbonyl)amino groups, $C_1$ to $C_6$ (alkylsulfonyl)amino groups or bis($C_1$ to $C_6$ alkylsulfonyl)amino groups, and further provided that the substituents of the phenyl group, the $C_3$ to $C_8$ cycloalkyl group, the $C_3$ to $C_8$ cycloalkenyl group, the benzyl group, the aromatic heterocyclic group, or the condensed ring may further be substituted by one or more halogen atoms, cyano groups, hydroxy groups, amino groups, trifluoromethyl groups, $C_1$ to $C_6$ alkyl groups, $C_1$ to $C_6$ alkoxy groups, $C_1$ to $C_6$ alkylthio groups, mono($C_1$ to $C_6$ alkyl)amino groups, or di($C_1$ to $C_6$ alkyl)amino groups; and wherein m+k is 3.

2. The method according to claim 1, wherein k is 1 and m is 2 in said formula (I).

* * * * *